US012570612B2

(12) United States Patent
Liu et al.

(10) Patent No.: US 12,570,612 B2
(45) Date of Patent: Mar. 10, 2026

(54) SUBSTITUTED NITROGEN HETEROCYCLIC COMPOUND AND ANESTHETIC EFFECT THEREOF

(71) Applicant: CHENGDU MFS PHARMA. CO., LTD., Chengdu (CN)

(72) Inventors: Jin Liu, Chengdu (CN); Wensheng Zhang, Chengdu (CN); Haijun Ma, Chengdu (CN); Changhua Wang, Chengdu (CN); Zhenbiao Xie, Chengdu (CN)

(73) Assignee: CHENGDU MFS PHARMA. CO., LTD., Chengdu (CN)

( * ) Notice: Subject to any disclaimer, the term of this patent is extended or adjusted under 35 U.S.C. 154(b) by 804 days.

(21) Appl. No.: 17/754,632

(22) PCT Filed: Oct. 10, 2020

(86) PCT No.: PCT/CN2020/120218

§ 371 (c)(1),
(2) Date: Apr. 7, 2022

(87) PCT Pub. No.: WO2021/068943

PCT Pub. Date: Apr. 15, 2021

(65) Prior Publication Data

US 2023/0026724 A1 Jan. 26, 2023

(30) Foreign Application Priority Data

Oct. 11, 2019 (CN) ......................... 201910964601.7
Oct. 11, 2019 (CN) ......................... 201910965229.1
Oct. 9, 2020 (CN) ......................... 202011073826.2
Oct. 9, 2020 (CN) ......................... 202011074987.3

(51) Int. Cl.

| | |
|---|---|
| ***C07D 231/14*** | (2006.01) |
| ***A61P 23/00*** | (2006.01) |
| ***C07D 207/333*** | (2006.01) |
| ***C07D 233/64*** | (2006.01) |
| ***C07D 249/04*** | (2006.01) |
| ***C07D 405/06*** | (2006.01) |
| ***C07D 405/12*** | (2006.01) |
| ***C07D 409/06*** | (2006.01) |
| ***C07D 409/12*** | (2006.01) |

(52) U.S. Cl.

CPC ............ *C07D 231/14* (2013.01); *A61P 23/00* (2018.01); *C07D 207/333* (2013.01); *C07D 233/64* (2013.01); *C07D 249/04* (2013.01); *C07D 405/06* (2013.01); *C07D 405/12* (2013.01); *C07D 409/06* (2013.01); *C07D 409/12* (2013.01)

(58) Field of Classification Search

None

See application file for complete search history.

(56) References Cited

U.S. PATENT DOCUMENTS

| | | | |
|---|---|---|---|
| 9,156,825 B2 | 10/2015 | Raines et al. | |
| 9,522,136 B2 * | 12/2016 | Raines ................ | C07D 233/54 |
| 9,718,789 B2 | 8/2017 | Ashweek et al. | |
| 11,434,205 B2 | 9/2022 | Ma | |

FOREIGN PATENT DOCUMENTS

| | | | |
|---|---|---|---|
| CN | 1066844 | A | 12/1992 |
| CN | 1747949 | A | 3/2006 |
| CN | 101146531 | A | 3/2008 |
| CN | 111153851 | A1 | 3/2015 |
| CN | 104540813 | A | 4/2015 |
| CN | 107382812 | A1 | 11/2017 |
| CN | 107382870 | A1 | 11/2017 |
| CN | 107522662 | A1 | 11/2017 |

(Continued)

OTHER PUBLICATIONS

Cotten, J. et al. Carboetomidate: A Pyrrole Analogue of Etomidate Designed Not To Suppress Adrenocortical Function . Anesthesiology. 2010, 112(3):637-644 (Year: 2010).*

Zalaru, C. et al. New Pyrazole Derivatives With Potential Local Anesthetic Activity. Revue Roumaine de Chimie, 2008, 53(4), 267-271 (Year: 2008).*

Woll, K. et al. Shedding Light on Anesthetic Mechanisms: Application of Photoaffinity Ligands. Anesth Analg. 2016, 123(5): 1253-1262 (Year: 2016).*

Lange, J. et al. Bioisosteric Replacements of the Pyrazole Moiety of Rimonabant: Synthesis, Biological Properties, and Molecular Modeling Investigations of Thiazoles, Triazoles, and Imidazoles as Potent and Selective CB1 Cannabinoid Receptor Antagonists J. Med. Chem. 2005, 48, 6, 1823-1838 (Year: 2005).*

Symonds, C. et al. Ultrafast photodissociation dynamics of pyrazole, imidazole and their deuterated derivatives using ab initio multiple cloning. Phys. Chem. Chem. Phys., 2019,21, 9987-9995 (Year: 2019).*

(Continued)

*Primary Examiner* — Clinton A Brooks
*Assistant Examiner* — Nicola Maria Bauer
(74) *Attorney, Agent, or Firm* — NKL Law; Bin Lu; Allen Xue

(57) ABSTRACT

Disclosed in the present invention are a substituted nitrogen heterocyclic compound and anesthetic action thereof. Specifically provided a chemical compound as shown in formula I, a stereoisomer thereof, a pharmaceutically acceptable salt thereof, a solvate thereof, a prodrug thereof, a metabolite thereof or a deuterated derivative thereof. The substituted nitrogen heterocyclic compound provided in the present application has good central nervous system inhibition effects, capable of generating sedative, hypnotic and/or general anesthetic effects, and capable of controlling status epilepticus; said substituted nitrogen heterocyclic compound is also characterized by rapid onset of action and rapid recovery, while maintaining positive anesthetic activity; in addition, said substituted nitrogen heterocyclic compound has almost no inhibitory effect on adrenocortical function, low side effects, and resolves technical difficulties in the art. The present invention provides a new selection for clinical screening and/or preparation of sedative, hypnotic and/or general anesthetic drugs and drugs controlling status epilepticus.

17 Claims, 17 Drawing Sheets

(56) References Cited

FOREIGN PATENT DOCUMENTS

| | | | | |
|---|---|---|---|---|
| CN | 107445898 | A1 | | 12/2017 |
| CN | 107641105 | A1 | | 1/2018 |
| CN | 109761906 | A1 | | 5/2019 |
| CN | 109776509 | A1 | | 5/2019 |
| CN | 109776510 | A1 | | 5/2019 |
| CN | 109776511 | A1 | | 5/2019 |
| CN | 109776512 | A1 | | 5/2019 |
| CN | 109824656 | A1 | | 5/2019 |
| CN | 110003188 | A1 | | 7/2019 |
| CN | 110669017 | A1 | | 1/2020 |
| CN | 110724106 | A | | 1/2020 |
| CN | 110724106 | A1 | | 1/2020 |
| JP | 06345728 | A | * | 12/1994 |
| JP | 2006131609 | A | | 5/2006 |
| WO | 2017059827 | A1 | | 4/2017 |

OTHER PUBLICATIONS

Husain, SS. et al. Modifying methoxycarbonyl etomidate inter-ester spacer optimizes in vitro metabolic stability and in vivo hypnotic potency and duration of action. Anesthesiology, Nov. 1, 2012, 117(5):1027-1036 (Year: 2012).*

Zhang et al. Drug metabolism in drug discovery and development. Acta Pharmaceutica Sinica B 2018; 8(5):72-732 (Year: 2018).*

Cotten, J. et al. Anesthesiology. 2010, 112(3):637-644 (Year: 2010).*

Zalaru, C. et al. Revue Roumaine de Chimie, 2008, 53(4), 267-271 (Year: 2008).*

Woll, K. et al. Anesth Analg. 2016, 123(5): 1253-1262 (Year: 2016).*

Lange, J. et al. J. Med. Chem. 2005, 48, 6, 1823-1838 (Year: 2005).*

Symonds, C. et al. Phys. Chem. Chem. Phys., 2019,21, 9987-9995 (Year: 2019).*

Japanese patent Application 2022-521590, mailed on Apr. 9, 2025.

Japanese patent Application 2022-521590, mailed on Apr. 16, 2024.

Chinese patent application 2019109664601.7, mailed on Sep. 5, 2021.

Chinese patent application 2019109664601.7, mailed on Jan. 19, 2023.

Japanese patent Application 2022-521590, mailed on Nov. 5, 2024.

European Patent Application No. 20875415.0, EP search report and EESR mailed on Oct. 10, 2023.

International Search Report, issued to PCT/CN2020/120218, date of mailing Jan. 11, 2021.

B. Kay; "A Dose-Response Relationship For Etomidate, With Some Observations on Cumulation", Br J Anaesth. 1976; 48(3): 213-6. PubMed: 1259887.

PA Janssen, et al; "Etomidate, a potent non-barbiturate hypnotic. Intravenous etomidate in mice, rats, guinea-pigs, rabbits and dogs", Archives Internationals de Pharmacodynamie et de Therapie, Mar. 1, 1975, 214(1):92-132 Abstract Only Provided; PubMed: 1156027.

Peter J. Zed, et al; "Intubating Conditions and Hemodynamic Effects of Etomidate for Rapid Sequence Intubation in the Emergency Department: An Observational Cohort Study", Acad Emerg Med. 2006; 13(4): 378-83. PubMed: 16531603.

Ledingham, et al; "Etomidate and Adrenocortical Function", Lancet. 1983; 1(8339): 1434. PubMed: 6134189.

Ryan Kamp, et al; "Etomidate, sepsis, and adrenal function: not as bad as we thought?", Crital Care. 2007; 11(3): 145. PubMed: 17610749.

Stuart a Forman, M.D., PhD: "Clinical and Molecular Pharmacology of Etomidate", Anesthesiology, Mar. 2011; 114(3): 695-707. PubMed: 21263301.

EA Bruder, et al; "Single induction dose of etomidate versus other induction agents for endotracheal intubation in critically ill patients (Review)" Cochrane Database of Systematic Reviews 2015; Issue 1: Art No. CD010225. PubMed: 25568981.

B. Allolio, et al; "Adrenocortical Suppression by a Single Induction Dose of Etomidate***", Klin Wochenschr. 1984; 62 (21): 1014-7. PubMed: 6096626.

Chee Man Chan, MD, MPH, et al; "Etomidate is associated with mortality and adrenal insufficiency in sepsis: A Meta-analysis*", Crit Care Med. 2012; 40(11): 2945-53. PubMed: 22971586.

R. Lee Wagner, M.D., et al; "Inhibition of Adrenal Steroidogenesis By The Anesthetic Etomidate", The New England Journal of Medicine, May 31, 1984; 310 (22): 1415-21 PubMed: 6325910.

F.H. De Jong, et al; "Etomidate Suppresses Adrenocortical Function by Inhibition of 11ß-Hydroxylation", Journal of Clinical Endocrinology and Metabolism; 1984; 59(6): 1143-7. PubMed: 6092411.

Luc Roumen, et al; "Construction of 3D models of the CYP11B family as a tool to predict ligand binding characteristics", J Comput Aided Mol Des. 2007; 21 (8): 455-71 PubMed: 48126; published online Jul. 24, 2007.

Ervin Pejo, B.S. et al; "Sedative-hypnotic Binding to 11ß-hydroxylase", Anesthesiology. 2016; 125 (5): 943-951 PubMed: 27541316.

Ryu Komatsu, et al; "Anesthetic Induction with Etomidate, Rather than Propofol, Is Associated with Increased 30-Day Mortality and Cardiovascular Morbidity After Noncardiac Surgery", Anesth Analg. 2013; 117(6): 1329-37. PubMed: 24257383.

Ladi. E. et al. "Design and Evaluation of Highly Selective Human Immunoproteasome Inhibitors Reveal a Compensatory Process That Preserves Immune Cell Viability" Journal of Medicinal Chemistry, vol. 62. No. 15. Jul. 8, 2019 (Jul. 8, 2019). ISSN: 0022-2623.

* cited by examiner

The relative percentage of cortisol in cell culture medium was determined by HPLC-MS

The relative percentage of corticosterone in cell culture medium was determined by HPLC-MS

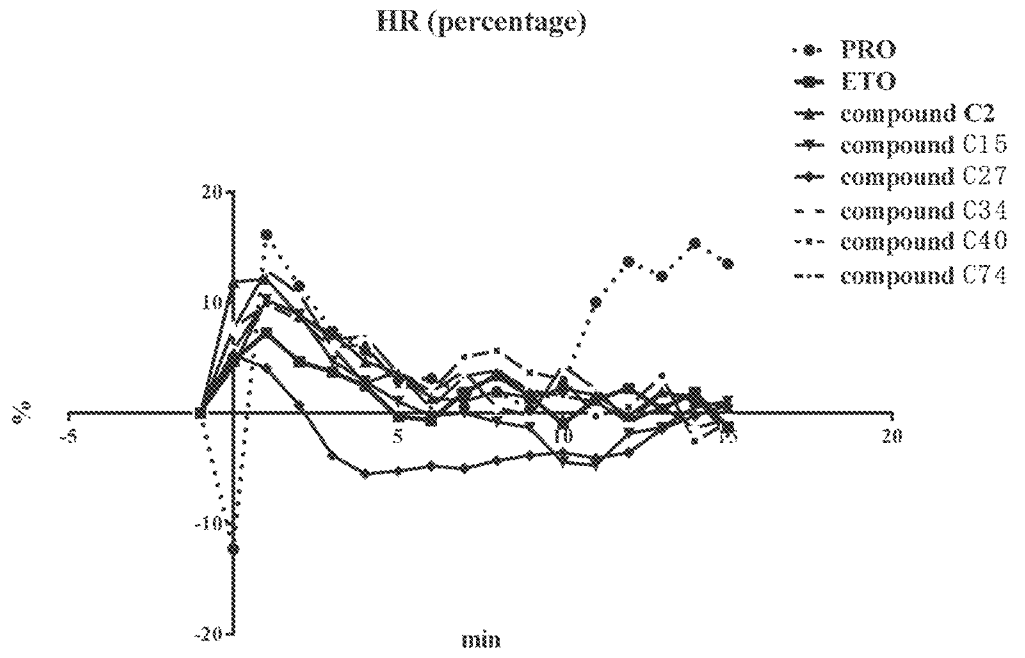
Figure 16
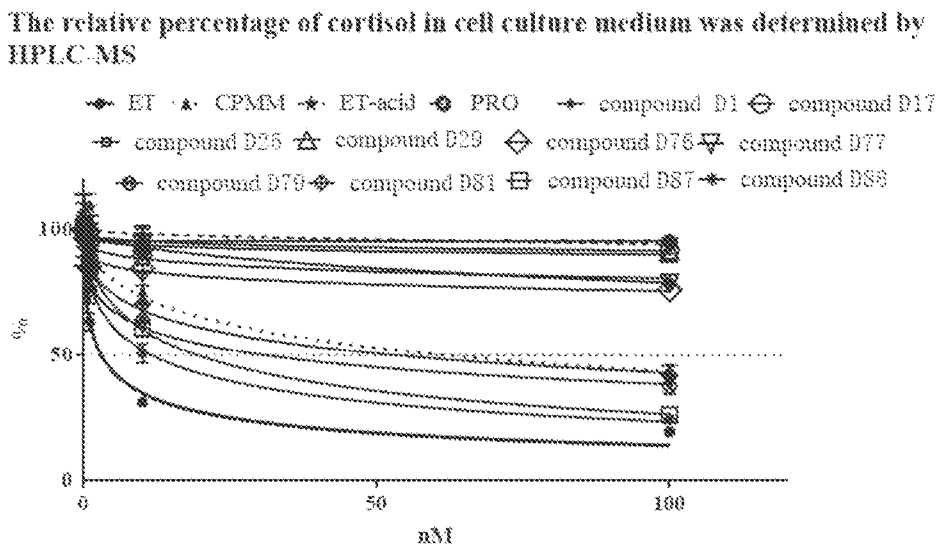

SUBSTITUTED NITROGEN HETEROCYCLIC COMPOUND AND ANESTHETIC EFFECT THEREOF

CROSS-REFERENCE TO RELATED APPLICATIONS

This application is a national stage entry of a PCT patent application No. PCT/CN2020/120218, filed Oct. 10, 2020, which claims the benefit and priority of CN patent application No. 201910964601.7 filed on Oct. 11, 2019, CN patent application No. 201910965229.1, filed on Oct. 11, 2019, CN patent application No. 202011073826.2, filed on Oct. 9, 2020, CN patent application No. 202011074987.3, filed on Oct. 9, 2020. The entire disclosures of the above applications are hereby incorporated herein by reference.

TECHNICAL FIELD

The present invention belongs to the field of medicinal chemistry, and in particular relates to a novel substituted nitrogen heterocyclic compounds, as well as the use of the compound in the preparation of drugs with sedative, hypnotic and/or general anesthetic effects, as well as drugs capable of controlling the status epilepticus.

BACKGROUND ART

Heterocyclic compounds are a class of cyclic organic compounds in which the atoms constituting the ring contain atoms other than carbon (including but not limited to N, O and S). Heterocyclic compounds are widely existed in nature. Most important compounds related to biology are heterocyclic compounds, such as nucleic acids, antibiotics, hormones, pigments and alkaloids etc. Heterocyclic compounds have various of structures, Common heterocyclic compounds include furan and its derivatives, thiophene and its derivatives, pyridine and its derivatives, pyrrole and its derivatives, benzofuran and its derivatives, benzothiophene and its derivatives etc. Due to the diverse structure of heterocyclic compounds, they have been widely used in many fields, such as drugs, fungicides, protease inhibitors etc.

Studies have found that some heterocyclic compounds with special structures have the effect of sedation and anesthesia. CN111153851A disclosed a quaternary ammonium salt heterocyclic compound and preparation method and use thereof. Heterocyclic compound have fastly the anesthetic effect, and it has the effect of long-term local anesthesia after a single administration, and the sensory nerve block time is greater than the motor nerve block time, and it has both long-acting local anesthesia and selective local anesthesia, and can be used as a long-acting local anesthetic. However, for some patients who require major surgery, general anesthetics are needed to suppress the patient's central nervous system and make the patient's consciousness disappear.

Etomidate is containing 5-membered heterocyclic group of imidazole derivative, which has the effects of sedation, hypnosis and anesthesia. It has been one of the commonly used drugs for anesthesia induction, and has been used in clinical practice for more than 30 years. Its pharmacological characteristics are outstanding: rapid induction of anesthesia, little impact on respiration and stable hemodynamics during single or continuous infusion. (Br J Anaesth. 1976; 48(3): 213-6. PubMed: 1259887; Arch Int Pharmacodyn Ther. 1975; 214(1): 92-132. PubMed: 1156027; Acad Emerg Med. 2006; 13(4): 378-83. PubMed: 16531603). The structure of etomidate is as follows, it is a ester substituted heterocyclic compound:

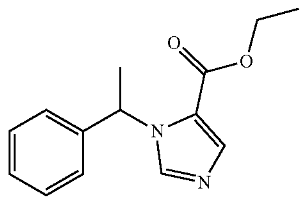 [SMILES: CCOC(=O)c1cncn1C(C)c1ccccc1]

However, the disadvantages of etomidate gradually was appeared when use in the clinical, which limits its application. For example, it's awakening quality is slightly worse than that of another general anesthetic propofol, which can reduce the survival rate of critically ill patients by inhibiting the function of adrenal cortex (Lancet. 1983; 1(8339): 1434. PubMed: 6134189; Crit Care. 2007; 11(3): 145. PubMed: 17610749; Anesthesiology. 2011; 114(3): 695-707. PubMed: 21263301); (Cochrane Database Syst Rev. 2015; 1: CD010225. PubMed: 25568981). It has been reported that a single injection of etomidate can also inhibit adrenal cortex function for up to 6 to 8 hours, increasing mortality in hospitalized patients (Klin Wochenschr. 1984; 62 (21): 1014-7. PubMed: 6096626) (Crit Care Med. 2012; 40(11): 2945-53. PubMed: 22971586; Anesth Analg. 2013; 117(6): 1329-37. PubMed: 24257383);

The literature suggests that etomidate can inhibit the key enzymes in the synthesis pathway of adrenocortical hormone (11β-Hydroxylase) to inhibit adrenocortical function (n Engl J Med. 1984; 310 (22): 1415-21 PubMed: 6325910; J Clin Endocrinol Metab. 1984; 59(6): 1143-7. PubMed: 6092411). Further studies showed that the inhibition was mainly due to the fact that the basic nitrogen on the imidazole ring in the molecular structure of etomidate could interact with 11β-Heme iron on hydroxylase binds to inhibit the activity of the enzyme (J compute aided mol des. 2007; 21 (8): 455-71 PubMed: 48126). However, in fact, not all heterocyclic compounds containing imidazole rings can inhibit the function of adrenal cortex, such as etomidate acid, the metabolite of etomidate, cyclopropyl methoxycarbonyl metamidate (CPMM), etc. (Anesthesiology. 2016; 125 (5): 943-951 PubMed: 27541316).

Therefore, it is of great clinical significance and wide application prospect to design a new compound which can not only keep the excellent characteristics of etomidate general anesthesia activity, but also not inhibit the synthesis of adrenocortical hormone.

CONTENT OF THE PRESENT INVENTION

In order to solve above problems, the present invention provides a novel series of substituted nitrogen heterocyclic compounds. The present invention further provides that the substituted nitrogen heterocyclic derivatives can use in the preparation of drugs with sedative, hypnotic and/or anesthetic effects, together with drugs capable of controlling the status epilepticus.

The present invention provides compounds of formula I, or stereoisomers thereof, or pharmaceutically acceptable salts thereof, or solvates thereof, or prodrugs thereof, or metabolites thereof, or deuterated derivatives thereof:

Formula I

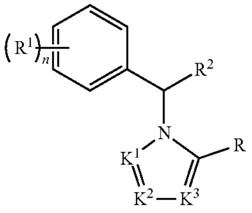

$R^1$ is independently selected from the group consisting of deuterium, halogen, —CN, —$NO_2$, —$OR^{32}$, —C(O)$R^{31}$, —$CO_2R^{31}$, —$CON(R^{32})_2$, —$N(R^{32})_2$, —OC(O)$R^{31}$, —$SO_2R^{31}$, substituted or unsubstituted 3~8-membered heterocyclic groups, substituted or unsubstituted $C_{1-8}$ alkyls, substituted or unsubstituted $C_{1-8}$ alkoxyl, substituted or unsubstituted $C_{2-8}$ alkenyls, substituted or unsubstituted $C_{2-8}$ alkynyls;

Wherein, $R^{31}$ is independently of each other selected from the group consisting of deuterium, $R^{32}$, substituted or unsubstituted $C_{2-8}$ alkenyls, substituted or unsubstituted $C_{2-8}$ alkynyls; $R^{32}$ is independently of each other selected from the group consisting of hydrogen, substituted or unsubstituted $C_{1-8}$ alkyls, substituted or unsubstituted $C_{3-8}$ cycloalkyls, substituted or unsubstituted 3~8-membered heterocyclic groups, substituted or unsubstituted aryls, and substituted or unsubstituted heteroaryls; said substituents are deuterium, cyano, hydroxyl, carboxyl, halogen, $C_{3-8}$ cycloalkyls or their halogenated or deuterated derivatives, 3~8-membered heterocyclic groups or their halogenated or deuterated derivatives, aryls or their halogenated or deuterated derivatives, and heteroaryls or their halogenated or deuterated derivatives;

For above $R^1$, $R^{31}$, $R^{32}$, said substituents are deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-8}$-membered cycloalkyls or their halogenated or deuterated derivatives, 3~8-membered heterocyclic groups or their halogenated or deuterated derivatives, aryls or their halogenated or deuterated derivatives, heteroaryls or their halogenated or deuterated derivatives;

n is an integer of 0~5;

$R^2$ is selected from the group consisting of hydrogen, deuterium, halogen, $C_{1-8}$ alkyls or their halogenated or deuterated derivatives, $C_{1-8}$ alkoxyl or their halogenated or deuterated derivatives, $C_{2-8}$ alkenyls or their halogenated or deuterated derivatives, $C_{2-8}$ alkynyls or their halogenated or deuterated derivatives, 3~8-membered heterocyclic groups or their halogenated or deuterated derivatives;

$K^1$ is selected from N or $CR^{k1}$, $K^2$ is selected from N or $CR^{k2}$;

$K^3$ is $CR^{k3}$, R is selected from

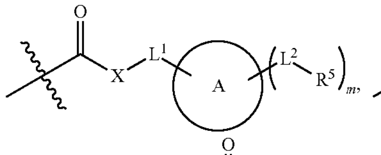, 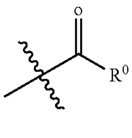,

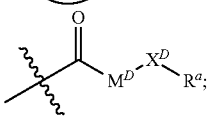;

or, $K^3$ is $CR^{k0}$, R is $R^{k3}$, $R^{k0}$ is selected from

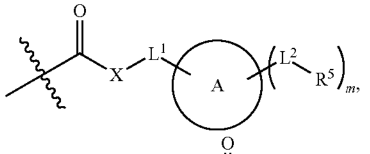, 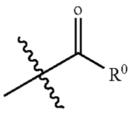,

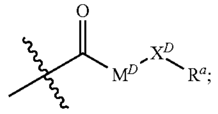;

$R^{k1}$, $R^{k2}$, $R^{k3}$ are independently selected from the group consisting of hydrogen, deuterium, halogen, substituted or unsubstituted $C_{1-8}$ alkyls, $N(R^{3k})_2$; said substituents are deuterium, halogen, $C_{1-8}$ alkyls or their halogenated or deuterated derivatives, $C_{1-8}$ alkoxyls or their halogenated or deuterated derivatives, $C_{3-8}$ cycloalkyls or their halogenated or deuterated derivatives, 3~8-membered heterocyclic groups or their halogenated or deuterated derivatives, aryls or their halogenated or deuterated derivatives, heteroaryls or their halogenated or deuterated derivatives, —$N(R^{3k})_2$, $R^{3k}$ is H or $C_{1-8}$ alkyls;

X is selected from O, S or $NR^{30}$, wherein, $R^{30}$ is selected from hydrogen or $C_{1-8}$ alkyls;

$L^1$ and $L^2$ are independently of each other selected from the group consisting of none, substituted or unsubstituted $C_{1-8}$ alkylenyls; said substituents are deuterium, cyano, hydroxyl, carboxyl, halogen, $C_{1-8}$ alkyls or their halogenated or deuterated derivatives, $C_{2-8}$ alkenyls or their halogenated or deuterated derivatives, $C_{2-8}$ alkynyls or their halogenated or deuterated derivatives, $C_{1-8}$ alkoxyls or their halogenated or deuterated derivatives, $C_{3-8}$ cycloalkyls or their halogenated or deuterated derivatives, 3~8-membered heterocyclic groups or their halogenated or deuterated derivatives, aryls or their halogenated or deuterated derivatives, heteroaryls or their halogenated or deuterated derivatives;

$L^1$ and $L^2$ can be connected to the homotopic or heterotopic atoms on the A ring;

m is an integer of 0~4;

Ring A is none, or, ring A is selected from 3~8-membered saturated carbocycles, 3~8-membered unsaturated carbocycles, 3~8-membered saturated heterocycles or 3~8-membered unsaturated heterocycles;

$R^5$ is selected from the group consisting of hydrogen, deuterium, halogen, propadienyl,

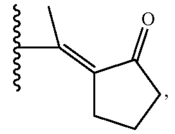 [SMILES: */C(C)=C1\CCCC1=O], substituted or unsubstituted $C_{1-8}$ alkyls, —$OR^{33}$, —$SR^{33}$, —OC(O)$R^{34}$, $C_{3-8}$-membered cycloalkyls, 3~8-membered heterocyclyls aryls, heteroaryls, —$N(R^{33})_2$, —C(O)$R^{34}$, —C(S)$R^{34}$, —S(O)$R^{34}$, —$CON(R^{33})_2$, —$SO_2R^{34}$, substituted or unsubstituted $C_{2-8}$ alkenyls, substituted or unsubstituted $C_{2-8}$ alkynyls, cyano, isocyano, isothiocyano, nitro, -$L^{33}$-$R^{36}$ or =$R^{39}$;

$L^{33}$ is selected from $C_{1-4}$ alkylenyls;

$R^{36}$ is selected from cyano, nitro, —OC(O) $R^{34}$, —C(O) $R^{34}$, —S(O)$R^{34}$, —C(O)N($R^{33}$)$_2$;

$R^{33}$ is selected from the group consisting of hydrogen, methylsulfonyl, -$L^{31}$-COO-$L^{32}$, and the following substituted or unsubstituted groups: $C_{1-8}$ alkyls, $C_{3-8}$ cycloalkyls, 3~8-membered heterocyclyls, aryls, heteroaryls;

$R^{34}$ is selected from the group consisting of $R^{33}$, deuterium, and the following substituted or unsubstituted groups: $C_{1-8}$ alkoxyl, $C_{2-8}$ alkenyls, $C_{2-8}$ alkynyls, or —S—$C_{1-8}$ alkyls;

$L^{31}$ is selected from the substituted or unsubstituted $C_{1-8}$ alkylenyls; $L^{32}$ is selected from the substituted or unsubstituted $C_{1-8}$ alkyls;

For above $R^5$, $R^{33}$, $R^{34}$, said substituents are selected from group consisting of deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-8}$-membered cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives, —S—$C_{1-4}$ alkyls, di-substituted cyclic carbonyls, =$R^{39}$, $C_{2-8}$ alkenyls or $C_{2-8}$ alkynyls;

$R^{39}$ is selected from O, S, $NR^{40}$ or C($R^{41}$)$_2$; $R^{40}$ is selected from hydrogen, halogen, $C_{1-4}$ alkyls or their halogenated or deuterated derivatives; $R^{41}$ is selected from $R^{40}$ or deuterium;

$R^0$ is selected from $L^{C3}R^{C4}$, $L^{C1}X^{C}L^{C2}R^{C5}$;

$L^{C3}$ is selected from none, substituted or unsubstituted $C_{1\sim4}$ alkylenyls, said substituents in $C_{1\sim4}$ alkylenyls are selected from the group consisting of $C_{1-5}$ alkyls, $C_{1\sim5}$ alkoxyl, halogen, hydroxyl;

$R^{C4}$ is selected from the group consisting of substituted or unsubstituted $C_{2\sim6}$ alkenyls, substituted or unsubstituted $C_{2-6}$ alkynyls, substituted or unsubstituted 3~6-membered saturated or unsaturated heterocyclyls, substituted or unsubstituted 3~6-membered saturated or unsaturated cycloalkyls, $COR^{4d}$; said substituents are independently of each other selected from $L^{C4}R^{4e}$; $R^{4d}$ is selected from $C_{1\sim6}$ alkyls;

$L^{C4}$ is selected from the group consisting of none, substituted or unsubstituted $C_{1-4}$ alkylenyls; $R^{4e}$ is selected from the group consisting of $C_{1\sim5}$ alkyls, $C_{1\sim5}$ alkoxyl, halogen, hydroxyl;

$L^{C1}$ is selected from substituted or unsubstituted $C_{1\sim3}$ alkylenyls, said substituents is selected from $C_{1-5}$ alkyls;

$X^C$ is O or S;

$L^{C2}$ is selected from none, substituted or unsubstituted $C_{1-3}$ alkylenyls, said substituents are selected from the group consisting of $C_{1\sim4}$ alkyls, $C_{1\sim4}$ alkoxyl, $L^{2a}R^{5g}$; $L^{2a}$ is selected from none, $C_{1\sim2}$ alkylenyls; $R^{5g}$ is selected from halogen, $C_{1\sim4}$ alkoxyls;

$R^{C5}$ is selected from the group consisting of hydrogen, halogen, $C_{1\sim5}$ alkyls, $C_{2\sim4}$ alkenyls, $C_{2\sim4}$ alkynyls, $COR^{4d}$, $C_{3\sim6}$ di-alkenyls, $C_{1\sim5}$ alkoxyl, 3~6-membered saturated or unsaturated heterocyclyls all of which are substituted by one or more $R^{5c}$, 3~6-membered saturated or unsaturated cycloalkyls all of which are substituted by one or more $R^{5c}$; $R^{4d}$ is selected $C_{1\sim6}$ alkyls, $R^{5c}$ is selected from the group consisting of halogen, =$R^{5d}$, $L^{1a}R^{5e}$, $C_{3\sim6}$ di-alkenyls; $R^{5d}$ is $CH_2$, O or S, $L^{1a}$ is $C_{1\sim3}$ alkylenyls, $R^{5e}$ is $C_{1\sim5}$ alkyls, $C_{1\sim5}$ alkoxyl;

$M^D$ is selected from CO or $CR^{D6}R^{D7}$, $R^{D6}$ is selected from hydrogen, $X^{Db}R^{D4b}$, $R^{D7}$ is selected from hydrogen, $R^{Dc}R^{D4c}$;

$X^D$ is O or S; $X^{Db}$ is O or S; $X^{Dc}$ is O or S;

$R^a$ is selected from the group consisting of substituted or unsubstituted $C_{1\sim6}$ alkyls, substituted or unsubstituted $C_{2\sim6}$ alkynyls, substituted or unsubstituted $C_{2\sim6}$ alkenyls, substituted or unsubstituted 3~6-membered saturated or unsaturated heterocyclyls, substituted or unsubstituted 3~6-membered saturated or unsaturated cycloalkyls; said substituents are independently of each other selected from the group consisting of $C_{3\sim6}$ di-alkenyls, $C_{1\sim5}$ alkyls, $C_{1\sim5}$ alkoxyl, halogen, hydroxyl;

$R^{D4b}$, $R^{D4c}$ are independently of each other selected from the group consisting of substituted or unsubstituted $C_{1\sim6}$ alkyls, substituted or unsubstituted $C_{2\sim6}$ alkynyls, substituted or unsubstituted $C_{2\sim6}$ alkenyls, $COR^{Df}$, substituted or unsubstituted 3~6-membered saturated or unsaturated heterocyclyls groups, substituted or unsubstituted 3~6-membered saturated or unsaturated cycloalkyls; said substituents are independently of each other selected from the group consisting of $C_{3\sim6}$ di-alkenyls, $C_{1\sim5}$ alkyls, $C_{1\sim5}$ alkoxyl, halogen, hydroxyl; $R^{Df}$ is selected from $C_{1\sim5}$ alkyls;

Or, when $M^D$ is $CR^{D6}R^{D7}$ and $R^{D6}$ is $X^{Db}R^{D4b}$, $R^{D4b}$ and $R^a$ is connected to get the substituted or unsubstituted 3~6-membered saturated or unsaturated heterocyclyls said saturated or unsaturated heterocyclic substituents is selected from the group consisting of halogenated or un-halogenated $C_{1\sim6}$ alkyls, halogenated or un-halogenated $C_{2\sim6}$ alkynyls, halogenated or un-halogenated $C_{2\sim6}$ alkenyls, $COR^{Df}$;

$R^{D7}$ is selected from the group consisting of hydrogen, $R^{Dc}R^{D4c}$, $X^{Dc}$ is O or S, $R^{D4c}$ is selected from the group consisting of substituted or unsubstituted $C_{1\sim6}$ alkyls, substituted or unsubstituted $C_{2\sim6}$ alkynyls, substituted or unsubstituted $C_{2\sim6}$ alkenyls, $COR^{Df}$, substituted or unsubstituted 3~6-membered saturated or unsaturated heterocycyls, substituted or unsubstituted 3~6-membered saturated or unsaturated cycloalkyls; said substituents are independently of each other selected from the group consisting of $C_{3\sim6}$ di-alkenyl, $C_{1\sim5}$ alkyls, $C_{1\sim5}$ alkoxyl, halogen, hydroxyl; $R^{Df}$ is selected from $C_{1\sim5}$ alkyls.

Further, said compound is represented by formula A-I:

Formula A-I

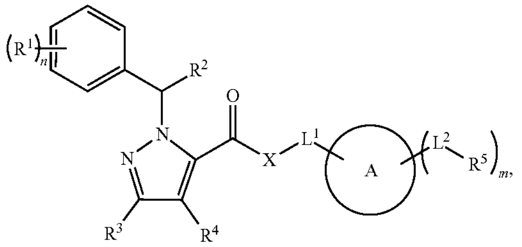

$R^1$ is independently of each other selected from the group consisting of deuterium, halogen, —CN, —$NO_2$, —$OR^{32}$, —C(O)$R^{31}$, —$CO_2R^{31}$, —CON($R^{32}$)$_2$, —N($R^{32}$)$_2$, —OC(O)$R^{31}$, —$SO_2R^{31}$, substituted or unsubstituted 3~8-membered heterocyclyls, substituted or unsubstituted $C_{1-8}$ alkyls, substituted or unsubstituted $C_{2-8}$ alkenyls, substituted or unsubstituted $C_{2-8}$ alkynyls;

Wherein, $R^{31}$ is independently of each other selected from the group consisting of deuterium, $R^{32}$, substituted or unsubstituted $C_{2-8}$ alkenyls, substituted or unsubstituted $C_{2-8}$ alkynyls, $R^{32}$ is independently of each other selected from the group consisting of hydrogen, substituted or unsubstituted $C_{1-8}$ alkyls, substituted or unsubstituted $C_{3-8}$ cycloalkyls, substituted or unsubstituted 3~8-membered heterocyclyls, substituted or unsubstituted aryls, and substituted or unsubstituted heteroaryls; said substituents are deuterium, cyano, hydroxyl, carboxyl, halogen, $C_{3-8}$ cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives;

For above $R^1$, $R^{31}$, $R^{32}$, said substituents are selected from the group consisting of deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-8}$-membered cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives;

n is an integer of 0~5;

$R^2$ is selected from the group consisting of hydrogen, deuterium, halogen, $C_{1-8}$ alkyls or their halogenated or deuterated derivatives, $C_{1-8}$ alkoxyl or their halogenated or deuterated derivatives, $C_{2-8}$ alkenyls or their halogenated or deuterated derivatives, $C_{2-8}$ alkynyls or their halogenated or deuterated derivatives, 3~8-membered heterocyclyls or their halogenated or deuterated derivatives;

$R^3$ and $R^4$ are independently of each other selected from the group consisting of hydrogen, deuterium, halogen, substituted or unsubstituted $C_{1-8}$ alkyls; said substituents is deuterium, halogen, $C_{1-8}$ alkyls or their halogenated or deuterated derivatives, $C_{1-8}$ alkoxyl or their halogenated or deuterated derivatives, $C_{3-8}$ cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives;

X is selected from O, S or $NR^{30}$, wherein, $R^{30}$ is selected from hydrogen, deuterium or $C_{1-8}$ alkyls;

$L^1$ and $L^2$ are independently of each other selected from the group consisting of none, substituted or unsubstituted $C_{1-8}$ alkylenyls; said substituents are deuterium, cyano, hydroxyl, carboxyl, halogen, $C_{1-8}$ alkyls or their halogenated or deuterated derivatives, $C_{2-8}$ alkenyls or their halogenated or deuterated derivatives, $C_{2-8}$ alkynyls or their halogenated or deuterated derivatives, $C_{1-8}$ alkoxyls or their halogenated or deuterated derivatives, $C_{3-8}$ cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives;

$L^1$ and $L^2$ can be connected to the homotopic or heterotopic atoms on the A ring; m is an integer of 0~4;

Ring A is none, or, ring A is selected from 3~8-membered saturated carbocycles, 3~8-membered unsaturated carbocycles, 3~8-membered saturated heterocycles or 3~8-membered unsaturated heterocycles;

$R^5$ is selected from the group consisting of hydrogen, deuterium, halogen, propadienyl,

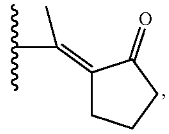 [SMILES: */C(C)=C1\CCCC1=O], substituted or unsubstituted $C_{1-8}$ alkyls, $—OR^{33}$, $—SR^{33}$, $—OC(O)R^{34}$, $C_{3-8}$-membered cycloalkyls, 3~8-membered heterocycyls, aryls, heteroaryls, $—N(R^{33})_2$, $—C(O)R^{34}$, $—C(S)R^{34}$, $—S(O)R^{34}$, $—CON(R^{33})_2$, $—SO_2R^{34}$, substituted or unsubstituted $C_{2-8}$ alkenyls, substituted or unsubstituted $C_{2-8}$ alkynyls, cyano, isocyano, isothiocyano, nitro, $-L^{33}-R^{36}$ or $=R^{39}$;

$L^{33}$ is selected from $C_{1-4}$ alkylenyls;

$R^{36}$ is selected from cyano, nitro, $—OC(O)R^{34}$, $—C(O)R^{34}$, $—S(O)R^{34}$, $—C(O)N(R^{33})_2$;

$R^{33}$ is selected from the group consisting of hydrogen, methylsulfonyl, $-L^{31}-COO-L^{32}$, the following substituted or unsubstituted groups: $C_{1-8}$ alkyls, $C_{3-8}$ cycloalkyls, 3~8-membered heterocyclyls, aryls, heteroaryls;

$R^{34}$ is selected from the group consisting of $R^{33}$, deuterium, the following substituted or unsubstituted groups: $C_{1-8}$ alkoxyl, $C_{2-8}$ alkenyls, $C_{2-8}$ alkynyls or $—S—C_{1-8}$ alkyls;

$L^{31}$ is selected from the substituted or unsubstituted $C_{1-8}$ alkylenyls; $L^{32}$ is selected from the substituted or unsubstituted $C_{1-8}$ alkyls;

For above $R^5$, $R^{33}$, $R^{34}$, said substituents are deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-8}$-membered cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives, $—S—C_{1-4}$ alkyls, di-substituted cyclic carbonyl, $=R^{39}$, $C_{2-8}$ alkenyls or $C_{2-8}$ alkynyls;

$R^{39}$ is selected from O, S, $NR^{40}$ or $C(R^{41})_2$, $R^{40}$ is selected from hydrogen, halogen, $C_{1-4}$ alkyls or their halogenated or deuterated derivatives; $R^{41}$ is selected from $R^{40}$ or deuterium;

Preferably:

Above $R^1$ is independently of each other selected from the group consisting of deuterium, halogen, —CN, $—NO_2$, $—OR^{32}$, $—C(O)R^{31}$, $—CO_2R^{31}$, $—CON(R^{32})_2$, $—N(R^{32})_2$, $—OC(O)R^{31}$, $C_{1-3}$ alkyls, $C_{2-3}$ alkenyls, $C_{2-3}$ alkynyls;

Wherein, $R^{31}$ is independently of each other selected from the group consisting of deuterium, $R^{32}$, $C_{2-3}$ alkenyls, $C_{2-3}$ alkynyls; $R^{32}$ is independently of each other selected from the group consisting of hydrogen, $C_{1-3}$ alkyls;

Or, n is an integer of 0~2;

Or, $R^2$ is selected from the group consisting of hydrogen, deuterium, halogen, $C_{1-3}$ alkyls or their halogenated or deuterated derivatives.

Further, said compound is represented by formula A-II:

Formula A-II

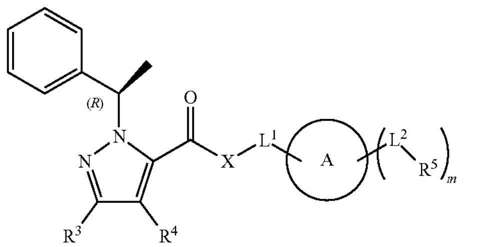

$R^3$ and $R^4$ are independently of each other selected from the group consisting of hydrogen, deuterium, halogen, substituted or unsubstituted $C_{1-4}$ alkyls; said substituents is deuterium, halogen, $C_{1-4}$ alkyls or their halogenated or deuterated derivatives, $C_{1-4}$ alkoxyl or their halogenated or deuterated derivatives, $C_{3-6}$ cycloalkyls or their halogenated or deuterated derivatives, 3~6-membered heterocyclyls or their halogenated or deuterated derivatives;

X is selected from O or S;

$L^1$ and $L^2$ are independently of each other selected from the group consisting of none, substituted or unsubstituted $C_{1-4}$ alkylenyls; said substituents are deuterium, cyano, hydroxyl, carboxyl, halogen, $C_{1-4}$ alkyls or their halogenated or deuterated derivatives, $C_{2-4}$ alkenyls or their halogenated or deuterated derivatives, $C_{2-4}$ alkynyls or their halogenated or deuterated derivatives, $C_{1-4}$ alkoxyls or their halogenated or deuterated derivatives, $C_{3-5}$ cycloalkyls or their halogenated or deuterated derivatives, 3~5-membered heterocyclyls or their halogenated or deuterated derivatives, aryls or their halogenated or deuterated derivatives, heteroaryls or their halogenated or deuterated derivatives;

$L^1$ and $L^2$ can be connected to the homotopic or heterotopic atoms on the A ring; m is an integer of 0~4;

Ring A is none, or, ring A is selected from 3~6-membered saturated carbocycles, 3~6-membered unsaturated carbocycles, 3~6-membered saturated heterocycles or 3~6-membered unsaturated heterocycles;

$R^5$ is selected from the group consisting of hydrogen, deuterium, halogen, propadienyl,

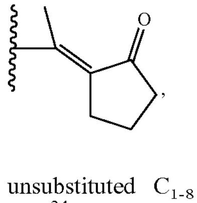

substituted or unsubstituted $C_{1-8}$ alkyls, —$OR^{33}$, —$SR^{33}$, —$OC(O)R^{34}$, $C_{3-8}$-membered cycloalkyls, 3~8-membered heterocyclyls, aryls, heteroaryls, —$N(R^{33})_2$, —$C(O)R^{34}$, —$C(S)R^{34}$, —$S(O)R^{34}$, —$CON(R^{33})_2$, —$SO_2R^{34}$, substituted or unsubstituted $C_{2-8}$ alkenyls, substituted or unsubstituted $C_{2-8}$ alkynyls, cyano, isocyano, isothiocyano, nitro, -$L^{33}$-$R^{36}$ or =$R^{39}$;

$L^{33}$ is selected from $C_{1-4}$ alkylenyls;

$R^{36}$ is selected from cyano, nitro, —$OC(O)$ $R^{34}$, —$C(O)$ $R^{34}$, —$S(O)R^{34}$, —$C(O)N(R^{33})_2$;

$R^{33}$ is selected from the group consisting of hydrogen, methyl sulfonyl, the following substituted or unsubstituted groups: $C_{1-8}$ alkyls, $C_{3-8}$ cycloalkyls, 3~8-membered heterocyclyls, aryls, heteroaryls;

$R^{34}$ is selected from the group consisting of $R^{33}$, deuterium, the following substituted or unsubstituted groups: $C_{1-8}$ alkoxyl, $C_{2-8}$ alkenyls, $C_{2-8}$ alkynyls;

For above $R^5$, $R^{33}$, $R^{34}$, said substituents thereof are selected from the group consisting of deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-8}$-membered cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives, —S—$C_{1-4}$ alkyls, di-substituted cyclic carbonyl, =$R^{39}$, $C_{2-6}$ alkenyls or $C_{2-6}$ alkynyls;

$R^{39}$ is selected from O, S, $NR^{40}$ or $C(R^{41})_2$, $R^{40}$ is selected from hydrogen, halogen, $C_{1-4}$ alkyls or their halogenated or deuterated derivatives; $R^{41}$ is selected from $R^{40}$ or deuterium;

Further, $R^3$ and $R^4$ are independently of each other selected from the group consisting of hydrogen, deuterium, halogen, substituted or unsubstituted $C_{1-4}$ alkyls; said substituents is deuterium, halogen, $C_{1-4}$ alkyls or their halogenated or deuterated derivatives, $C_{1-4}$ alkoxyl or their halogenated or deuterated derivatives, $C_{3-6}$ cycloalkyls or their halogenated or deuterated derivatives, 3~6-membered heterocycles or their halogenated or deuterated derivatives;

Or, $L^1$ and $L^2$ are independently of each other selected from the group consisting of none, substituted or unsubstituted $C_{1-4}$ alkylenyls; said substituents are deuterium, cyano, hydroxyl, carboxyl, halogen, $C_{1-4}$ alkyls or their halogenated or deuterated derivatives, $C_{2-4}$ alkenyls or their halogenated or deuterated derivatives, $C_{2-4}$ alkynyls or their halogenated or deuterated derivatives, $C_{1-4}$ alkoxyls or their halogenated or deuterated derivatives, $C_{3-5}$ cycloalkyls or their halogenated or deuterated derivatives, 3~5-membered heterocycles or their halogenated or deuterated derivatives, aryls or their halogenated or deuterated derivatives, heteroaryls or their halogenated or deuterated derivatives;

m is an integer of 0~4;

Or, ring A is none, or, ring A is selected from 3~6-membered saturated carbocycles, 3~6-membered unsaturated carbocycles, 3~6-membered saturated heterocycles or 3~6-membered unsaturated heterocycles;

Or, $R^5$ is selected from the group consisting of hydrogen, deuterium, halogen, propadienyl,

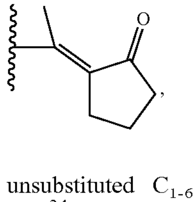

substituted or unsubstituted $C_{1-6}$ alkyls, —$OR^{33}$, —$SR^{33}$, —$OC(O)R^{34}$, $C_{3-8}$-membered cycloalkyls, 3~8-membered heterocyclyls, aryls, heteroaryls, —$N(R^{33})_2$, —$C(O)R^{34}$, —$C(S)R^{34}$, —$S(O)R^{34}$, —$CON(R^{33})_2$, —$SO_2R^{34}$, substituted or unsubstituted $C_{2-6}$ alkenyls, substituted or unsubstituted $C_{2-6}$ alkynyls, cyano, isocyano, isothiocyano, =$R^{39}$; $R^{33}$ is selected from the group consisting of hydrogen, methylsulfonyl, the following substituted or unsubstituted groups: $C_{1-4}$ alkyls, $C_{3-8}$ cycloalkyls, 3~8-membered heterocyclyls, aryls, heteroaryls;

$R^{34}$ is selected from the group consisting of $R^{33}$, deuterium, the following substituted or unsubstituted groups: $C_{1-4}$ alkoxyl, $C_{2-4}$ alkenyls, $C_{2-4}$ alkynyls;

For above $R^5$, $R^{33}$, $R^{34}$, said substituents are selected from the group consisting of deuterium, cyano, hydroxyl, carboxyl, halogen, $C_{1-4}$ alkyls, $C_{1-4}$ alkoxyl, $C_{3-8}$-membered cycloalkyls, 3~8-membered heterocyclyls, aryls, heteroaryls, —S—$C_{1-4}$ alkyls, di-substituted carbonyls, =$R^{39}$, $C_{2-4}$ alkenyls or $C_{2-4}$ alkynyls;

$R^{39}$ is selected from O, S, $NR^{40}$ or $C(R^{41})_2$, $R^{40}$ is selected from hydrogen, halogen, $C_{1-4}$ alkyls or their halogenated or deuterated derivatives; $R^{41}$ is selected from $R^{40}$ or deuterium;

Preferably:

For above $R^3$ and $R^4$ are independently of each other selected from the group consisting of hydrogen, deuterium, halogen, substituted or unsubstituted $C_{1-2}$ alkyls; said substituents are deuterium, halogen, $C_{1-2}$ alkyls or their halogenated or deuterated derivatives, $C_{1-2}$ alkoxyl or their halogenated or deuterated derivatives;

Or, $L^1$ and $L^2$ are independently of each other selected from the group consisting of none, substituted or unsubstituted $C_{1-3}$ alkylenyls; said substituents are deuterium, halogen, $C_{1-3}$ alkyls or their halogenated or deuterated derivatives, $C_{2-3}$ alkenyls or their halogenated or deuterated derivatives, $C_{2-3}$ alkynyls or their halogenated or deuterated derivatives, $C_{1-3}$ alkoxyl or their halogenated or deuterated derivatives;

m is an integer of 0~3;

or, ring A is none, or, ring A is selected from 3~6-membered saturated carbocycles, 3~6-membered unsaturated carbocycles, 3~6-membered saturated heterocycles;

or, $R^5$ is selected from the group consisting of hydrogen, deuterium, halogen, propadienyl,

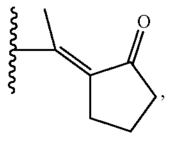 [SMILES: */C(C)=C1\CCCC1=O]

substituted or unsubstituted $C_{1-4}$ alkyls, —$OR^{33}$, —$SR^{33}$, —$OC(O)R^{34}$, $C_{3-8}$-membered cycloalkyls, $C_{3-8}$-membered cycloalkyls, 3~8-membered heterocyclyls, aryls, heteroaryls, —$N(R^{33})_2$, —$C(O)R^{34}$, —$C(S)R^{34}$, —$S(O)R^{34}$, —$CON(R^{33})_2$, —$SO_2R^{34}$, substituted or unsubstituted $C_{2-4}$ alkenyls, substituted or unsubstituted $C_{2-4}$ alkynyls, cyano, isocyano, isothiocyano, =$R^{39}$;

$R^{33}$ is selected from the group consisting of hydrogen, methylsulfonyl, the following substituted or unsubstituted groups: $C_{1-3}$ alkyls, $C_{3-6}$ cycloalkyls, 3~6-membered heterocyclyls, aryls, heteroaryls;

$R^{34}$ is selected from the group consisting of $R^{33}$, deuterium, substituted or unsubstituted $C_{1-3}$ alkoxyl;

For above $R^5$, $R^{33}$, $R^{34}$, said substituents are selected from the group consisting of deuterium, halogen, cyano, $C_{1-2}$ alkyls, $C_{1-2}$ alkoxyl, $C_{3-6}$-membered cycloalkyls, 3~6-membered heterocycyls, aryls, heteroaryls, —S—$C_{1-2}$ alkyls, di-substituted cyclic carbonyl, =$R^{39}$, $C_{2-4}$ alkenyls or $C_{2-4}$ alkynyls;

$R^{39}$ is selected from O, S, $NR^{40}$ or $C(R^{41})_2$, $R^{40}$ is selected from hydrogen, halogen, $C_{1-3}$ alkyls or their halogenated or deuterated derivatives; $R^{41}$ is selected from $R^{40}$ or deuterium;

More Preferably:

For above $R^3$ and $R^4$ are independently of each other selected from the group consisting of hydrogen, deuterium, halogen, halogenated or un-halogenated methyl groups;

Or, $L^1$ and $L^2$ are independently of each other selected from the group consisting of none, substituted or unsubstituted $C_{1-2}$ alkylenyls; said substituents are deuterium, halogen, $C_{1-2}$ alkyls, $C_{2-3}$ alkenyls, $C_{2-3}$ alkynyls;

m is an integer of 0~2;

or, ring A is none, or, ring A is selected from 3~6-membered saturated carbocycles, 3~6-membered unsaturated carbocycles or 3~6-membered saturated heterocycles;

Or, $R^5$ is selected from the group consisting of hydrogen, deuterium, halogen, propadienyl,

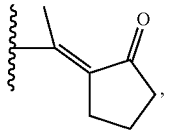 [SMILES: */C(C)=C1\CCCC1=O]

substituted or unsubstituted $C_{1-3}$ alkyls, —$OR^{33}$, —$SR^{33}$, —$OC(O)R^{34}$, $C_{3-8}$-membered cycloalkyls, 3~8-membered heterocyclyls, aryls, heteroaryls, —$N(R^{33})_2$, —$C(O)R^{34}$, —$C(S)R^{34}$, —$S(O)R^{34}$, —$CON(R^{33})_2$, —$SO_2R^{34}$, substituted or unsubstituted $C_{2-3}$ alkenyls, substituted or unsubstituted $C_{2-3}$ alkynyls, cyano, isocyano, isothiocyano, =$R^{39}$;

$R^{33}$ is selected from the group consisting of hydrogen, methylsulfonyl, acetyl, $C_{1-3}$ alkyls;

$R^{34}$ is selected from the group consisting of $R^{33}$, deuterium, $C_{1-3}$ alkoxyl;

For above $R^5$, said substituents are selected from the group consisting of deuterium, halogen, cyano, $C_{1-2}$ alkyls, 3~5-membered heterocyclyls, —S—$CH_3$, di-substituted carbonyl, =$R^{39}$, $C_{2-4}$ alkenyls or $C_{2-4}$ alkynyls;

$R^{39}$ is selected from O, S, $NR^{40}$ or $C(R^{41})_2$, $R^{40}$ is selected from hydrogen, halogen, $C_{1-3}$ alkyls; $R^{41}$ is selected from $R^{40}$ or deuterium;

Further, the compound is represented by formula A-II:

Formula A-II

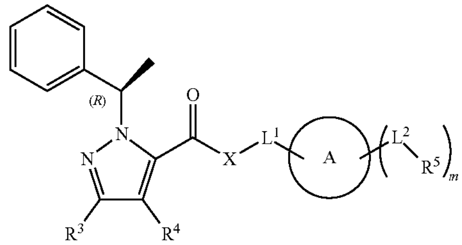

In formula A-II:

Ring A is 3~6-membered saturated carbocycles;

X is selected from O, S; m is an integer of 0~2;

$R^3$ and $R^4$ are independently of each other selected from the group consisting of hydrogen, deuterium, halogen, halogenated or un-halogenated methyl, preferably, $R^3$ and $R^4$ are independently of each other selected from the group consisting of hydrogen, deuterium, F, Cl, $CF_3$;

$L^1$ and $L^2$ are independently of each other selected from the group consisting of none, substituted by 1~2 substituents or unsubstituted methylene; said substituents are deuterium, $C_{1-4}$ alkyls, $C_{2-3}$ alkenyls, $C_{2-3}$ alkynyls;

$L^1$ and $L^2$ can be connected to the homotopic or heterotopic atoms on the A ring;

$R^5$ is selected from the group consisting of hydrogen, deuterium, $C_{1-2}$ alkyls, propadienyl, substituted or unsubstituted $C_{2-4}$ alkenyls, substituted or unsubstituted $C_{2-4}$ alkynyls, —$OR^{33}$, —$C(O)R^{34}$, halogen, =$R^{39}$;

$R^{33}$ is selected from the $C_{1-3}$ alkyls;

$R^{34}$ is selected from the group consisting of $R^{33}$, deuterium, $C_{1-3}$ alkoxyl;

Said substituents of $R^5$ are selected from the group consisting of =$R^{39}$, $C_{2-4}$ alkenyls or $C_{2-4}$ alkynyls;

$R^{39}$ is selected from O, S, $CH_2$,

Or, in formula A-II:

Ring A is selected from 3~6-membered saturated heterocycles; preferably, ring A is

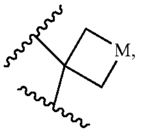

M is O or S;

X is selected from O or S; m is an integer of 0~2;

$R^3$ and $R^4$ are independently of each other selected from the group consisting of hydrogen, deuterium, halogen, halogenated or un-halogenated methyl, preferably, $R^3$ and $R^4$ are independently of each other selected from the group consisting of hydrogen, deuterium, F, Cl, $CF_3$;

$L^1$ and $L^2$ are independently of each other selected from the group consisting of none, substituted by 1~2 substituents or unsubstituted methylene; said substituents are deuterium, $C_{1-4}$ alkyls, $C_{2-3}$ alkenyls, $C_{2-3}$ alkynyls;

$R^5$ is selected from the group consisting of hydrogen, deuterium, $C_{1-2}$ alkyls, propadienyl, substituted or unsubstituted $C_{2-4}$ alkenyls, substituted or unsubstituted $C_{2-4}$ alkynyls, —$OR^{33}$, —$C(O)R^{34}$, halogen, =$R^{39}$;

$R^{33}$ is selected from $C_{1-3}$ alkyls, $R^{34}$ is selected from the group consisting of $R^{33}$, deuterium, $C_{1-3}$ alkoxyl;

Said substituents $R^5$ are selected from the group consisting of =$R^{39}$, $C_{2-4}$ alkenyls or $C_{2-4}$ alkynyls;

$R^{39}$ is selected from O, S, $CH_2$, or, in formula A-II:

Ring A is 5~6-membered unsaturated carbocycles; preferably, ring A is

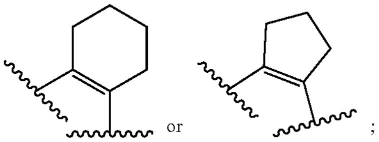 [SMILES: *C1=C(*)CCCC1 ; *C1=C(*)CCC1]

X is selected from O, S; m is an integer of 0~1;

$R^3$ and $R^4$ are independently of each other selected from the group consisting of hydrogen, deuterium, halogen, halogenated or un-halogenated methyl, preferably, $R^3$ and $R^4$ are independently of each other selected from the group consisting of hydrogen, deuterium, F, Cl, $CF_3$;

$L^1$ and $L^2$ are independently of each other selected from the group consisting of none, substituted by 1~2 substituents or unsubstituted methylene; said substituents are deuterium, $C_{1-4}$ alkyls, $C_{2-3}$ alkenyls, $C_{2-3}$ alkynyls;

$R^5$ is selected from —$C(O)R^{34}$, $R^{34}$ is selected from the group consisting of deuterium, $R^{33}$, $C_{1-2}$ alkoxyl, $R^{33}$ is selected from the group consisting hydrogen, $C_{1-2}$ alkyl, Or, in formula A-II:

Ring A is none;

X is selected from O, S; m is an integer of 0~1;

$R^3$ and $R^4$ are independently of each other selected from the group consisting of hydrogen, deuterium, halogen, halogenated or un-halogenated methyl, preferably, $R^3$ and $R^4$ are independently of each other selected from the group consisting of hydrogen, deuterium, F, Cl, $CF_3$;

$L^1$ and $L^2$ are independently of each other selected from the group consisting of none, substituted by 1~2 substituents or unsubstituted methylene; said substituents are deuterium, $C_{1-4}$ alkyls, $C_{2-3}$ alkenyls, $C_{2-3}$ alkynyls;

$R^5$ is selected from the group consisting of hydrogen, deuterium, $C_{1-4}$ alkyls, propadienyl,

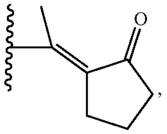 [SMILES: */C(C)=C1\CCCC1=O]

substituted or unsubstituted $C_{2-4}$ alkenyls, substituted or unsubstituted $C_{2-4}$ alkynyls, —$OR^{33}$, —$OC(O)R^{34}$;

$R^{33}$ is selected from $C_{1-3}$ alkyls, $R^{34}$ is selected from the group consisting of deuterium, $R^{33}$, $C_{1-3}$ alkoxyl; Said substituents of $R^5$ are selected from the group consisting of di-substituted cyclic carbonyls, =$R^{39}$, $C_{2-4}$ alkenyls or $C_{2-4}$ alkynyls, $R^{39}$ is selected from O, S, $CH_2$.

Further, the compound is represented by formula B—I:

Formula B-I

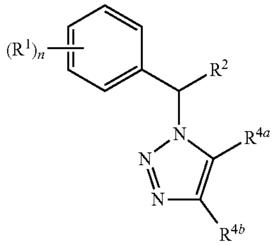

$R^1$ is independently of each other selected from the group consisting of deuterium, halogen, —CN, —$NO_2$, —$OR^{32}$, —$C(O)R^{31}$, —$CO_2R^{31}$, —$CON(R^{32})_2$, —$N(R^{32})_2$, —$OC(O)R^{31}$, —$SO_2R^{31}$, substituted or unsubstituted 3~8-membered heterocyclyls, substituted or unsubstituted $C_{1-8}$ alkyls, substituted or unsubstituted $C_{2-8}$ alkenyls, substituted or unsubstituted $C_{2-8}$ alkynyls;

Wherein, $R^{31}$ is independently of each other selected from the group consisting of deuterium, $R^{32}$, substituted or unsubstituted $C_{2-8}$ alkenyls, substituted or unsubstituted $C_{2-8}$ alkynyls, $R^{32}$ is independently of each other selected from the group consisting of hydrogen, substituted or unsubstituted $C_{1-8}$ alkyls, substituted or unsubstituted $C_{3-8}$ cycloalkyls, substituted or unsubstituted 3~8-membered heterocyclyls, substituted or unsubstituted aryls, substituted or unsubstituted heteroaryls; said substituents are deuterium, cyano, hydroxyl, carboxyl, halogen, $C_{3-8}$ cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives;

For above $R^1$, $R^{31}$, $R^{32}$, said substituents are deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-8}$-membered cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives;

n is an integer of 0~5;

$R^2$ is selected from the group consisting of hydrogen, deuterium, halogen, $C_{1-8}$ alkyls or their halogenated or deuterated derivatives, $C_{1-8}$ alkoxyl or their halogenated or deuterated derivatives, $C_{2-8}$ alkenyls or their halogenated or deuterated derivatives, $C_{2-8}$ alkynyls or their halogenated or deuterated derivatives, 3~8-membered heterocyclyls or their halogenated or deuterated derivatives;

In $R^{4a}$ and $R^{4b}$, one is $R^4$, other is

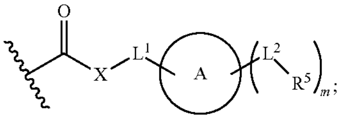;

Wherein, $R^4$ is selected from the group consisting of hydrogen, deuterium, halogen, substituted or unsubstituted $C_{1-8}$ alkyls, $N(R^3)_2$; said substituents are deuterium, halogen, $C_{1-8}$ alkyls or their halogenated or deuterated derivatives, $C_{1-8}$ alkoxyls or their halogenated or deuterated derivatives, $C_{3-8}$ cycloalkyls or their halogenated or deuterated derivatives, 3~8-membered heterocyclyl or their halogenated or deuterated derivatives, aryls or their halogenated or deuterated derivatives, heteroaryls or their halogenated or deuterated derivatives, —$N(R^3)_2$, $R^3$ is H or $C_{1-8}$ alkyls;

X is selected from O, S, or $NR^{30}$, wherein, $R^{30}$ is selected from hydrogen or $C_{1-8}$ alkyls;

$L^1$ and $L^2$ are independently of each other selected from the group consisting of none, substituted or unsubstituted $C_{1-8}$ alkylenyls; said substituents are deuterium, cyano, hydroxyl, carboxyl, halogen, $C_{1-8}$ alkyls or their halogenated or deuterated derivatives, $C_{2-8}$ alkenyls or their halogenated or deuterated derivatives, $C_{2-8}$ alkynyls or their halogenated or deuterated derivatives, $C_{1-8}$ alkoxyls or their halogenated or deuterated derivatives, $C_{3-8}$ cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives;

$L^1$ and $L^2$ can be connected to the homotopic or heterotopic atoms on the A ring;

m is an integer of 0~4;

Ring A is none, or, ring A is selected from 3~8-membered saturated carbocycles, 3~8-membered unsaturated carbocycles, 3~8-membered saturated heterocycles or 3~8-membered unsaturated heterocycles;

$R^5$ is selected from the group consisting of hydrogen, deuterium, halogen, propadienyl,

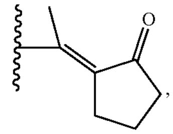, substituted or unsubstituted $C_{1-8}$ alkyls, —$OR^{33}$, —$SR^{33}$, —$OC(O)R^{34}$, $C_{3-8}$-membered cycloalkyls, 3~8-membered heterocyclyls, aryls, heteroaryls, —$N(R^{33})_2$, —$C(O)R^{34}$, —$C(S)R^{34}$, —$S(O)R^{34}$, —$CON(R^{33})_2$, —$SO_2R^{34}$, substituted or unsubstituted $C_{2-8}$ alkenyls, substituted or unsubstituted $C_{2-8}$ alkynyls, cyano, isocyano, isothiocyano, nitro, -$L^{33}$-$R^{36}$ or =$R^{39}$;

$L^{33}$ is selected from $C_{1-4}$ alkylenyls;

$R^{36}$ is selected from cyano, nitro, —$OC(O)R^{34}$, —$C(O)R^{34}$, —$S(O)R^{34}$, —$C(O)N(R^{33})_2$;

$R^{33}$ is selected from the group consisting of hydrogen, methylsulfonyl, -$L^{31}$-COO-$L^{32}$, the following substituted or unsubstituted groups: $C_{1-8}$ alkyls, $C_{3-8}$ cycloalkyls, 3~8-membered heterocyclyls, aryls, heteroaryls;

$R^{34}$ is selected from the group consisting of $R^{33}$, deuterium, the following substituted or unsubstituted groups: $C_{1-8}$ alkoxyl, $C_{2-8}$ alkenyls, $C_{2-8}$ alkynyls, or —S—$C_{1-8}$ alkyls;

$L^{31}$ is selected from the substituted or unsubstituted $C_{1-8}$ alkylenyls; $L^{32}$ is selected from the substituted or unsubstituted $C_{1-8}$ alkyls;

For above $R^5$, $R^{33}$, $R^{34}$, said substituents are deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-8}$-membered cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives, —S—$C_{1-4}$ alkyls, di-substituted cyclic carbonyl, =$R^{39}$, $C_{2-8}$ alkenyls or $C_{2-8}$ alkynyls;

$R^{39}$ is selected from O, S, $NR^{40}$ or $C(R^{41})_2$, $R^{40}$ is selected from hydrogen, halogen, $C_{1-4}$ alkyls or their halogenated or deuterated derivatives; $R^{41}$ is selected from $R^{40}$ or deuterium;

Preferably:

For above $R^1$ is independently of each other selected from the group consisting of deuterium, halogen, —CN, —$NO_2$, —$OR^{32}$, —C(O)$R^{31}$, —$CO_2R^{31}$, —CON$(R^{32})_2$, —N$(R^{32})_2$, —OC(O)$R^{31}$, $C_{1-3}$ alkyls, $C_{2-3}$ alkenyls, $C_{2-3}$ alkynyls;

Wherein, $R^{31}$ is independently of each other selected from the group consisting of deuterium, $R^{32}$, $C_{2-3}$ alkenyls, $C_{2-3}$ alkynyls; $R^{32}$ is independently of each other selected from of hydrogen, $C_{1-3}$ alkyls;

Or, n is an integer of 0~2;

Or, $R^2$ is selected from the group consisting of hydrogen, deuterium, halogen, $C_{1-3}$ alkyls or their halogenated or deuterated derivatives;

Further, said the compound is represented by formula B-II-1 or B-II-2:

Formula B-II-1

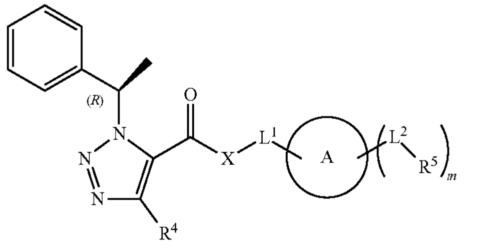

Formula B-II-2

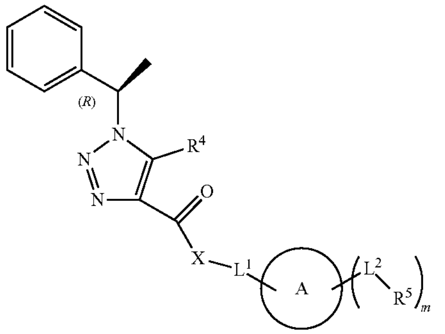

$R^4$ is selected from the group consisting of hydrogen, deuterium, halogen, substituted or unsubstituted $C_{1-4}$ alkyls, N$(R^3)_2$; Said substituents are deuterium, halogen, $C_{1-4}$ alkyls or their halogenated or deuterated derivatives, $C_{1-4}$ alkoxyl or their halogenated or deuterated derivatives, $C_{3-6}$ cycloalkyls or their halogenated or deuterated derivatives, 3~6-membered heterocyclyls or their halogenated or deuterated derivatives, —N$(R^3)_2$, $R^3$ is H or $C_{1-4}$ alkyls;

X is selected from O or S;

$L^1$ and $L^2$ are independently of each other selected from the group consisting of none, substituted or unsubstituted $C_{1-4}$ alkylenyls; said substituents are deuterium, cyano, hydroxyl, carboxyl, halogen, $C_{1-4}$ alkyls or their halogenated or deuterated derivatives, $C_{2-4}$ alkenyls or their halogenated or deuterated derivatives, $C_{2-4}$ alkynyls or their halogenated or deuterated derivatives, $C_{1-4}$ alkoxyls or their halogenated or deuterated derivatives, $C_{3-5}$ cycloalkyls or their halogenated or deuterated derivatives, 3~5-membered heterocyclyls or their halogenated or deuterated derivatives, aryls or their halogenated or deuterated derivatives, heteroaryls or their halogenated or deuterated derivatives;

$L^1$ and $L^2$ can be connected to the homotopic or heterotopic atoms on the A ring; m is an integer of 0~4;

Ring A is none, or, ring A is selected from 3~6-membered saturated carbocycles, 3~6-membered unsaturated carbocycles, 3~6-membered saturated heterocycles or 3~6-membered unsaturated heterocycles;

$R^5$ is selected from the group consisting of hydrogen, deuterium, halogen, propadienyl,

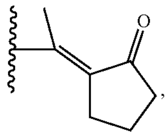 [SMILES: */C(C)=C1\CCCC1=O], substituted or unsubstituted $C_{1-8}$ alkyls, —$OR^{33}$, —$SR^{33}$, —OC(O)$R^{34}$, $C_{3-8}$-membered cycloalkyls, 3~8-membered heterocyclyls, aryls, heteroaryls, —N$(R^{33})_2$, —C(O)$R^{34}$, —C(S)$R^{34}$, —S(O)$R^{34}$, —CON$(R^{33})_2$, —$SO_2R^{34}$, substituted or unsubstituted $C_{2-8}$ alkenyls, substituted or unsubstituted $C_{2-8}$ alkynyls, cyano, isocyano, isothiocyano, nitro, -$L^{33}$-$R^{36}$ or =$R^{39}$;

$L^{33}$ is selected from $C_{1-4}$ alkylenyls;

$R^{36}$ is selected from cyano, nitro, —OC(O) $R^{34}$, —C(O) $R^{34}$, —S(O)$R^{34}$, —C(O)N$(R^{33})_2$;

$R^{34}$ is selected from the group consisting of deuterium or $R^{33}$, $R^{33}$ is selected from the group consisting of hydrogen, methyl sulfonyl, the following substituted or unsubstituted groups: $C_{1-8}$ alkyls, $C_{3-8}$ cycloalkyls, 3~8-membered heterocyclyls, heteroaryls;

$R^{34}$ is selected from the group consisting of $R^{33}$, deuterium, the following substituted or unsubstituted groups: $C_{1-8}$ alkoxyl, $C_{2-8}$ alkenyls, $C_{2-8}$ alkynyls;

For above $R^5$, $R^{33}$, $R^{34}$, said substituents are deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-8}$-membered cycloalkyls or their halogenated or deuterated derivatives, 3~8-membered heterocyclyls or their halogenated or deuterated derivatives, aryls or their halogenated or deuterated derivatives, heteroaryls or their halogenated or deuterated derivatives, —S—$C_{1-4}$ alkyls, si-substituted carbonyl, =$R^{39}$, $C_{2-6}$ alkenyls or $C_{2-6}$ alkynyls;

$R^{39}$ is selected from O, S, $NR^{40}$ or C$(R^{41})_2$; $R^{40}$ is selected from hydrogen, halogen, $C_{1-4}$ alkyls or their halogenated or deuterated derivatives; $R^{41}$ is selected from $R^{40}$ or deuterium.

Further, $R^4$ is selected from the group consisting of hydrogen, deuterium, halogen, substituted or unsubstituted $C_{1-4}$ alkyls, N$(R^3)_2$; Said substituents is deuterium, halogen, $C_{1-4}$ alkyls or their halogenated or deuterated derivatives, $C_{1-4}$ alkoxyl or their halogenated or deuterated derivatives, $C_{3-6}$ cycloalkyls or their halogenated or deuterated derivatives, 3~6-membered heterocyclyls or their halogenated or deuterated derivatives, —N$(R^3)_2$, $R^3$ is H or $C_{1-4}$ alkyls;

Or, $L^1$ and $L^2$ are independently of each other selected from the group consisting of none, substituted or unsubstituted $C_{1-4}$ alkylenyls; said substituents are deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{2-4}$ alkenyls or their halogenated or deuterated derivatives, $C_{2-4}$ alkynyls or their halogenated or deuterated derivatives, $C_{3-5}$ cycloalkyls or their halogenated or deuterated derivatives, 3~5-membered heterocyclyls or their halogenated or deuterated derivative, aryls or their halogenated or deuterated derivatives, heteroaryls or their halogenated or deuterated derivatives;

m is an integer of 0~4;

Or, ring A is none, or, ring A is selected from 3~6-membered saturated carbocycles, 3~6-membered unsaturated carbocycles, 3~6-membered saturated heterocycles or 3~6-membered unsaturated heterocycles;

or, $R^5$ is selected from the group consisting of hydrogen, deuterium, halogen, propadienyl,

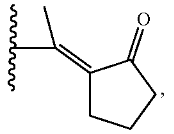 [SMILES: */C(C)=C1\CCCC1=O]
, substituted or unsubstituted $C_{1-6}$ alkyls, —$OR^{33}$, —$SR^{33}$, —$OC(O)R^{34}$, $C_{3-8}$-membered cycloalkyls, 3~8-membered heterocyclyls, aryls, heteroaryls, —$N(R^{33})_2$, —$C(O)R^{34}$, —$C(S)R^{34}$, —$S(O)R^{34}$, —$CON(R^{33})_2$, —$SO_2R^{34}$, substituted or unsubstituted $C_{2-6}$ alkenyls, substituted or unsubstituted $C_{2-6}$ alkynyls, cyano, isocyano, isothiocyano, $=R^{39}$;

$R^{33}$ is selected from the group consisting of hydrogen, methyl sulfonyl, the following substituted or unsubstituted groups: $C_{1-4}$ alkyls, $C_{3-8}$ cycloalkyls, 3~8-membered heterocyclyls, aryls, heteroaryls;

$R^{34}$ is selected from the group consisting of $R^{33}$, deuterium, the following substituted or unsubstituted groups: $C_{1-4}$ alkoxyl, $C_{2-4}$ alkenyls, $C_{2-4}$ alkynyls;

For above $R^5$, $R^{33}$, $R^{34}$, said substituents are deuterium, cyano, hydroxyl, carboxyl, halogen, $C_{1-4}$ alkyls, $C_{1-4}$ alkoxyl, $C_{3-8}$-membered cycloalkyls, 3~8-membered heterocyclyls, aryls, heteroaryls, —S—$C_{1-4}$ alkyls, di-substituted cyclic carbonyl, $=R^{39}$, $C_{2-4}$ alkenyls or $C_{2-4}$ alkynyls;

$R^{39}$ is selected from O, S, $NR^{40}$ or $C(R^{41})_2$, $R^{40}$ is selected from hydrogen, halogen, $C_{1-4}$ alkyls or their halogenated or deuterated derivatives; $R^{41}$ is selected from $R^{40}$ or deuterium;

Preferably:

For above $R^4$ is selected from the group consisting of hydrogen, deuterium, halogen, substituted or unsubstituted $C_{1-2}$ alkyls, —$N(R^3)_2$; Said substituents is deuterium, halogen, $C_{1-2}$ alkyls or their halogenated or deuterated derivatives, $C_{1-2}$ alkoxyl or their halogenated or deuterated derivatives, —$N(R^3)_2$, $R^3$ is H or $C_{1-4}$ alkyls;

Or, $L^1$ and $L^2$ are independently of each other selected from the group consisting of none, substituted or unsubstituted $C_{1-3}$ alkylenyls; said substituents is deuterium, halogen, $C_{1-4}$ alkyls or their halogenated or deuterated derivatives, $C_{2-3}$ alkenyls or their halogenated or deuterated derivatives, $C_{2-3}$ alkynyls or their halogenated or deuterated derivatives, $C_{1-3}$ alkoxyl or their halogenated or deuterated derivatives;

m is an integer of 0~3;

or, ring A is none, or, ring A is selected from 3~6-membered saturated carbocycles, 3~6-membered unsaturated carbocycles or 3~6-membered saturated heterocycles;

or, $R^5$ is selected from the group consisting of hydrogen, deuterium, halogen, propadienyl,

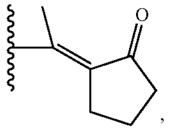 [SMILES: */C(C)=C1\CCCC1=O]
, substituted or unsubstituted $C_{1-4}$ alkyls, —$OR^{33}$, —$SR^{33}$, —$OC(O)R^{34}$, $C_{3-8}$-membered cycloalkyls, 3~8-membered heterocyclyls, aryls, heteroaryls, —$N(R^{33})_2$, —$C(O)R^{34}$, —$C(S)R^{34}$, —$S(O)R^{34}$, —$CON(R^{33})_2$, —$SO_2R^{34}$, substituted or unsubstituted $C_{2-4}$ alkenyls, substituted or unsubstituted $C_{2-4}$ alkynyls, cyano, isocyano, isothiocyano, $=R^{39}$;

$R^{33}$ is selected from the group consisting of hydrogen, methylsulfonyl, the following substituted or unsubstituted groups: $C_{1-3}$ alkyls, $C_{3-6}$ cycloalkyls, 3~6-membered heterocyclyls, aryls, heteroaryls;

$R^{34}$ is selected from the group consisting of $R^{33}$, deuterium, substituted or unsubstituted $C_{1-3}$ alkoxyl;

For above $R^5$, $R^{33}$ and $R^{34}$, said substituents are deuterium, halogen, cyano, $C_{1-2}$ alkyls, $C_{1-2}$ alkoxyls, $C_{3-6}$-membered cycloalkyls, 3~6-membered heterocyclyls, aryls, heteroaryls, —S—$C_{1-2}$ alkyls, di-substituted cyclic carbonyl, $=R^{39}$, $C_{2-4}$ alkenyls or $C_{2-4}$ alkynyls;

$R^{39}$ is selected from O, S, $NR^{40}$ or $C(R^{41})_2$, $R^{40}$ is selected from hydrogen, halogen, $C_{1-3}$ alkyls or their halogenated or deuterated derivatives; $R^{41}$ is selected from $R^{40}$ or deuterium;

More Preferably:

For above $R^4$ is selected from the group consisting of hydrogen, deuterium, halogen, halogenated or un-halogenated methyl, —$N(R^3)_2$, $R^3$ is H or $C_{1-2}$ alkyl;

Or, $L^1$ and $L^2$ are independently of each other selected from none, substituted or unsubstituted $C_{1-2}$ alkylenyls; said substituents are deuterium, halogen, $C_{1-4}$ alkyls, $C_{2-3}$ alkenyls, $C_{2-3}$ alkynyls;

m is an integer of 0~2;

Or, ring A is none, or, ring A is selected from 3~6-membered saturated carbocycles, 3~6-membered unsaturated carbocycles, 3~6-membered saturated heterocycles;

or, $R^5$ is selected from the group consisting of hydrogen, deuterium, halogen, propadienyl,

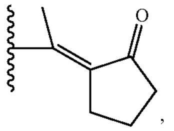 [SMILES: */C(C)=C1\CCCC1=O]
, substituted or unsubstituted $C_{1-3}$ alkyls, —$OR^{33}$, —$SR^{33}$, —$OC(O)R^{34}$, $C_{3-8}$-membered cycloalkyls, 3~8-membered heterocyclyls, aryls, heteroaryls, —$N(R^{33})_2$, —$C(O)R^{34}$, —$C(S)R^{34}$, —$S(O)R^{34}$, —$CON(R^{33})_2$, —$SO_2R^{34}$, substituted or unsubstituted $C_{2-3}$ alkenyls, substituted or unsubstituted $C_{2-3}$ alkynyls, cyano, isocyano, isothiocyano, $=R^{39}$;

$R^{33}$ is selected from the group consisting of hydrogen, methyl sulfonyl, acetyl, $C_{1-3}$ alkyls;

$R^{34}$ is selected from the group consisting of $R^{33}$, deuterium, $C_{1-3}$ alkoxyl; For above $R^5$ is selected from of the group deuterium, halogen, cyano, $C_{1-2}$ alkyls, 3~5-membered heterocyclyls, —S—$CH_3$, di-substituted cyclic carbonyl, =$R^{39}$, $C_{2-4}$ alkenyls or $C_{2-4}$ alkynyls;

$R^{39}$ is selected from O, S, $NR^{40}$ or $C(R^{41})_2$, $R^{40}$ is selected from hydrogen, halogen, $C_{1-3}$ alkyls; $R^{41}$ is selected from $R^{40}$ or deuterium;

Further, said the compound is represented by formula B-II-1 or B-II-2:

Formula B-II-1

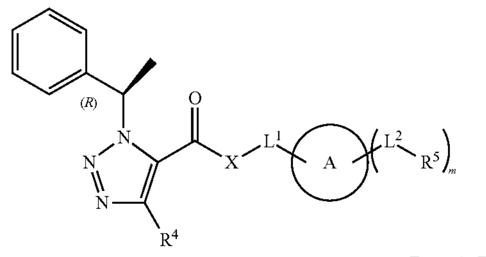

Formula B-II-2

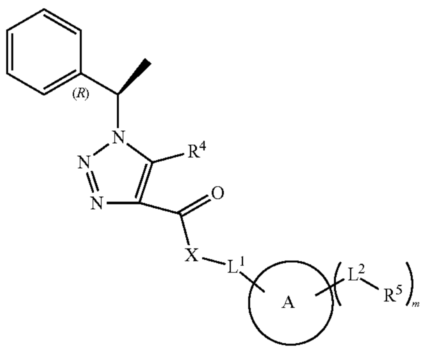

Wherein:

Ring A is 3~6-membered saturated carbocycles;

X is selected from O, S; m is an integer of 0~2;

$R^4$ is selected from the group consisting of hydrogen, deuterium, halogen, halogenated or un-halogenated methyls, $N(R^3)_2$; $R^3$ is H or $C_{1-2}$ alkyls; preferably, $R^4$ is selected from the group consisting of hydrogen, deuterium, F, Cl, Br, I, $CF_3$, —$N(CH_3)_2$;

$L^1$ and $L^2$ are independently of each other selected from the group consisting of none, substituted by 1~2 substituents or unsubstituted methylenes; said substituents are deuterium, $C_{1-4}$ alkyls, $C_{2-3}$ alkenyls, $C_{2-3}$ alkynyls;

$L^1$ and $L^2$ can be connected to the homotopic or heterotopic atoms on the A ring;

$R^5$ is selected from the group consisting of hydrogen, deuterium, $C_{1-2}$ alkyls, propadienyl, substituted or unsubstituted $C_{2-4}$ alkenyls, substituted or unsubstituted $C_{2-4}$ alkynyls, —$OR^{33}$, —$SR^{33}$, —$C(O)R^{34}$, halogen, =$R^{39}$;

$R^{33}$ is selected from the $C_{1-3}$ alkyls;

$R^{34}$ is selected from the group consisting of $R^{33}$, deuterium, $C_{1-3}$ alkoxyls;

$R^5$ said substituents are selected from the group consisting of =$R^{39}$, $C_{2-4}$ alkenyls or $C_{2-4}$ alkynyls;

Or, wherein:

Ring A is selected from 3~6-membered saturated heterocycles; preferably, ring A is

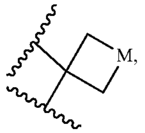

M is s O or S;

X is selected from O or S; m is an integer of 0~2;

$R^4$ is selected from the group consisting of hydrogen, deuterium, halogen, halogenated or un-halogenated methyls, $N(R^3)_2$, $R^3$ is H or $C_{1-2}$ alkyls; preferably, $R^4$ is selected from the group consisting of hydrogen, deuterium, F, Cl, Br, I, $CF_3$, —$N(CH_3)_2$;

$L^1$ and $L^2$ are independently of each other selected from the group consisting of none, substituted by 1~2 substituents or unsubstituted $C_{1-2}$ methylene; Said substituents are deuterium, $C_{1-4}$ alkyls, $C_{2-3}$ alkenyls, $C_{2-3}$ alkynyls;

$R^5$ is selected from the group consisting of hydrogen, deuterium, $C_{1-2}$ alkyls, propadienyl, substituted or unsubstituted $C_{2-4}$ alkenyls, substituted or unsubstituted $C_{2-4}$ alkynyls, —$OR^{33}$, —$SR^{33}$, —$C(O)R^{34}$, halogen, =$R^{39}$;

$R^{33}$ is selected from the $C_{1-3}$ alkyls;

$R^{34}$ is selected from the group consisting of $R^{33}$, deuterium, $C_{1-3}$ alkoxyl;

$R^5$ said substituents is selected from the group consisting of =$R^{39}$, $C_{2-4}$ alkenyls or $C_{2-4}$ alkynyls;

$R^{39}$ is selected from the O, S, $CH_2$;

Or, wherein:

Ring A is selected from 5~6-membered unsaturated carbocycles; preferably, Ring A is

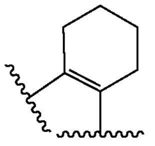

or

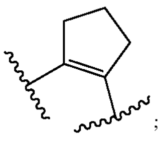

;

X is selected from O or S; m is an integer of 0~1;

$R^4$ is selected from the group consisting of hydrogen, deuterium, halogen, halogenated or un-halogenated methyls, $N(R^3)_2$; $R^3$ is H or $C_{1-2}$ alkyls; Preferably, $R^4$ is selected from the group consisting of hydrogen, deuterium, F, Cl, Br, I, $CF_3$, —$N(CH_3)_2$;

$L^1$ and $L^2$ are independently of each other selected from the group consisting of none, substituted by 1~2 substituents or unsubstituted $C_{1-2}$ methylene; said substituents are deuterium, $C_{1-4}$ alkyls, $C_{2-3}$ alkenyls, $C_{2-3}$ alkynyls;

$R^5$ is selected from —$C(O)R^{34}$, $R^{34}$ is selected from the group consisting of deuterium, $R^{33}$, $C_{1-2}$ alkoxyl; $R^{33}$ is selected from hydrogen, $C_{1-2}$ alkyls, Or, wherein:

Ring A is none,

X is selected from O, S; m is an integer of 0~1;

$R^4$ is independently of each other selected from the group consisting of hydrogen, deuterium, halogen, halogenated or un-halogenated methyl, —$N(R^3)_2$, $R^3$ is H or $C_{1-2}$ alkyls; Preferably, $R^4$ is selected from the group consisting of hydrogen, deuterium, F, Cl, Br, I, $CF_3$, —$N(CH_3)_2$;

$L^1$ and $L^2$ are independently of each other selected from the group consisting of none, substituted by 1~2 substituents or unsubstituted $C_{1-2}$ methylene; said substituents are deuterium, $C_{1-4}$ alkyls, $C_{2-3}$ alkenyls, $C_{2-3}$ alkynyls;

$R^5$ is selected from the group consisting of hydrogen, deuterium, $C_{1-4}$ alkyls, substituted by 1~3 halogens alkyls, propadienyl,

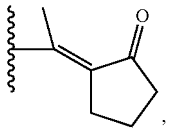

, substituted or unsubstituted $C_{2-4}$ alkenyls, substituted or unsubstituted $C_{2-4}$ alkynyls, —$OR^{33}$, —$SR^{33}$, —$C(O)R^{34}$;

$R^{33}$ is selected from the $C_{1-3}$ alkyls, $R^{34}$ is selected from the group consisting of deuterium, $R^{33}$, $C_{1-3}$ alkoxyls;

Said substituents of $R^5$ are selected from the group consisting of di-substituted cyclopentanoyls, $=R^{39}$, $C_{2-4}$ alkenyls or $C_{2-4}$ alkynyls, $R^{39}$ is selected from O, S, $CH_2$, Further, said the compound is represented by formula C-I:

Formula C-I

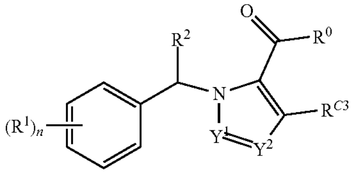

Wherein, n is an integer of 0~3;

$R^1$ is selected from the group consisting of halogens, $C_{1-5}$ alkyls, $C_{1-5}$ alkoxyls;

$R^2$ is selected from the group consisting of halogens, $C_{1-5}$ alkyls, $C_{1-5}$ alkoxyls;

$Y^1$ is selected from N or $CR^{c5a}$, $Y^2$ is selected from N or $CR^{c5b}$;

$R^{c5a}$, $R^{c5b}$, $R^{c3}$ are independently selected from the group consisting of hydrogen, halogens, $C_{1-5}$ alkyls, $R^0$ is selected from $L^{C3}R^{C4}$, $L^{C1}X^CL^{C2}R^{C5}$;

$L^{C3}$ is selected from the group consisting of none, substituted or unsubstituted $C_{1-4}$ alkylenyls; said substituents of $C_{1-4}$ alkylenyls are selected from the group consisting of $C_{1-5}$ alkyls, $C_{1-5}$ alkoxyls, halogens, hydroxyl;

$R^{C4}$ is selected from the group consisting of substituted or unsubstituted $C_{2-6}$ alkenyls, substituted or unsubstituted $C_{2-6}$ alkynyls, substituted or unsubstituted 3~6-membered saturated or unsaturated heterocyclyls, substituted or unsubstituted 3~6-membered saturated or unsaturated cycloalkyls, $COR^{4d}$; said substituents independently of each other selected from $L^{C4}R^{4e}$; $R^{4d}$ is selected $C_{1-6}$ alkyls; $L^{C4}$ is selected from the group consisting of none, substituted or unsubstituted $C_{1-4}$ alkylenyl; $R^{4e}$ is selected from the group consisting of $C_{1-5}$ alkyls, $C_{1-5}$ alkoxyl, halogen, hydroxyl;

$L^{C1}$ is selected from the substituted or unsubstituted $C_{1-3}$ alkylenyls, said substituents are selected from the $C_{1-5}$ alkyls;

$X^C$ is O or S;

$L^{C2}$ is selected from the group consisting of none, substituted or unsubstituted $C_{1-3}$ alkylenyls, said substituents are selected from the $C_{1-4}$ alkyls, $C_{1-4}$ alkoxyls, $L^{2a}R^{5g}$;

$L^{2a}$ is selected from the group consisting of none, $C_{1-2}$ alkylenyls, $R^{5g}$ is selected from halogen, $C_{1-4}$ alkoxyls;

$R^{c5}$ is selected from the group consisting of hydrogen, halogen, $C_{1-5}$ alkyls, $C_{2-4}$ alkenyls, $C_{2-4}$ alkynyls, $COR^{4d}$, $C_{3-6}$ dienyls, $C_{1-5}$ alkoxyl, substituted by one or more $R^{5c}$ 3~6-membered saturated or unsaturated heterocyclyls; substituted by one or more $R^{5c}$ 3~6-membered saturated or unsaturated cycloalkyls; $R^{4d}$ is selected from $C_{1-6}$ alkyls, $R^{5c}$ is selected from the group consisting of halogen, $=R^{5d}$, $L^{1a}R^{5e}$, $C_{3-6}$ dienyls;

$R^{5d}$ is $CH_2$, O or S; $L^{1a}$ is $C_{1-3}$ alkylenyls; $R^{5e}$ is $C_{1-5}$ alkyls, $C_{1-5}$ alkoxyls.

Further, said the compound is represented by formula C-II:

Formula C-II

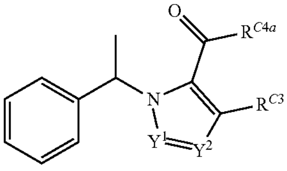

In formula C-II, $R^{C4a}$ is selected from the group consisting of substituted or unsubstituted $C_{2-6}$ alkenyls, substituted or unsubstituted $C_{2-6}$ alkynyls, substituted or unsubstituted 3~6-membered saturated or unsaturated heterocyclyls, substituted or unsubstituted 3~6-membered saturated or unsaturated cycloalkyls; Said substituents are independently of each other selected from the group consisting of $C_{1-5}$ alkyls, $C_{1-5}$ alkoxyl, halogen, hydroxyl;

$Y^1$ is selected from N or $CR^{C5a}$, $Y^2$ is selected from N or $CR^{C5b}$; Preferably, $Y^1$ and $Y^2$ aren't N at the same time;

$R^{C5a}$, $R^{C5b}$, $R^{C3}$ are independently of each other selected from the group consisting of hydrogen, halogen, $C_{1-5}$ alkyls;

Or, said the compounds are represented by formula C-III-a or formula C-III-b:

Formula C-III-a

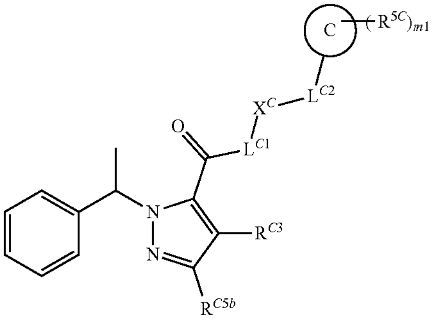

-continued

Formula C-III-b

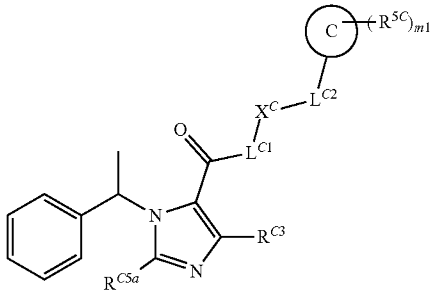

Wherein, $X^C$ is O or S;

$L^{C1}$ is selected from substituted or unsubstituted $C_{1-3}$ alkylenyls, said substituents are selected from the $C_{1-3}$ alkyls; preferably, $L^{C1}$ is methylene;

$L^{C2}$ is selected from the group consisting of none, substituted or unsubstituted $C_{1-2}$ alkylenyls, said substituents are selected from the $C_{1-3}$ alkyls;

Ring C is selected from 3~4-membered saturated heterocyclyls, 3~4-membered saturated cycloalkyls;

m1 is selected from 0, 1, 2; $R^{5c}$ is selected from the group consisting of halogen, $=R^{5d}$, $L^{1a}R^{5e}$, propadienyl; $R^{5d}$ is $CH_2$; $L^{1a}$ is $C_{1\sim3}$ alkylenyls, $R^{5e}$ is $C_{1\sim3}$ alkyls, $C_{1\sim3}$ alkoxyls; said halogen is selected to be F preferably;

$R^{C5a}$, $R^{C5b}$, $R^{C3}$ are independently of each other selected from the group consisting of hydrogen, halogen, $C_{1\sim3}$ alkyls; said halogen is selected to be F preferably;

or, said the compounds are represented by formula C-III-c or formula C-III-d:

Formula C-III-c

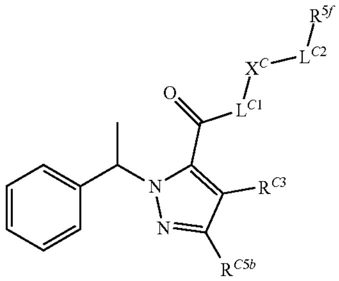

Formula C-III-d

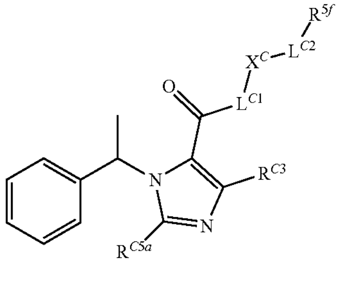

Wherein, $X^C$ is O or S;

$L^{C1}$ is selected from substituted or unsubstituted $C_{1-3}$ alkylenyls, said substituents are selected from the $C_{1-3}$ alkyls, preferably, $L^{C1}$ is selected from $C_{1\sim2}$ alkylenyls;

$L^{C2}$ is selected from the group consisting of none, substituted or unsubstituted $C_{1-2}$ alkylenyls, said substituents are selected from the $C_{1-4}$ alkyls, $C_{1-4}$ alkoxyls, $L^{2a}R^{5g}$;

$L^{2a}$ is selected from none, $C_{1-2}$ alkylenyls; $R^{5g}$ is selected from halogen, $C_{1-4}$ alkoxyls;

$R^{5f}$ is selected from the group consisting of hydrogen, halogen, $C_{1-4}$ alkyls, $C_{2-3}$ alkenyls, $C_{2-3}$ alkynyls, $COR^{4d}$, propadienyl, $C_{1\sim4}$ alkoxyls; $R^{4d}$ is selected from $C_{1\sim4}$ alkyls;

$R^{C5a}$, $R^{C5b}$, $R^{C3}$ are independently of each other selected from the group consisting of hydrogen, halogen, $C_{1\sim3}$ alkyls; said halogen is selected to be F preferably;

or, said the compounds are represented by formula C-IV:

Formula C-IV

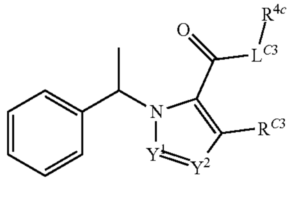

In formula C-IV, $L^{C3}$ is selected from substituted or unsubstituted $C_{1-4}$ alkylenyls, said substituents are selected from the group consisting of $C_{1-5}$ alkyls, $C_{1-5}$ alkoxyl, halogen, hydroxyl;

$R^{4c}$ is selected from the group consisting of substituted or unsubstituted $C_{2-6}$ alkenyls, substituted or unsubstituted $C_{2-6}$ alkynyls, substituted or unsubstituted 3~6-membered saturated cycloalkyls, substituted or unsubstituted 3~6-membered saturated heterocyclyls, $COR^{4d}$; said substituents are independently of each other selected from $L^{C4}R^{4e}$, $R^{4d}$ is selected from $C_{1\sim5}$ alkyls, $L^{C4}$ is selected from none or $C_{1-3}$ alkylenyls; $R^{4e}$ is selected from the group consisting of $C_{1\sim5}$ alkyls, $C_{1\sim5}$ alkoxyls, halogen, hydroxyl;

$Y^1$ is selected from N or $CR^{C5a}$, $Y^2$ is selected from N or $CR^{C5b}$, preferably, $Y^1$ and $Y^2$ aren't N at the same time.

$R^{C5a}$, $R^{C5b}$, $R^{C3}$ are independently of each other selected from the group consisting of hydrogen, halogen, $C_{1\sim5}$ alkyls;

Further, Said the compound C-II is represented by formula C-II-a or formula C-II-b:

Formula C-II-a

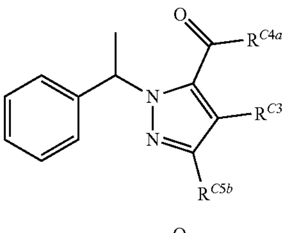

Formula C-II-b

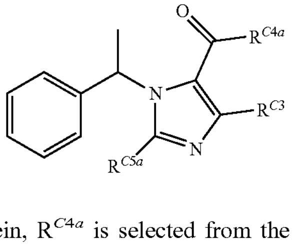

Wherein, $R^{C4a}$ is selected from the group consisting of substituted or unsubstituted $C_{2-3}$ alkenyls, substituted or unsubstituted $C_{2-3}$ alkynyls, substituted or unsubstituted 3~4-membered saturated epoxy's; said substituents are independently of each other selected from $C_{1-3}$ alkyls;

$R^{C5a}$, $R^{C5b}$, $R^{C3}$ are independently of each other selected from the group consisting of hydrogen, halogen, $C_{1\sim3}$ alkyls; said halogen is selected to be F preferably;

Or, the said compound C-IV is represented by formula C-IV-a or formula C-IV-b:

Formula C-IV-a

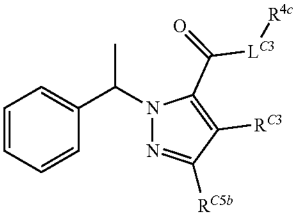

Formula C-IV-b

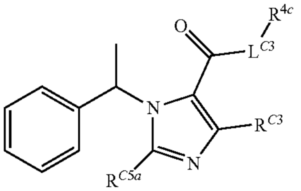

Wherein, $L^{C3}$ is selected from substituted or unsubstituted $C_{1-3}$ alkylenyls, said substituents is selected from the group consisting of $C_{1-3}$ alkyls, $C_{1-3}$ alkoxyl;

$R^{4c}$ is selected from the group consisting of substituted or unsubstituted $C_{2-4}$ alkenyls, substituted or unsubstituted $C_{2-4}$ alkynyls, substituted or unsubstituted 4-membered saturated cycloalkyls, $COR^{4d}$; Said substituents are independently of each other selected from $L^{C4}R^{4e}$, $R^{4d}$ is selected from $C_{1\sim3}$ alkyls, $L^{C4}$ is selected from the group consisting of none or $C_{1-2}$ alkylenyls; $R^{4e}$ is selected from $C_{1\sim3}$ alkyls, $C_{1\sim3}$ alkoxyl;

$R^{C5a}$, $R^{C5b}$, $R^{C3}$ are independently of each other selected from the group consisting of hydrogen, halogen, $C_{1\sim3}$ alkyls; said halogen is selected to be F preferably.

Further, said the compound is represented by formula D-I:

Formula D-I

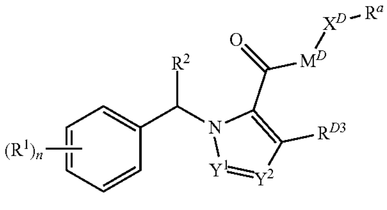

Wherein, n is an integer of 0~3;

$R^1$ is selected from the group consisting of halogen, $C_{1-5}$ alkyls, $C_{1-5}$ alkoxyls;

$R^2$ is selected from the group consisting of halogen, $C_{1-5}$ alkyls, $C_{1-5}$ alkoxyls;

$Y^1$ is selected from N or $CR^{D5a}$, $Y^2$ is selected from N or $CR^{D5b}$;

$R^{D5a}$, $R^{D5b}$, $R^{D3}$ are independently selected from the group consisting of hydrogen, halogen, $C_{1-5}$ alkyls, $M^D$ is selected from CO or $CR^{D6}R^{D7}$; $R^{D6}$ is selected from hydrogen, $X^{Db}R^{D4b}$; $R_7$ is selected from hydrogen, $X^{Dc}R^{D4c}$;

$X^D$ is O or S; $X^{Db}$ is O or S; $X^{Dc}$ is O or S;

$R^a$ is selected from the group consisting of substituted or unsubstituted $C_{1-6}$ alkyls, substituted or unsubstituted $C_{2-6}$ alkynyls, substituted or unsubstituted $C_{2-6}$ alkenyls, substituted or unsubstituted 3~6-membered saturated or unsaturated heterocyclyls, substituted or unsubstituted 3~6-membered saturated or unsaturated cycloalkyls; said substituents are independently of each other selected from the group consisting of $C_{3-6}$dienyls, $C_{1\sim5}$ alkyls, $C_{1\sim5}$ alkoxyl, halogen, hydroxyl;

$R^{D4b}$, $R^{D4c}$ are independently of each other selected from the group consisting of substituted or unsubstituted $C_{1\sim6}$ alkyls, substituted or unsubstituted $C_{2-6}$ alkynyls, substituted or unsubstituted $C_{2-6}$ alkenyls, $COR^{Df}$, substituted or unsubstituted 3~6-membered saturated or unsaturated heterocyclyls, substituted or unsubstituted 3~6-membered saturated or unsaturated cycloalkyls; said substituents are independently of each other selected from the group consisting of $C_{3-6}$dienyls, $C_{1\sim5}$ alkyls, $C_{1\sim5}$ alkoxyl, halogen, hydroxyl; $R^{Df}$ is selected from $C_{1\sim5}$ alkyls;

Or, when $M^D$ is $CR^{D6}R^{D7}$ and $R^{D6}$ is $X^{Db}R^{D4b}$, $R^{D4b}$ and $R^a$ are connected to get substituted or unsubstituted 3~6-membered saturated or unsaturated heterocyclyls, said substituents of saturated or unsaturated heterocyclyls are selected from halogenated or unhalogenated $C_{1\sim6}$ alkyls, halogenated or unhalogenated $C_{2-6}$ alkynyls, halogenated or unhalogenated $C_{2-6}$ alkenyls, $COR^{Df}$;

$R^{D7}$ is selected from hydrogen, $X^{Dc}R^{D4c}$; $X^{Dc}$ is O or S, $R^{D4c}$ is selected from the group consisting of substituted or unsubstituted $C_{1-6}$ alkyls, substituted or unsubstituted $C_{2-6}$ alkynyls, substituted or unsubstituted $C_{2-6}$ alkenyls, $COR^{Df}$, substituted or unsubstituted 3~6-membered saturated or unsaturated heterocyclyls, substituted or unsubstituted 3~6-membered saturated or unsaturated cycloalkyls, said substituents are independently of each other selected from the group consisting of $C_{3-6}$ dienyls, $C_{1\sim5}$ alkyls, $C_{1\sim5}$ alkoxyl, halogen, hydroxyl; $R^{Df}$ is selected from $C_{1\sim5}$ alkyls;

Further, said the compound is represented by formula D-II:

Formula D-II

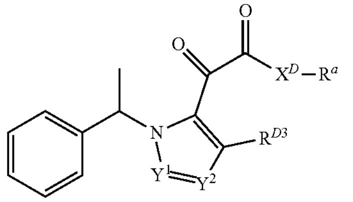

In formula D-II, $X^D$ is O or S;

$R^a$ is selected from the group consisting of substituted or unsubstituted $C_{1-6}$ alkyls, substituted or unsubstituted $C_{2-6}$ alkynyls, substituted or unsubstituted $C_{2-6}$ alkenyls, substituted or unsubstituted 3~6-membered saturated or unsaturated heterocyclyls, substituted or unsubstituted 3~6-membered saturated or unsaturated cycloalkyls; said substituents are independently of each other selected from the group consisting of $C_{3-6}$dienyls, $C_{1\sim5}$ alkyls, $C_{1\sim5}$ alkoxyls, halogen, hydroxyl;

$Y^1$ is selected from N or $CR^{C5a}$, $Y^2$ is selected from N or $CR^{C5b}$;

$R^{D5a}$, $R^{D5b}$, $R^{D3}$ are independently of each other selected from the group consisting of hydrogen, halogen, $C_{1-5}$ alkyls;

Or, said the compound is represented by formula D-III:

Formula D-III

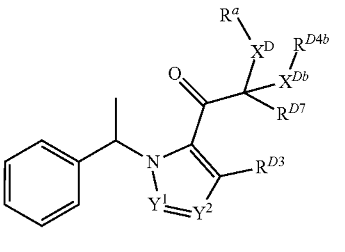

Wherein, $R^{D7}$ is selected from hydrogen or $X^{Dc}R^{D4c}$;

$X^D$, $X^{Db}$, $X^{Dc}$ are independently selected from O or S, $R^a$, $R^{D4b}$, $R^{D4c}$ are independently of each other selected from the group consisting of $C_{1-6}$ alkyls, $C_{2-6}$ alkynyls, $C_{2-6}$ alkenyls, substituted or unsubstituted 3~6-membered saturated or unsaturated heterocyclyls, substituted or unsubstituted 3~6-membered saturated or unsaturated cycloalkyls; said substituents are independently of each other selected from the group consisting of $C_{1\sim3}$ alkyls, $C_{1\sim3}$ alkoxyl, halogen, hydroxyl;

$Y^1$ is selected from N or $CR^{D5a}$, $Y^2$ is selected from N or $CR^{D5b}$;

$R^{D5a}$, $R^{D5b}$, $R^{D3}$ are independently of each other selected from the group consisting of hydrogen, halogen, $C_{1\sim5}$ alkyls;

Or, said the compound is represented by formula D-IV:

Formula D-IV

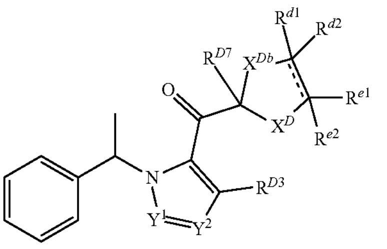

In formula D-IV, $R^{D7}$ is selected from hydrogen, $X^{Dc}R^{D4c}$;

$X^{Db}$, $X^D$, $X^{D4c}$ are independently selected from O or S, $R^{D4c}$ is selected from the group consisting of $C_{1-6}$ alkyls, $C_{2-6}$ alkynyls, $C_{2-6}$ alkenyls, $COR^{Df}$; $R^{Df}$ is selected from $C_{1-5}$ alkyls;

$R^{d1}$ and $R^{e1}$ are independently of each other selected from the group consisting of hydrogen, halogenated or un-halogenated $C_{1-6}$ alkyls, $C_{2-6}$ alkynyls, $C_{2-6}$ alkenyls, $COR^{Df}$; $R^{Df}$ is selected from $C_{1-5}$ alkyls;

$R^{d2}$ and $R^{e2}$ are independently of each other selected from the group consisting of none, hydrogen, halogenated or un-halogenated $C_{1-6}$ alkyls, $C_{2-6}$ alkynyls, $C_{2-6}$ alkenyls, $COR^{Df}$; $R^{Df}$ is selected from $C_{1-5}$ alkyls;

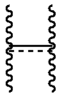

is single bond or double bond; when

is double bond, $R^{d2}$ and $R^{e2}$ are none;

$Y^1$ is selected from N or $CR^{D5a}$, $Y^2$ is selected from N or $CR^{D5b}$;

$R^{D5a}$, $R^{D5b}$, $R^{D3}$ are independently of each other selected from the group consisting of hydrogen, halogen, $C_{1\sim5}$ alkyls.

Further, Said the compound D-II is represented by formula D-II-1, formula D-II-2, formula D-II-3 or formula D-II-4:

Formula D-II-1

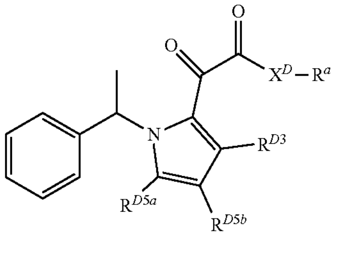

Formula D-II-2

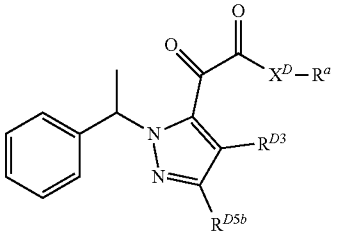

Formula D-II-3

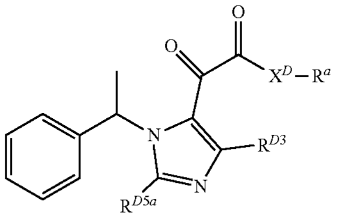

Formula D-II-4

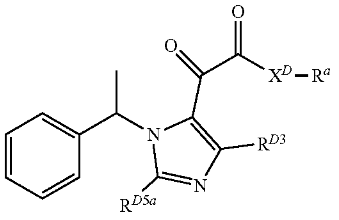

Wherein, $X^D$ is O or S, preferable selection is O;

$R^a$ is selected from the group consisting of substituted or unsubstituted $C_{1-5}$ alkyls, substituted or unsubstituted $C_{2-4}$ alkynyls, substituted or unsubstituted $C_{2-4}$ alkenyls, substituted or unsubstituted 4-membered saturated epoxyls groups, substituted or unsubstituted 4-membered saturated cycloalkyls; Said substituents are independently of each other selected from the group consisting of propadienyl, $C_{1\sim3}$ alkyls, $C_{1\sim3}$ alkoxys;

$R^{D5a}$, $R^{D5b}$, $R^{D3}$ are independently of each other selected from the group consisting of hydrogen, halogen, $C_{1\sim3}$ alkyls; Said halogen is selected to be F, Cl, Br preferably;

Or, said the compound D-III is represented by formula D-III-1, formula D-III-2, formula D-III-3 or formula D-III-4:

Formula D-III-1

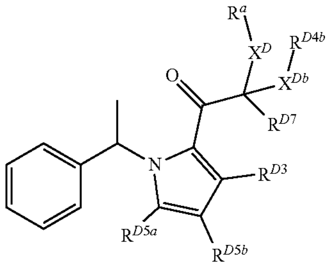

Formula D-III-2

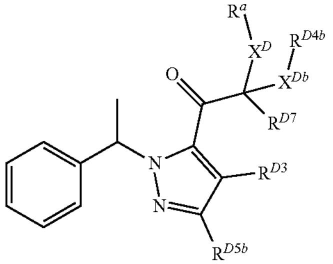

Formula D-III-3

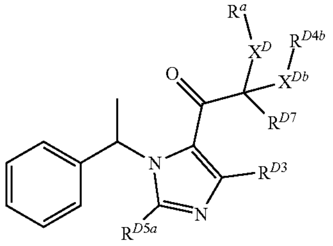

Formula D-III-4

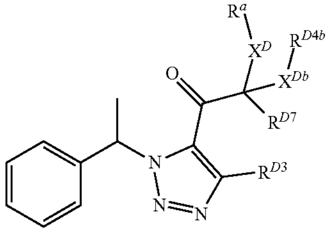

Wherein, $R^{D7}$ is selected from hydrogen or $X^{Dc}R^{D4c}$;

$X^{D}$, $X^{Db}$, $X^{Dc}$ are independently selected from O or S, $R^{a}$, $R^{D4b}$, $R^{D4c}$ are independently of each other selected from the group consisting of $C_{1-5}$ alkyls, $C_{2-4}$ alkynyls, $C_{2-3}$ alkenyls, 4-membered saturated cycloalkyls;

$R^{D5a}$, $R^{D5b}$, $R^{D3}$ are independently of each other selected from the group consisting of hydrogen, halogen, $C_{1-3}$ alkyls; Said halogen is selected to be F, Cl, Br preferably;

Or, said the compound D-IV is represented by formula D-IV-1, formula D-IV-2, formula D-IV-3 or formula D-IV-4:

Formula D-IV-1

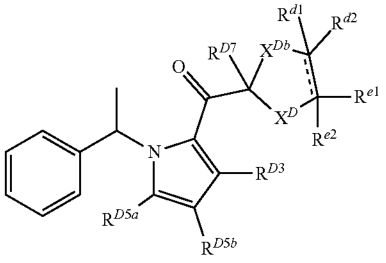

Formula D-IV-2

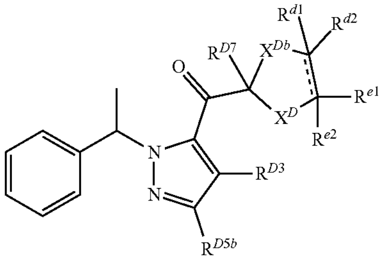

Formula D-IV-3

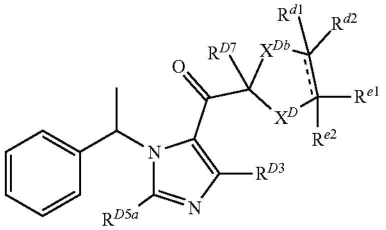

Formula D-IV-4

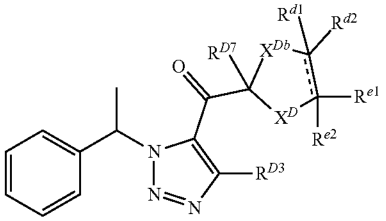

Wherein, $R^{D7}$ is selected from hydrogen, $X^{Dc}R^{D4c}$;

$X^{Db}$, $X^{D}$, $X^{Dc}$ are independently of each other selected from O or S;

$R^{D4c}$ is selected from the group consisting of $C_{1-5}$ alkyls, $C_{2-4}$ alkynyls, $C_{2-3}$ alkenyls;

$R^{d1}$ and $R^{e1}$ are independently of each other selected from the group consisting of hydrogen, halogenated or un-halogenated $C_{1-5}$ alkyls, $COR^{Df}$; $R^{Df}$ is selected from $C_{1-3}$ alkyls; Preferably, said halogenated $C_{1-5}$ alkyls are $CF_3$;

$R^{d2}$ and $R^{e2}$ are independently of each other selected from the group consisting of none, hydrogen, halogenated or un-halogenated $C_{1-5}$ alkyls, $COR^{Df}$; $R^{Df}$ is selected from $C_{1-3}$ alkyls; Preferably, said halogenated $C_{1-5}$ alkyls are $CF_3$;

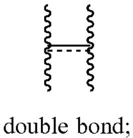

is single bond or double bond; when is double bond,

is double, $R^{d2}$ and $R^{e2}$ are none;

$R^{D5a}$, $R^{D5b}$, $R^{D3}$ are independently of each other selected from the group consisting of hydrogen, halogen, $C_{1\sim3}$ alkyls; said halogen is selected to be F, Cl, Br preferably.

Further, the compound is one of the following compounds:

Compound A1

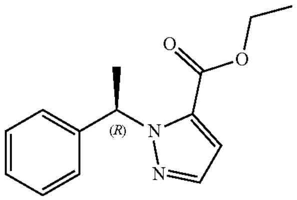

Compound A2

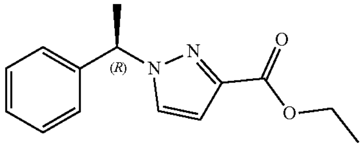

Compound A3

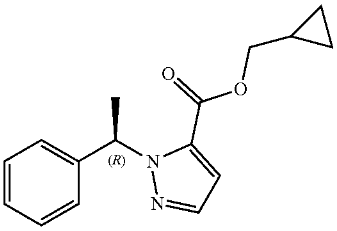

Compound A4

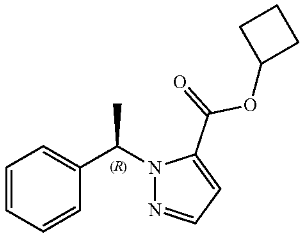

Compound A5

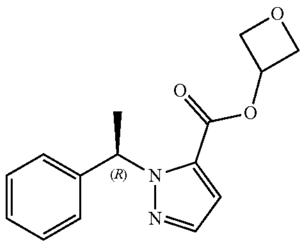

-continued

Compound A6

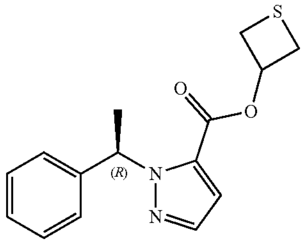

Compound A7

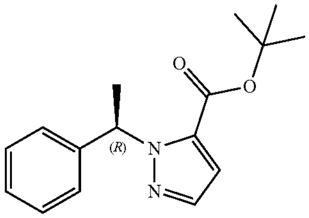

Compound A8

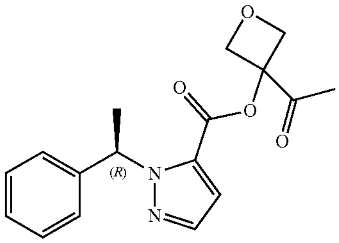

Compound A9

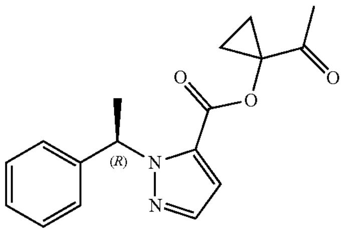

Compound A10

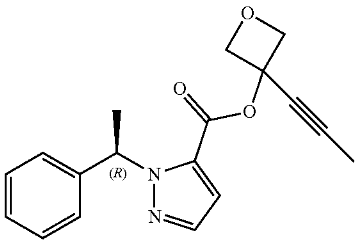

Compound A11

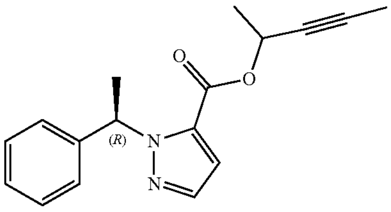

-continued
Compound A12
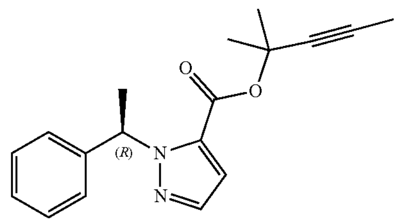
Compound A13
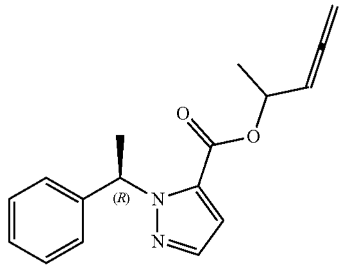
Compound A14
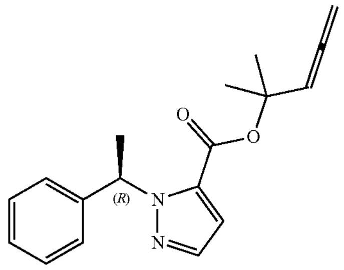
Compound A15
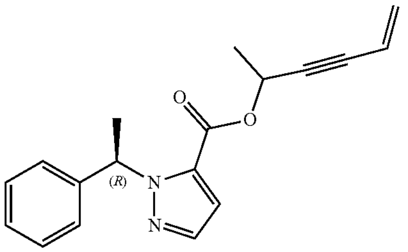
Compound A16
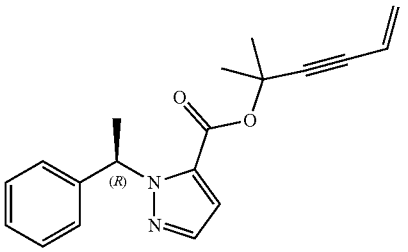
Compound A17
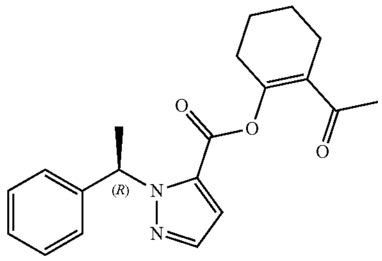
-continued
Compound A18
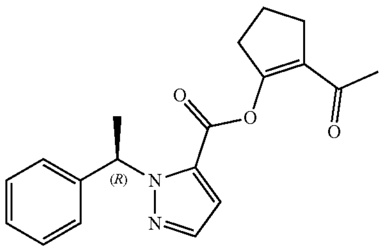
Compound A19
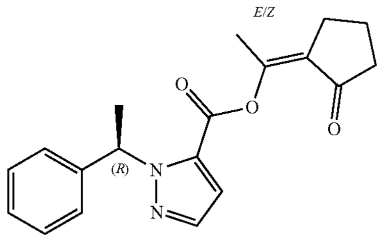
Compound A20
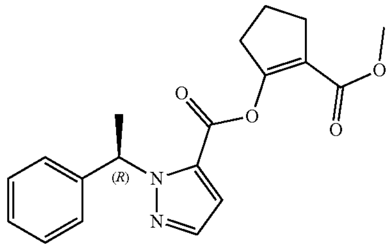
Compound A21
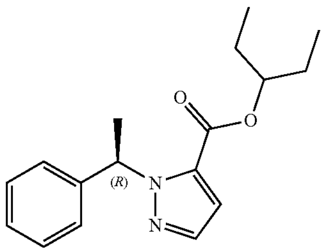
Compound A22
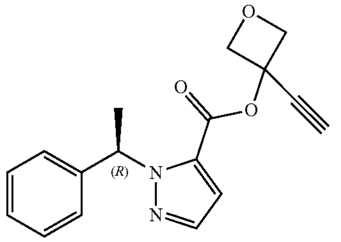
Compound A23
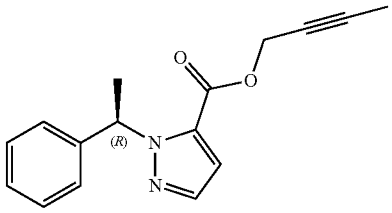

-continued
Compound A24
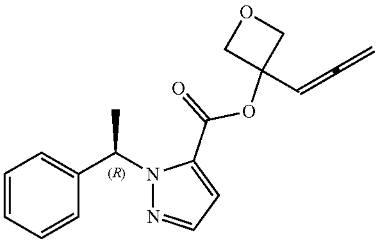
Compound A25
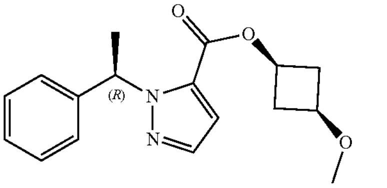
Compound A26
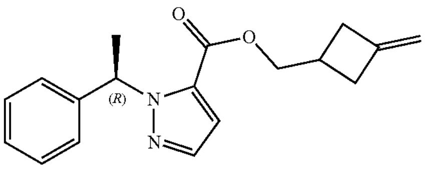
Compound A27
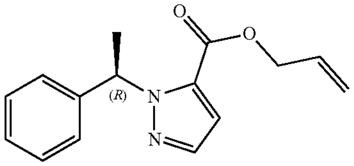
Compound A28
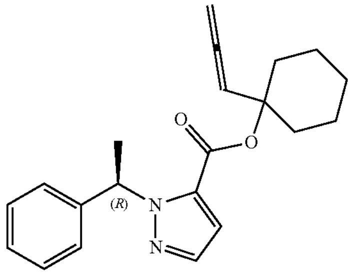
Compound A29
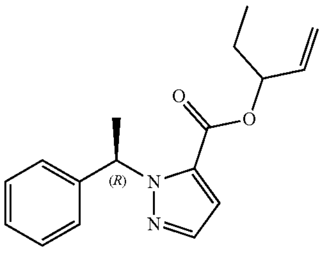
Compound A30
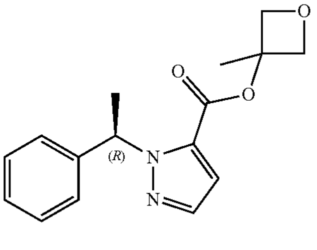
-continued
Compound A31
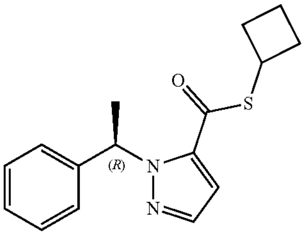
Compound A32
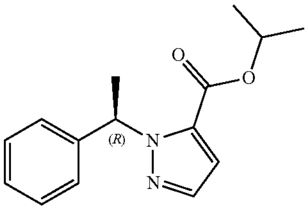
Compound A33
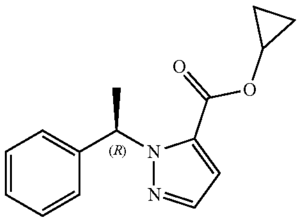
Compound A34
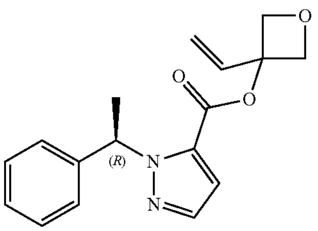
Compound A35
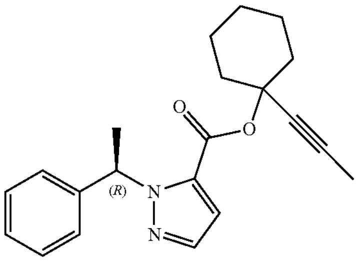
Compound A36
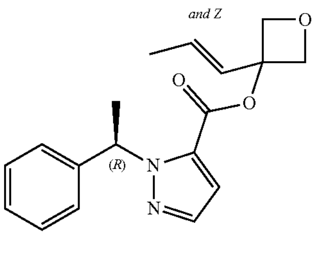

-continued
Compound A37
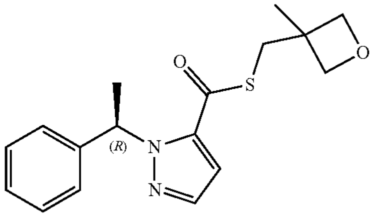
Compound A38
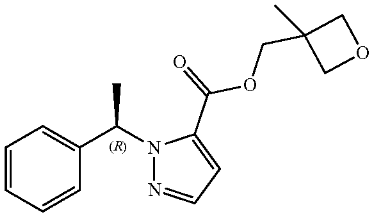
Compound A39
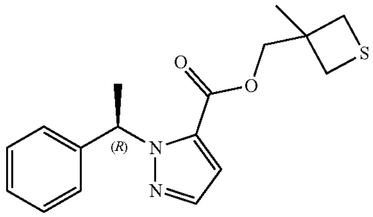
Compound A40
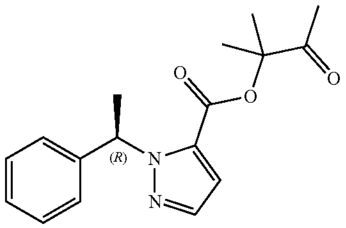
Compound A41
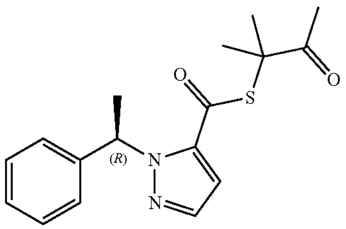
Compound A42
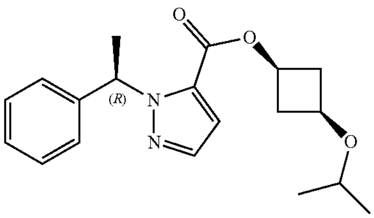
-continued
Compound A43
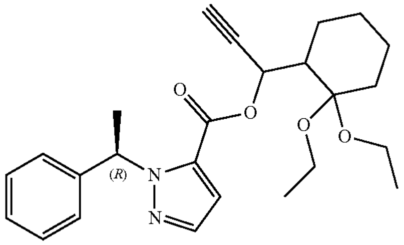
Compound A44
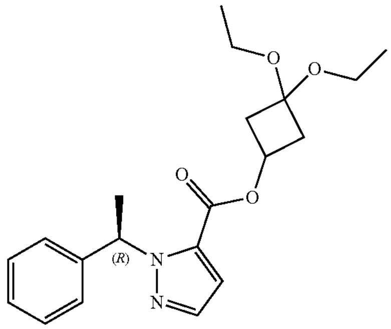
Compound A45
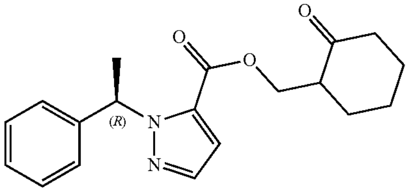
Compound A46
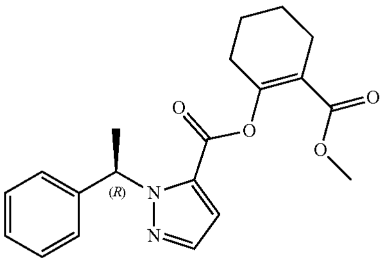
Compound A47
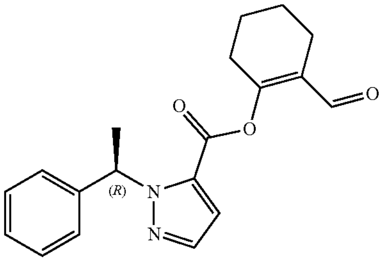

-continued
Compound A48
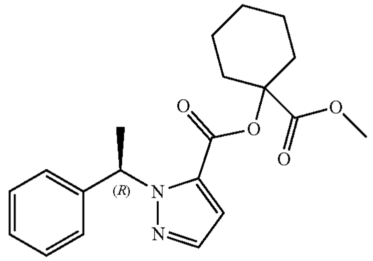
Compound A49
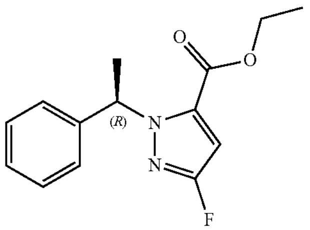
Compound A50
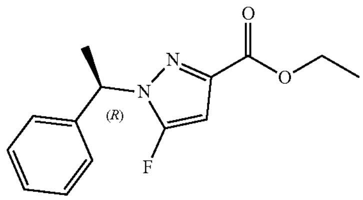
Compound A51
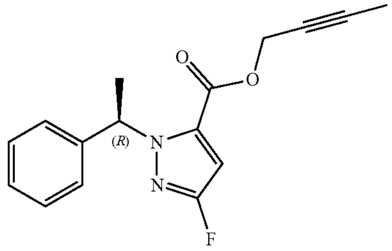
Compound A52
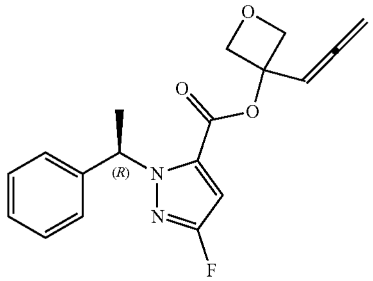
Compound A53
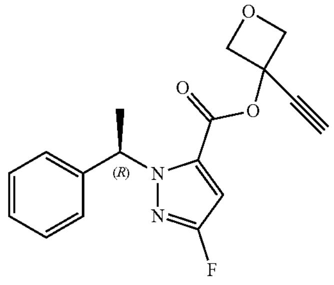
-continued
Compound A54
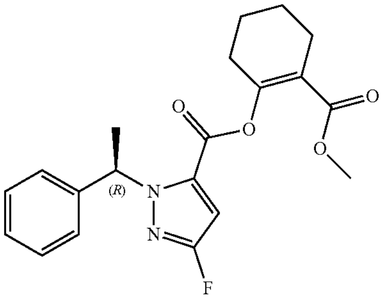
Compound A55
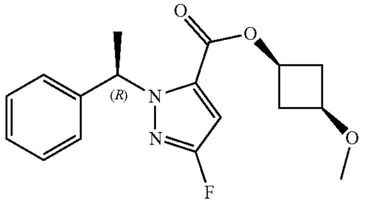
Compound A56
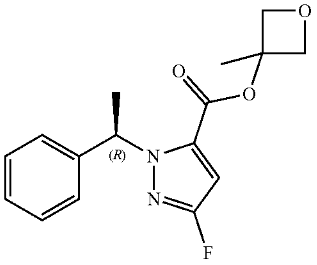
Compound A57
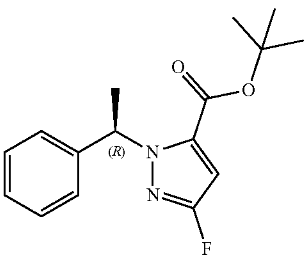
Compound A58
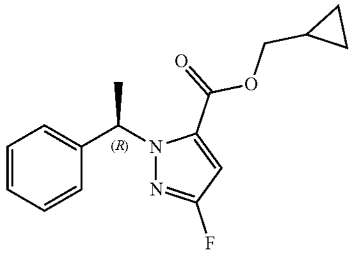
Compound A59
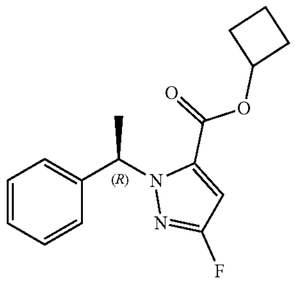

-continued
Compound A60
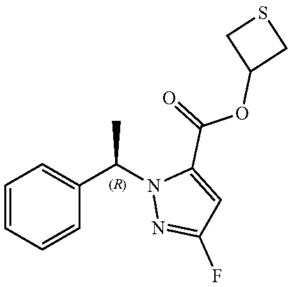
Compound A61
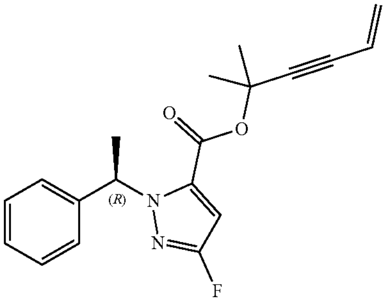
Compound A62
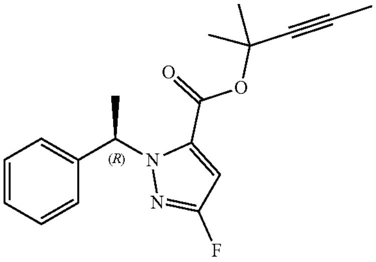
Compound A63
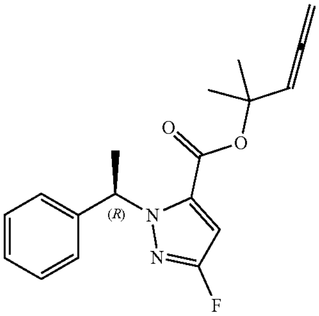
Compound A64
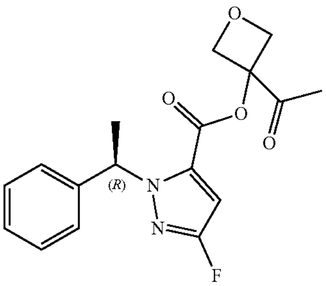
-continued
Compound A65
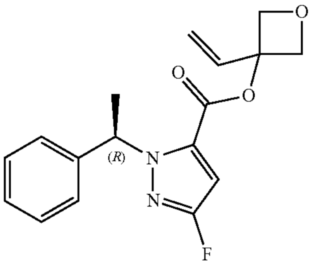
Compound A66
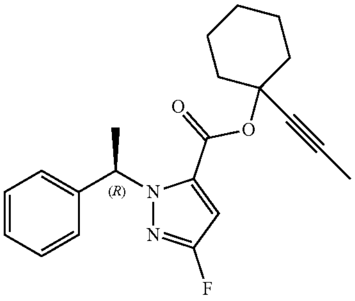
Compound A67
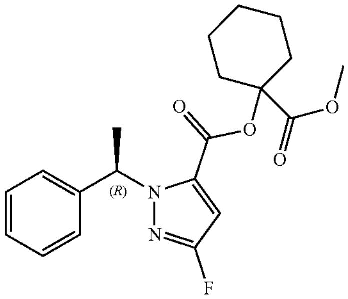
Compound A68
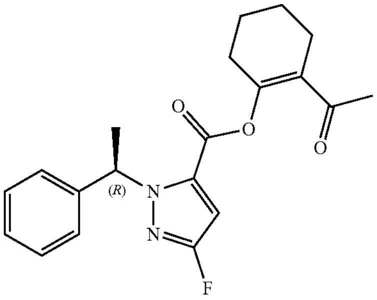
Compound A69
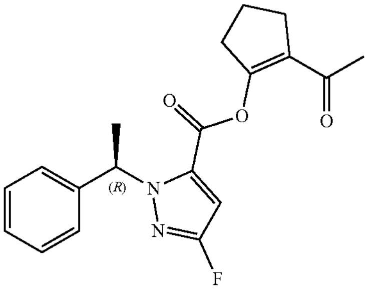

-continued
Compound A70
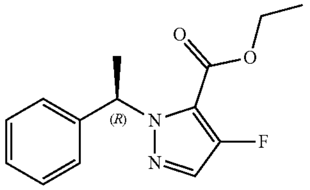
Compound A71
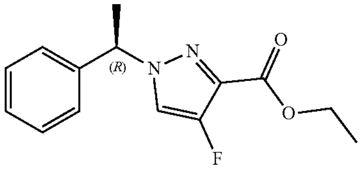
Compound A72
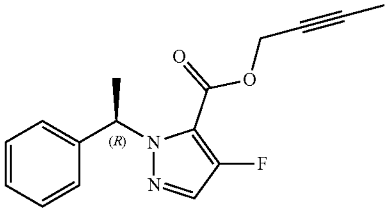
Compound A73
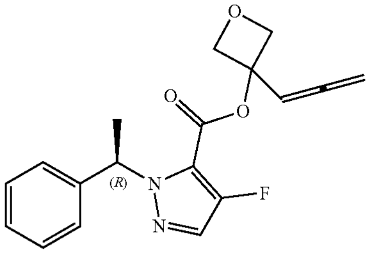
Compound A74
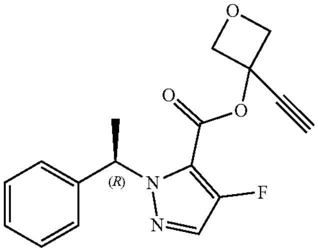
Compound A75
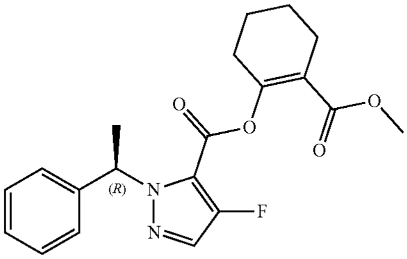
-continued
Compound A76
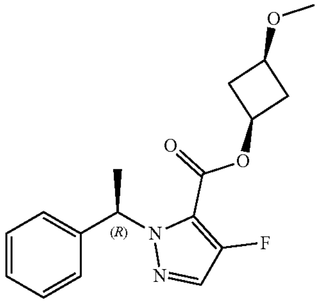
Compound A77
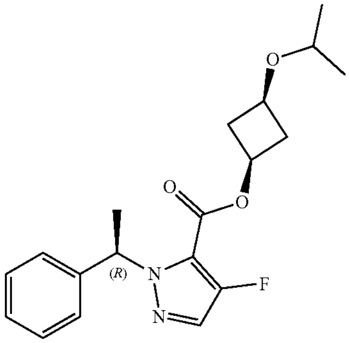
Compound A78
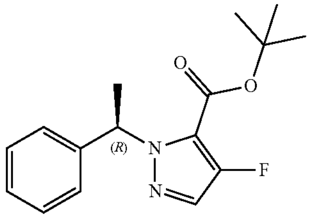
Compound A79
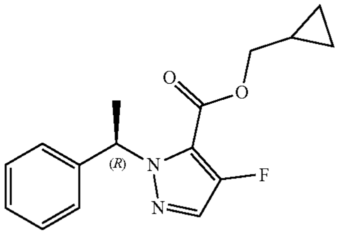
Compound A80
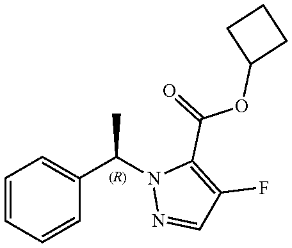

-continued
Compound A81
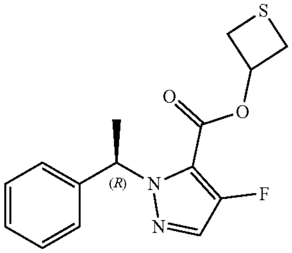
Compound A82
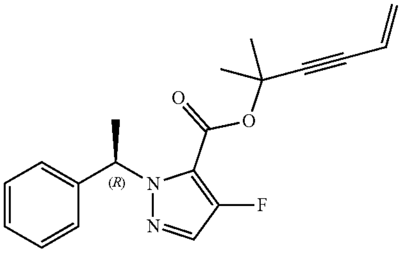
Compound A83
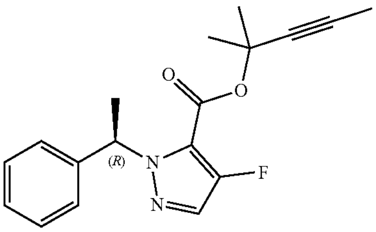
Compound A84
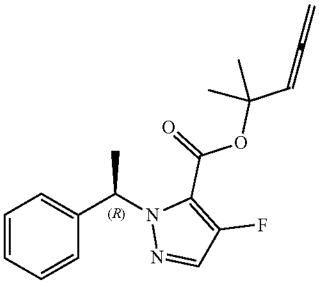
Compound A85
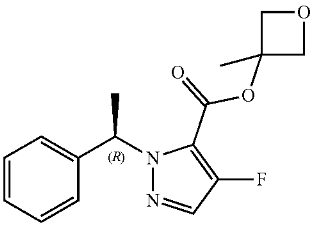
Compound A86
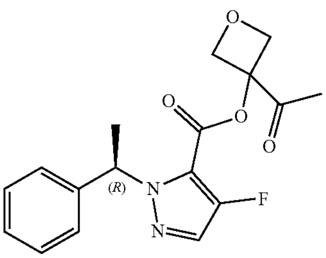
-continued
Compound A87
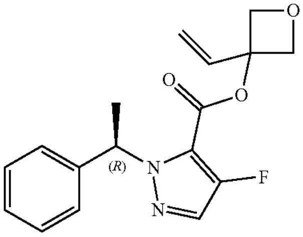
Compound A88
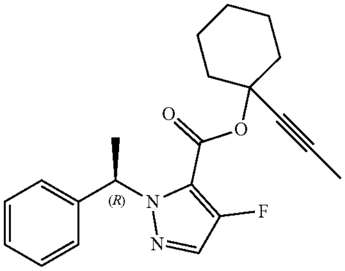
Compound A89
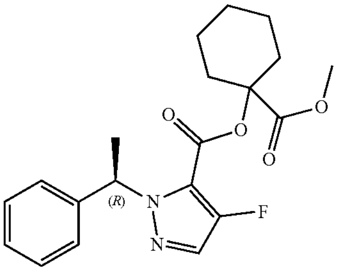
Compound A90
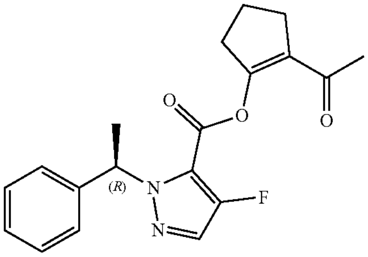
Compound A91
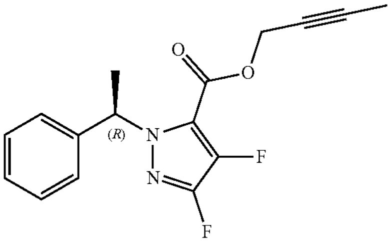
Compound A92
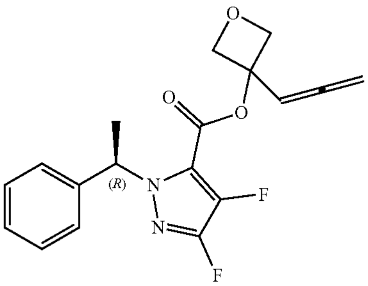

-continued
Compound A93
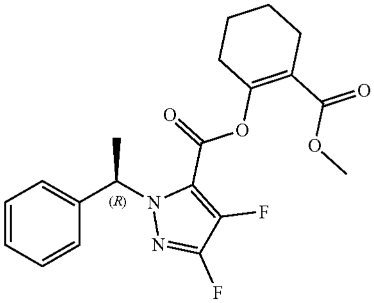
Compound A94
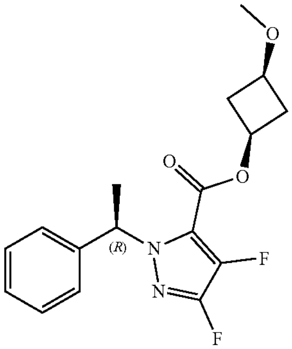
Compound A95
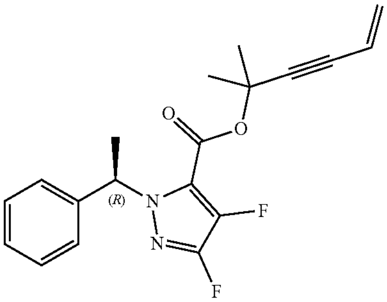
Compound A96
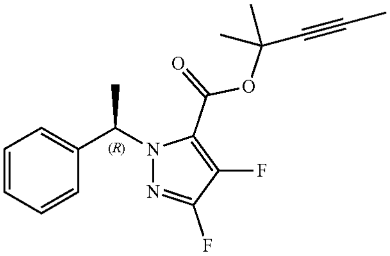
Compound A97
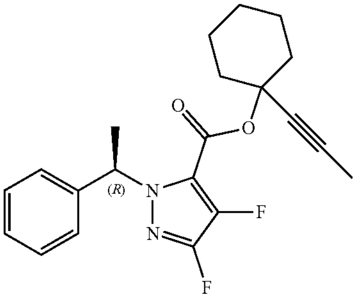
-continued
Compound A98
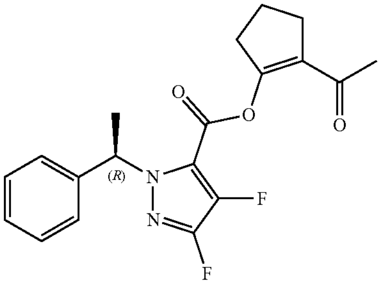
Compound A99
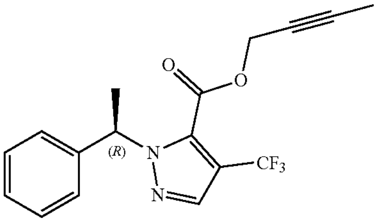
Compound A100
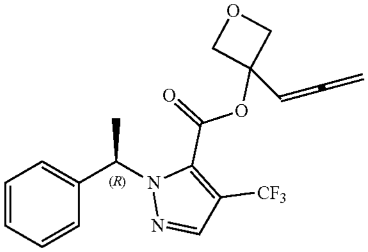
Compound A101
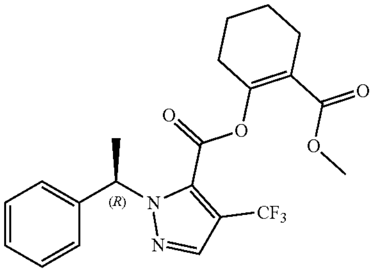
Compound A102
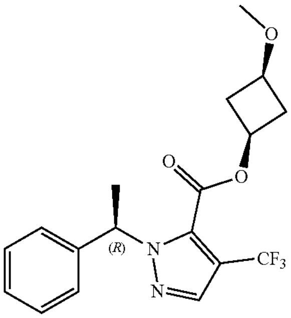

-continued
Compound A103
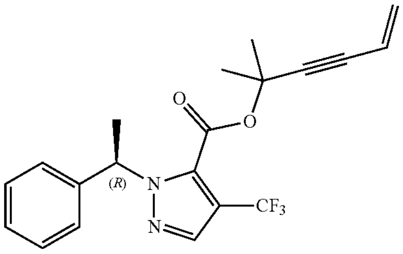
Compound A104
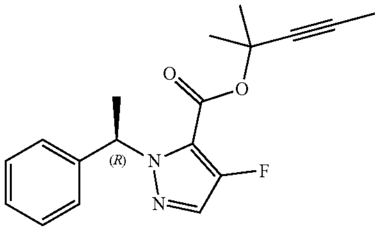
Compound A105
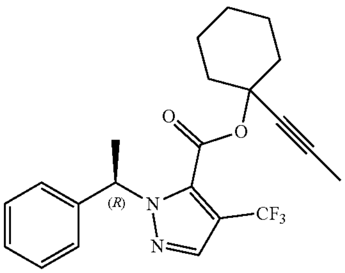
Compound A106
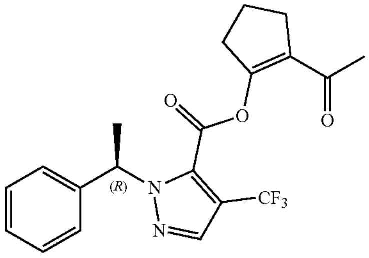
Compound A107
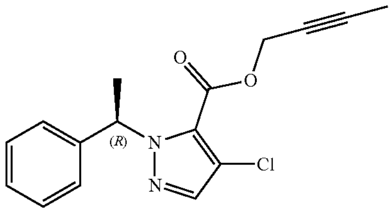
Compound A108
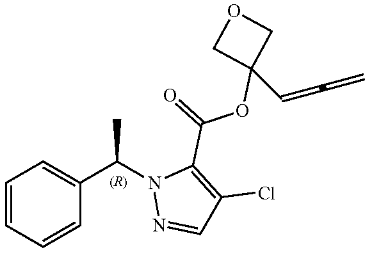
-continued
Compound A109
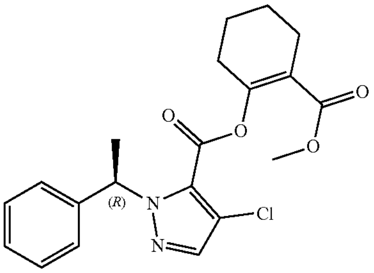
Compound A110
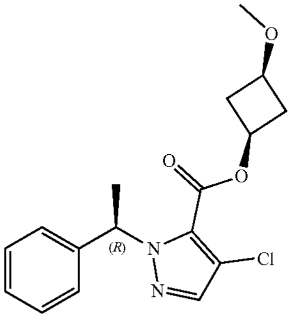
Compound A111
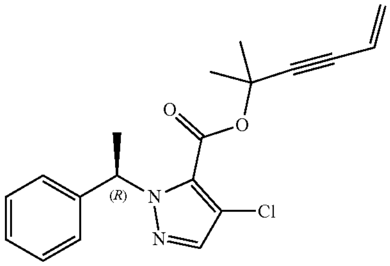
Compound A112
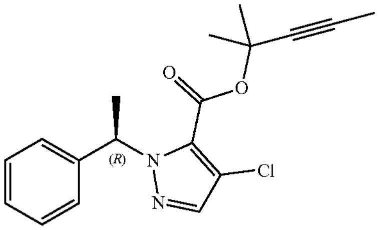
Compound A113
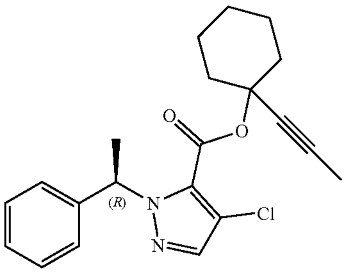

-continued
Compound A114
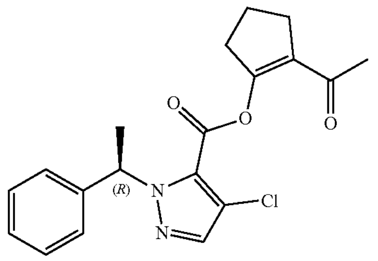
Compound B1
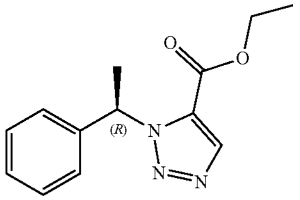
Compound B2
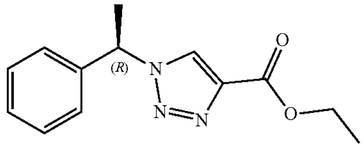
Compound B3
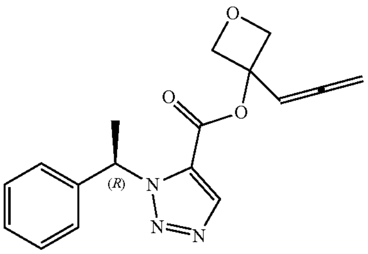
Compound B4
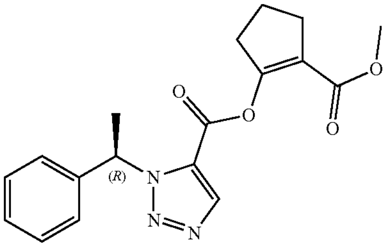
Compound B5
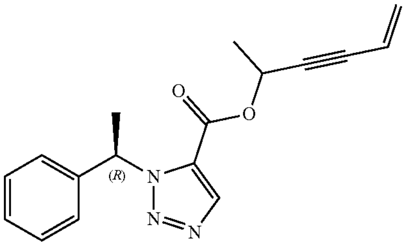
-continued
Compound B6
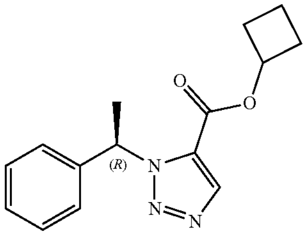
Compound B7
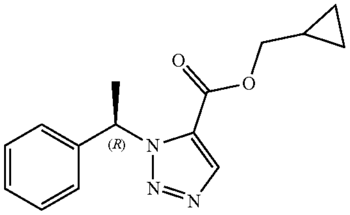
Compound B8
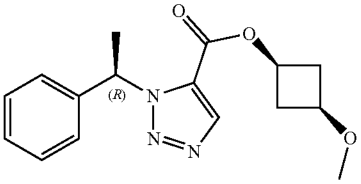
Compound B9
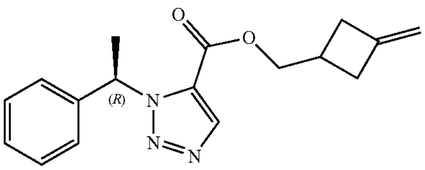
Compound B10
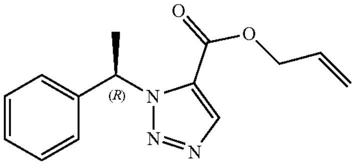
Compound B11
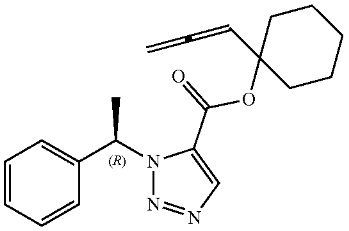
Compound B12
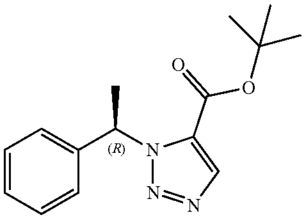

-continued
Compound B13
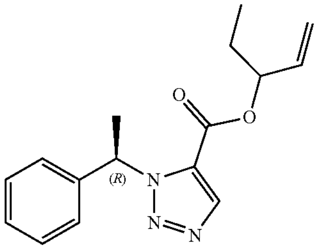
Compound B14
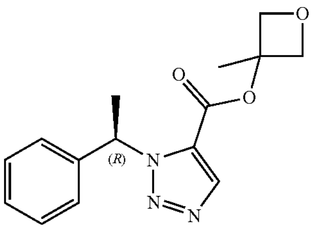
Compound B15
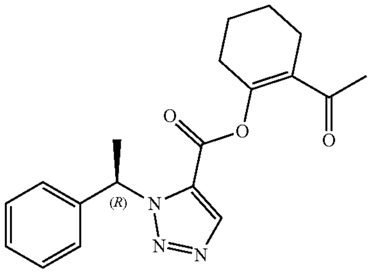
Compound B16
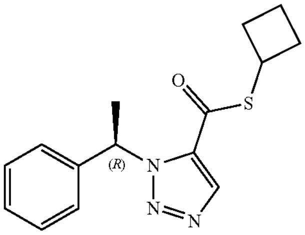
Compound B17
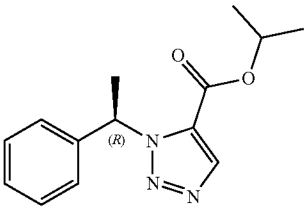
Compound B18
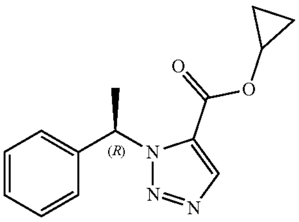
-continued
Compound B19
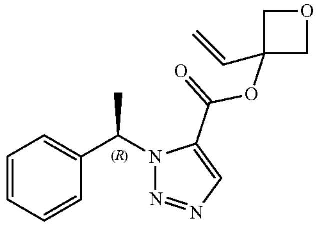
Compound B20
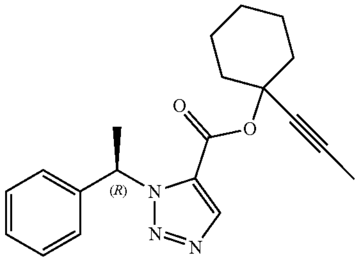
Compound B21
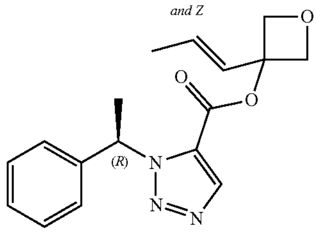
Compound B22
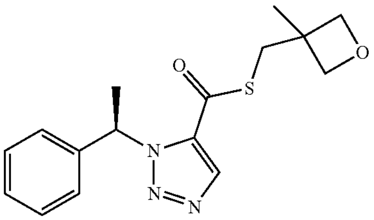
Compound B23
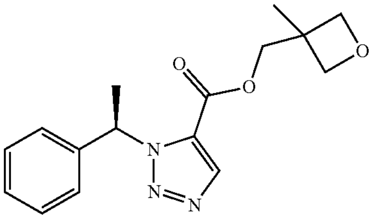
Compound B24
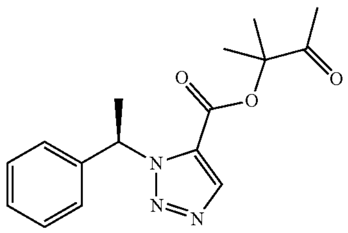

-continued
Compound B25
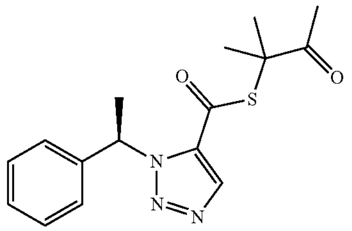
Compound B26
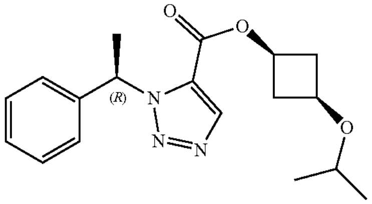
Compound B27
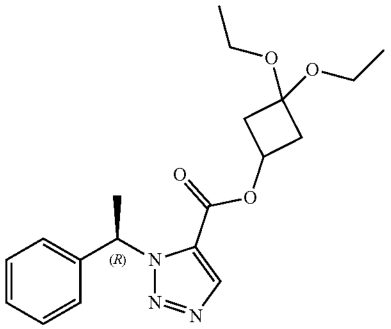
Compound B28
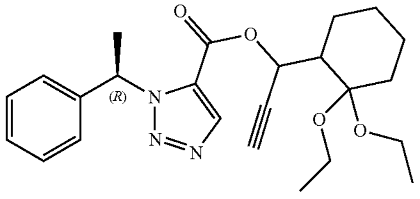
Compound B29
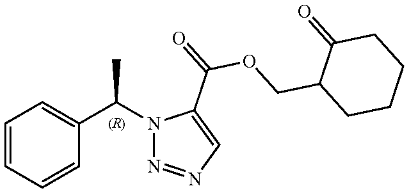
Compound B30
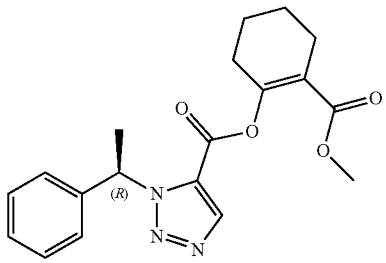
-continued
Compound B31
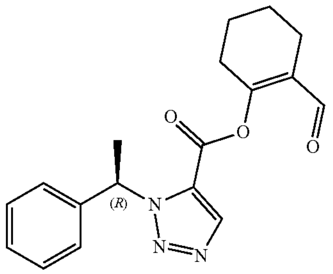
Compound B32
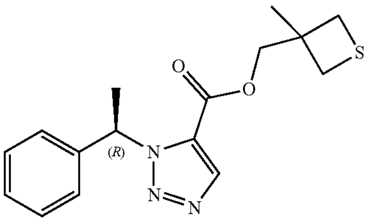
Compound B33
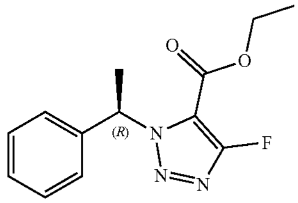
Compound B34
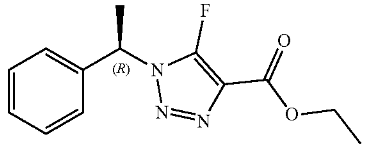
Compound B35
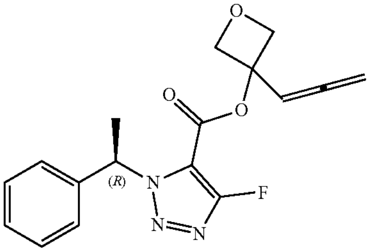
Compound B36
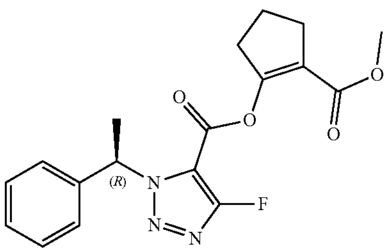

-continued
Compound B37
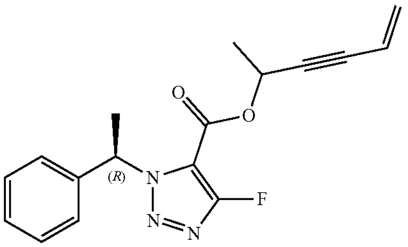
Compound B38
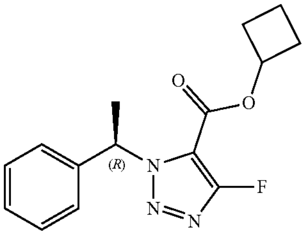
Compound B39
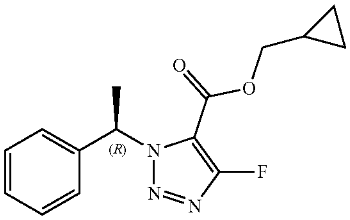
Compound B40
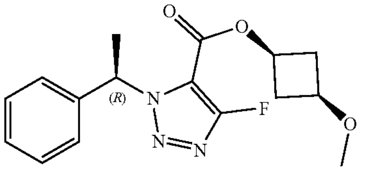
Compound B41
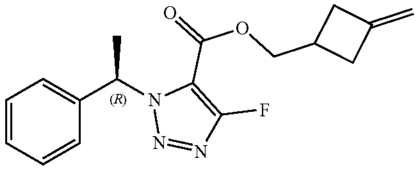
Compound B42
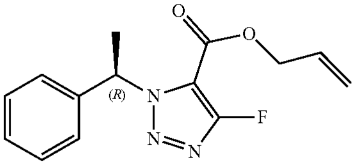
Compound B43
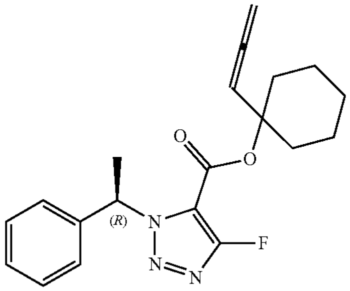
-continued
Compound B44
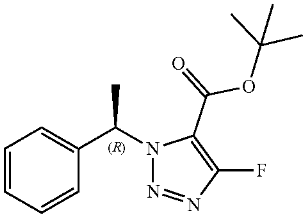
Compound B45
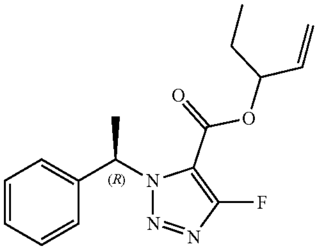
Compound B46
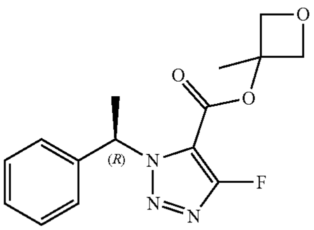
Compound B47
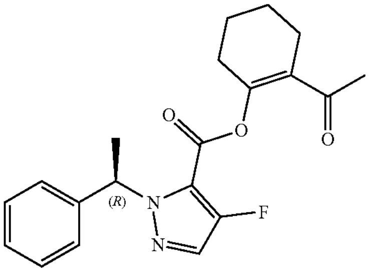
Compound B48
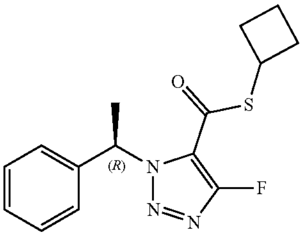
Compound B49
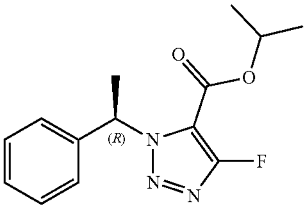

-continued
Compound B50
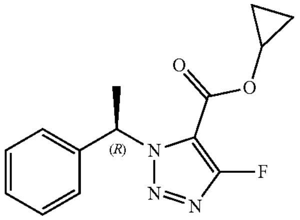
Compound B51
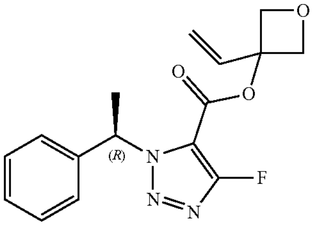
Compound B52
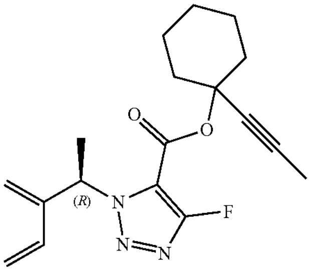
Compound B53
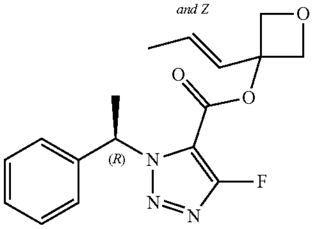
Compound B54
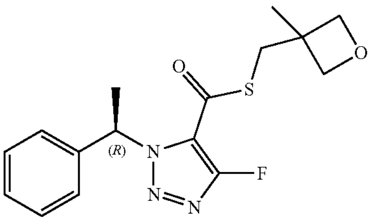
Compound B55
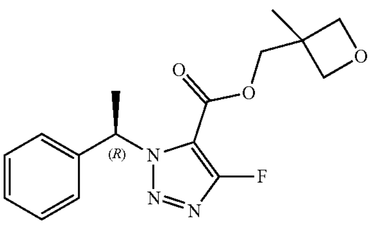
-continued
Compound B56
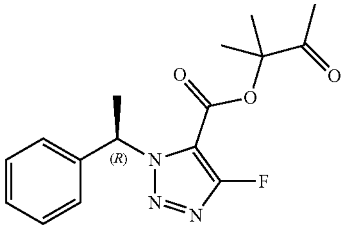
Compound B57
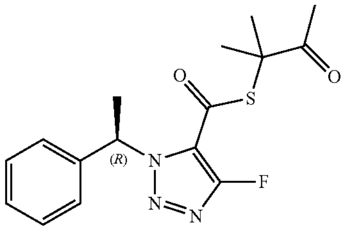
Compound B58
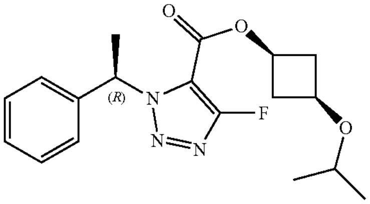
Compound B59
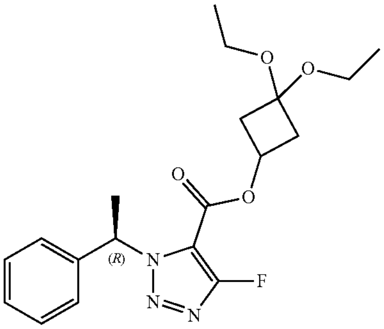
Compound B60
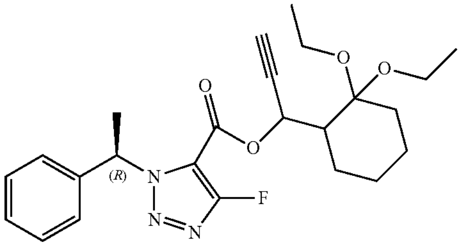
Compound B61
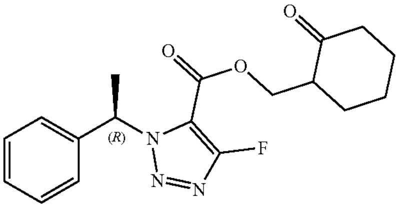

-continued
Compound B62
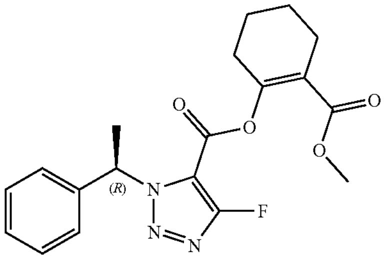
Compound B63
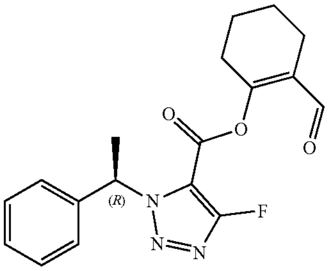
Compound B64
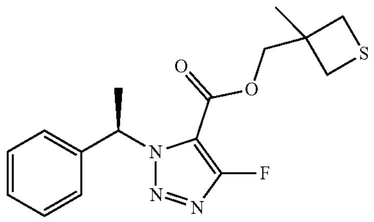
Compound B65
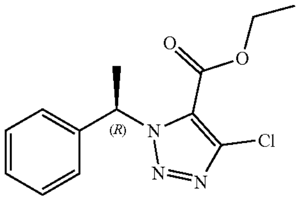
Compound B66
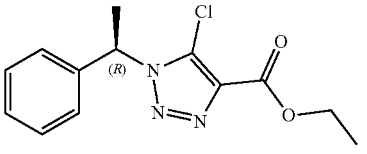
Compound B67
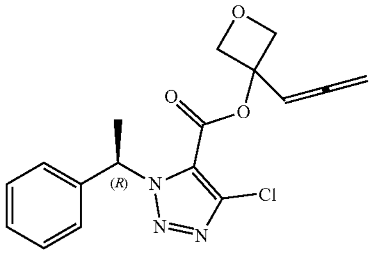
-continued
Compound B68
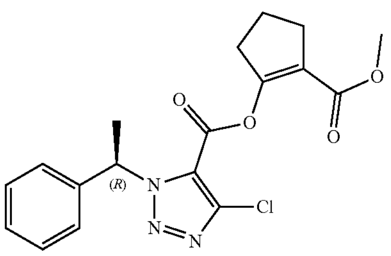
Compound B69
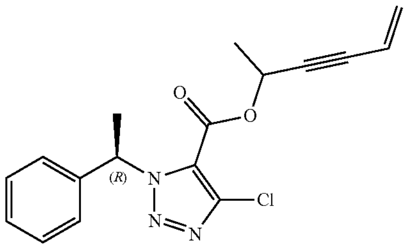
Compound B70
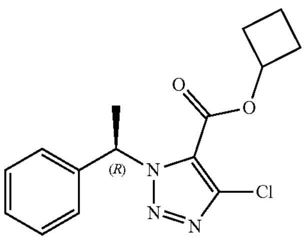
Compound B71
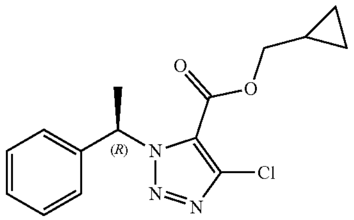
Compound B72
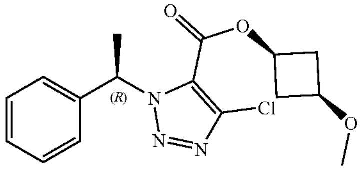
Compound B73
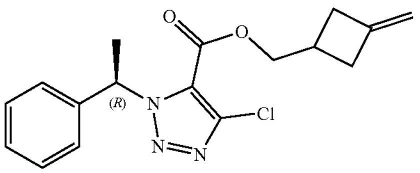
Compound B74
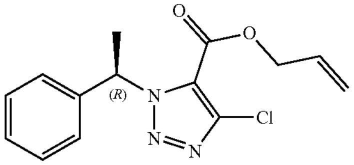

-continued
Compound B75
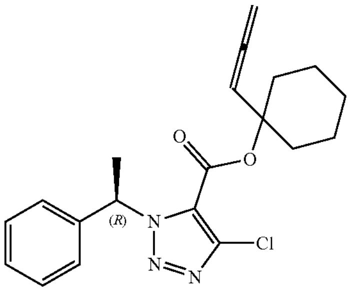
Compound B76
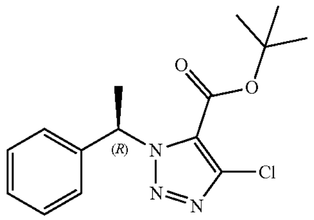
Compound B77
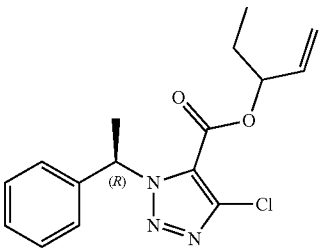
Compound B78
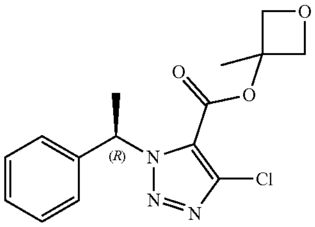
Compound B79
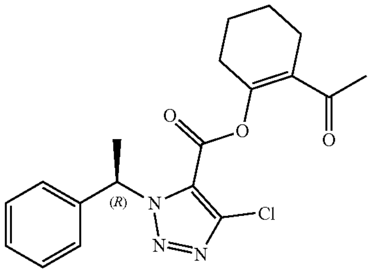
Compound B80
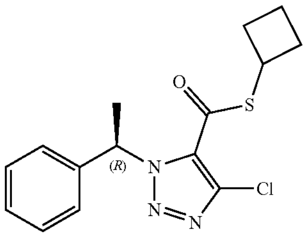
-continued
Compound B81
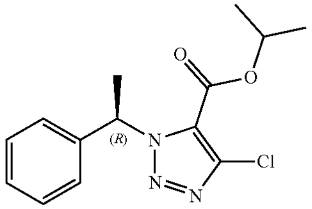
Compound B82
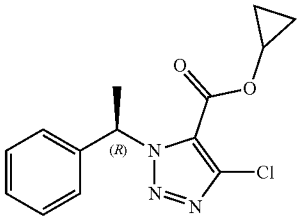
Compound B83
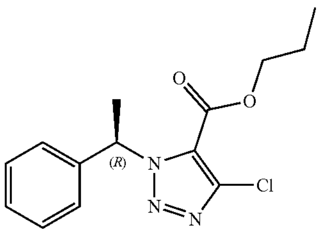
Compound B84
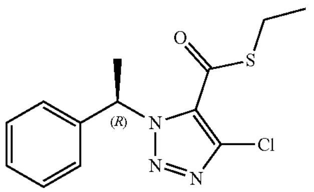
Compound B85
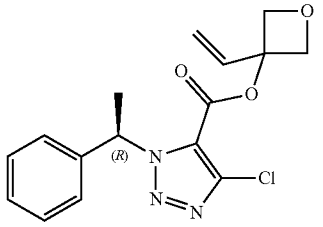
Compound B86
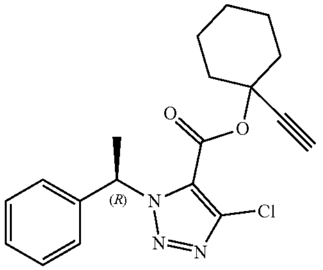
Compound B87
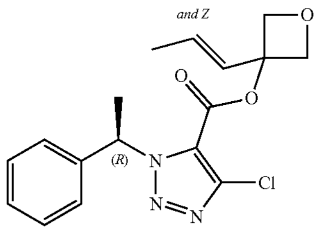

-continued
Compound B88
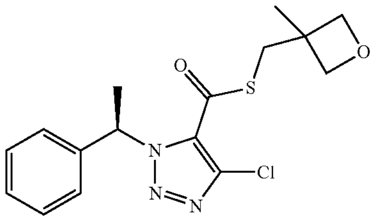
Compound B89
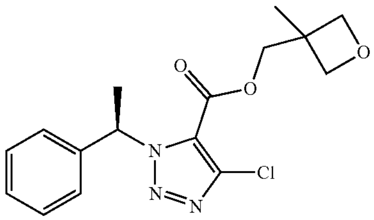
Compound B90
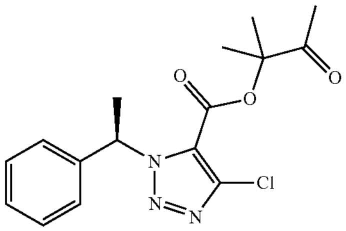
Compound B91
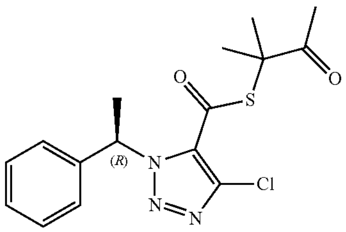
Compound B92
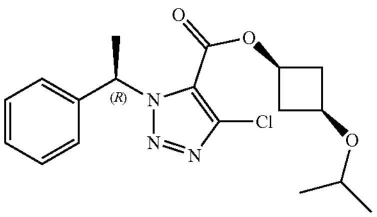
Compound B93
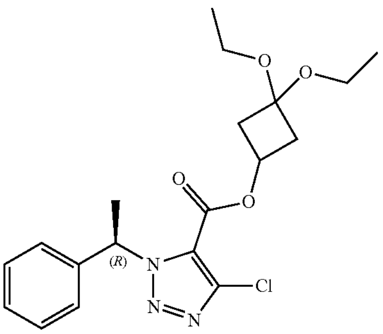
-continued
Compound B94
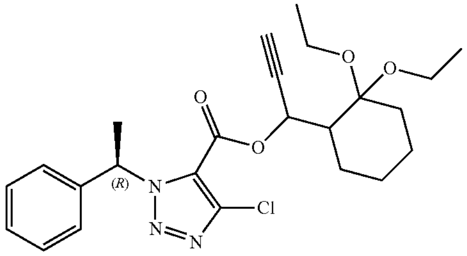
Compound B95
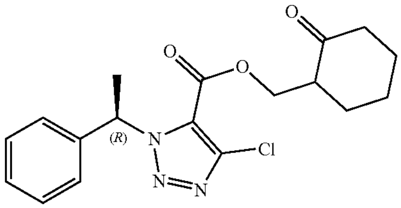
Compound B96
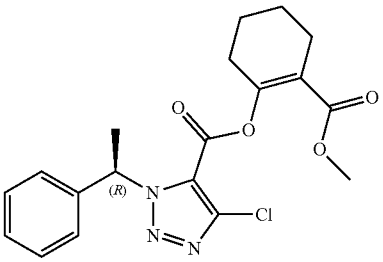
Compound B97
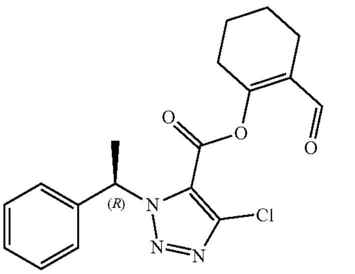
Compound B98
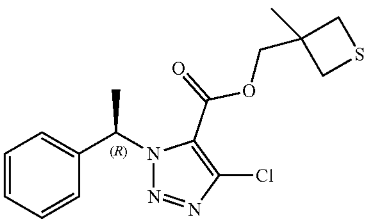
Compound B99
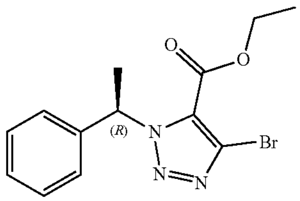

-continued
Compound B100
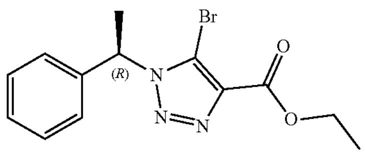
Compound B101
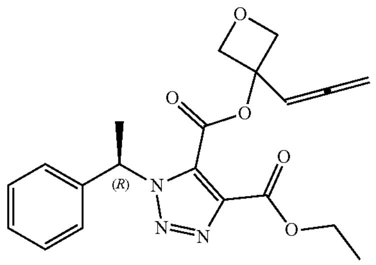
Compound B102
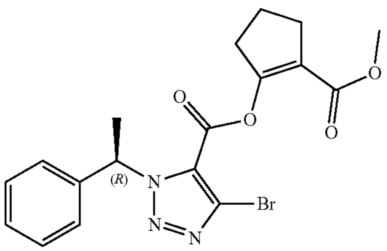
Compound B103
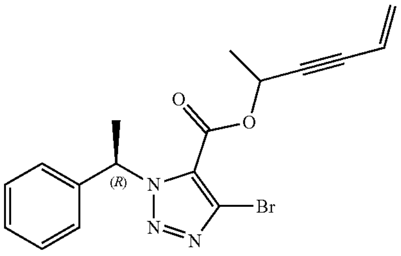
Compound B104
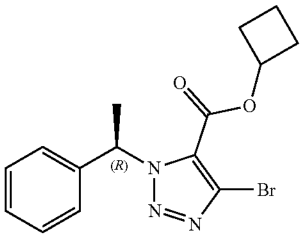
Compound B105
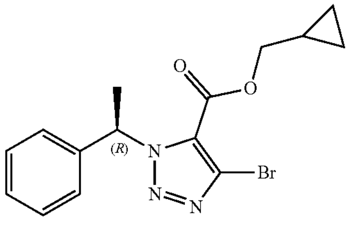
-continued
Compound B106
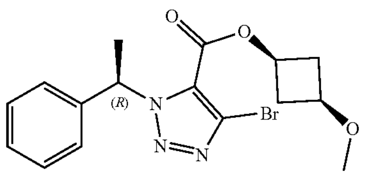
Compound B107
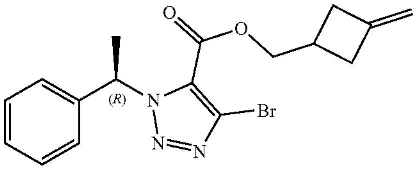
Compound B108
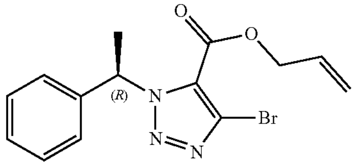
Compound B109
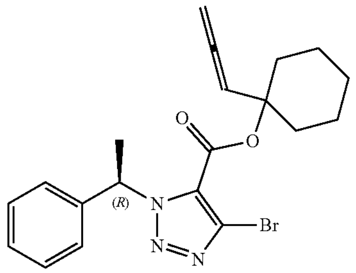
Compound B110
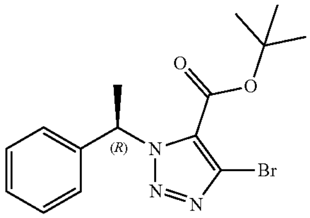
Compound B111
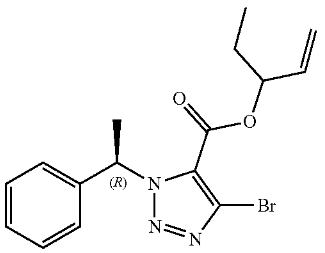
Compound B112
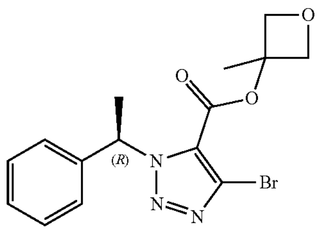

-continued
Compound B113
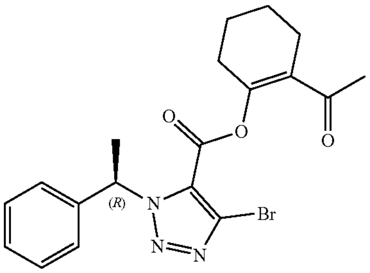
Compound B114
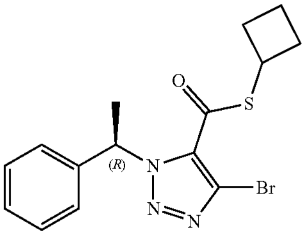
Compound B115
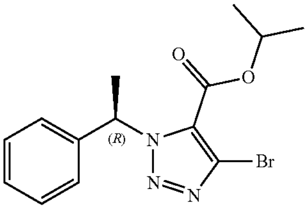
Compound B116
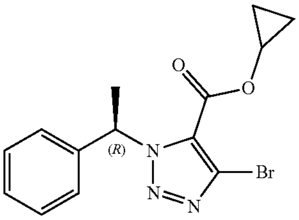
Compound B117
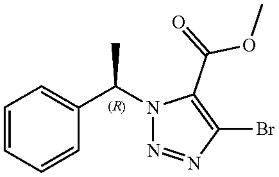
Compound B118
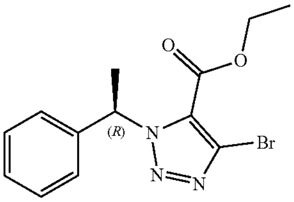
Compound B119
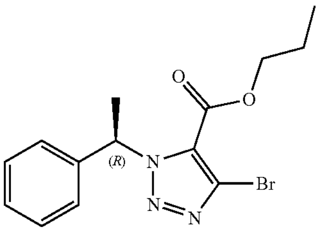
-continued
Compound B120
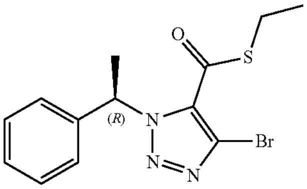
Compound B121
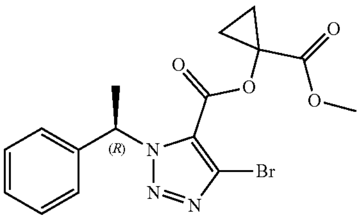
Compound B122
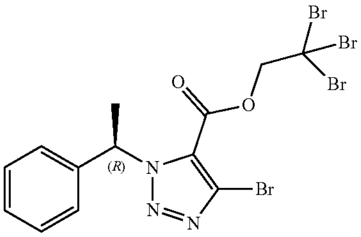
Compound B123
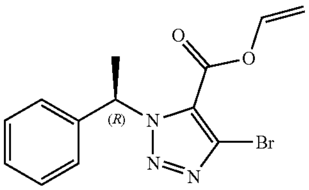
Compound B124
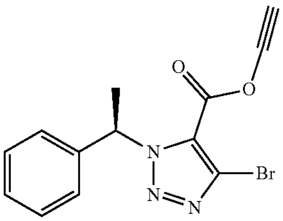
Compound B125
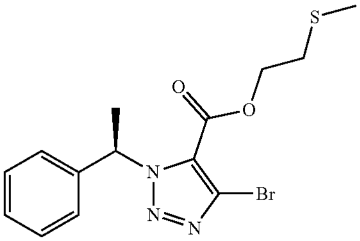

-continued
Compound B126
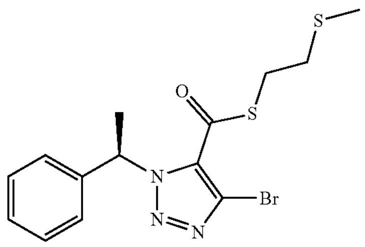
Compound B127
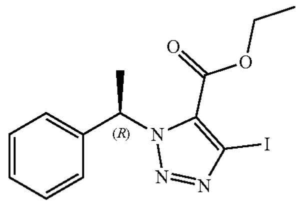
Compound B128
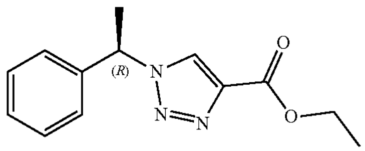
Compound B129
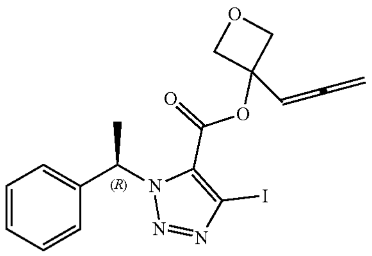
Compound B130
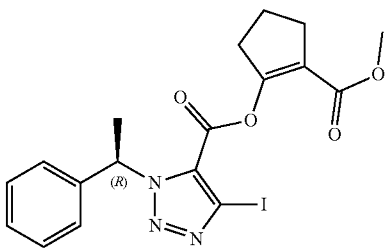
Compound B131
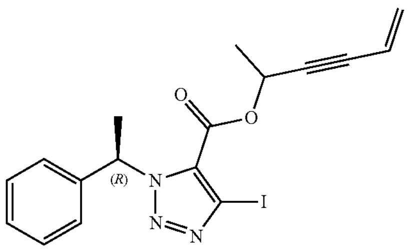
-continued
Compound B132
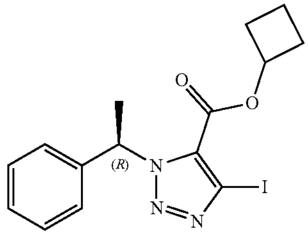
Compound B133
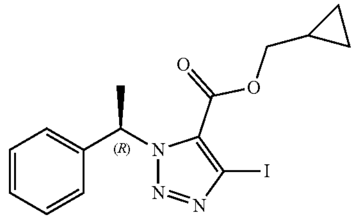
Compound B134
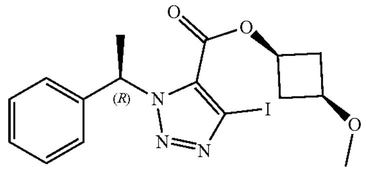
Compound B135
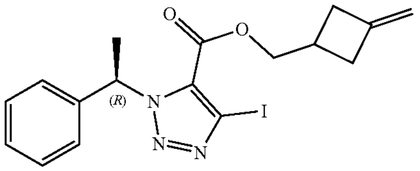
Compound B136
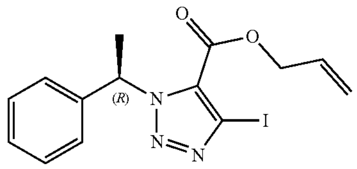
Compound B137
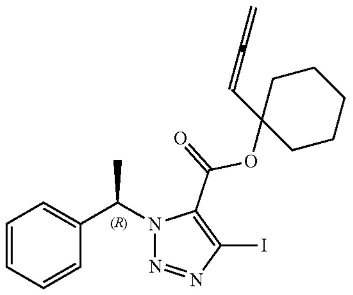
Compound B138
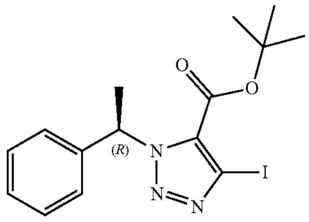

-continued
Compound B139
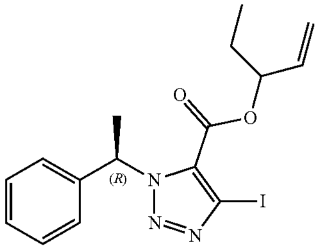
Compound B140
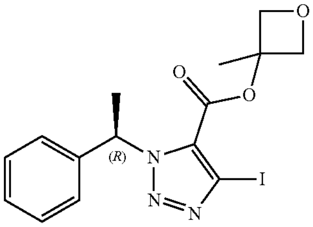
Compound B141
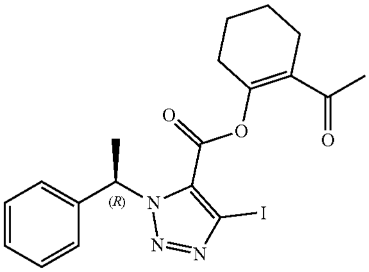
Compound B142
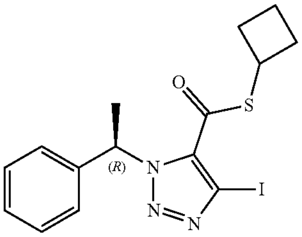
Compound B143
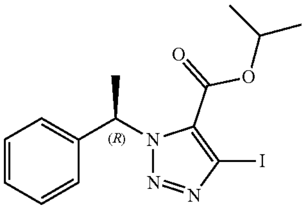
Compound B144
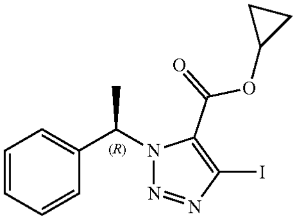
-continued
Compound B145
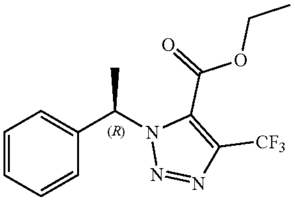
Compound B146
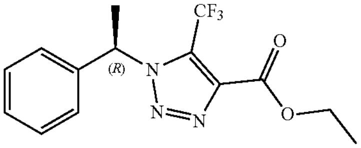
Compound B147
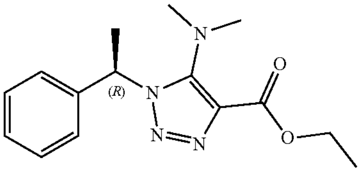
Compound C1
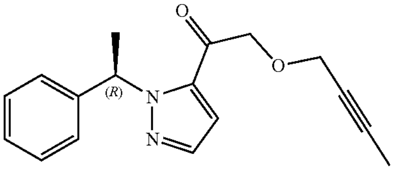
Compound C2
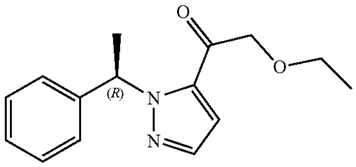
Compound C3
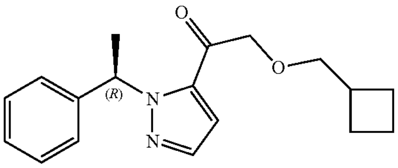
Compound C4
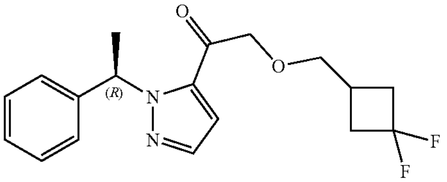
Compound C5
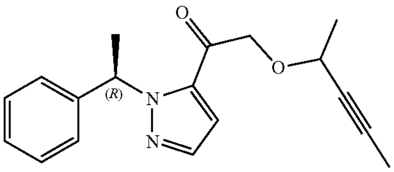

-continued
Compound C6
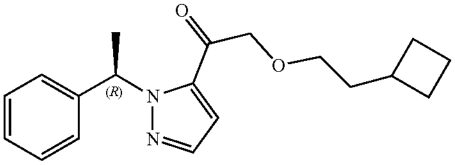
Compound C7
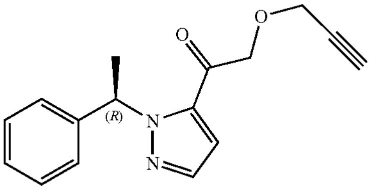
Compound C8
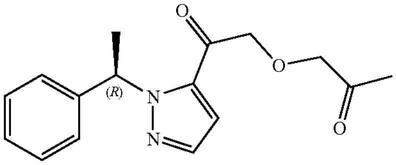
Compound C9
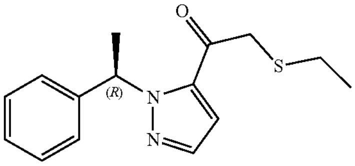
Compound C10
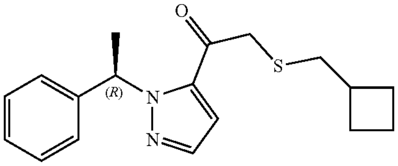
Compound C11
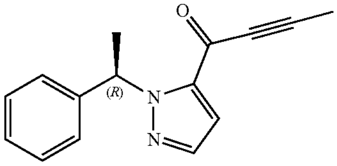
Compound C12
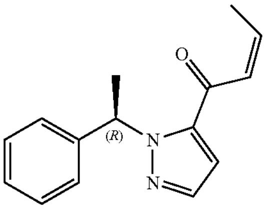
Compound C13
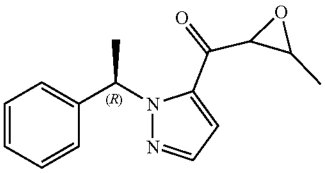
-continued
Compound C14
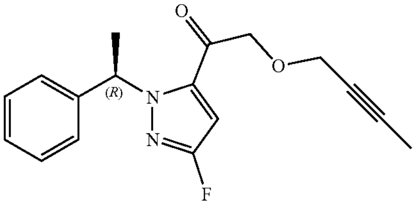
Compound C15
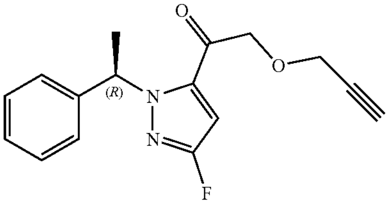
Compound C16
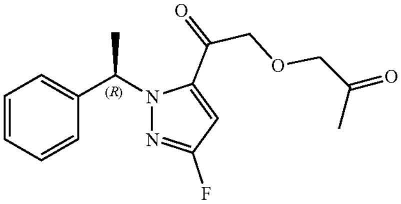
Compound C17
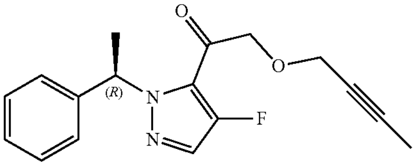
Compound C18
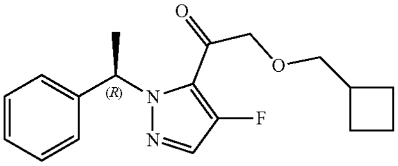
Compound C19
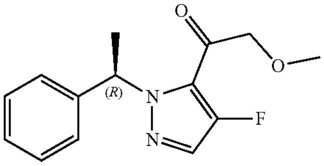
Compound C20
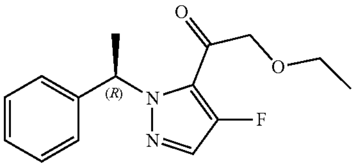
Compound C21
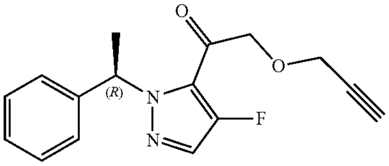

-continued
Compound C22
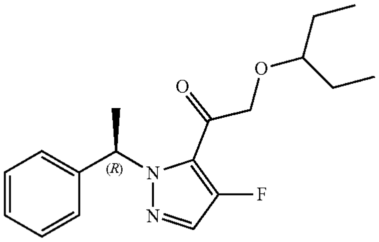
Compound C23
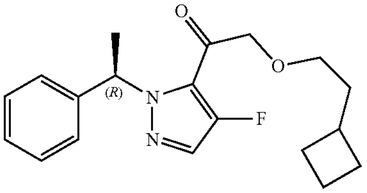
Compound C24
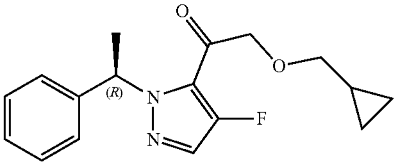
Compound C25
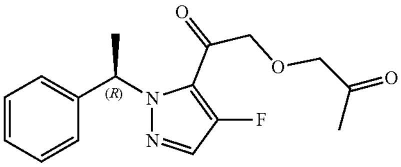
Compound C26
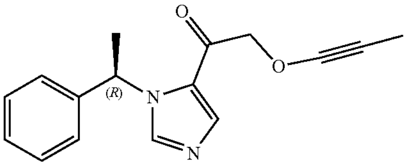
Compound C27
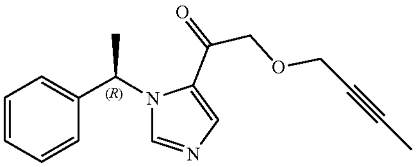
Compound C28
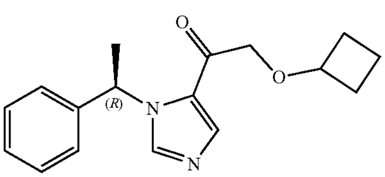
Compound C29
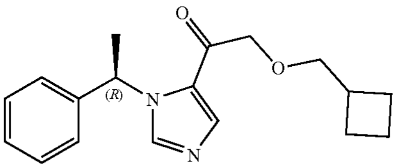
-continued
Compound C30
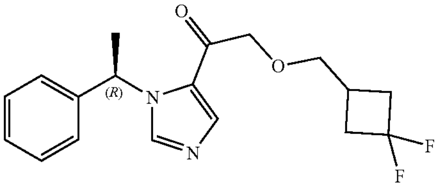
Compound C31
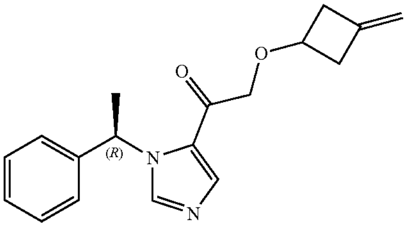
Compound C32
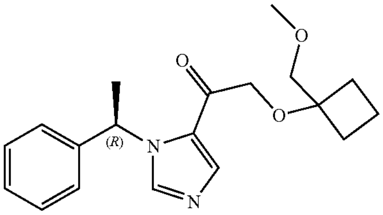
Compound C33
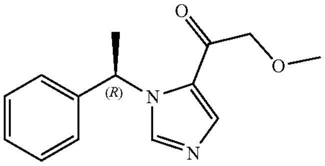
Compound C34
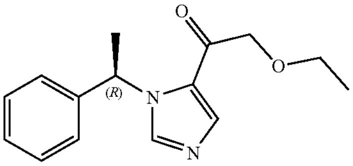
Compound C35
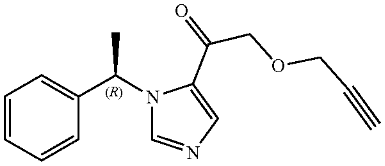
Compound C36
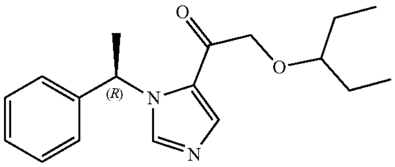
Compound C37
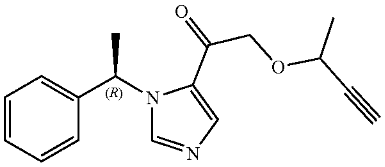

-continued
Compound C38
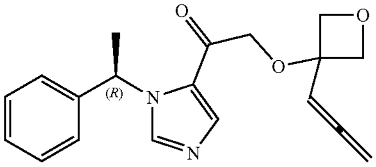
Compound C39
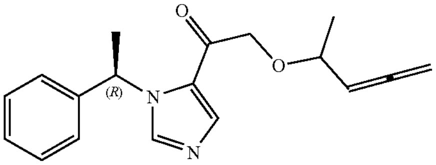
Compound C40
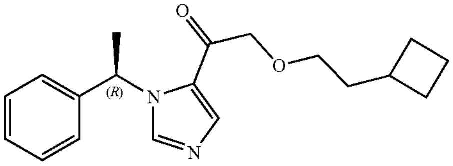
Compound C41
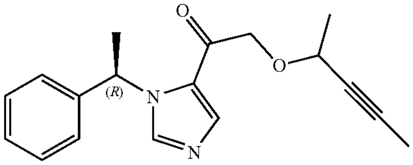
Compound C42
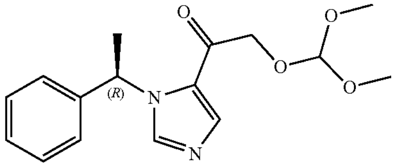
Compound C43
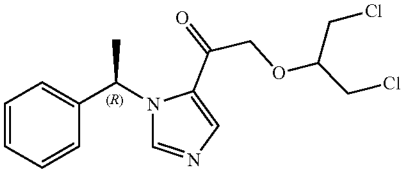
Compound C44
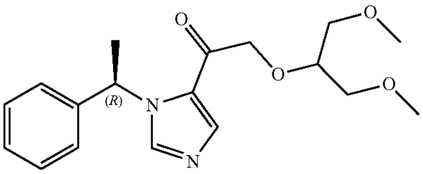
Compound C45
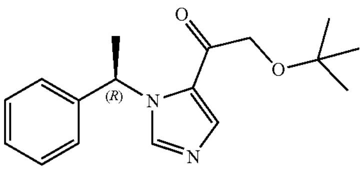
-continued
Compound C46
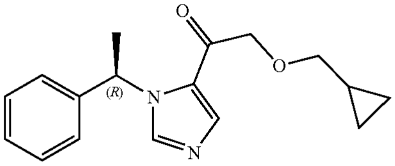
Compound C47
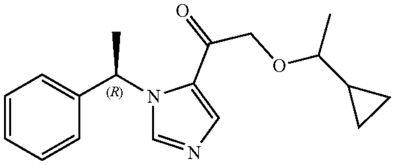
Compound C48
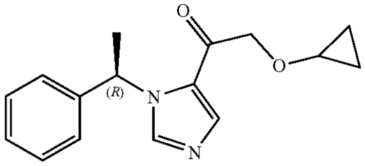
Compound C49
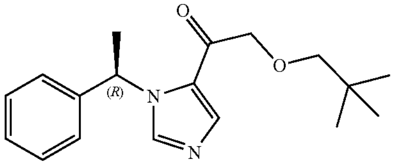
Compound C50
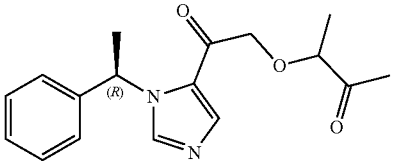
Compound C51
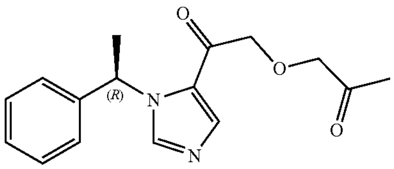
Compound C52
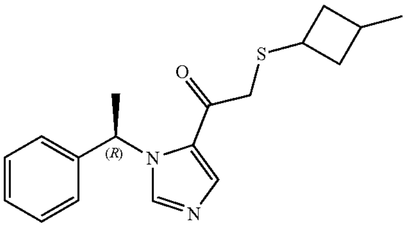
Compound C53
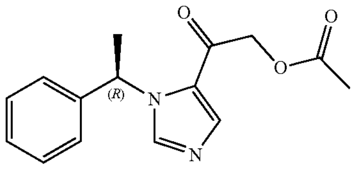

-continued
Compound C54
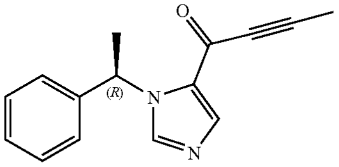
Compound C55
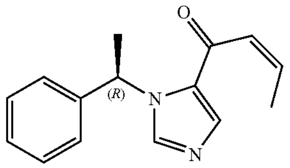
Compound C56
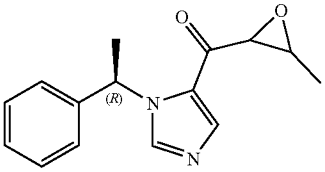
Compound C57
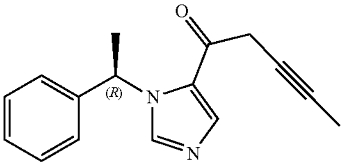
Compound C58
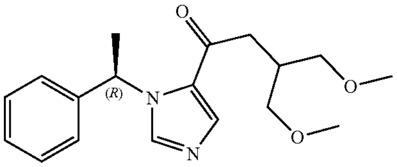
Compound C59
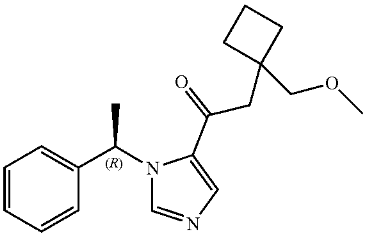
Compound C60
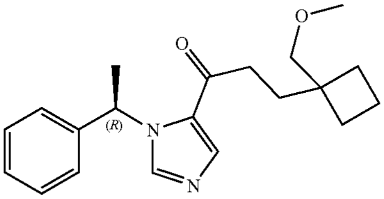
Compound C61
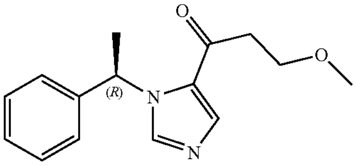
-continued
Compound C62
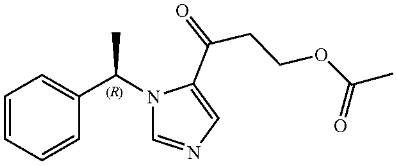
Compound C63
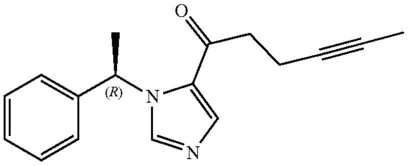
Compound C64
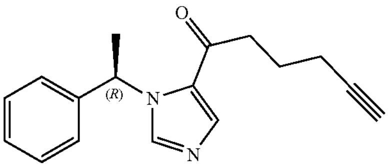
Compound C65
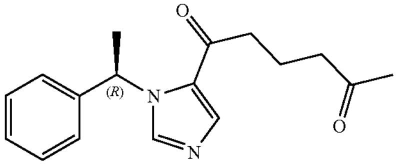
Compound C66
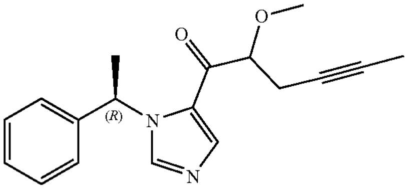
Compound C67
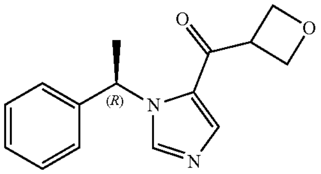
Compound C68
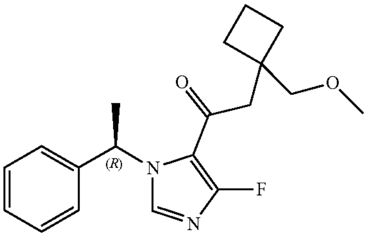
Compound C69
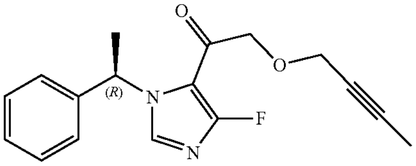

-continued
Compound C70
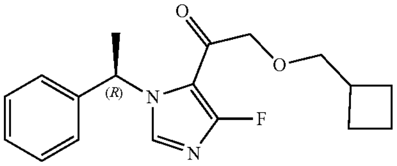
Compound C71
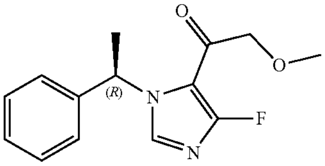
Compound C72
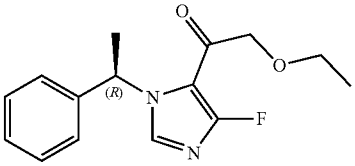
Compound C73
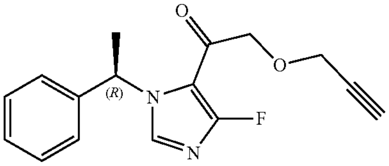
Compound C74
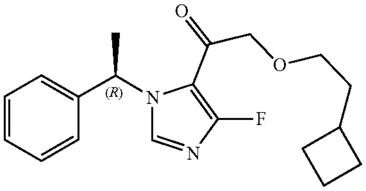
Compound C75
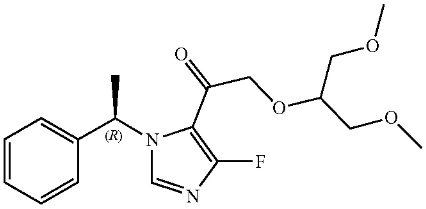
Compound C76
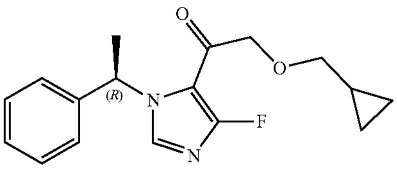
Compound C77
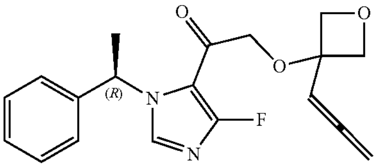
-continued
Compound C78
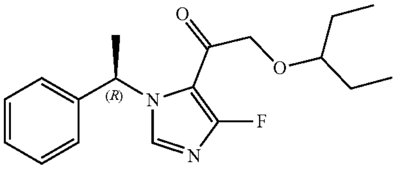
Compound C79
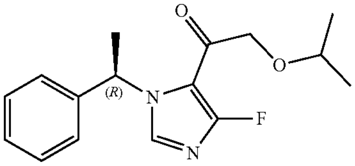
Compound C80
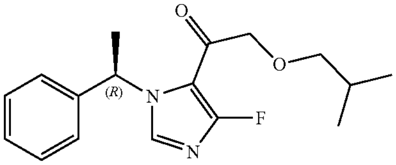
Compound C81
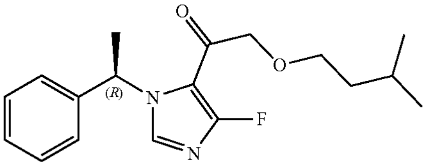
Compound C82
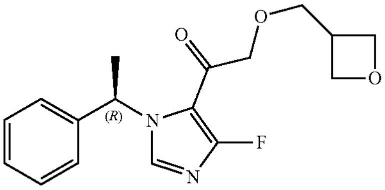
Compound C83
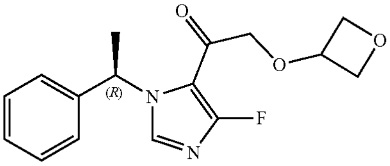
Compound C84
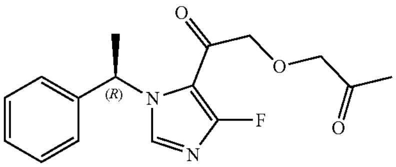
Compound C85
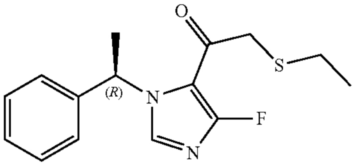

Compound D1
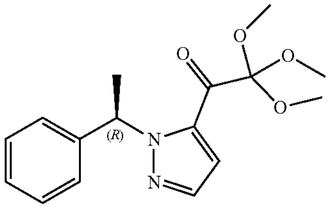
Compound D2
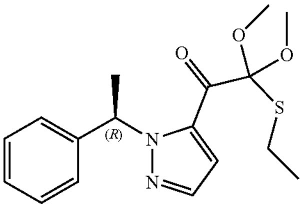
Compound D3
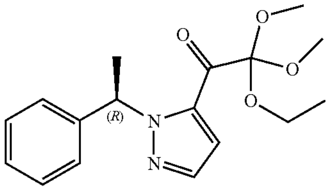
Compound D4
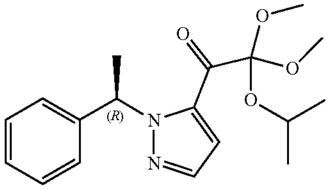
Compound D5
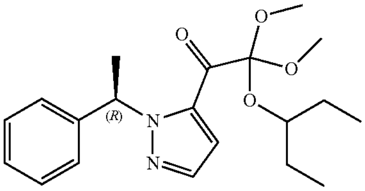
Compound D6
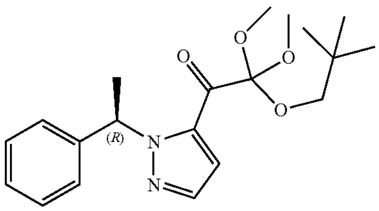
Compound D7
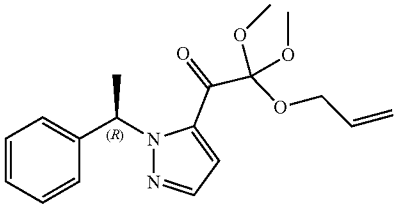
Compound D8
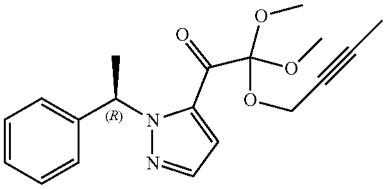
Compound D9
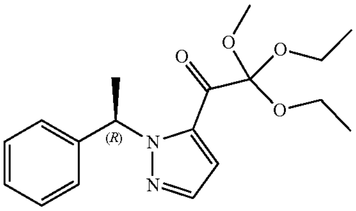
Compound D10
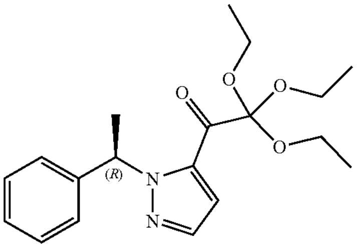
Compound D11
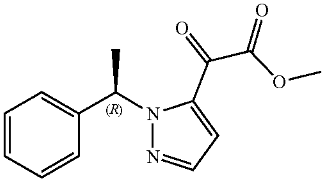
Compound D12
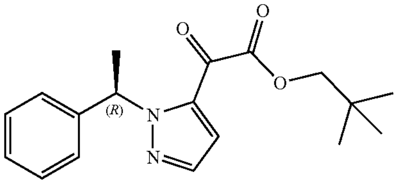
Compound D13
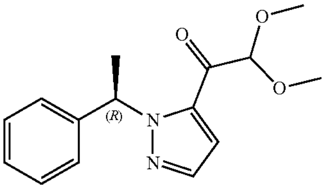
Compound D14
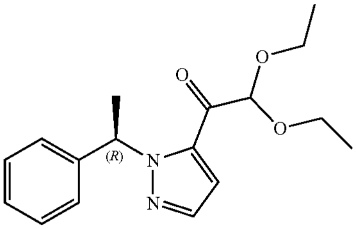

Compound D15
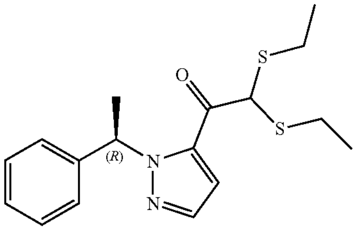
Compound D16
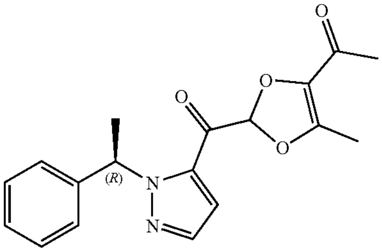
Compound D17
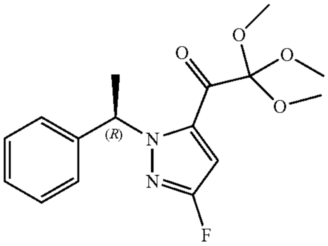
Compound D18
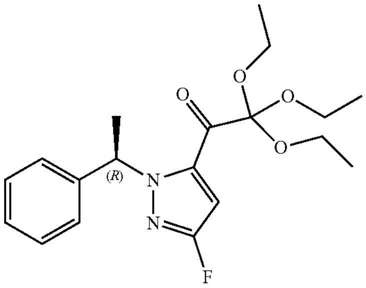
Compound D19
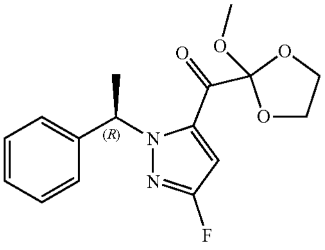
Compound D20
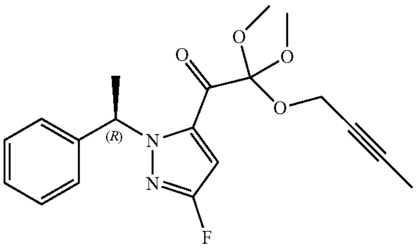
Compound D21
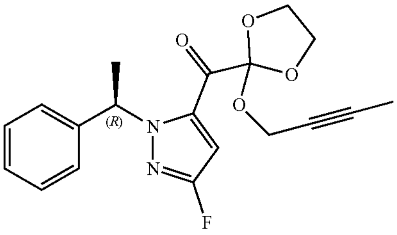
Compound D22
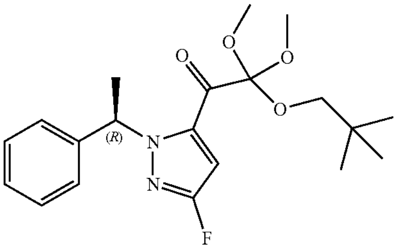
Compound D23
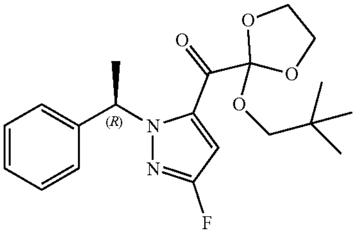
Compound D24
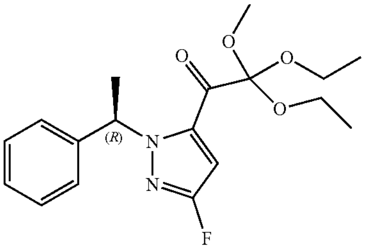
Compound D25
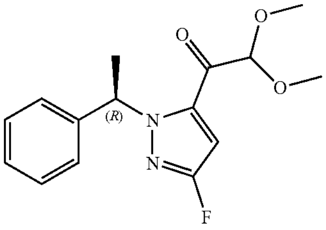
Compound D26
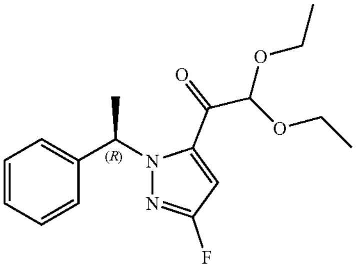

-continued
Compound D27
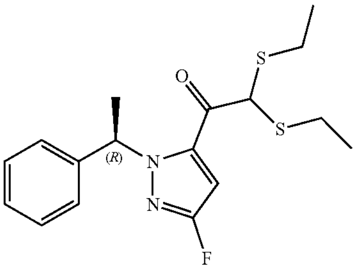
Compound D28
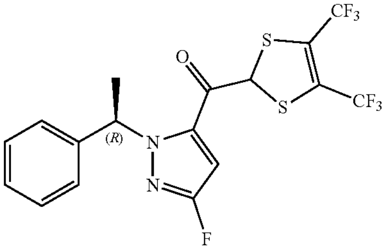
Compound D29
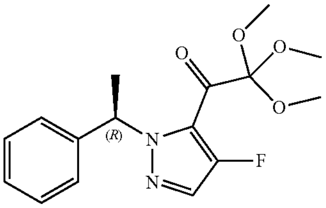
Compound D30
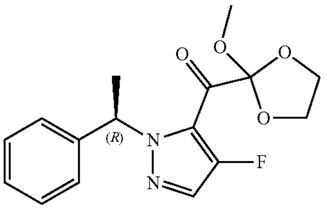
Compound D31
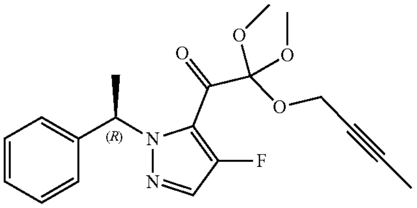
Compound D32
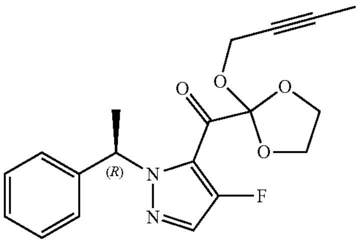
-continued
Compound D33
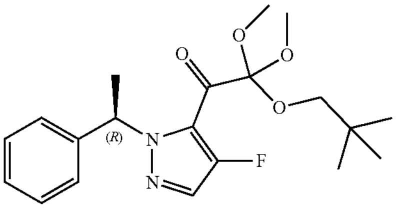
Compound D34
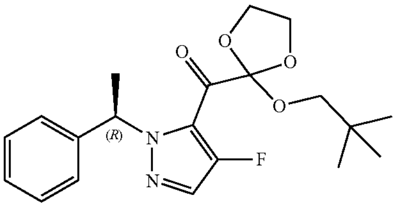
Compound D35
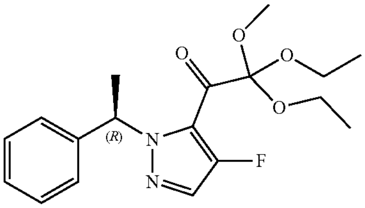
Compound D36
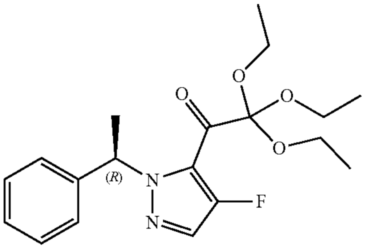
Compound D37
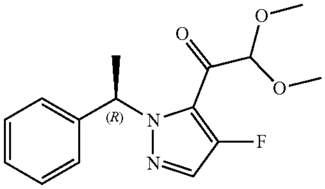
Compound D38
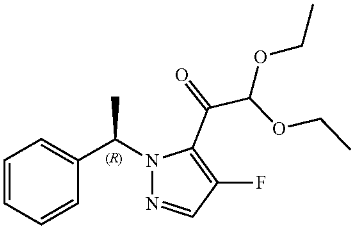
Compound D39
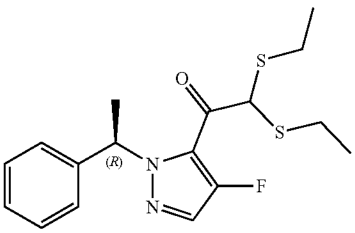

-continued
Compound D40
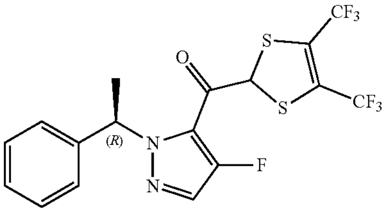
Compound D41
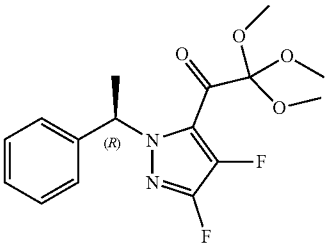
Compound D42
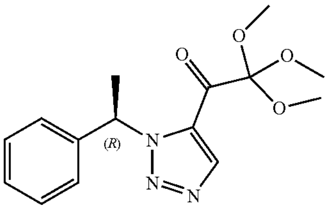
Compound D43
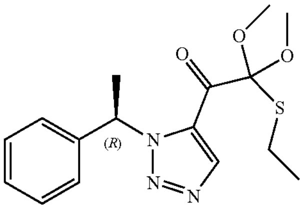
Compound D44
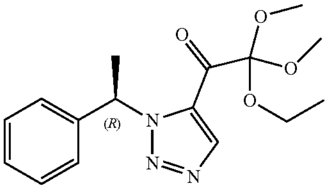
Compound D45
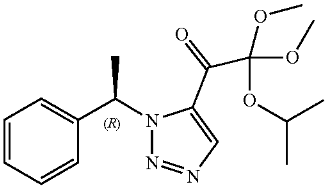
Compound D46
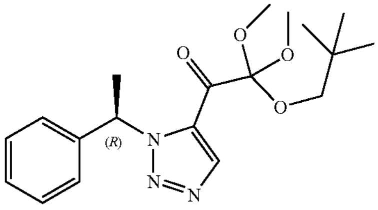
-continued
Compound D47
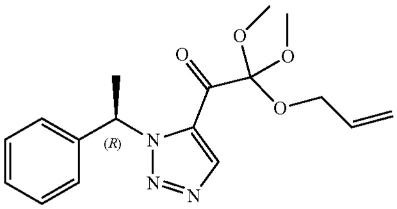
Compound D48
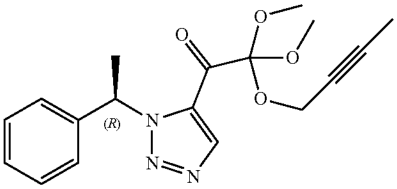
Compound D49
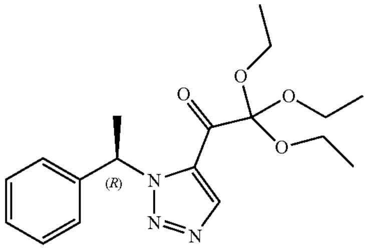
Compound D50
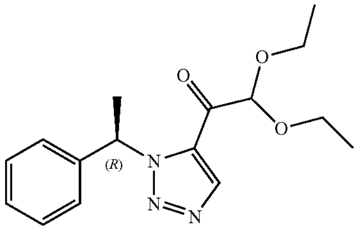
Compound D51
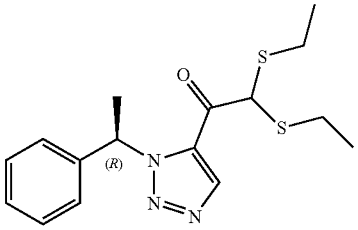
Compound D52
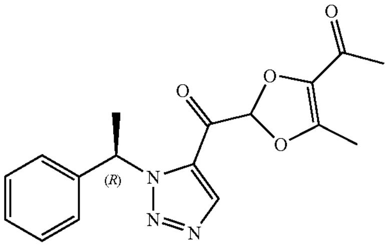

-continued
Compound D53
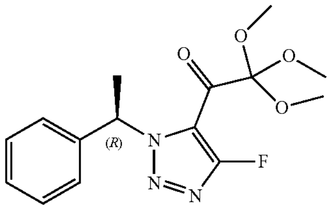
Compound D54
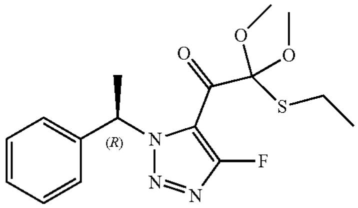
Compound D55
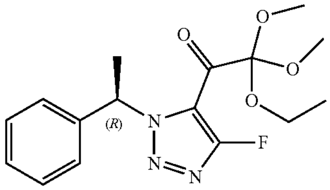
Compound D56
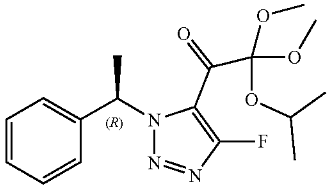
Compound D57
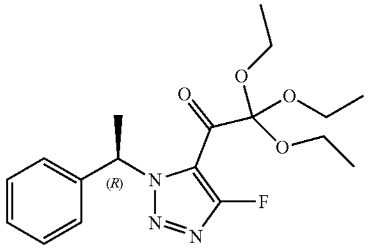
Compound D58
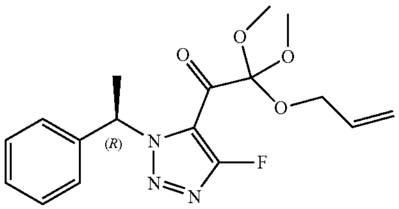
Compound D59
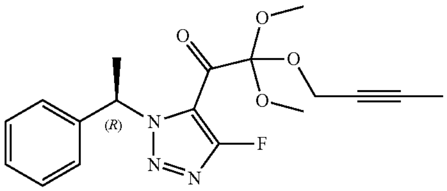
-continued
Compound D60
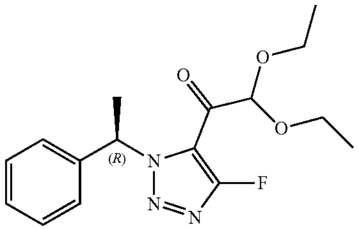
Compound D61
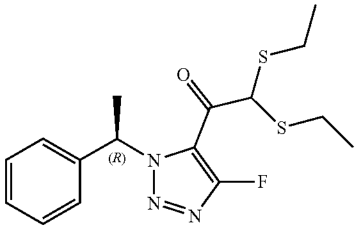
Compound D62
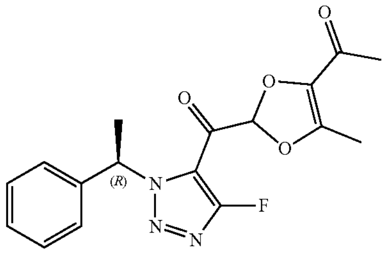
Compound D63
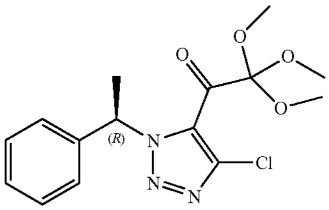
Compound D64
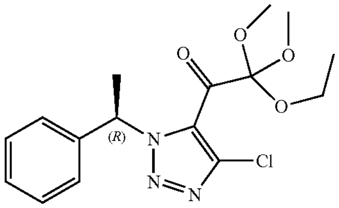
Compound D65
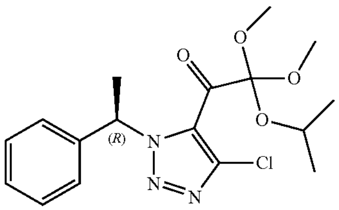
Compound D66
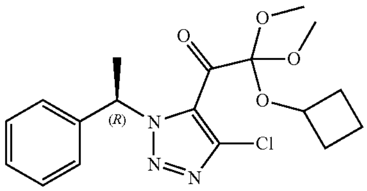

-continued
Compound D67
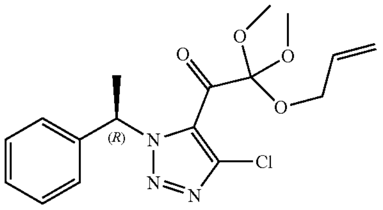
Compound D68
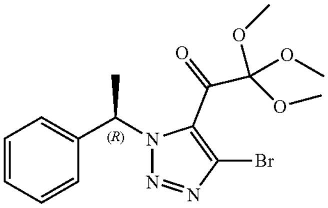
Compound D69
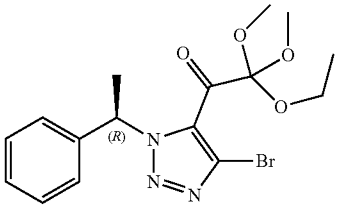
Compound D70
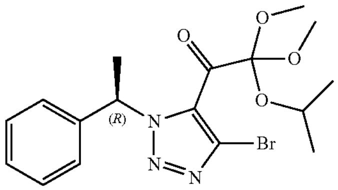
Compound D71
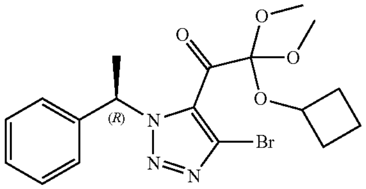
Compound D72
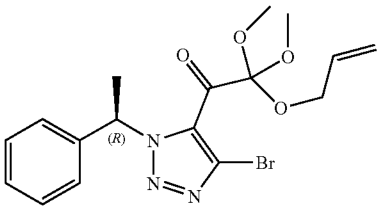
Compound D73
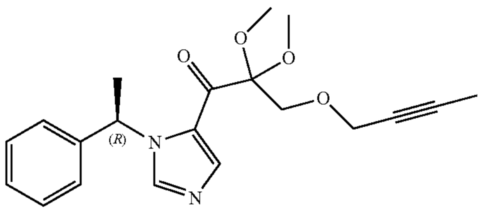
-continued
Compound D74
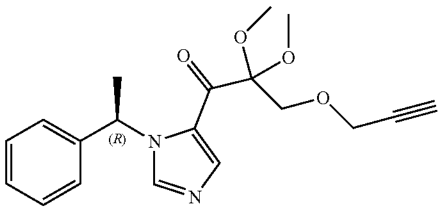
Compound D75
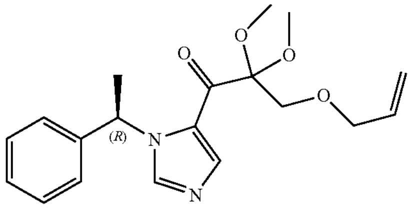
Compound D76
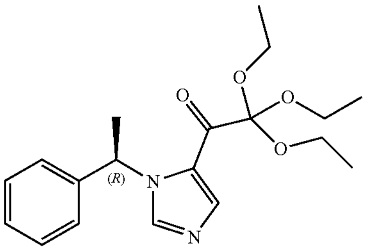
Compound D77
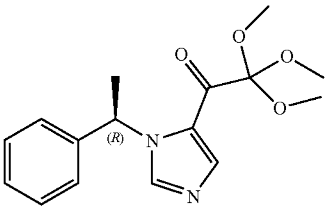
Compound D78
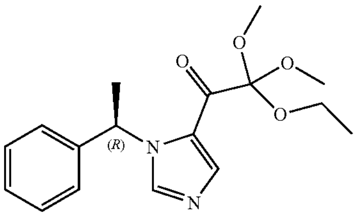
Compound D79
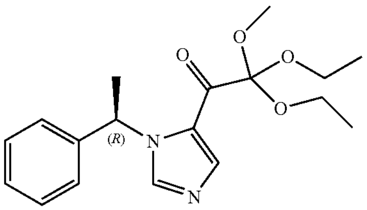
Compound D80
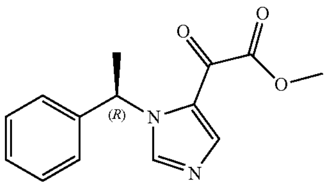

-continued
Compound D81
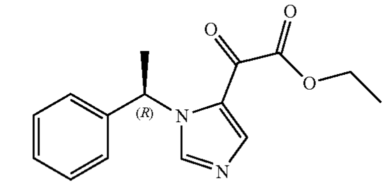
Compound D82
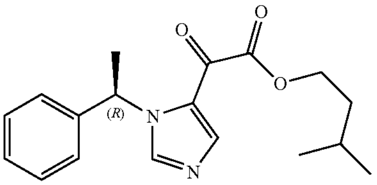
Compound D83
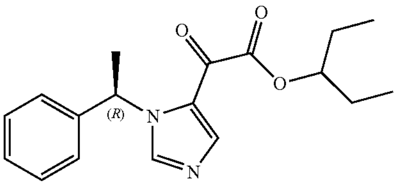
Compound D84
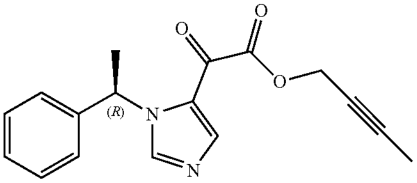
Compound D85
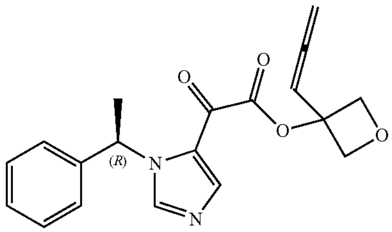
Compound D86
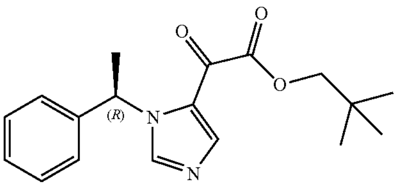
Compound D87
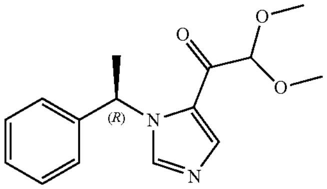
-continued
Compound D88
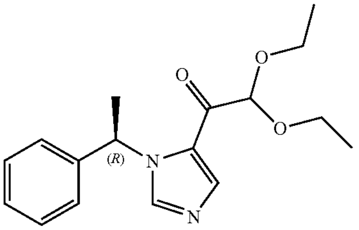
Compound D89
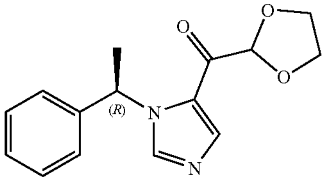
Compound D90
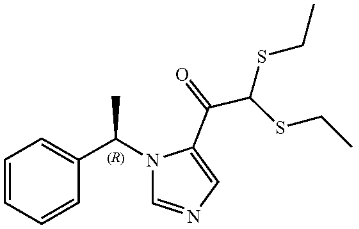
Compound D91
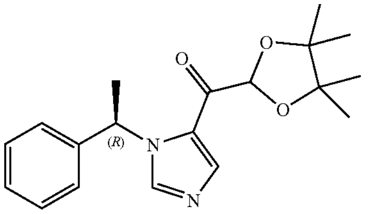
Compound D92
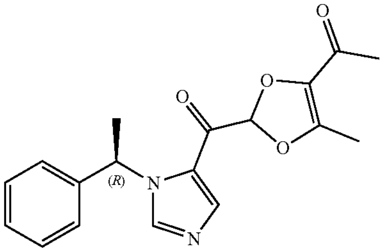
Compound D93
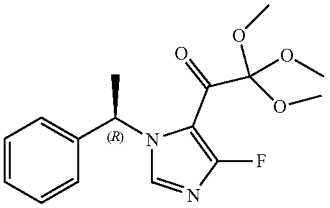
Compound D94
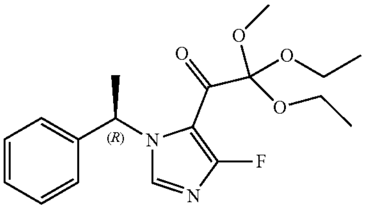

-continued
Compound D95
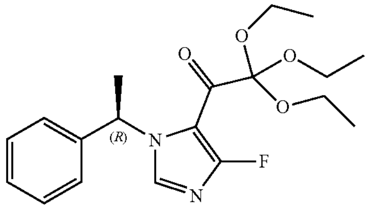
Compound D96
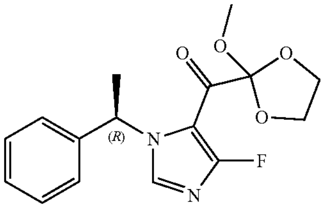
Compound D97
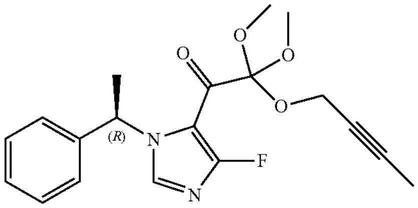
Compound D98
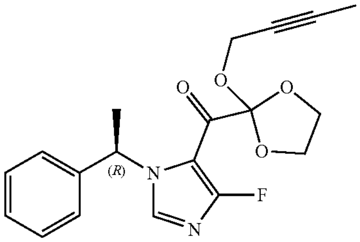
Compound D99
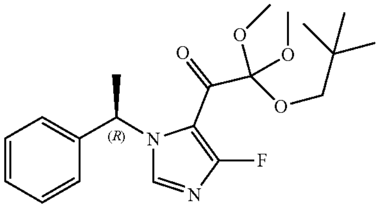
Compound D100
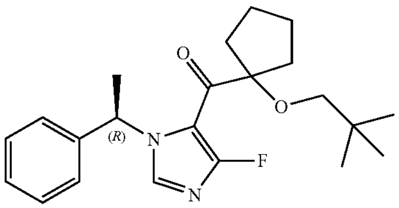
Compound D101
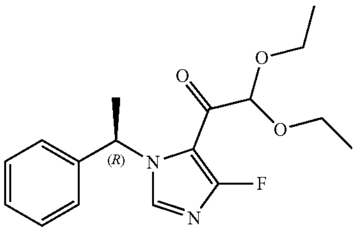
-continued
Compound D102
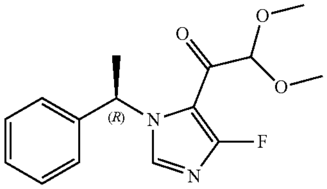
Compound D103
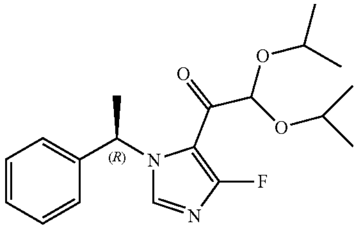
Compound D104
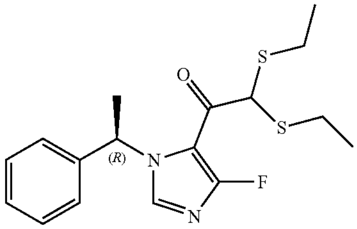
Compound D105
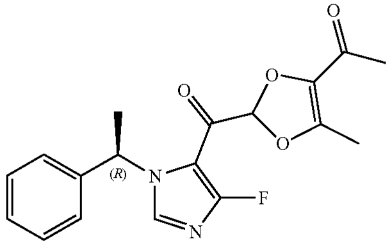
Compound D106
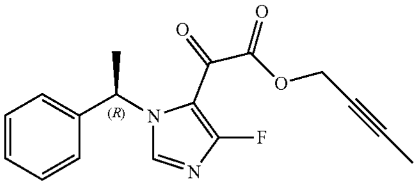
Compound D107
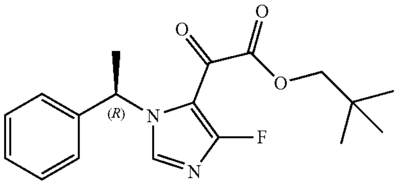
Compound D108
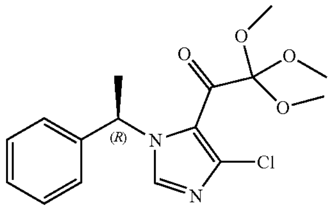

-continued
Compound D109
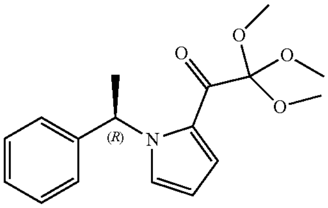
Compound D110
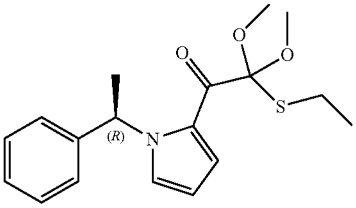
Compound D111
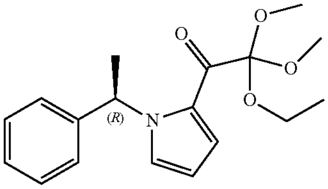
Compound D112
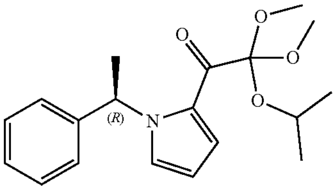
Compound D113
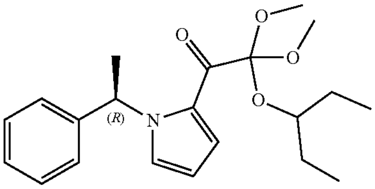
Compound D114
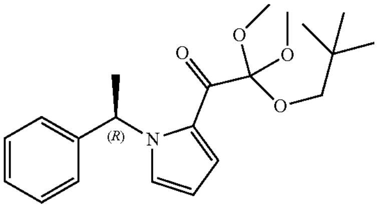
Compound D115
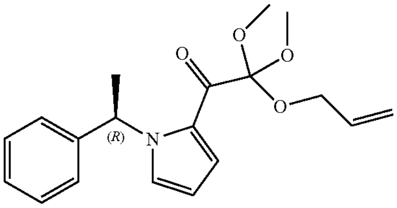
-continued
Compound D116
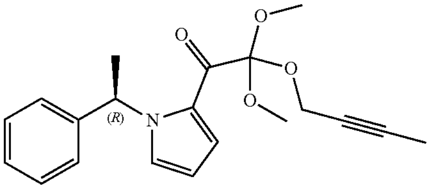
Compound D117
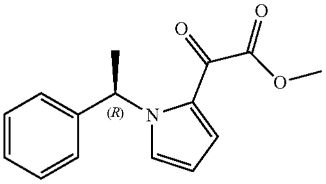
Compound D118
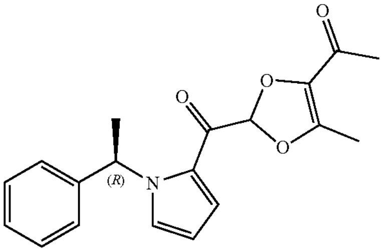
Compound D119
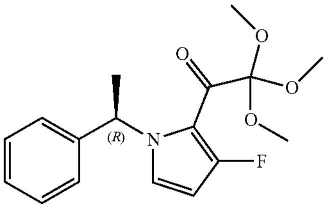
Compound D120
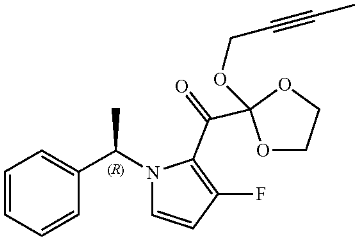
Compound D121
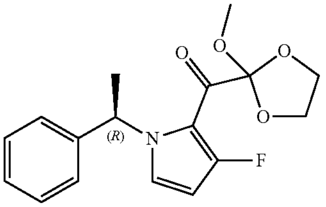
Compound D122
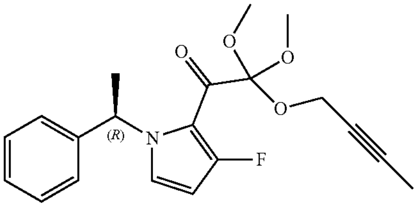

Compound D123
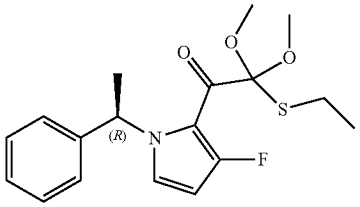
Compound D124
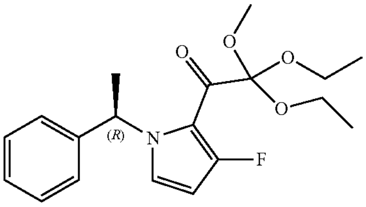
Compound D125
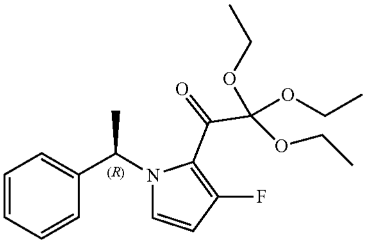
Compound D126
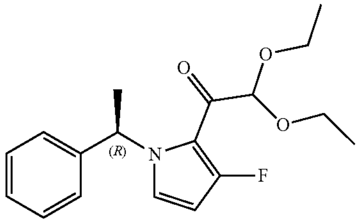
Compound D127
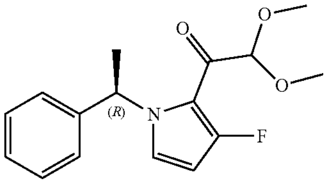
Compound D128
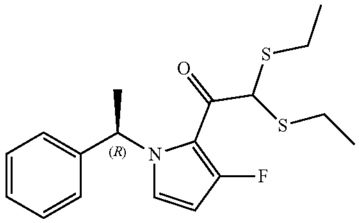
Compound D129
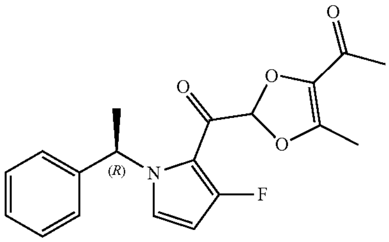
Compound D130
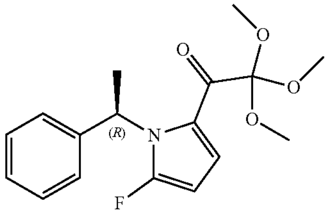
Compound D131
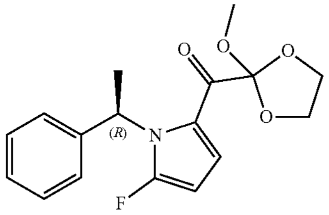
Compound D132
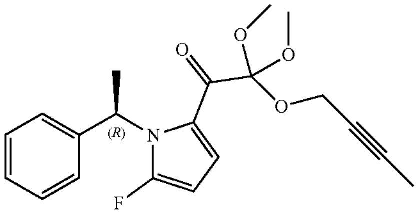
Compound D133
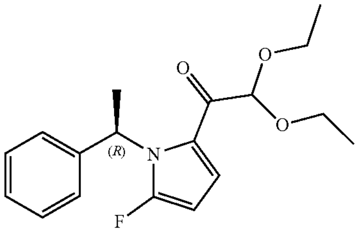
Compound D134
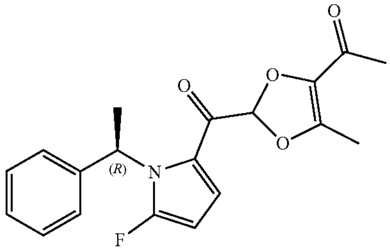
Compound D135
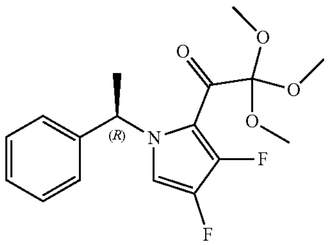

-continued

Compound D136

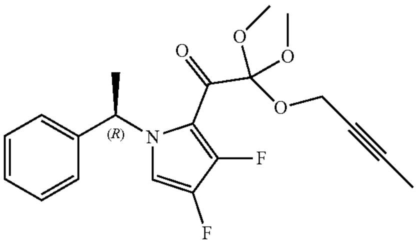

Compound D137

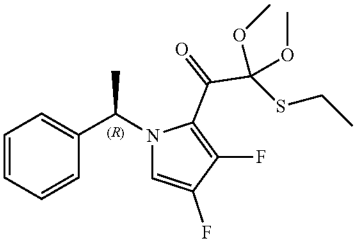

Compound D138

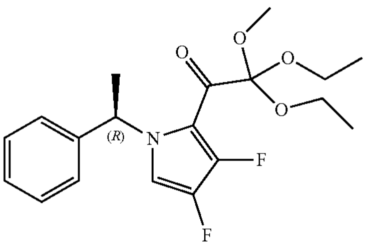

Compound D139

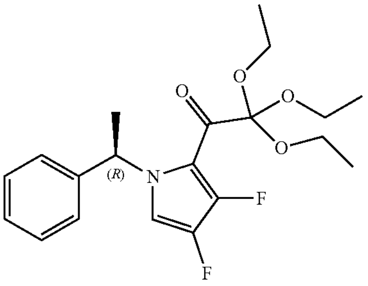

Compound D140

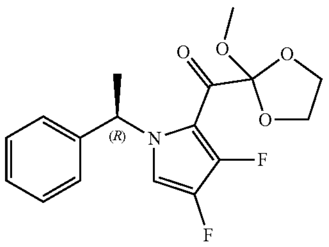

-continued

Compound D141

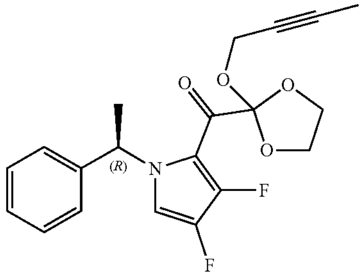

Compound D142

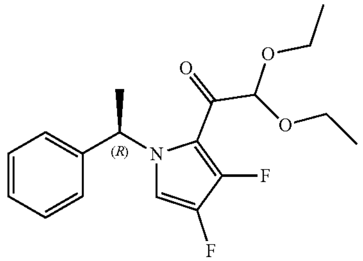

Compound D143

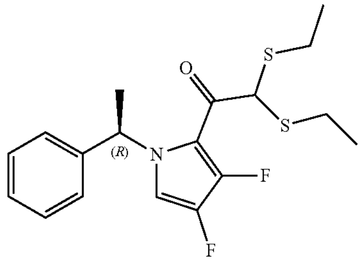

Compound D144

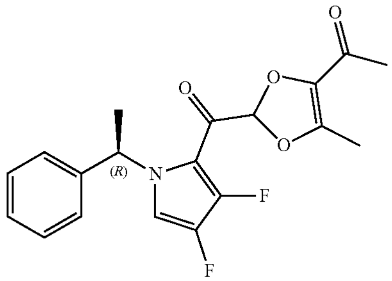

The present invention also provides a drug, it is prepared by anyone of the above compounds, or stereoisomers thereof, or pharmaceutically acceptable salts thereof, or solvates thereof, or prodrugs thereof, or metabolites thereof, or deuterated derivatives thereof, or their combinations as active ingredients, with addition of pharmaceutically acceptable excipients.

The present invention also provides the use of anyone of the above compounds, or stereoisomers thereof, or pharmaceutically acceptable salts thereof, or solvates thereof, or prodrugs thereof, or metabolites thereof, or deuterated derivatives thereof, or their combinations in preparation of drugs having sedative, hypnotic, and/or anesthetic effects and/or drugs that can be used to control epileptic status.

The said "sedative drug" in the present invention is a kind of drug that has a sedative effect and can effectively help sleep and improve sleep, and this drug can avoid the serious harm of insomnia to human body, treat insomnia and improve sleep quality.

The said "hypnotic drug" in the present invention denotes a drug that has a hypnotic effect, which can induce drowsiness and promote sleep. The drug has an effect of the central nervous system inhibition, and small dose causes sedation and excessive dose results in general anesthesia.

The said "anesthetic drug" in the present invention denotes a kind of drug that has a hypnotic effect, which can produce a reversible functional inhibition of the central nervous system and/or peripheral nervous system and this inhibition is mainly characterized by loss of sensation, especially sense of pain.

Preferably, the anesthesia is general anesthesia.

The "general anesthesia" mentioned in the present invention denotes that the anesthetics inside the vivo cause the temporary inhibition of central nervous system. The clinical manifestations are loss of consciouseness, disappearance of generalized sense of pain, amnesia, inhibitory reflex and skeletal muscle relaxation.

The compounds mentioned above, or stereoisomers thereof, or pharmaceutically acceptable salts thereof, or solvates thereof, or prodrugs thereof, or metabolites thereof are used in preparation of the drugs that could control the status epilepticus.

The "status epilepticus." mentioned in the present invention denotes the epilepsy frequently recurs without complete recovery of consciousness between successive seizures and or does not stop automatically after the seizure lasts for more than 30 minutes. Long-lasting seizure of epilepsy, if not be treated in time, would lead to irreversible brain injury due to high fever, circulatory failure or neuronal excitotoxic injury with high disability rate and mortality, so epilepsy is a common emergency in internal medicine.

The present invention provides a drug, that is prepared by using compounds mentioned above, or stereoisomers thereof, or pharmaceutically acceptable salts thereof, or solvates thereof, or prodrugs thereof, or metabolites thereof, or deuterated derivatives thereof as active ingredients, with addition of pharmaceutically acceptable excipients.

The compounds and derivatives provided in the present invention can be named according to IUPAC (International Union of Pure and Applied Chemistry) or CAS (Chemical Abstracting Service, Columbus, OH) naming system.

For the definition of term used in the present invention: unless otherwise specified, the initial definition provided for the group or the term herein is applicable to those in the whole specification; for terms not specifically defined herein, according to the disclosure content and the context, the term should have the meaning commonly given by those skilled in the field.

"Substitution" means that one or more hydrogen atoms in a molecule are replaced by other atoms or molecules that are not hydrogen, including one or more substitutions on the homotopic atoms or heterotopic atoms in the molecule.

The structures of the compounds mentioned in the present invention denote the stable existence structures.

"Deuterium" denotes the isotope of hydrogen (H), also known as heavy hydrogen, and the elemental symbol is generally D or 2H.

In the present invention, the structure of substituent "—$C(O)R^{32}$" is:

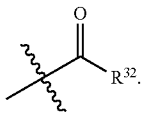

In the present invention, the structure of substituent "—$CO_2R^{32}$" is:

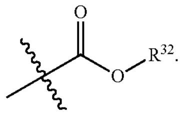

In the present invention, the structure of substituent "—$CON(R^{32})_2$" is:

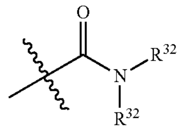

In the present invention, the structure of substituent "—$OC(O)R^{32}$" is:

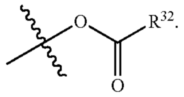

In the present invention, the structure of substituent "—$SO_2R^{32}$" is:

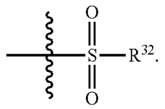

In the present invention, the structure of substituent "—$C(S)R^{34}$" is:

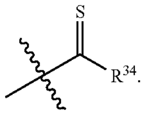

In the present invention, the structure of substituent "—$S(O)R^{34}$" is:

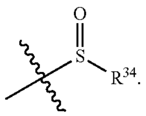

The minimum and the maximum number of carbon atoms in hydrocarbon groups are represented by prefixes, for example, the prefix ($C_a$~$C_b$) alkyls indicate any alkyls containing "a"~"b" carbon atoms. Therefore, for example, $C_1$~$C_8$ alkyls denote alkyls containing 1~8 carbon atoms. $C_1$~$C_8$ alkyls are linear or branched hydrocarbon chains containing 1~8 carbon atoms.

"Alkyls" is a hydrocarbon group formed by losing one hydrogen in an alkane molecule, such as methyl —$CH_3$, ethyl —$CH_3CH_2$, etc.

"Alkylenyls" denotes the hydrocarbon group formed by losing two hydrogens in the alkane molecule, such as methylene-$CH_2$—, ethylidene-$CH_2CH_2$—, etc. "$C_{1-8}$ alkylenyls" denotes a linear or branched hydrocarbon chain containing 1~8 carbon atoms.

"Substituted or unsubstituted $C_{1-8}$ alkyls" denotes $C_{1-8}$ alkyls that can be substituted or not be substituted.

When the ring A of the compounds in the present invention is

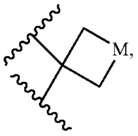

"  " indicate the separate linkage sites of $L^1$ and $L^2$ Similarly, when the ring A of the compounds in the present invention is

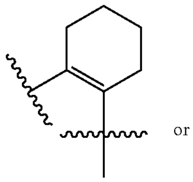

or

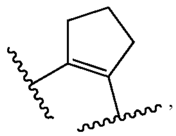

,

"  " indicate the separate linkage sites of $L^1$ and $L^2$.

"Ring A is none of" in the present invention denotes $L^1$ and $L^2$ are connected directly by chemical bonds.

"3~6-membered saturated carbocycles" in "ring A is 3~6-membered saturated carbocycles" mentioned in the present invention denotes a carbocycle consisting of 3~6 carbons, in which no double bond exists.

"3~6-membered unsaturated carbocycles" in "ring A is 3~6-membered unsaturated carbocycles" mentioned in the present invention denotes a carbocycle consisting of 3~6 carbons, in which double bond exists.

"3~6-membered saturated heterocycles" in "ring A is 3~6-membered saturated heterocycles" mentioned in the present invention denotes a saturated heterocycle without double bonds, in which there is at least one atom selected from O, S, or substituted N, and the remaining ring atoms are carbons.

"3~6-membered unsaturated heterocycles" in "ring A is 3~6-membered unsaturated heterocycles" mentioned in the present invention denotes a saturated heterocycle without double bonds, in which there is at least one atom selected from O, S, or substituted N, and the remaining ring atoms are carbons.

"Alkynyls" denotes aliphatic hydrocarbon groups with at least one CC triple bond. Said alkynyls can be linear or branched chain. When there is a limited carbon numbers before alkynyls (such as $C_{2-8}$ alkynyls), for example, the term "$C_{2-8}$ alkynyls" denotes a linear or branched alkynyls with 2-8 carbons.

"Alkenyls" denotes aliphatic hydrocarbon groups with at least one C═C double bond. Said alkenyls can be linear or branched chain. When there is a limited carbon numbers before alkenyls (such as $C_{2-8}$ alkenyls), for example, the term "$C_{2-8}$ alkenyls" denotes a linear or branched alkenyls with 2-8 carbons.

"dienyls" denotes aliphatic hydrocarbon groups with two double bonds among carbons. Said dienyls could be linear or branched chain. When there is a limited carbon numbers before "dienyls", for example, "$C_{3-6}$ dienyls" denotes a linear or branched dienyls with 3~6 carbons, such as the structures of "propadienyls" are

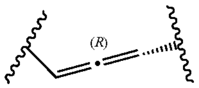

and/or

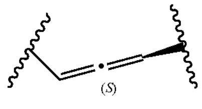

。

Halogen is fluorine, chlorine, bromine, or iodine.

"Aryls" denote all-carbon monocyclic or fused polycyclic (i.e. ring sharing adjacent carbon atom pairs) groups with conjugated π electron system, such as phenyl and naphthyl. Said aryl ring can be fused to other cyclic groups (including saturated and unsaturated rings), but can not contain hetero atoms such as nitrogen, oxygen, or sulfur. At the same time, the site connected with the parent must be on the carbon in the ring having the conjugated π electron system. Aryls can be substituted or unsubstituted.

"Heteroaryls" denote the heteroaromatic group containing one or more heteroatoms. The heteroatoms mentioned herein include oxygen, sulfur, and nitrogen. For example, furanyl, thienyl, pyridinyl, pyrazolyl, pyrrolyl, N-alkylpyrrolyl, pyrimidinyl, pyrazinyl, imidazolyl, tetrazolyl, etc. The heteroaromatic ring can be fused to aryls, heterocyclic group or cycloalkyl ring, in which the ring connected with the parent structure is heteroaromatic ring. Heteroaryls can be substituted or unsubstituted.

"Cycloalkyls" denote saturated or unsaturated cyclic hydrocarbon substituents; cyclic hydrocarbon can have one or more rings. For example, "$C_{3-8}$ cycloalkyls" denote cycloalkyls having 3~8 carbons. Heterocyclyls denotes saturated or unsaturated cyclic hydrocarbon substituents; cyclic hydrocarbon can have one or more rings with at least one heteroatom (including but not limited to O, S or N). For example, "$C_{3-8}$ heterocyclyls" denote saturated or unsaturated cyclic hydrocarbon substituents; cyclic hydrocarbon could be mono cyclic and poly cyclic containing at least one atom selected from O, S or substituted N, other ring atoms are carbons.

"$C_{1-4}$ alkyls, or halogenated or deuterated derivatives thereof" denotes $C_{1-4}$ alkyls, halogenated or deuterated $C_{1-4}$ alkyls. Other related terms "or halogenated or deuterated derivatives thereof" have the similar definition.

For all the compounds of the present invention, each chiral carbon atom (chiral center) can be optionally R-configurated or S-configurated, or a mixture of R-configuration and S-configuration.

"Pharmaceutically acceptable carriers" denote one or more compatible solid or liquid filling materials or gel substances, which are suitable for human use and must be of sufficient purity and low toxicity. "Compatibility" herein means that each component in the composition can be mixed with the compounds of the present invention without reducing the efficacy of the compounds obviously. Some examples of pharmaceutically acceptable carriers are cellulose and its derivatives (such as carboxymethylcellulose sodium, ethylcellulose sodium, cellulose acetate, etc.), gelatin, talcum, solid lubricants (such as stearic acid, magnesium stearate), calcium sulfate, vegetable oil (such as soybean oil, sesame oil, peanut oil, olive oil, etc.), polyols (such as propylene glycol, glycerin, mannitol, sorbitol, etc.), emulsifier (such as Tween®), wetting agent (such as sodium dodecyl sulfate), colorant, seasoning agent, stabilizer, antioxidant, preservative, pyrogen free water, etc.

The term "pharmaceutically acceptable salt" denotes the salt formed by the compounds of the present invention and pharmaceutically acceptable inorganic and organic acids, which is suitable for contacting the tissue of the object (e.g. human) without undue side effects. Among them, the preferred inorganic acids include (but not limited to) hydrochloric acid, hydrobromic acid, phosphoric acid, nitric acid, sulfuric acid; the preferred organic acids include (but not limited to) formic acid, acetic acid, propionic acid, succinic acid, naphthalene disulfonic acid (1,5), asiatic acid, oxalic acid, tartaric acid, lactic acid, salicylic acid, benzoic acid, valeric acid, diethylacetic acid, malonic acid, succinic acid, fumaric acid, pimelic acid, adipic acid, maleic acid, malic acid, sulfamic acid, phenylpropionic acid, gluconic acid, ascorbic acid, niacin, isoniacin, methanesulfonic acid, p-toluenesulfonic acid, citric acid, and amino acids.

The term "pharmaceutically acceptable solvate" denotes the solvate formed by the compounds of the present invention and pharmaceutically acceptable solvents, in which the pharmaceutically acceptable solvent includes (but not limited to) water, ethanol, methanol, isopropanol, propylene glycol, tetrahydrofuran, and dichloromethane.

As used herein, the term "pharmaceutically acceptable stereoisomer" means that the chiral carbon atom involved in the compounds of the present invention may be R-configuration, S-configuration, or a combination thereof.

The compounds of the present invention or composition thereof, as well as the use method thereof:

The compounds of the present invention, and various crystal forms, pharmaceutically acceptable inorganic or organic salts, hydrates or solvates thereof, as well as the pharmaceutical composition containing the compounds of the present invention as the main active ingredients can be used for sedation, hypnosis and/or general anesthesia.

The compounds of the present invention can also be used for controlling epileptic persistent state and the like.

The pharmaceutical composition of the present invention includes a compound of the present invention or a pharmaceutically acceptable salt thereof within a safe and effective amount, as well as a pharmaceutically acceptable excipient or carrier thereof. The administration ways for the compound or pharmaceutical composition of the present invention include (but not limited to) intragastric, intraintestinal, extragastrointestinal (intravenous, intramuscular or subcutaneous), oral and various local administration.

The composition for extragastrointestinal injection (intravenous, intramuscular, subcutaneous) may contain physiologically acceptable sterile aqueous or anhydrous solutions, dispersions, suspensions or emulsions, and sterile powder used for reconstitution into sterile injectable solutions or dispersions. Suitable aqueous and non-aqueous carriers, diluents, solvents or excipients include water, ethanol, polyols and their suitable mixtures.

Solid dosage forms for oral administration include capsules, tablets, pills, powders and granules. In these solid dosage forms, the active compound is mixed with at least one conventional inert excipient (or carrier), such as sodium citrate or dicalcium phosphate, or mixed with following ingredients: (a) bulking agent or compatibilizer, such as starch, lactose, sucrose, glucose, mannitol and silicic acid; (b) binding agent, such as hydroxymethylcellulose, alginate, gelatin, polyvinylpyrrolidone, sucrose and gum arabic; (c) moisturing agent, such as glycerin; (d) disintegrating agent, such as agar, calcium carbonate, potato starch or cassava starch, alginate, some complex silicates, and sodium carbonate; (e) solvents, such as paraffin; (f) absorption accelerators, such as quaternary amine compounds; (g) wetting agents, such as cetyl alcohol and glycerin monostearate; (h) adsorbents, such as kaolin; and (i) lubricants, such as talc, calcium stearate, magnesium stearate, solid polyethylene glycol, sodium dodecyl sulfate, or mixtures thereof. In capsules, tablets and pills, the dosage form may also include buffers. The liquid dosage forms used for oral administration include pharmaceutically acceptable emulsion, solution, suspension, syrup or tincture. In addition to the active compounds, the liquid dosage form may comprise inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide and oil, especially cottonseed oil, peanut oil, corn germ oil, olive oil, castor oil and sesame oil or the mixture thereof, etc.

Solid dosage forms such as tablets, sugar pills, capsules, pills and granules can be prepared by coating and shell materials, such as casing and other materials known in the art. They may comprise an opaque agent, and the release of the active compound or compound in the composition may be delayed in a certain part of the digestive tract.

Examples of embedding components that can be used are polymers and waxes. If necessary, the active compound may also form a microcapsule form with one or more of above excipients.

The dosage form of the compound of the present invention for local administration includes ointment, powder, patch, spray and inhalant. The active ingredient is mixed in sterile conditions with a biologically acceptable carrier and any preservatives, buffers, or propellants that may be required if necessary.

Except for these inert diluents, the composition may also include auxiliaries such as wetting agents, emulsifiers and suspensions, sweeteners, flavoring agents and perfumes.

Except for the active compounds, the suspension may contain a suspending agent, such as ethoxylated isooctadecanol, polyoxyethylene sorbitol and dehydrated sorbitol ester, microcrystalline cellulose, aluminum methoxide and agar or the mixture thereof, etc.

The compound of the present invention can be administered alone or in combination with other pharmaceutically acceptable compounds.

When the pharmaceutical composition is used, the safe and effective amount of the compound of the present invention is administrated to the mammal (such as human) in need thereof, in which the dosage is the pharmaceutically acceptable safe and effective dosage.

When the pharmaceutical composition is used, the safe and effective amount of the compound of the present invention is administrated to the mammal (such as human) that need to be treated, in which the pharmaceutically effective dosage is given. For the person with 60 kg body weight, the daily dosage is usually 1-2000 mg, preferably 5-500 mg. Of course, the specific dose should be adjusted dependent on the route of administration, the health status of patients and other factors, that are all within the scope of technical skill of practical physicians.

Said "room temperature" of the present invention is 25±5° C.

Said "overnight" of the present invention is 12±1 hours.

Said "1N HCl" of the invention is 1 mol/L HCl.

The experimental results show that the present invention of substituted nitrogen heterocyclic compounds have better depressant effects on the central nervous system and produce sedative, hypnotic and/or anesthetic action as well as control of epilepsy persistence; The substituted nitrogen heterocyclic compounds not only maintain excellent anesthetic activity, but also has the characteristics of rapid onset and rapid recovery; At the same time, the substituted nitrogen heterocyclic compounds have almost no inhibitory effect on the function of adrenal cortex and has little side effects, which solves the technical problems in the field. The present invention provides a new choice for clinically screening and/or preparing sedative, hypnotic and/or general anesthesia drugs and drugs for controlling status epilepticus.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

Compound B21: 251 s (4.19 min); Compound B36: 214 s (3.57 min); Compound B51: 132 s (2.20 min); Compound B80: 203 s (3.39 min); Compound B99: 127 s (2.12 min); Compound B108: 100 s (1.63 min); Compound B127: 116 s (1.93 min).

Figure 10:
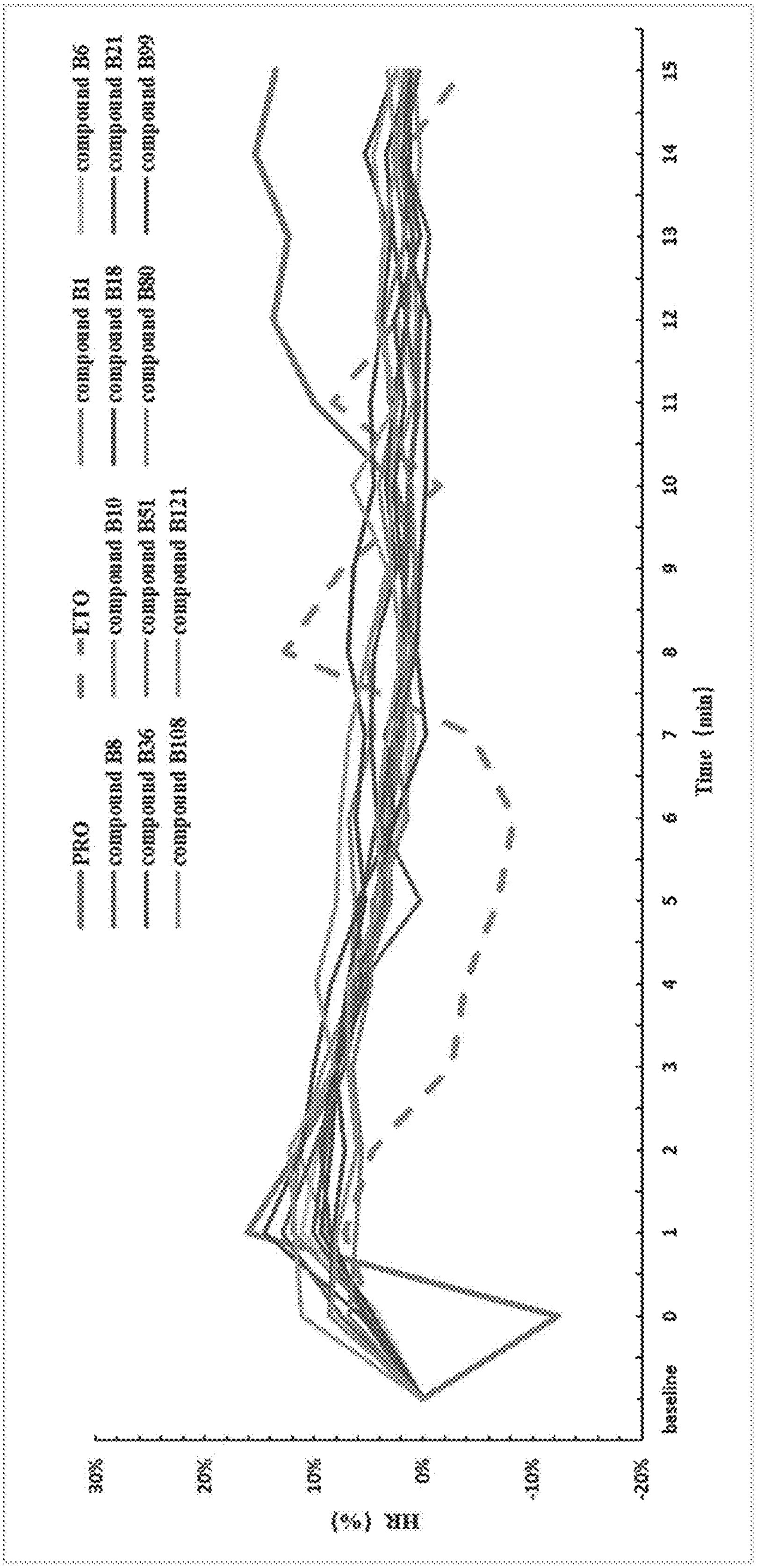

FIG. 10: Effects (rate of change) of the compounds of the present invention on heart rate (HR). Notes: (1) All the test animals' righting reflex disappeared within 1 min after the administration; (2) The 0 min on the abscissa in the figure represents the end of administration; (3) The recovery time of the test animals' righting reflex for compounds or drugs were PRO: 645 s (10.75 min); ETO: 440 s (7.33 min); Compound B1: 120.6 s (2.01 min); Compound B6: 133 s (2.22 min); Compound B8: 139 s (2.32 min); Compound B10: 80 s (1.34 min); Compound B18: 186 s (3.10 min); Compound B21: 251 s (4.19 min); Compound B36: 214 s (3.57 min); Compound B51: 132 s (2.20 min); Compound B80: 203 s (3.39 min); Compound B99: 127 s (2.12 min); Compound B108: 100 s (1.63 min); Compound B127: 116 s (1.93 min).

Figure 11:
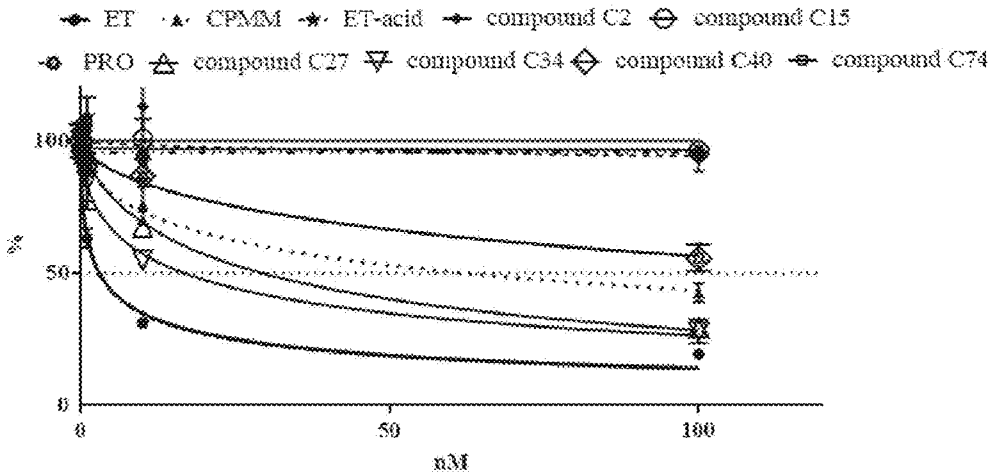
Figure 11:
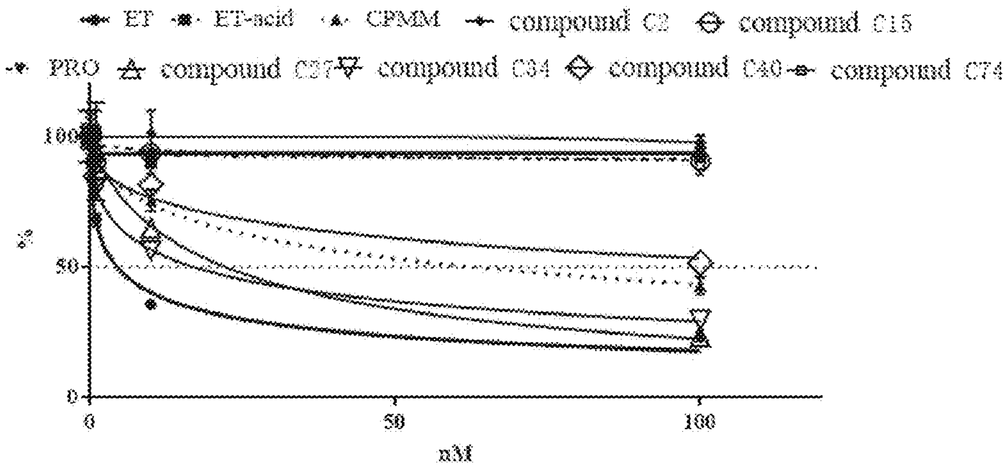

FIG. 11 shows the compound effect the invention on the function of adrenal cortex.

Figure 12:
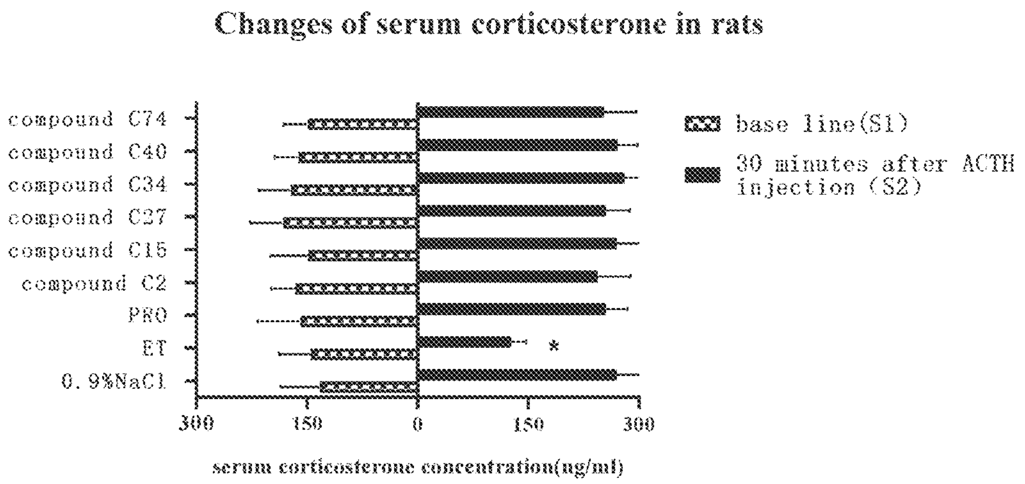

FIG. 12 shows the compound effect the invention on the function of adrenal cortex. Notes: "*" means that it is statistically significant compared with 0.9% NaCl group.

Figure 13:
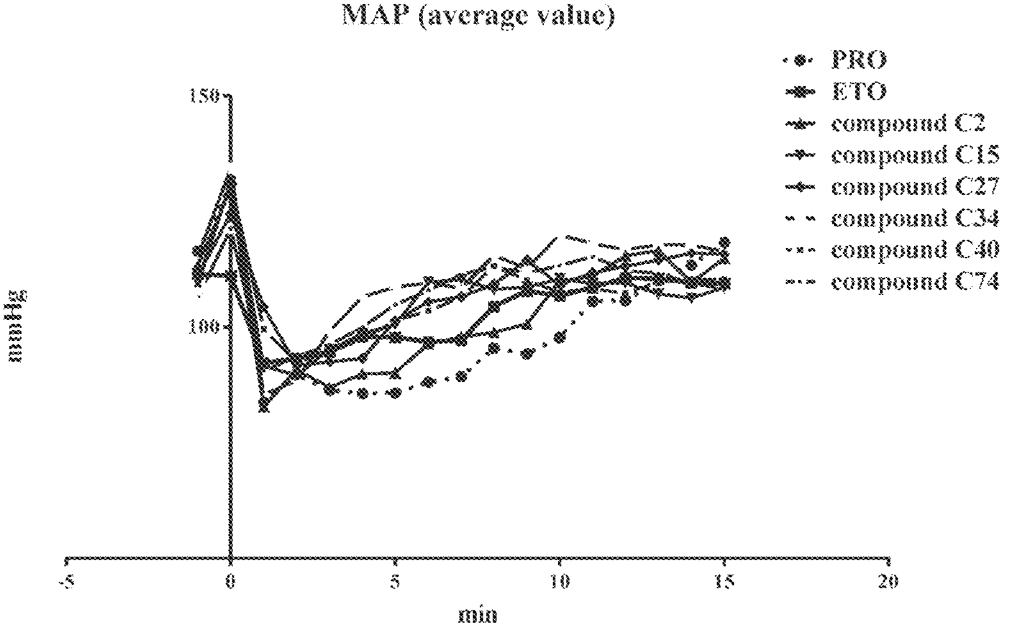

FIG. 13 shows the compound effect the invention on circulatory function of rats (MAP)

Figure 14:
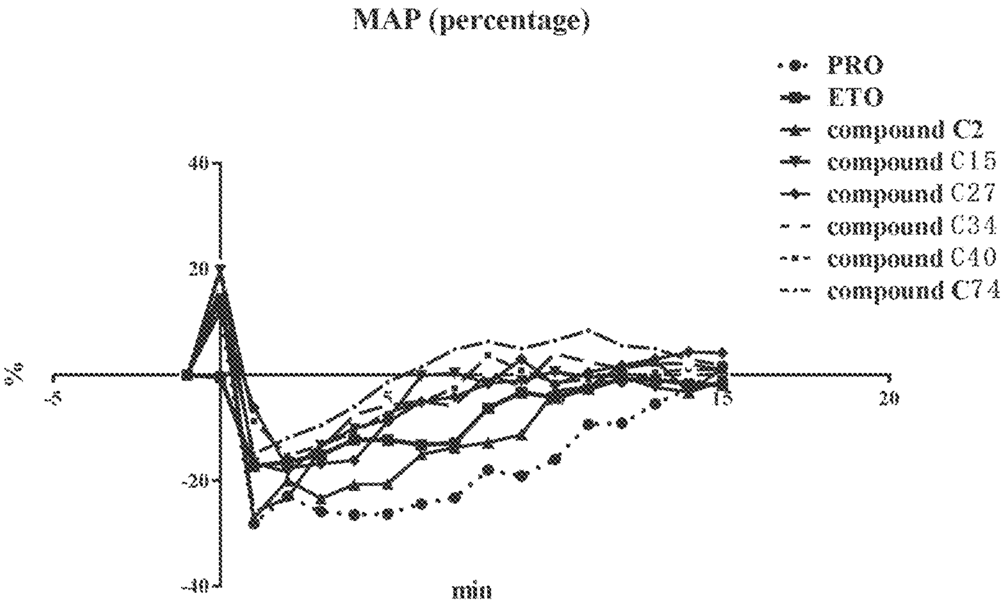

FIG. 14 shows the compound effect the invention on circulatory function of rats (MAP,%).

Figure 15:
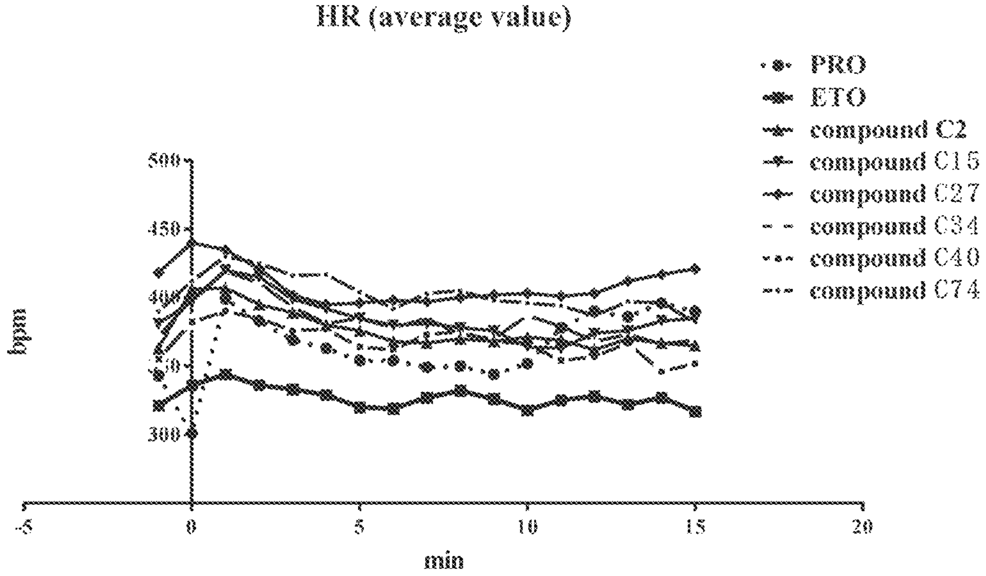

FIG. 15 shows effect of the compound of which the invention on circulatory function of rats (HR).

FIG. 16 shows effect of the compound of which the invention on circulatory function of rats (HR, %).

Figure 17:
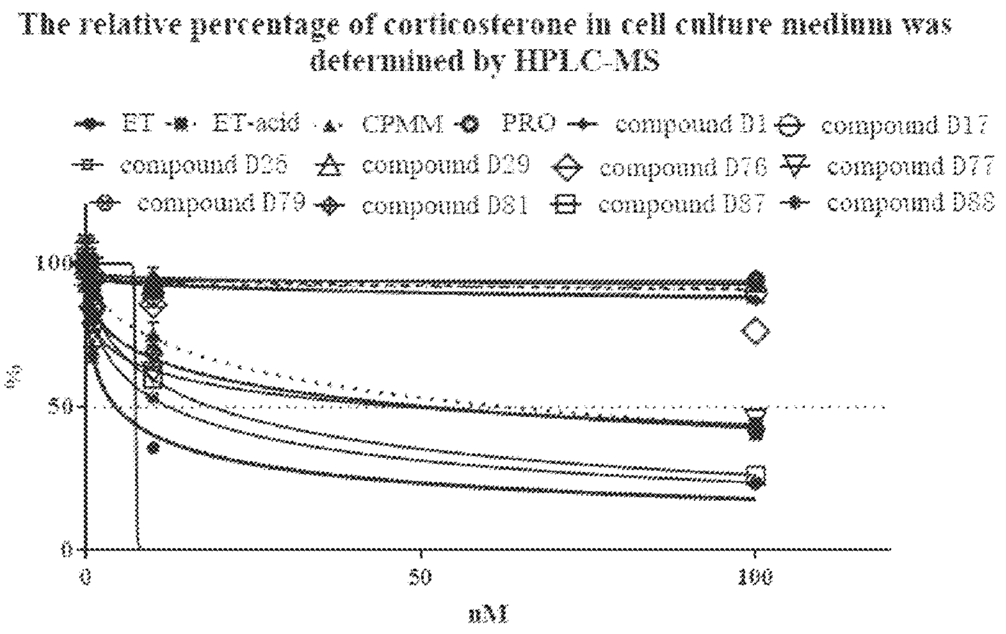

FIG. 17 shows the effect of the compound of the invention on the function of adrenal cortex in vitro.

Figure 18:
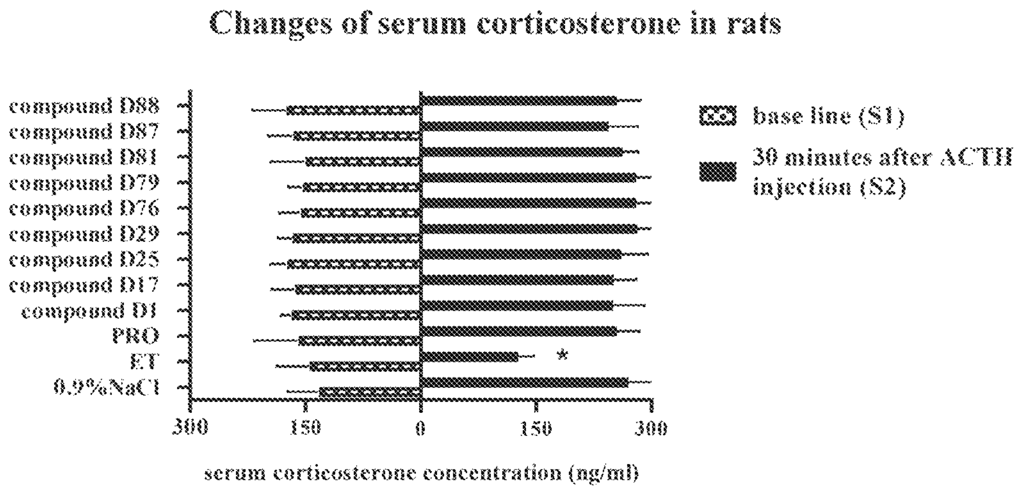

FIG. 18 shows Compound Effect on the function of adrenal cortex in rats; Note: * indicates that it is statistically significant compared with 0.9% NaCl group.

Figure 19:
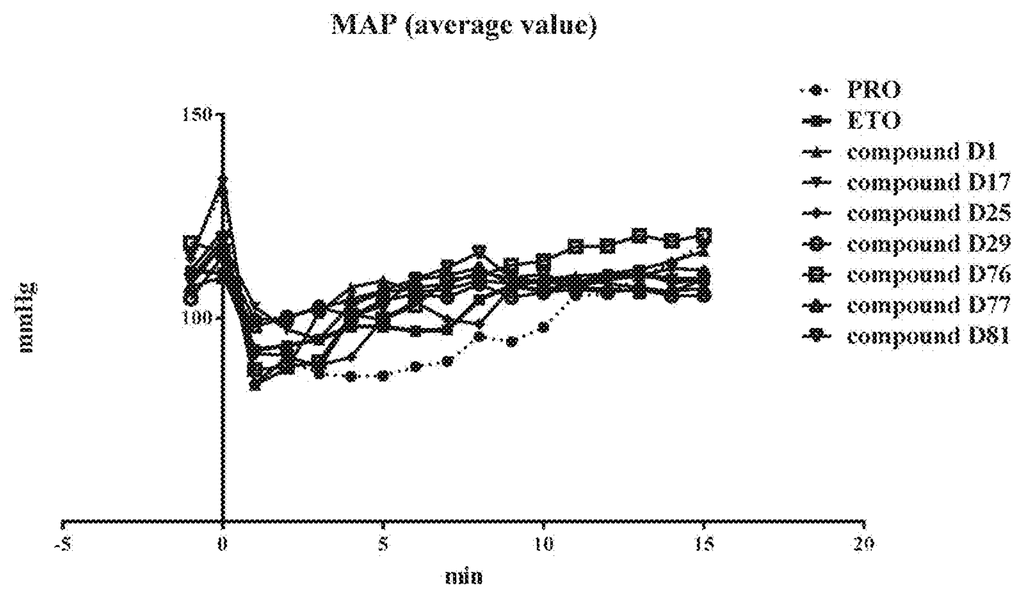

FIG. 19 shows the compound effect the invention on circulatory function of rats (MAP).

Figure 20:
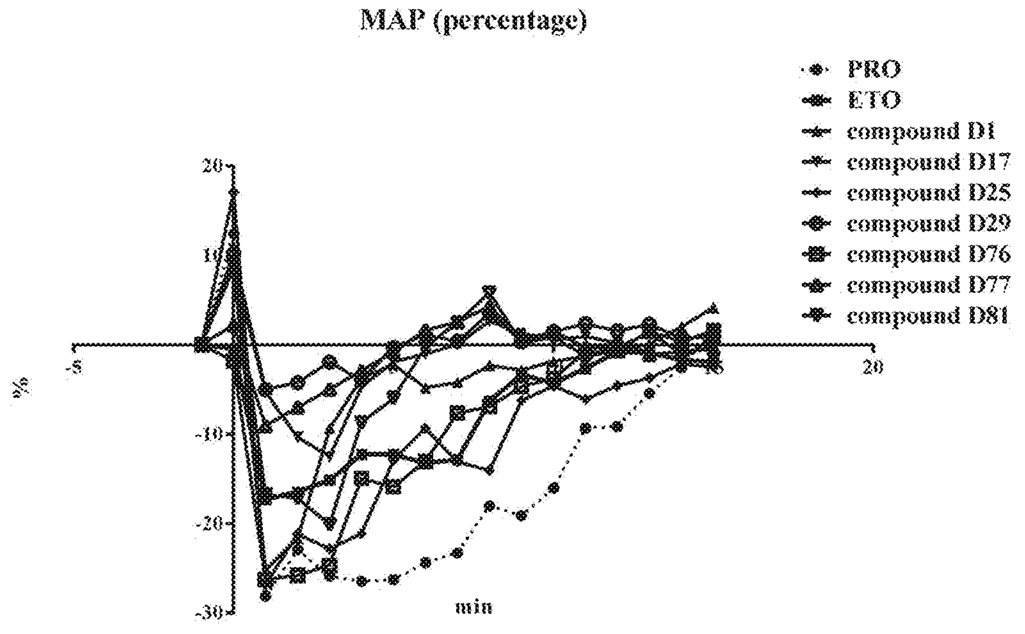

FIG. 20 shows the compound effect the invention on circulatory function of rats (MAP,%).

Figure 21:
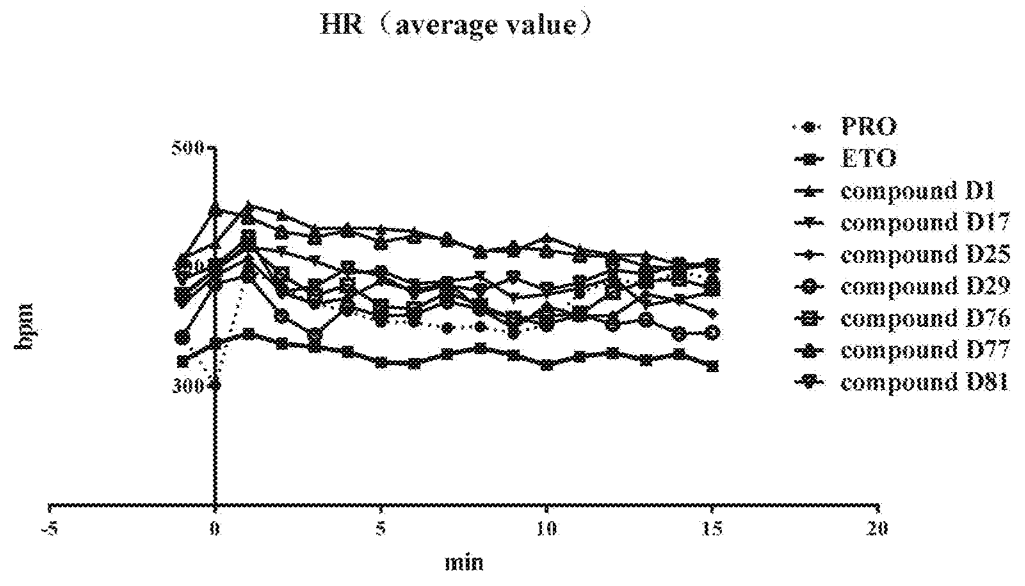

FIG. 21 shows effect of the compound of which the invention on circulatory function of rats (HR).

Figure 22:
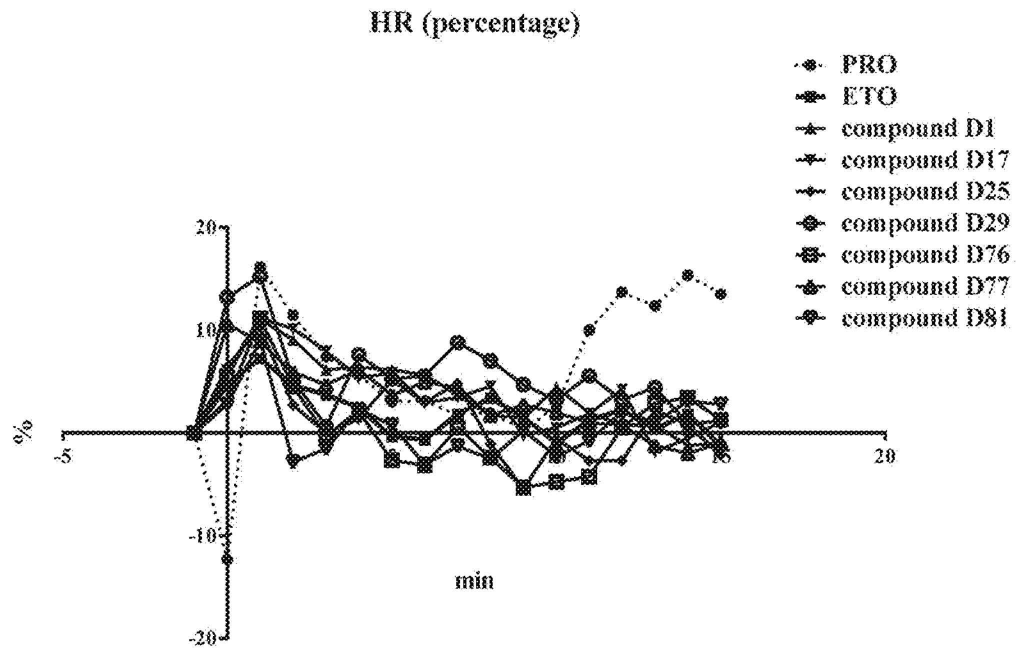

FIG. 22 shows effect of the compound of which the invention on circulatory function of rats (HR, %).

EXAMPLES

All starting materials and equipments used in the present invention were known products, acquired by purchasing commercially available products.

The structures of the compounds were confirmed by $^1$H NMR and/or MS spectra. NMR spectra were recorded on a Bruker NMR 400 Avance III spectrometer, using $d_6$-DMSO, $CDCl_3$ or $CD_3OD$ as deuterated solvent. NMR Chemical shift (δ) was given in part per million (ppm) relative to the internal standard of tetramethylsilane (TMS).

Agilent LCMS 1260-6110 (ESI) was used in the present invention. Column: Waters X-Bridge C18 (50 mm×4.6 mm×3.5 μm). Column temperature: 40° C.; Flow rate: 2.0 mL/min; Chromatographic analysis was performed in gradient mode. The mobile phases were composed of 0.05% TFA in water (A) and 0.05% TFA in Acetonitrile (B). A gradient elution was applied from 95% A and 5% B to 0% A and 100% B within 3 mins, then extended for another 1 min, and at end changed back to 95% A and 5% B within 0.05 mins and kept eluting for another 0.7 mins 1) Materials and Reagents The silica gel plate (HSGF254) for thin layer chromatography was bought from Yantai Xinnuo Chemical Co., Ltd, with the thickness of 1 mm Thin layer chromatography (TLC) was bought from Yantai Jiangyou silicone Development Co., Ltd., with the thickness of 0.2±0.03 mm Silica gel used for column chromatography was mostly made by Rushan Sun Desiccant Co., Ltd. (Weihai, Shandong) with 100-200 meshes or 200-300 meshes.

2) The Main Instruments

Electronic Balance JA2003N (manufactured by Shanghai Yoke Instrument Co., Ltd);

Magnetic Stirrer (model: 98-2, manufactured by Shanghai Sile Instrument Co., Ltd);

Contact Voltage Regulator (manufacturer: Zhejiang Tianzheng Electric Co., Ltd);

Temperature Controller (made by Shanghai Lulin Electric Co., Ltd);

Three-function Ultraviolet Analysis (model: ZF-2, manufactured by Shanghai Anting Electronic Instrument Factory);

Rotary Evaporator R-201 (manufactured by Shanghai Shenshun Biological Technology Co., Ltd)

Constant Temperature Water Bath (model: W201D, manufactured by Shanghai Shenshun Biological Technology Co., Ltd).

Circulating Water Vacuum Pump SHB-III (manufactured by Zhengzhou Huicheng Technology Industry and Trade Co., Ltd).

Mobile Water Pump SHB—B95 (manufactured by Zhengzhou Huicheng Technology Industry and Trade Co., Ltd).

Low-temperature Cooling Liquid Circulating Pump (manufactured by Gongyi Yuhua Instrument Co., Ltd).

Rotary Vane Vacuum Pump (manufactured by Linhai Yonghao Vacuum Equipment Co., Ltd).

Ultraviolet High-pressure Mercury Lamp (manufactured by Beijing Tianmai Henghui Lamp-house Electric Appliances Co., Ltd).

General Procedure A:

At room temperature, R-1-(1-phenethyl)-1H-pyrazole-5-carboxylic acid/R-1-(1-phenethyl)-1H-triazole-5-carboxylic acid or its derivatized acids (1 eq), DCC (1.5 eq) and DMAP (1.5 eq) were dissolved in dichloromethane. After stirring 5 min, Alcohol or Thiol was added dropwise into above mixture using a syringe and the mixture was stirred at room temperature overnight. The reaction was monitored by TLC until completion, then it was concentrated under reduced pressure. Methyl tert-butyl ether was added into the residue and stirred, filtered, the filter cake was washed with methyl tert-butyl ether, the filtrate was concentrated under reduced pressure. The residue was purified by silica gel column chromatography or Prep-TLC to give the desired product. The following are the specific preparation methods for the four groups (A, B, C, D) target compounds of the present invention.

Examples of Group A compounds are as follows:

Example 1 Preparation of Compounds A1 and A2

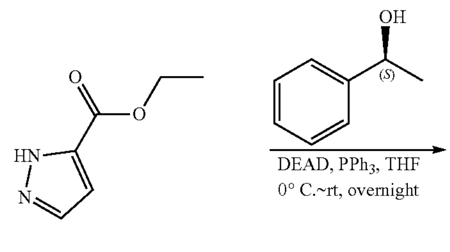

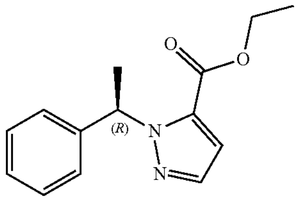

Compound A1

+

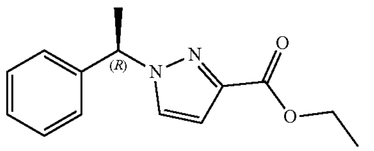

Compound A2

In an ice-water bath, DEAD (3.7 g, 21.2 mmol) in THF (10 mL) was added dropwise into a solution of S-1-phenylethan-1-ol (2.3 g, 18.8 mmol), ethyl 1H-pyrazole-5-carboxylate (6.78 g, 25.5 mmol) and $PPh_3$ (5.6 g, 21.4 mmol) in the THF (50 mL) at 0° C. at the rate of 1 mmol/min, then the mixture was warmed slowly to room temperature and stirred at this temperature overnight. The reaction was monitored by TLC until completion, then it was quenched with the saturated brine (50 mL) and extracted with ethyl acetate (3×15 mL). The combined organic layers were washed with saturated brine (30 mL), dried over anhydrous sodium sulfate, filtered and concentrated under reduced pressure to give crude product. The residue was purified by silica gel column chromatography (ethyl acetate/petroleum ether (v/v)=1/20~1/10) and the eluate was monitored by TLC (ethyl acetate/petroleum ether (v/v)=1/2). The fraction with Rf=0.5~0.6 was collected and dried to give products A1 (610 mg, yield 18%) and A2 (91 mg, yield 3%).

The compound A1: ESI$[M+H]^+$=245.1

$^1$H NMR (400 MHz, $CDCl_3$) δ 7.57 (d, J=1.9 Hz, 1H), 7.33-7.27 (m, 4H), 7.25-7.18 (m, 1H), 6.86 (d, J=2.0 Hz, 1H), 6.59 (q, J=7.1 Hz, 1H), 4.42-4.16 (m, 2H), 1.92 (d, J=7.1 Hz, 3H), 1.33 (t, J=7.1 Hz, 3H).

The compound A2: ESI$[M+H]^+$=245.1

$^1$H NMR (400 MHz, $CDCl_3$) δ 7.39-7.28 (m, 4H), 7.25-7.20 (m, 2H), 6.81 (d, J=2.4 Hz, 1H), 5.68 (q, J=7.1 Hz, 1H), 4.41 (q, J=7.1 Hz, 2H), 1.92 (d, J=7.1 Hz, 3H), 1.40 (t, J=7.1 Hz, 3H).

Example 2 Preparation of Compounds A3~A48

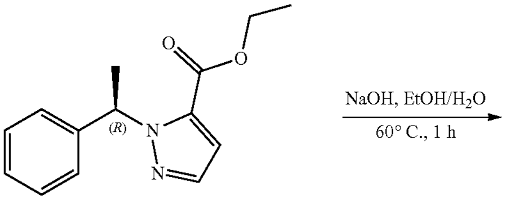

Compound A1

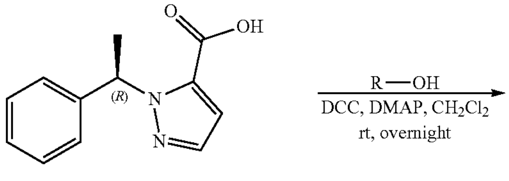

A

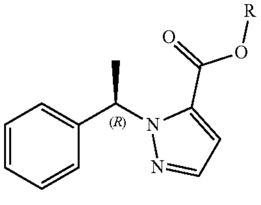

Compound A3~A48

1. Preparation of (R)-1-(1-phenylethyl)-1H-pyrazole-5-carboxylic acid (A)

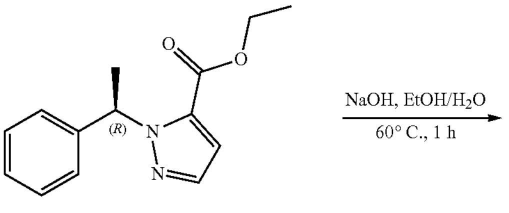

Compound A1

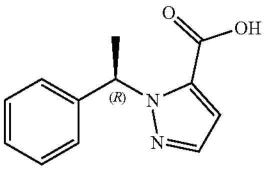

A

At room temperature, NaOH (3.1 g, 77.5 mmol) and A1 (9.5 g, 38.9 mmol) were dissolved in EtOH/$H_2O$ (25 mL, 1/1), and then it was stirred at 60° C. for 1 hour. The reaction was monitored by TLC until completion, the mixture was concentrated under reduced pressure, cooled and adjusted pH to 4~5 with 1 N HCl solution, then it was extracted with dichloromethane (3×15 mL). The combined organic layers were dried over anhydrous sodium sulfate, filtered and concentrated under reduced pressure to give compound A (6.7 g, yield 80%). ESI$[M+H]^+$=217.1

$^1$H NMR (400 MHz, $CDCl_3$) δ 7.62 (d, J=2.0 Hz, 1H), 7.39-7.16 (m, 5H), 7.00 (d, J=2.0 Hz, 1H), 6.56 (q, J=7.0 Hz, 1H), 1.93 (d, J=7.1 Hz, 3H).

2. Preparation of Compounds A3~A48

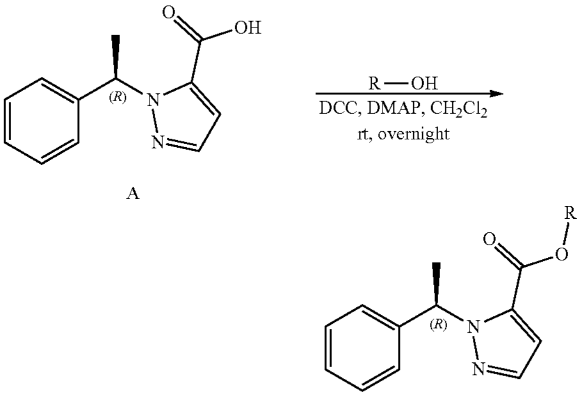

A

Compound A3~A48

The target compounds A3~A48 were prepared according to the general procedure A, using A (100 mg, 0.41 mmol) and corresponding alcohol (0.61 mmol) as starting materials. The crude product was purified by Prep-TLC (ethyl acetate/petroleum ether (v/v)=1/5) and the fraction with Rf=0.4~0.6 was collected and dried to give target compounds as colorless oil.

The compound A3: 104 mg, ESI[M+H]$^+$=271.1

$^1$H NMR (400 MHz, $CDCl_3$) δ 7.57 (d, J=1.8 Hz, 1H), 7.33-7.27 (m, 4H), 7.25-7.19 (m, 1H), 6.90 (d, J=1.9 Hz, 1H), 6.59 (q, J=7.0 Hz, 1H), 4.18-3.94 (m, 2H), 1.92 (d, J=7.1 Hz, 3H), 1.26-1.09 (m, 1H), 0.66-0.48 (m, 2H), 0.40-0.21 (m, 2H).

The compound A4: 28 mg, ESI[M+H]$^+$=271.1

$^1$H NMR (400 MHz, $CDCl_3$) δ 7.56 (s, 1H), 7.31-7.27 (m, 4H), 7.25-7.20 (m, 1H), 6.87 (s, 1H), 6.67-6.51 (m, 1H), 5.20-5.05 (m, 1H), 2.49-2.31 (m, 2H), 2.22-2.02 (m, 2H), 1.91 (d, J=7.0 Hz, 3H), 1.88-1.78 (m, 1H), 1.75-1.59 (m, 1H).

The compound A5: 65 mg, ESI[M+H]$^+$=273.1

$^1$H NMR (400 MHz, $CDCl_3$) δ 7.60 (d, J=1.9 Hz, 1H), 7.33-7.20 (m, 5H), 6.95 (d, J=1.9 Hz, 1H), 6.50 (q, J=7.1 Hz, 1H), 5.64-5.52 (m, 1H), 4.99-4.87 (m, 2H), 4.76-4.62 (m, 2H), 1.92 (d, J=7.1 Hz, 3H).

The compound A6: 46 mg, ESI[M+H]$^+$=289.0

$^1$H NMR (400 MHz, $CDCl_3$) δ 7.58 (d, J=1.9 Hz, 1H), 7.36-7.16 (m, 5H), 6.88 (d, J=1.9 Hz, 1H), 6.51 (q, J=7.0 Hz, 1H), 5.77 (p, J=8.0 Hz, 1H), 3.65-3.45 (m, 2H), 3.43-3.22 (m, 2H), 1.91 (d, J=7.1 Hz, 3H).

The compound A7: 83 mg, ESI[M+H]$^+$=273.1

$^1$H NMR (400 MHz, $CDCl_3$) δ 7.54 (s, 1H), 7.33-7.27 (m, 4H), 7.25-7.19 (m, 1H), 6.77 (s, 1H), 6.59 (q, J=7.1 Hz, 1H), 1.92 (d, J=7.0 Hz, 3H), 1.52 (s, 9H).

The compound A8: 36 mg, ESI[M+H]$^+$=315.1 $^1$H NMR (400 MHz, $CDCl_3$) δ 7.63 (d, J=1.8 Hz, 1H), 7.32-7.16 (m, 5H), 7.01 (d, J=1.8 Hz, 1H), 6.41 (q, J=7.0 Hz, 1H), 4.96 (dd, J=24.8, 7.7 Hz, 2H), 4.77 (dd, J=21.8, 7.7 Hz, 2H), 2.19 (s, 3H), 1.92 (d, J=7.0 Hz, 3H).

The compound A9: 27 mg, ESI[M+H]$^+$=299.1

$^1$H NMR (400 MHz, $CDCl_3$) δ 7.60 (s, 1H), 7.35-7.14 (m, 5H), 7.00 (d, J=1.6 Hz, 1H), 6.54 (q, J=7.0 Hz, 1H), 1.91 (d, J=7.1 Hz, 3H), 1.89 (s, 3H), 1.60-1.45 (m, 2H), 1.38-1.10 (m, 2H).

The compound A10: 113 mg, ESI[M+H]$^+$=311.0

$^1$H NMR (400 MHz, $CDCl_3$) δ 7.59 (s, 1H), 7.34-7.17 (m, 5H), 6.91 (d, J=1.4 Hz, 1H), 6.53 (q, J=7.0 Hz, 1H), 5.16-4.43 (m, 4H), 1.93 (d, J=7.0 Hz, 3H), 1.89 (s, 3H).

The compound A11: 69 mg, ESI[M+H]$^+$=283.0

$^1$H NMR (400 MHz, $CDCl_3$) δ 7.57 (s, 1H), 7.36-7.17 (m, 5H), 6.95-6.83 (m, 1H), 6.68-6.50 (m, 1H), 5.67-5.42 (m, 1H), 1.92 (d, J=7.0 Hz, 3H), 1.84 (dd, J=12.9, 2.1 Hz, 3H), 1.52 (t, J=6.6 Hz, 3H).

The compound A12: 52 mg, ESI[M+H]$^+$=297.1

$^1$H NMR (400 MHz, $CDCl_3$) δ 7.54 (s, 1H), 7.37-7.14 (m, 5H), 6.79 (s, 1H), 6.63 (q, J=6.9 Hz, 1H), 1.92 (d, J=7.0 Hz, 3H), 1.84 (s, 3H), 1.71 (s, 3H), 1.69 (s, 3H).

The compound A13: 86 mg, ESI[M+H]$^+$=283.1

$^1$H NMR (400 MHz, $CDCl_3$) δ 7.57 (s, 1H), 7.33-7.19 (m, 5H), 6.87 (t, 1H), 6.66-6.50 (m, 1H), 5.60-5.47 (m, 1H), 5.39-5.25 (m, 1H), 4.97-4.72 (m, 2H), 1.92 (d, J=7.1 Hz, 3H), 1.45-1.38 (m, 3H).

The compound A14: 21 mg, ESI[M+H]$^+$=297.1

$^1$H NMR (400 MHz, $CDCl_3$) δ 7.61 (d, J=1.7 Hz, 1H), 7.37-7.16 (m, 5H), 6.98-6.87 (m, 1H), 6.62-6.49 (m, 1H), 6.17-5.55 (m, 1H), 5.45-4.69 (m, 2H), 2.06-1.85 (m, 6H), 1.82-1.59 (m, 3H).

The compound A15: 79 mg, ESI[M+H]$^+$=295.1

$^1$H NMR (400 MHz, $CDCl_3$) δ 7.57 (t, J=1.7 Hz, 1H), 7.35-7.18 (m, 5H), 6.97-6.84 (m, 1H), 6.66-6.48 (m, 1H), 5.89-5.60 (m, 3H), 5.59-5.34 (m, 1H), 1.92 (d, J=7.1 Hz, 3H), 1.57 (t, J=6.5 Hz, 3H).

The compound A16: 66 mg, ESI[M+H]$^+$=309.1

$^1$H NMR (400 MHz, $CDCl_3$) δ 7.54 (s, 1H), 7.36-7.18 (m, 5H), 6.80 (s, 1H), 6.62 (q, J=7.0 Hz, 1H), 5.91-5.75 (m, 1H), 5.68-5.58 (m, 1H), 5.53-5.44 (m, 1H), 1.92 (d, J=7.0 Hz, 3H), 1.76 (s, 3H), 1.73 (s, 3H).

The compound A17: 90 mg, ESI[M+H]$^+$=339.1

$^1$H NMR (400 MHz, $CDCl_3$) δ 7.62 (d, J=1.5 Hz, 1H), 7.32-7.18 (m, 5H), 6.95 (d, J=1.3 Hz, 1H), 6.51 (q, J=6.9 Hz, 1H), 2.43-2.22 (m, 4H), 2.07 (s, 3H), 1.94 (d, J=7.1 Hz, 3H), 1.81-1.71 (m, 2H), 1.72-1.63 (m, 2H).

The compound A18: 56 mg, ESI[M+H]$^+$=325.0

$^1$H NMR (400 MHz, $CDCl_3$) δ 7.62 (d, J=1.3 Hz, 1H), 7.34-7.20 (m, 5H), 6.95 (d, J=1.2 Hz, 1H), 6.48 (q, J=7.0 Hz, 1H), 2.51-2.31 (m, 7H), 1.94 (d, J=7.0 Hz, 3H), 1.88-1.76 (m, 2H).

The compound A19: 8 mg, ESI[M+H]$^+$=325.0

$^1$H NMR (400 MHz, $CDCl_3$) δ 7.67-7.58 (m, 1H), 7.36-7.27 (m, 4H), 7.25-7.20 (m, 1H), 7.02-6.92 (m, 1H), 6.55-6.45 (m, 1H), 2.89-2.69 (m, 2H), 2.67-2.57 (m, 1H), 2.42-2.29 (m, 2H), 2.19 (s, 1H), 2.05-1.90 (m, 6H).

The compound A20: 61 mg, ESI[M+H]$^+$=341.0

$^1$H NMR (400 MHz, $CDCl_3$) δ 7.62 (s, 1H), 7.34-7.19 (m, 5H), 7.02 (s, 1H), 6.57-6.47 (m, 1H), 3.55 (s, 3H), 2.76-2.63 (m, 4H), 2.07-1.95 (m, 2H), 1.94 (d, J=7.0 Hz, 3H).

The compound A21: 94 mg, ESI[M+H]$^+$=287.1

$^1$H NMR (400 MHz, $CDCl_3$) δ 7.56 (s, 1H), 7.34-7.27 (m, 4H), 7.25-7.18 (m, 1H), 6.85 (s, 1H), 6.60 (q, J=6.5 Hz, 1H), 5.01-4.76 (m, 1H), 1.93 (d, J=6.9 Hz, 3H), 1.69-1.55 (m, 4H), 0.90 (t, J=7.4 Hz, 3H), 0.85 (t, J=7.4 Hz, 3H).

The compound A22: 102 mg, ESI[M+H]$^+$=297.1

$^1$H NMR (400 MHz, $CDCl_3$) δ 7.60 (d, J=2.0 Hz, 1H), 7.34-7.19 (m, 5H), 6.92 (d, J=2.0 Hz, 1H), 6.52 (q, J=7.0 Hz, 1H), 5.03-4.70 (m, 4H), 2.79 (s, 1H), 1.93 (d, J=7.1 Hz, 3H).

The compound A23: 105.3 mg, ESI[M+H]$^+$=269.1

$^1$H NMR (400 MHz, $CDCl_3$) δ 7.57 (d, J=1.9 Hz, 1H), 7.35-7.19 (m, 5H), 6.92 (d, J=1.9 Hz, 1H), 6.57 (q, J=7.1 Hz, 1H), 4.96-4.63 (m, 2H), 1.92 (d, J=7.1 Hz, 3H), 1.86 (t, J=2.4 Hz, 3H).

The compound A24: 95.6 mg, ESI$[M+H]^+$=311.0

$^1$H NMR (400 MHz, $CDCl_3$) δ 7.58 (d, J=2.0 Hz, 1H), 7.35-7.20 (m, 5H), 6.89 (d, J=2.0 Hz, 1H), 6.49 (q, J=7.1 Hz, 1H), 5.65 (t, J=6.6 Hz, 1H), 5.05-4.70 (m, 6H), 1.92 (d, J=7.1 Hz, 3H).

The compound A25: 79 mg, ESI$[M+H]^+$=301.0

$^1$H NMR (400 MHz, $CDCl_3$) δ 7.61 (d, J=1.4 Hz, 1H), 7.35-7.17 (m, 5H), 6.94 (d, J=1.3 Hz, 1H), 6.52 (q, J=7.1 Hz, 1H), 4.80-4.74 (m, 1H), 3.65-3.55 (m, 1H), 3.24 (s, 3H), 2.88-2.74 (m, 2H), 2.15-2.03 (m, 2H), 1.92 (d, J=7.1 Hz, 3H).

The compound A26: 23 mg, ESI$[M+H]^+$=297.1

$^1$H NMR (400 MHz, $CDCl_3$) δ 7.61 (d, J=1.8 Hz, 1H), 7.35-7.18 (m, 5H), 6.91 (d, J=1.6 Hz, 1H), 6.51 (q, J=7.0 Hz, 1H), 4.88-4.70 (m, 2H), 4.36-4.15 (m, 2H), 2.89-2.74 (m, 2H), 2.75-2.39 (m, 3H), 1.92 (d, J=7.1 Hz, 3H).

The compound A27: 85 mg, ESI$[M+H]^+$=257.0

$^1$H NMR (400 MHz, $CDCl_3$) δ 7.60 (d, J=2.0 Hz, 1H), 7.39-7.16 (m, 5H), 6.89 (d, J=2.0 Hz, 1H), 6.50 (q, J=7.0 Hz, 1H), 6.08-5.80 (m, 1H), 5.52-5.19 (m, 1H), 4.98-4.58 (m, 1H), 1.92 (d, J=7.0 Hz, 3H).

The compound A28: 27 mg, ESI$[M+H]^+$=337.1

$^1$H NMR (400 MHz, $CDCl_3$) δ 7.59 (d, J=1.8 Hz, 1H), 7.38-7.19 (m, 5H), 6.90 (d, J=1.8 Hz, 1H), 6.51 (q, J=7.1 Hz, 1H), 5.61 (s, 1H), 4.98-4.86 (m, 2H), 2.38-2.25 (m, 2H), 2.13 (t, J=5.7 Hz, 2H), 1.93 (d, J=7.1 Hz, 3H), 1.65-1.48 (m, 6H).

The compound A29: 112 mg, ESI$[M+H]^+$=285.0

$^1$H NMR (400 MHz, $CDCl_3$) δ 7.60 (d, J=2.0 Hz, 1H), 7.35-7.18 (m, 5H), 6.91 (d, J=2.0 Hz, 1H), 6.52 (q, J=7.0 Hz, 1H), 5.88-5.72 (m, 1H), 5.45-5.17 (m, 3H), 1.92 (d, J=7.1 Hz, 3H), 1.80-1.71 (m, 2H), 1.05-0.82 (m, 3H).

The compound A30: 75 mg, ESI$[M+H]^+$=287.0

$^1$H NMR (400 MHz, $CDCl_3$) δ 7.61 (d, J=1.8 Hz, 1H), 7.37-7.15 (m, 5H), 6.90 (d, J=1.8 Hz, 1H), 6.51 (q, J=7.1 Hz, 1H), 4.86-4.77 (m, 2H), 4.60-4.49 (m, 2H), 1.91 (d, J=7.1 Hz, 3H), 1.75 (s, 3H).

The compound A31: 84 mg, ESI$[M+H]^+$=287.0

$^1$H NMR (400 MHz, $CDCl_3$) δ 7.60 (d, J=2.0 Hz, 1H), 7.38-7.15 (m, 5H), 6.92 (d, J=2.0 Hz, 1H), 6.52 (q, J=7.0 Hz, 1H), 4.29-4.20 (m, 1H), 2.59-2.42 (m, 2H), 2.27-2.00 (m, 4H), 2.06 (d, J=7.1 Hz, 3H), 1.90 (d, J=7.0 Hz, 3H).

The compound A32: 103 mg, ESI$[M+H]^+$=259.0

$^1$H NMR (400 MHz, $CDCl_3$) δ 7.61 (d, J=1.6 Hz, 1H), 7.39-7.14 (m, 5H), 6.90 (d, J=2.1 Hz, 1H), 6.50 (q, J=7.1 Hz, 1H), 5.27-5.17 (m, 1H), 1.91 (d, J=7.1 Hz, 3H), 1.36 (d, J=6.2 Hz, 3H), 1.32 (d, J=6.3 Hz, 3H).

The compound A33: 83 mg, ESI$[M+H]^+$=257.0

$^1$H NMR (400 MHz, $CDCl_3$) δ 7.59 (d, J=2.0 Hz, 1H), 7.38-7.14 (m, 5H), 6.89 (d, J=2.0 Hz, 1H), 6.52 (q, J=7.0 Hz, 1H), 4.35-4.25 (m, 1H), 1.90 (d, J=7.1 Hz, 3H), 0.90-0.70 (m, 4H).

The compound A34: 31 mg, ESI$[M+H]^+$=299.0

$^1$H NMR (400 MHz, $CDCl_3$) δ 7.61 (d, J=2.0 Hz, 1H), 7.38-7.15 (m, 5H), 6.89 (d, J=2.1 Hz, 1H), 6.51 (q, J=7.1 Hz, 1H), 6.27-6.23 (m, 1H), 5.36-5.30 (m, 2H), 4.94-4.77 (m, 4H), 1.92 (d, J=6.9 Hz, 3H).

The compound A35: 84 mg, ESI$[M+H]^+$=337.1

$^1$H NMR (400 MHz, $CDCl_3$) δ 7.60 (d, J=1.6 Hz, 1H), 7.37-7.14 (m, 5H), 6.90 (d, J=1.8 Hz, 1H), 6.52 (q, J=7.0 Hz, 1H), 2.18-1.92 (m, 4H), 1.91 (d, J=7.0 Hz, 3H), 1.86 (s, 3H), 1.69-1.24 (m, 6H).

The compound A36: 51 mg, ESI$[M+H]^+$=313.1

$^1$H NMR (400 MHz, $CDCl_3$) δ 7.61 (d, J=1.8 Hz, 1H), 7.34-7.15 (m, 5H), 6.92 (d, J=2.0 Hz, 1H), 6.51 (q, J=7.1 Hz, 1H), 5.95-5.64 (m, 2H), 5.02-4.77 (m, 3H), 4.72 (d, J=8.0 Hz, 1H), 1.90-1.82 (m, 3H), 1.75-1.57 (m, 3H).

The compound A37: 76 mg, ESI$[M+H]^+$=317.0

$^1$H NMR (400 MHz, $CDCl_3$) δ 7.60 (d, J=1.8 Hz, 1H), 7.35-7.16 (m, 5H), 6.90 (d, J=1.8 Hz, 1H), 6.50 (q, J=7.0 Hz, 1H), 4.45-4.39 (m, 2H), 4.35-4.30 (m, 2H), 3.34 (s, 2H), 1.90 (d, J=7.1 Hz, 3H), 1.33 (s, 3H).

The compound A38: 99 mg, ESI$[M+H]^+$=301.0

$^1$H NMR (400 MHz, $CDCl_3$) δ 7.61 (d, J=2.0 Hz, 1H), 7.38-7.15 (m, 5H), 6.91 (d, J=2.0 Hz, 1H), 6.50 (q, J=7.1 Hz, 1H), 4.51 (dd, J=6.1, 2.0 Hz, 2H), 4.42 (dd, J=6.1, 1.5 Hz, 2H), 4.39-4.30 (m, 2H), 1.91 (d, J=7.1 Hz, 3H), 1.35 (s, 3H).

The compound A39: 101 mg, ESI$[M+H]^+$=317.0

$^1$H NMR (400 MHz, $CDCl_3$) δ 7.62 (d, J=1.6 Hz, 1H), 7.35-7.15 (m, 5H), 6.89 (d, J=2.0 Hz, 1H), 6.49 (q, J=7.1 Hz, 1H), 4.25 (q, J=10.9 Hz, 2H), 3.07 (d, J=9.4 Hz, 2H), 2.94 (dd, J=9.4, 1.1 Hz, 2H), 1.89 (d, J=7.1 Hz, 3H), 1.33 (s, 3H).

The compound A40: 82 mg, ESI$[M+H]^+$=301.0

$^1$H NMR (400 MHz, $CDCl_3$) δ 7.60 (d, J=2.0 Hz, 1H), 7.37-7.15 (m, 5H), 6.90 (d, J=2.0 Hz, 1H), 6.50 (q, J=7.1 Hz, 1H), 1.91 (s, 3H), 1.88 (d, J=7.1 Hz, 3H), 1.53 (s, 3H), 1.46 (s, 3H).

The compound A41: 38 mg, ESI$[M+H]^+$=317.1

$^1$H NMR (400 MHz, $CDCl_3$) δ 7.59 (d, J=2.0 Hz, 1H), 7.38-7.13 (m, 5H), 6.92 (d, J=2.0 Hz, 1H), 6.51 (q, J=7.1 Hz, 1H), 2.13 (s, 3H), 1.89 (d, J=7.1 Hz, 3H), 1.55 (s, 3H), 1.46 (s, 3H).

The compound A42: 70 mg, ESI$[M+H]^+$=329.1

$^1$H NMR (400 MHz, $CDCl_3$) δ 7.61 (d, J=2.0 Hz, 1H), 7.37-7.14 (m, 5H), 6.90 (d, J=2.0 Hz, 1H), 6.52 (q, J=7.1 Hz, 1H), 4.82-4.71 (m, 1H), 3.80-3.69 (m, 1H), 3.65-3.54 (m, 1H), 2.89-2.74 (m, 2H), 2.20-2.07 (m, 2H), 1.86 (d, J=7.1 Hz, 3H), 1.15 (d, J=6.1 Hz, 6H).

The compound A43: 15 mg, ESI$[M+H]^+$=425.2

$^1$H NMR (400 MHz, $CDCl_3$) δ 7.60 (d, J=2.0 Hz, 1H), 7.35-7.15 (m, 5H), 6.91 (d, J=2.0 Hz, 1H), 6.52 (q, J=7.1 Hz, 1H), 6.15-5.80 (m, 1H), 3.87-3.13 (m, 4H), 2.58-2.35 (m, 1H), 2.18-1.11 (m, 18H).

The compound A44: 22 mg, ESI$[M+H]^+$=359.2

$^1$H NMR (400 MHz, $CDCl_3$) δ 7.61 (d, J=2.0 Hz, 1H), 7.38-7.13 (m, 5H), 6.91 (d, J=1.8 Hz, 1H), 6.51 (q, J=7.1 Hz, 1H), 5.09-4.94 (m, 1H), 3.50-3.36 (m, 4H), 2.82-2.65 (m, 2H), 2.35-2.20 (m, 2H), 1.90 (d, J=7.1 Hz, 3H), 1.19 (q, J=7.0 Hz, 6H).

The compound A45: 54 mg, ESI$[M+H]^+$=327.1

$^1$H NMR (400 MHz, $CDCl_3$) δ 7.62 (d, J=1.6 Hz, 1H), 7.35-7.18 (m, 5H), 6.94 (d, J=1.6 Hz, 1H), 6.51 (q, J=7.0 Hz, 1H), 4.65-4.49 (m, 1H), 4.34-4.15 (m, 1H), 2.82-2.64 (m, 1H), 2.50-1.93 (m, 5H), 1.90 (d, J=7.1 Hz, 3H), 1.78-1.35 (m, 3H).

The compound A46: 95 mg, ESI$[M+H]^+$=355.1

$^1$H NMR (400 MHz, $CDCl_3$) δ 7.60 (d, J=1.8 Hz, 1H), 7.38-7.15 (m, 5H), 6.92 (d, J=1.8 Hz, 1H), 6.51 (q, J=7.1 Hz, 1H), 3.51 (s, 3H), 2.48-2.35 (m, 2H), 2.35-2.20 (m, 2H), 1.90 (d, J=7.1 Hz, 3H), 1.81-1.75 (m, 2H), 1.73-1.65 (m, 2H).

The compound A47: 76 mg, ESI$[M+H]^+$=325.0

$^1$H NMR (400 MHz, $CDCl_3$) δ 8.09 (s, 1H), 7.61 (d, J=1.9 Hz, 1H), 7.36-7.15 (m, 5H), 6.91 (d, J=1.8 Hz, 1H), 6.51 (q, J=7.1 Hz, 1H), 2.67-2.63 (m, 2H), 2.46 (t, J=6.6 Hz, 2H), 1.91 (d, J=7.1 Hz, 3H), 1.88-1.84 (m, 2H), 1.80-1.72 (m, 2H).

The compound A48: 85 mg, ESI$[M+H]^+$=357.1

$^1$H NMR (400 MHz, $CDCl_3$) δ 7.59 (d, J=1.6 Hz, 1H), 7.37-7.15 (m, 5H), 6.90 (d, J=2.0 Hz, 1H), 6.50 (q, J=7.1 Hz, 1H), 3.55 (s, 3H), 2.28-2.05 (m, 2H), 1.94-1.76 (m, 5H), 1.74-1.20 (m, 6H).

Example 3 Preparation of Compounds A49 and A50

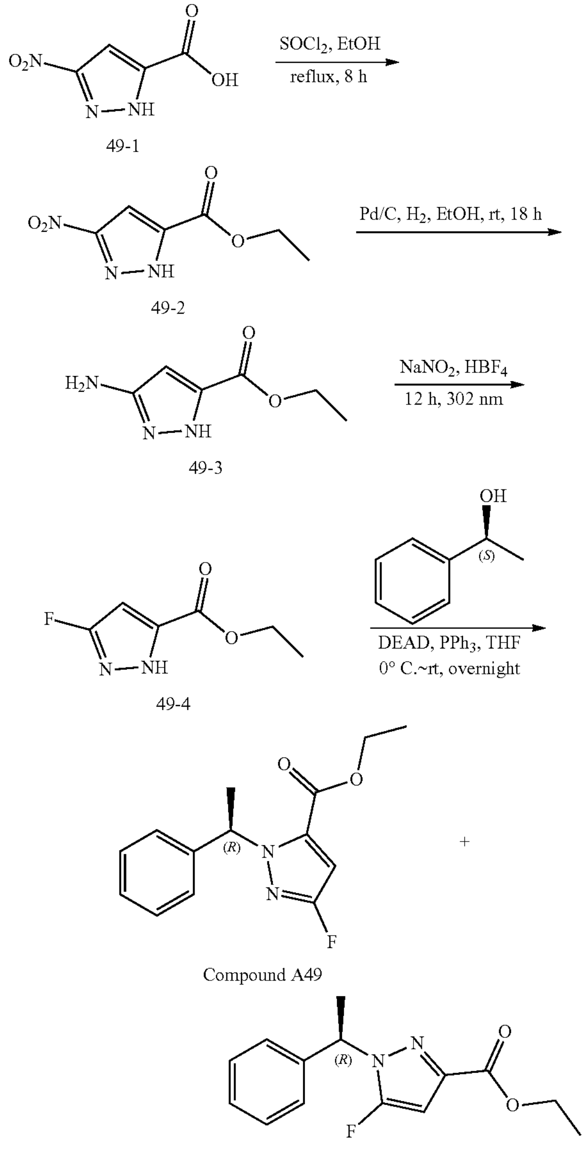

49-1

49-2

49-3

49-4

Compound A49

Compound A50

1. Preparation of ethyl 3-nitro-1H-pyrazole-5-carboxylate (49-2)

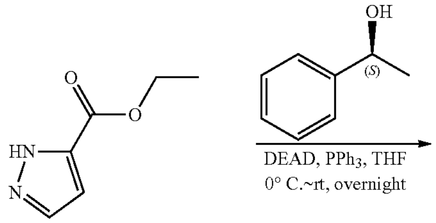

-continued

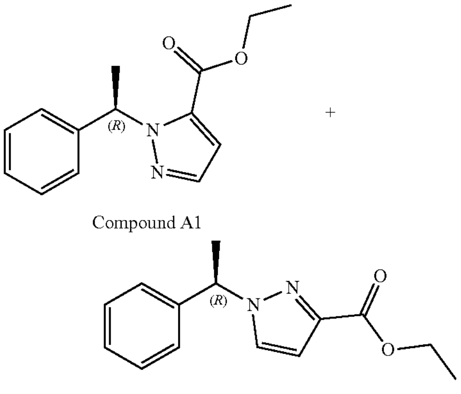

Compound A1

Compound A2

At room temperature, 49-1 (50 g, 318.3 mmol) was dissolved in ethanol (300 mL), and the mixture was cooled to 0° C. by an ice-salt bath. $SOCl_2$ (49 g, 412 mmol) was added dropwise into the mixture, then it was stirred at 85° C. for 10 hrs. The reaction was monitored by TLC until completion and concentrated under reduced pressure. The residue was dissolved in dichloromethane (3 mL) and adjusted pH to 8 with sat $NaHCO_3$ solution. The mixture was extracted with dichloromethane (3×30 mL). The combined organic layers were washed with saturated brine (50 mL), dried over anhydrous sodium sulfate, filtered and concentrated under reduced pressure to give compound 49-2 (58.7 g, yield 99.6%) as a white solid. ESI[M+H]$^+$=186.1

2. Preparation of ethyl 3-amino-1H-pyrazole-5-carboxylate (49-3)

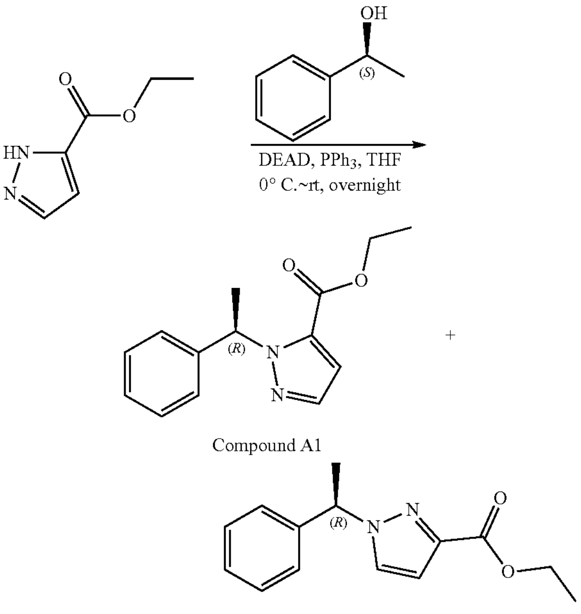

Compound A1

Compound A2

At room temperature, 49-2 (58.7 g, 317 mmol) and 10% wet palladium on carbon (6 g) were dissolved in EtOH (200 mL), the system was replaced with hydrogen three times and stirred under hydrogen for 18 hrs. The reaction was monitored by TLC until completion, filtered and the filter cake was washed with ethanol (3×30 mL). The filtrate was concentrated under reduced pressure to give a crude product. The crude product was purified by silica gel column chromatography with ethyl acetate/petroleum ether (v/v=1/5) and the eluate was monitored by TLC (ethyl acetate/petroleum ether (v/v)=1/1). The fraction with Rf=0.4~0.5 was collected to give 49-3 (43.5 g, yield 88%) as a gray solid. ESI[M+H]$^+$156.1

3. Preparation of ethyl 3-fluoro-1H-pyrazole-5-carboxylate (49-4)

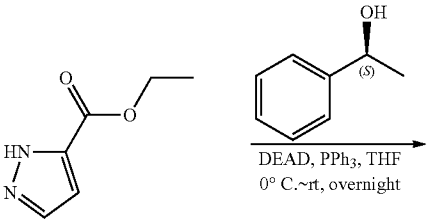

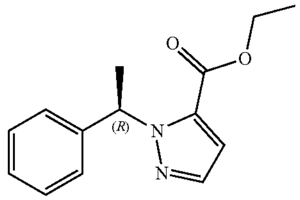

Compound A1

+

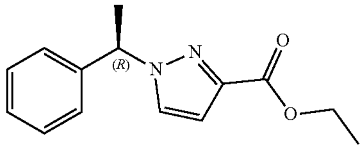

Compound A2

In an ice-salt bath, 49-3 (43.5 g, 280 mmol) was dissolved in the $HBF_4$ (40%), and then $NaNO_2$ (20.3 g, 294 mmol) in the water (30 mL) was added dropwise into solution at −10° C. The mixture was allowed to react under the irradiation of a mercury lamp (254 nm) for 12 hrs. The reaction was monitored by TLC until completion, and then the reaction solution was adjusted pH to 7 with 1N NaOH solution in an ice-water bath. The mixture was extracted with ethyl acetate (3×50 mL). The combined organic layers were washed with saturated brine, dried over anhydrous sodium sulfate, filtered and concentrated under reduced pressure. The crude product was purified by silica gel column chromatography with ethyl acetate/petroleum ether (v/v=1/1) and the eluate was monitored by TLC (ethyl acetate/petroleum ether (v/v)=1/1). The fraction with Rf=0.4~0.5 was collected to give 49-4 (3.4 g, yield 8%) as a gray solid.

4. Preparation of Compounds A49 and A50

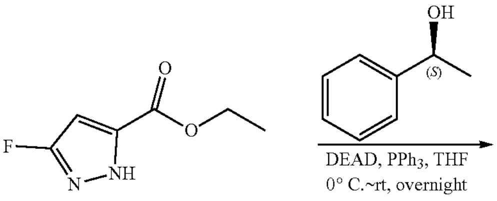

49-4

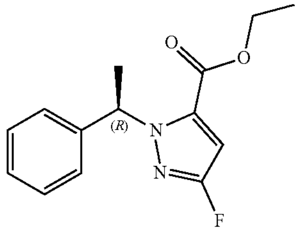

Compound A49

+

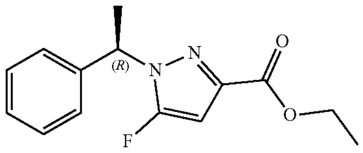

Compound A50

In an ice-water bath, S-1-phenylethan-1-ol (3.4 g, 27.8 mmol), 49-4 (3.4 g, 21.5 mmol) and $PPh_3$ (8.4 g, 32.0 mmol) were dissolved in THF (50 mL) at 0° C., then DEAD (5.6 g, 32.2 mmol) was added into mixture at the rate of 0.5 mmol/min. The mixture was warmed slowly to room temperature and stirred at this temperature overnight. The reaction was monitored by TLC until completion, then it was quenched with saturated brine (30 mL) and extracted with ethyl acetate (3×15 mL). The combined organic layers were washed with saturated brine (30 mL), dried over anhydrous sodium sulfate, filtered and concentrated under reduced pressure to give crude product. The crude product was purified by silica gel column chromatography with ethyl acetate/petroleum ether (v/v=1/20~1/10) and the eluate was monitored by TLC (ethyl acetate/petroleum ether (v/v)=1/2). The fraction with Rf=0.5~0.6 was collected to give the products A49 (4.2 g, yield 74%) and A50 (400 mg, yield 7%).

The compound A49: ESI[M+H]$^+$=263.1

$^1$H NMR (400 MHz, $CDCl_3$) δ 7.35-7.21 (m, 5H), 6.56-6.47 (m, 1H), 6.33 (d, J=6.3 Hz, 1H), 4.41-4.17 (m, 2H), 1.85 (d, J=7.1 Hz, 3H), 1.33 (t, J=7.1 Hz, 3H).

The compound A50: ESI[M+H]$^+$=263.0

$^1$H NMR (400 MHz, $CDCl_3$) δ 7.37-7.27 (m, 5H), 6.26 (d, J=5.6 Hz, 1H), 5.58 (q, J=7.2 Hz, 1H), 4.40 (q, J=7.1 Hz, 2H), 1.95 (d, J=7.2 Hz, 3H), 1.39 (t, J=7.1 Hz, 3H).

Example 4 Preparation of Compounds A51~A69

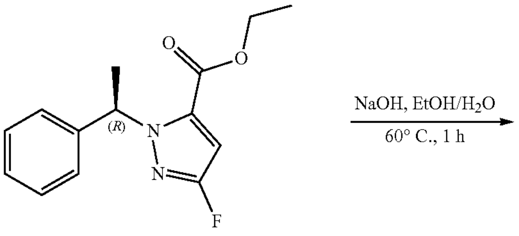

Compound A49

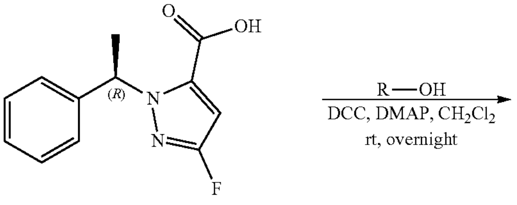

B

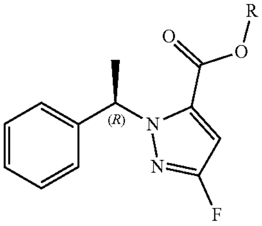

Compound A51~A69

1. Preparation of (R)-3-fluoro-1-(1-phenylethyl)-1H-pyrazole-5-carboxylic acid (B)

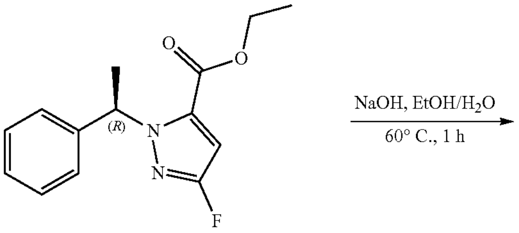

Compound A49

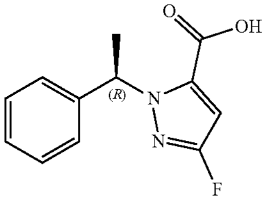

B

At room temperature, NaOH (1.3 g, 32.5 mmol) and A49 (4.2 g, 16.0 mmol) were dissolved in ethanol/water (20 mL, v/v=1/1), and then it was reacted at 60° C. for 1 hour. The reaction was monitored by TLC until completion, then it was concentrated under reduced pressure. The residue was dissolved in $H_2O$ (20 mL) and adjusted pH to 4-5 with 1 N HCl solution. The mixture was extracted with dichloromethane (3×15 mL). The combined organic layers were washed with saturated brine, dried over anhydrous sodium sulfate, filtered and concentrated under reduced pressure to give compound B (2.8 g, yield 75%) as a white solid. ESI[M+H]$^+$=234.9

$^1$H NMR (400 MHz, $CDCl_3$) δ 7.41-7.14 (m, 6H), 6.55-6.36 (m, 2H), 1.87 (d, J=7.0 Hz, 3H).

2. Preparation of Compounds A51~A69

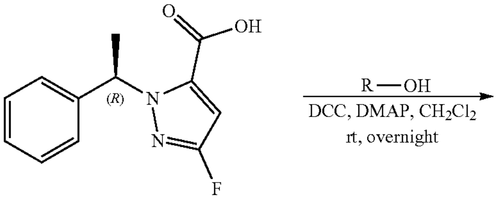

B

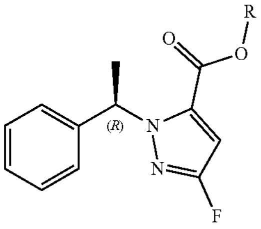

Compound A51~A69

The target compounds A51~A69 were prepared according to the general procedure A, using B (100 mg, 0.43 mmol) and corresponding alcohol (0.64 mmol) as starting materials. The crude product was purified by Prep-TLC (ethyl acetate/petroleum ether (v/v)=1/5) and the fraction with Rf=0.4~0.6 was collected and dried to give target compounds as colorless oil.

The compound A51: 84 mg, ESI[M+H]$^+$=287.0

$^1$H NMR (400 MHz, $CDCl_3$) δ 7.37-7.21 (m, 5H), 6.54-6.44 (m, 1H), 6.39 (d, J=6.3 Hz, 1H), 4.91-4.71 (m, 2H), 1.87 (d, J=2.4 Hz, 3H), 1.85 (d, J=7.2 Hz, 3H).

The compound A52: 89 mg, ESI[M+H]$^+$=329.0

$^1$H NMR (400 MHz, $CDCl_3$) δ 7.58-7.14 (m, 5H), 6.49-6.39 (m, 1H), 6.37 (d, J=6.3 Hz, 1H), 5.64 (t, J=6.6 Hz, 1H), 5.08-4.70 (m, 6H), 1.85 (d, J=7.0 Hz, 3H).

The compound A53: 32 mg, ESI[M+H]$^+$=315.0

$^1$H NMR (400 MHz, $CDCl_3$) δ 7.41-7.19 (m, 6H), 6.48-6.41 (m, 1H), 6.40 (d, J=6.3 Hz, 1H), 5.09-4.59 (m, 4H), 2.81 (s, 1H), 1.86 (d, J=7.0 Hz, 3H).

The compound A54: 84 mg, ESI[M+H]$^+$=373.0

$^1$H NMR (400 MHz, $CDCl_3$) δ 7.40-7.18 (m, 5H), 6.52-6.43 (m, 1H), 6.41 (d, J=6.3 Hz, 1H), 3.46 (s, 3H), 2.51-2.37 (m, 2H), 2.34-2.21 (m, 2H), 1.87 (d, J=7.0 Hz, 3H), 1.82-1.73 (m, 2H), 1.73-1.64 (m, 2H).

The compound A55: 88 mg, ESI[M+H]$^+$=319.0

$^1$H NMR (400 MHz, $CDCl_3$) δ 7.36-7.21 (m, 5H), 6.52-6.42 (m, 1H), 6.34 (d, J=6.3 Hz, 1H), 4.80 (p, J=7.3 Hz, 1H), 3.63 (p, J=6.9 Hz, 1H), 3.26 (s, 3H), 2.95-2.73 (m, 2H), 2.17-2.02 (m, 2H), 1.84 (d, J=7.0 Hz, 3H).

The compound A56: 39 mg, ESI[M+H]$^+$=305.0

$^1$H NMR (400 MHz, $CDCl_3$) δ 7.35-7.21 (m, 5H), 6.48-6.38 (m, 1H), 6.33 (d, J=6.3 Hz, 1H), 4.80 (dd, J=24.7, 7.3 Hz, 2H), 4.55 (t, J=6.7 Hz, 2H), 1.85 (d, J=7.0 Hz, 3H), 1.75 (s, 3H).

The compound A57: 70 mg, ESI[M+H]$^+$=291.1

$^1$H NMR (400 MHz, $CDCl_3$) δ 7.37-7.20 (m, 5H), 6.58-6.45 (m, 1H), 6.23 (d, J=6.3 Hz, 1H), 1.84 (d, J=7.1 Hz, 3H), 1.52 (s, 9H).

The compound A58: 99 mg, ESI[M+H]$^+$=289.0

$^1$H NMR (400 MHz, $CDCl_3$) δ 7.36-7.18 (m, 5H), 6.50-6.41 (m, 1H), 6.35 (d, J=6.3 Hz, 1H), 4.20-3.95 (m, 2H), 1.85 (d, J=7.1 Hz, 3H), 1.27-1.00 (m, 1H), 0.68-0.48 (m, 2H), 0.45-0.20 (m, 2H).

The compound A59: 86 mg, ESI[M+H]$^+$=289.0

$^1$H NMR (400 MHz, $CDCl_3$) δ 7.37-7.19 (m, 5H), 6.50-6.40 (m, 1H), 6.32 (d, J=6.3 Hz, 1H), 5.19-5.04 (m, 1H), 2.47-2.30 (m, 2H), 2.25-2.01 (m, 2H), 1.86 (d, J=7.1 Hz, 3H), 1.86-1.59 (m, 2H).

The compound A60: 62 mg, ESI[M+H]$^+$=307.1

$^1$H NMR (400 MHz, $CDCl_3$) δ 7.39-7.18 (m, 5H), 6.48-6.37 (m, 1H), 6.28 (d, J=6.3 Hz, 1H), 5.75 (p, J=8.0 Hz, 1H), 3.61-3.20 (m, 4H), 1.87 (d, J=7.1 Hz, 3H).

The compound A61: 51 mg, ESI[M+H]$^+$=327.1

$^1$H NMR (400 MHz, $CDCl_3$) δ 7.41-7.16 (m, 5H), 6.50-6.37 (m, 1H), 6.30 (d, J=6.3 Hz, 1H), 5.92-5.74 (m, 1H), 5.70-5.59 (m, 1H), 5.55-5.40 (m, 1H), 1.88 (d, J=7.0 Hz, 3H), 1.77 (s, 3H), 1.74 (s, 3H).

The compound A62: 47 mg, ESI[M+H]$^+$=315.0

$^1$H NMR (400 MHz, $CDCl_3$) δ 7.45-7.16 (m, 5H), 6.49-6.38 (m, 1H), 6.29 (d, J=6.3 Hz, 1H), 1.89 (d, J=7.1 Hz, 3H), 1.85 (s, 3H), 1.72 (s, 3H), 1.68 (s, 3H).

The compound A63: 39 mg, ESI[M+H]$^+$=315.0

$^1$H NMR (400 MHz, $CDCl_3$) δ 7.48-7.16 (m, 5H), 6.50-6.38 (m, 1H), 6.32 (d, J=6.3 Hz, 1H), 5.87-5.51 (m, 1H), 5.23-4.68 (m, 2H), 2.12-1.85 (m, 6H), 1.80-1.59 (m, 3H).

The compound A64: 50 mg, ESI[M+H]$^+$=333.0

$^1$H NMR (400 MHz, $CDCl_3$) δ 7.47-7.16 (m, 5H), 6.48-6.38 (m, 1H), 6.29 (d, J=6.3 Hz, 1H), 5.05-4.90 (m, 2H), 4.81-4.70 (m, 2H), 2.21 (s, 3H), 1.88 (d, J=7.1 Hz, 3H).

The compound A65: 27 mg, ESI[M+H]$^+$=317.0

$^1$H NMR (400 MHz, $CDCl_3$) δ 7.50-7.15 (m, 5H), 6.55-6.41 (m, 1H), 6.30 (d, J=6.3 Hz, 1H), 6.26-6.18 (m, 1H), 5.35-5.21 (m, 2H), 4.97-4.71 (m, 4H), 1.88 (d, J=7.0 Hz, 3H).

The compound A66: 49 mg, ESI[M+H]$^+$=355.1

$^1$H NMR (400 MHz, $CDCl_3$) δ 7.49-7.18 (m, 5H), 6.50-6.41 (m, 1H), 6.33 (d, J=6.3 Hz, 1H), 2.21-1.90 (m, 4H), 1.89 (d, J=7.0 Hz, 3H), 1.85 (s, 3H), 1.70-1.29 (m, 6H).

The compound A67: 93 mg, ESI[M+H]$^+$=375.1

$^1$H NMR (400 MHz, $CDCl_3$) δ 7.50-7.17 (m, 5H), 6.48-6.45 (m, 1H), 6.28 (d, J=6.3 Hz, 1H), 3.54 (s, 3H), 2.30-2.05 (m, 2H), 1.96-1.20 (m, 11H).

The compound A68: 58 mg, ESI[M+H]$^+$=357.0

$^1$H NMR (400 MHz, $CDCl_3$) δ 7.47-7.15 (m, 5H), 6.50-6.42 (m, 1H), 6.31 (d, J=6.3 Hz, 1H), 2.45-2.21 (m, 4H), 2.09 (s, 3H), 1.89 (d, J=7.1 Hz, 3H), 1.80-1.561 (m, 4H).

The compound A69: 32 mg, ESI[M+H]$^+$=343.0

$^1$H NMR (400 MHz, $CDCl_3$) δ 7.50-7.17 (m, 5H), 6.49-6.44 (m, 1H), 6.27 (d, J=6.3 Hz, 1H), 2.50-2.31 (m, 7H), 1.89 (d, J=7.1 Hz, 3H), 1.88-1.74 (m, 2H).

Example 5 Preparation of Compounds A70 and A71

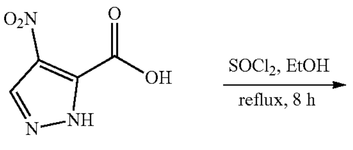

70-1

-continued

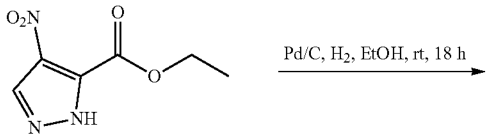

70-2

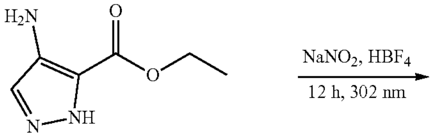

70-3

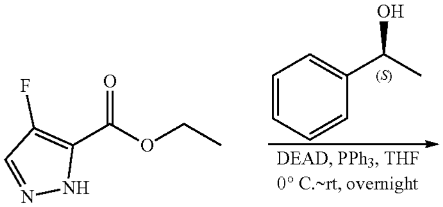

70-4

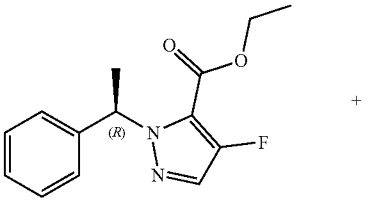

Compound A70

+

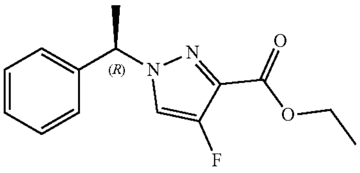

Compound A71

1. Preparation of Ethyl 4-nitro-1H-pyrazole-5-carboxylate (70-2)

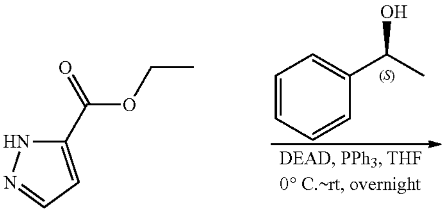

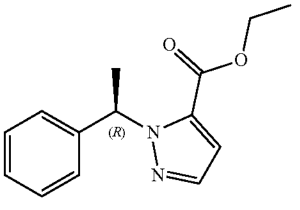

+

Compound A1

-continued

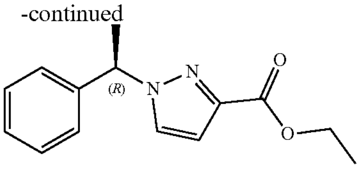

Compound A2

At room temperature, 70-1 (50 g, 318.3 mmol) was dissolved in ethanol (300 mL), the mixture was cooled to 0° C. by an ice-salt bath. $SOCl_2$ (49 g, 412 mmol) was added dropwise into the mixture, then it was stirred at 85° C. for 10 hrs. The reaction was monitored by TLC until completion and concentrated under reduced pressure. The residue was dissolved in dichloromethane (30 mL) and adjusted pH to 8 with sat $NaHCO_3$. The mixture was extracted with dichloromethane (3×30 mL). The combined organic layers were washed with saturated brine (50 mL), dried over anhydrous sodium sulfate, filtered and concentrated under reduced pressure to give compound 70-2 (54.8 g, yield 93%) as a white solid. ESI$[M+H]^+$=186.1

2. Preparation of Ethyl 4-amino-1H-pyrazole-5-carboxylate (70-3)

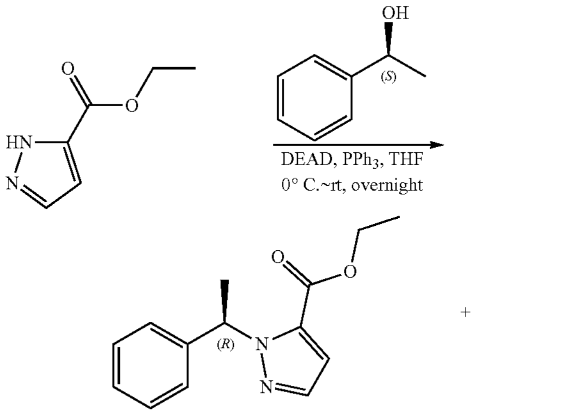

Compound A1

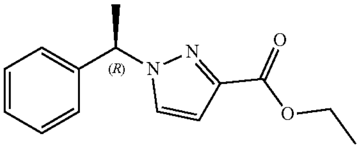

Compound A2

At room temperature, 70-2 (54.8 g, 296 mmol) and 10% wet palladium on carbon (5 g) were dissolved in EtOH (200 mL), the system was replaced with hydrogen three times and stirred under hydrogen for 18 hrs. The reaction was monitored by TLC until completion, filtered and the filter cake was washed with ethanol (3×30 mL). The filtrate was concentrated under reduced pressure to give a crude product. The crude product was purified by silica gel column chromatography with ethyl acetate/petroleum ether (v/v=1/5) and the eluate was monitored by TLC (ethyl acetate/petroleum ether (v/v)=1/1). The fraction with Rf=0.4~0.5 was collected to give 70-3 (41.1 g, yield 89%) as a gray solid. ESI$[M+H]^+$156.1

3. Preparation of Ethyl 4-fluoro-1H-pyrazole-5-carboxylate (70-4)

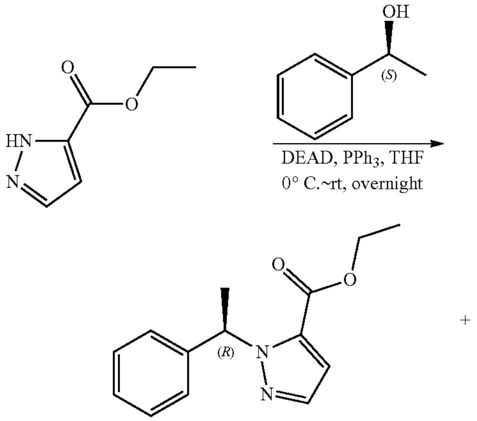

Compound A1

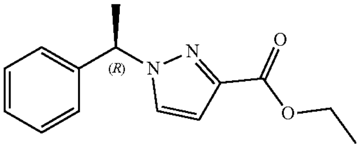

Compound A2

In an ice-salt bath, 70-3 (35 g, 226 mmol) was dissolved in the $HBF_4$ (40%), and then $NaNO_2$ (16.4 g, 238 mmol) in the water (30 mL) was added dropwise into solution at −10° C. The mixture was allowed to react under the irradiation of a mercury lamp (302 nm) for 12 hrs. The reaction was monitored by TLC until completion, and then the reaction solution was adjusted pH to 7 with 1N NaOH solution in an ice-water bath. The mixture was extracted with ethyl acetate (3×50 mL). The combined organic layers were washed with saturated brine, dried over anhydrous sodium sulfate, filtered and concentrated under reduced pressure. The crude product was purified by silica gel column chromatography with ethyl acetate/petroleum ether (v/v=1/1) and the eluate was monitored by TLC (ethyl acetate/petroleum ether (v/v)=1/1). The fraction with Rf=0.4~0.5 was collected to give 70-4 (6 g, yield 17%) as a gray solid.

4. Preparation of Compounds A70 and A71

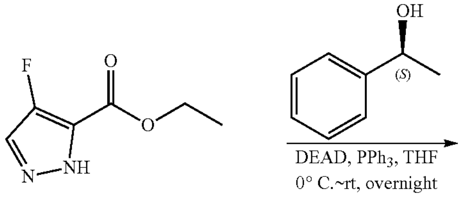

70-4

-continued

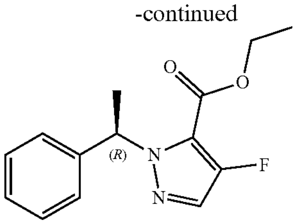

+

Compound A70

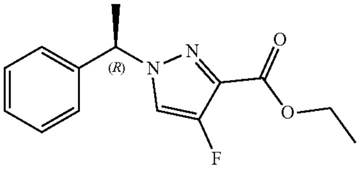

Compound A71

In an ice-water bath, S-1-phenylethan-1-ol (3.4 g, 27.8 mmol), 70-4 (6 g, 37.9 mmol), and $PPh_3$ (14.9 g, 56.8 mmol) were dissolved in THF (50 mL) at 0° C., then DEAD (9.9 g, 56.8 mmol) in THF (15 mL) was added in to mixture at the rate of 0.5 mmol/min, then the mixture was warmed slowly to room temperature and stirred at this temperature overnight. The reaction was monitored by TLC until completion, then it was quenched with the saturated brine (30 mL) and extracted with ethyl acetate (3×15 mL). The combined organic layers were washed with saturated brine (30 mL), dried over anhydrous sodium sulfate, filtered and concentrated under reduced pressure to give crude product. The crude product was purified by silica gel column chromatography with ethyl acetate/petroleum ether (v/v=1/20~1/10) and the eluate was monitored by TLC (ethyl acetate/petroleum ether (v/v)=1/2). The fraction with Rf=0.5~0.6 was collected to give the products A70 (5.9 g, yield 59%) and A71 (1.5 g, yield 15%).

The compound A70: ESI$[M+H]^+$=263.1

$^1$H NMR (400 MHz, $CDCl_3$) δ 7.44 (d, J=4.5 Hz, 1H), 7.35-7.20 (m, 5H), 6.46 (q, J=7.1 Hz, 1H), 4.53-4.09 (m, 2H), 1.88 (d, J=7.1 Hz, 3H), 1.34 (t, J=7.1 Hz, 3H).

The compound A71: ESI$[M+H]^+$=263.0

$^1$H NMR (400 MHz, $CDCl_3$) δ 7.41-7.29 (m, 3H), 7.27-7.23 (m, 2H), 7.21 (d, J=4.8 Hz, 1H), 5.55 (q, J=7.1 Hz, 1H), 4.43 (q, J=7.1 Hz, 2H), 1.89 (d, J=7.1 Hz, 3H), 1.40 (t, J=7.1 Hz, 3H).

Example 6 Preparation of Compounds A72~A90

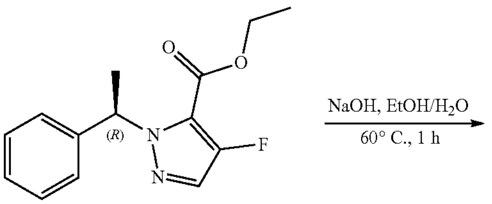

Compound A70

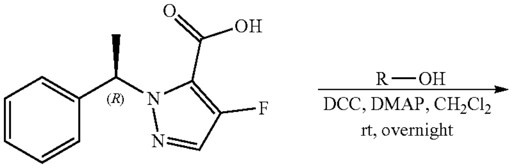

C

-continued

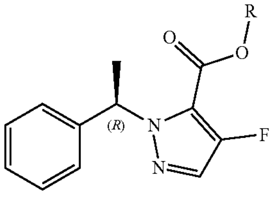

Compound A72~A90

1. Preparation of (R)-4-fluoro-1-(1-phenylethyl)-1H-pyrazole-5-carboxylic acid (C)

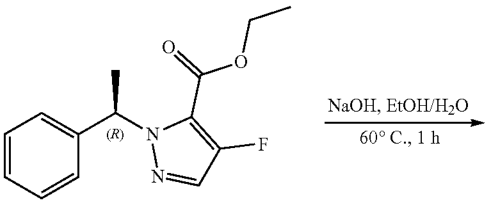

Compound A70

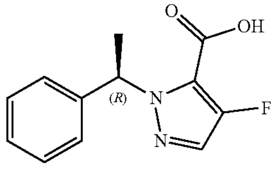

C

At room temperature, NaOH (1.8 g, 45.0 mmol) and A70 (5.9 g, 22.5 mmol) were dissolved in EtOH/$H_2O$ (20 mL, 1/1), and then it was stirred at 60° C. for 1 hour. The reaction was monitored by TLC until completion, the mixture was concentrated under reduced pressure, cooled and adjusted pH to 4~5 with 1 N HCl solution. The mixture was extracted with dichloromethane (3×15 mL). The combined organic layers were dried over anhydrous sodium sulfate, filtered and concentrated under reduced pressure to give compound C (3.8 g, yield 72%). ESI$[M+H]^+$=235.2

$^1$H NMR (400 MHz, $CDCl_3$) δ 7.50 (d, J=4.5 Hz, 1H), 7.36-7.20 (m, 5H), 6.43 (q, J=7.0 Hz, 1H), 1.89 (d, J=7.1 Hz, 3H).

2. Preparation of Compounds A72~A90

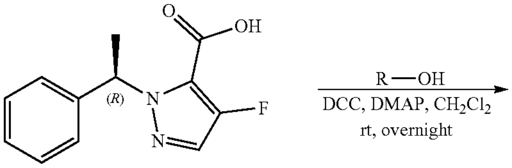

C

-continued

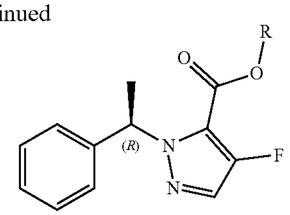

Compound A72~A90

The target compounds A72~A90 were prepared according to the general procedure A, using C (100 mg, 0.43 mmol) and corresponding alcohol (0.64 mmol) as starting materials. The crude product was purified by Prep-TLC (ethyl acetate/petroleum ether (v/v)=1/5) and the fraction with Rf=0.4~0.6 was collected and dried to give target compounds as colorless oil.

The compound A72: 40 mg, ESI$[M+H]^+$=287.2

$^1$H NMR (400 MHz, $CDCl_3$) δ 7.45 (d, J=4.5 Hz, 1H), 7.33-7.20 (m, 5H), 6.44 (q, J=6.9 Hz, 1H), 4.92-4.71 (m, 2H), 1.90-1.85 (m, 6H).

The compound A73: 52 mg, ESI$[M+H]^+$=329.2

$^1$H NMR (400 MHz, $CDCl_3$) δ 7.46 (d, J=4.5 Hz, 1H), 7.35-7.18 (m, 5H), 6.37 (q, J=7.1 Hz, 1H), 5.63 (t, J=6.6 Hz, 1H), 5.03-4.95 (m, 1H), 4.95-4.87 (m, 2H), 4.85-4.74 (m, 3H), 1.88 (d, J=7.1 Hz, 3H).

The compound A74: 76 mg, ESI$[M+H]^+$=315.2

$^1$H NMR (400 MHz, $CDCl_3$) δ 7.45 (d, J=4.5 Hz, 1H), 7.34-7.18 (m, 5H), 6.43 (q, J=7.1 Hz, 1H), 5.05-4.72 (m, 4H), 2.80 (s, 1H), 1.89 (d, J=7.1 Hz, 3H).

The compound A75: 109 mg, ESI$[M+H]^+$=373.2

$^1$H NMR (400 MHz, $CDCl_3$) δ 7.43 (d, J=4.5 Hz, 1H), 7.35-7.16 (m, 5H), 6.41 (q, J=7.0 Hz, 1H), 3.50 (s, 3H), 2.48-2.19 (m, 4H), 1.88 (d, J=7.1 Hz, 3H), 1.82-1.63 (m, 4H).

The compound A76: 57 mg, ESI$[M+H]^+$=319.1

$^1$H NMR (400 MHz, $CDCl_3$) δ 7.43 (d, J=4.5 Hz, 1H), 7.35-7.16 (m, 5H), 6.41 (q, J=7.0 Hz, 1H), 4.84-4.72 (m, 1H), 3.68-3.54 (m, 1H), 3.24 (s, 3H), 2.93-2.70 (m, 2H), 2.19-2.01 (m, 2H), 1.87 (d, J=7.1 Hz, 3H).

The compound A77: 76 mg, ESI$[M+H]^+$=347.2

$^1$H NMR (400 MHz, $CDCl_3$) δ 7.44 (d, J=4.5 Hz, 1H), 7.38-7.14 (m, 5H), 6.36 (q, J=7.1 Hz, 1H), 4.84-4.68 (m, 1H), 3.78-3.52 (m, 2H), 2.84-2.71 (m, 2H), 2.24-2.00 (m, 2H), 1.87 (d, J=7.1 Hz, 3H), 1.17 (d, J=6.1 Hz, 6H).

The compound A78: 31 mg, ESI$[M+H]^+$=291.1

$^1$H NMR (400 MHz, $CDCl_3$) δ 7.45 (d, J=4.5 Hz, 1H), 7.35-7.14 (m, 5H), 6.41 (q, J=7.1 Hz, 1H), 1.89 (d, J=7.1 Hz, 3H), 1.53 (s, 9H).

The compound A79: 105 mg, ESI$[M+H]^+$=289.2

$^1$H NMR (400 MHz, $CDCl_3$) δ 7.43 (d, J=4.5 Hz, 1H), 7.37-7.16 (m, 5H), 6.45 (q, J=7.0 Hz, 1H), 4.20-3.94 (m, 2H), 1.90 (d, J=7.1 Hz, 3H), 1.24-1.01 (m, 1H), 0.64-0.20 (m, 4H).

The compound A80: 92 mg, ESI$[M+H]^+$=289.1

$^1$H NMR (400 MHz, $CDCl_3$) δ 7.45 (d, J=4.5 Hz, 1H), 7.36-7.12 (m, 5H), 6.39 (q, J=7.1 Hz, 1H), 5.18-5.07 (m, 1H), 2.45-2.05 (m, 4H), 1.87 (d, J=7.1 Hz, 3H), 1.86-1.58 (m, 2H).

The compound A81: 67 mg, ESI$[M+H]^+$=307.0

$^1$H NMR (400 MHz, $CDCl_3$) δ 7.44 (d, J=4.5 Hz, 1H), 7.39-7.15 (m, 5H), 6.42 (q, J=7.1 Hz, 1H), 5.80-5.73 (m, 1H), 3.69-3.19 (m, 4H), 1.88 (d, J=7.1 Hz, 3H).

The compound A82: 25 mg, ESI$[M+H]^+$=327.2

$^1$H NMR (400 MHz, $CDCl_3$) δ 7.45 (d, J=4.5 Hz, 1H), 7.37-7.18 (m, 5H), 6.45 (q, J=7.1 Hz, 1H), 5.90-5.40 (m, 3H), 1.88 (d, J=7.1 Hz, 3H), 1.78 (s, 3H), 1.75 (s, 3H).

The compound A83: 61 mg, ESI$[M+H]^+$=315.0

$^1$H NMR (400 MHz, $CDCl_3$) δ 7.43 (d, J=4.5 Hz, 1H), 7.38-7.16 (m, 5H), 6.40 (q, J=7.1 Hz, 1H), 1.89 (d, J=7.1 Hz, 3H), 1.86 (s, 3H), 1.74 (s, 3H), 1.69 (s, 3H).

The compound A84: 16 mg, ESI$[M+H]^+$=315.2

$^1$H NMR (400 MHz, $CDCl_3$) δ 7.44 (d, J=4.5 Hz, 1H), 7.35-7.15 (m, 5H), 6.41 (q, J=7.1 Hz, 1H), 5.77-5.50 (m, 1H), 5.34-4.64 (m, 2H), 2.08-1.84 (m, 6H), 1.78-1.55 (m, 3H).

The compound A85: 82 mg, ESI$[M+H]^+$=305.2

$^1$H NMR (400 MHz, $CDCl_3$) δ 7.45 (d, J=4.5 Hz, 1H), 7.38-7.15 (m, 5H), 6.38 (q, J=7.1 Hz, 1H), 4.89-4.74 (m, 2H), 4.61-4.44 (m, 2H), 1.86 (d, J=7.1 Hz, 3H), 1.74 (s, 3H).

The compound A86: 59 mg, ESI$[M+H]^+$=333.1

$^1$H NMR (400 MHz, $CDCl_3$) δ 7.47 (d, J=4.5 Hz, 1H), 7.36-7.15 (m, 5H), 6.42 (q, J=7.1 Hz, 1H), 5.01-4.91 (m, 2H), 4.85-4.66 (m, 2H), 2.24 (s, 3H), 1.89 (d, J=7.1 Hz, 3H).

The compound A87: 33 mg, ESI$[M+H]^+$=317.2

$^1$H NMR (400 MHz, $CDCl_3$) δ 7.46 (d, J=4.5 Hz, 1H), 7.39-7.15 (m, 5H), 6.38 (q, J=7.1 Hz, 1H), 6.29-6.17 (m, 1H), 5.36-5.20 (m, 2H), 4.94-4.56 (m, 4H), 1.88 (d, J=7.0 Hz, 3H).

The compound A88: 79 mg, ESI$[M+H]^+$=355.2

$^1$H NMR (400 MHz, $CDCl_3$) δ 7.45 (d, J=4.5 Hz, 1H), 7.40-7.16 (m, 5H), 6.41 (q, J=7.1 Hz, 1H), 2.21-1.92 (m, 4H), 1.88 (d, J=7.1 Hz, 3H), 1.86 (s, 3H), 1.72-1.24 (m, 6H).

The compound A89: 101 mg, ESI$[M+H]^+$=375.2

$^1$H NMR (400 MHz, $CDCl_3$) δ 7.41 (d, J=4.5 Hz, 1H), 7.36-7.15 (m, 5H), 6.37 (q, J=7.1 Hz, 1H), 3.52 (s, 3H), 2.33-2.01 (m, 2H), 1.94-1.22 (m, 11H).

The compound A90: 49 mg, ESI$[M+H]^+$=343.2

$^1$H NMR (400 MHz, $CDCl_3$) δ 7.40 (d, J=4.5 Hz, 1H), 7.35-7.12 (m, 5H), 6.39 (q, J=7.1 Hz, 1H), 2.51-2.28 (m, 7H), 1.88 (d, J=7.1 Hz, 3H), 1.84-1.70 (m, 2H).

The preparation method of the target compounds A91~A114 was the similar as the compounds A1, A49 and A70. 3,4-Difluoro-1H-pyrazole-5 carboxylic acid ethyl ester, 4-chloro-1H-pyrazole-5-carboxylate ethyl ester or 4-trifluoromethyl-1H-pyrazole-5 carboxylic acid ethyl ester reacted with S-1-phenylethan-1-ol under $PPh_3$ and DEAD to give corresponding intermediates, which were hydrolyzed by NaOH to give the corresponding carboxylic acid. The carboxylic acid reacted with a series of alcohols by DCC condensation according to general procedure A to give the target compounds.

The compound A91: 89 mg, ESI$[M+H]^+$=305.1

$^1$H NMR (400 MHz, $CDCl_3$) δ 7.35-7.18 (m, 5H), 6.52-6.44 (m, 1H), 4.90-4.69 (m, 2H), 1.88 (d, J=2.2 Hz, 3H), 1.88 (d, J=7.1 Hz, 3H).

The compound A92: 20 mg, ESI$[M+H]^+$=347.2

$^1$H NMR (400 MHz, $CDCl_3$) δ 7.35-7.20 (m, 5H), 6.53-6.41 (m, 1H), 5.67 (t, J=6.5 Hz, 1H), 5.05-4.64 (m, 6H), 1.86 (d, J=7.1 Hz, 3H).

The compound A93: 77 mg, ESI$[M+H]^+$=391.1

$^1$H NMR (400 MHz, $CDCl_3$) δ 7.34-7.21 (m, 5H), 6.51-6.40 (m, 1H), 3.55 (s, 3H), 2.50-2.17 (m, 4H), 1.85 (d, J=7.0 Hz, 3H), 1.81-1.60 (m, 4H).

The compound A94: 60 mg, ESI$[M+H]^+$=337.2

$^1$H NMR (400 MHz, $CDCl_3$) δ 7.36-7.21 (m, 5H), 6.54-6.38 (m, 1H), 4.87-4.76 (m, 1H), 3.70-3.55 (m, 1H), 3.27 (s, 3H), 2.97-2.73 (m, 2H), 2.20-2.03 (m, 2H), 1.84 (d, J=7.1 Hz, 3H).

The compound A95: 26 mg, ESI[M+H]$^+$=345.2

$^1$H NMR (400 MHz, $CDCl_3$) δ 7.34-7.20 (m, 5H), 6.51-6.34 (m, 1H), 6.00-5.77 (m, 1H), 5.68-5.41 (m, 2H), 1.88 (d, J=7.0 Hz, 3H), 1.78 (s, 3H), 1.74 (s, 3H).

The compound A96: 20 mg, ESI[M+H]$^+$=333.1

$^1$H NMR (400 MHz, $CDCl_3$) δ 7.35-7.23 (m, 5H), 6.50-6.33 (m, 1H), 1.87 (d, J=7.1 Hz, 3H), 1.84 (s, 3H), 1.74 (s, 3H), 1.65 (s, 3H).

The compound A97: 76 mg, ESI[M+H]$^+$=373.2

$^1$H NMR (400 MHz, $CDCl_3$) δ 7.34-7.21 (m, 5H), 6.51-6.32 (m, 1H), 2.25-1.92 (m, 4H), 1.86 (d, J=7.1 Hz, 3H), 1.84 (s, 3H), 1.72-1.24 (m, 6H).

The compound A98: 64 mg, ESI[M+H]$^+$=361.2

$^1$H NMR (400 MHz, $CDCl_3$) δ 7.36-7.20 (m, 5H), 6.49-6.37 (m, 1H), 2.53-2.30 (m, 7H), 1.86 (d, J=7.1 Hz, 3H), 1.86-1.74 (m, 2H).

The compound A99: 20 mg, ESI[M+H]$^+$=337.2

$^1$H NMR (400 MHz, $CDCl_3$) δ 7.62 (s, 1H), 7.35-7.20 (m, 5H), 6.48 (q, J=7.1 Hz, 1H), 4.97-4.69 (m, 2H), 1.92-1.81 (m, 6H).

The compound A100: 35 mg, ESI[M+H]$^+$=379.2

$^1$H NMR (400 MHz, $CDCl_3$) δ 7.64 (s, 1H), 7.37-7.23 (m, 5H), 6.51 (q, J=7.1 Hz, 1H), 5.64 (t, J=6.7 Hz, 1H), 5.05-4.72 (m, 6H), 1.87 (d, J=7.1 Hz, 3H).

The compound A101: 35 mg, ESI[M+H]$^+$=423.3

$^1$H NMR (400 MHz, $CDCl_3$) δ 7.66 (s, 1H), 7.35-7.21 (m, 5H), 6.47 (q, J=7.1 Hz, 1H), 3.52 (s, 3H), 2.50-2.16 (m, 4H), 1.84 (d, J=7.1 Hz, 3H), 1.80-1.58 (m, 4H).

The compound A102: 72 mg, ESI[M+H]$^+$=369.2

$^1$H NMR (400 MHz, $CDCl_3$) δ 7.60 (s, 1H), 7.34-7.20 (m, 5H), 6.51 (q, J=7.1 Hz, 1H), 4.85-4.70 (m, 1H), 3.70-3.52 (m, 1H), 3.22 (s, 3H), 2.91-2.68 (m, 2H), 2.22-2.01 (m, 2H), 1.85 (d, J=7.1 Hz, 3H).

The compound A103: 28 mg, ESI[M+H]$^+$=377.2

$^1$H NMR (400 MHz, $CDCl_3$) δ 7.64 (s, 1H), 7.35-7.19 (m, 5H), 6.47 (q, J=7.1 Hz, 1H), 5.88-5.40 (m, 3H), 1.86 (d, J=7.1 Hz, 3H), 1.77 (s, 3H), 1.75 (s, 3H).

The compound A104: 62 mg, ESI[M+H]$^+$=365.2

$^1$H NMR (400 MHz, $CDCl_3$) δ 7.62 (s, 1H), 7.36-7.23 (m, 5H), 6.52 (q, J=7.1 Hz, 1H), 1.87 (d, J=7.1 Hz, 3H), 1.85 (s, 3H), 1.73 (s, 3H), 1.68 (s, 3H).

The compound A105: 35 mg, ESI[M+H]$^+$=405.2

$^1$H NMR (400 MHz, $CDCl_3$) δ 7.63 (s, 1H), 7.36-7.20 (m, 5H), 6.50 (q, J=7.1 Hz, 1H), 2.20-1.89 (m, 4H), 1.86 (d, J=7.1 Hz, 3H), 1.85 (s, 3H), 1.70-1.21 (m, 6H).

The compound A106: 43 mg, ESI[M+H]$^+$=393.2

$^1$H NMR (400 MHz, $CDCl_3$) δ 7.66 (s, 1H), 7.38-7.19 (m, 5H), 6.48 (q, J=7.1 Hz, 1H), 2.50-2.20 (m, 7H), 1.87 (d, J=7.1 Hz, 3H), 1.85-1.66 (m, 2H).

The compound A107: 109 mg, ESI[M+H]$^+$=303.0

$^1$H NMR (400 MHz, $CDCl_3$) δ 7.44 (s, 1H), 7.35-7.20 (m, 5H), 6.46 (q, J=6.9 Hz, 1H), 4.88-4.70 (m, 2H), 1.89-1.83 (m, 6H).

The compound A108: 19 mg, ESI[M+H]$^+$=345.2

$^1$H NMR (400 MHz, $CDCl_3$) δ 7.44 (s, 1H), 7.36-7.17 (m, 5H), 6.40 (q, J=7.1 Hz, 1H), 5.64 (t, J=6.5 Hz, 1H), 5.00-4.70 (m, 6H), 1.86 (d, J=7.1 Hz, 3H).

The compound A109: 77 mg, ESI[M+H]$^+$=389.2

$^1$H NMR (400 MHz, $CDCl_3$) δ 7.45 (s, 1H), 7.34-7.15 (m, 5H), 6.45 (q, J=7.1 Hz, 1H), 3.52 (s, 3H), 2.45-2.15 (m, 4H), 1.84 (d, J=7.1 Hz, 3H), 1.80-1.52 (m, 4H).

The compound A110: 109 mg, ESI[M+H]$^+$=335.1

$^1$H NMR (400 MHz, $CDCl_3$) δ 7.43 (s, 1H), 7.35-7.11 (m, 5H), 6.46 (q, J=7.1 Hz, 1H), 4.85-4.70 (m, 1H), 3.69-3.51 (m, 1H), 3.22 (s, 3H), 2.91-2.65 (m, 2H), 2.20-2.01 (m, 2H), 1.85 (d, J=7.1 Hz, 3H).

The compound A111: 26 mg, ESI[M+H]$^+$=343.2

$^1$H NMR (400 MHz, $CDCl_3$) δ 7.46 (s, 1H), 7.37-7.15 (m, 5H), 6.48 (q, J=7.1 Hz, 1H), 5.91-5.45 (m, 3H), 1.86 (d, J=7.1 Hz, 3H), 1.77 (s, 3H), 1.75 (s, 3H).

The compound A112: 53 mg, ESI[M+H]$^+$=331.1

$^1$H NMR (400 MHz, $CDCl_3$) δ 7.45 (s, 1H), 7.35-7.16 (m, 5H), 6.46 (q, J=7.1 Hz, 1H), 1.88 (d, J=7.1 Hz, 3H), 1.85 (s, 3H), 1.74 (s, 3H), 1.67 (s, 3H).

The compound A113: 29 mg, ESI[M+H]$^+$=371.2

$^1$H NMR (400 MHz, $CDCl_3$) δ 7.45 (s, 1H), 7.38-7.15 (m, 5H), 6.48 (q, J=7.1 Hz, 1H), 2.25-1.91 (m, 4H), 1.87 (d, J=7.1 Hz, 3H), 1.85 (s, 3H), 1.78-1.21 (m, 6H).

The compound A114: 45 mg, ESI[M+H]$^+$=359.1

$^1$H NMR (400 MHz, $CDCl_3$) δ 7.44 (s, 1H), 7.37-7.12 (m, 5H), 6.50 (q, J=7.1 Hz, 1H), 2.55-2.24 (m, 7H), 1.86 (d, J=7.1 Hz, 3H), 1.83-1.65 (m, 2H).

Examples of Group B compounds are as follows:

Example 1 Preparation of Compounds B1 and B2

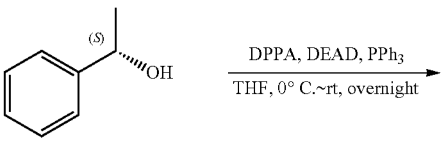

1-1

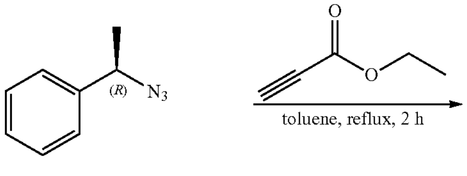

1-2

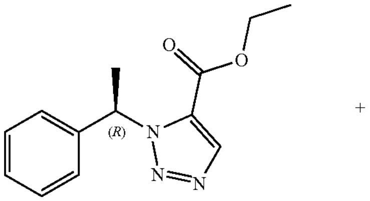

Compound B1

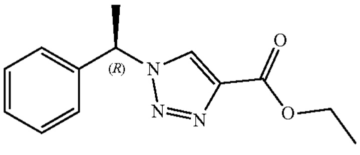

Compound B2

1. Preparation of (R)-(1-Azidoethyl)benzene (1-2)

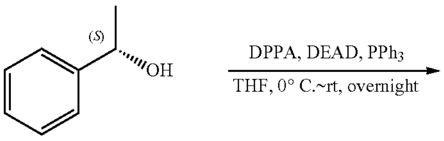

1-1

-continued

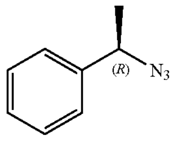

1-2

In an ice bath, (S)-1-phenylethan-1-ol (1-1) (20 g, 164 mmol) and $PPh_3$ (85.9 g, 328 mmol) were dissolved in THF (300 mL) at 0° C. DEAD (57.1 g, 328 mmol) in THF (50 mL) was added dropwise into the mixture at the rate of 10 mmol/min, then DPPA (54.1 g, 197 mmol) was added dropwise into the mixture at the rate of 6 mmol/min. The mixture was warmed to room temperature slowly and allowed to react for overnight. The reaction was monitored by TLC until completion, then it was quenched with brine (150 mL) and extracted with hexane (3×50 mL). The mixture was divided into three layers, collected the top layer. The combined organic layers were washed with saturated brine (50 mL), dried over anhydrous sodium sulfate, filtered and concentrated under reduced pressure. The residue was purified by silica gel column chromatography (ethyl acetate/petroleum ether (v/v)=1/100~1/50) and the eluate was monitored by TLC (ethyl acetate/petroleum ether (v/v)=1/10). The fraction with Rf=0.5~0.6 was collected and dried to give compound 1-2 (20.0 g, yield 83%).

2. Preparation of Compounds B1 and B2

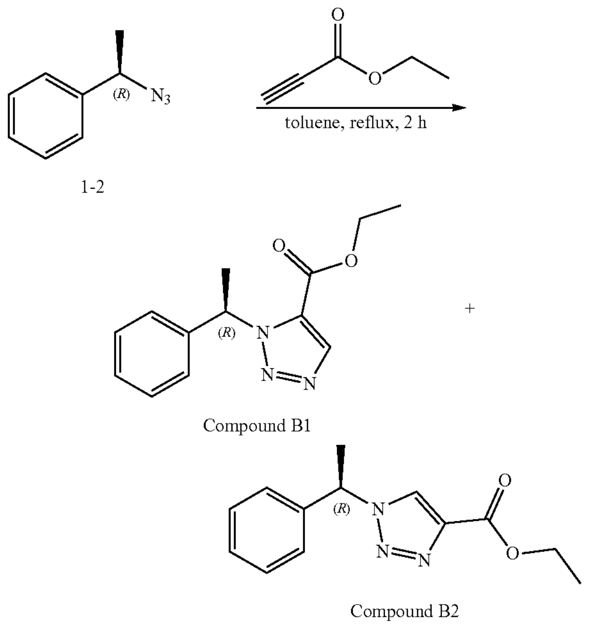

1-2

Compound B1

Compound B2

At room temperature, (R)-(1-azidoethyl)benzene 1-2 (4.8 g, 32.6 mmol) and ethyl propiolate (6.4 g, 65.2 mmol) were dissolved in toluene (100 mL), then the mixture was refluxed for 2 hrs. The reaction was monitored by TLC until completion, then it was quenched with the saturated brine (30 mL) and extracted with ethyl acetate (3×50 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v)=1/10-1/1) and the eluate was monitored by TLC (ethyl acetate/petroleum ether (v/v)=1/5). The fraction with Rf=0.5~0.6 was collected and dried to give the products B1 (1.3 g, yield 16%) and B2 (4.0 g, yield 50%).

The compound B1: ESI$[M+H]^+$=246.3

$^1$H NMR (400 MHz, $CDCl_3$) δ 8.17 (s, 1H), 7.42-7.29 (m, 5H), 6.58 (q, J=7.1 Hz, 1H), 4.45-4.26 (m, 2H), 2.08 (d, J=7.1 Hz, 3H), 1.37 (t, J=7.1 Hz, 3H).

The compound B2: ESI$[M+H]^+$=246.3

$^1$H NMR (400 MHz, $CDCl_3$) δ 7.97 (s, 1H), 7.46-7.36 (m, 3H), 7.35-7.29 (m, 2H), 5.91 (q, J=7.1 Hz, 1H), 4.42 (q, J=7.1 Hz, 2H), 2.03 (d, J=7.1 Hz, 3H), 1.41 (t, J=7.1 Hz, 3H).

Example 2 Preparation of Compounds B3~B32

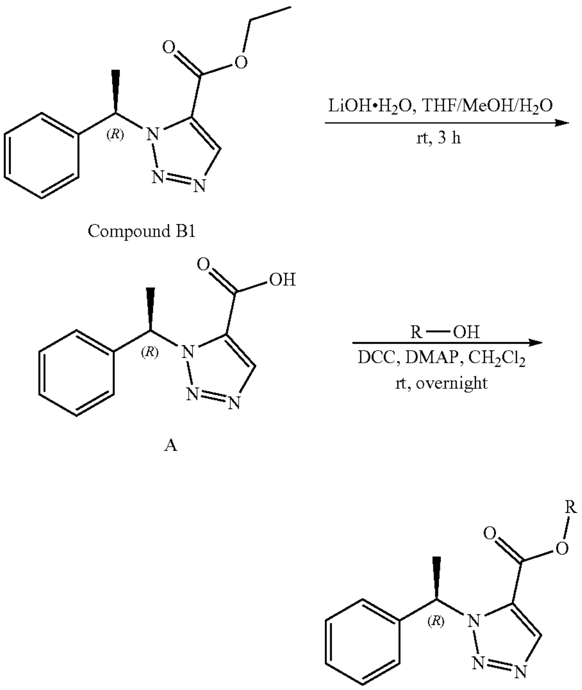

Compound B1

A

Compound B3~B32

1. Preparation of (R)-1-(1-phenylethyl)-1H-1,2,3-triazole-5-carboxylic acid (A)

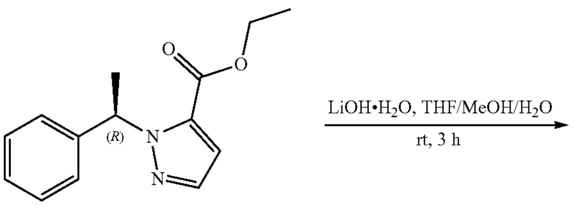

Compound B1

-continued

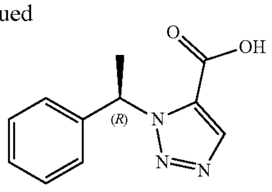

A

At room temperature, $LiOH{\cdot}H_2O$ (220 mg, 5.24 mmol) was added into the mixture of B1 (643 mg, 2.62 mmol) in $MeOH/THF/H_2O$ (3 mL, 1/1/1), then it was stirred at room temperature overnight. The reaction was monitored by TLC until completion. The mixture was concentrated under reduced pressure and $H_2O$ (10 mL) was added. The mixture was adjusted to PH=4-5 with 1 N hydrochloric acid and extracted with dichloromethane (3×15 mL). The combined organic layers were washed with saturated brine (50 mL), dried over anhydrous sodium sulfate, filtered and concentrated under reduced pressure to give compound A (545 mg, yield 96%) as a white solid. $ESI[M+H]^+$=218.2

$^1H$ NMR (400 MHz, $CDCl_3$) δ 8.25 (s, 1H), 7.38-7.30 (m, 5H), 6.58-6.52 (m, 1H), 2.10 (d, J=7.0 Hz, 3H).

2. The Preparation of Compounds B3~B32

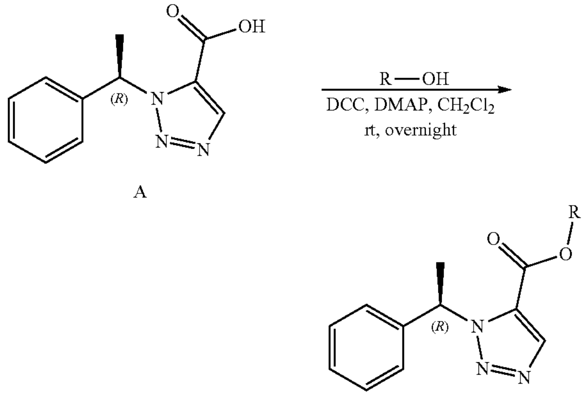

A

Compound B3~B32

The target compounds B3~B32 were prepared according to the general procedure A, using (R)-1-(1-phenylethyl)-1H-1,2,3-triazole-5-carboxylic acid A (100 mg, 0.46 mmol) and corresponding alcohols (0.69 mmol) as starting materials. The crude product was purified by Prep-TLC (ethyl acetate/petroleum ether (v/v)=1/5) and the fraction with Rf=0.4~0.6 was collected and dried to give target compounds as colorless oil.

The compound B3: 21 mg, $ESI[M+H]^+$=312.3

$^1H$ NMR (400 MHz, $CDCl_3$) δ 8.19 (s, 1H), 7.39-7.29 (m, 5H), 6.48 (q, J=7.0 Hz, 1H), 5.64 (t, J=6.6 Hz, 1H), 5.04-4.75 (m, 6H), 2.09 (d, J=7.1 Hz, 3H).

The compound B4: 82 mg, $ESI[M+H]^+$=342.1

$^1H$ NMR (400 MHz, $CDCl_3$) δ 8.18 (s, 1H), 7.38-7.29 (m, 5H), 6.46 (q, J=7.0 Hz, 1H), 3.57 (s, 3H), 2.82-2.55 (m, 4H), 2.05-1.88 (m, 2H), 2.07 (d, J=7.1 Hz, 3H).

The compound B5: 77 mg, $ESI[M+H]^+$=296.1

$^1H$ NMR (400 MHz, $CDCl_3$) δ 8.16 (s, 1H), 7.39-7.28 (m, 5H), 6.47 (q, J=7.0 Hz, 1H), 5.87-5.60 (m, 3H), 5.59-5.23 (m, 1H), 2.07 (d, J=7.1 Hz, 3H), 1.66 (t, J=6.0 Hz, 3H).

The compound B6: 105 mg, $ESI[M+H]^+$=272.2

$^1H$ NMR (400 MHz, $CDCl_3$) δ 8.16 (s, 1H), 7.41-7.29 (m, 5H), 6.56 (q, J=7.1 Hz, 1H), 5.17 (p, J=7.5 Hz, 1H), 2.51-2.34 (m, 2H), 2.25-2.11 (m, 2H), 2.08 (d, J=7.1 Hz, 3H), 1.94-1.82 (m, 1H), 1.77-1.63 (m, 1H).

The compound B7: 96 mg, $ESI[M+H]^+$=272.2

$^1H$ NMR (400 MHz, $CDCl_3$) δ 8.19 (s, 1H), 7.39-7.29 (m, 5H), 6.58 (q, J=7.0 Hz, 1H), 4.21-4.04 (m, 2H), 2.09 (d, J=7.1 Hz, 3H), 1.26-1.14 (m, 1H), 0.69-0.58 (m, 2H), 0.42-0.28 (m, 2H).

The compound B8: 46 mg, $ESI[M+H]^+$=302.2

$^1H$ NMR (400 MHz, $CDCl_3$) δ 8.17 (s, 1H), 7.40-7.30 (m, 5H), 6.54 (q, J=7.0 Hz, 1H), 4.89-4.80 (m, 1H), 3.70-3.61 (m, 1H), 3.28 (s, 3H), 2.95-2.78 (m, 2H), 2.18-2.10 (m, 2H), 2.08 (d, J=7.1 Hz, 3H).

The compound B9: 33 mg, $ESI[M+H]^+$=298.0

$^1H$ NMR (400 MHz, $CDCl_3$) δ 7.97 (s, 1H), 7.46-7.36 (m, 3H), 7.35-7.29 (m, 2H), 5.91 (q, J=7.1 Hz, 1H), 4.85-4.73 (m, 2H), 4.35-4.18 (m, 2H), 2.89-2.71 (m, 2H), 2.74-2.29 (m, 3H), 2.03 (d, J=7.1 Hz, 3H).

The compound B10: 85 mg, $ESI[M+H]^+$=258.3

$^1H$ NMR (400 MHz, $CDCl_3$) δ 8.19 (s, 1H), 7.40-7.29 (m, 5H), 6.57 (q, J=7.3 Hz, 1H), 6.05-5.90 (m, 1H), 5.44-5.28 (m, 2H), 4.87-4.71 (m, 2H), 2.09 (d, J=7.1 Hz, 3H).

The compound B11: 20 mg, $ESI[M+H]^+$=338.2

$^1H$ NMR (400 MHz, $CDCl_3$) δ 8.24 (s, 1H), 7.41-7.29 (m, 5H), 6.55 (q, J=7.1 Hz, 1H), 5.60 (s, 1H), 4.93 (d, J=3.8 Hz, 2H), 2.35-2.18 (m, 2H), 2.17-2.03 (m, 5H), 1.62-1.49 (m, 4H), 1.46-1.33 (m, 2H).

The compound B12: 39 mg, $ESI[M+H]^+$=274.3

$^1H$ NMR (400 MHz, $CDCl_3$) δ 8.08 (s, 1H), 7.40-7.30 (m, 5H), 6.59 (q, J=6.7 Hz, 1H), 2.08 (d, J=7.0 Hz, 3H), 1.55 (s, 9H).

The compound B13: 94 mg, $ESI[M+H]^+$=286.3

$^1H$ NMR (400 MHz, $CDCl_3$) δ 8.17 (s, 1H), 7.42-7.28 (m, 5H), 6.58 (q, J=7.5 Hz, 1H), 5.89-5.74 (m, 1H), 5.41-5.17 (m, 3H), 2.13-2.03 (m, 3H), 1.77-1.67 (m, 2H), 1.00-0.87 (m, 3H).

The compound B14: 55 mg, $ESI[M+H]^+$=288.3

$^1H$ NMR (400 MHz, $CDCl_3$) δ 8.16 (s, 1H), 7.41-7.29 (m, 5H), 6.48 (q, J=7.1 Hz, 1H), 4.81 (dd, J=27.0, 7.3 Hz, 2H), 4.57 (t, J=6.6 Hz, 2H), 2.09 (d, J=7.1 Hz, 3H), 1.77 (s, 3H).

The compound B15: 15 mg, $ESI[M+H]^+$=340.3

$^1H$ NMR (400 MHz, $CDCl_3$) δ 8.24 (s, 1H), 7.37-7.30 (m, 5H), 6.50 (q, J=7.2 Hz, 1H), 2.45-2.38 (m, 2H), 2.36-2.28 (m, 2H), 2.12 (d, J=7.0 Hz, 3H), 2.06 (s, 3H), 1.83-1.76 (m, 2H), 1.75-1.68 (m, 2H).

The compound B16: 15 mg, $ESI[M+H]^+$=288.2

$^1H$ NMR (400 MHz, $CDCl_3$) δ 8.19 (s, 1H), 7.38-7.29 (m, 5H), 6.42 (q, J=7.2 Hz, 1H), 4.29-4.21 (m, 1H), 2.59-2.44 (m, 2H), 2.25-2.07 (m, 4H), 2.06 (d, J=7.1 Hz, 3H).

The compound B17: 86 mg, $ESI[M+H]^+$=260.2

$^1H$ NMR (400 MHz, $CDCl_3$) δ 8.14 (s, 1H), 7.43-7.29 (m, 5H), 6.58 (q, J=7.1 Hz, 1H), 5.29-5.13 (m, 1H), 2.08 (d, J=7.1 Hz, 3H), 1.35 (d, J=6.2 Hz, 3H), 1.32 (d, J=6.3 Hz, 3H).

The compound B18: 98 mg, $ESI[M+H]^+$=258.3

$^1H$ NMR (400 MHz, $CDCl_3$) δ 8.10 (s, 1H), 7.42-7.28 (m, 5H), 6.55 (q, J=7.1 Hz, 1H), 4.36-4.25 (m, 1H), 2.08 (d, J=7.1 Hz, 3H), 0.92-0.70 (m, 4H).

The compound B19: 102 mg, $ESI[M+H]^+$=300.2

$^1H$ NMR (400 MHz, $CDCl_3$) δ 8.12 (s, 1H), 7.43-7.28 (m, 5H), 6.54 (q, J=7.1 Hz, 1H), 6.24-6.13 (m, 1H), 5.37-5.14 (m, 2H), 4.97-4.61 (m, 4H), 2.08 (d, J=7.1 Hz, 3H).

The compound B20: 56 mg, ESI$[M+H]^+$=338.3

$^1$H NMR (400 MHz, $CDCl_3$) δ 8.11 (s, 1H), 7.41-7.25 (m, 5H), 6.56 (q, J=7.1 Hz, 1H), 2.17-2.02 (m, 5H), 2.01-1.90 (m, 2H), 1.87 (s, 3H), 1.69-1.25 (m, 6H).

The compound B21: 49 mg, ESI$[M+H]^+$=314.2

$^1$H NMR (400 MHz, $CDCl_3$) δ 8.13 (s, 1H), 7.44-7.28 (m, 5H), 6.52 (q, J=7.1 Hz, 1H), 5.97-5.61 (m, 2H), 5.03-4.71 (m, 3H), 4.71 (d, J=8.0 Hz, 1H), 2.08 (d, J=7.1 Hz, 3H), 1.73-1.60 (m, 3H).

The compound B22: 34 mg, ESI$[M+H]^+$=318.2

$^1$H NMR (400 MHz, $CDCl_3$) δ 8.12 (s, 1H), 7.43-7.28 (m, 5H), 6.53 (q, J=7.1 Hz, 1H), 4.41-4.33 (m, 4H), 3.33 (s, 2H), 2.08 (d, J=7.1 Hz, 3H), 1.31 (s, 3H).

The compound B23: 75 mg, ESI$[M+H]^+$=302.2

$^1$H NMR (400 MHz, $CDCl_3$) δ 8.11 (s, 1H), 7.42-7.29 (m, 5H), 6.53 (q, J=7.1 Hz, 1H), 4.52-4.32 (m, 6H), 2.08 (d, J=7.1 Hz, 3H), 1.31 (s, 3H).

The compound B24: 29 mg, ESI$[M+H]^+$=302.2

$^1$H NMR (400 MHz, $CDCl_3$) δ 8.12 (s, 1H), 7.43-7.28 (m, 5H), 6.55 (q, J=7.1 Hz, 1H), 2.08 (d, J=7.1 Hz, 3H), 2.03 (s, 3H), 1.49 (s, 3H), 1.45 (s, 3H).

The compound B25: 54 mg, ESI$[M+H]^+$=318.2

$^1$H NMR (400 MHz, $CDCl_3$) δ 8.13 (s, 1H), 7.45-7.29 (m, 5H), 6.53 (q, J=7.1 Hz, 1H), 2.12 (s, 3H), 2.05 (d, J=7.1 Hz, 3H), 1.55 (s, 3H), 1.44 (s, 3H).

The compound B26: 45 mg, ESI$[M+H]^+$=330.3

$^1$H NMR (400 MHz, $CDCl_3$) δ 8.12 (s, 1H), 7.43-7.29 (m, 5H), 6.52 (q, J=7.1 Hz, 1H), 4.76 (t, J=7.4 Hz, 1H), 3.74 (t, J=7.0 Hz, 1H), 3.64-3.58 (m, 1H), 2.89-2.72 (m, 2H), 2.21-2.07 (m, 2H), 2.10 (d, J=7.1 Hz, 3H), 1.15 (d, J=8.0 Hz, 6H).

The compound B27: 34 mg, ESI$[M+H]^+$=360.3

$^1$H NMR (400 MHz, $CDCl_3$) δ 8.11 (s, 1H), 7.41-7.27 (m, 5H), 6.54 (q, J=7.1 Hz, 1H), 5.07-4.95 (m, 1H), 3.49-3.36 (m, 4H), 2.81-2.66 (m, 2H), 2.32-2.22 (m, 2H), 2.08 (d, J=7.1 Hz, 3H), 1.20 (q, J=7.0 Hz, 6H).

The compound B28: 17 mg, ESI$[M+H]^+$=426.3

$^1$H NMR (400 MHz, $CDCl_3$) δ 8.10 (s, 1H), 7.42-7.28 (m, 5H), 6.55 (q, J=7.1 Hz, 1H), 6.14-5.81 (m, 1H), 3.85-3.62 (m, 1H), 3.59-3.13 (m, 3H), 2.55-2.39 (m, 1H), 2.18-1.92 (m, 7H), 1.91-1.83 (m, 3H), 1.82-1.41 (m, 2H), 1.28-1.14 (m, 4H), 1.08-0.88 (m, 2H).

The compound B29: 38 mg, ESI$[M+H]^+$=328.3

$^1$H NMR (400 MHz, $CDCl_3$) δ 8.12 (s, 1H), 7.44-7.29 (m, 5H), 6.55 (q, J=7.1 Hz, 1H), 4.63-4.49 (m, 1H), 4.32-4.16 (m, 1H), 2.80-2.61 (m, 1H), 2.50-2.01 (m, 7H), 1.98-1.91 (m, 1H), 1.77-1.31 (m, 3H).

The compound B30: 78 mg, ESI$[M+H]^+$=356.3

$^1$H NMR (400 MHz, $CDCl_3$) δ 8.11 (s, 1H), 7.43-7.29 (m, 5H), 6.55 (q, J=7.1 Hz, 1H), 3.50 (s, 3H), 2.48-2.23 (m, 4H), 2.08 (d, J=7.1 Hz, 3H), 1.81-1.63 (m, 4H).

The compound B31: 46 mg, ESI$[M+H]^+$=326.2

$^1$H NMR (400 MHz, $CDCl_3$) δ 8.10 (s, 1H), 7.42-7.28 (m, 5H), 6.55 (q, J=7.1 Hz, 1H), 2.67-2.64 (m, 2H), 2.46-2.44 (m, 2H), 2.08 (d, J=7.1 Hz, 3H), 1.88-1.71 (m, 4H), 1.81-1.72 (m, 2H).

The compound B32: 47 mg, ESI$[M+H]^+$=318.2

$^1$H NMR (400 MHz, $CDCl_3$) δ 8.10 (s, 1H), 7.42-7.28 (m, 5H), 6.55 (q, J=7.1 Hz, 1H), 4.23-4.20 (m, 2H), 3.09-3.07 (m, 2H), 2.94-2.91 (m, 2H), 2.08 (d, J=7.1 Hz, 3H), 1.33 (s, 3H).

Example 3 Preparation of Compounds B33 and B34

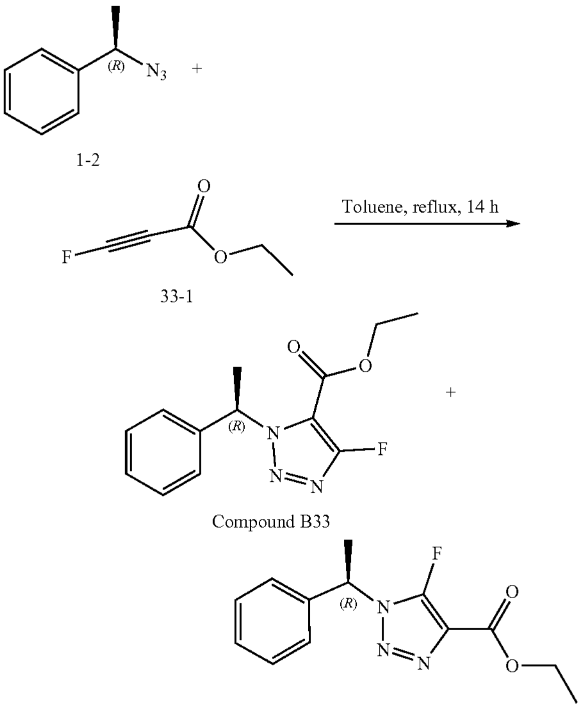

1-2

33-1

Compound B33

Compound B34

At room temperature, (R)-(1-azidoethyl)benzene 1-2 (5.1 g, 34.7 mmol) and ethyl 3-fluoropropiolate (8.1 g, 69.8 mmol) were dissolved in toluene (50 mL), then the mixture was refluxed for 14 hrs. The reaction was monitored by TLC until completion and concentrated under reduced pressure. The residue was purified by silica gel column chromatography (ethyl acetate/petroleum ether (v/v)=1/10-1/1) and the eluate was monitored by TLC (ethyl acetate/petroleum ether (v/v)=1/5). The fraction with Rf=0.5-0.6 was collected and dried to give the products B33 (890 mg, yield 10%) and the B34 (1.2 g, yield 13%).

The compound B33: ESI$[M+H]^+$=264.3

$^1$H NMR (400 MHz, $CDCl_3$) δ 7.42-7.21 (m, 5H), 6.57-6.53 (m, 1H), 4.45-4.26 (m, 2H), 2.02 (d, J=7.1 Hz, 3H), 1.37 (t, J=7.1 Hz, 3H).

The compound B34: ESI$[M+H]^+$=264.3

$^1$H NMR (400 MHz, $CDCl_3$) δ 7.41-7.23 (m, 5H), 6.54-6.51 (m, 1H), 4.41-4.21 (m, 2H), 2.03 (d, J=7.1 Hz, 3H), 1.33 (t, J=7.1 Hz, 3H).

Example 4 Preparation of Compounds B35~B64

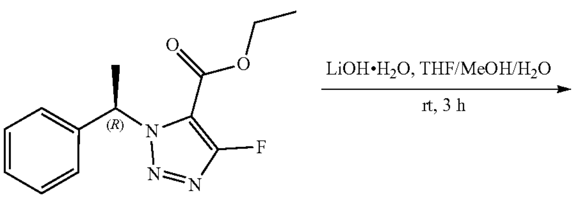

Compound B33

-continued

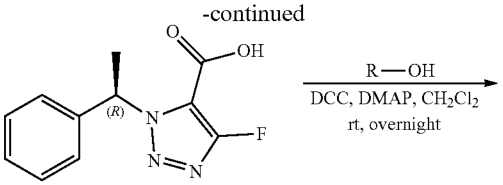

B

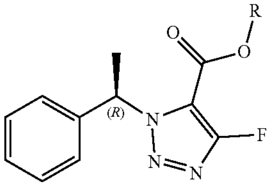

Compound B35~B64

1. Preparation of (R)-4-fluoro-1-(1-phenylethyl-1H-1,2,3-triazole-5-carboxylic acid (B)

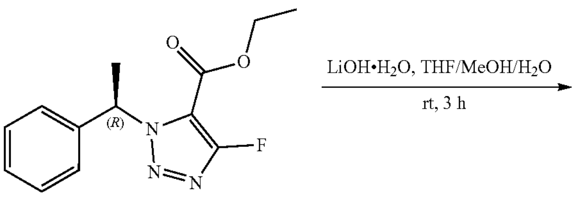

Compound B33

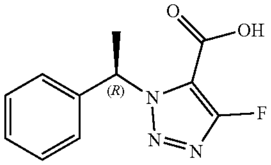

B

At room temperature, LiOH·$H_2O$ (223 mg, 5.32 mmol) was added into the mixture of B33 (700 mg, 2.66 mmol) in MeOH/THF/$H_2O$ (3 mL, 1/1/1), then it was stirred at room temperature overnight. The reaction was monitored by TLC until completion. The mixture was concentrated under reduced pressure and $H_2O$ (10 mL) was added. The mixture was adjusted to PH=4-5 with 1 N hydrochloric acid and extracted with dichloromethane (3×15 mL). The combined organic layers were washed with saturated brine (50 mL), dried over anhydrous sodium sulfate, filtered and concentrated under reduced pressure to give compound A (586 mg, yield 94%) as a white solid. ESI[M+H]$^+$=236.1

$^1$H NMR (400 MHz, $CDCl_3$) δ 7.41-7.14 (m, 5H), 6.55-6.49 (m, 1H), 2.03 (d, J=7.1 Hz, 3H).

2. The Preparation of Compounds B35~B64

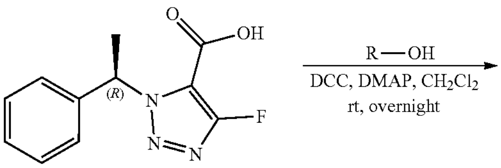

B

-continued

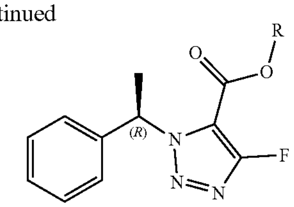

Compound B35~B64

The target compounds B35~B64 were prepared according to the general procedure A, using (R)-4-fluoro-1-(1-phenylethyl)-1H-1,2,3-triazole-5-carboxylic acid B (100 mg, 0.46 mmol) and corresponding alcohols (0.69 mmol) as starting materials. The crude product was purified by Prep-TLC (ethyl acetate/petroleum ether (v/v)=1/5) and the fraction with Rf=0.4~0.6 was collected and dried to give target compounds as colorless oil.

The compound B35: 36 mg, ESI[M+H]$^+$=330.3

$^1$H NMR (400 MHz, $CDCl_3$) δ 7.42-7.28 (m, 5H), 6.57-6.53 (m, 1H), 5.63 (t, J=6.4 Hz, 1H), 5.03-4.75 (m, 6H), 2.02 (d, J=7.1 Hz, 3H).

The compound B36: 52 mg, ESI[M+H]$^+$=360.2

$^1$H NMR (400 MHz, $CDCl_3$) δ 7.41-7.28 (m, 5H), 6.55-6.52 (m, 1H), 3.58 (s, 3H), 2.82-2.55 (m, 4H), 2.05-1.88 (m, 5H).

The compound B37: 48 mg, ESI[M+H]$^+$=314.2

$^1$H NMR (400 MHz, $CDCl_3$) δ 7.42-7.28 (m, 5H), 6.57-6.51 (m, 1H), 5.87-5.69 (m, 3H), 5.61-5.54 (m, 1H), 2.04 (d, J=7.1 Hz, 3H), 1.65 (t, J=5.9 Hz, 3H).

The compound B38: 66 mg, ESI[M+H]$^+$=290.3

$^1$H NMR (400 MHz, $CDCl_3$) δ 7.41-7.27 (m, 5H), 6.57-6.53 (m, 1H), 5.20-5.01 (m, 1H), 2.51-2.34 (m, 2H), 2.24-2.08 (m, 2H), 2.02 (d, J=7.1 Hz, 3H), 1.93-1.62 (m, 2H), 1.77-1.63 (m, 1H).

The compound B39: 67 mg, ESI[M+H]$^+$=290.3

$^1$H NMR (400 MHz, $CDCl_3$) δ 7.43-7.28 (m, 5H), 6.58-6.53 (m, 1H), 4.21-4.04 (m, 2H), 2.01 (d, J=7.1 Hz, 3H), 1.26-1.14 (m, 1H), 0.68-0.28 (m, 4H).

The compound B40: 88 mg, ESI[M+H]$^+$=320.2

$^1$H NMR (400 MHz, $CDCl_3$) δ 7.41-7.27 (m, 5H), 6.56-6.52 (m, 1H), 4.88-4.80 (m, 1H), 3.70-3.60 (m, 1H), 3.29 (s, 3H), 2.94-2.78 (m, 2H), 2.17-2.10 (m, 2H), 2.03 (d, J=7.1 Hz, 3H).

The compound B41: 38 mg, ESI[M+H]$^+$=316.2

$^1$H NMR (400 MHz, $CDCl_3$) δ 7.41-7.26 (m, 5H), 6.57-6.53 (m, 1H), 4.85-4.74 (m, 2H), 4.35-4.17 (m, 2H), 2.85-2.75 (m, 2H), 2.74-2.59 (m, 1H), 2.53-2.39 (m, 2H), 2.01 (d, J=7.1 Hz, 3H).

The compound B42: 45 mg, ESI[M+H]$^+$=276.2

$^1$H NMR (400 MHz, $CDCl_3$) δ 7.42-7.28 (m, 5H), 6.57-6.53 (m, 1H), 6.05-5.90 (m, 1H), 5.44-5.28 (m, 2H), 4.87-4.71 (m, 2H), 2.04 (d, J=7.1 Hz, 3H).

The compound B43: 25 mg, ESI[M+H]$^+$=356.3

$^1$H NMR (400 MHz, $CDCl_3$) δ 7.44-7.29 (m, 5H), 6.56-6.52 (m, 1H), 5.61 (s, 1H), 4.91 (d, J=3.8 Hz, 2H), 2.35-2.18 (m, 2H), 2.17-2.02 (m, 5H), 1.62-1.33 (m, 6H).

The compound B44: 47 mg, ESI[M+H]$^+$=292.2

$^1$H NMR (400 MHz, $CDCl_3$) δ 7.41-7.28 (m, 5H), 6.55-6.51 (m, 1H), 2.02 (d, J=7.1 Hz, 3H), 1.55 (s, 9H).

The compound B45: 39 mg, ESI[M+H]$^+$=304.3

$^1$H NMR (400 MHz, $CDCl_3$) δ 7.41-7.28 (m, 5H), 6.55-6.53 (m, 1H), 5.88-5.73 (m, 1H), 5.40-5.17 (m, 3H), 2.01 (d, J=7.1 Hz, 3H), 1.77-1.67 (m, 2H), 1.03-0.81 (m, 3H).

The compound B46: 67 mg, ESI[M+H]$^+$=306.2

$^1$H NMR (400 MHz, $CDCl_3$) δ 7.43-7.28 (m, 5H), 6.57-6.53 (m, 1H), 4.87-4.70 (m, 2H), 4.60-4.41 (m, 2H), 2.02 (d, J=7.1 Hz, 3H), 1.77 (s, 3H).

The compound B47: 74 mg, ESI[M+H]$^+$=358.2

$^1$H NMR (400 MHz, $CDCl_3$) δ 7.44-7.29 (m, 5H), 6.58-6.54 (m, 1H), 2.45-2.38 (m, 2H), 2.36-2.28 (m, 2H), 2.06 (s, 3H), 2.01 (d, J=7.1 Hz, 3H), 1.83-1.63 (m, 4H).

The compound B48: 46 mg, ESI[M+H]$^+$=306.2

$^1$H NMR (400 MHz, $CDCl_3$) δ 7.42-7.27 (m, 5H), 6.56-6.53 (m, 1H), 4.28-4.21 (m, 1H), 2.56-2.44 (m, 2H), 2.25-2.08 (m, 4H), 2.01 (d, J=7.0 Hz, 3H).

The compound B49: 75 mg, ESI[M+H]$^+$=278.3

$^1$H NMR (400 MHz, $CDCl_3$) δ 7.42-7.28 (m, 5H), 6.57-6.53 (m, 1H), 5.29-5.13 (m, 1H), 2.02 (d, J=7.1 Hz, 3H), 1.36 (d, J=6.3 Hz, 3H), 1.33 (d, J=6.3 Hz, 3H).

The compound B50: 42 mg, ESI[M+H]$^+$=276.2

$^1$H NMR (400 MHz, $CDCl_3$) δ 7.43-7.26 (m, 5H), 6.58-6.54 (m, 1H), 4.36-4.25 (m, 1H), 2.02 (d, J=7.1 Hz, 3H), 0.92-0.70 (m, 4H).

The compound B51: 28 mg, ESI[M+H]$^+$=318.3

$^1$H NMR (400 MHz, $CDCl_3$) δ 7.42-7.28 (m, 5H), 6.57-6.53 (m, 1H), 6.24-6.13 (m, 1H), 5.22-5.14 (m, 2H), 4.79-4.63 (m, 4H), 2.03 (d, J=7.1 Hz, 3H).

The compound B52: 92 mg, ESI[M+H]$^+$=356.3

$^1$H NMR (400 MHz, $CDCl_3$) δ 7.40-7.28 (m, 5H), 6.56-6.53 (m, 1H), 2.16-2.02 (m, 5H), 2.01-1.90 (m, 2H), 1.86 (s, 3H), 1.69-1.25 (m, 6H).

The compound B53: 46 mg, ESI[M+H]$^+$=332.3

$^1$H NMR (400 MHz, $CDCl_3$) δ 7.42-7.28 (m, 5H), 6.57-6.53 (m, 1H), 5.95-5.64 (m, 2H), 5.02-4.72 (m, 4H), 2.02 (d, J=7.1 Hz, 3H), 1.73-1.60 (m, 3H).

The compound B54: 47 mg, ESI[M+H]$^+$=336.2

$^1$H NMR (400 MHz, $CDCl_3$) δ 7.43-7.25 (m, 5H), 6.55-6.51 (m, 1H), 4.41-4.30 (m, 4H), 3.33 (s, 2H), 2.02 (d, J=7.1 Hz, 3H), 1.31 (s, 3H).

The compound B55: 56 mg, ESI[M+H]$^+$=320.3

$^1$H NMR (400 MHz, $CDCl_3$) δ 7.42-7.28 (m, 5H), 6.57-6.53 (m, 1H), 4.52-4.31 (m, 6H), 2.02 (d, J=7.1 Hz, 3H), 1.36 (s, 3H), The compound B56: 24 mg, ESI[M+H]$^+$=320.3

$^1$H NMR (400 MHz, $CDCl_3$) δ 7.41-7.28 (m, 5H), 6.58-6.53 (m, 1H), 2.04 (d, J=7.1 Hz, 3H), 1.98 (s, 3H), 1.54 (s, 3H), 1.47 (s, 3H).

The compound B57: 16 mg, ESI[M+H]$^+$=336.2

$^1$H NMR (400 MHz, $CDCl_3$) δ 7.42-7.27 (m, 5H), 6.57-6.52 (m, 1H), 2.15 (s, 3H), 2.01 (d, J=7.0 Hz, 3H), 1.57 (s, 3H), 1.48 (s, 3H).

The compound B58: 60 mg, ESI[M+H]$^+$=348.3

$^1$H NMR (400 MHz, $CDCl_3$) δ 7.43-7.29 (m, 5H), 6.56-6.52 (m, 1H), 4.85-4.69 (m, 1H), 3.82-3.521 (m, 2H), 2.90-2.76 (m, 2H), 2.22-2.08 (m, 2H), 2.10 (d, J=7.1 Hz, 3H), 1.18 (d, J=6.1 Hz, 6H).

The compound B59: 31 mg, ESI[M+H]$^+$=378.3

$^1$H NMR (400 MHz, $CDCl_3$) δ 7.42-7.26 (m, 5H), 6.57-6.51 (m, 1H), 5.08-4.95 (m, 1H), 3.48-3.34 (m, 4H), 2.81-2.62 (m, 2H), 2.32-2.22 (m, 2H), 2.01 (d, J=7.1 Hz, 3H), 1.20 (q, J=7.0 Hz, 6H).

The compound B60: 35 mg, ESI[M+H]$^+$=444.3

$^1$H NMR (400 MHz, $CDCl_3$) δ 7.43-7.27 (m, 5H), 6.59-6.54 (m, 1H), 6.15-5.80 (m, 1H), 3.87-3.13 (m, 4H), 2.58-2.35 (m, 1H), 2.18-0.88 (m, 18H).

The compound B61: 42 mg, ESI[M+H]$^+$=346.2

$^1$H NMR (400 MHz, $CDCl_3$) δ 7.42-7.28 (m, 5H), 6.57-6.53 (m, 1H), 4.65-4.11 (m, 2H), 2.82-2.64 (m, 1H), 2.50-1.90 (m, 8H), 1.78-1.31 (m, 3H).

The compound B62: 86 mg, ESI[M+H]$^+$=374.2

$^1$H NMR (400 MHz, $CDCl_3$) δ 7.41-7.27 (m, 5H), 6.57-6.53 (m, 1H), 3.55 (s, 3H), 2.49-2.19 (m, 4H), 2.01 (d, J=7.1 Hz, 3H), 1.82-1.61 (m, 4H).

The compound B63: 88 mg, ESI[M+H]$^+$=344.3

$^1$H NMR (400 MHz, $CDCl_3$) δ 8.11 (s, 1H), 7.43-7.29 (m, 5H), 6.58-6.53 (m, 1H), 2.67-2.61 (m, 2H), 2.46-2.40 (m, 2H), 2.01 (d, J=7.1 Hz, 3H), 1.89-1.85 (m, 2H), 1.81-1.70 (m, 2H).

The compound B64: 88 mg, ESI[M+H]$^+$=336.2

$^1$H NMR (400 MHz, $CDCl_3$) δ 7.42-7.28 (m, 5H), 6.58-6.53 (m, 1H), 4.23-4.20 (m, 2H), 3.09-3.05 (m, 2H), 2.99-2.85 (m, 2H), 2.01 (d, J=7.1 Hz, 3H), 1.33 (s, 3H).

Example 5 Preparation of Compounds B65 and B66

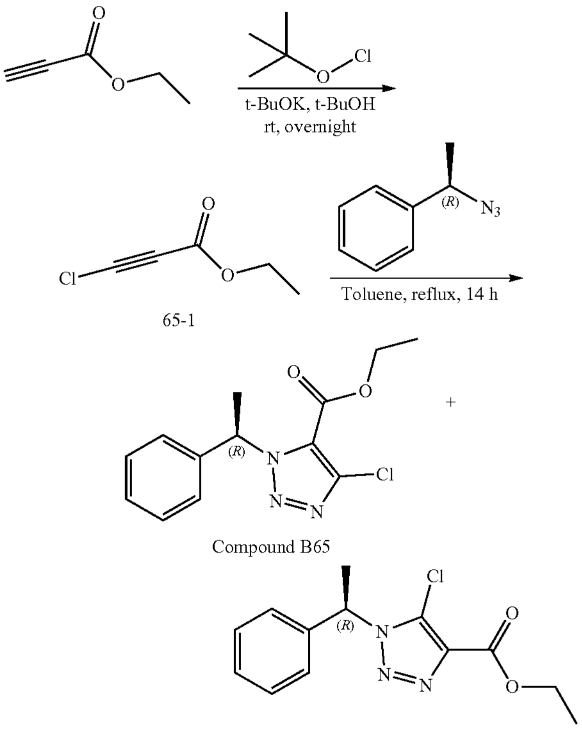

65-1

Compound B65

Compound B66

1. Preparation of ethyl 3-chloropropionate (65-1)

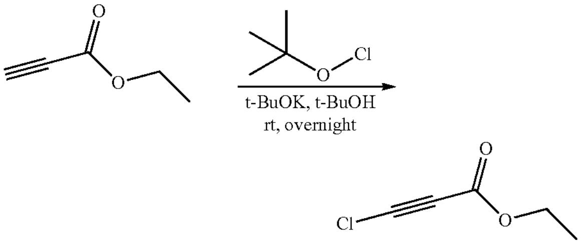

65-1

At room temperature, ethyl propiolate (9.0 g, 91.7 mmol) and tert-butyl hypochlorite (10 g, 92.1 mmol) were dissolved in t-BuOH (100 mL). t-BuOK (2.0 g, 17.8 mmol) was added into the mixture twice within 5 minutes, then it was stirred at room temperature overnight. The reaction was monitored by TLC until completion. The mixture was filtered and concentrated under reduced pressure to give crude product 65-1, which was used for next step directly without further purification.

2. Preparation of Compounds B65 and B66

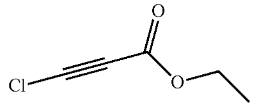

65-1

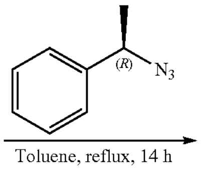

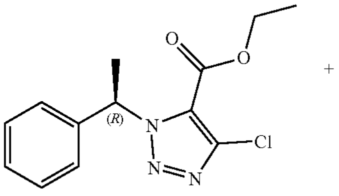

+

Compound B65

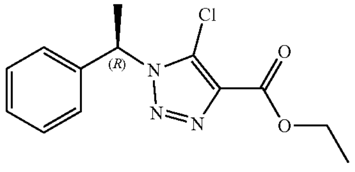

Compound B66

At room temperature, Ethyl 3-chloropropionate (65-1) and (R)-(1-azidoethyl)benzene 1-2 (3.2 g, 21.7 mmol) were dissolved in toluene (100 mL), then the mixture was refluxed for 14 hrs. The reaction was monitored by TLC until completion. The mixture was quenched with the saturated brine (30 mL) and extracted with ethyl acetate (3×30 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v)=1/10-1/1), with TLC (ethyl acetate/petroleum ether (v/v)=1/5) monitoring, and collecting the fraction with Rf=0.5~0.6 to give the products B65 (620 mg, yield 10%) and B66 (3.2 g, yield 53%).

The compound B65: ESI[M+H]$^+$=280.1

$^1$H NMR (400 MHz, $CDCl_3$) δ 7.38-7.29 (m, 5H), 6.52 (q, J=7.1 Hz, 1H), 4.43-4.33 (m, 2H), 2.07 (d, J=7.1 Hz, 3H), 1.38 (t, J=7.1 Hz, 3H).

The compound B66: ESI[M+H]$^+$=280.1

$^1$H NMR (400 MHz, $CDCl_3$) δ 7.40-7.29 (m, 5H), 5.76 (q, J=7.1 Hz, 1H), 4.45 (q, J=7.1 Hz, 2H), 2.11 (d, J=7.1 Hz, 3H), 1.43 (t, J=7.1 Hz, 3H).

Example 6 Preparation of Compounds B67~98

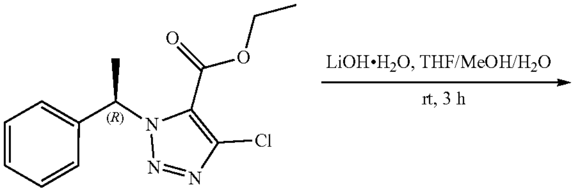

Compound B65

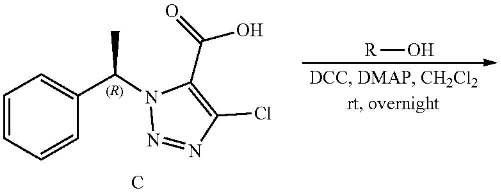

C

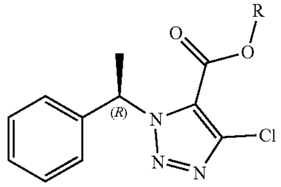

Compound B67~B98

1. Preparation of (R)-4-chloro-1-(1-phenylethyl)-1H-1,2,3-triazole-5-carboxylic acid (C)

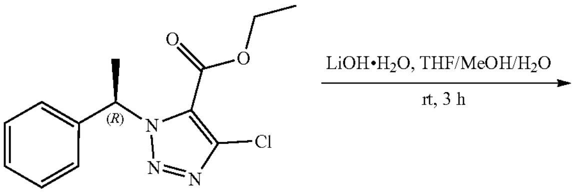

Compound B65

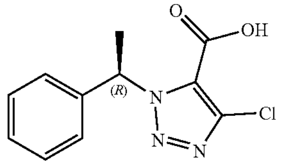

C

At room temperature, $LiOH·H_2O$ (156 mg, 3.72 mmol) was added into the mixture of B65 (520 mg, 1.86 mmol) in $MeOH/THF/H_2O$ (3 mL, 1/1/1), then it was stirred at room temperature overnight. The reaction was monitored by TLC until completion. The mixture was concentrated under reduced pressure and $H_2O$ (10 mL) was added. The mixture was adjusted to PH=4~5 with 1 N hydrochloric acid and extracted with dichloromethane (3×15 mL). The combined organic layers were dried over anhydrous sodium sulfate, filtered and concentrated under reduced pressure to give compound C (445 mg, yield 95%) as a white solid. ESI[M+Na]$^+$=274.1, [M+H−105]$^+$=148.1

$^1$H NMR (400 MHz, $CDCl_3$) δ 7.39-7.29 (m, 5H), 6.52 (q, J=7.1 Hz, 1H), 2.08 (d, J=7.0 Hz, 3H).

2. Preparation of Compounds B67~B98

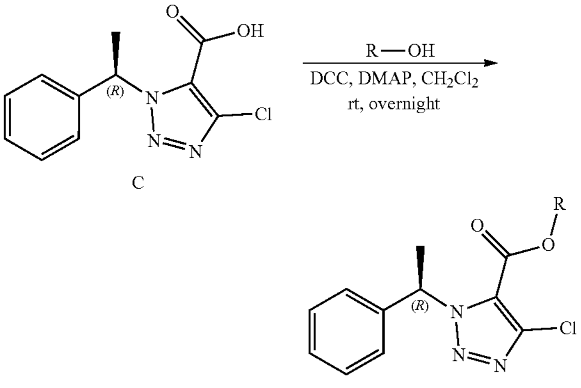

Compound B67~B98

The target compounds B67~B98 were prepared according to the general procedure A, using (R)-4-chloro-1-(1-phenylethyl)-1H-1,2,3-triazole-5-carboxylic acid C (80 mg, 0.32 mmol) and corresponding alcohols (0.48 mmol) as starting materials. The crude product was purified by Prep-TLC (ethyl acetate/petroleum ether (v/v)=1/5) and the fraction with Rf=0.4~0.6 was collected and dried to give target compounds as colorless oil.

The compound B67: 47 mg, ESI[M+H]$^+$=346.1

$^1$H NMR (400 MHz, $CDCl_3$) δ 7.37-7.29 (m, 5H), 6.51 (q, J=7.1 Hz, 1H), 5.64 (t, J=6.6 Hz, 1H), 5.04-4.75 (m, 6H), 2.09 (d, J=7.1 Hz, 3H).

The compound B68: 82 mg, ESI[M+H]$^+$=376.1

$^1$H NMR (400 MHz, $CDCl_3$) δ 7.38-7.29 (m, 5H), 6.52 (q, J=7.1 Hz, 1H), 3.56 (s, 3H), 2.82-2.55 (m, 4H), 2.07 (d, J=7.1 Hz, 3H), 2.05-1.88 (m, 2H).

The compound B69: 28 mg, ESI[M+H]$^+$=330.1

$^1$H NMR (400 MHz, $CDCl_3$) δ 7.39-7.28 (m, 5H), 6.53 (q, J=7.1 Hz, 1H), 5.86-5.68 (m, 3H), 5.61-5.54 (m, 1H), 2.08 (d, J=7.1 Hz, 3H), 1.66 (t, J=5.9 Hz, 3H).

The compound B70: 28 mg, ESI[M+H]$^+$=306.2

$^1$H NMR (400 MHz, $CDCl_3$) δ 7.37-7.26 (m, 5H), 6.50 (q, J=7.1 Hz, 1H), 5.23-5.14 (m, 1H), 2.51-2.37 (m, 2H), 2.26-2.13 (m, 2H), 2.06 (d, J=7.1 Hz, 3H), 1.95-1.85 (m, 1H), 1.77-1.66 (m, 1H).

The compound B71: 80 mg, ESI[M+H]$^+$=306.1

$^1$H NMR (400 MHz, $CDCl_3$) δ 7.36-7.25 (m, 5H), 6.52 (q, J=7.1 Hz, 1H), 4.20-4.03 (m, 2H), 2.08 (d, J=7.1 Hz, 3H), 1.27-1.14 (m, 1H), 0.69-0.25 (m, 4H).

The compound B72: 54 mg, ESI[M+H]$^+$=336.1

$^1$H NMR (400 MHz, $CDCl_3$) δ 7.38-7.30 (m, 5H), 6.52 (q, J=7.1 Hz, 1H), 4.88-4.80 (m, 1H), 3.71-3.61 (m, 1H), 3.27 (s, 3H), 2.96-2.78 (m, 2H), 2.18-2.10 (m, 2H), 2.07 (d, J=7.1 Hz, 3H).

The compound B73: 29 mg, ESI[M+H]$^+$=332.1

$^1$H NMR (400 MHz, $CDCl_3$) δ 7.39-7.29 (m, 5H), 6.53 (q, J=7.1 Hz, 1H), 4.85-4.73 (m, 2H), 4.35-4.18 (m, 2H), 2.89-2.75 (m, 2H), 2.74-2.59 (m, 1H), 2.53-2.39 (m, 2H), 2.07 (d, J=7.1 Hz, 3H).

The compound B74: 22 mg, ESI[M+H]$^+$=292.2

$^1$H NMR (400 MHz, $CDCl_3$) δ 7.40-7.29 (m, 5H), 6.50 (q, J=7.1 Hz, 1H), 6.03-5.91 (m, 1H), 5.48-5.30 (m, 2H), 4.88-4.75 (m, 2H), 2.07 (d, J=7.1 Hz, 3H).

The compound B75: 66 mg, ESI[M+H]$^+$=372.1

$^1$H NMR (400 MHz, $CDCl_3$) δ 7.37-7.27 (m, 5H), 6.52 (q, J=7.1 Hz, 1H), 5.63 (s, 1H), 4.99-4.86 (m, 2H), 2.36-2.18 (m, 2H), 2.15-2.03 (m, 5H), 1.61-1.431 (m, 6H).

The compound B76: 23 mg, ESI[M+H]$^+$=308.1

$^1$H NMR (400 MHz, $CDCl_3$) δ 7.39-7.26 (m, 5H), 6.53 (q, J=7.1 Hz, 1H), 2.07 (d, J=7.1 Hz, 3H), 1.56 (s, 9H).

The compound B77: 33 mg, ESI[M+H]$^+$=320.1

$^1$H NMR (400 MHz, $CDCl_3$) δ 7.39-7.28 (m, 5H), 6.52 (q, J=7.1 Hz, 1H), 5.89-5.75 (m, 1H), 5.42-5.17 (m, 3H), 2.14-2.03 (m, 3H), 1.78-1.67 (m, 2H), 1.01-0.87 (m, 3H).

The compound B78: 46 mg, ESI[M+H]$^+$=322.1

$^1$H NMR (400 MHz, $CDCl_3$) δ 7.36-7.26 (m, 5H), 6.50 (q, J=7.1 Hz, 1H), 4.82-4.80 (m, 2H), 4.59-4.56 (m, 2H), 2.08 (d, J=7.1 Hz, 3H), 1.77 (s, 3H).

The compound B79: 89 mg, ESI[M+H]$^+$=374.1

$^1$H NMR (400 MHz, $CDCl_3$) δ 7.37-7.29 (m, 5H), 6.52 (q, J=7.1 Hz, 1H), 2.46-2.21 (m, 4H), 2.07 (d, J=7.0 Hz, 3H), 2.05 (s, 3H), 1.84-1.61 (m, 4H).

The compound B80: 35 mg, ESI[M+H]$^+$=322.1

$^1$H NMR (400 MHz, $CDCl_3$) δ 7.37-7.29 (m, 5H), 6.38 (q, J=7.2 Hz, 1H), 4.27-4.20 (m, 1H), 2.59-2.44 (m, 2H), 2.23-2.06 (m, 4H), 2.04 (d, J=7.1 Hz, 3H).

The compound B81: 27 mg, ESI[M+H]$^+$=294.3

$^1$H NMR (400 MHz, $CDCl_3$) δ 7.37-7.30 (m, 5H), 6.50 (q, J=7.2 Hz, 1H), 5.27-5.17 (m, 1H), 2.07 (d, J=7.1 Hz, 3H), 1.36 (d, J=6.2 Hz, 3H), 1.32 (d, J=6.3 Hz, 3H).

The compound B82: 55 mg, ESI[M+H]$^+$=292.1

$^1$H NMR (400 MHz, $CDCl_3$) δ 7.38-7.29 (m, 5H), 6.52 (q, J=7.1 Hz, 1H), 4.36-4.25 (m, 1H), 2.08 (d, J=7.1 Hz, 3H), 0.94-0.58 (m, 4H).

The compound B83: 24 mg, ESI[M+H]$^+$=294.2

$^1$H NMR (400 MHz, $CDCl_3$) δ 7.38-7.30 (m, 5H), 6.53 (q, J=7.1 Hz, 1H), 4.34-4.23 (m, 2H), 2.07 (d, J=7.1 Hz, 3H), 1.82-1.72 (m, 2H), 1.02 (t, J=7.4 Hz, 3H).

The compound B84: 39 mg, ESI[M+H]$^+$=296.1

$^1$H NMR (400 MHz, $CDCl_3$) δ 7.36-7.30 (m, 5H), 6.40 (q, J=7.1 Hz, 1H), 3.06 (q, J=7.4 Hz, 2H), 2.05 (d, J=7.1 Hz, 3H), 1.31 (t, J=7.4 Hz, 3H).

The compound B85: 54 mg, ESI[M+H]$^+$=334.1

$^1$H NMR (400 MHz, $CDCl_3$) δ 7.38-7.29 (m, 5H), 6.52 (q, J=7.1 Hz, 1H), 6.25-6.13 (m, 1H), 5.22-5.14 (m, 2H), 4.79-4.63 (m, 4H), 2.07 (d, J=7.1 Hz, 3H).

The compound B86: 67 mg, ESI[M+H]$^+$=372.1

$^1$H NMR (400 MHz, $CDCl_3$) δ 7.37-7.29 (m, 5H), 6.52 (q, J=7.1 Hz, 1H), 2.17-1.90 (m, 7H), 1.88 (s, 3H), 1.69-1.21 (m, 6H).

The compound B87: 77 mg, ESI[M+H]$^+$=348.1

$^1$H NMR (400 MHz, $CDCl_3$) δ 7.38-7.28 (m, 5H), 6.53 (q, J=7.1 Hz, 1H), 5.96-5.64 (m, 2H), 5.05-4.77 (m, 3H), 4.74 (d, J=8.0 Hz, 1H), 2.08 (d, J=7.1 Hz, 3H), 1.73-1.60 (m, 3H).

The compound B88: 42 mg, ESI[M+H]$^+$=352.1

$^1$H NMR (400 MHz, $CDCl_3$) δ 7.36-7.29 (m, 5H), 6.51 (q, J=7.1 Hz, 1H), 4.41-4.33 (m, 4H), 3.33 (s, 2H), 2.06 (d, J=7.1 Hz, 3H), 1.32 (s, 3H).

The compound B89: 68 mg, ESI[M+H]$^+$=336.1

$^1$H NMR (400 MHz, $CDCl_3$) δ 7.39-7.29 (m, 5H), 6.52 (q, J=7.1 Hz, 1H), 4.52-4.32 (m, 6H), 2.08 (d, J=7.1 Hz, 3H), 1.32 (s, 3H).

The compound B90: 24 mg, ESI[M+H]$^+$=336.1

$^1$H NMR (400 MHz, $CDCl_3$) δ 7.37-7.27 (m, 5H), 6.50 (q, J=7.1 Hz, 1H), 2.04 (d, J=7.1 Hz, 3H). 2.00 (s, 3H), 1.49 (s, 3H), 1.45 (s, 3H).

The compound B91: 16 mg, ESI[M+H]$^+$=352.1

$^1$H NMR (400 MHz, $CDCl_3$) δ 7.38-7.28 (m, 5H), 6.52 (q, J=7.1 Hz, 1H), 2.12 (s, 3H), 2.07 (d, J=7.1 Hz, 3H), 1.56 (s, 3H), 1.47 (s, 3H).

The compound B92: 35 mg, ESI[M+H]$^+$=364.1

$^1$H NMR (400 MHz, $CDCl_3$) δ 7.39-7.27 (m, 5H), 6.53 (q, J=7.1 Hz, 1H), 4.76 (t, J=7.4 Hz, 1H), 3.75 (t, J=7.0 Hz, 1H), 3.64-3.58 (m, 1H), 2.88-2.72 (m, 2H), 2.21-2.07 (m, 2H), 2.08 (d, J=7.1 Hz, 3H), 1.15 (d, J=8.0 Hz, 6H).

The compound B93: 28 mg, ESI[M+H]$^+$=394.1

$^1$H NMR (400 MHz, $CDCl_3$) δ 7.37-7.28 (m, 5H), 6.55 (q, J=7.1 Hz, 1H), 5.07-4.95 (m, 1H), 3.48-3.36 (m, 4H), 2.83-2.66 (m, 2H), 2.33-2.22 (m, 2H), 2.07 (d, J=7.1 Hz, 3H), 1.20 (q, J=7.0 Hz, 6H).

The compound B94: 26 mg, ESI[M+H]$^+$=460.2

$^1$H NMR (400 MHz, $CDCl_3$) δ 7.37-7.29 (m, 5H), 6.51 (q, J=7.1 Hz, 1H), 6.15-5.81 (m, 1H), 3.86-3.62 (m, 1H), 3.58-3.13 (m, 3H), 2.55-2.39 (m, 1H), 2.19-1.92 (m, 7H), 1.90-1.83 (m, 3H), 1.82-1.42 (m, 2H), 1.28-1.14 (m, 4H), 1.09-0.88 (m, 2H).

The compound B95: 29 mg, ESI[M+H]$^+$=362.1

$^1$H NMR (400 MHz, $CDCl_3$) δ 7.37-7.29 (m, 5H), 6.54 (q, J=7.1 Hz, 1H), 4.64-4.49 (m, 1H), 4.33-4.16 (m, 1H), 2.80-2.64 (m, 1H), 2.51-2.26 (m, 2H), 2.24-2.03 (m, 5H), 1.99-1.91 (m, 1H), 1.76-1.25 (m, 3H).

The compound B96: 88 mg, ESI[M+H]$^+$=390.1

$^1$H NMR (400 MHz, $CDCl_3$) δ 7.38-7.28 (m, 5H), 6.52 (q, J=7.1 Hz, 1H), 3.51 (s, 3H), 2.48-2.21 (m, 4H), 2.07 (d, J=7.1 Hz, 3H), 1.82-1.63 (m, 4H).

The compound B97: 48 mg, ESI[M+H]$^+$=360.1

$^1$H NMR (400 MHz, $CDCl_3$) δ 8.18 (t, J=2.0 Hz, 1H), 7.39-7.29 (m, 5H), 6.52 (q, J=7.1 Hz, 1H), 2.68-2.64 (m, 2H), 2.47-2.44 (m, 2H), 2.06 (d, J=7.1 Hz, 3H), 1.89-1.85 (m, 2H), 1.81-1.72 (m, 2H).

The compound B98: 28 mg, ESI[M+H]$^+$=352.1

$^1$H NMR (400 MHz, $CDCl_3$) δ 7.38-7.29 (m, 5H), 6.52 (q, J=7.1 Hz, 1H), 4.23-4.20 (m, 2H), 3.09-3.07 (m, 2H), 2.96-2.90 (m, 2H), 2.07 (d, J=7.1 Hz, 3H), 1.35 (s, 3H).

Example 7 Preparation of Compounds B99 and B100

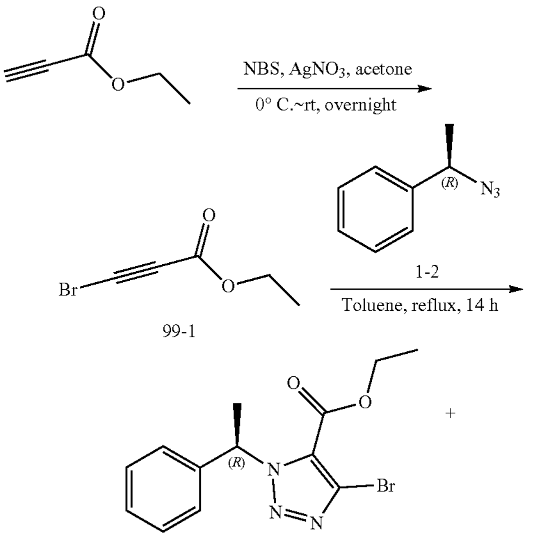

99-1

Compound B99

-continued

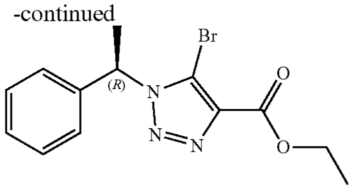

Compound B100

1. Preparation of ethyl 3-bromopropionate (99-1)

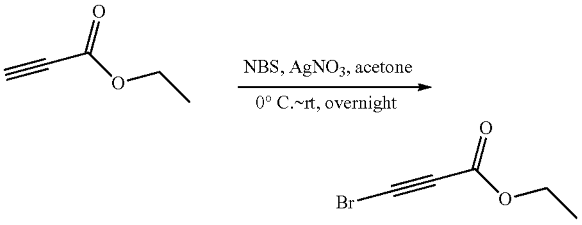

99-1

At room temperature, ethyl propiolate (12.0 g, 122 mmol), NBS (26.2 g, 147 mmol) and AgNO3 (10.4 g, 61 mmol) were dissolved in acetone (400 mL). Then the mixture was stirred at room temperature overnight. The reaction was monitored by TLC until completion. The mixture was filtered and concentrated under reduced pressure to give the crude product 99-1, which was used for next step directly without further purification.

2. Preparation of Compounds B99 and B100

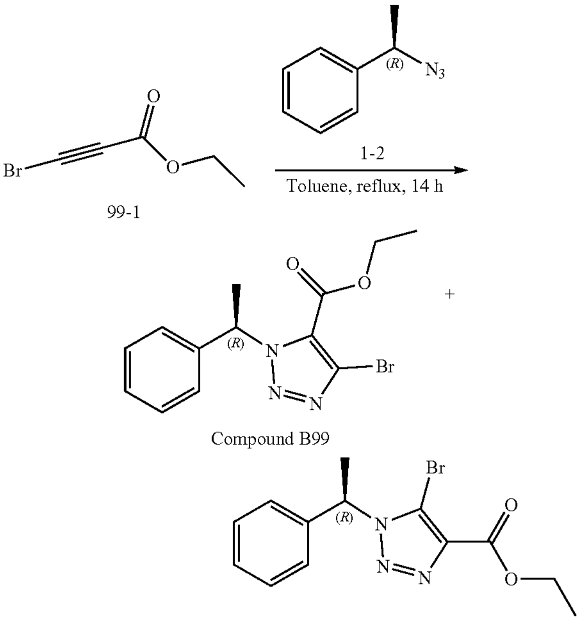

99-1

Compound B99

Compound B100

At room temperature, ethyl 3-bromopropionate (99-1) and (R)-(1-azidoethyl)benzene 1-2 (7.1 g, 48.2 mmol) were dissolved in toluene (100 mL), then the mixture was refluxed for 14 hrs. The reaction was monitored by TLC until completion. The mixture was quenched with the saturated brine (30 mL) and extracted with ethyl acetate (3×30 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v)=1/10~1/1), with TLC (ethyl acetate/petroleum ether (v/v)=1/5) monitoring, and collecting the fraction with Rf=0.5~0.6 to give the products B99 (2.3 g, yield 15%) and B100 (6.0 g, yield 38%).

The compound B99: ESI[M+H]$^+$=324.1

$^1$H NMR (400 MHz, $CDCl_3$) δ 7.40-7.29 (m, 5H), 6.53 (q, J=7.1 Hz, 1H), 4.45-4.31 (m, 2H), 2.07 (d, J=7.1 Hz, 3H), 1.39 (t, J=7.1 Hz, 3H).

The compound B100: ESI[M+H]$^+$=324.1

$^1$H NMR (400 MHz, $CDCl_3$) δ 7.40-7.29 (m, 5H), 5.80 (q, J=7.1 Hz, 1H), 4.45 (q, J=7.1 Hz, 2H), 2.12 (d, J=7.1 Hz, 3H), 1.44 (t, J=7.1 Hz, 3H).

Example 8 Preparation of Compounds B101~B126

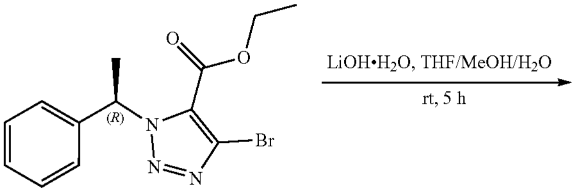

Compound B100

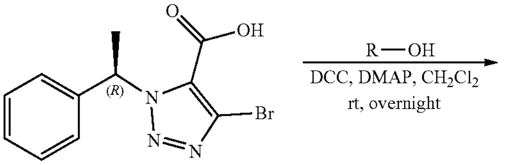

D

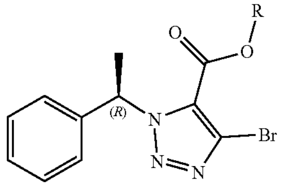

Compound B101~B126

1. Preparation of (R)-4-bromo-1-(1-phenylethyl)-1H-1,2,3-triazole-5-carboxylic acid (D)

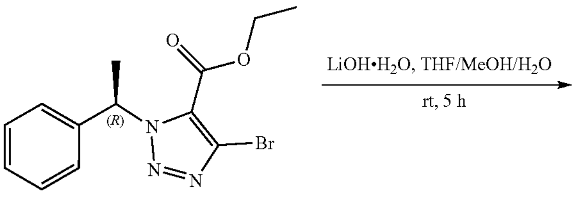

Compound B100

-continued

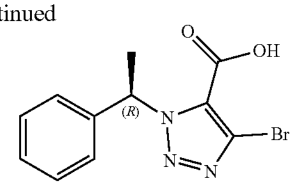

D

At room temperature, LiOH·$H_2O$ (337 mg, 8.0 mmol) was added into the mixture of B100 (1.3 g, 4.0 mmol) in MeOH/THF/$H_2O$ (15 mL, 1/1/1), then it was stirred at room temperature overnight. The reaction was monitored by TLC until completion. The mixture was concentrated under reduced pressure and $H_2O$ (10 mL) was added. The mixture was adjusted to PH=4-5 with 1 N hydrochloric acid and extracted with dichloromethane (3×15 mL). The combined organic layers were dried over anhydrous sodium sulfate, filtered and concentrated under reduced pressure $^1$H NMR (400 MHz, $CD_3OD$) δ 7.48-7.13 (m, 5H), 6.76-6.65 (m, 1H), 2.00 (d, J=5.5 Hz, 3H).

2. Preparation of Compounds B101~B126

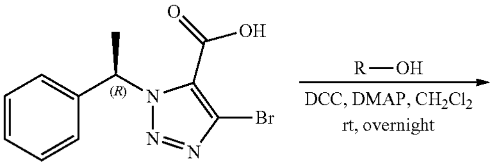

D

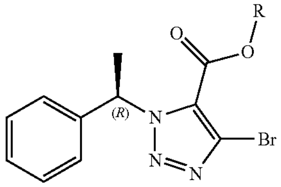

Compound B101~B126

The target compounds B101~B126 were prepared according to the general procedure A, using (R)-4-bromo-1-(1-phenylethyl)-1H-1,2,3-triazole-5-carboxylic acid (D) (100 mg, 0.34 mmol) and corresponding alcohols (0.51 mmol) as starting materials. The crude product was purified by Prep-TLC (ethyl acetate/petroleum ether (v/v)=1/5) and the fraction with Rf=0.4~0.6 was collected and dried to give target compounds as colorless oil.

The compound B101: 16.8 mg, ESI[M+H]$^+$=390.1

$^1$H NMR (400 MHz, $CDCl_3$) δ 7.39-7.24 (m, 5H), 6.44 (q, J=7.1 Hz, 1H), 5.60 (t, J=6.6 Hz, 1H), 5.09-4.76 (m, 6H), 2.07 (d, J=7.1 Hz, 3H).

The compound B102: 80 mg, ESI[M+H]$^+$=420.1

$^1$H NMR (400 MHz, $CDCl_3$) δ 7.40-7.28 (m, 5H), 6.41 (q, J=7.1 Hz, 1H), 3.57 (s, 3H), 2.82-2.55 (m, 4H), 2.12 (d, J=7.1 Hz, 3H), 2.05-1.88 (m, 2H).

The compound B103: 66 mg, ESI[M+H]$^+$=374.1

$^1$H NMR (400 MHz, $CDCl_3$) δ 7.40-7.29 (m, 5H), 6.42 (q, J=7.1 Hz, 1H), 5.88-5.69 (m, 3H), 5.60-5.54 (m, 1H), 2.11 (d, J=7.1 Hz, 3H), 1.65 (t, J=5.9 Hz, 3H).

The compound B104: 62 mg, ESI[M+H]$^+$=246.1

$^1$H NMR (400 MHz, $CDCl_3$) δ 7.38-7.29 (m, 5H), 6.51 (q, J=7.1 Hz, 1H), 5.24-5.14 (m, 1H), 2.54-2.37 (m, 2H), 2.27-2.14 (m, 2H), 2.06 (d, J=7.1 Hz, 3H), 1.96-1.85 (m, 1H), 1.78-1.66 (m, 1H).

The compound B105: 55 mg, ESI$[M+H]^+$=350.1

$^1$H NMR (400 MHz, $CDCl_3$) δ 7.39-7.29 (m, 5H), 6.53 (q, J=7.1 Hz, 1H), 4.23-4.10 (m, 2H), 2.07 (d, J=7.1 Hz, 3H), 1.27-1.17 (m, 1H), 0.69-0.59 (m, 2H), 0.41-0.32 (m, 2H).

The compound B106: 56 mg, ESI$[M+H]^+$=380.2

$^1$H NMR (400 MHz, $CDCl_3$) δ 7.41-7.28 (m, 5H), 6.51 (q, J=7.1 Hz, 1H), 4.89-4.80 (m, 1H), 3.71-3.61 (m, 1H), 3.28 (s, 3H), 2.96-2.78 (m, 2H), 2.18-2.02 (m, 5H).

The compound B107: 33 mg, ESI$[M+H]^+$=376.2

$^1$H NMR (400 MHz, $CDCl_3$) δ 7.41-7.29 (m, 5H), 6.49 (q, J=7.1 Hz, 1H), 4.86-4.73 (m, 2H), 4.36-4.18 (m, 2H), 2.89-2.76 (m, 2H), 2.74-2.59 (m, 1H), 2.54-2.39 (m, 2H), 2.06 (d, J=7.1 Hz, 3H).

The compound B108: 63 mg, ESI$[M+H]^+$=336.1

$^1$H NMR (400 MHz, $CDCl_3$) δ 7.38-7.29 (m, 5H), 6.52 (q, J=7.1 Hz, 1H), 6.04-5.91 (m, 1H), 5.50-5.30 (m, 2H), 4.89-4.74 (m, 2H), 2.07 (d, J=7.1 Hz, 3H).

The compound B109: 51 mg, ESI$[M+H]^+$=416.2

$^1$H NMR (400 MHz, $CDCl_3$) δ 7.42-7.29 (m, 5H), 6.48 (q, J=7.1 Hz, 1H), 5.61 (s, 1H), 4.92 (d, J=3.8 Hz, 2H), 2.34-2.18 (m, 2H), 2.17-2.02 (m, 5H), 1.63-1.49 (m, 4H), 1.46-1.33 (m, 2H).

The compound B110: 66 mg, ESI$[M+H]^+$=352.1

$^1$H NMR (400 MHz, $CDCl_3$) δ 7.37-7.30 (m, 5H), 6.52 (q, J=7.1 Hz, 1H), 2.06 (d, J=7.1 Hz, 3H), 1.56 (s, 9H).

The compound B111: 56 mg, ESI$[M+H]^+$=364.1

$^1$H NMR (400 MHz, $CDCl_3$) δ 7.40-7.28 (m, 5H), 6.51 (q, J=7.1 Hz, 1H), 5.89-5.72 (m, 1H), 5.41-5.16 (m, 3H), 2.15-2.02 (m, 3H), 1.77-1.68 (m, 2H), 1.00-0.66 (m, 3H).

The compound B112: 46 mg, ESI$[M+H]^+$=366.1

$^1$H NMR (400 MHz, $CDCl_3$) δ 7.40-7.29 (m, 5H), 6.49 (q, J=7.1 Hz, 1H), 4.82-4.79 (m, 2H), 4.59-4.56 (m, 2H), 2.10 (d, J=7.1 Hz, 3H), 1.77 (s, 3H).

The compound B113: 79 mg, ESI$[M+H]^+$=418.2

$^1$H NMR (400 MHz, $CDCl_3$) δ 7.42-7.29 (m, 5H), 6.50 (q, J=7.1 Hz, 1H), 2.46-2.38 (m, 2H), 2.35-2.27 (m, 2H), 2.06 (d, J=7.0 Hz, 3H), 2.07 (s, 3H), 1.84-1.76 (m, 2H), 1.75-1.68 (m, 2H).

The compound B114: 35 mg, ESI$[M+H]^+$=366.1

$^1$H NMR (400 MHz, $CDCl_3$) δ 7.37-7.25 (m, 5H), 6.35 (q, J=7.1 Hz, 1H), 4.29-4.20 (m, 1H), 2.59-2.42 (m, 2H), 2.23-2.05 (m, 4H), 2.04 (d, J=7.1 Hz, 3H).

The compound B115: 57 mg, ESI$[M+H]^+$=338.1

$^1$H NMR (400 MHz, $CDCl_3$) δ 7.37-7.29 (m, 5H), 6.52 (q, J=7.2 Hz, 1H), 5.25-5.19 (m, 1H), 2.07 (d, J=7.1 Hz, 3H), 1.37 (d, J=6.2 Hz, 3H), 1.33 (d, J=6.3 Hz, 3H).

The compound B116: 67 mg, ESI$[M+H]^+$=336.0

$^1$H NMR (400 MHz, $CDCl_3$) δ 7.39-7.29 (m, 5H), 6.51 (q, J=7.1 Hz, 1H), 4.41-4.29 (m, 1H), 2.07 (d, J=7.1 Hz, 3H), 0.89-0.80 (m, 4H).

The compound B117: 39 mg, ESI$[M+H]^+$=310.1

$^1$H NMR (400 MHz, $CDCl_3$) δ 7.41-7.29 (m, 5H), 6.52 (q, J=7.1 Hz, 1H), 3.92 (s, 3H), 2.07 (d, J=7.1 Hz, 3H).

The compound B118: 238 mg, ESI$[M+H]^+$=324.1

$^1$H NMR (400 MHz, $CDCl_3$) δ 7.38-7.29 (m, 5H), 6.53 (q, J=7.1 Hz, 1H), 4.45-4.31 (m, 2H), 2.07 (d, J=7.1 Hz, 3H), 1.39 (t, J=7.1 Hz, 3H).

The compound B119: 63 mg, ESI$[M+H]^+$=338.1

$^1$H NMR (400 MHz, $CDCl_3$) δ 7.40-7.30 (m, 5H), 6.55 (q, J=7.2 Hz, 1H), 4.35-4.22 (m, 2H), 2.07 (d, J=7.1 Hz, 3H), 1.84-1.72 (m, 2H), 1.03 (t, J=7.4 Hz, 3H).

The compound B120: 82 mg, ESI$[M+H]^+$=340.1

$^1$H NMR (400 MHz, $CDCl_3$) δ 7.37-7.29 (m, 5H), 6.37 (q, J=7.0 Hz, 1H), 3.09-3.01 (m, 2H), 2.05 (d, J=7.1 Hz, 3H), 1.30 (t, J=7.4 Hz, 3H).

The compound B121: 99 mg, ESI$[M+H]^+$=394.1

$^1$H NMR (400 MHz, $CDCl_3$) δ 7.39-7.29 (m, 5H), 6.47 (q, J=7.1 Hz, 1H), 3.70 (s, 3H), 2.08 (d, J=7.1 Hz, 3H), 1.71-1.60 (m, 2H), 1.35-1.21 (m, 2H).

The compound B122: 194 mg, ESI$[M+H]^+$=558.0

$^1$H NMR (400 MHz, $CDCl_3$) δ 7.37-7.30 (m, 5H), 6.56 (q, J=7.2 Hz, 0H), 5.16 (s, 0H), 2.10 (d, J=7.1 Hz, 1H).

The compound B123: 32 mg, ESI$[M+H]^+$=322.1

$^1$H NMR (400 MHz, $CDCl_3$) δ 7.40-7.31 (m, 5H), 6.51 (q, J=7.2 Hz, 1H), 5.16 (dd, J=13.8, 2.1 Hz, 1H), 4.82 (dd, J=6.1, 2.1 Hz, 1H), 2.08 (d, J=7.1 Hz, 3H).

The compound B124: 26 mg, ESI$[M+H]^+$=320.1

$^1$H NMR (400 MHz, $CDCl_3$) δ 7.40-7.29 (m, 5H), 6.52 (q, J=7.1 Hz, 1H), 2.55 (s, 1H), 2.12 (d, J=7.1 Hz, 3H).

The compound B125: 48 mg, ESI$[M+H]^+$=370.1

$^1$H NMR (400 MHz, $CDCl_3$) δ 7.41-7.29 (m, 5H), 6.48 (q, J=7.1 Hz, 1H), 4.51-4.34 (m, 2H), 2.80 (t, J=6.9 Hz, 2H), 2.18 (s, 3H), 2.10 (d, J=7.1 Hz, 3H).

The compound B126: 37 mg, ESI$[M+H]^+$=386.1

$^1$H NMR (400 MHz, $CDCl_3$) δ 7.41-7.29 (m, 5H), 6.51 (q, J=7.1 Hz, 1H), 3.38-2.95 (m, 2H), 2.78-2.59 (m, 2H), 2.18 (s, 3H), 2.11 (d, J=7.1 Hz, 3H).

Example 9 Preparation of Compound B127 and Compound B128

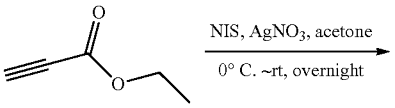

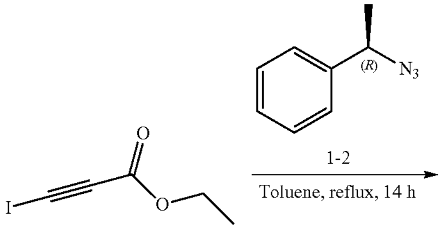

127-1

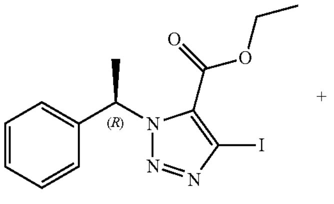

Compound B127

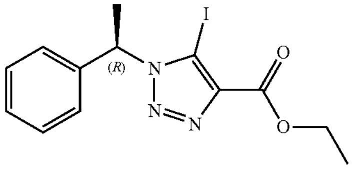

Compound B128

1. Preparation of ethyl 3-iodopropiolate (127-1)

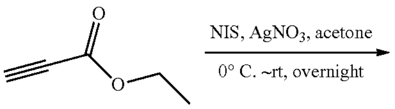

-continued

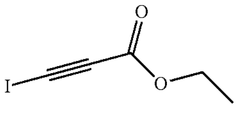

127-1

At room temperature, ethyl propiolate (12.0 g, 122 mmol), NIS (33.1 g, 147 mmol) and AgNO3 (10.4 g, 61 mmol) were dissolved in acetone (400 mL). Then the mixture was stirred at room temperature overnight. The reaction was monitored by TLC until completion. The mixture was filtered and concentrated under reduced pressure to give the crude product 127-1, which was used for next step directly without further purification.

2. Preparation of Compounds B12 and B128

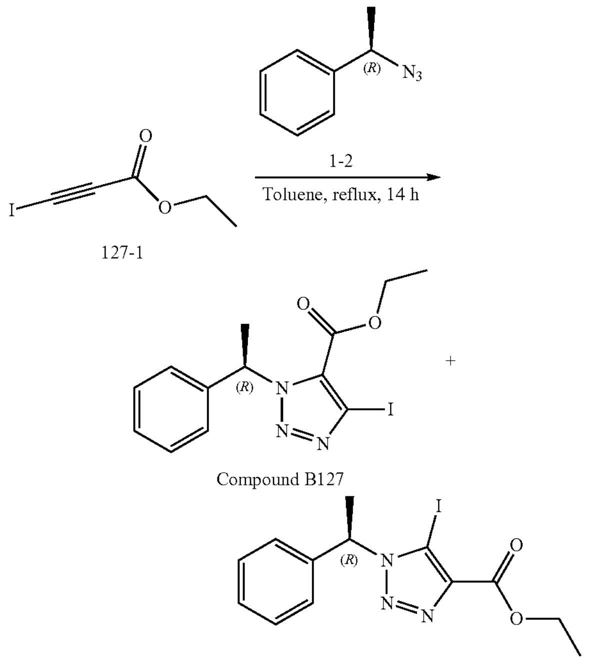

127-1

Compound B127

Compound B128

At room temperature, ethyl 3-iodopropiolate (127-1) and (R)-(1-azidoethyl)benzene 1-2 (4.5 g, 30.6 mmol) were dissolved in toluene (100 mL), then the mixture was refluxed for 14 hrs. The reaction was monitored by TLC until completion. The mixture was quenched with the saturated brine (30 mL) and extracted with ethyl acetate (3×50 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v)=1/10~1/1), with TLC (ethyl acetate/petroleum ether (v/v)=1/5) monitoring, and collecting the fraction with Rf=0.5~0.6 to give the products B127 (4.5 g, yield 40%) and B128 (4.9 g, yield 43%).

The compound B127: ESI$[M+H]^+$=372.1

$^1H$ NMR (400 MHz, $CDCl_3$) δ 7.39-7.29 (m, 5H), 6.55 (q, J=7.1 Hz, 1H), 4.46-4.30 (m, 2H), 2.06 (d, J=7.1 Hz, 3H), 1.41 (t, J=7.1 Hz, 3H).

The compound B128: ESI$[M+H]^+$=372.1

$^1H$ NMR (400 MHz, $CDCl_3$) δ 7.42-7.29 (m, 5H), 5.83 (q, J=7.0 Hz, 1H), 4.46 (q, J=7.1 Hz, 2H), 2.13 (d, J=7.1 Hz, 3H), 1.45 (t, J=7.1 Hz, 3H).

Example 10 Preparation of Compounds B129~B144

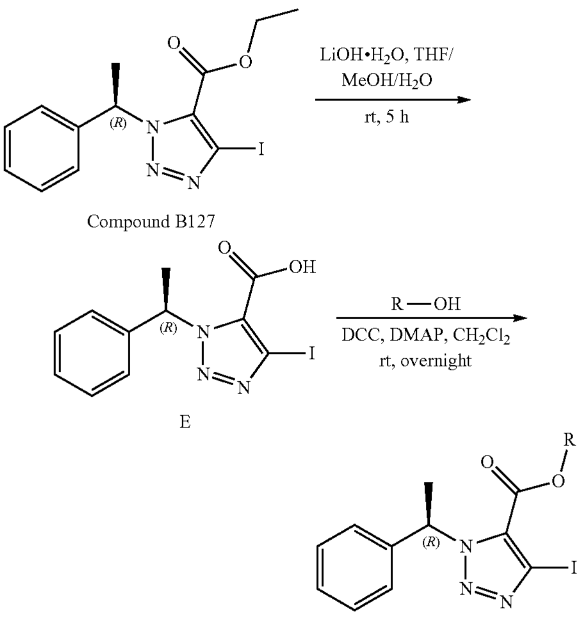

Compound B127

E

Compound B129~B144

1. Preparation of (R)-4-iodo-1-(1-phenylethyl)-1H-1,2,3-triazole-5-carboxylic acid (E)

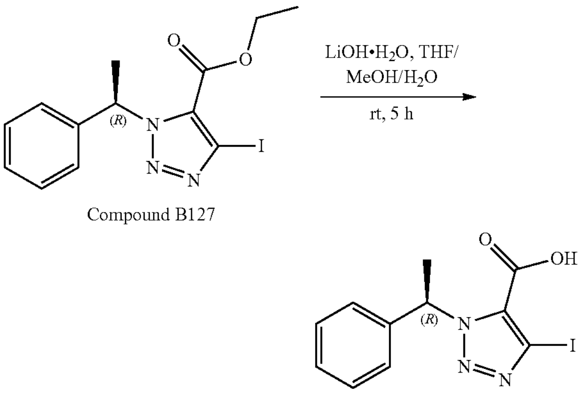

Compound B127

E

At room temperature, $LiOH \cdot H_2O$ (906 mg, 21.6 mmol) was added into the mixture of B127 (4.0 g, 10.8 mmol) in $MeOH/THF/H_2O$ (30 mL, 1/1/1), then it was stirred at room temperature overnight. The reaction was monitored by TLC until completion. The mixture was concentrated under reduced pressure and $H_2O$ (10 mL) was added. The mixture was adjusted to PH=4~5 with 1 N hydrochloric acid and extracted with dichloromethane (3×10 mL). The combined organic layers were dried over anhydrous sodium sulfate, filtered and concentrated under reduced pressure to give compound E (3.0 g, yield 81%) as a white solid. ESI[M+H]$^+$=344.0, [M+H−=105]$^+$=240.1

$^1$H NMR (400 MHz, $CD_3OD$) δ 7.39-7.22 (m, 5H), 6.74-6.64 (m, 1H), 1.99 (d, J=6.0 Hz, 3H).

2. Preparation of Compounds B129~B144

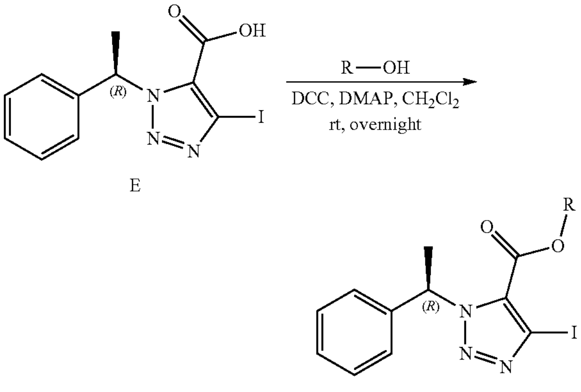

E

Compound B129~B144

The target compounds B129~B144 were prepared according to the general procedure A, using (R)-4-iodo-1-(1-phenylethyl)-1H-1,2,3-triazole-5-carboxylic acid (E) (100 mg, 0.29 mmol) and corresponding alcohols (0.44 mmol) as starting materials. The crude product was purified by Prep-TLC (ethyl acetate/petroleum ether (v/v)=1/5) and the fraction with Rf=0.4~0.6 was collected and dried to give target compounds as colorless oil.

The compound B129: 37 mg, ESI[M+H]$^+$=438.1

$^1$H NMR (400 MHz, $CDCl_3$) δ 7.46-7.29 (m, 5H), 6.46 (q, J=7.3 Hz, 1H), 5.61 (t, J=6.9 Hz, 1H), 5.10-4.69 (m, 6H), 2.07 (d, J=7.6 Hz, 3H).

The compound B130: 82 mg, ESI[M+H]$^+$=468.1

$^1$H NMR (400 MHz, $CDCl_3$) δ 7.46-7.29 (m, 5H), 6.46 (q, J=7.1 Hz, 1H), 3.57 (s, 3H), 2.82-2.55 (m, 4H), 2.07 (d, J=7.1 Hz, 3H), 2.05-1.88 (m, 2H).

The compound B131: 49 mg, ESI[M+H]$^+$=422.0

$^1$H NMR (400 MHz, $CDCl_3$) δ 7.39-7.30 (m, 5H), 6.59-6.49 (m, 1H), 5.87-5.69 (m, 3H), 5.61-5.54 (m, 1H), 2.07 (d, J=6.9 Hz, 3H), 1.65 (t, J=5.9 Hz, 3H).

The compound B132: 68 mg, ESI[M+H]$^+$=398.0

$^1$H NMR (400 MHz, $CDCl_3$) δ 7.40-7.29 (m, 5H), 6.53 (q, J=7.2 Hz, 1H), 5.26-5.15 (m, 1H), 2.53-2.37 (m, 2H), 2.31-2.18 (m, 2H), 2.05 (d, J=7.1 Hz, 3H), 1.98-1.85 (m, 1H), 1.80-1.65 (m, 1H).

The compound B133: 72 mg, ESI[M+H]$^+$=398.1

$^1$H NMR (400 MHz, $CDCl_3$) δ 7.38-7.29 (m, 5H), 6.62-6.50 (m, 1H), 4.25-4.09 (m, 2H), 2.07 (d, J=6.2 Hz, 3H), 1.28-1.19 (m, 1H), 0.72-0.60 (m, 2H), 0.44-0.33 (m, 2H).

The compound B134: 33 mg, ESI[M+H]$^+$=428.0

$^1$H NMR (400 MHz, $CDCl_3$) δ 7.37-7.29 (m, 5H), 6.52 (q, J=7.1 Hz, 1H), 4.92-4.82 (m, 1H), 3.71-3.62 (m, 1H), 3.29 (s, 3H), 2.95-2.79 (m, 2H), 2.26-2.15 (m, 2H), 2.06 (d, J=7.1 Hz, 3H).

The compound B135: 72 mg, ESI[M+H]$^+$=424.1

$^1$H NMR (400 MHz, $CDCl_3$) δ 7.39-7.28 (m, 5H), 6.53 (q, J=7.1 Hz, 1H), 4.86-4.73 (m, 2H), 4.36-4.18 (m, 2H), 2.90-2.77 (m, 2H), 2.74-2.56 (m, 1H), 2.53-2.39 (m, 2H), 2.07 (d, J=7.1 Hz, 3H).

The compound B136: 66 mg, ESI[M+H]$^+$=384.1

$^1$H NMR (400 MHz, $CDCl_3$) δ 7.38-7.29 (m, 5H), 6.54 (q, J=7.0 Hz, 1H), 6.06-5.94 (m, 1H), 5.49-5.41 (m, 1H), 5.38-5.31 (m, 1H), 4.89-4.75 (m, 2H), 2.06 (d, J=7.1 Hz, 3H).

The compound B137: 21 mg, ESI[M+H]$^+$=464.1

$^1$H NMR (400 MHz, $CDCl_3$) δ 7.37-7.30 (m, 5H), 6.53 (q, J=7.0 Hz, 1H), 5.57 (s, 1H), 4.96-4.90 (m, 2H), 2.35-2.21 (m, 2H), 2.16-2.10 (m, 2H), 2.07 (d, J=7.1 Hz, 3H), 1.56-1.49 (m, 2H), 1.49-1.37 (m, 2H).

The compound B138: 17 mg, ESI[M+H]$^+$=400.1

$^1$H NMR (400 MHz, $CDCl_3$) δ 7.39-7.29 (m, 5H), 6.53 (q, J=6.9 Hz, 1H), 2.05 (d, J=7.1 Hz, 3H), 1.57 (s, 9H).

The compound B139: 80 mg, ESI[M+H]$^+$=412.1

$^1$H NMR (400 MHz, $CDCl_3$) δ 7.37-7.30 (m, 5H), 6.61-6.52 (m, 1H), 5.91-5.75 (m, 1H), 5.45-5.17 (m, 3H), 2.11-1.99 (m, 3H), 1.88-1.70 (m, 2H), 1.03-0.90 (m, 3H).

The compound B140: 28 mg, ESI[M+H]$^+$=414.1

$^1$H NMR (400 MHz, $CDCl_3$) δ 7.38-7.23 (m, 5H), 6.45 (q, J=7.1 Hz, 1H), 4.93-4.79 (m, 2H), 4.63-4.52 (m, 2H), 2.07 (d, J=7.1 Hz, 3H), 1.75 (s, 3H).

The compound B141: 51 mg, ESI[M+H]$^+$=466.1

$^1$H NMR (400 MHz, $CDCl_3$) δ 7.37-7.22 (m, 5H), 6.50 (q, J=7.1 Hz, 1H), 2.55-2.15 (m, 4H), 2.09 (d, J=7.1 Hz, 3H), 2.00 (s, 3H), 1.87-1.67 (m, 4H).

The compound B142: 72 mg, ESI[M+H]$^+$=414.1

$^1$H NMR (400 MHz, $CDCl_3$) δ 7.36-7.24 (m, 5H), 6.29 (q, J=7.1 Hz, 1H), 4.31-4.17 (m, 1H), 2.59-2.42 (m, 2H), 2.23-2.05 (m, 4H), 2.04 (d, J=7.1 Hz, 3H).

The compound B143: 76 mg, ESI[M+H]$^+$=386.0

$^1$H NMR (400 MHz, $CDCl_3$) δ 7.37-7.29 (m, 5H), 6.54 (q, J=7.2 Hz, 1H), 5.29-5.18 (m, 1H), 2.06 (d, J=7.1 Hz, 3H), 1.39 (d, J=6.3 Hz, 3H), 1.35 (d, J=6.3 Hz, 3H).

The compound B144: 102 mg, ESI[M+H]$^+$=384.1

$^1$H NMR (400 MHz, $CDCl_3$) δ 7.39-7.29 (m, 5H), 6.53 (q, J=7.1 Hz, 1H), 4.42-4.34 (m, 1H), 2.06 (d, J=7.1 Hz, 3H), 0.94-0.78 (m, 4H).

Example 11 Preparation of Compounds B145 and B146

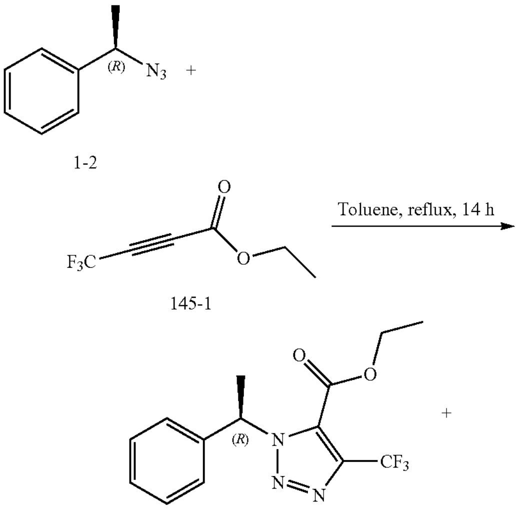

1-2

145-1

Compound B145

-continued

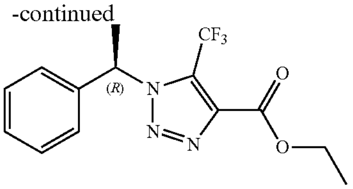

Compound B146

At room temperature, (R)-(1-azidoethyl)benzene 1-2 (200 mg, 1.36 mmol) and ethyl 4,4,4-trifluorobut-2-ynoate 145-1 (452 mg, 2.72 mmol) were dissolved in toluene (100 mL), then the mixture was refluxed for 14 hrs. The reaction was monitored by TLC until completion. The mixture concentrated under reduced pressure. The residue was purified by Prep-TLC (ethyl acetate/petroleum ether (v/v)~1/5), collecting the fraction with Rf=0.4~0.6 to give the product B145 (230 mg, yield 54%) and the product B146 (192 mg, yield 45%) as colorless oil.

The compound B145: ESI[M+H]$^+$=314.1

$^1$H NMR (400 MHz, $CDCl_3$) δ 7.41-7.31 (m, 5H), 6.52 (q, J=7.1 Hz, 1H), 4.47-4.31 (m, 2H), 2.11 (d, J=7.1 Hz, 3H), 1.36 (t, J=7.2 Hz, 3H).

The compound B146: ESI[M+Na]$^+$=336.1

$^1$H NMR (400 MHz, $CDCl_3$) δ 7.41-7.29 (m, 5H), 5.90 (q, J=7.0 Hz, 1H), 4.46 (q, J=7.1 Hz, 2H), 2.13 (d, J=7.0 Hz, 3H), 1.42 (t, J=7.1 Hz, 3H).

Example 12 Preparation of Compound B147

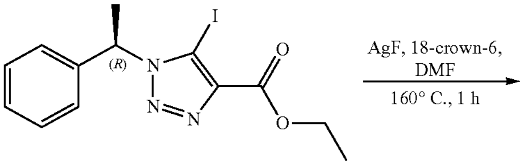

Compound B128

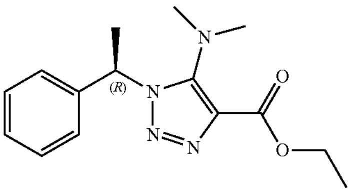

Compound B147

At room temperature, compound B128 (200 mg, 0.54 mmol), 18-crown-6 (29 mg, 0.11 mmol) and AgF (69 mg, 0.54 mmol) were dissolved in DMF (2 mL), then the mixture was stirred at 160° C. for 1 hour. The reaction was monitored by TLC until completion. The mixture concentrated under reduced pressure. The residue was purified by Prep-TLC (ethyl acetate/petroleum ether (v/v)=1/1) and the fraction with Rf=0.4~0.6 was collected and dried to give target compound B147 (20 mg, yield 13%) as colorless oil. ESI [M+H]$^+$=289.3

$^1$H NMR (400 MHz, $CDCl_3$) δ 7.38-7.29 (m, 5H), 5.79 (q, J=7.2 Hz, 1H), 4.44 (q, J=7.1 Hz, 2H), 2.66 (s, 6H), 2.02 (d, J=7.2 Hz, 3H), 1.45 (t, J=7.1 Hz, 3H).

Examples of Group C compounds are as follows:

Example 1 Preparation of Compounds C1~C7

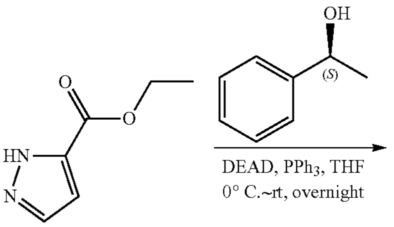

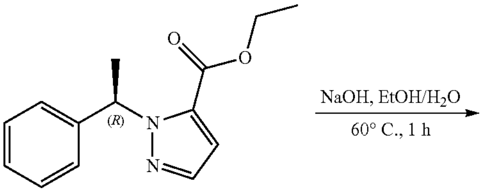

A-1

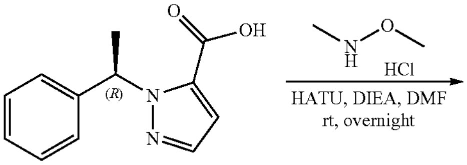

A-2

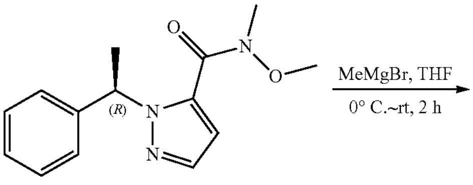

A-3

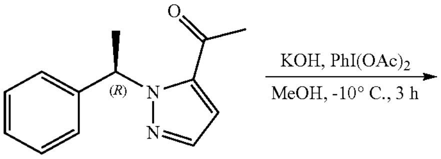

A-4

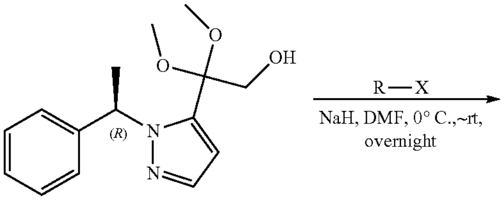

A

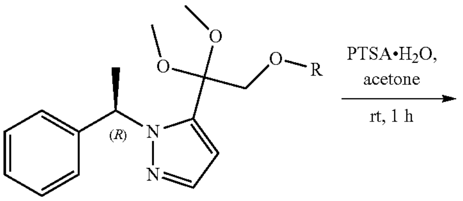

1-1~7-1

-continued

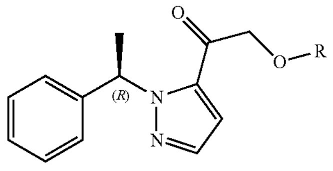

Compound C1~C7

1. Preparation of ethyl (R)-1-(1-phenylethyl)-1H-pyrazole-5-carboxylate (A-1)

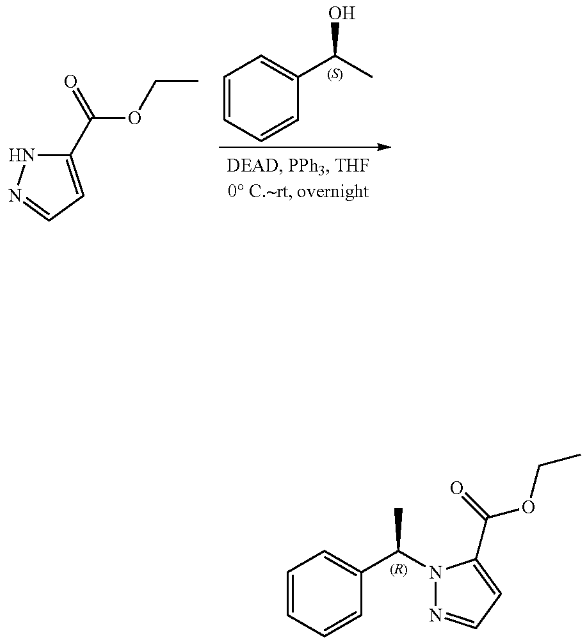

A-1

In an ice-water bath, S-1-phenylethan-1-ol (8.38 g, 68.6 mmol), ethyl 1H-pyrazole-5-carboxylate (7.4 g, 52.8 mmol) and PPh3 (20.8 g, 79.3 mmol) were dissolved in THF (15 mL) at 0° C., then DEAD (5.6 g, 32.2 mmol) in THF (15 mL) was added into mixture at the rate of 2.0 mmol/min. The mixture was warmed slowly to room temperature and stirred at this temperature overnight. The reaction was monitored by TLC until completion. The mixture was quenched with the saturated brine (100 mL) and extracted with ethyl acetate (3x30 mL). The combined organic layers were washed with saturated brine (30 mL), dried over anhydrous sodium sulfate, filtered and concentrated under reduced pressure. The residue was purified by silica gel column chromatography (ethyl acetate/petroleum ether (v/v)= 1/20~1/10), with TLC (ethyl acetate/petroleum ether (v/v)=1/2) monitoring, and collecting the fraction with Rf=0.5~0.6 to give compound A-1 (9.5 g, yield 73.7%). ESI$[M+H]^+$=245.1

$^1$H NMR (400 MHz, $CDCl_3$) δ 7.57 (d, J=1.9 Hz, 1H), 7.33-7.27 (m, 4H), 7.25-7.18 (m, 1H), 6.86 (d, J=2.0 Hz, 1H), 6.59 (q, J=7.1 Hz, 1H), 4.42-4.16 (m, 2H), 1.92 (d, J=7.1 Hz, 3H), 1.33 (t, J=7.1 Hz, 3H).

2. Preparation of (R)-1-(1-phenylethyl)-1H-pyrazole-5-carboxylic acid (A-2)

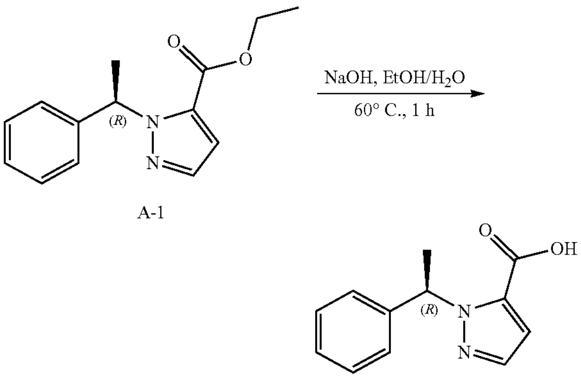

A-2

At room temperature, NaOH (3.1 g, 77.5 mmol) was added into the mixture ethyl (R)-1-(1-phenylethyl)-1H-pyrazole-5-carboxylate A-1 (9.5 g, 38.9 mmol) in EtOH/$H_2O$ (25 mL, 1/1), then it was stirred at 60° C. for 1 hour. The reaction was monitored by TLC until completion. The mixture was concentrated under reduced pressure and $H_2O$ (20 mL) was added. The mixture was adjusted to PH=4-5 with 1 N hydrochloric acid and extracted with dichloromethane (3×15 mL). The combined organic layers were dried over anhydrous sodium sulfate, filtered and concentrated under reduced pressure to give compound A-2 (6.7 mg, yield 80%) as a white solid. ESI$[M+H]^+$=217.1

$^1$H NMR (400 MHz, $CDCl_3$) δ 7.62 (d, J=2.0 Hz, 1H), 7.39-7.16 (m, 5H), 7.00 (d, J=2.0 Hz, 1H), 6.56 (q, J=7.0 Hz, 1H), 1.93 (d, J=7.1 Hz, 3H).

3. Preparation of (R)—N-methoxy-N-methyl-1-(1-phenylethyl)-1H-pyrazole-5-carboxamide (A-3)

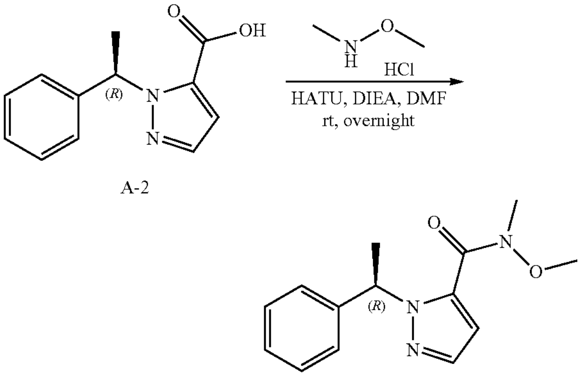

A-3

At room temperature, (R)-1-(1-phenylethyl)-1H-pyrazole-5-carboxylic acid A-2 (3.5 g, 16.2 mmol), N, O-dimethylhydroxylamine hydrochloride (2.4 g, 24.6 mmol), DIEA (3.2 g, 24.8 mmol) and HATU (9.2 g, 24.2 mmol) were dissolved in DMF (100 mL). Then the mixture was stirred at room temperature overnight. The reaction was monitored by TLC until completion, $H_2O$ (100 mL) was added, and extracted with ethyl acetate (3×15 mL). The combined organic layers were dried over anhydrous sodium sulfate, filtered and concentrated under reduced pressure. The residue was purified by silica gel column chromatography (ethyl acetate/petroleum ether (v/v)=1/10~1/3) and the eluate was monitored by TLC (ethyl acetate/petroleum ether (v/v)=1/1). The fraction with Rf=0.5~0.6 was collected and dried to give the product A-3 (4.1 g, yield 64%) as a white solid. ESI[M+H]$^+$=260.2

4. Preparation of (R)-1-(1-(1-phenylethyl)-1H-pyrazol-5-yl)ethan-1-one (A-4)

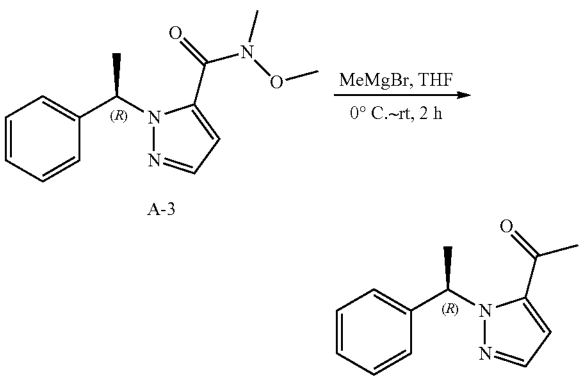

A-3

A-4

At room temperature, (R)—N-methoxy-N-methyl-1-(1-phenylethyl)-1H-pyrazole-5-carboxamide A-3 (4.1 g, 15.8 mmol) was dissolved in anhydrous THF (20 mL). The mixture was cooled to 0° C. with an ice-water bath. MeMgBr (23.7 mL, 1 mol/L in THF, 23.7 mmol) was added dropwise into the mixture at the rate of 2 mmol/min. Then the mixture was warmed to room temperature slowly and allowed to react for 2 hrs. The reaction was monitored by TLC until completion, then it was cooled to 0° C. with an ice-water bath. The mixture was quenched with the saturated ammonium chloride solution (50 mL) and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10) and the eluate was monitored by TLC (ethyl acetate/petroleum ether (v/v)=1/5). The fraction with Rf=0.5~0.6 was collected and dried to give compound A-4 (3.1 g, yield 92%) as a white solid. ESI[M+H]$^+$=215.1

5. Preparation of (R)-2,2-dimethoxy-2-(1-(1-phenylethyl)-1H-pyrazol-5-yl)ethan-1-ol (A)

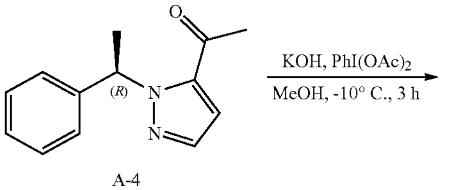

A-4

-continued

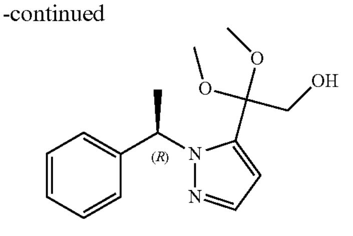

A

At room temperature, (R)-1-(1-(1-phenylethyl)-1H-pyrazol-5-yl)ethan-1-one A-4 (3.1 g, 14.5 mmol) and $PhI(OAc)_2$ (7.0 g, 21.7 mmol) were dissolved in MeOH (50 mL). The mixture was cooled to −10° C. with an ice-brine bath. KOH (9.8 g, 175 mol) was added in portions into the mixture within 30 minutes. Then the mixture was stirred at −10° C. for 3 hrs. The reaction was monitored by TLC until completion, the saturated brine (100 mL) was added slowly into the mixture and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5-0.6 to give compound A-4 (3.6 g, yield 90%) as a white solid. ESI[M+H]$^+$=277.1

6. Preparation of Compound C1

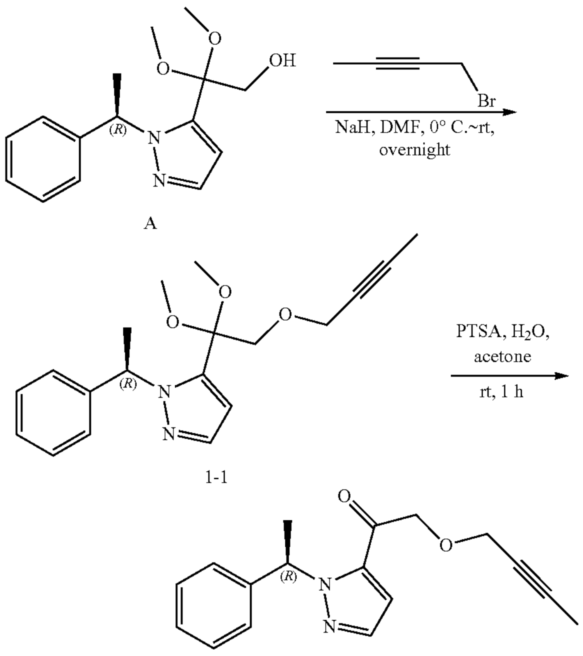

A 1-1

Compound C1

In an ice bath, NaH (26.0 mg, 60% in mineral oil, 0.65 mmol) was added into the solution of compound A (150 mg, 0.54 mmol) in anhydrous DMF (25 mL), the mixture was stirred at 0° C. for 30 minutes. 1-bromobut-2-yne (108 mg, 0.81 mmol) was added slowly into the mixture using a syringe, then the mixture was stirred at room temperature overnight. The reaction was monitored by TLC until completion, ice-water (10 mL) was added slowly into the mixture and extracted with ethyl acetate (3×10 mL). The combined organic layers were washed with saturated brine (10 mL), dried over anhydrous sodium sulfate, filtered and concentrated under reduced pressure to give the crude product 1-1 (171 mg), which was used for next step directly without further purification. ESI[M+H]$^+$=329.1

At room temperature, PTSA.$H_2O$ (99 mg, 0.52 mmol) was added into the solution of the crude product 1-1 (171 mg) in acetone (5 mL). Then the mixture was stirred at room temperature for 1 hour. The reaction was monitored by TLC until completion, the ice-water (10 mL) was added slowly into the mixture and extracted with ethyl acetate (3×5 mL). The combined organic layers were washed with saturated brine (10 mL), dried over anhydrous sodium sulfate, filtered and concentrated under reduced pressure. The crude product was purified by Prep-TLC (ethyl acetate/petroleum ether (v/v)=1/5) and the fraction with Rf=0.4~0.6 was collected and dried to give the product C1 (88 mg, two steps yield 58%) as colorless oil. ESI[M+H]$^+$=283.0

$^1$H NMR (400 MHz, $CDCl_3$) δ 7.59 (d, J=2.0 Hz, 1H), 7.35-7.27 (m, 3H), 7.26-7.19 (m, 2H), 6.91 (d, J=2.0 Hz, 1H), 6.60 (q, J=7.1 Hz, 1H), 4.59 (q, J=16.6 Hz, 2H), 4.25 (q, J=2.3 Hz, 2H), 1.91 (d, J=7.1 Hz, 3H), 1.83 (t, J=2.3 Hz, 3H).

7. Preparation of Compounds C2~C7

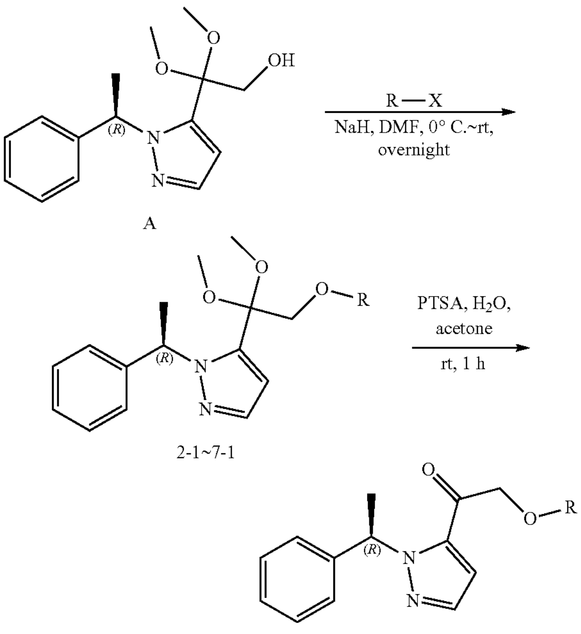

A 2-1~7-1

Compound C2~C7

The target compounds C2~C7 were prepared according to the operation method of preparing compound C1. Compound A reacted with corresponding halides under NaH condition to give intermediate compounds 2-1~7-1, which were deprotected with PTSA.$H_2O$ to give target compounds C2~C7.

The compound C2: 91 mg, ESI[M+H]$^+$=259.1

$^1$H NMR (400 MHz, $CDCl_3$) δ 7.58 (d, J=2.1 Hz, 1H), 7.35-7.18 (m, 5H), 6.89 (d, J=2.1 Hz, 1H), 6.61 (q, J=7.1 Hz, 1H), 4.59-4.33 (m, 2H), 3.65-3.42 (m, 2H), 1.91 (d, J=7.1 Hz, 3H), 1.25 (t, J=7.0 Hz, 3H).

The compound C3: 39 mg, ESI[M+H]$^+$=299.1

$^1$H NMR (400 MHz, $CDCl_3$) δ 7.57 (d, J=2.1 Hz, 1H), 7.37-7.19 (m, 5H), 6.89 (d, J=2.1 Hz, 1H), 6.62 (q, J=7.1 Hz, 1H), 4.59-4.33 (m, 2H), 3.48 (d, J=6.9 Hz, 2H), 2.71-2.56 (m, 1H), 2.12-2.01 (m, 2H), 1.98-1.84 (m, 5H), 1.79-1.69 (m, 2H).

The compound C4: 37 mg, ESI[M+H]$^+$=335.0

$^1$H NMR (400 MHz, $CDCl_3$) δ 7.56 (d, J=2.1 Hz, 1H), 7.35-7.18 (m, 5H), 6.87 (d, J=2.1 Hz, 1H), 6.63 (q, J=7.1 Hz, 1H), 4.59-4.33 (m, 2H), 4.28-4.14 (m, 2H), 2.75-2.58 (m, 2H), 2.58-2.29 (m, 3H), 1.92 (d, J=7.1 Hz, 3H).

The compound C5: 23 mg, ESI[M+H]$^+$=297.0

$^1$H NMR (400 MHz, $CDCl_3$) δ 7.58 (d, J=2.1 Hz, 1H), 7.35-7.18 (m, 5H), 6.89 (d, J=2.1 Hz, 1H), 6.61 (q, J=7.1 Hz, 1H), 4.60-4.41 (m, 3H), 1.88 (d, J=7.1 Hz, 3H), 1.86-1.84 (m, 6H).

The compound C6: 48 mg, ESI[M+H]$^+$=313.1

$^1$H NMR (400 MHz, $CDCl_3$) δ 7.56 (d, J=2.1 Hz, 1H), 7.37-7.18 (m, 5H), 6.88 (d, J=2.1 Hz, 1H), 6.62 (q, J=7.1 Hz, 1H), 4.58-4.33 (m, 2H), 3.42 (t, J=6.9 Hz, 2H), 2.43-2.29 (m, 1H), 2.11-1.96 (m, 2H), 1.91 (d, J=7.1 Hz, 3H), 1.90-1.85 (m, 1H), 1.81-1.77 (m, 1H), 1.76-1.69 (m, 2H), 1.68-1.58 (m, 2H).

The compound C7: 46 mg, ESI[M+H]$^+$=269.0

$^1$H NMR (400 MHz, $CDCl_3$) δ 7.57 (d, J=2.1 Hz, 1H), 7.36-7.18 (m, 5H), 6.85 (d, J=2.1 Hz, 1H), 6.64 (q, J=7.1 Hz, 1H), 4.56-4.31 (m, 2H), 4.28 (d, J=2.4 Hz, 2H), 2.45 (t, J=2.4 Hz, 1H), 1.92 (d, J=7.1 Hz, 3H).

Example 2 Preparation of Compound C8

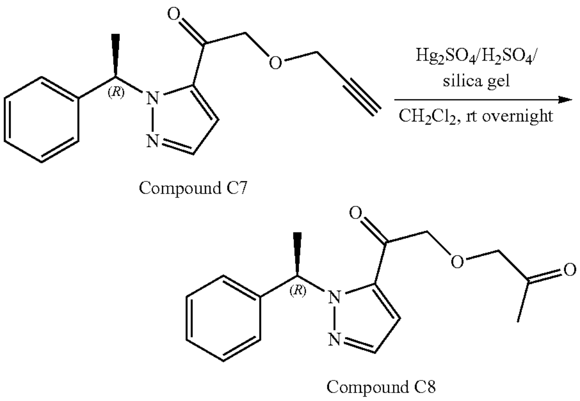

Compound C7

Compound C8

At room temperature, the compound C7 (100 mg, 0.37 mmol) and $Hg_2SO_4$/$H_2SO_4$/silica gel (200 mg) was dissolved in $CH_2Cl_2$ (5 mL). Then the mixture was stirred at room temperature overnight. The reaction was monitored by TLC until completion, the saturated $NaHCO_3$ solution was added into the mixture and extracted with $CH_2Cl_2$ (3×5 mL). The combined organic layers were washed with saturated brine (10 mL), dried over anhydrous sodium sulfate, filtered and concentrated under reduced pressure. The residue was purified by Prep-TLC (ethyl acetate/petroleum ether (v/v) ~1/3) and the fraction with Rf=0.4~0.5 was collected and dried to give the product $C_8$ (69 mg, yield 65%) as colorless oil. ESI[M+H]$^+$=287.0

$^1H$ NMR (400 MHz, $CDCl_3$) δ 7.55 (d, J=2.1 Hz, 1H), 7.35-7.18 (m, 5H), 6.86 (d, J=2.1 Hz, 1H), 6.60 (q, J=7.1 Hz, 1H), 4.57-4.33 (m, 2H), 4.21 (s, 2H), 2.15 (s, 3H), 1.91 (d, J=7.1 Hz, 3H).

Example 3 Preparation of Compounds C9~C10

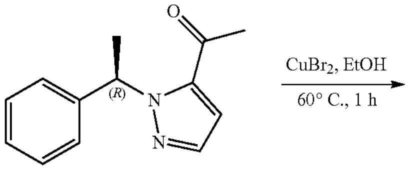

A-4

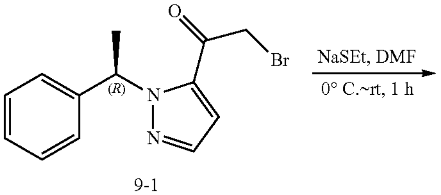

9-1

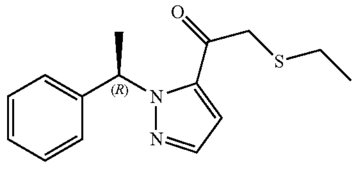

Compound C9

1. Preparation of (R)-2-bromo-1-(1-(1-phenylethyl)-1H-pyrazol-5-yl)ethan-1-one (9-1)

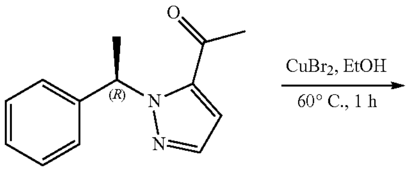

A-4

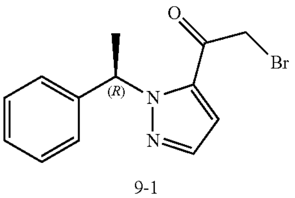

9-1

At room temperature, $CuBr_2$ (4.17 g, 18.7 mmol) was added into the solution of (R)-1-(1-(1-phenylethyl)-1H-pyrazol-5-yl)ethan-1-one A-4 (2.0 g, 9.3 mmol) in EtOH (50 mL). Then the mixture was stirred at 60° C. for 1 hour. The reaction was monitored by TLC until completion, then it was cooled to room temperature, quenched with $H_2O$ (50 mL) and extracted with ethyl acetate (3×10 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5-0.6 to give the compound 9-1 (2.2 g, yield 81%) as colorless oil. ESI$[M+H]^+$=293.0

2. Preparation of Compounds C9~C10

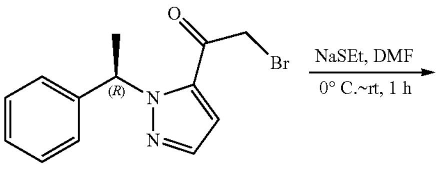

9-1

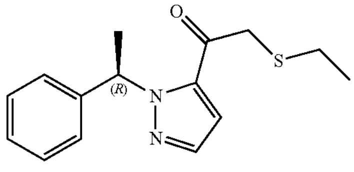

Compound C9

At an ice bath, NaSEt (631 mg, 7.5 mmol) was added into the solution of (R)-2-bromo-1-(1-(1-phenylethyl)-1H-pyrazol-5-yl)ethan-1-one 9-1 (2.2 g, 7.5 mmol) in DMF (30 mL). Then the mixture was stirred at room temperature for 1 hour. The reaction was monitored by TLC until completion. The mixture was quenched with the ice-water (10 mL) and extracted with ethyl acetate (3×5 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.4-0.6 to give the compound C9 (1.26 g, yield 61%). ESI$[M+H]^+$=275.2

$^1H$ NMR (400 MHz, $CDCl_3$) δ 7.61 (d, J=1.9 Hz, 1H), 7.34-7.20 (m, 5H), 6.88 (d, J=2.0 Hz, 1H), 6.59 (q, J=7.0 Hz, 1H), 3.60 (s, 2H), 2.49-2.35 (m, 2H), 1.94 (d, J=7.1 Hz, 3H), 1.18 (t, J=7.4 Hz, 3H).

The target compound C10 were prepared according to the operation method of preparing compound C9. compound 9-1 reacted with sodium cyclobutyl methanethiolate to give the compound C10 (87 mg, yield 43%). ESI$[M+H]^+$=315.2

$^1H$ NMR (400 MHz, $CDCl_3$) δ 7.62 (d, J=1.9 Hz, 1H), 7.37-7.25 (m, 5H), 6.88 (d, J=2.0 Hz, 1H), 6.58 (q, J=7.0 Hz, 1H), 3.61 (s, 2H), 2.71-2.56 (m, 1H), 2.48-2.36 (m, 2H), 2.12-2.01 (m, 2H), 1.98-1.84 (m, 5H), 1.79-1.69 (m, 2H).

Example 4 Preparation of Compounds C11~C13

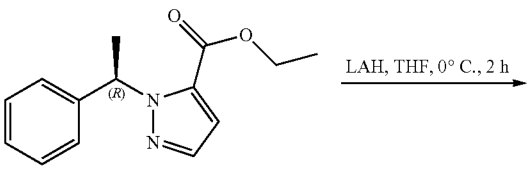

A-1

-continued

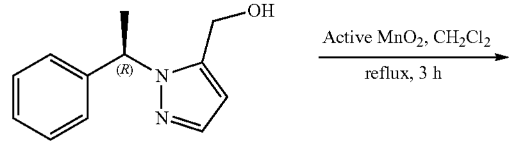

11-1

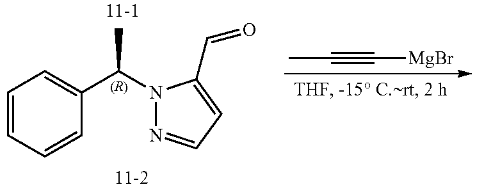

11-2

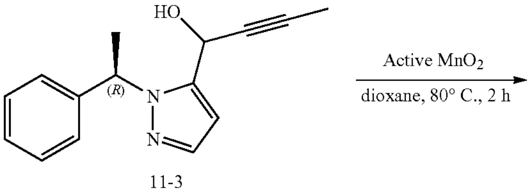

11-3

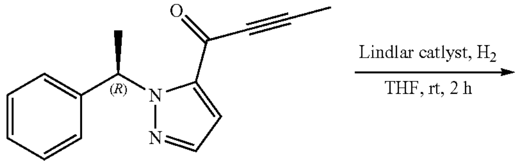

Compound C11

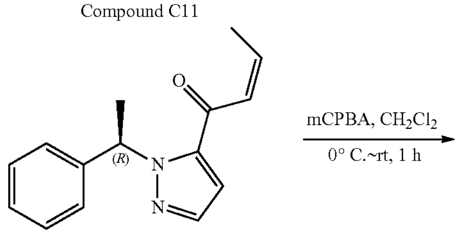

Compound C12

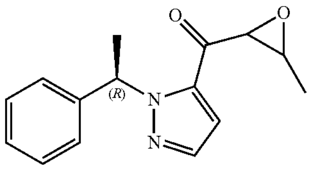

Compound C13

1. Preparation of (R)-(1-(1-phenylethyl)-1H-pyrazol-5-yl)methanol (11-1)

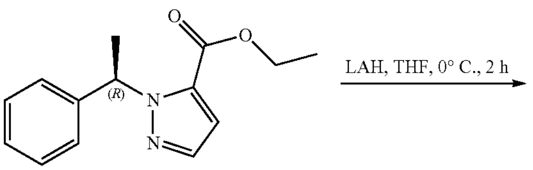

A-1

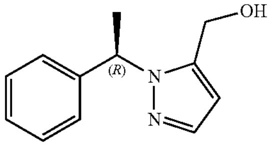

11-1

In an ice-water bath, LAH (133 mg, 3.5 mmol) was added in two portions into the mixture of ethyl (R)-1-(1-phenylethyl)-1H-pyrazole-5-carboxylate A-1 (854 mg, 3.5 mmol) in THF (20 mL) within 10 min. The mixture was allowed to react at 0° C. for 2 hrs. The reaction was monitored by TLC until completion. $Na_2SO_4.10H_2O$ (1.12 g, 3.5 mmol) was added slowly into the mixture at 0° C., then it was filtered and the filter cake was washed with THF (3×10 mL). The filtrate was dried over anhydrous sodium sulfate, filtered and concentrated under reduced pressure to give the crude product 11-1, which was used for next step directly without further purification. ESI$[M+H]^+$=203.1

2. Preparation of (R)-1-(1-phenylethyl)-1H-pyrazole-5-carbaldehyde (11-2)

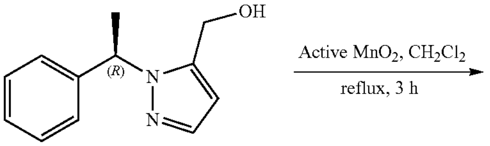

11-1

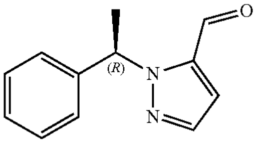

11-2

At room temperature, active $MnO_2$ (12.2 g, 140 mmol) was added into the solution of (R)-(1-(1-phenylethyl)-1H-pyrazol-5-yl)methanol 11-1 in $CH_2Cl_2$ (100 mL), then it was refluxed for 3 hrs. The reaction was monitored by TLC until completion, then it was cooled to room temperature, filtered and the filter cake was washed with $CH_2Cl_2$ (300 mL). The filtrate was concentrated under reduced pressure and the residue was purified by silica gel column chromatography (ethyl acetate/petroleum ether (v/v)=1/20~1/5), with TLC (ethyl acetate/petroleum ether (v/v)=1/5) monitoring, and collecting the fraction with Rf=0.5~0.6 to give the product 11-2 (451 mg, two steps yield 64%) as colorless oil. ESI $[M+H]^+$=201.1

3. Preparation of 1-(1-((R)-1-phenylethyl)-1H-pyrazol-5-yl)but-2-yn-1-ol (11-3)

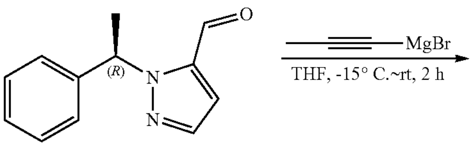

11-2

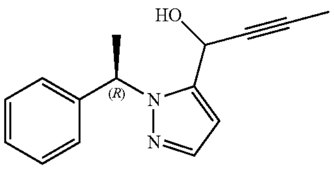

11-3

At room temperature, (R)-1-(1-phenylethyl)-1H-pyrazole-5-carbaldehyde 11-2 (451 mg, 2.25 mmol) was dissolved in anhydrous THF (20 mL). The mixture was replaced with nitrogen and cooled to −15° C. with an ice-brine bath. Prop-1-yn-1-ylmagnesium bromide (3.4 mL, 0.5 mol/L in THF, 2.70 mmol) was added dropwise into the mixture at the rate of 0.5 mmol/min at −15° C. Then the mixture was warmed to room temperature slowly and allowed to react for 2 hrs. The reaction was monitored by TLC until completion, the mixture was quenched with the saturated ammonium chloride (50 mL) and extracted with ethyl acetate (3×10 mL). The combined organic layers were washed with saturated brine (50 mL), dried over anhydrous sodium sulfate, filtered and concentrated under reduced pressure to give the crude product 11-3 as colorless oil, which was used for next step directly without further purification.

4. Preparation of Compound C11

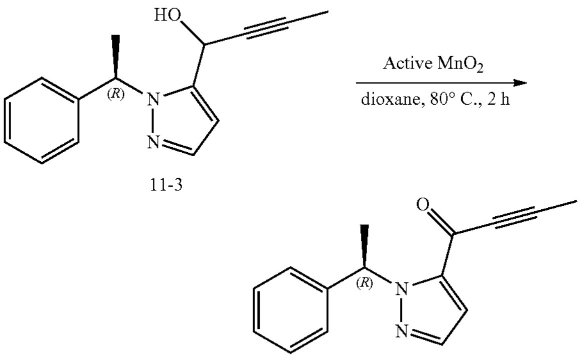

11-3

Compound C11

At room temperature, active $MnO_2$ (7.8 g, 90 mmol) was added in portions into the solution of crude 11-3 in dioxane (50 mL). The mixture was stirred at 80° C. for 2 hrs. The reaction was monitored by TLC until completion. The mixture was cooled to room temperature, filtered and the filter cake was washed with $CH_2Cl_2$ (300 mL). The filtrate was concentrated under reduced pressure and the residue was purified by silica gel column chromatography (ethyl acetate/petroleum ether (v/v)=1/20~1/5), with TLC (ethyl acetate/petroleum ether (v/v)=1/5) monitoring, and collecting the fraction with Rf=0.5~0.6 to give the product C11 (365 mg, two steps yield 68%). ESI[M+H]$^+$=239.1

$^1$H NMR (400 MHz, $CDCl_3$) δ 7.55 (d, J=2.1 Hz, 1H), 7.34-7.18 (m, 5H), 6.88 (d, J=2.1 Hz, 1H), 6.63 (q, J=7.1 Hz, 1H), 2.09 (s, 3H), 1.92 (d, J=7.1 Hz, 3H).

5. Preparation of Compound C12

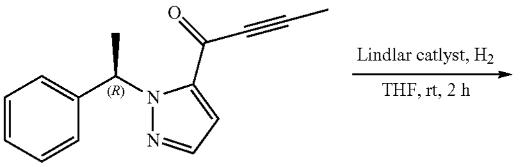

Compound C11

-continued

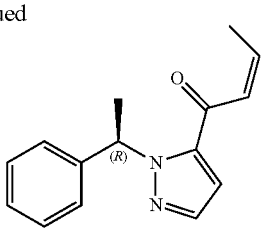

Compound C12

At room temperature, the compound C11 (300 mg, 1.26 mmol) and Lindlar catalyst (15 mg) were dissolved in THF (10 mL). The mixture was replaced three times with hydrogen, then it was allowed to react at room temperature for 2 hrs under hydrogen. The reaction was monitored by TLC until completion. The mixture was concentrated under reduced pressure and the residue was purified by Prep-TLC (ethyl acetate/petroleum ether (v/v)~1/3) and the fraction with Rf=0.4~0.5 was collected and dried to give the product C12 (217 mg, yield 72%). ESI[M+H]$^+$=241.2

$^1$H NMR (400 MHz, $CDCl_3$) δ 7.56 (d, J=2.1 Hz, 1H), 7.36-7.18 (m, 5H), 6.85 (d, J=2.1 Hz, 1H), 6.68 (q, J=7.1 Hz, 1H), 6.73-6.53 (m, 1H), 6.45-6.30 (m, 1H), 2.15 (dd, J=7.3, 1.7 Hz, 3H), 1.89 (d, J=7.1 Hz, 3H).

6. Preparation of Compound C13

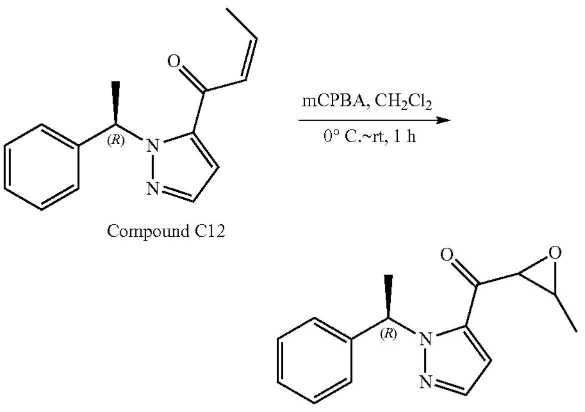

Compound C12

Compound C13

In an ice-water bath, m-CPBA (162 mg, 0.94 mmol) was added in portions into the mixture of compound C12 (150 mg, 0.62 mmol) in $CH_2Cl_2$ (5 mL) at the rate of 0.5 mmol/min. Then the mixture was warmed to room temperature and stirred for 1 hour. The reaction was monitored by TLC until completion. The mixture was quenched with $H_2O$ (10 mL) and extracted with $CH_2Cl_2$ (3×5 mL). The combined organic layers were washed with saturated brine (20 mL), dried over anhydrous sodium sulfate, filtered and concentrated under reduced pressure. The residue was purified by Prep-TLC (ethyl acetate/petroleum ether (v/v)~1/3) and the fraction with Rf=0.4~0.5 was collected and dried to give the product C13 (89 mg, yield 37%). ESI[M+H]$^+$=257.2

$^1$H NMR (400 MHz, $CDCl_3$) δ 7.54 (d, J=2.1 Hz, 1H), 7.35-7.18 (m, 5H), 6.89 (d, J=2.1 Hz, 1H), 6.63 (q, J=7.1 Hz, 1H), 3.42-3.28 (m, 1H), 2.92-2.80 (m, 1H), 1.92 (d, J=7.1 Hz, 3H), 1.19-1.15 (m, 3H).

Example 5 Preparation of Compound C14~C15

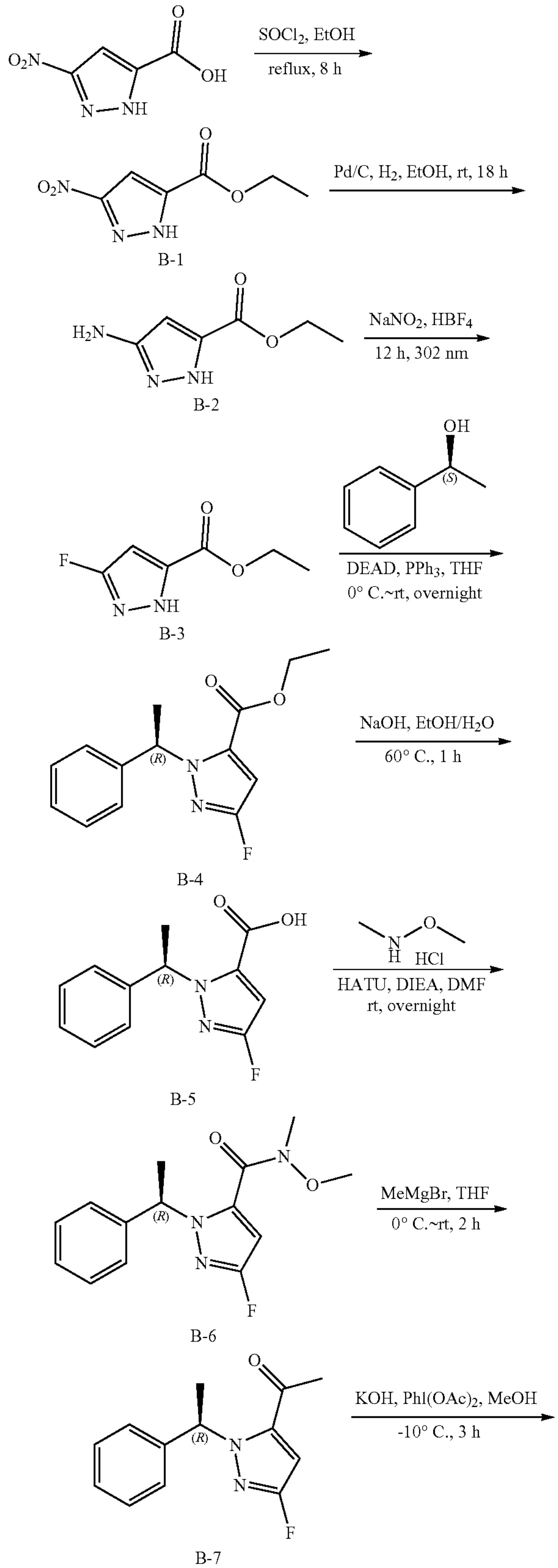

B-1

B-2

B-3

B-4

B-5

B-6

B-7

-continued

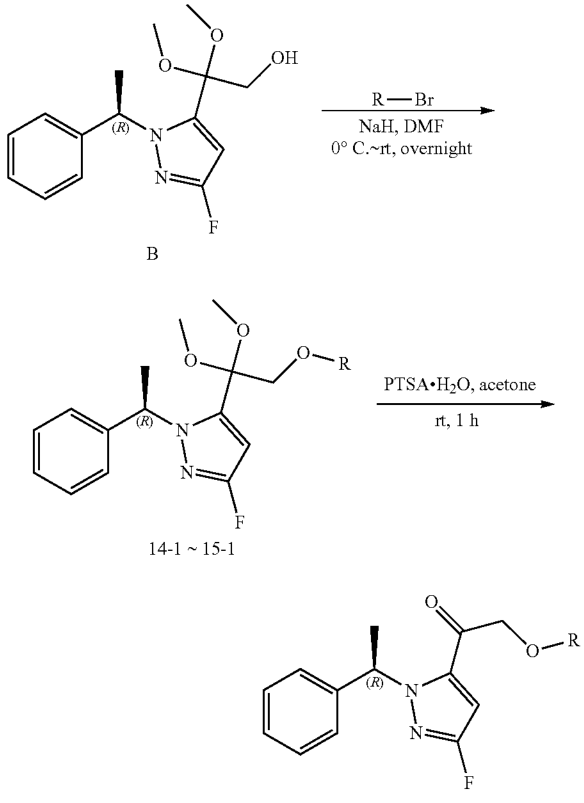

B 14-1 ~ 15-1

Compound C14~C15

1. Preparation of ethyl 3-nitro-1H-pyrazole-5-carboxylate (B-1)

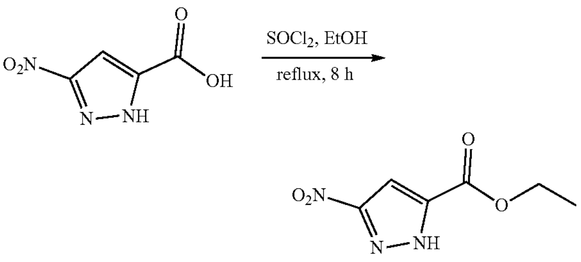

B-1

At room temperature, 3-nitro-1H-pyrazole-5-carboxylic acid (50 g, 318.3 mmol) was dissolved in EtOH (300 mL). $SOCl_2$ (49 g, 412 mmol) was added dropwise slowly into above mixture, then the mixture was refluxed for 8 hrs. The reaction was monitored by TLC until completion. The mixture was concentrated under reduced pressure and the residue was dissolved in $CH_2Cl_2$ (30 mL). The mixture was adjusted to PH=8~9 with saturated sodium bicarbonate solution and extracted with dichloromethane (3x30 mL). The combined organic layers were washed with saturated brine (50 mL), dried over anhydrous sodium sulfate, filtered and concentrated under reduced pressure to give the product B-1 (58.7 g, yield 99.6%) as a white solid. ESI[M+H]$^+$= 186.1

2. Preparation of ethyl 3-amino-1H-pyrazole-5-carboxylate (B-2)

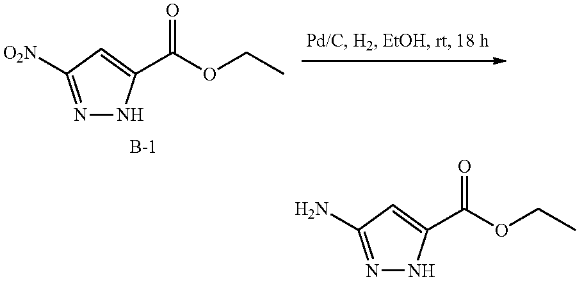

B-1

B-2

At room temperature, ethyl 3-nitro-1H-pyrazole-5-carboxylate B-1 (58.7 g, 317 mmol) and 10% Pd/C (6 g) were dissolved in EtOH (200 mL), the system was replaced with hydrogen three times and stirred under hydrogen for 18 hrs. The reaction was monitored by TLC until completion, filtered and the filter cake was washed with ethanol (3×30 mL). The filtrate was concentrated under reduced pressure and the residue was purified by silica gel column chromatography (ethyl acetate/petroleum ether (v/v)=1/10~1/1), with TLC (ethyl acetate/petroleum ether (v/v)=1/1) monitoring, and collecting the fraction with Rf=0.4~0.5 to give the product B-2 (43.5 g, yield 88%) as a gray solid. ESI[M+H]$^+$=156.1

3. Preparation of ethyl 3-fluoro-1H-pyrazole-5-carboxylate (B-3)

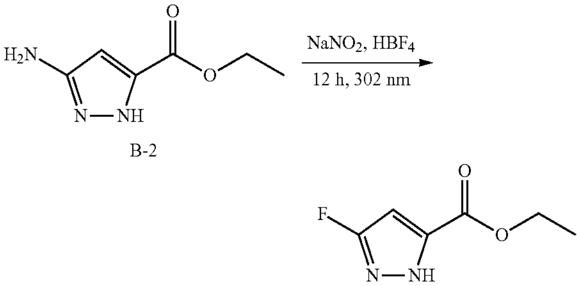

B-2

B-3

At an ice-brine bath, ethyl 3-amino-1H-pyrazole-5-carboxylate B-2 (43.5 g, 280 mmol) was dissolved in the 40% $HBF_4$. $NaNO_2$ (20.3 g, 294 mmol) in $H_2O$ (30 mL) was added into above mixture. The mixture was stirred under high pressure mercury lamp (302 nm) for 12 hrs. The reaction was monitored by TLC until completion. The mixture was adjusted to PH=8~9 with 1 N NaOH and extracted with ethyl acetate (3×50 mL). The combined organic layers were washed with saturated brine (50 mL), dried over anhydrous sodium sulfate, filtered and concentrated under reduced pressure. the residue was purified by silica gel column chromatography (ethyl acetate/petroleum ether (v/v)=1/10~1/1), with TLC (ethyl acetate/petroleum ether (v/v)=1/1) monitoring, and collecting the fraction with Rf=0.4~0.5 to give the product B-3 (3.4 g, yield 8%) as a gray solid.

4. Preparation of ethyl (R)-3-fluoro-1-(1-phenylethyl)-1H-pyrazole-5-carboxylate (B-4)

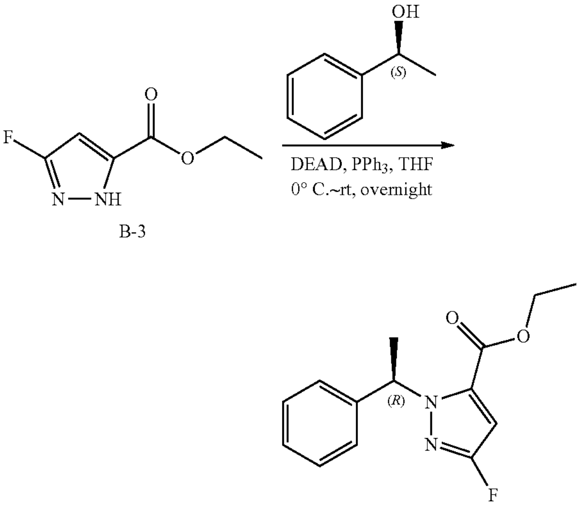

B-3

B-4

In an ice-water bath, S-1-phenylethan-1-ol (3.4 g, 27.8 mmol), ethyl 3-fluoro-1H-pyrazole-5-carboxylate B-3 (3.4 g, 21.5 mmol) and $PPh_3$ (8.4 g, 32.0 mmol) were dissolved in THF (15 mL) at 0° C., then DEAD (5.6 g, 32.2 mmol) in THF (15 mL) was added into mixture at the rate of 0.5 mmol/min. The mixture was warmed slowly to room temperature and stirred at this temperature overnight. The reaction was monitored by TLC until completion. The mixture was quenched with the saturated brine (30 mL) and extracted with ethyl acetate (3×15 mL). The combined organic layers were washed with saturated brine (30 mL), dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/2) monitoring, and collecting the fraction with Rf=0.5-0.6 to give compound B-4 (4.2 g, yield 74%). ESI[M+H]$^+$=263.1

$^1$H NMR (400 MHz, $CDCl_3$) δ 7.35-7.21 (m, 5H), 6.56-6.47 (m, 1H), 6.33 (d, J=6.3 Hz, 1H), 4.41-4.17 (m, 2H), 1.85 (d, J=7.1 Hz, 3H), 1.33 (t, J=7.1 Hz, 3H).

5. Preparation of (R)-3-fluoro-1-(1-phenylethyl)-1H-pyrazole-5-carboxylic acid (B-5)

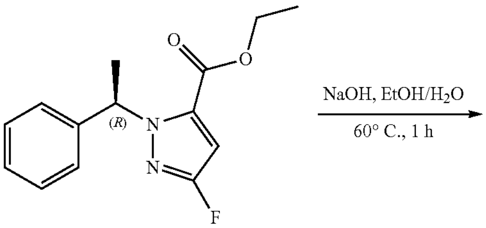

B-4

-continued

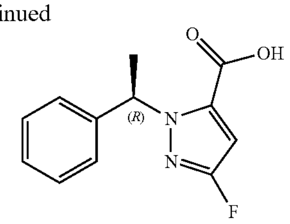

B-5

At room temperature, NaOH (1.3 g, 32.5 mmol) was added into the mixture ethyl (R)-3-fluoro-1-(1-phenylethyl)-1H-pyrazole-5-carboxylate B-4 (4.2 g, 16.0 mmol) in EtOH/$H_2O$ (25 mL, 1/1), then it was stirred at 60° C. for 1 hour. The reaction was monitored by TLC until completion. The mixture was concentrated under reduced pressure and $H_2O$ (20 mL) was added. The mixture was adjusted to PH=4-5 with 1 N hydrochloric acid and extracted with dichloromethane (3×15 mL). The combined organic layers were dried over anhydrous sodium sulfate, filtered and concentrated under reduced pressure to give compound B-5 (2.8 g, yield 75%) as a white solid.

ESI[M+H]$^+$=234.9

$^1$H NMR (400 MHz, $CDCl_3$) δ 7.41-7.14 (m, 6H), 6.55-6.36 (m, 2H), 1.87 (d, J=7.0 Hz, 3H).

6. Preparation of (R)-3-fluoro-N-methoxy-N-methyl-1-(1-phenylethyl)-1H-pyrazole-5-carboxamide (B-6)

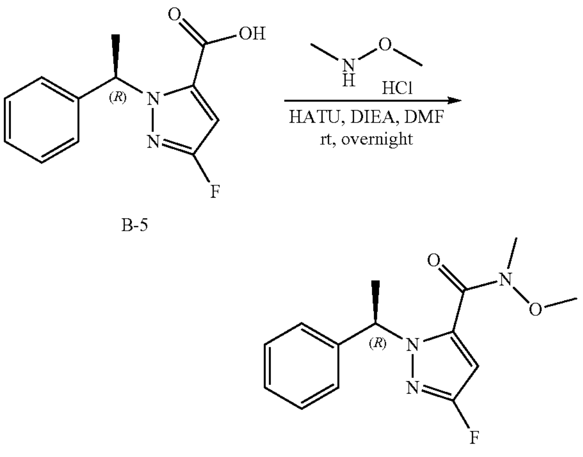

B-5

B-6

At room temperature, (R)-3-fluoro-1-(1-phenylethyl)-1H-pyrazole-5-carboxylic acid B-5 (2.0 g, 8.5 mmol), N, O-dimethylhydroxylamine hydrochloride (1.2 g, 12.3 mmol), DIEA (1.7 g, 13.2 mmol) and HATU (4.7 g, 12.4 mmol) were dissolved in DMF (30 mL), then it was stirred at room temperature overnight. The reaction was monitored by TLC until completion, $H_2O$ (100 mL) was added, and extracted with ethyl acetate (3×30 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5~0.6 to give the product B-6 (1.8 g, yield 76%) as a white solid. ESI[M+H]$^+$=278.1

7. Preparation of (R)-1-(3-fluoro-1-(1-phenylethyl)-1H-pyrazol-5-yl)ethan-1-one (B-7)

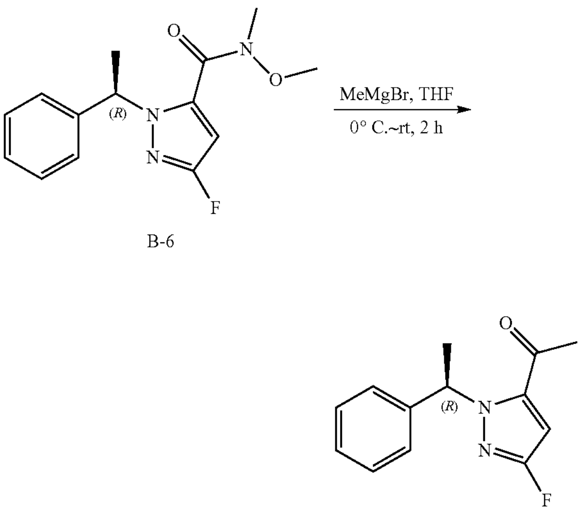

B-6

B-7

At room temperature, (R)-3-fluoro-N-methoxy-N-methyl-1-(1-phenylethyl)-1H-pyrazole-5-carboxamide B-6 (1.8 g, 6.5 mmol) was dissolved in anhydrous THF (20 mL). The mixture was cooled to 0° C. with an ice-water bath. MeMgBr (13 mL, 1 mol/L in THF, 13.0 mmol) was added dropwise into the mixture at the rate of 2 mmol/min. Then the mixture was warmed to room temperature slowly and allowed to react for 2 hrs. The reaction was monitored by TLC until completion, then it was cooled to 0° C. with an ice-water bath, quenched with saturated ammonium chloride (50 mL) and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give compound B-7 (1.2 g, yield 79%) as a white solid. ESI[M+H]$^+$=233.1

8. Preparation of (R)-2-(3-fluoro-1-(1-phenylethyl)-1H-pyrazol-5-yl)-2,2-dimethoxyethan-1-ol (B)

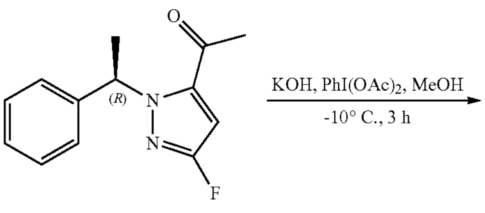

B-7

-continued

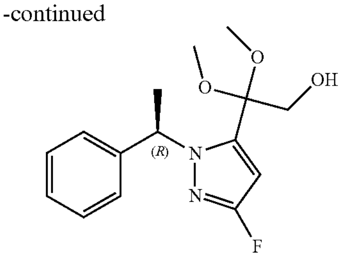

B

At room temperature, (R)-1-(3-fluoro-1-(1-phenylethyl)-1H-pyrazol-5-yl) ethan-1-one B-7 (1.2 g, 5.2 mmol) and $PhI(OAc)_2$ (2.5 g, 7.8 mmol) were dissolved in MeOH (30 mL). The mixture was cooled to −10° C. with an ice-brine bath. KOH (3.5 g, 62.4 mol) was added in portions into the mixture within 30 minutes, then it was stirred at −10° C. for 3 hrs. The reaction was monitored by TLC until completion, the saturated brine (100 mL) was added slowly into the mixture and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5-0.6 to give compound B (1.3 g, yield 85%) as colorless oil. ESI[M+H]$^+$=295.2

9. Preparation of Compounds C14~C15

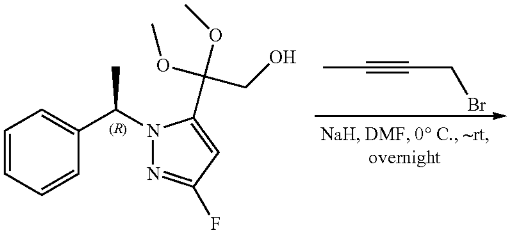

B

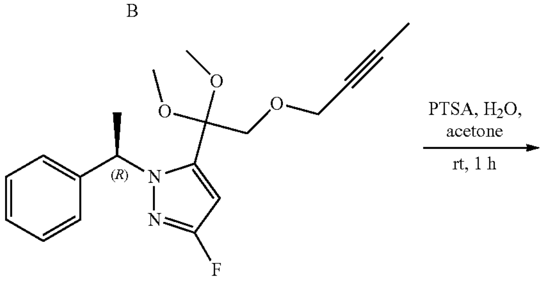

14-1

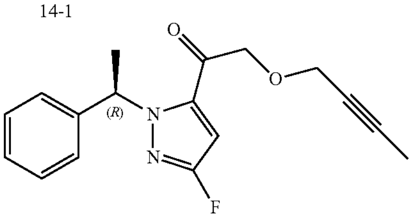

Compound C14

-continued

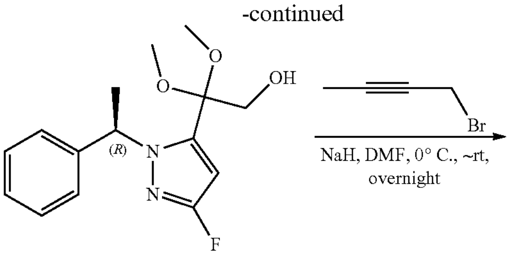

B

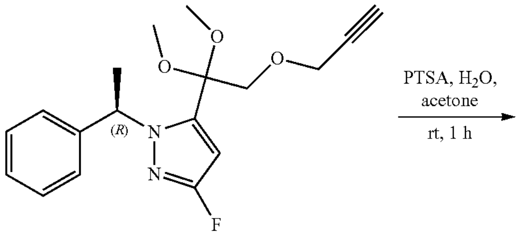

15-1

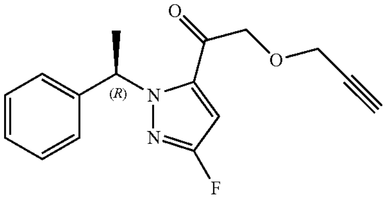

Compound C15

The target compounds C14 and C15 were prepared according to the operation method of preparing compound C1. Compound B reacted with corresponding halides under NaH condition to give intermediate compounds 14-1 and 15-1, which were deprotected with $PTSA.H_2O$ to give target compounds C14 and C15.

The compound C14: 85 mg, ESI[M+H]$^+$=301.0

$^1H$ NMR (400 MHz, $CDCl_3$) δ 7.39-7.19 (m, 5H), 6.55-6.45 (m, 1H), 6.41 (d, J=6.2 Hz, 1H), 4.51 (q, J=16.6 Hz, 2H), 4.24 (q, J=2.3 Hz, 2H), 1.84 (d, J=7.0 Hz, 3H), 1.83 (d, J=2.3 Hz, 3H).

The compound C15: 34 mg, ESI[M+H]$^+$=287.2

$^1H$ NMR (400 MHz, $CDCl_3$) δ 7.39-7.20 (m, 5H), 6.55-6.44 (m, 1H), 6.40 (d, J=6.2 Hz, 1H), 4.54 (q, J=16.6 Hz, 2H), 4.32-4.25 (m, 2H), 2.43 (t, J=2.4 Hz, 1H), 1.85 (d, J=7.0 Hz, 3H).

Example 6 Preparation of Compound C16

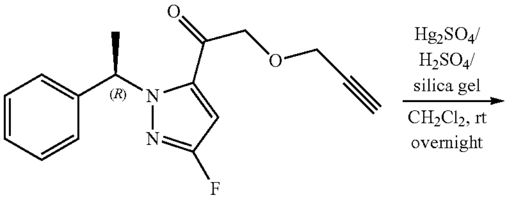

Compound C15

-continued

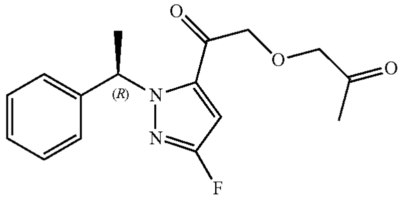

Compound C16

At room temperature, compound C15 (66 mg, 0.23 mmol) and $Hg_2SO_4/H_2SO_4$/silica gel (200 mg) was dissolved in $CH_2Cl_2$ (5 mL). Then the mixture was stirred at room temperature overnight. The reaction was monitored by TLC until completion, the saturated $NaHCO_3$ solution was added into the mixture and extracted with $CH_2Cl_2$ (3×5 mL). The combined organic layers were washed with saturated brine (10 mL), dried over anhydrous sodium sulfate, filtered and concentrated under reduced pressure. The residue was purified by Prep-TLC (ethyl acetate/petroleum ether (v/v)~1/3) and the fraction with Rf=0.4~0.5 was collected and dried to give the product C16 (33 mg, yield 47%) as colorless oil. ESI$[M+H]^+$=305.0

$^1H$ NMR (400 MHz, $CDCl_3$) δ 7.38-7.18 (m, 5H), 6.52-6.43 (m, 1H), 6.38 (d, J=6.2 Hz, 1H), 4.54 (q, J=16.7 Hz, 2H), 4.23-4.08 (m, 2H), 2.15 (s, 3H), 1.84 (d, J=7.0 Hz, 3H).

Example 7 Preparation of Compounds C17~C24

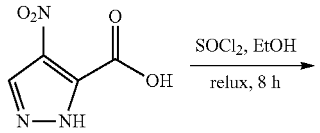

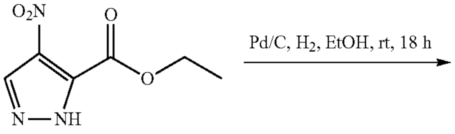

C-1

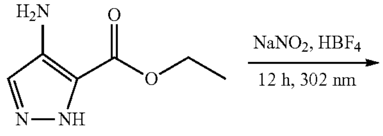

C-2

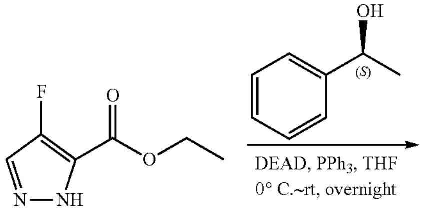

C-3

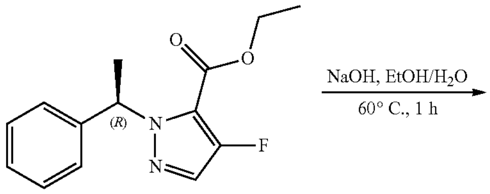

C-4

-continued

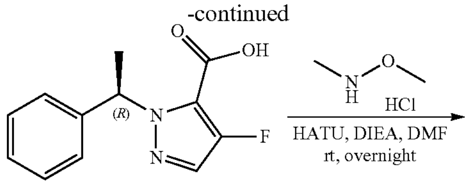

C-5

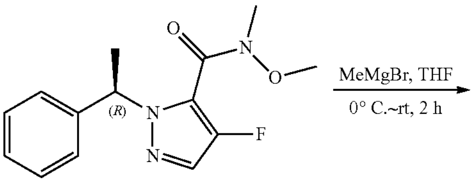

C-6

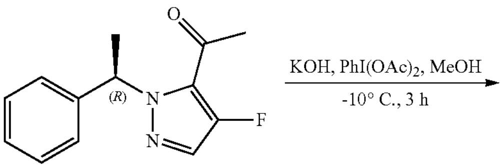

C-7

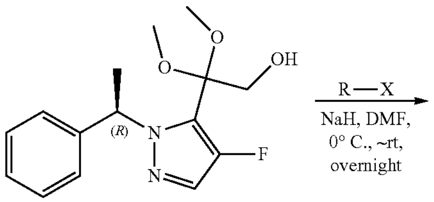

C

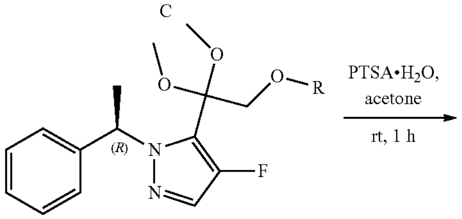

17-1~24-1

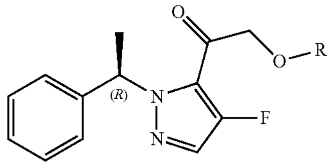

Compound C17~C24

1. Preparation of ethyl 4-nitro-1H-pyrazole-5-carboxylate (C-1)

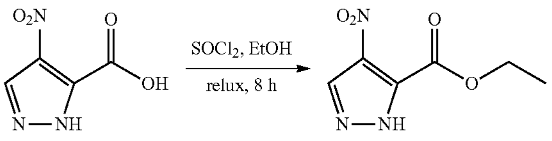

C-1

At room temperature, 4-nitro-1H-pyrazole-5-carboxylic acid (50 g, 318.3 mmol) was dissolved in EtOH (300 mL).

$SOCl_2$ (49 g, 412 mmol) was added dropwise into mixture at 0° C., then it was refluxed for 8 hrs. The reaction was monitored by TLC until completion. The mixture was concentrated under reduced pressure and the residue was dissolved in $CH_2Cl_2$ (30 mL). Then it was adjusted to PH=8~9 with saturated sodium bicarbonate solution and extracted with dichloromethane (3×30 mL). The combined organic layers were washed with saturated brine (50 mL), dried over anhydrous sodium sulfate, filtered and concentrated under reduced pressure to give compound C-1 (54.8 g, yield 93%) as a white solid. ESI$[M+H]^+$=186.1

2. Preparation of ethyl 4-amino-1H-pyrazole-5-carboxylate (C-2)

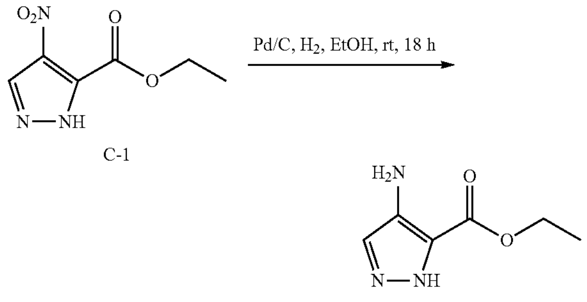

C-1
C-2

At room temperature, ethyl 4-nitro-1H-pyrazole-5-carboxylate C-1 (54.8 g, 296 mmol) and 10% Pd/C (5 g) were dissolved in EtOH (200 mL), the system was replaced with hydrogen three times and stirred under hydrogen for 18 hrs. The reaction was monitored by TLC until completion, filtered and the filter cake was washed with ethanol (3×30 mL). The filtrate was concentrated under reduced pressure and the residue was purified by silica gel column chromatography (ethyl acetate/petroleum ether (v/v)=1/10~1/1), with TLC (ethyl acetate/petroleum ether (v/v)=1/1) monitoring, and collecting the fraction with Rf=0.4~0.5 to give the product C-2 (41.1 g, yield 89%) as a gray solid. ESI$[M+H]^+$=156.1

3. Preparation of ethyl 4-fluoro-1H-pyrazole-5-carboxylate (C-3)

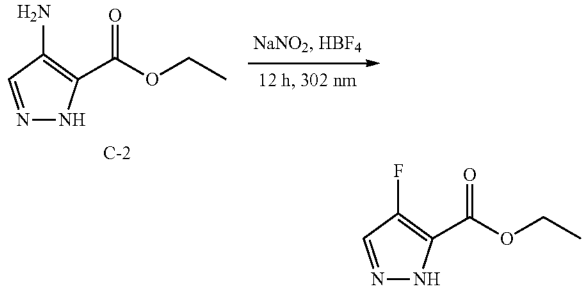

C-2
C-3

At an ice-brine bath, ethyl 4-amino-1H-pyrazole-5-carboxylate C-2 (35 g, 226 mmol) was dissolved in the 40% $HBF_4$. $NaNO_2$ (16.4 g, 238 mmol) in $H_2O$ (30 mL) was added into above mixture. The mixture was stirred under high pressure mercury lamp (302 nm) for 12 hrs. The reaction was monitored by TLC until completion. The mixture was adjusted to PH=8-9 with 1 N NaOH and extracted with ethyl acetate (3×50 mL). The combined organic layers were washed with saturated brine (50 mL), dried over anhydrous sodium sulfate, filtered and concentrated under reduced pressure. the residue was purified by silica gel column chromatography (ethyl acetate/petroleum ether (v/v)=1/10~1/1), with TLC (ethyl acetate/petroleum ether (v/v)=1/1) monitoring, and collecting the fraction with Rf=0.4~0.5 to give the product C-3 (6 g, yield 17%) as a gray solid.

4. Preparation of ethyl (R)-4-fluoro-1-(1-phenylethyl)-1H-pyrazole-5-carboxylate (C-4)

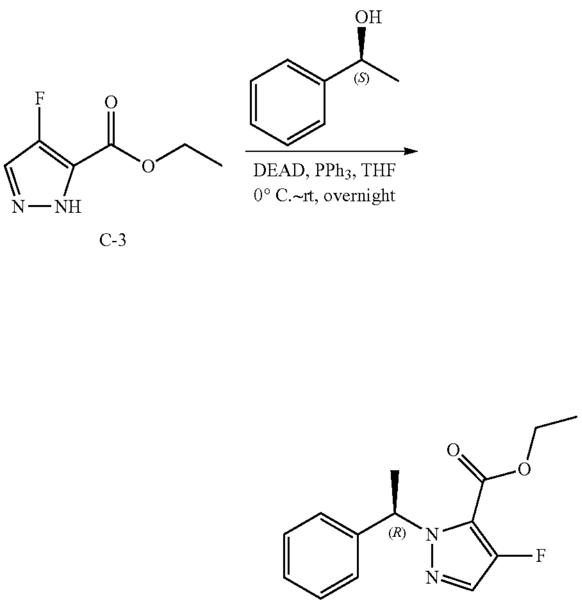

C-3
C-4

In an ice-water bath, S-1-phenylethan-1-ol (6.0 g, 49.1 mmol), ethyl 4-fluoro-1H-pyrazole-5-carboxylate C-3 (6 g, 37.9 mmol) and $PPh_3$ (14.9 g, 56.8 mmol) were dissolved in THF (50 mL) at 0° C., then DEAD (9.9 g, 56.8 mmol) in THF (15 mL) was added into mixture at the rate of 0.5 mmol/min. The mixture was warmed slowly to room temperature and stirred at this temperature overnight. The reaction was monitored by TLC until completion. The mixture was quenched with the saturated brine (30 mL) and extracted with ethyl acetate (3×15 mL). The combined organic layers were washed with saturated brine (30 mL), dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/2) monitoring, and collecting the fraction with Rf=0.5~0.6 to give compound C-4 (5.9 g, yield 59%). ESI$[M+H]^+$=263.1

$^1H$ NMR (400 MHz, $CDCl_3$) δ 7.44 (d, J=4.5 Hz, 1H), 7.35-7.20 (m, 5H), 6.46 (q, J=7.1 Hz, 1H), 4.53-4.09 (m, 2H), 1.88 (d, J=7.1 Hz, 3H), 1.34 (t, J=7.1 Hz, 3H).

5. Preparation of (R)-4-fluoro-1-(1-phenylethyl)-1H-pyrazole-5-carboxylic acid (C-5)

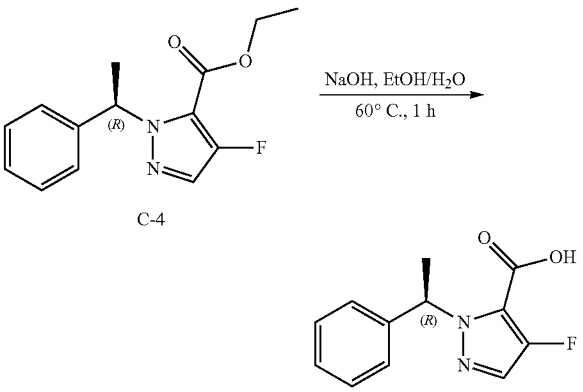

C-4

C-5

At room temperature, NaOH (3.1 g, 77.5 mmol) was added into the mixture ethyl (R)-4-fluoro-1-(1-phenylethyl)-1H-pyrazole-5-carboxylate C-4 (9.5 g, 38.9 mmol) in EtOH/$H_2O$ (25 mL, 1/1), then it was stirred at 60° C. for 1 hour. The reaction was monitored by TLC until completion. The mixture was concentrated under reduced pressure and $H_2O$ (20 mL) was added. The mixture was adjusted to PH=4-5 with 1 N hydrochloric acid and extracted with dichloromethane (3×15 mL). The combined organic layers were dried over anhydrous sodium sulfate, filtered and concentrated under reduced pressure to give compound C-5 (6.7 g, yield 80%) as a white solid. ESI$[M+H]^+$=234.1

$^1H$ NMR (400 MHz, $CDCl_3$) δ 7.62 (d, J=2.0 Hz, 1H), 7.39-7.16 (m, 5H), 7.00 (d, J=2.0 Hz, 1H), 6.56 (q, J=7.0 Hz, 1H), 1.93 (d, J=7.1 Hz, 3H).

6. Preparation of (R)-4-fluoro-N-methoxy-N-methyl-1-(1-phenylethyl)-1H-pyrazole-5-carboxamide (C-6)

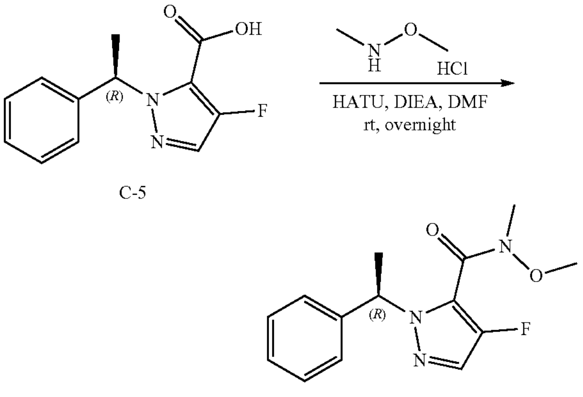

C-5

C-6

At room temperature, (R)-4-fluoro-1-(1-phenylethyl)-1H-pyrazole-5-carboxylic acid C-5 (2.0 g, 8.5 mmol), N,O-dimethylhydroxylamine hydrochloride (1.2 g, 12.3 mmol), DIEA (1.7 g, 13.2 mmol) and HATU (4.7 g, 12.4 mmol) were dissolved in DMF (30 mL). Then the mixture was stirred at room temperature overnight. The reaction was monitored by TLC until completion, $H_2O$ (100 mL) was added, and extracted with ethyl acetate (3×30 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5~0.6 to give the product C-6 (1.8 g, yield 76%) as a white solid. ESI$[M+H]^+$=278.1

7. Preparation of (R)-1-(4-fluoro-1-(1-phenylethyl)-1H-pyrazol-5-yl)ethan-1-one (C-7)

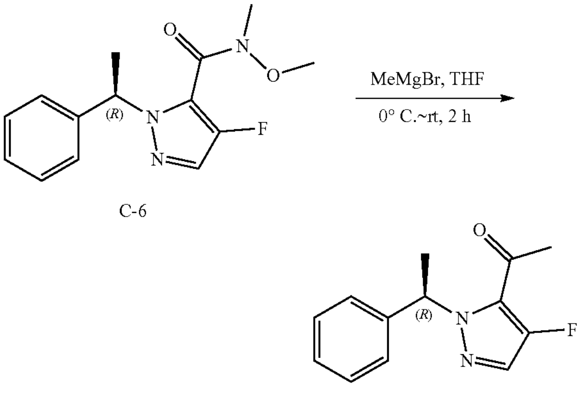

C-6

C-7

At room temperature, Preparation of (R)-4-fluoro-N-methoxy-N-methyl-1-(1-phenylethyl)-1H-pyrazole-5-carboxamide C-6 (1.8 g, 6.5 mmol) were dissolved in anhydrous THF (20 mL). The mixture was cooled to 0° C. with an ice-water bath. MeMgBr (13 mL, 1 mol/L in THF, 13.0 mmol) was added dropwise into the mixture at the rate of 2 mmol/min. Then the mixture was warmed to room temperature slowly and allowed to react for 2 hrs. The reaction was monitored by TLC until completion, the mixture was cooled to 0° C. with an ice-water bath. The mixture was quenched with the saturated ammonium chloride solution (50 mL) and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give compound C-7 (1.2 g, yield 79%) as a white solid. ESI$[M+H]^+$=233.1

8. Preparation of (R)-2-(4-fluoro-1-(1-phenylethyl)-1H-pyrazol-5-yl)-2,2-dimethoxyethan-1-ol (C)

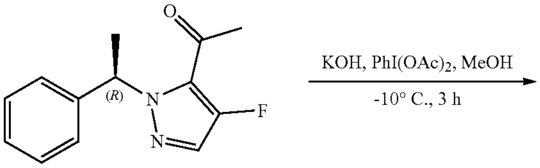

C-7

-continued

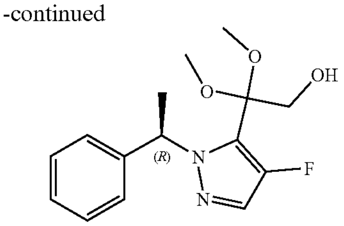

C

At room temperature, (R)-1-(4-fluoro-1-(1-phenylethyl)-1H-pyrazol-5-yl)ethan-1-one C-7 (1.2 g, 5.2 mmol) and $PhI(OAc)_2$ (2.5 g, 7.8 mmol) were dissolved in MeOH (30 mL). The mixture was cooled to −10° C. with an ice-brine bath. KOH (3.5 g, 62.4 mol) was added in portions into the mixture within 30 minutes. Then the mixture was stirred at −10° C. for 3 hrs. The reaction was monitored by TLC until completion, saturated brine (100 mL) was added slowly into the mixture and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5-0.6 to give compound C (1.3 g, yield 85%) as colorless oil. ESI[M+H]$^+$=295.2

9. Preparation of Compound C17~C24

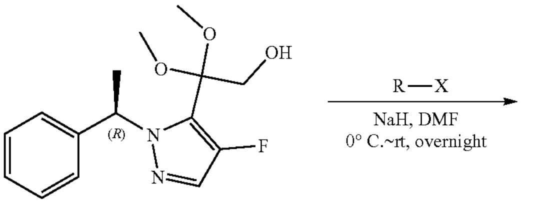

C

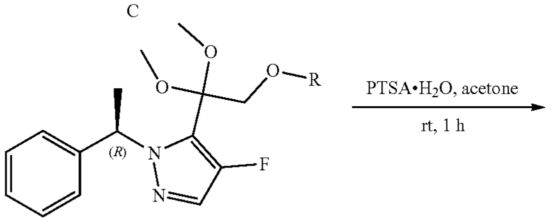

17-1~24.1

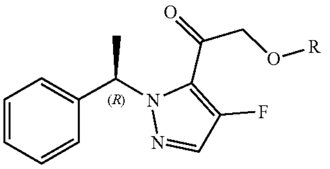

Compound C17~C24

The target compounds C17~C24 were prepared according to the operation method of preparing compound C1. Compound C reacted with corresponding halides under NaH condition to give intermediate compounds 17-1~24-1, which were deprotected with $PTSA.H_2O$ to give target compounds C17~C24.

The compound C17: 29 mg, ESI[M+H]$^+$=301.0

$^1$H NMR (400 MHz, $CDCl_3$) δ 7.44 (d, J=4.5 Hz, 1H), 7.35-7.20 (m, 5H), 6.46 (q, J=7.1 Hz, 1H), 4.54 (q, J=16.7 Hz, 2H), 4.25 (q, J=2.3 Hz, 2H), 1.90 (d, J=7.1 Hz, 3H), 1.83 (t, J=2.3 Hz, 3H).

The compound C18: 22 mg, ESI[M+H]$^+$=317.1

$^1$H NMR (400 MHz, $CDCl_3$) δ 7.43 (d, J=4.5 Hz, 1H), 7.34-7.20 (m, 5H), 6.45 (q, J=7.1 Hz, 1H), 4.54 (q, J=16.7 Hz, 2H), 3.48 (d, J=6.9 Hz, 2H), 2.71-2.56 (m, 1H), 2.12-2.01 (m, 2H), 1.98-1.84 (m, 5H), 1.79-1.69 (m, 2H).

The compound C19: 26 mg, ESI[M+H]$^+$=263.0

$^1$H NMR (400 MHz, $CDCl_3$) δ 7.45 (d, J=4.5 Hz, 1H), 7.33-7.20 (m, 5H), 6.44 (q, J=7.1 Hz, 1H), 4.53 (q, J=16.7 Hz, 2H), 3.45 (s, 3H), 1.88 (d, J=7.1 Hz, 3H).

The compound C20: 66 mg, ESI[M+H]$^+$=277.0

$^1$H NMR (400 MHz, $CDCl_3$) δ 7.46 (d, J=4.5 Hz, 1H), 7.37-7.22 (m, 5H), 6.46 (q, J=7.1 Hz, 1H), 4.52 (q, J=16.7 Hz, 2H), 3.65-3.42 (m, 2H), 1.89 (d, J=7.1 Hz, 3H), 1.25 (t, J=7.0 Hz, 3H).

The compound C21: 36 mg, ESI[M+H]$^+$=287.2

$^1$H NMR (400 MHz, $CDCl_3$) δ 7.45 (d, J=4.5 Hz, 1H), 7.35-7.20 (m, 5H), 6.44 (q, J=7.1 Hz, 1H), 4.53 (q, J=16.7 Hz, 2H), 4.32-4.25 (m, 2H), 2.43 (t, J=2.4 Hz, 1H), 1.85 (d, J=7.1 Hz, 3H).

The compound C22: 54 mg, ESI[M+H]$^+$319.1

$^1$H NMR (400 MHz, $CDCl_3$) δ 7.42 (d, J=4.5 Hz, 1H), 7.32-7.20 (m, 5H), 6.43 (q, J=7.1 Hz, 1H), 5.01-4.76 (m, 1H), 4.52 (q, J=16.7 Hz, 2H), 3.21 (p, J=5.8 Hz, 1H), 1.86 (d, J=7.1 Hz, 3H), 1.60-1.46 (m, 4H), 0.93-0.78 (m, 6H).

The compound C23: 36 mg, ESI[M+H]$^+$331.1

$^1$H NMR (400 MHz, $CDCl_3$) δ 7.45 (d, J=4.5 Hz, 1H), 7.35-7.20 (m, 5H), 6.44 (q, J=7.1 Hz, 1H), 4.54 (q, J=16.7 Hz, 2H), 3.42 (t, J=6.9 Hz, 2H), 2.43-2.29 (m, 1H), 2.11-1.96 (m, 2H), 1.90-1.85 (m, 4H), 1.81-1.78 (m, 1H), 1.76-1.69 (m, 2H), 1.67-1.58 (m, 2H).

The compound C24: 29 mg, ESI[M+H]$^+$=303.1

$^1$H NMR (400 MHz, $CDCl_3$) δ 7.43 (d, J=4.5 Hz, 1H), 7.34-7.20 (m, 5H), 6.46 (q, J=7.1 Hz, 1H), 4.53 (q, J=16.7 Hz, 2H), 4.18-3.94 (m, 2H), 1.87 (d, J=7.1 Hz, 3H), 1.26-1.09 (m, 1H), 0.66-0.48 (m, 2H), 0.40-0.21 (m, 2H).

Example 8 Preparation of Compound C25

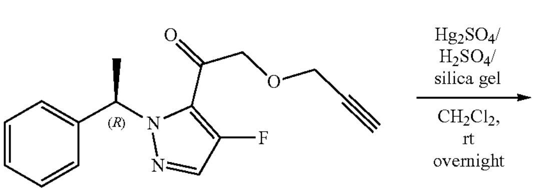

Compound C21

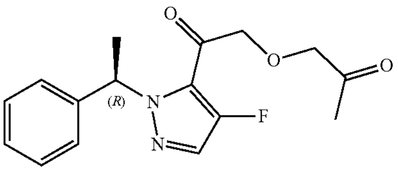

Compound C25

At room temperature, compound C21 (100 mg, 0.35 mmol) and $Hg_2SO_4/H_2SO_4$/silica gel (200 mg) was dissolved in $CH_2Cl_2$ (5 mL). Then the mixture was stirred at room temperature overnight. The reaction was monitored by TLC until completion, the saturated $NaHCO_3$ solution was added into the mixture and extracted with $CH_2Cl_2$ (3×5 mL). The combined organic layers were washed with saturated brine (10 mL), dried over anhydrous sodium sulfate, filtered and concentrated under reduced pressure. The residue was purified by Prep-TLC (ethyl acetate/petroleum ether (v/v) ~1/3), collecting the fraction with Rf=0.4~0.5 to give the product $C_{25}$ (65 mg, yield 61%). ESI[M+H]$^+$305.1

$^1$H NMR (400 MHz, $CDCl_3$) δ 7.46 (d, J=4.5 Hz, 1H), 7.37-7.23 (m, 5H), 6.46 (q, J=7.1 Hz, 1H), 4.55 (q, J=16.7 Hz, 2H), 4.21 (s, 2H), 2.15 (s, 3H), 1.88 (d, J=7.1 Hz, 3H).

Example 9 Preparation of Compounds C26~C49

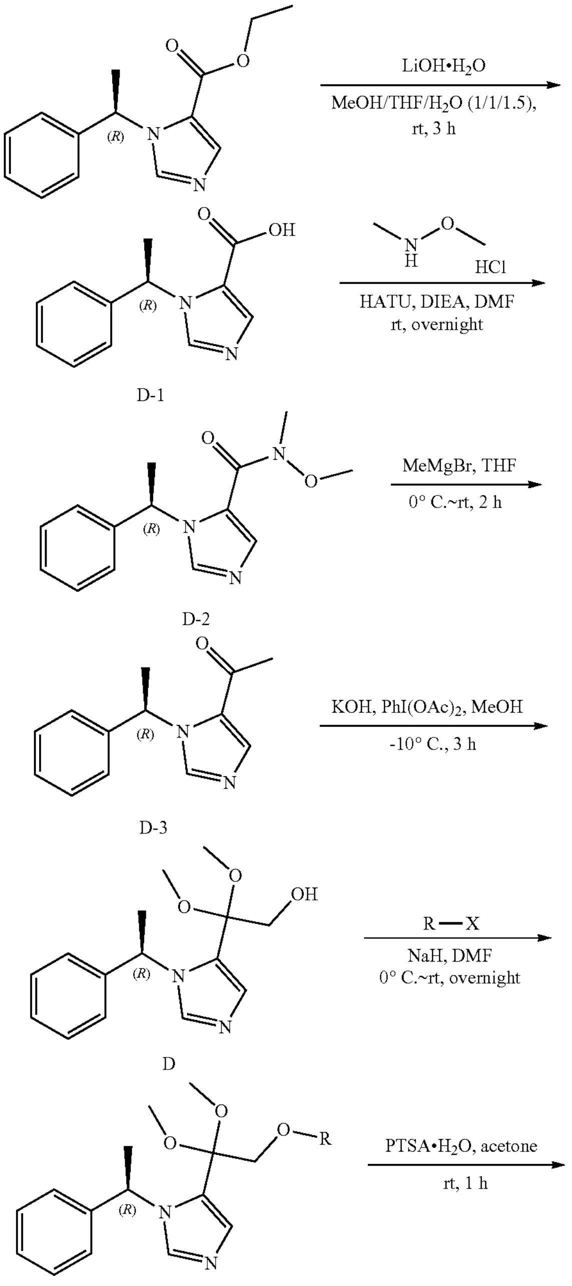

D-1

D-2

D-3

D 26-1~49-1

-continued

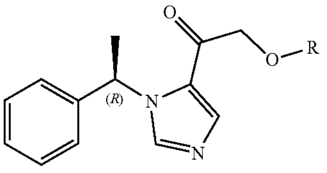

Compound C26~C49

1. Preparation of (R)-1-(1-phenylethyl)-1H-imidazole-5-carboxylic acid (D-1)

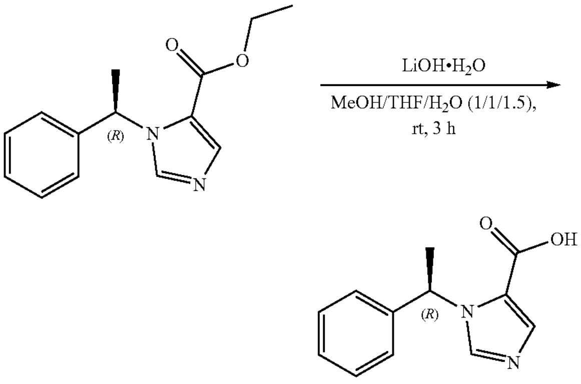

D-1

At room temperature, LiOH·$H_2O$ (6.9 g, 164.4 mmol) was added into the mixture of (R)-1-(1-phenylethyl)-1H-imidazole-5-carboxylate (20.0 g, 81.9 mmol) in MeOH/THF/$H_2O$ (80 mL, 1/1/1.5), then it was stirred at room temperature for 3 hrs. The reaction was monitored by TLC until completion. The mixture was concentrated under reduced pressure and $H_2O$ (50 mL) was added. The mixture was adjusted to PH=4~5 with 1 N hydrochloric acid and extracted with dichloromethane (5×30 mL). The combined organic layers were dried over anhydrous sodium sulfate, filtered and concentrated under reduced pressure. The residue was washed with tert-Butyl methyl ether to give compound D-1 (15 mg, yield 85%) as a white solid. ESI[M+H]$^+$=217.3

$^1$H NMR (400 MHz, $CDCl_3$) δ 9.73 (brs, 1H), 7.89 (s, 1H), 7.87 (s, 1H), 7.39-7.27 (m, 3H), 7.26-7.18 (m, 2H), 6.55 (q, J=7.1 Hz, 1H), 1.87 (d, J=7.1 Hz, 3H).

2. Preparation of (R)—N-methoxy-N-methyl-1-(1-phenylethyl)-1H-imidazole-5-carboxamide (D-2)

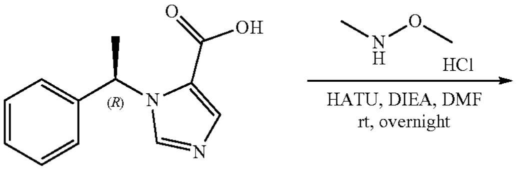

D-1

-continued

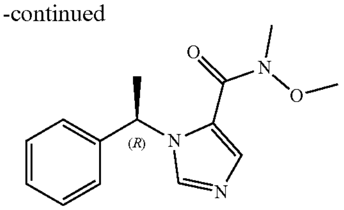

D-2

At room temperature, (R)-1-(1-phenylethyl)-1H-imidazole-5-carboxylic acid D-1 (13 g, 60 mmol), N,O-dimethylhydroxylamine hydrochloride (11.7 g, 120 mmol), DIEA (15.5 g, 120 mmol) and HATU (45.6 g, 120 mmol) were dissolved in DMF (200 mL). Then the mixture was stirred at room temperature overnight. The reaction was monitored by TLC until completion, $H_2O$ (500 mL) was added, and extracted with ethyl acetate (4×50 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5~0.6 to give the product D-2 (13 g, yield 84%) as a white solid. ESI$[M+H]^+$=260.1

3. Preparation of (R)-1-(1-(1-phenylethyl)-1H-imidazol-5-yl)ethan-1-one (D-3)

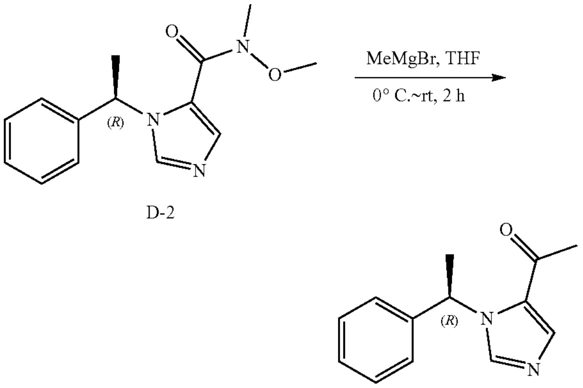

D-2

D-3

At room temperature, (R)—N-methoxy-N-methyl-1-(1-phenylethyl)-1H-imidazole-5-carboxamide D-2 (13 g, 50.1 mmol) were dissolved in anhydrous THF (100 mL). The mixture was cooled to 0° C. with an ice-water bath. MeMgBr (100.2 mL, 1 mol/L in THF, 100.2 mmol) was added dropwise into the mixture at the rate of 5 mmol/min. Then the mixture was warmed to room temperature slowly and allowed to react for 2 hrs. The reaction was monitored by TLC until completion, the mixture was cooled to 0° C. with an ice-water bath. The mixture was quenched with the saturated ammonium chloride solution (100 mL) and extracted with ethyl acetate (3×50 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give compound D-3 (9.1 g, yield 85%) as a white solid. ESI$[M+H]^+$=215.1

4. Preparation of (R)-2,2-dimethoxy-2-(1-(1-phenylethyl)-1H-imidazol-5-yl)ethan-1-ol (D)

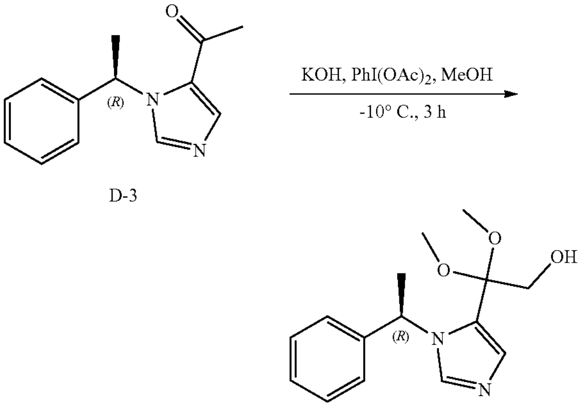

D-3

D

At room temperature, (R)-1-(1-(1-phenylethyl)-1H-imidazol-5-yl)ethan-1-one D-3 (9 g, 42 mmol) and $PhI(OAc)_2$ (20.3 g, 63 mmol) were dissolved in MeOH (100 mL). The mixture was cooled to −10° C. with an ice-brine bath. KOH (28.3 g, 504 mol) was added in portions into the mixture within 50 minutes. Then the mixture was stirred at −10° C. for 3 hrs. The reaction was monitored by TLC until completion, the saturated brine (200 mL) was added slowly into the mixture and extracted with ethyl acetate (3×50 mL). The combined organic layers were dried over anhydrous sodium sulfate, filtered and concentrated under reduced pressure. The residue was purified by silica gel column chromatography (ethyl acetate/petroleum ether (v/v)=1/20~1/5), with TLC (ethyl acetate/petroleum ether (v/v)=1/3) monitoring, and collecting the fraction with Rf=0.5~0.6 to give compound D (7.4 g, yield 64%) as a white solid. ESI$[M+H]^+$=277.2

5. Preparation of Compounds C26~C49

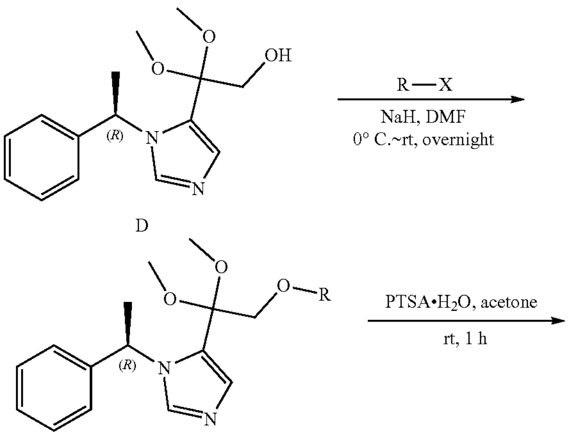

D 26-1~49-1

-continued

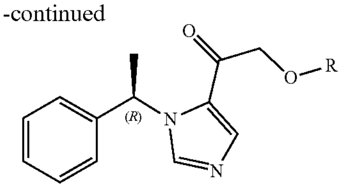

Compound C26~C49

The target compounds C26~C49 were prepared according to the operation method of preparing compound C1. Compound D reacted with corresponding halides under NaH condition to give intermediate compounds 26-1~49-1, which were deprotected with PTSA.$H_2O$ to give target compounds C26~C49.

The compound C26: 37 mg, ESI$[M+H]^+$=269.0

$^1$H NMR (400 MHz, $CDCl_3$) δ 8.00 (s, 1H), 7.86 (s, 1H), 7.38-7.28 (m, 3H), 7.24-7.15 (m, 2H), 6.44 (q, J=7.1 Hz, 1H), 4.32 (s, 2H), 1.86 (d, J=7.0 Hz, 3H), 1.80 (s, 3H).

The compound C27: 70 mg, ESI$[M+H]^+$=283.2

$^1$H NMR (400 MHz, $CDCl_3$) δ 7.96 (s, 1H), 7.81 (s, 1H), 7.38-7.27 (m, 3H), 7.24-7.17 (m, 2H), 6.43 (q, J=7.1 Hz, 1H), 4.54 (q, J=15.8 Hz, 2H), 4.23 (q, J=2.3 Hz, 2H), 1.86-1.84 (m, 6H).

The compound C28: 16 mg, ESI$[M+H]^+$=285.1

$^1$H NMR (400 MHz, $CDCl_3$) δ 8.02 (s, 1H), 7.88 (s, 1H), 7.39-7.28 (m, 3H), 7.24-7.15 (m, 2H), 6.45 (q, 6.6 Hz, 1H), 4.33 (s, 2H), 3.97 (p, J=7.1 Hz, 1H), 2.26-2.12 (m, 2H), 2.05-1.90 (m, 2H), 1.86 (d, J=7.0 Hz, 3H), 1.77-1.64 (m, 1H), 1.55-1.39 (m, 1H).

The compound C29: 23 mg, ESI$[M+H]^+$=299.1

$^1$H NMR (400 MHz, $CDCl_3$) δ 8.00 (s, 1H), 7.83 (s, 1H), 7.38-7.27 (m, 3H), 7.24-7.14 (m, 2H), 6.45 (q, J=6.5 Hz, 1H), 4.40 (s, 2H), 3.45 (p, J=9.3 Hz, 2H), 2.68-2.51 (m, 1H), 2.10-2.01 (m, 2H), 1.98-1.88 (m, 2H), 1.85 (d, J=6.9 Hz, 3H), 1.78-1.66 (m, 2H).

The compound C30: 38 mg, ESI$[M+H]^+$=335.0

$^1$H NMR (400 MHz, $CDCl_3$) δ 8.01 (s, 1H), 7.85 (s, 1H), 7.38-7.28 (m, 3H), 7.23-7.15 (m, 2H), 6.45 (q, J=7.1 Hz, 1H), 4.33 (s, 2H), 4.28-4.14 (m, 2H), 2.75-2.58 (m, 2H), 2.58-2.29 (m, 3H), 1.85 (d, J=7.0 Hz, 3H).

The compound C31: 26 mg, ESI$[M+H]^+$=297.1

$^1$H NMR (400 MHz, $CDCl_3$) δ 7.98 (s, 1H), 7.82 (s, 1H), 7.37-7.26 (m, 3H), 7.23-7.14 (m, 2H), 6.43 (q, J=7.1 Hz, 1H), 4.32 (s, 2H), 5.23-5.09 (m, 1H), 4.92 (s, 2H), 3.18-2.97 (m, 2H), 2.93-2.78 (m, 2H), 1.87 (d, J=7.0 Hz, 3H).

The compound C32: 17 mg, ESI$[M+H]^+$=329.1

$^1$H NMR (400 MHz, $CDCl_3$) δ 8.00 (s, 1H), 7.86 (s, 1H), 7.39-7.28 (m, 3H), 7.24-7.15 (m, 2H), 6.45 (q, J=7.1 Hz, 1H), 4.33 (s, 2H), 3.40 (s, 2H), 3.33 (s, 3H), 1.98-1.86 (m, 6H), 1.85 (d, J=7.0 Hz, 3H).

The compound C33: 78 mg, ESI$[M+H]^+$=245.1

$^1$H NMR (400 MHz, $CDCl_3$) δ 7.93 (s, 1H), 7.82 (s, 1H), 7.37-7.27 (m, 3H), 7.23-7.16 (m, 2H), 6.44 (q, J=7.1 Hz, 1H), 4.51-4.29 (m, 2H), 3.43 (s, 3H), 1.85 (d, J=7.1 Hz, 3H).

The compound C34: 73 mg, ESI$[M+H]^+$=259.1

$^1$H NMR (400 MHz, $CDCl_3$) δ 7.97 (s, 1H), 7.81 (s, 1H), 7.38-7.27 (m, 3H), 7.20 (d, J=6.9 Hz, 2H), 6.44 (q, J=7.1 Hz, 1H), 4.54-4.33 (m, 2H), 3.56 (qd, J=7.0, 1.1 Hz, 2H), 1.85 (d, J=7.1 Hz, 3H), 1.25 (t, J=7.0 Hz, 3H).

The compound C35: 35 mg, ESI$[M+H]^+$=269.0

$^1$H NMR (400 MHz, $CDCl_3$) δ 7.94 (s, 1H), 7.82 (s, 1H), 7.37-7.27 (m, 3H), 7.24-7.16 (m, 2H), 6.42 (q, J=7.2 Hz, 1H), 4.57 (q, J=15.8 Hz, 2H), 4.28 (d, J=2.4 Hz, 2H), 2.45 (t, J=2.4 Hz, 1H), 1.85 (d, J=7.1 Hz, 3H).

The compound C36: 55 mg, ESI$[M+H]^+$=301.1

$^1$H NMR (400 MHz, $CDCl_3$) δ 8.07 (s, 1H), 7.89 (s, 1H), 7.41-7.28 (m, 3H), 7.24-7.16 (m, 2H), 6.47 (q, J=7.1 Hz, 1H), 4.40 (s, 2H), 3.21 (p, J=5.8 Hz, 1H), 1.86 (d, J=7.1 Hz, 3H), 1.60-1.46 (m, 4H), 0.93-0.78 (m, 6H).

The compound C37: 23 mg, ESI$[M+H]^+$=283.0

$^1$H NMR (400 MHz, $CDCl_3$) δ 8.01 (s, 1H), 7.83 (s, 1H), 7.39-7.28 (m, 3H), 7.22-7.15 (m, 2H), 6.42 (q, J=6.6 Hz, 1H), 4.46-4.38 (m, 1H), 4.33 (s, 2H), 2.49 (dd, J=8.8, 2.1 Hz, 1H), 1.88 (d, J=7.1 Hz, 3H), 1.57 (dd, J=6.7, 3.8 Hz, 3H).

The compound C38: 24 mg, ESI$[M+H]^+$=325.0

$^1$H NMR (400 MHz, $CDCl_3$) δ 8.00 (s, 1H), 7.85 (s, 1H), 7.38-7.27 (m, 3H), 7.24-7.15 (m, 2H), 6.45 (q, J=6.6 Hz, 1H), 5.61 (t, J=6.9 Hz, 1H), 5.10-4.69 (m, 6H), 4.33 (s, 2H), 1.86 (d, J=7.0 Hz, 3H).

The compound C39: 26 mg, ESI$[M+H]^+$=297.1

$^1$H NMR (400 MHz, $CDCl_3$) δ 8.02 (s, 1H), 7.88 (s, 1H), 7.39-7.28 (m, 3H), 7.26-7.17 (m, 2H), 6.47 (q, J=6.6 Hz, 1H), 5.39-5.25 (m, 1H), 4.97-4.72 (m, 3H), 4.33 (s, 2H), 1.87 (d, J=7.0 Hz, 3H), 1.45-1.38 (m, 3H).

The compound C40: 70 mg, ESI$[M+H]^+$=313.1

$^1$H NMR (400 MHz, $CDCl_3$) δ 7.98 (s, 1H), 7.82 (s, 1H), 7.38-7.27 (m, 3H), 7.22-7.16 (m, 2H), 6.44 (q, J=7.1 Hz, 1H), 4.39 (s, 2H), 3.40 (t, J=6.9 Hz, 2H), 2.41-2.31 (m, 1H), 2.08-1.97 (m, 2H), 1.90-1.76 (m, 5H), 1.71 (q, J=7.0 Hz, 2H), 1.66-1.55 (m, 2H).

The compound C41: 11 mg, ESI$[M+H]^+$=297.1

$^1$H NMR (400 MHz, $CDCl_3$) δ 8.00 (s, 1H), 7.86 (s, 1H), 7.39-7.28 (m, 3H), 7.24-7.15 (m, 2H), 6.45 (q, J=6.6 Hz, 1H), 4.51-4.42 (m, 1H), 4.33 (s, 2H), 1.86 (d, J=7.0 Hz, 3H), 1.84 (dd, J=12.9, 2.1 Hz, 3H), 1.52 (t, J=6.6 Hz, 3H).

The compound C42: 20 mg, ESI$[M+H]^+$=305.0

$^1$H NMR (400 MHz, $CDCl_3$) δ 8.01 (s, 1H), 7.87 (s, 1H), 7.40-7.28 (m, 3H), 7.25-7.15 (m, 2H), 6.45 (q, J=7.1 Hz, 1H), 5.23-5.12 (m, 1H), 4.33 (s, 2H), 3.33 (s, 6H), 1.86 (d, J=7.0 Hz, 3H).

The compound C43: 18 mg, ESI$[M+H]^+$=341.0

$^1$H NMR (400 MHz, $CDCl_3$) δ 8.02 (s, 1H), 7.86 (s, 1H), 7.39-7.27 (m, 3H), 7.24-7.15 (m, 2H), 6.46 (q, J=7.1 Hz, 1H), 3.93-3.88 (m, 1H), 4.31 (s, 2H), 3.48 (s, 4H), 1.85 (d, J=7.0 Hz, 3H).

The compound C44: 32 mg, ESI$[M+H]^+$=333.1

$^1$H NMR (400 MHz, $CDCl_3$) δ 8.03 (s, 1H), 7.88 (s, 1H), 7.41-7.30 (m, 3H), 7.26-7.17 (m, 2H), 6.47 (q, J=7.1 Hz, 1H), 4.33 (s, 2H), 3.72-3.68 (m, 1H), 3.51-3.46 (m, 4H), 3.31 (s, 6H), 1.87 (d, J=7.0 Hz, 3H).

The compound C45: 195 mg, ESI$[M+H]^+$=287.1

$^1$H NMR (400 MHz, $CDCl_3$) δ 8.05 (s, 1H), 7.78 (s, 1H), 7.36-7.24 (m, 3H), 7.23-7.15 (m, 2H), 6.45 (q, J=7.1 Hz, 1H), 4.44-4.24 (m, 2H), 1.84 (d, J=7.1 Hz, 3H), 1.23 (s, 9H).

The compound C46: 66 mg, ESI$[M+H]^+$=285.1

$^1$H NMR (400 MHz, $CDCl_3$) δ 8.03 (s, 1H), 7.87 (s, 1H), 7.40-7.27 (m, 3H), 7.24-7.15 (m, 2H), 6.45 (q, J=7.1 Hz, 1H), 4.45 (s, 2H), 3.43-3.23 (m, 2H), 1.85 (d, J=7.1 Hz, 3H), 1.13-1.01 (m, 1H), 0.58-0.48 (m, 2H), 0.24-0.13 (m, 2H).

The compound C47: 19 mg, ESI$[M+H]^+$=299.1

$^1$H NMR (400 MHz, $CDCl_3$) δ 8.00 (s, 1H), 7.86 (s, 1H), 7.38-7.27 (m, 3H), 7.24-7.15 (m, 2H), 6.44 (q, J=7.1 Hz, 1H), 4.32 (s, 2H), 3.51-3.46 (m, 1H), 1.86 (d, J=7.0 Hz, 3H), 1.19-1.00 (m, 4H), 0.63-0.43 (m, 2H), 0.26-0.09 (m, 2H).

The compound C48: 35 mg, ESI$[M+H]^+$=271.0

$^1$H NMR (400 MHz, $CDCl_3$) δ 8.02 (s, 1H), 7.86 (s, 1H), 7.41-7.28 (m, 3H), 7.24-7.15 (m, 2H), 6.46 (q, J=7.1 Hz, 1H), 4.33 (s, 2H), 3.42-3.34 (m, 1H), 0.67-0.45 (m, 4H), 1.88 (d, J=7.0 Hz, 3H).

The compound C49: 35 mg, ESI$[M+H]^+$=301.1

$^1H$ NMR (400 MHz, $CDCl_3$) δ 8.00 (s, 1H), 7.86 (s, 1H), 7.39-7.28 (m, 3H), 7.24-7.15 (m, 2H), 6.45 (q, J=7.1 Hz, 1H), 4.33 (s, 2H), 3.82-3.76 (m, 2H), 1.88 (d, J=7.0 Hz, 3H), 1.01 (s, 9H).

Example 10 Preparation of Compounds C50~C51

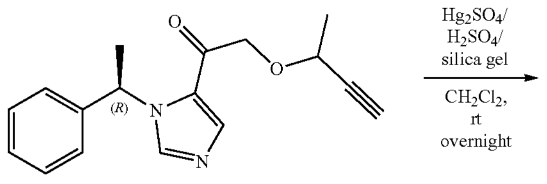

Compound C37

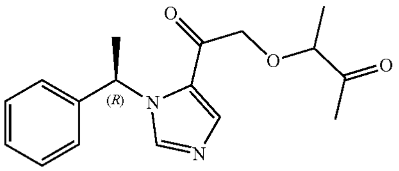

Compound C50

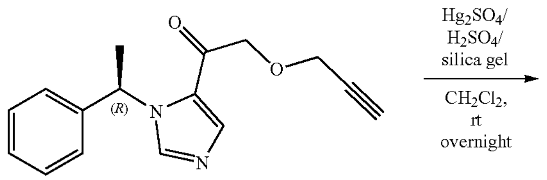

Compound C35

-continued

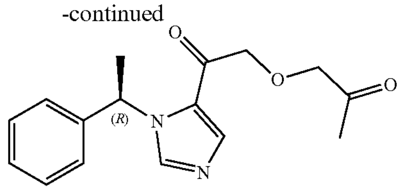

Compound C51

The target compounds C50~C51 were prepared according to the operation method of preparing compound C8 described in Example 2. Compounds C37 or C35 reacted with $Hg_2SO_4/H_2SO_4$/silica gel, then it was purified by Prep-TLC.

The compound C50: 32 mg, ESI$[M+H]^+$=301.1

$^1H$ NMR (400 MHz, $CDCl_3$) δ 8.00 (s, 1H), 7.86 (s, 1H), 7.39-7.28 (m, 3H), 7.24-7.15 (m, 2H), 6.45 (q, J=7.1 Hz, 1H), 4.33 (s, 2H), 4.31-4.25 (m, 1H), 2.03 (s, 3H), 1.86 (d, J=7.0 Hz, 3H), 1.33-1.21 (m, 3H),

The compound C51: 150 mg, ESI$[M+H]^+$=287.0

$^1H$ NMR (400 MHz, $CDCl_3$) δ 8.17 (s, 1H), 8.05 (s, 1H), 7.42-7.31 (m, 3H), 7.25-7.20 (m, 2H), 6.51-6.42 (m, 1H), 4.53 (s, 2H), 4.21 (s, 2H), 2.15 (s, 3H), 1.89 (d, J=6.4 Hz, 3H).

Example 11 Preparation of Compounds C52~C53

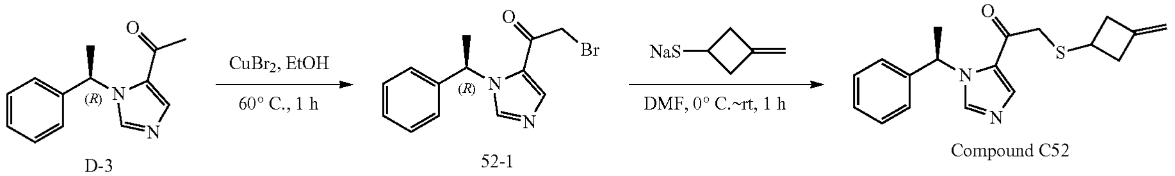

D-3

52-1

Compound C52

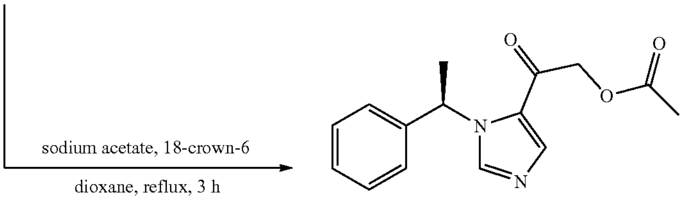

Compound C53

The target compounds C52~C53 were prepared according to the operation method of preparing compound C9 described in Example 3. D-3 worked with $CuBr_2$ to give 52-1, which worked with sodium 3-methylenecyclobutane-1-thiolate or sodium acetate to give target compounds C52 and C53

The compound C52: 35 mg, ESI$[M+H]^+$=313.0

$^1$H NMR (400 MHz, $CDCl_3$) δ 8.00 (s, 1H), 7.86 (s, 1H), 7.39-7.28 (m, 3H), 7.24-7.15 (m, 2H), 6.45 (q, J=7.1 Hz, 1H), 4.82 (s, 2H), 3.60 (s, 2H), 2.62-2.59 (m, 1H), 2.43-2.39 (m, 2H), 2.21-2.15 (m, 2H), 1.87 (d, J=7.0 Hz, 3H).

The compound C53: 18 mg, ESI$[M+H]^+$=273.1

$^1$H NMR (400 MHz, $CDCl_3$) δ 7.88 (s, 1H), 7.78 (s, 1H), 7.42-7.27 (m, 3H), 7.25-7.16 (m, 2H), 6.39 (q, J=7.1 Hz, 1H), 5.08 (dd, J=69.5, 15.8 Hz, 2H), 2.20 (s, 3H), 1.84 (d, J=7.1 Hz, 3H).

Example 12 Preparation of Compounds C54~C56

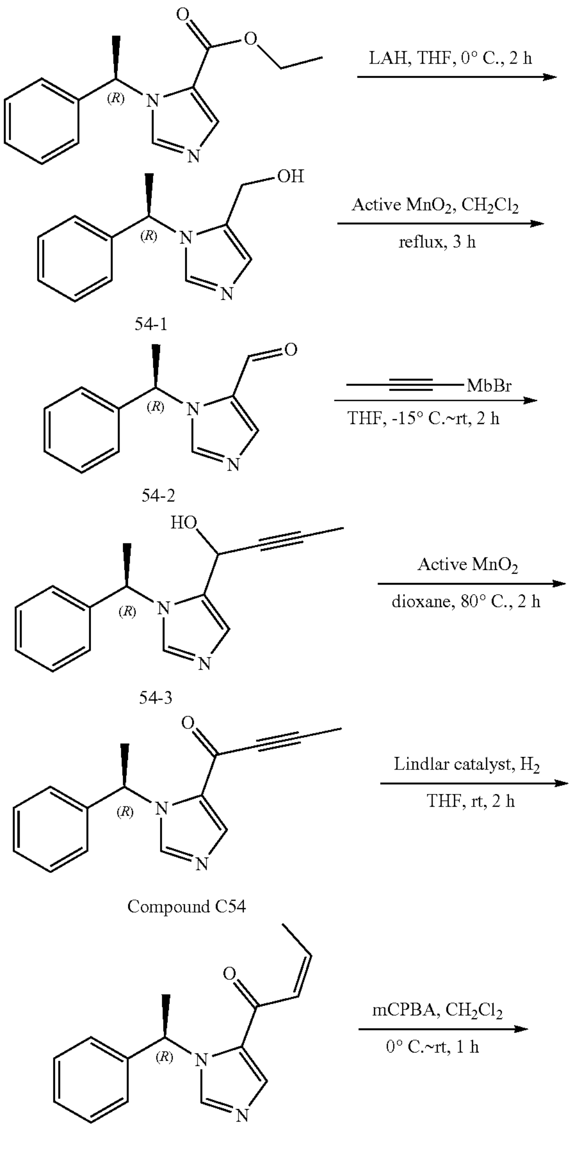

54-1

54-2

54-3

Compound C54

Compound C55

-continued

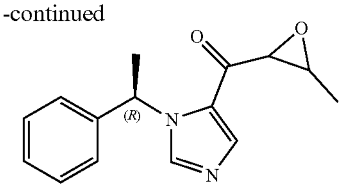

Compound C56

The target compounds C54~C56 were prepared according to the operation method of preparing compounds C11~C13 described in Example 4.

Etomidate was reduced by LAH, then oxidized by active $MnO_2$ to give compound 54-2, which worked with prop-1-yn-1-ylmagnesium bromide followed by active $MnO_2$ to give the compound C54. The compound C54 was reduced by Lindlar catalyst to give compound C55, which was oxidized by m-CPBA to give the compound C56.

The compound C54: 57 mg, ESI$[M+H]^+$=239.4

$^1$H NMR (400 MHz, $CDCl_3$) δ 7.99 (s, 1H), 7.77 (s, 1H), 7.40-7.27 (m, 3H), 7.25-7.15 (m, 2H), 6.41 (q, J=7.0 Hz, 1H), 2.09 (s, 3H), 1.84 (d, J=7.1 Hz, 3H).

The compound C55: 95 mg, ESI$[M+H]^+$=241.3

$^1$H NMR (400 MHz, $CDCl_3$) δ 7.82 (s, 1H), 7.79 (s, 1H), 7.40-7.30 (m, 3H), 7.26-7.21 (m, 2H), 6.73-6.53 (m, 2H), 6.44-6.30 (m, 1H), 2.15 (dd, J=7.3, 1.7 Hz, 3H), 1.87 (d, J=7.1 Hz, 3H).

The compound C56: 13 mg, ESI$[M+H]^+$=257.2

$^1$H NMR (400 MHz, $CDCl_3$) δ 8.13 (s, 1H), 7.85 (s, 1H), 7.38-7.27 (m, 3H), 7.23-7.13 (m, 2H), 6.51-6.32 (m, 1H), 3.63 (d, J=12.7 Hz, 1H), 3.23-3.09 (m, 1H), 1.84 (d, J=5.3 Hz, 3H), 1.44 (d, J=4.8 Hz, 3H).

Example 13 Preparation of Compounds C57~C67

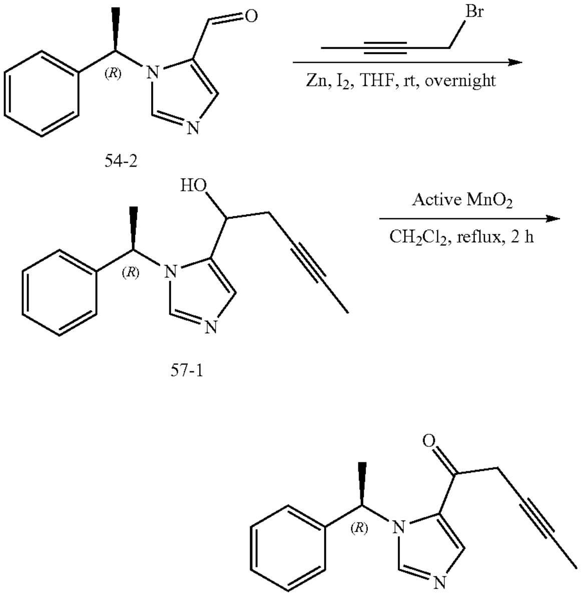

54-2

57-1

Compound C57

1. Preparation of (R)-1-(1-(1-phenylethyl)-1H-imidazol-5-yl)pent-3-yn-1-one (57-1)

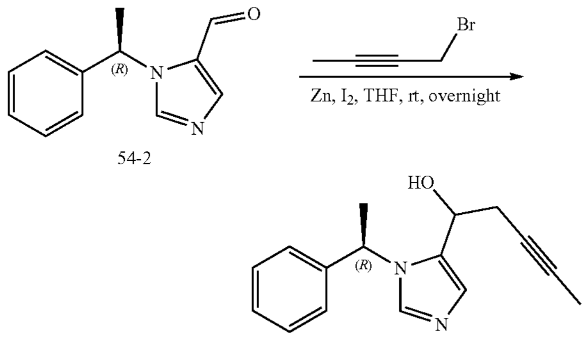

54-2

57-1

At room temperature, Zn (245 mg, 3.75 mmol) and $I_2$ (190 mg, 0.75 mmol) was dissolved in anhydrous THF (15 mL). The mixture was replaced with nitrogen twice. The solution of the compound 54-2 (150 mg, 0.75 mmol) and 1-bromobut-2-yne (120 mg, 0.90 mmol) in THF (5 mL) was added dropwise into the mixture at the rate of 1 mL/min using a syringe. Then the mixture was warmed to room temperature slowly and allowed to react overnight. The reaction was monitored by TLC until completion, and then it was cooled to 0° C., quenched with the saturated ammonium chloride solution (10 mL) and extracted with ethyl acetate (3×10 mL). The combined organic layers were dried over anhydrous sodium sulfate, filtered and concentrated under reduced pressure to give the crude product 57-1, which was used for next step directly without further purification.

2. Preparation of Compound C57

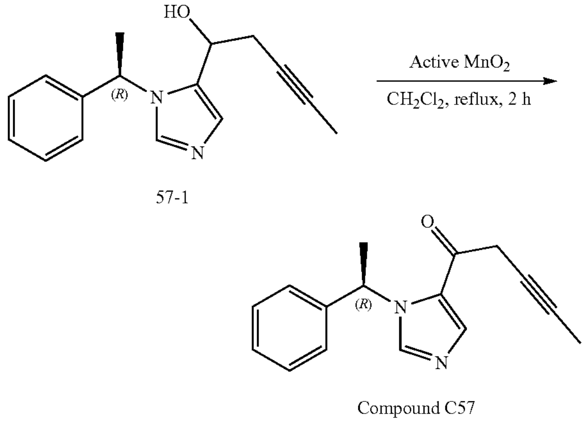

57-1

Compound C57

At room temperature, active $MnO_2$ (2.6 g, 30 mmol) was added into the solution of crude 57-1 in $CH_2Cl_2$ (50 mL). The mixture was refluxed for 2 hrs. The reaction was monitored by TLC until completion. The mixture was cooled to room temperature, filtered and the filter cake was washed with $CH_2Cl_2$ (30 mL). The filtrate was concentrated under reduced pressure and the residue was purified by Prep-TLC (ethyl acetate/petroleum ether (v/v)~1/3), collecting the fraction with Rf=0.4~0.5 to give the product $C_{57}$ (12 mg, two steps yield 6.3%). ESI[M+H]$^+$=253.3

$^1$H NMR (400 MHz, $CDCl_3$) δ 7.84 (s, 1H), 7.73 (s, 1H), 7.40-7.28 (m, 3H), 7.22-7.12 (m, 2H), 6.32 (q, J=7.1 Hz, 1H), 5.19-5.05 (m, 2H), 1.91 (t, J=3.0 Hz, 3H), 1.85 (d, J=7.1 Hz, 3H).

3. Preparation of Compounds C58~C67

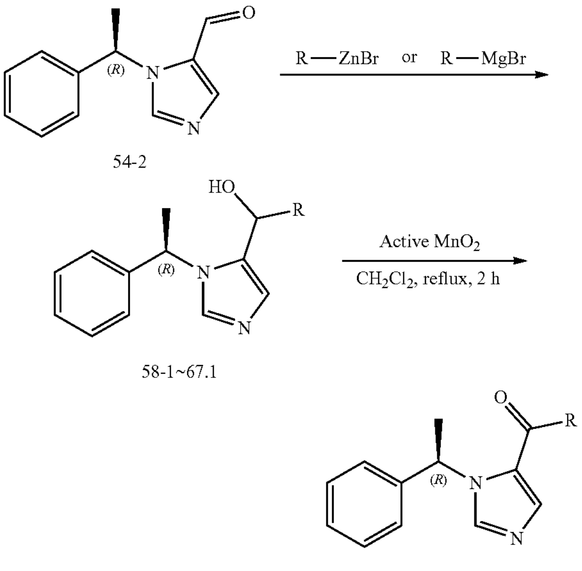

54-2

58-1~67.1

Compound C58~C67

The target compounds C58~C67 were prepared according to the operation method of preparing compound C57.

Compound 54-2 worked with corresponding zinc reagents or grignard reagents to give 58-1~67-1, which was oxidized by active $MnO_2$ to give $C_{58}$~C67.

The compound C58: 15 mg, ESI[M+H]$^+$=317.1

$^1$H NMR (400 MHz, $CDCl_3$) δ 8.01 (s, 1H), 7.85 (s, 1H), 7.39-7.28 (m, 3H), 7.24-7.15 (m, 2H), 6.43 (q, J=7.1 Hz, 1H), 3.43-3.31 (m, 4H), 3.33 (s, 6H), 2.43-2.31 (m, 2H), 2.14-2.03 (m, 1H), 1.87 (d, J=7.0 Hz, 3H).

The compound C59: 35 mg, ESI[M+H]$^+$=313.3

$^1$H NMR (400 MHz, $CDCl_3$) δ 8.01 (s, 1H), 7.84 (s, 1H), 7.39-7.28 (m, 3H), 7.26-7.15 (m, 2H), 6.45 (q, J=7.1 Hz, 1H), 3.37 (s, 2H), 3.33 (s, 3H), 2.31-2.17 (m, 2H), 1.94-1.83 (m, 9H).

The compound C60: 16 mg, ESI[M+H]$^+$=327.1

$^1$H NMR (400 MHz, $CDCl_3$) δ 8.00 (s, 1H), 7.86 (s, 1H), 7.39-7.28 (m, 3H), 7.24-7.15 (m, 2H), 6.45 (q, J=7.1 Hz, 1H), 3.37 (s, 2H), 3.33 (s, 3H), 2.31-2.17 (m, 2H), 1.94-1.83 (m, 9H), 1.65-1.46 (m, 2H).

The compound C61: 15 mg, ESI[M+H]$^+$=259.0

$^1$H NMR (400 MHz, $CDCl_3$) δ 8.02 (s, 1H), 7.86 (s, 1H), 7.39-7.28 (m, 3H), 7.24-7.15 (m, 2H), 6.43 (q, J=7.1 Hz, 1H), 3.68-3.57 (m, 2H), 3.33 (s, 3H), 2.58-2.47 (m, 2H), 1.84 (d, J=7.0 Hz, 3H).

The compound C62: 14 mg, ESI[M+H]$^+$=287.0

$^1$H NMR (400 MHz, $CDCl_3$) δ 8.00 (s, 1H), 7.86 (s, 1H), 7.39-7.28 (m, 3H), 7.24-7.15 (m, 2H), 6.45 (q, J=7.1 Hz, 1H), 4.15-4.03 (m, 2H), 2.58-2.47 (m, 2H), 2.04 (s, 3H), 1.84 (d, J=7.0 Hz, 3H).

The compound C63: 15 mg, ESI[M+H]$^+$=267.2

$^1$H NMR (400 MHz, $CDCl_3$) δ 7.95 (s, 1H), 7.82 (s, 1H), 7.35-7.28 (m, 3H), 7.24-7.15 (m, 2H), 6.41 (q, J=7.1 Hz, 1H), 2.58-2.47 (m, 2H), 2.35-2.28 (m, 2H), 1.84 (d, J=7.0 Hz, 3H), 1.82 (t, J=3.0 Hz, 3H).

The compound C64: 18 mg, ESI[M+H]$^+$=267.2

$^1$H NMR (400 MHz, $CDCl_3$) δ 8.00 (s, 1H), 7.86 (s, 1H), 7.39-7.28 (m, 3H), 7.24-7.15 (m, 2H), 6.45 (q, J=7.1 Hz, 1H), 2.58-2.47 (m, 2H), 2.44 (t, J=2.4 Hz, 1H), 2.43-2.36 (m, 2H), 1.84 (d, J=7.0 Hz, 3H), 1.82-1.75 (m, 2H).

The compound C65: 22 mg, ESI[M+H]$^+$=285.1

$^1$H NMR (400 MHz, $CDCl_3$) δ 8.01 (s, 1H), 7.87 (s, 1H), 7.39-7.28 (m, 3H), 7.24-7.15 (m, 2H), 6.46 (q, J=7.1 Hz, 1H), 2.58-2.47 (m, 2H), 2.45-2.41 (m, 2H), 2.15 (s, 3H), 1.98-1.79 (m, 5H).

The compound C66: 23 mg, ESI[M+H]$^+$=297.1

$^1$H NMR (400 MHz, $CDCl_3$) δ 8.02 (s, 1H), 7.86 (s, 1H), 7.39-7.28 (m, 3H), 7.25-7.15 (m, 2H), 6.44 (q, J=7.1 Hz, 1H), 3.95-3.90 (m, 1H), 3.35 (s, 3H), 2.56-2.31 (m, 2H), 1.98-1.79 (m, 6H).

The compound C67: 22 mg, ESI[M+H]$^+$=257.1

$^1$H NMR (400 MHz, $CDCl_3$) δ 8.04 (s, 1H), 7.88 (s, 1H), 7.43-7.28 (m, 3H), 7.24-7.15 (m, 2H), 6.45 (q, J=7.1 Hz, 1H), 4.89-4.71 (m, 1H), 3.98-3.84 (m, 3H), 3.59-3.54 (m, 1H), 1.86 (d, J=7.0 Hz, 3H).

Example 14 Preparation of Compounds C68~C83

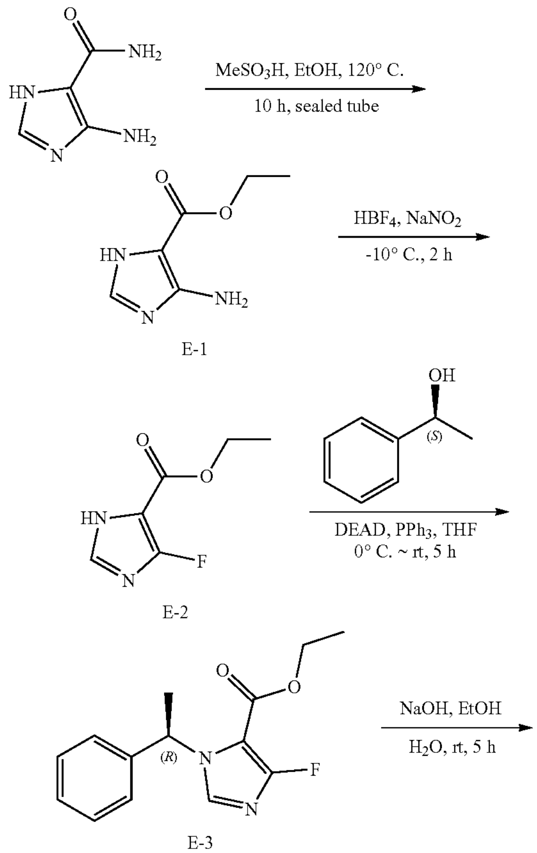

E-1

E-2

E-3

-continued

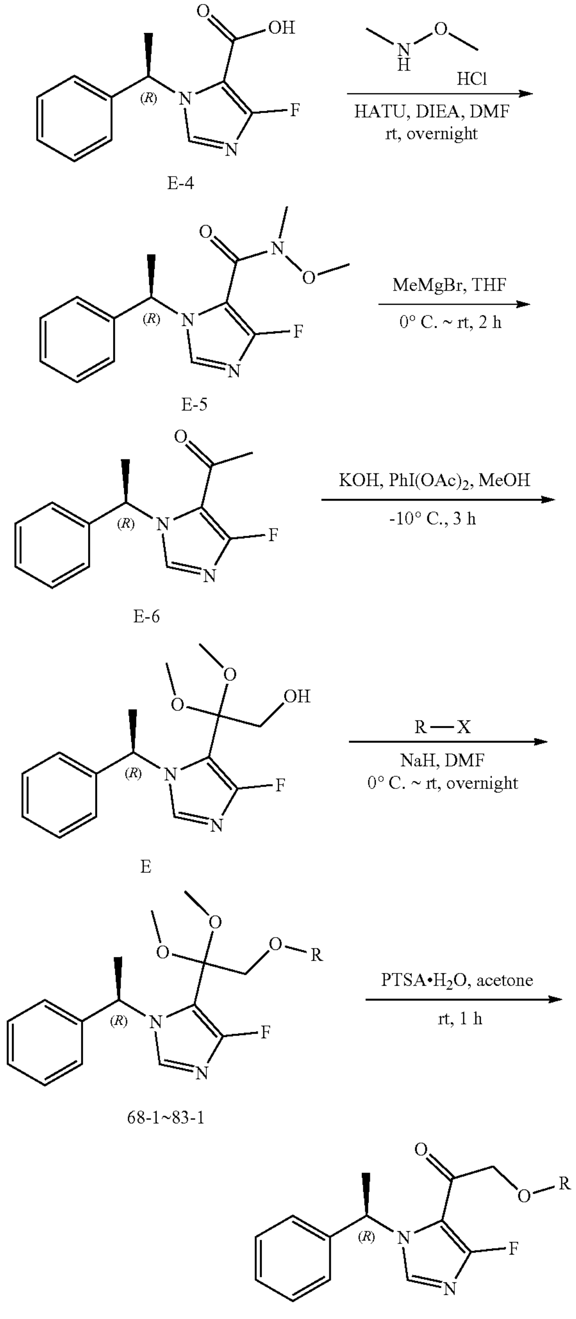

E-4

E-5

E-6

E 68-1~83-1

Compound C68~C83

1. Preparation of ethyl 4-amino-1H-imidazole-5-carboxylate (E-1)

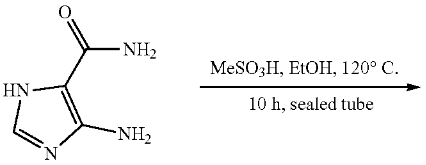

-continued

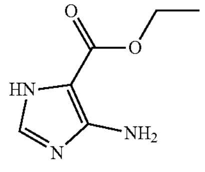

E-1

At room temperature, 4-amino-1H-imidazole-5-carboxamide (3.0 g, 23.8 mmol), $MeSO_3H$ (6 mL) and EtOH (30 mL) were added into sealed tube, then it was stirred at 120° C. for 10 hrs. The reaction was monitored by TLC until completion and concentrated under reduced pressure. The residue was adjusted to PH=8~9 with saturated $NaHCO_3$ solution and extracted with ethyl acetate (3×150 mL). The combined organic layers were washed with saturated brine (100 mL), dried over anhydrous sodium sulfate, filtered and concentrated under reduced pressure to give the product E-1 (3.0 g, yield 81%).

2. Preparation of ethyl 4-fluoro-1H-imidazole-5-carboxylate (E-2)

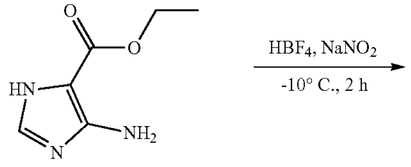

E-1

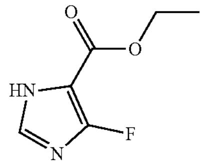

E-2

At an ice-brine bath, E-1 (250 mg, 1.61 mmol) was dissolved in the $HBF_4$ (40%), and then $NaNO_2$ (117 mg, 1.69 mmol) in $H_2O$ (0.15 mL) was added into solution at −10° C. The mixture was stirred under high pressure mercury lamp (302 nm) for 2 hrs. The reaction was monitored by TLC until completion. The mixture was adjusted to PH=8~9 with 1 N NaOH and extracted with ethyl acetate (3×10 mL). The combined organic layers were washed with saturated brine (10 mL), dried over anhydrous sodium sulfate, filtered and concentrated under reduced pressure. the residue was purified by silica gel column chromatography (ethyl acetate/petroleum ether (v/v)=1/10~1/1), with TLC (ethyl acetate/petroleum ether (v/v)=1/1) monitoring, and collecting the fraction with Rf=0.4~0.5 to give the product E-2 (100 mg, yield 39%) as colorless oil.

3. Preparation of ethyl (R)-4-fluoro-1-(1-phenylethyl)-1H-imidazole-5-carboxylate (E-3)

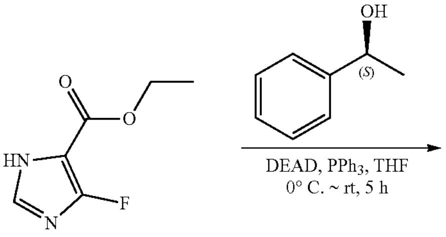

E-2

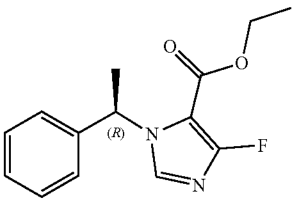

E-3

In an ice-water bath, S-1-phenylethan-1-ol (134 mg, 1.1 mmol), ethyl 4-fluoro-1H-imidazole-5-carboxylate E-2 (158 mg, 1.1 mmol) and $PPh_3$ (346 mg, 1.32 mmol) were dissolved in THF (10 mL) at 0° C., then DEAD (230 mg, 1.32 mmol) in THF (1 mL) was added into mixture at the rate of 0.5 mmol/min. The mixture was warmed to room temperature slowly and stirred for 5 hrs. The reaction was monitored by TLC until completion. The mixture was concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5~0.6 to give compound E-3 (70 mg, yield 27%). as colorless oil. ESI$[M+H]^+$=263.0

$^1H$ NMR (400 MHz, $CDCl_3$) δ 7.42-7.28 (m, 4H), 7.23-7.16 (m, 2H), 6.28 (q, J=7.1 Hz, 1H), 4.39-4.17 (m, 2H), 1.84 (d, J=7.1 Hz, 3H), 1.32 (t, J=7.1 Hz, 3H).

4. Preparation of (R)-4-fluoro-1-(1-phenylethyl)-1H-imidazole-5-carboxylic acid (E-4)

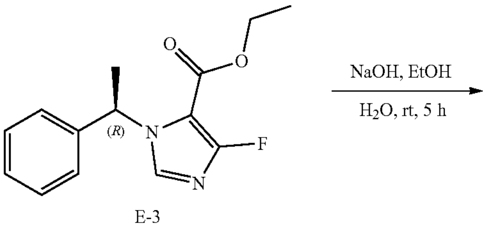

E-3

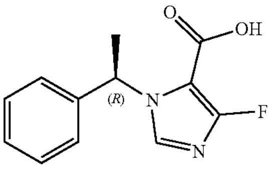

E-4

At room temperature, NaOH (21.6 mg, 0.54 mmol) was added into the mixture ethyl (R)-4-fluoro-1-(1-phenylethyl)-

1H-imidazole-5-carboxylate E-3 (70 mg, 0.27 mmol) in EtOH/$H_2O$ (10 mL, 1/1), then it was stirred at room temperature for 5 hrs. The reaction was monitored by TLC until completion. The mixture was concentrated under reduced pressure. The mixture was adjusted to PH=4-5 with 1 N hydrochloric acid and extracted with ethyl acetate (3×20 mL). The combined organic layers were dried over anhydrous sodium sulfate, filtered and concentrated under reduced pressure to give compound E-4 (58 mg, yield 93%) as a gray solid. ESI[M+H]$^+$=235.0

$^1$H NMR (400 MHz, $CDCl_3$) δ 7.43-7.28 (m, 4H), 7.24-7.16 (m, 2H), 6.24 (q, J=7.0 Hz, 1H), 1.85 (d, J=7.1 Hz, 3H).

5. Preparation of (R)-4-fluoro-N-methoxy-N-methyl-1-(1-phenylethyl)-1H-imidazole-5-carboxamide (E-5)

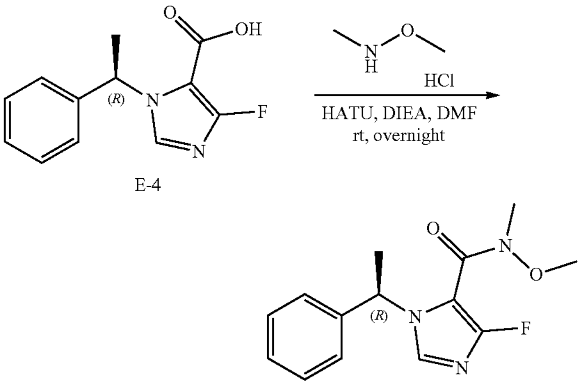

E-4

E-5

At room temperature, (R)-4-fluoro-1-(1-phenylethyl)-1H-imidazole-5-carboxylic acid E-4 (4.4 g, 18.8 mmol), N, O-dimethylhydroxylamine hydrochloride (2.8 g, 28.7 mmol), DIEA (3.7 g, 28.6 mmol) and HATU (10.9 g, 28.7 mmol) were dissolved in DMF (50 mL). Then the mixture was stirred at room temperature overnight. The reaction was monitored by TLC until completion, $H_2O$ (100 mL) was added, and extracted with ethyl acetate (4×30 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5~0.6 to give the product E-5 (4.7 g, yield 90%) as a white solid. ESI[M+H]$^+$=278.1

6. Preparation of (R)-1-(4-fluoro-1-(1-phenylethyl)-1H-imidazol-5-yl)ethan-1-one (E-6)

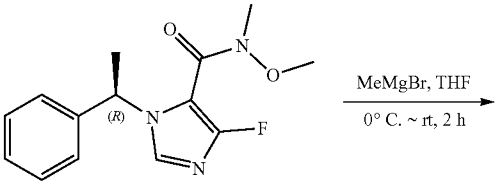

E-5

-continued

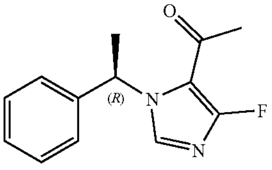

E-6

At room temperature, (R)-4-fluoro-N-methoxy-N-methyl-1-(1-phenylethyl)-1H-imidazole-5-carboxamide E-5 (4.7 g, 16.9 mmol) were dissolved in anhydrous THF (20 mL). The mixture was cooled to 0° C. with an ice-water bath. MeMgBr (33.9 mL, 1 mol/L in THF, 33.9 mmol) was added dropwise into the mixture at the rate of 3 mmol/min. Then the mixture was warmed to room temperature slowly and allowed to react for 2 hrs. The reaction was monitored by TLC until completion, the mixture was cooled to 0° C. with an ice-water bath. The mixture was quenched with the saturated ammonium chloride solution (100 mL) and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5-0.6 to give compound E-6 (3.9 g, yield 99%) as a white solid. ESI[M+H]$^+$=233.1

7. Preparation of (R)-2-(4-fluoro-1-(1-phenylethyl)-1H-imidazol-5-yl)-2,2-dimethoxyethan-1-ol (E)

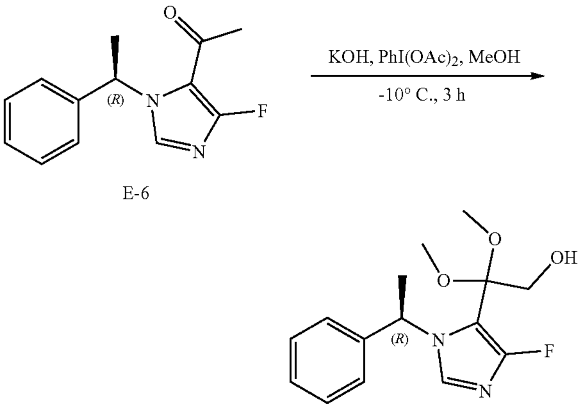

E-6

E

At room temperature, (R)-1-(4-fluoro-1-(1-phenylethyl)-1H-imidazol-5-yl)eth an-1-one E-6 (3.9 g, 16.8 mmol) and $PhI(OAc)_2$ (8.1 g, 25.1 mmol) were dissolved in MeOH (30 mL). The mixture was cooled to −10° C. with an ice-brine bath. KOH (11.3 g, 201.4 mol) was added in portions into the mixture within 30 minutes. Then the mixture was stirred at −10° C. for 3 hrs. The reaction was monitored by TLC until completion, the saturated brine (200 mL) was added slowly into the mixture and extracted with ethyl acetate (3×50 mL). The combined organic layers were dried over anhydrous sodium sulfate, filtered and concentrated under reduced pressure. The residue was purified by silica gel column chromatography (ethyl acetate/petroleum ether (v/v)= 1/20~1/5), with TLC (ethyl acetate/petroleum ether (v/v)=1/3) monitoring, and collecting the fraction with Rf=0.5~0.6 to give compound A-4 (684 mg, yield 14%) as a white solid. ESI[M+H]$^+$=295.2

8. Preparation of Compounds C68~C83

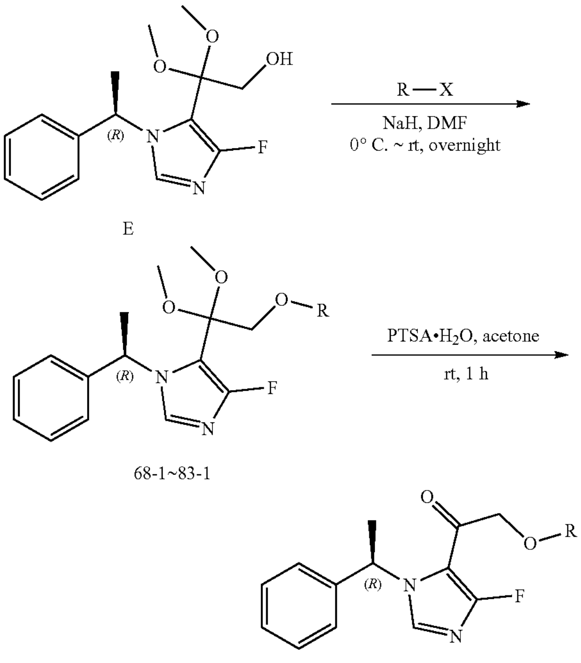

E 68-1~83-1

Compound C68~C83

The target compounds C68~C83 were prepared according to the operation method of preparing compound C1. Compound E reacted with corresponding halides under NaH condition to give intermediate compounds 68-1~83-1, which were deprotected with PTSA.$H_2O$ to give target compounds C68~C83.

The compound C68: 30 mg, ESI[M+H]$^+$=331.2

$^1$H NMR (400 MHz, $CDCl_3$) δ 7.41 (s, 1H), 7.36-7.11 (m, 5H), 6.40 (q, J=7.1 Hz, 1H), 3.38 (s, 2H), 3.34 (s, 3H), 2.35-2.14 (m, 2H), 1.97-1.81 (m, 9H).

The compound C69: 59 mg, ESI[M+H]$^+$=301.0

$^1$H NMR (400 MHz, $CDCl_3$) δ 7.40 (d, J=1.1 Hz, 1H), 7.38-7.28 (m, 3H), 7.25-7.21 (m, 2H), 6.37 (d, J=7.0 Hz, 1H), 4.57 (qd, J=17.1, 2.3 Hz, 2H), 4.25 (q, J=2.3 Hz, 2H), 1.86-1.81 (m, 6H).

The compound C70: 52 mg, ESI[M+H]$^+$=317.1

$^1$H NMR (400 MHz, $CDCl_3$) δ 7.43 (s, 1H), 7.39-7.28 (m, 3H), 7.26-7.18 (m, 2H), 6.37 (q, J=7.0 Hz, 1H), 4.52-4.32 (m, 2H), 3.45 (p, J=9.3 Hz, 2H), 2.68-2.51 (m, 1H), 2.10-2.01 (m, 2H), 1.98-1.88 (m, 2H), 1.85 (d, J=7.1 Hz, 3H), 1.78-1.66 (m, 2H).

The compound C71: 64 mg, ESI[M+H]$^+$=263.0

$^1$H NMR (400 MHz, $CDCl_3$) δ 7.42 (s, 1H), 7.39-7.28 (m, 3H), 7.26-7.18 (m, 2H), 6.38 (q, J=7.0 Hz, 1H), 4.52-4.32 (m, 2H), 3.44 (s, 3H), 1.83 (d, J=7.1 Hz, 3H).

The compound C72: 56 mg, ESI[M+H]$^+$=277.1

$^1$H NMR (400 MHz, $CDCl_3$) δ 7.38 (s, 1H), 7.37-7.28 (m, 3H), 7.26-7.18 (m, 2H), 6.39 (q, J=6.9 Hz, 1H), 4.60-4.36 (m, 2H), 3.58 (q, J=7.0 Hz, 2H), 1.83 (d, J=7.0 Hz, 3H), 1.26 (t, J=7.0 Hz, 3H).

The compound C73: 60 mg, ESI[M+H]$^+$=287.0

$^1$H NMR (400 MHz, $CDCl_3$) δ 7.41 (d, J=1.2 Hz, 1H), 7.39-7.28 (m, 3H), 7.26-7.18 (m, 2H), 6.36 (q, J=7.0 Hz, 1H), 4.69-4.51 (m, 2H), 4.30 (d, J=2.3 Hz, 2H), 2.45 (t, J=2.4 Hz, 1H), 1.83 (d, J=7.1 Hz, 3H).

The compound C74: 29 mg, ESI[M+H]$^+$=331.1

$^1$H NMR (400 MHz, $CDCl_3$) δ 7.41-7.28 (m, 4H), 7.26-7.19 (m, 2H), 6.39 (q, J=7.1 Hz, 1H), 4.52-4.35 (m, 2H), 3.42 (t, J=6.9 Hz, 2H), 2.43-2.29 (m, 1H), 2.11-1.97 (m, 2H), 1.91-1.84 (m, 1H), 1.82 (d, J=7.0 Hz, 3H), 1.81-1.77 (m, 1H), 1.76-1.69 (m, 2H), 1.68-1.58 (m, 2H).

The compound C75: 19 mg, ESI[M+H]$^+$=351.0

$^1$H NMR (400 MHz, $CDCl_3$) δ 7.43 (s, 1H), 7.38-7.28 (m, 3H), 7.27-7.18 (m, 2H), 6.38 (q, J=7.0 Hz, 1H), 4.33 (s, 2H), 3.72-3.68 (m, 1H), 3.51-3.46 (m, 4H), 3.31 (s, 6H), 1.87 (d, J=7.0 Hz, 3H).

The compound C76: 108 mg, ESI[M+H]$^+$=303.2

$^1$H NMR (400 MHz, $CDCl_3$) δ 7.44-7.27 (m, 4H), 7.26-7.20 (m, 2H), 6.39 (q, J=7.0 Hz, 1H), 4.70-4.33 (m, 2H), 3.36 (d, J=7.0 Hz, 2H), 1.83 (d, J=7.1 Hz, 3H), 1.19-1.00 (m, 1H), 0.63-0.43 (m, 2H), 0.26-0.09 (m, 2H).

The compound C77: 39 mg, ESI[M+H]$^+$=343.0

$^1$H NMR (400 MHz, $CDCl_3$) δ 7.44 (s, 1H), 7.39-7.29 (m, 3H), 7.26-7.18 (m, 2H), 6.39 (q, J=7.0 Hz, 1H), 5.61 (t, J=6.9 Hz, 1H), 5.11-4.69 (m, 6H), 4.35 (s, 2H), 1.86 (d, J=7.1 Hz, 3H).

The compound C78: 22 mg, ESI[M+H]$^+$=319.1

$^1$H NMR (400 MHz, $CDCl_3$) δ 7.37 (s, 1H), 7.36-7.28 (m, 3H), 7.27-7.18 (m, 2H), 6.54-6.25 (m, 1H), 4.60-4.24 (m, 2H), 3.20 (p, J=5.8 Hz, 1H), 1.82 (d, J=7.0 Hz, 3H), 1.55-1.47 (m, 4H), 0.98-0.79 (m, 6H).

The compound C79: 29 mg, ESI[M+H]$^+$=291.0

$^1$H NMR (400 MHz, $CDCl_3$) δ 7.42 (s, 1H), 7.39-7.28 (m, 3H), 7.26-7.18 (m, 2H), 6.38 (q, J=7.0 Hz, 1H), 4.52-4.32 (m, 2H), 3.31-3.19 (m, 1H), 1.82 (d, J=7.1 Hz, 3H), 1.41-1.27 (m, 6H).

The compound C80: 32 mg, ESI[M+H]$^+$=305.0

$^1$H NMR (400 MHz, $CDCl_3$) δ 7.43 (s, 1H), 7.36-7.28 (m, 3H), 7.26-7.18 (m, 2H), 6.36 (q, J=7.0 Hz, 1H), 4.52-4.32 (m, 2H), 3.52-3.38 (m, 2H), 1.84 (d, J=7.1 Hz, 3H), 1.81-1.67 (m, 1H), 1.01-0.88 (m, 6H).

The compound C81: 39 mg, ESI[M+H]$^+$=319.1

$^1$H NMR (400 MHz, $CDCl_3$) δ 7.44 (s, 1H), 7.38-7.28 (m, 3H), 7.27-7.18 (m, 2H), 6.38 (q, J=7.0 Hz, 1H), 4.52-4.32 (m, 2H), 3.51-3.39 (m, 2H), 1.83 (d, J=7.1 Hz, 3H), 1.80-1.69 (m, 1H), 1.69-1.39 (m, 2H), 1.01-0.90 (m, 6H).

The compound C82: 24 mg, ESI[M+H]$^+$=305.0

$^1$H NMR (400 MHz, $CDCl_3$) δ 7.43 (s, 1H), 7.37-7.28 (m, 3H), 7.26-7.18 (m, 2H), 6.39 (q, J=7.0 Hz, 1H), 5.11-4.69 (m, 5H), 4.51-4.32 (m, 2H), 1.83 (d, J=7.1 Hz, 3H).

The compound C83: 32 mg, ESI[M+H]$^+$=319.0

$^1$H NMR (400 MHz, $CDCl_3$) δ 7.44 (s, 1H), 7.39-7.28 (m, 3H), 7.26-7.18 (m, 2H), 6.36 (q, J=7.0 Hz, 1H), 4.52-4.32 (m, 6H), 3.47-3.37 (m, 2H), 2.96-2.88 (m, 1H), 1.83 (d, J=7.1 Hz, 3H).

Example 15 Preparation of Compound C84

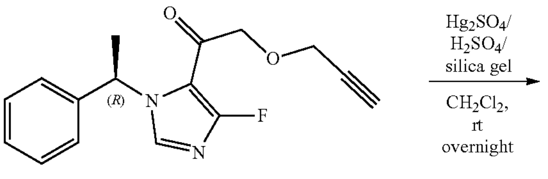

Compound C73

-continued

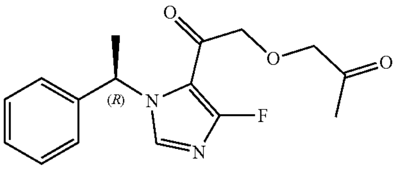

Compound C84

At room temperature, compound C73 (100 mg, 0.35 mmol) and $Hg_2SO_4/H_2SO_4$/silica gel (200 mg) was dissolved in $CH_2Cl_2$ (5 mL). Then the mixture was stirred at room temperature overnight. The reaction was monitored by TLC until completion, the saturated $NaHCO_3$ solution was added into the mixture and extracted with $CH_2Cl_2$ (3×5 mL). The combined organic layers were washed with saturated brine (10 mL), dried over anhydrous sodium sulfate, filtered and concentrated under reduced pressure. The residue was purified by Prep-TLC (ethyl acetate/petroleum ether (v/v) ~1/3), collecting the fraction with Rf=0.4~0.5 to give the product C84 (53 mg, yield 50%) as colorless oil. ESI[M+H]$^+$=305.0

$^1$H NMR (400 MHz, $CDCl_3$) δ 7.41 (s, 1H), 7.39-7.28 (m, 3H), 7.25-7.19 (m, 2H), 6.41-6.20 (m, 1H), 4.58 (q, J=17.5 Hz, 2H), 4.16 (s, 2H), 2.18 (s, 3H), 1.83 (d, J=6.8 Hz, 3H).

Example 16 Preparation of Compound C85

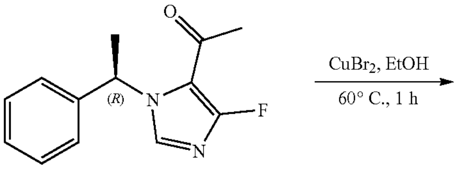

E-6

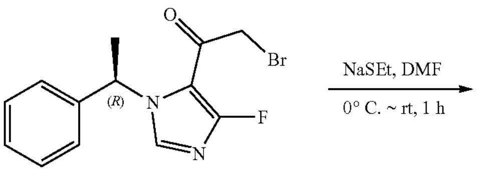

85-1

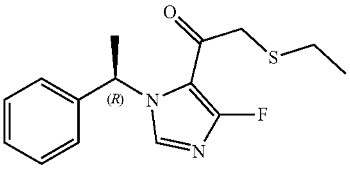

Compound C85

1. Preparation of (R)-2-bromo-1-(4-fluoro-1-(1-phenylethyl)-1H-imidazol-5-yl)ethan-1-one (85-1)

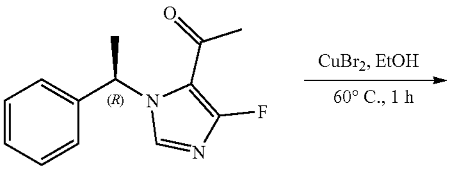

E-6

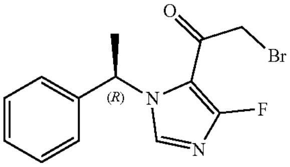

85-1

At room temperature, $CuBr_2$ (1.9 g, 8.5 mmol) was added into the solution of (R)-1-(4-fluoro-1-(1-phenylethyl)-1H-imidazol-5-yl)ethan-1-one E-6 (1.0 g, 4.3 mmol) in EtOH (50 mL). Then the mixture was stirred at 60° C. for 1 hour. The reaction was monitored by TLC until completion, cooled to room temperature and quenched with $H_2O$ (30 mL) and extracted with ethyl acetate (3×10 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/20~1/5), with TLC (ethyl acetate/petroleum ether (v/v)=1/5) monitoring, and collecting the fraction with Rf=0.5-0.6 to give the compound 85-1 (703 mg, yield 53%) as colorless oil. ESI[M+H]$^+$=311.1

2. Preparation of Compound C85

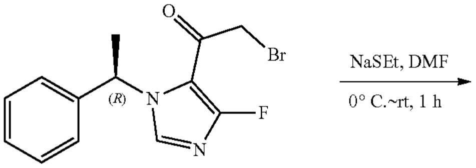

85-1

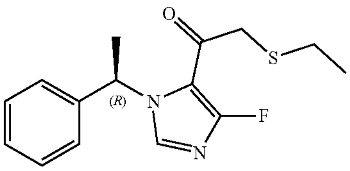

Compound C85

At an ice bath, NaSEt (49 mg, 0.58 mmol) was added into the solution of 85-1 (150 mg, 0.48 mmol) in DMF (5 mL) at 0° C. Then the mixture was stirred at room temperature for 1 hour. The reaction was monitored by TLC until completion. The mixture was quenched with the ice-water (10 mL) and extracted with ethyl acetate (3×5 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.4~0.6 to give the compound C85 (73 mg, yield 52%). ESI[M+H]$^+$=293.1

$^1$H NMR (400 MHz, $CDCl_3$) δ 7.41 (s, 1H), 7.37-7.28 (m, 3H), 7.26-7.18 (m, 2H), 6.35 (q, J=7.0 Hz, 1H), 3.75-3.64 (m, 2H), 2.51-2.44 (m, 2H), 1.83 (d, J=7.1 Hz, 3H), 1.21-1.14 (m, 3H).

Examples of Group D compounds are as follows:

Example 1 Preparation of Compound D1

Method A

Method A:

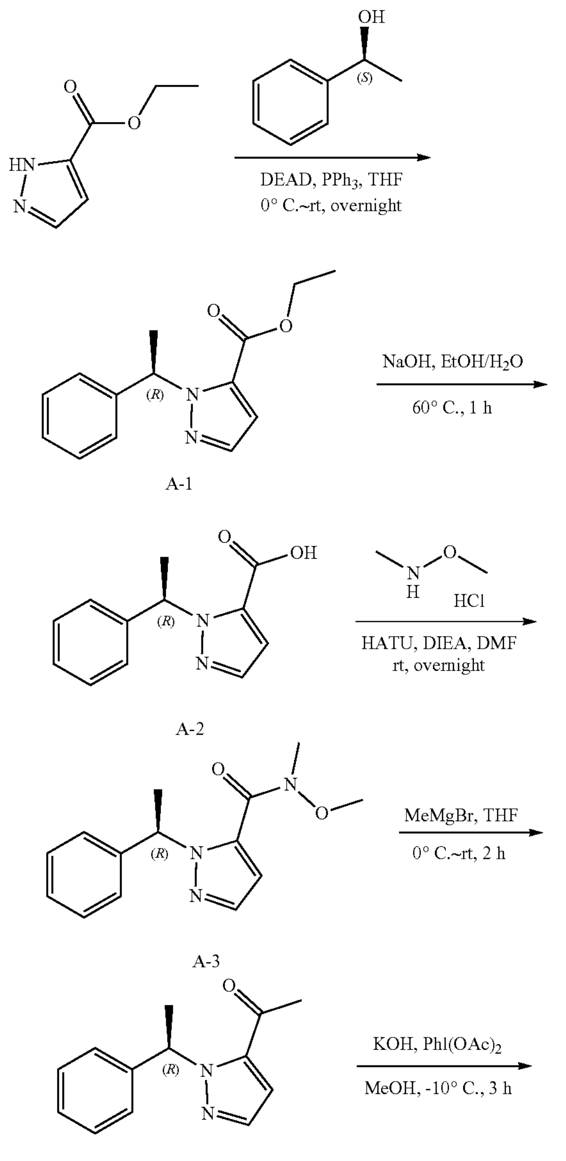

A-4

-continued

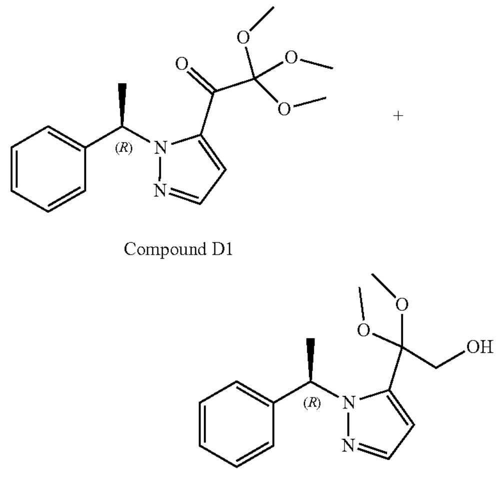

A-5

Method B:

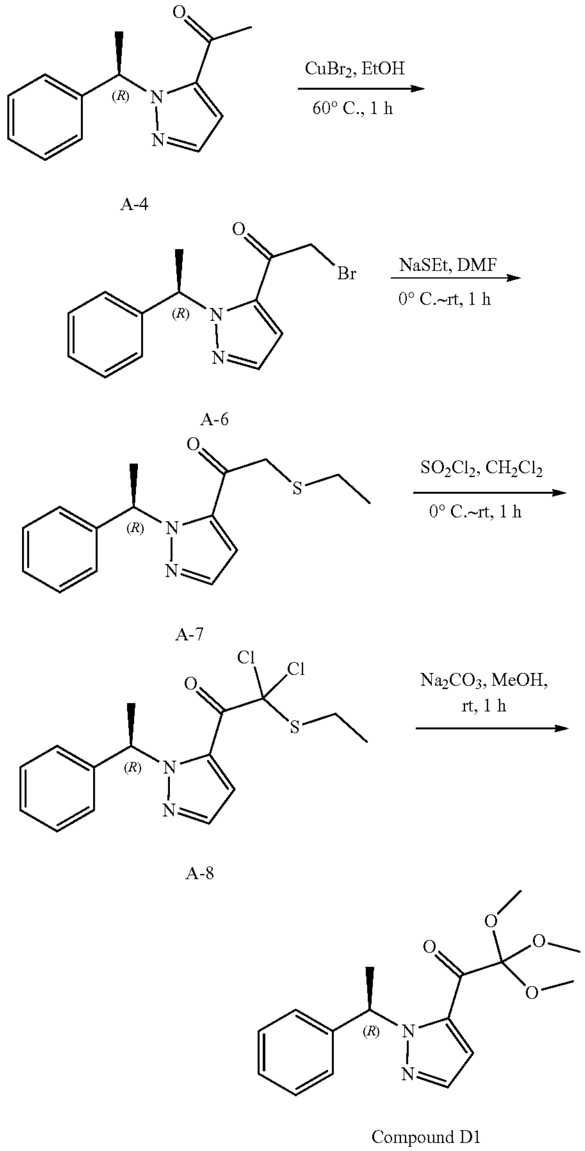

Compound D1

1. Preparation of ethyl (R)-1-(1-phenylethyl)-1H-pyrazole-5-carboxylate (A-1)

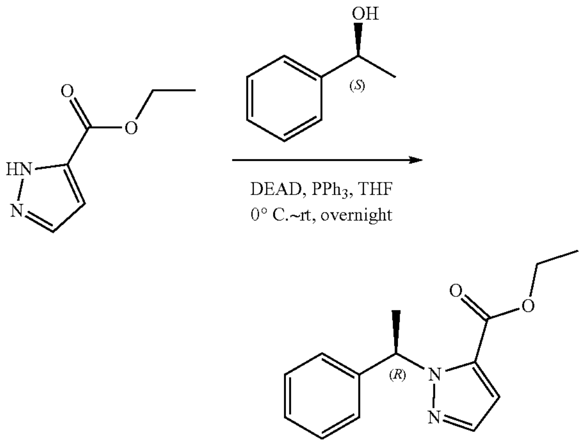

A-1

In an ice-water bath, (S)-1-phenylethan-1-ol (8.38 g, 68.6 mmol) was added into the mixture of ethyl 1H-pyrazole-5-carboxylate (7.4 g, 52.8 mmol) and $PPh_3$ (20.8 g, 79.3 mmol in THF (50 mL), then solution of DEAD (13.8 g, 79.2 mmol) in THF (150 mL) was added slowly into the mixture at the rate of 2 mmol/min After addition, the reaction mixture was warmed slowly to room temperature and stirred overnight. The reaction was monitored by TLC until completion. The reaction mixture was quenched with the saturated brine (100 mL) and extracted with ethyl acetate (3x30 mL). The combined organic layers were washed with saturated brine (50 mL), dried over anhydrous sodium sulfate, filtered and concentrated under reduced pressure to give crude product. The crude product was purified by silica gel column chromatography (ethyl acetate/petroleum ether (v/v)=1/20~1/10), with TLC (ethyl acetate/petroleum ether (v/v)=1/2) monitoring, and collecting the fraction with Rf=0.5~0.6 to give compound A-1 (9.5 g, yield 74%) as colorless oil. ESI$[M+H]^+$=245.1

$^1H$ NMR (400 MHz, $CDCl_3$) δ 7.57 (d, J=1.9 Hz, 1H), 7.33-7.27 (m, 4H), 7.25-7.18 (m, 1H), 6.86 (d, J=2.0 Hz, 1H), 6.59 (q, J=7.1 Hz, 1H), 4.42-4.16 (m, 2H), 1.92 (d, J=7.1 Hz, 3H), 1.33 (t, J=7.1 Hz, 3H).

2. Preparation of (R)-1-(1-phenylethyl)-1H-pyrazole-5-carboxylic acid (A-2)

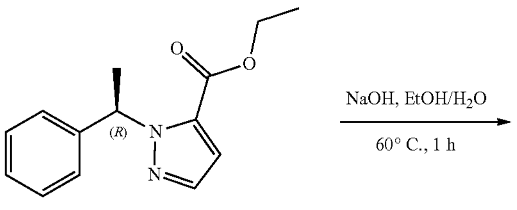

A-1

-continued

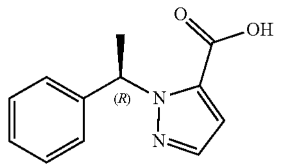

A-2

At room temperature, the solution of NaOH (3.1 g, 77.5 mmol) in water (12 mL) was added into the solution of A-1 (9.5 g, 38.9 mmol) in ethanol (12 mL), then the mixture was stirred at 60° C. for 1 hour. The reaction was monitored by TLC until completion. The reaction mixture was concentrated under reduced pressure. Water (20 mL) was poured into the residue. The mixture was adjusted pH to 4~5 using 1N HCl and extracted with dichloromethane (3x15 mL). The combined organic layers were dried over anhydrous sodium sulfate, filtered and concentrated to give the compound A-2 (6.70 g, yield 80%) as a white solid. ESI$[M+H]^+$=217.1

$^1H$ NMR (400 MHz, $CDCl_3$) δ 7.62 (d, J=2.0 Hz, 1H), 7.39-7.16 (m, 5H), 7.00 (d, J=2.0 Hz, 1H), 6.56 (q, J=7.0 Hz, 1H), 1.93 (d, J=7.1 Hz, 3H).

3. Preparation of (R)—N-methoxy-N-methyl-1-(1-phenylethyl)-1H-pyrazole-5-carboxamide (A-3)

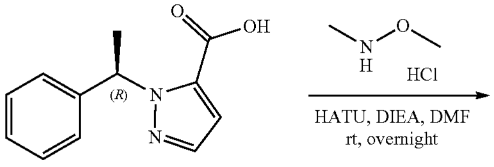

A-2

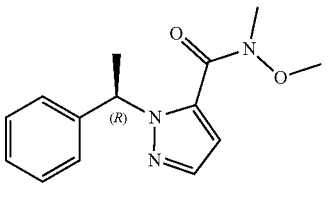

A-3

At room temperature, A-2 (3.5 g, 16.2 mmol), N, O-dimethylhydroxylamine hydrochloride (2.4 g, 24.6 mmol), DIEA (3.2 g, 24.8 mmol) and HATU (9.2 g, 24.2 mmol) were dissolved in DMF (100 mL), then the mixture was stirred at room temperature overnight. The reaction was monitored by TLC until completion. The mixture was quenched with water (100 mL) and extracted with ethyl acetate (3x30 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5-0.6 to give the title compound A-3 (4.10 g, yield 64%) as a white solid. ESI$[M+H]^+$=260.2

4. Preparation of (R)-1-(1-(1-phenylethyl)-1H-pyrazol-5-yl)ethan-1-one (A-4)

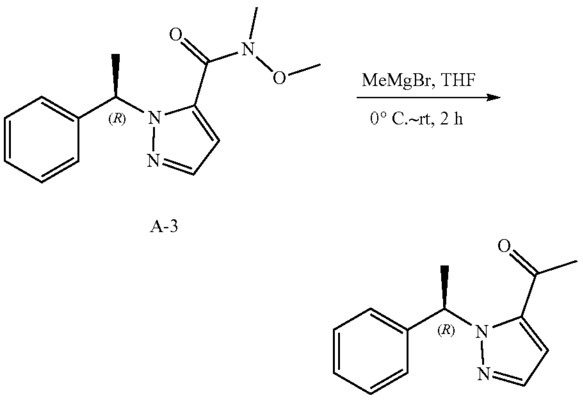

A-3

A-4

At room temperature, A-3 (4.1 g, 15.8 mmol) was dissolved in anhydrous THF (20 mL). The mixture was cooled to 0° C. with an ice-water bath. Methylmagnesium bromide (23.7 mL, 1 mol/L in THF, 23.7 mmol) was added dropwise into the mixture at the rate of 2 mmol/min, then the mixture was reacted at room temperature for 2 hrs. The reaction was monitored by TLC until completion. The reaction mixture was cooled to 0° C., quenched with saturated ammonium chloride solution (50 mL) and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)= 1/20~1/10), with TLC (ethyl acetate/petroleum ether (v/v)=1/5) monitoring, and collecting the fraction with Rf=0.5~0.6 to give the title compound A-4 (3.10 g, yield 92%) as a white solid. ESI[M+H]$^+$=215.1

5. Preparation of (R)-2-bromo-1-(1-(1-phenylethyl)-1H-pyrazol-5-yl)ethan-1-one (A-6)

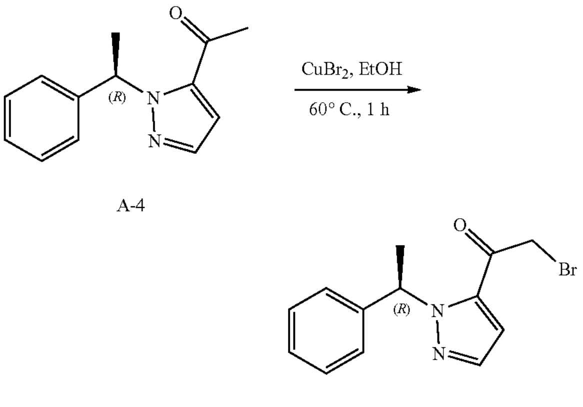

A-4

A-6

At room temperature, $CuBr_2$ (4.17 g, 18.7 mmol) was added into the solution of A-4 (2.0 g, 9.3 mmol) in ethanol (50 mL), then the mixture was stirred at 60° C. for 1 hour. The reaction was monitored by TLC until completion. The reaction mixture was cooled to 0° C., quenched with water (50 mL) and extracted with ethyl acetate (3×10 mL). The combined organic layers were washed with saturated brine (20 mL), dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give the title compound A-6 (2.2 g, yield 81%) as a white solid. ESI[M+H]$^+$=293.0

6. Preparation of (R)-2-(ethylthio)-1-(1-(1-phenylethyl)-1H-pyrazol-5-yl)ethan-1-one (A-7)

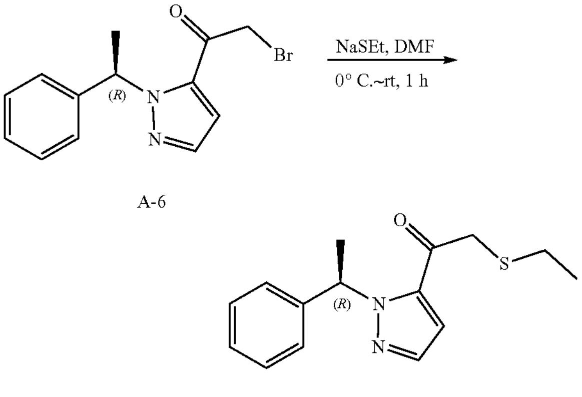

A-6

A-7

In an ice-water bath, NaSEt (631 mg, 7.5 mmol) was added into the solution of A-6 (2.2 g, 7.5 mmol) in DMF (30 mL) at 0° C., then the mixture was stirred at room temperature for 1 hour. The reaction was monitored by TLC until completion. The reaction mixture was quenched with ice-water (10 mL) and extracted with ethyl acetate (3×5 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/10~1/3) and collecting the fraction with Rf=0.4~0.6 to give the title compound A-7 (1.26 g, yield 61%). ESI[M+H]$^+$=275.2

$^1$H NMR (400 MHz, $CDCl_3$) δ 7.61 (d, J=1.9 Hz, 1H), 7.34-7.20 (m, 5H), 6.88 (d, J=2.0 Hz, 1H), 6.59 (q, J=7.0 Hz, 1H), 3.60 (s, 2H), 2.49-2.35 (m, 2H), 1.94 (d, J=7.1 Hz, 3H), 1.18 (t, J=7.4 Hz, 3H).

7. Preparation of (R)-2,2-dichloro-2-(ethylthio)-1-(1-(1-phenylethyl)-1H-pyrazol-5-yl)ethan-1-one (A-8)

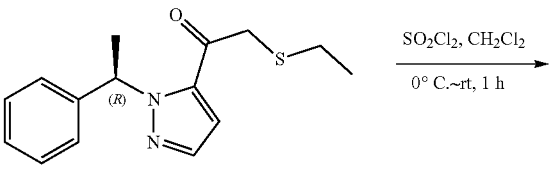

A-7

-continued

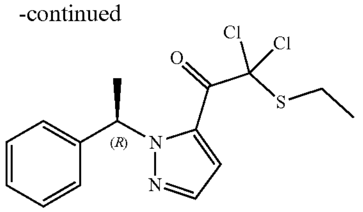

A-8

In an ice-water bath, $SO_2Cl_2$ (1.24 g, 9.18 mmol) was added into the solution of A-7 (1.26 g, 4.59 mmol) in dichloromethane (30 mL) at 0° C., then the mixture was stirred at room temperature for 1 hour. The reaction was monitored by TLC until completion. The reaction mixture was concentrated under reduced pressure to give A-8 (1.4 g, crude), which was used for next step directly without further purification.

8. Preparation of Compound D1

Method A

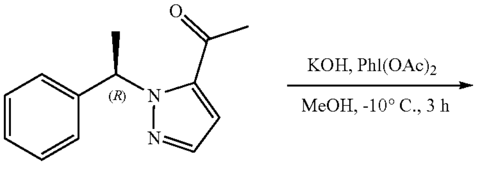

A-4

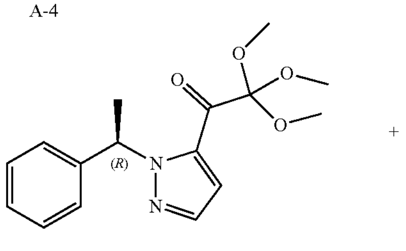

Compound D1

+

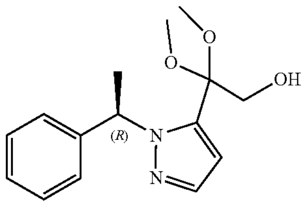

A-5

At room temperature, A-4 (3.1 g, 14.5 mmol) and PhI $(OAc)_2$ (7.0 g, 21.7 mmol) were dissolved in methanol (50 mL), then the mixture was cooled to −10° C. with an ice-salt bath. KOH (9.8 g, 175 mmol) was added in portions into the mixture within 30 mins, then the reaction mixture was reacted at −10° C. for 3 hrs. The reaction was monitored by TLC until completion. The reaction mixture was quenched with saturated brine (100 mL) and extracted with ethyl acetate (3×20 mL). The combined organic layers were dried over anhydrous sodium sulfate, filtered, and concentrated under reduced pressure. The residue was purified by Prep-TLC (ethyl acetate/petroleum ether (v/v)=1/5) and the fraction with Rf=0.5~0.6 was collected to give the title compound D1 (196 mg, yield 4%). The fraction with Rf=0.2~0.3 was collected to give the title compound A-5 (3.6 g, yield 87%).

Method B

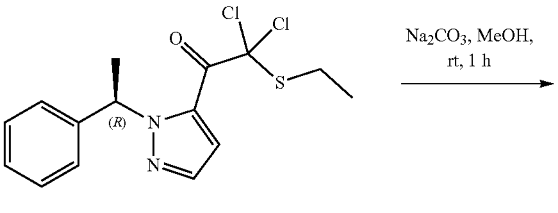

A-8

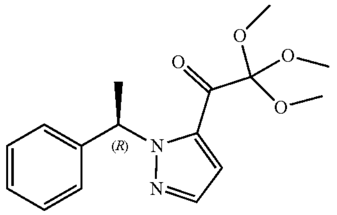

Compound D1

At room temperature, crude compound A-8 (150 mg, 0.44 mmol) and $Na_2CO_3$ (70 mg, 0.66 mmol) were dissolved methanol (10 mL), then the mixture was stirred at room temperature for 1 hour. The reaction was monitored by TLC until completion. In an ice-water bath, the reaction mixture was quenched with saturated sodium bicarbonate solution (10 mL) at 0° C. and extracted with ethyl acetate (3×20 mL). The combined organic layers were dried over anhydrous sodium sulfate, filtered and concentrated under reduced pressure. The residue was purified by Prep-TLC (ethyl acetate/petroleum ether (v/v)=1/5) and the fraction with Rf=0.5~0.6 was collected to give the title compound D1 (89 mg, yield 66%). ESI$[M+H]^+$=305.0

$^1H$ NMR (400 MHz, $CDCl_3$) δ 7.64 (d, J=2.1 Hz, 0.2H), 7.60 (d, J=2.1 Hz, 0.8H), 7.35-7.11 (m, 6H), 6.78-5.98 (m, 1H), 3.92 (s, 0.7H), 3.49 (s, 1.3H), 3.13 (s, 7H), 1.99-1.87 (m, 3H).

Example 2 Preparation of Compounds D2~D10

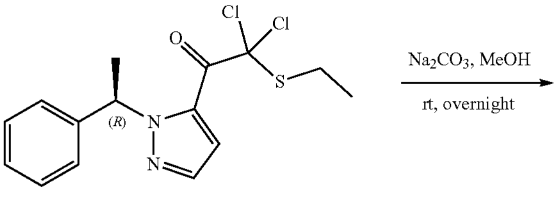

A-8

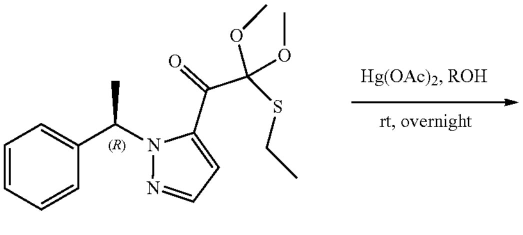

Compound D2

-continued

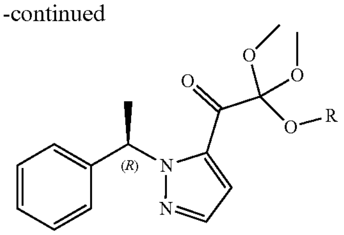

Compound D3~D10

1. Preparation of Compound D2

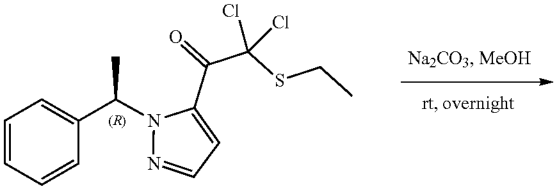

A-8

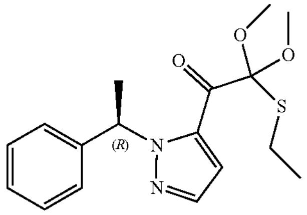

Compound D2

At room temperature, crude compound A-8 (1.4 g, 4.08 mmol) and $Na_2CO_3$ (865 mg, 8.16 mmol) were dissolved methanol (10 mL), then the mixture was stirred at room temperature overnight. The reaction was monitored by TLC until completion. The mixture was quenched with saturated brine (20 mL) and extracted with ethyl acetate (3×10 mL). The combined organic layers were dried over anhydrous sodium sulfate, filtered and concentrated under reduced pressure. The residue was purified by silica gel column chromatography (ethyl acetate/petroleum ether (v/v)=1/20~1/8), with TLC (ethyl acetate/petroleum ether (v/v)=1/5) monitoring, and collecting the fraction with Rf=0.5~0.6 to give title compound D2 (1.30 g, yield 95%). ESI[M+H]$^+$=335.0

$^1$H NMR (400 MHz, $CDCl_3$) δ 7.62 (d, J=2.0 Hz, 1H), 7.34-7.16 (m, 6H), 6.61-6.50 (m, 1H), 3.35 (s, 3H), 3.24 (s, 3H), 2.31-2.17 (m, 1H), 2.14-2.01 (m, 1H), 1.96 (d, J=7.0 Hz, 3H), 0.99 (t, J=7.5 Hz, 3H).

2. Preparation of Compound D3

Method A

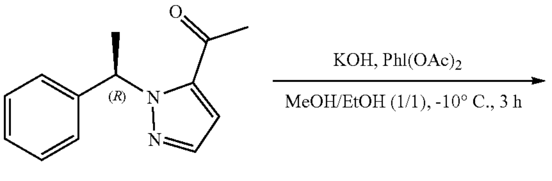

A-4

-continued

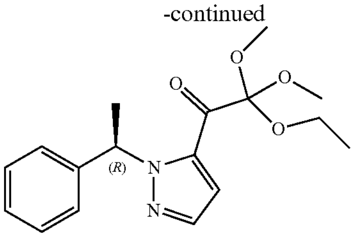

Compound D3

+

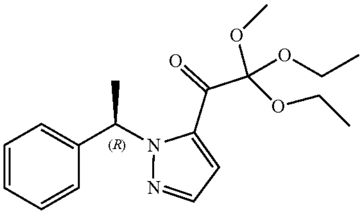

Compound D9

Method B

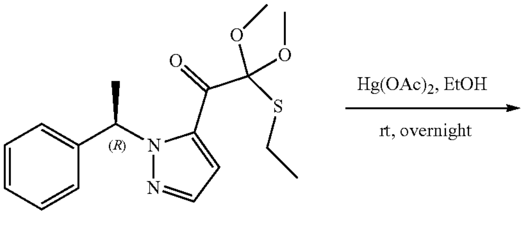

Compound D2

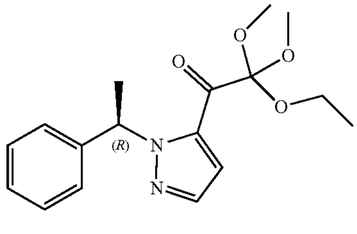

Compound D3

Method A

At room temperature, A-4 (1.0 g, 4.67 mmol) and PhI(OAc)$_2$ (2.3 g, 7.14 mmol) were dissolved in MeOH/EtOH (10 mL, v/v=1/1), then the mixture was cooled to −10° C. with an ice-salt bath. KOH (3.14 g, 56 mmol) was added in portions into the mixture within 30 mins, then the reaction mixture was reacted at −10° C. for 3 hrs. The reaction was monitored by TLC until completion. The reaction mixture was quenched with saturated brine (50 mL) and extracted with ethyl acetate (3×10 mL). The combined organic layers were dried over anhydrous sodium sulfate, filtered, and concentrated under reduced pressure. The residue was purified by silica gel column chromatography (ethyl acetate/petroleum ether (v/v)=1/20~1/10), with TLC (ethyl acetate/petroleum ether (v/v)=1/8) monitoring, and collecting the fraction with Rf=0.5~0.6 to give the title compound D3 (89 mg, yield 6%) and the title compound D9 (28 mg, yield 1.8%). Method B:

At room temperature, D2 (100 mg, 0.30 mmol) and Hg(OAc)$_2$ (143 mg, 0.45 mmol) were dissolved in EtOH (2 mL), then the mixture was stirred at room temperature overnight. The reaction was monitored by TLC until completion. The reaction mixture was quenched with saturated brine (10 mL) and extracted with ethyl acetate (3×5 mL). The combined organic layers were dried over anhydrous sodium sulfate, filtered, and concentrated under reduced pressure. The residue was purified by Prep-TLC (ethyl acetate/petroleum ether (v/v)=1/5) and the fraction with Rf=0.5~0.6 was collected to give the title compound D3 (39 mg, yield 41%). ESI[M+H]$^+$=319.1

$^1$H NMR (400 MHz, $CDCl_3$) δ 7.66 (s, 1H), 7.35-7.30 (m, 5H), 7.29-7.26 (m, 1H), 6.54 (d, J=7.1 Hz, 1H), 4.43-4.40 (m, 2H), 3.95 (s, 1H), 3.78-3.71 (m, 1.5H), 3.52 (s, 3.5H), 1.95 (d, J=7.0 Hz, 3H), 1.42 (t, J=7.1 Hz, 1.5H), 1.27 (t, J=7.0 Hz, 1.5H).

3. Preparation of Compounds D4~D8

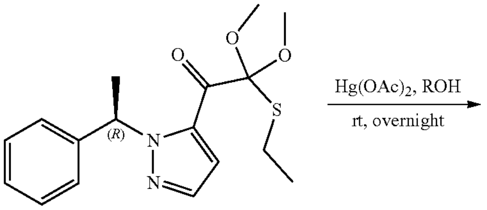

Compound D2

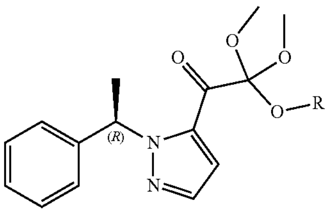

Compound D4~D8

The title compounds D4~D8 were prepared according to the operation method B of preparing compound D3. Compound D2, $Hg(OAc)_2$ and corresponding alcohols were stirred at room temperature overnight. The crude product was purified by Prep-TLC to give the title compounds.

Compound D4: 34 mg, ESI[M+H]$^+$=333.1

$^1$H NMR (400 MHz, $CDCl_3$) δ 7.66 (d, J=2.1 Hz, 1H), 7.37-7.30 (m, 5H), 7.28-7.21 (m, 1H), 6.56-6.52 (m, 1H), 5.35-5.30 (m, 1H), 3.95 (s, 1H), 3.52 (s, 5H), 1.95 (d, J=7.0 Hz, 3H), 1.55 (d, J=6.5 Hz, 1H), 1.46-1.40 (m, 3H), 1.25 (t, J=10.2 Hz, 2H).

Compound D5: 28 mg, ESI[M+H]$^+$=361.0

$^1$H NMR (400 MHz, $CDCl_3$) δ 7.68 (d, J=2.0 Hz, 1H), 7.38-7.32 (m, 4H), 7.29-7.22 (m, 1H), 6.57 (dd, J=14.4, 7.3 Hz, 1H), 4.87 (s, 1H), 3.95 (s, 1H), 3.51 (s, 5H), 1.92 (dd, J=7.0, 3.5 Hz, 3H), 1.65-1.62 (m, 2.5H), 1.60-1.55 (m, 1.5H), 1.50-1.45 (m, 1.5H), 1.40-1.35 (m, 3.5H), 1.25-1.20 (m, 1H).

Compound D6: 27 mg, ESI[M+H]$^+$=361.1

$^1$H NMR (400 MHz, $CDCl_3$) δ 7.66 (s, 1H), 7.32-7.19 (m, 6H), 6.59-6.52 (m, 1H), 4.04 (s, 1.5H), 3.95 (s, 1H), 3.52 (s, 4.5H), 3.32 (s, 1H), 1.95 (d, J=7.0 Hz, 3H), 1.02 (s, 5.5H), 0.94 (s, 3.5H).

Compound D7: 41 mg, ESI[M+H]$^+$=331.1

$^1$H NMR (400 MHz, $CDCl_3$) δ 7.72-7.44 (m, 2H), 7.39-7.30 (m, 4H), 7.26-7.16 (m, 1H), 6.65-6.49 (m, 1H), 6.17-5.89 (m, 1H), 5.51-4.83 (m, 2H), 4.21-4.18 (m, 1.5H), 3.94 (s, 1.5H), 3.45 (m, 3H), 3.26-3.09 (m, 2H), 2.06-1.87 (m, 3H).

Compound D8: 48 mg, ESI[M+H]$^+$=343.1

$^1$H NMR (400 MHz, $CDCl_3$) δ 7.75-7.46 (m, 2H), 7.38-7.32 (m, 3H), 7.28-7.19 (m, 2H), 6.66-6.47 (m, 1H), 4.22-4.18 (m, 1.5H), 3.96 (s, 2H), 3.48 (s, 3H), 3.28-3.08 (m, 1.5H), 2.04-1.82 (m, 6H).

4. Preparation of Compound D9

Method A

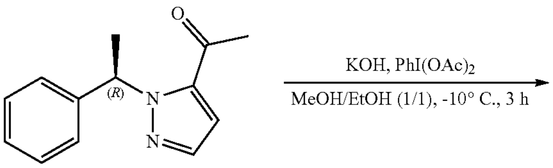

A-4

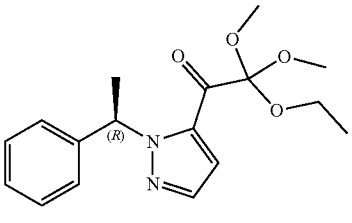

Compound D3

+

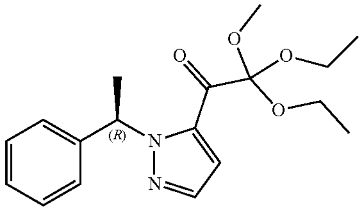

Compound D9

Method B

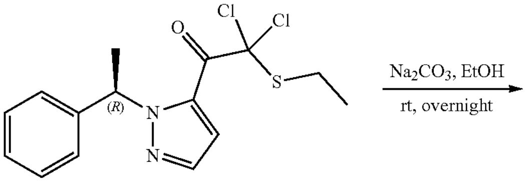

A-8

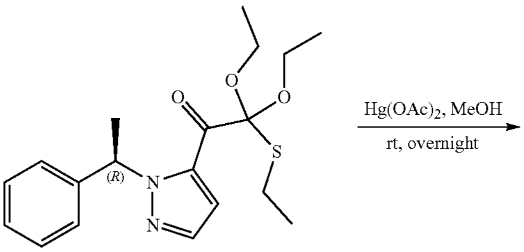

9-1

-continued

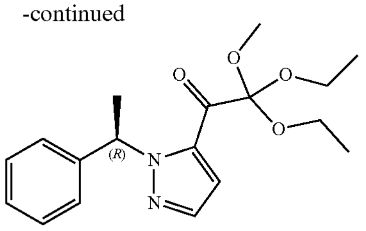

Compound D9

Method A

At room temperature, A-4 (1.0 g, 4.67 mmol) and $PhI(OAc)_2$ (2.3 g, 7.14 mmol) were dissolved in MeOH/EtOH (10 mL, v/v=1/1), then the mixture was cooled to −10° C. with an ice-salt bath. KOH (3.14 g, 56 mmol) was added in portions into the mixture within 30 mins, then the reaction mixture was stirred at −10° C. for 3 hrs. The reaction was monitored by TLC until completion. The reaction mixture was quenched with saturated brine (50 mL) and extracted with ethyl acetate (3×10 mL). The combined organic layers were dried over anhydrous sodium sulfate, filtered, and concentrated under reduced pressure. The residue was purified by silica gel column chromatography (ethyl acetate/petroleum ether (v/v)=1/20~1/10), with TLC (ethyl acetate/petroleum ether (v/v)=1/8) monitoring, and collecting the fraction with Rf=0.5~0.6 to give the title compound D3 (89 mg, yield 6%) and the title compound D9 (28 mg, yield 1.8%).

Method B

At room temperature, crude compound A-8 (1.4 g, 4.08 mmol) and $Na_2CO_3$ (865 mg, 8.16 mmol) were dissolved ethanol (10 mL), then the mixture was stirred at room temperature overnight. The reaction was monitored by TLC until completion. The mixture was quenched with saturated brine (20 mL) and extracted with ethyl acetate (3×10 mL). The combined organic layers were dried over anhydrous sodium sulfate, filtered and concentrated under reduced pressure. The residue was purified by silica gel column chromatography (ethyl acetate/petroleum ether (v/v)=1/20~1/8), with TLC (ethyl acetate/petroleum ether (v/v)=1/5) monitoring, and collecting the fraction with Rf=0.5~0.6 to give title compound 9-1 (1.0 g, yield 68%). ESI$[M+H]^+$=363.1

At room temperature, 9-1 (100 mg, 0.28 mmol) and $Hg(OAc)_2$ (131 mg, 0.41 mmol) were dissolved in methanol (2 mL), then the mixture was stirred at room temperature overnight. The reaction was monitored by TLC until completion. The reaction mixture was quenched with saturated brine (10 mL) and extracted with ethyl acetate (3×5 mL). The combined organic layers were dried over anhydrous sodium sulfate, filtered, and concentrated under reduced pressure. The residue was purified by Prep-TLC (ethyl acetate/petroleum ether (v/v)=1/5) and the fraction with Rf=0.5~0.6 was collected to give the title compound D9 (27 mg, yield 29%). ESI$[M+H]^+$=333.1

$^1H$ NMR (400 MHz, $CDCl_3$) δ 7.63 (s, 1H), 7.31-7.27 (m, 5H), 7.26-7.24 (m, 1H), 6.52 (d, J=7.1 Hz, 2H), 4.43-4.40 (m, 2H), 3.95 (s, 1H), 3.77-3.71 (m, 1.5H), 3.54 (s, 2.5H), 1.94 (d, J=7.0 Hz, 3H), 1.44-1.40 (m, 3H), 1.28-1.24 (m, 3H).

5. Preparation of Compound D10

Method A

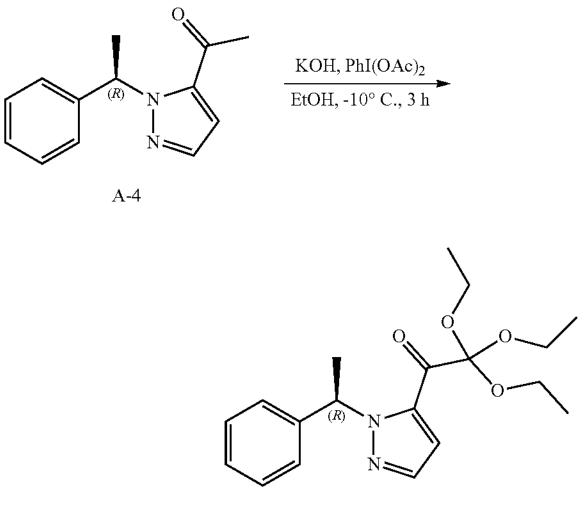

A-4

Compound D10

Method B

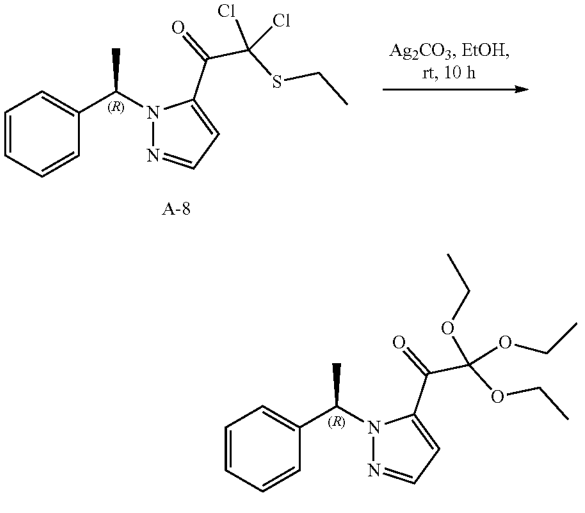

A-8

Compound D10

The title compound D10 was prepared according to the operation method A and B of preparing compound D1 described in Example 1, using A-4 and A-8 as the raw materials respectively.

34 mg of compound D10 was obtained in 34% yield by using method B. ESI$[M+H]^+$=347.1

$^1H$ NMR (400 MHz, $CDCl_3$) δ 7.61 (s, 1H), 7.30-7.26 (m, 5H), 7.24-7.22 (m, 1H), 6.50 (d, J=7.1 Hz, 2H), 4.42-4.40 (m, 1H), 3.94 (s, 1H), 3.75-3.70 (m, 1.5H), 3.52 (s, 2.5H), 1.92 (d, J=7.0 Hz, 3H), 1.43-1.41 (m, 4.5H), 1.25-1.22 (m, 4.5H).

Example 3 Preparation of Compounds D11~D12

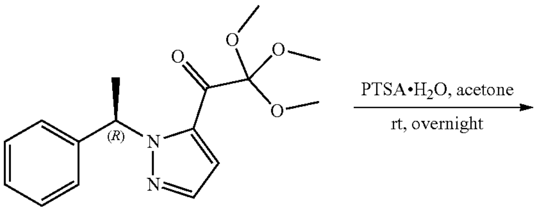

Compound D1

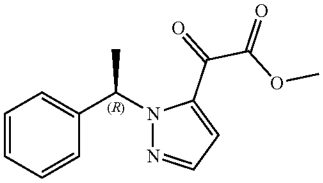

Compound D11

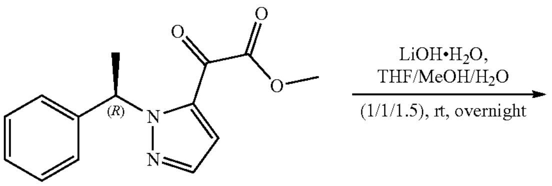

Compound D11

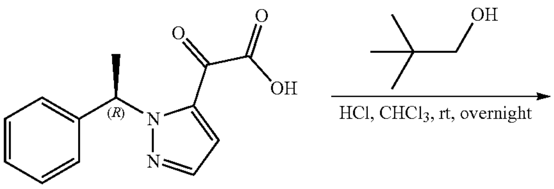

12-1

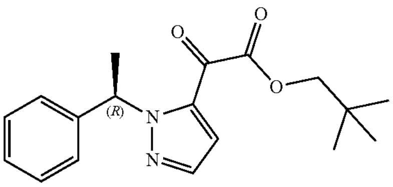

Compound D12

1. Preparation of Compound D11

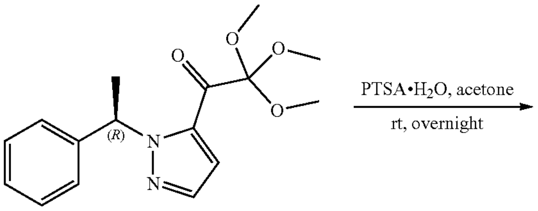

Compound D1

-continued

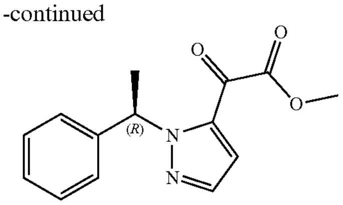

Compound D11

At room temperature, PTSA.$H_2O$ (1.2 g, 6.31 mmol) was added into the solution of D1 (600 mg, 1.97 mmol) in acetone (15 mL), then the mixture was stirred at room temperature overnight. The reaction was monitored by TLC until completion. The mixture was quenched with ice-water (10 mL) and extracted with ethyl acetate (3×15 mL). The combined organic layers were washed with saturated brine (10 mL), dried over anhydrous sodium sulfate, filtered and concentrated under reduced pressure. The residue was purified by Prep-TLC (ethyl acetate/petroleum ether (v/v)=1/3) and the fraction with Rf=0.4~0.6 was collected to give the title compound D11 (305 mg, yield 60%). ESI$[M+H]^+$=259.0

$^1H$ NMR (400 MHz, $CDCl_3$) δ 7.67 (d, J=2.1 Hz, 1H), 7.44-7.16 (m, 6H), 6.54 (q, J=7.0 Hz, 1H), 3.94 (s, 3H), 1.95 (d, J=7.0 Hz, 3H).

2. Preparation of Compound D12

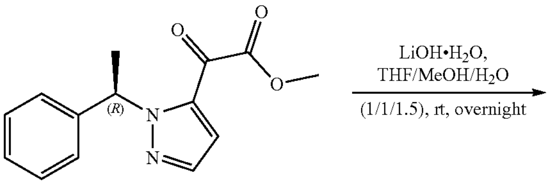

Compound D11

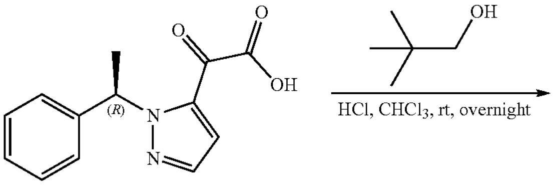

12-1

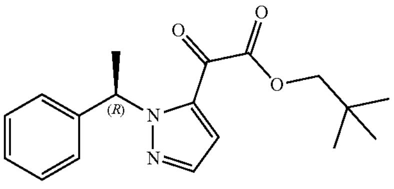

Compound D12

At room temperature, LiOH·$H_2O$ (81 mg, 1.93 mmol) was added into the solution of D11 (250 mg, 0.97 mmol) in MeOH/THF/$H_2O$ (7 mL, v/v/v=1/1/1.5), then the mixture was stirred at room temperature overnight. The reaction was monitored by TLC until completion. The reaction mixture was adjusted pH to 4~5 using 1N HCl and extracted with ethyl acetate (3×5 mL). The combined organic layers were washed with saturated brine (10 mL), dried over anhydrous sodium sulfate, filtered and concentrated to give the compound 12-1 (162 mg, yield 68%). ESI$[M+H]^+$=245.0

At room temperature, 12-1 (150 mg, 0.61 mmol) and 2,2-dimethylpropan-1-ol (162 mg, 1.84 mmol) were dissolved in chloroform (5 mL). Five drops of concentrated hydrochloric acid were added into the mixture using a syringe, and then the mixture was stirred at room temperature overnight. The reaction was monitored by TLC until completion. The reaction mixture was concentrated under reduced pressure. The crude product was purified by Prep-TLC (ethyl acetate/petroleum ether (v/v)=1/3) and the fraction with Rf=0.4~0.6 was collected and dried to give the title product D12 (74 mg, yield 39%). ESI[M+H]$^+$=315.1

$^1$H NMR (400 MHz, $CDCl_3$) δ 7.69 (d, J=2.1 Hz, 1H), 7.46-7.18 (m, 6H), 6.55 (q, J=7.0 Hz, 1H), 4.23 (s, 2H), 1.94 (d, J=7.0 Hz, 3H), 1.23 (s, 9H).

Example 4 Preparation of Compounds D13~D16

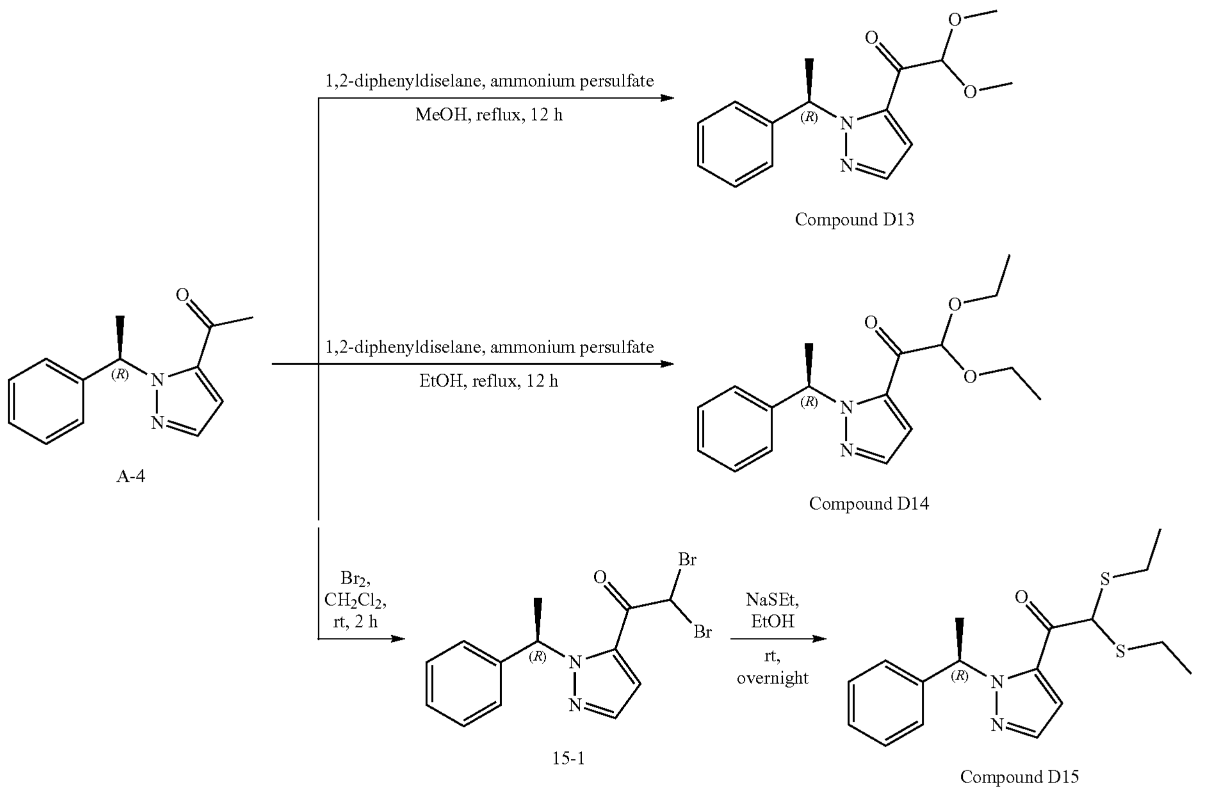

A-4

Compound D13

Compound D14

15-1

Compound D15

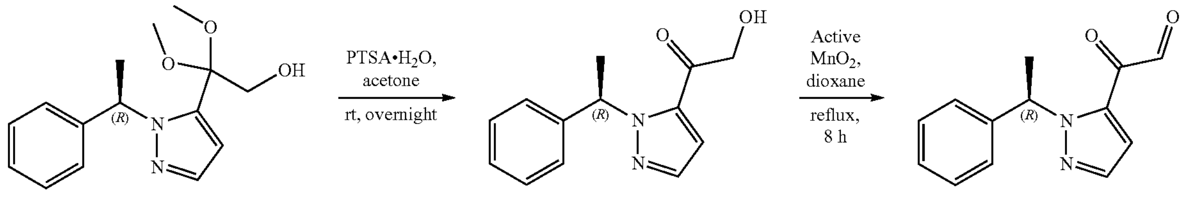

A-5

16-1

16-2

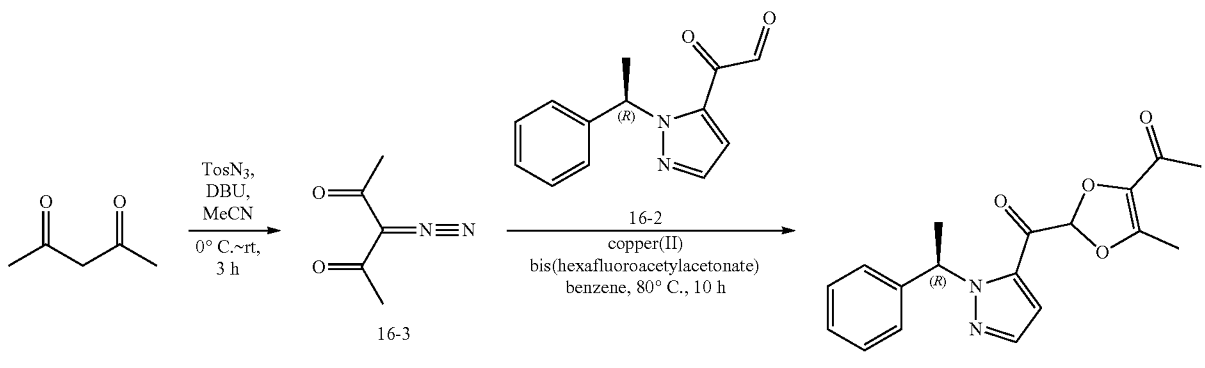

16-3

Compound D16

1. Preparation of Compounds D13 and D14

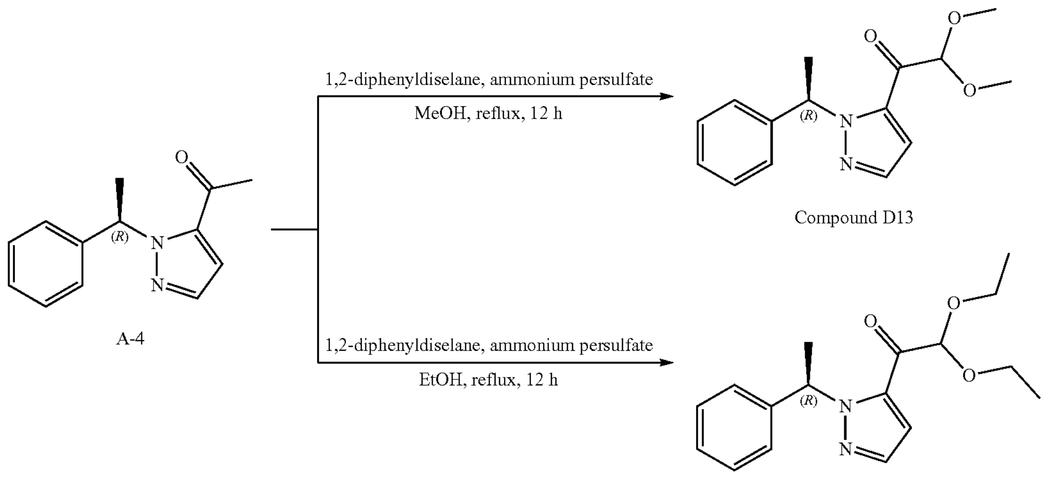

A-4

Compound D13

Compound D14

A-4 (214 mg, 1.0 mmol) and 1,2-diphenyldiselane (1.56 g, 5.0 mmol) were dissolved in methanol or ethanol (10 mL), then the mixture was heated to reflux for 12 hrs. The reaction was monitored by TLC until completion. The reaction mixture was quenched with water (30 mL) and extracted with ethyl acetate (3×10 mL). The combined organic layers were dried over anhydrous sodium sulfate, filtered, and concentrated under reduced pressure. The residue was purified by Prep-TLC (methyl tert-butyl ether/petroleum ether (v/v)=1/30) and the fraction with Rf=0.4~0.6 was collected to give the title compound D13 and the title compound D14.

Compound D13: 91 mg, yield 33%, ESI[M+H]$^+$=275.0

$^1$H NMR (400 MHz, $CDCl_3$) δ 7.64 (s, 1H), 7.30-7.26 (m, 5H), 7.26-7.23 (m, 1H), 6.51 (d, J=7.1 Hz, 2H), 5.08 (s, 1H), 3.35 (s, 3H), 3.30 (s, 3H), 1.92 (d, J=7.0 Hz, 3H).

Compound D14: 138 mg, yield 46%, ESI[M+H]$^+$=303.2

$^1$H NMR (400 MHz, $CDCl_3$) δ 7.63 (s, 1H), 7.31-7.26 (m, 5H), 7.25-7.23 (m, 1H), 6.49 (d, J=7.1 Hz, 2H), 5.04 (s, 1H), 3.50-3.46 (m, 4H), 1.92 (d, J=7.0 Hz, 3H), 1.19-1.15 (m, 6H).

2. Preparation of Compound D15

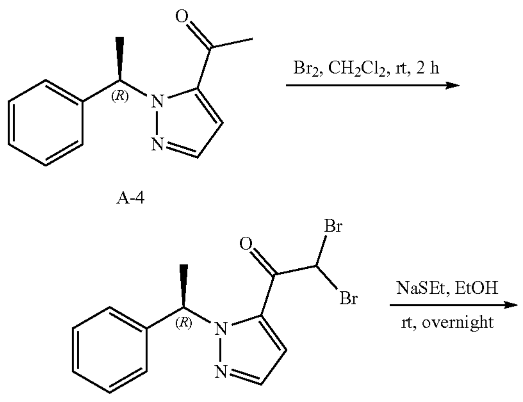

A-4

15-1

-continued

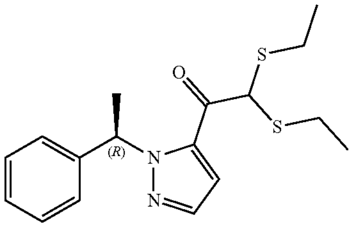

Compound D15

At room temperature, A-4 (400 mg, 1.87 mmol) was dissolved in dichloromethane (10 mL), then the mixture was cooled to 0° C. with an ice-water bath. The solution of $Br_2$ (597 mg, 3.74 mmol) in dichloromethane (5 mL) was added slowly into the above mixture using a syringe. The reaction mixture was stirred at room temperature for 2 hrs. The reaction was monitored by TLC until completion. The reaction mixture was concentrated under reduced pressure to give crude compound 15-1, which was used for next step directly without further purification.

At room temperature, NaSEt (472 mg, 5.61 mmol) was added into the solution of crude 15-1 (1.87 mmol) in ethanol (30 mL), then the mixture was stirred at room temperature overnight. The reaction was monitored by TLC until completion. The reaction mixture was quenched with ice-water (10 mL) and extracted with ethyl acetate (3×5 mL). The combined organic layers were washed with saturated brine (10 mL), dried over anhydrous sodium sulfate, filtered, and concentrated under reduced pressure. The residue was purified by silica gel column chromatography (ethyl acetate/petroleum ether (v/v)=1/20~1/3), with TLC (ethyl acetate/petroleum ether (v/v)=1/5) monitoring, and collecting the fraction with Rf=0.4~0.6 to give the title compound D15 (46 mg, yield 7.4% for 2 steps). ESI[M+H]$^+$=335.1

$^1$H NMR (400 MHz, $CDCl_3$) δ 7.62 (s, 1H), 7.30-7.24 (m, 5H), 7.22-7.20 (m, 1H), 6.45 (d, J=7.1 Hz, 2H), 5.13 (s, 1H), 2.79-2.40 (m, 4H), 1.90 (d, J=7.0 Hz, 3H), 1.16-1.13 (m, 6H). 3. Preparation of Compound D16

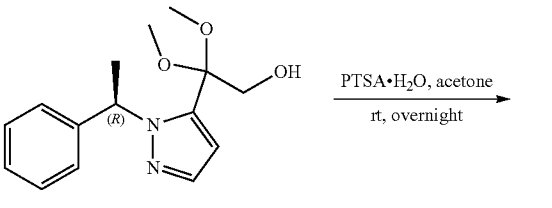

A-5

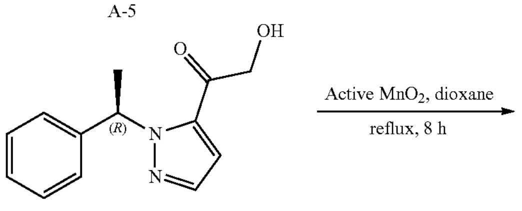

16-1

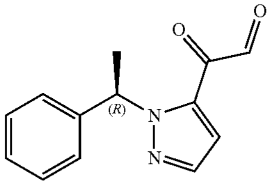

16-2

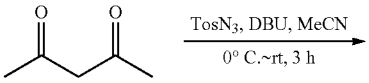

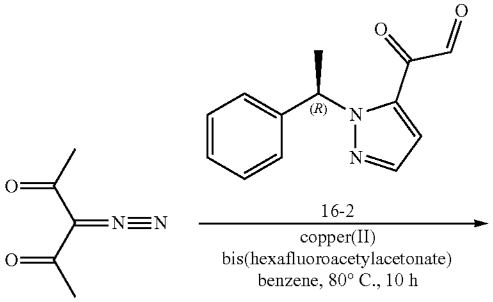

16-3

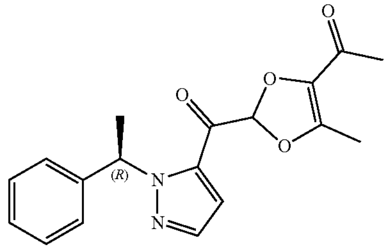

Compound D16

At room temperature, PTSA.$H_2O$ (4.1 g, 21.6 mmol) was added into the solution of A-5 (3.0 g, 10.9 mmol) in acetone (50 mL), then the mixture was stirred at room temperature overnight. The reaction was monitored by TLC until completion. The mixture was quenched with ice-water (50 mL) and extracted with ethyl acetate (3×15 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/20~1/5), with TLC (ethyl acetate/petroleum ether (v/v)=1/2) monitoring, and collecting the fraction with Rf=0.5~0.6 to give compound 16-1 (1.7 g, yield 68%). ESI$[M+H]^+$=231.1

At room temperature, active $MnO_2$ (26.6 g, 91%, 278 mmol) was added in portions into the solution of 16-1 (1.6 g, 6.9 mmol) in dioxane (150 mL), then the mixture was heated to reflux for 8 hrs. The reaction was monitored by TLC until completion. The reaction mixture was cooled to room temperature and filtered. The filter cake was washed with dichloromethane (300 mL). The filtrate was concentrated under reduced pressure. The crude product was purified by silica gel column chromatography (ethyl acetate/petroleum ether (v/v)=1/20~1/5), with TLC (ethyl acetate/petroleum ether (v/v)=1/2) monitoring, and collecting the fraction with Rf=0.5~0.6 to give compound 16-2 (1.2 g, yield 76%). ESI$[M+H]^+$=229.1

At room temperature, acetylacetone (1.5 g, 15.0 mmol) and 4-methylbenzenesulfonyl azide (2.9 g, 14.7 mmol) were dissolved in acetonitrile (100 mL), then the mixture was cooled to 0° C. with an ice-water bath. DBU (6.9 g, 45 mmol) was added into the mixture using a syringe within 10 mins. After addition, the ice-water bath was removed, and the mixture was allowed to react at room temperature for 3 hrs. The reaction was monitored by TLC until completion. The reaction mixture was filtered, and the filtrate was concentrated under reduced pressure. The residue was heated with ethyl acetate/petroleum ether (v/v=1/1) and filtered. The filtrate was concentrated under reduced pressure. The crude product was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give compound 16-3 (1.3 g, yield 29%).

At room temperature, 16-2 (500 mg, 2.2 mmol) and 16-3 (277 mg, 2.2 mmol) were dissolved in benzene (5 mL), then the mixture was stirred at 80° C. for 10 hrs. The reaction was monitored by TLC until completion. The reaction mixture was concentrated under reduced pressure. The residue was purified by Prep-TLC (ethyl acetate/petroleum ether (v/v)=1/3) and the fraction with Rf=0.4~0.6 was collected to give the title compound D16 (79 mg, yield 11%). ESI$[M+H]^+$=327.1

$^1H$ NMR (400 MHz, $CDCl_3$) δ 7.65 (s, 1H), 7.32-7.29 (m, 5H), 7.25-7.22 (m, 1H), 6.69 (s, 1H), 6.44 (d, J=7.1 Hz, 1H), 2.21 (s, 6H), 1.91 (d, J=7.0 Hz, 3H).

Example 5 Preparation of Compound D17

Method A

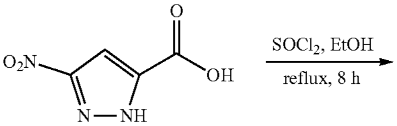

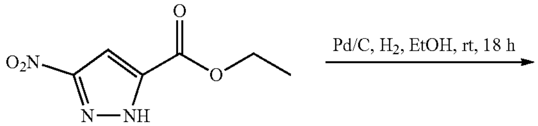

B-1

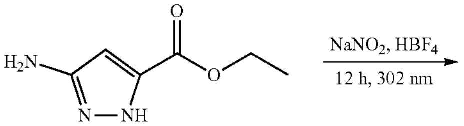

B-2

-continued
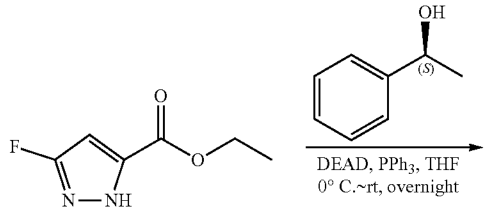
B-3
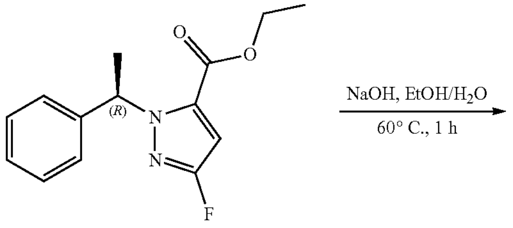
B-4
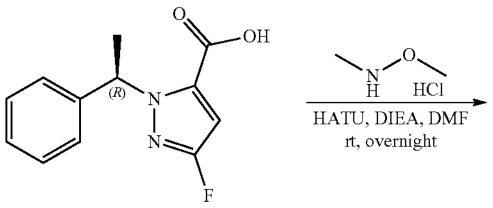
B-5
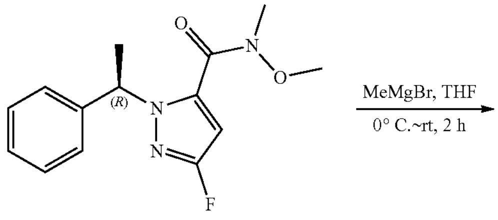
B-6
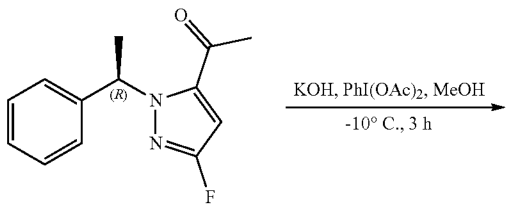
B-7
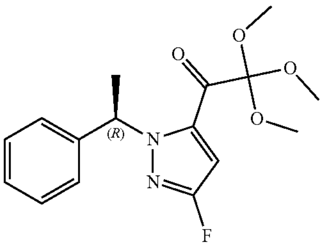
Compound D17
+
-continued
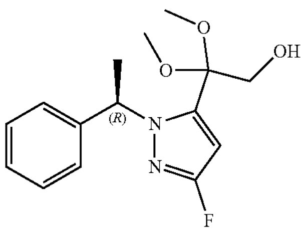
B-8
Method B
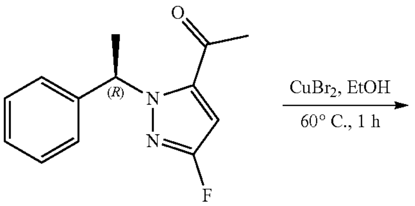
B-7
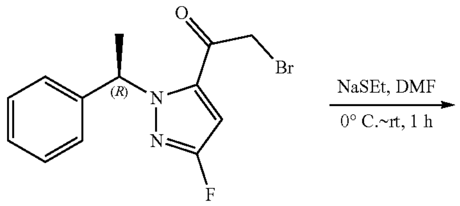
B-9
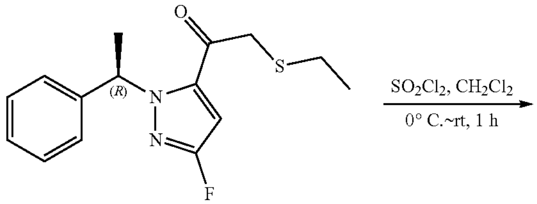
B-10
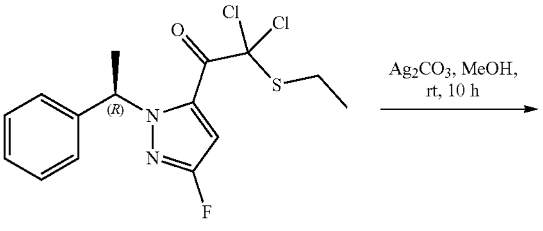
B-11
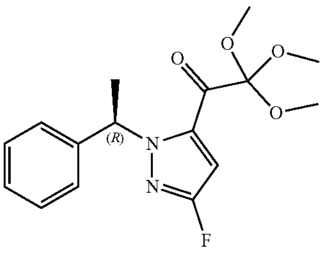
Compound D17

1. Preparation of ethyl 3-nitro-1H-pyrazole-5-carboxylate (B-1)

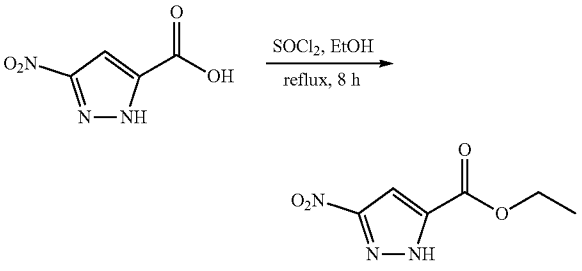

B-1

At room temperature, 3-nitro-1H-pyrazole-5-carboxylic acid (50 g, 318.3 mmol was dissolved in ethanol (300 mL). In an ice-water bath, $SOCl_2$ (49 g, 412 mmol) was added dropwise into the mixture. After addition, the mixture was heated to reflux for 8 hrs. The reaction was monitored by TLC until completion. The reaction mixture was concentrated under reduced pressure. The residue was dissolved in dichloromethane (30 mL) and adjusted pH to 7~8 with saturated sodium bicarbonate solution. The mixture was extracted with dichloromethane (3×30 mL). The combined organic layers were washed with saturated brine (10 mL), dried over anhydrous sodium sulfate, filtered and concentrated under reduced pressure to give compound B-1 (58.7 g, yield 99.6%) as a white solid. ESI$[M+H]^+$=186.1

2. Preparation of ethyl 3-amino-1H-pyrazole-5-carboxylate (B-2)

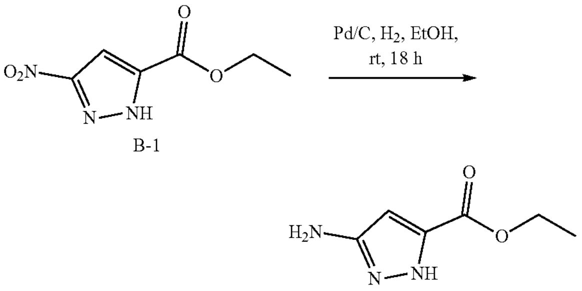

B-1

B-2

B-1 (58.7 g, 317 mmol) and 10% wet palladium carbon (6 g) were dissolved in ethanol (200 mL). The system was replaced three times with hydrogen, then the reaction mixture was allowed to react at room temperature for 18 hrs under hydrogen. The reaction was monitored by TLC until completion. The reaction mixture was filtered. The filter cake was washed with ethanol (3×30 mL). The filtrate was concentrated under reduced pressure. The crude product was purified by silica gel column chromatography (ethyl acetate/petroleum ether (v/v)=1/20~1/1), with TLC (ethyl acetate/petroleum ether (v/v)=1/1) monitoring, and collecting the fraction with Rf=0.4~0.5 to give compound B-2 (43.5 g, yield 88%). ESI$[M+H]^+$=156.1

3. Preparation of ethyl 3-fluoro-1H-pyrazole-5-carboxylate (B-3)

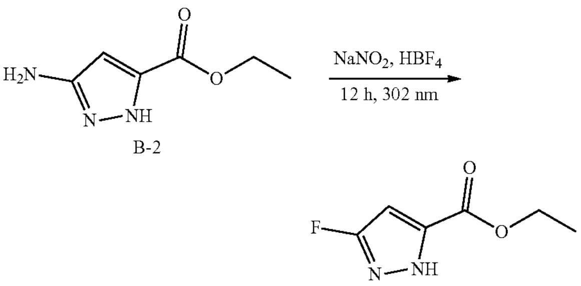

B-2

B-3

In an ice-salt bath, B-2 (43.5 g, 280 mmol) was dissolved in $HBF_4$ (40%) at −10° C., and then the solution of $NaNO_2$ (20.3 g, 294 mmol) in water (30 mL) was added into the mixture. The mixture was allowed to react under the irradiation of a mercury lamp (302 nm) for 12 hrs. The reaction was monitored by TLC until completion, and then the reaction solution was adjusted pH to 7~8 with 1N NaOH solution in an ice-water bath. The mixture was extracted with ethyl acetate (3×50 mL). The combined organic layers were washed with saturated brine (20 mL), dried over anhydrous sodium sulfate, filtered and concentrated under reduced pressure. The crude product was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.4~0.5 to give compound B-3 (3.4 g, yield 8%) as a grey solid compound.

4. Preparation of ethyl (R)-3-fluoro-1-(1-phenylethyl)-1H-pyrazole-5-carboxylate (B-4)

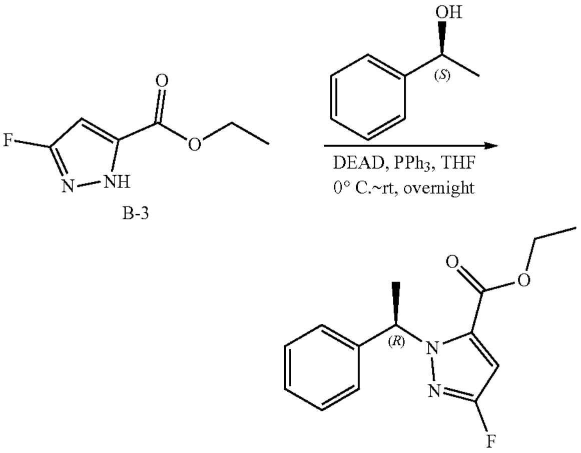

B-3

B-4

In an ice-water bath, (S)-1-phenylethan-1-ol (3.4 g, 27.8 mmol) was added into the mixture of B-3 (3.4 g, 21.5 mmol) and $PPh_3$ (8.4 g, 32.0 mmol) in THF (50 mL) at 0° C., then the solution of DEAD (5.6 g, 32.2 mmol) in THF (15 mL) was added dropwise into the mixture at the rate of 1 mmol/min After addition, the reaction mixture was warmed slowly to room temperature and stirred overnight. The reaction was monitored by TLC until completion. The reaction mixture was quenched with the saturated brine (100 mL) and extracted with ethyl acetate (3×15 mL). The combined organic layers were washed with saturated brine (30 mL), dried over anhydrous sodium sulfate, filtered and concentrated under reduced pressure to give crude product. The crude product was purified by silica gel column chromatography (ethyl acetate/petroleum ether (v/v)=1/20~1/10), with TLC (ethyl acetate/petroleum ether (v/v)=1/2) monitoring, and collecting the fraction with Rf=0.5~0.6 to give the product B-4 (4.2 g, yield 74%). ESI[M+H]$^+$=263.1

$^1$H NMR (400 MHz, $CDCl_3$) δ 7.35-7.21 (m, 5H), 6.56-6.47 (m, 1H), 6.33 (d, J=6.3 Hz, 1H), 4.41-4.17 (m, 2H), 1.85 (d, J=7.1 Hz, 3H), 1.33 (t, J=7.1 Hz, 3H).

5. Preparation of (R)-3-fluoro-1-(1-phenylethyl)-1H-pyrazole-5-carboxylic acid (B-5)

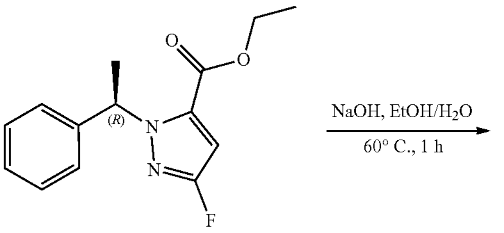

B-4

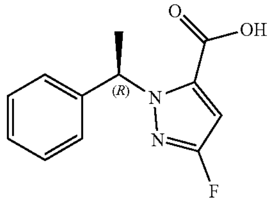

B-5

At room temperature, the solution of NaOH (1.3 g, 32.5 mmol) in water (10 mL) was added into the solution of B-4 (4.2 g, 16.0 mmol) in ethanol (10 mL), then the mixture was stirred at 60° C. for 1 hour. The reaction was monitored by TLC until completion. The reaction mixture was concentrated under reduced pressure. Water (20 mL) was poured into the residue. The mixture was adjusted pH to 4~5 with 1N HCl and extracted with dichloromethane (3×15 mL). The combined organic layers were dried over anhydrous sodium sulfate, filtered and concentrated to give the compound B-5 (2.8 g, yield 75%) as a white solid. ESI[M+H]$^+$=234.9

$^1$H NMR (400 MHz, $CDCl_3$) δ 7.41-7.14 (m, 6H), 6.55-6.36 (m, 2H), 1.87 (d, J=7.0 Hz, 3H).

6. Preparation of (R)-3-fluoro-N-methoxy-N-methyl-1-(1-phenylethyl)-1H-pyrazole-5-carboxamide (B-6)

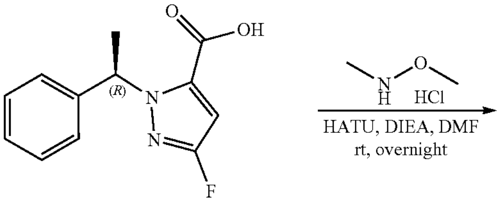

B-5

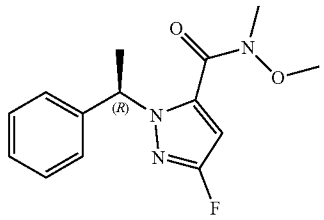

B-6

At room temperature, B-5 (2.0 g, 8.5 mmol), N,O-dimethylhydroxylamine hydrochloride (1.2 g, 12.3 mmol), DIEA (1.7 g, 13.2 mmol) and HATU (4.7 g, 12.4 mmol) were dissolved in DMF (30 mL), then the mixture was stirred at room temperature overnight. The reaction was monitored by TLC until completion. The mixture was quenched with water (100 mL) and extracted with ethyl acetate (3×30 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5~0.6 to give the title compound B-6 (1.8 g, yield 76%) as a white solid. ESI[M+H]$^+$=278.1

7. Preparation of (R)-1-(3-fluoro-1-(1-phenylethyl)-1H-pyrazol-5-yl)ethan-1-one (B-7)

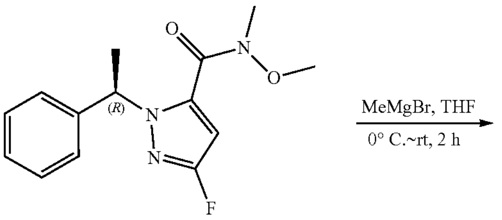

B-6

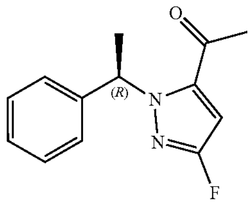

B-7

At room temperature, B-6 (1.8 g, 6.5 mmol) was dissolved in anhydrous THF (20 mL). The mixture was cooled to 0° C. with an ice-water bath. Methylmagnesium bromide (13 mL, 1 mol/L in THF, 13.0 mmol) was added dropwise into the mixture at the rate of 2 mmol/min, then the mixture was reacted at room temperature for 2 hrs. The reaction was monitored by TLC until completion. The mixture was cooled to 0° C. with an ice-water bath, quenched with saturated ammonium chloride solution (50 mL) and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give the title compound B-7 (1.2 g, yield 79%) as a white solid. ESI[M+H]$^+$=233.1

8. Preparation of (R)-2-bromo-1-(3-fluoro-1-(1-phenylethyl)-1H-pyrazol-5-yl) ethan-1-one (B-9)

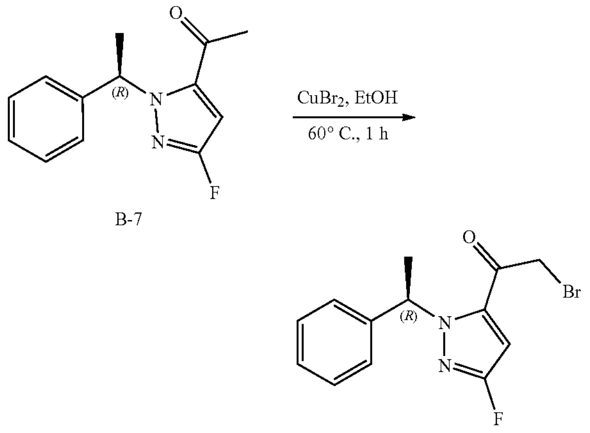

B-7

B-9

At room temperature, $CuBr_2$ (4.5 g, 20 mmol) was added into the solution of B-7 (2.3 g, 10 mmol) in ethanol (50 mL), then the mixture was stirred at 60° C. for 1 hour. The reaction was monitored by TLC until completion. The mixture was cooled to room temperature, quenched with water (50 mL) and extracted with ethyl acetate (3×10 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give the title compound B-9 (2.3 g, yield 74%) as light-yellow oil. ESI[M+H]$^+$=311.0

9. Preparation of (R)-2-(ethylthio)-1-(3-fluoro-1-(1-phenylethyl)-1H-pyrazol-5-yl)ethan-1-one (B-10)

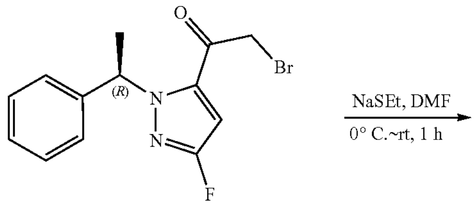

B-9

-continued

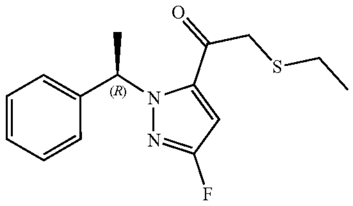

B-10

In an ice-water bath, NaSEt (595 mg, 7.07 mmol) was added into the solution of B-9 (2.2 g, 7.07 mmol) in DMF (30 mL) at 0° C., then the mixture was reacted at room temperature for 1 hour. The reaction was monitored by TLC until completion. The mixture was quenched with ice-water (10 mL) and extracted with ethyl acetate (3×5 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/10~1/3), with collecting the fraction with Rf=0.4~0.6 to give the title compound B-10 (1.1 g, yield 53%). ESI[M+H]$^+$=293.0

10. Preparation of (R)-2,2-dichloro-2-(ethylthio)-1-(3-fluoro-1-(1-phenylethyl)-1H-pyrazol-5-yl)ethan-1-one (B-11)

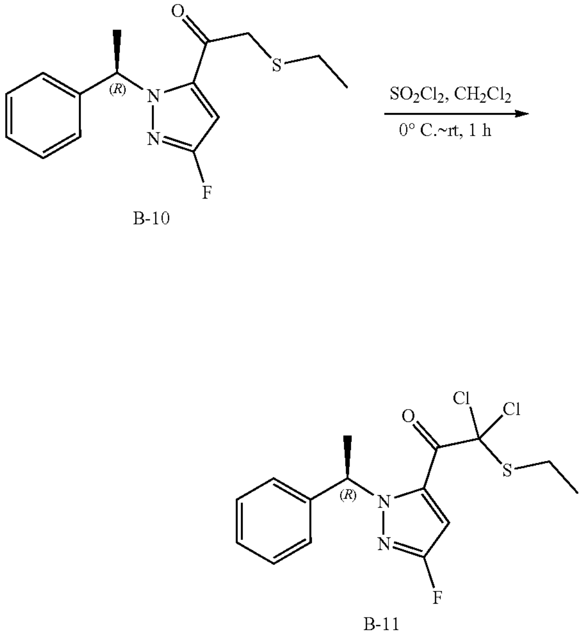

B-10

B-11

In an ice-water bath, $SO_2Cl_2$ (923 mg, 6.84 mmol) was added into the solution of B-10 (1.0 g, 3.42 mmol) in dichloromethane (10 mL) at 0° C., then the mixture was stirred at room temperature for 1 hour. The reaction was monitored by TLC until completion. The reaction mixture was concentrated under reduced pressure to give the crude compound B-11 (1.2 g), which was used for next step directly without further purification.

11. Preparation of Compound D17

Method A

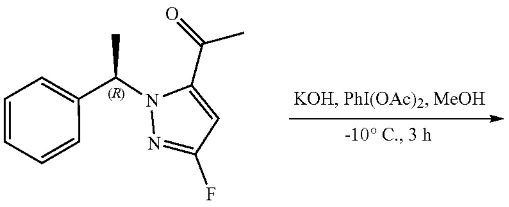

B-7

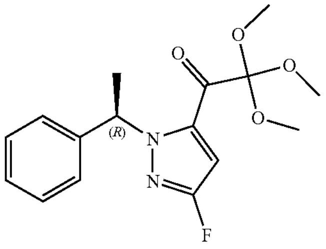

Compound D17

At room temperature, B-7 (1 g, 4.3 mmol) and $PhI(OAc)_2$ (2.1 g, 6.5 mmol) were dissolved in methanol (20 mL), then the mixture was cooled to −10° C. with an ice-salt bath. KOH (2.9 g, 52 mmol) was added in portions into the mixture within 30 mins, then the reaction mixture was reacted at −10° C. for 3 hrs. The reaction was monitored by TLC until completion. The reaction mixture was quenched with saturated brine (50 mL) and extracted with ethyl acetate (3×20 mL). The combined organic layers were dried over anhydrous sodium sulfate, filtered, and concentrated under reduced pressure. The crude product was purified by silica gel column chromatography (ethyl acetate/petroleum ether (v/v)=1/20~1/10), with TLC (ethyl acetate/petroleum ether (v/v)=1/8) monitoring, and collecting the fraction with Rf=0.5~0.6 to give title compound D17 (36 mg, yield 2.6%).

Method B

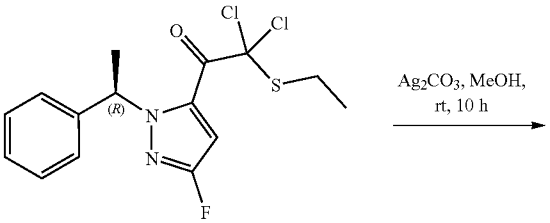

B-11

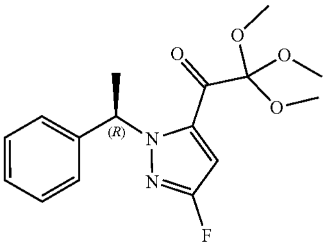

Compound D17

At room temperature, B-11 (200 mg, 0.55 mmol) and $Ag_2CO_3$ (229 mg, 0.83 mmol) were dissolved methanol (10 mL), then the mixture was stirred at room temperature for 10 hrs. The reaction was monitored by TLC until completion. In an ice-water bath, the mixture was quenched with saturated sodium bicarbonate solution (10 mL) at 0° C. and extracted with ethyl acetate (3×10 mL). The combined organic layers were dried over anhydrous sodium sulfate, filtered and concentrated under reduced pressure. The residue was purified by Prep-TLC (ethyl acetate/petroleum ether (v/v)=1/5) and the fraction with Rf=0.5~0.6 was collected to give the title compound D17 (67 mg, yield 38%). ESI$[M+H]^+$=323.0

$^1$H NMR (400 MHz, $CDCl_3$) δ 7.35-7.21 (m, 5H), 6.79 (d, J=6.2 Hz, 1H), 6.47-6.37 (m, 1H), 3.92 (s, 3H), 3.50 (s, 6H), 1.87 (d, J=7.0 Hz, 3H).

Example 6 Preparation of Compounds D18~D28

1. Preparation of Compound D18

Method A

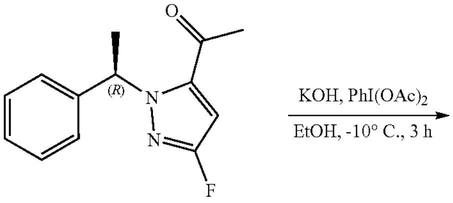

B-7

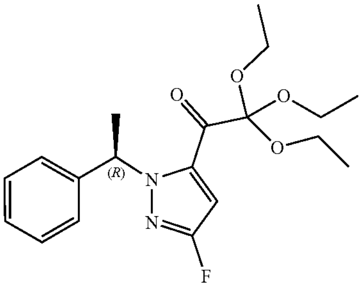

Compound D18

Method B

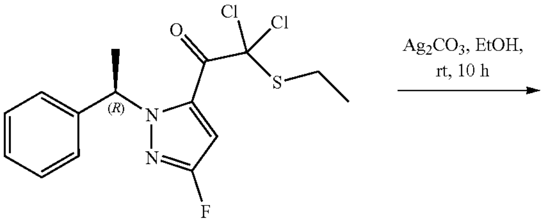

B-11

-continued

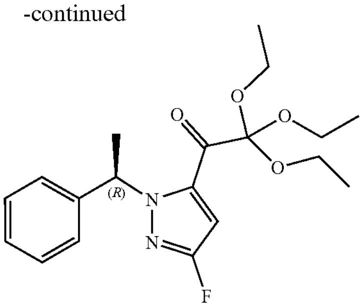

Compound D18

The title compound D18 was prepared according to the operation method A and B of preparing compound D10 described in Example 2, using B-7 and B-11 as the raw materials respectively.

Compound D18: 43 mg, ESI[M+H]$^+$=365.1

$^1$H NMR (400 MHz, $CDCl_3$) δ 7.34-7.20 (m, 5H), 6.75 (d, J=6.2 Hz, 1H), 6.47-6.39 (m, 1H), 4.42-4.40 (m, 1H), 3.93 (s, 1H), 3.75-3.70 (m, 1.5H), 3.53 (s, 2.5H), 1.88 (d, J=7.0 Hz, 3H), 1.43-1.40 (m, 4.5H), 1.25-1.22 (m, 4.5H).

2. Preparation of Compounds D19~D24

The title compounds D19~D24 were prepared according to the operation method of preparing compounds D2~D10 described in Example 2.

Compound D19: 26 mg, ESI[M+H]$^+$=321.0

$^1$H NMR (400 MHz, $CDCl_3$) δ 7.37-7.25 (m, 5H), 6.77 (d, J=6.2 Hz, 1H), 6.49-6.38 (m, 1H), 4.07-3.78 (m, 4H), 3.26 (s, 3H), 1.86 (d, J=7.0 Hz, 3H).

Compound D20: 16 mg, ESI[M+H]$^+$=361.0

$^1$H NMR (400 MHz, $CDCl_3$) δ 7.35-7.21 (m, 5H), 6.79 (d, J=6.2 Hz, 1H), 6.47-6.37 (m, 1H), 4.23-4.16 (m, 1.5H), 3.95 (s, 2H), 3.47 (m, 3H), 3.27-3.08 (m, 1.5H), 2.03-1.82 (m, 6H).

Compound D21: 22 mg, ESI[M+H]$^+$=359.0

$^1$H NMR (400 MHz, $CDCl_3$) δ 7.35-7.21 (m, 5H), 6.79 (d, J=6.2 Hz, 1H), 6.47-6.37 (m, 1H), 4.07-3.78 (m, 6H), 2.03-1.82 (m, 6H).

Compound D22: 54 mg, ESI[M+H]$^+$=379.1

$^1$H NMR (400 MHz, $CDCl_3$) δ 7.32-7.21 (m, 5H), 6.75 (d, J=6.2 Hz, 1H), 6.45-6.34 (m, 1H), 4.03 (s, 1.5H), 3.95 (s, 1H), 3.53 (s, 4.5H), 3.31 (s, 1H), 1.93 (d, J=7.0 Hz, 3H), 1.01 (s, 5.5H), 0.94 (s, 3.5H).

Compound D23: 36 mg, ESI[M+H]$^+$=377.1

$^1$H NMR (400 MHz, $CDCl_3$) δ 7.36-7.25 (m, 5H), 6.75 (d, J=6.2 Hz, 1H), 6.48-6.38 (m, 1H), 4.07-3.78 (m, 5H), 3.30 (s, 1H), 1.92 (d, J=7.0 Hz, 3H), 1.03 (s, 5.5H), 0.95 (s, 3.5H).

Compound D24: 29 mg, ESI[M+H]$^+$=351.1

$^1$H NMR (400 MHz, $CDCl_3$) δ 7.37-7.21 (m, 5H), 6.79 (d, J=6.2 Hz, 1H), 6.46-6.37 (m, 1H), 4.44-4.40 (m, 2H), 3.96 (s, 1H), 3.77-3.72 (m, 1.5H), 3.54 (s, 2.5H), 1.86 (d, J=7.0 Hz, 3H), 1.45-1.41 (m, 3H), 1.27-1.24 (m, 3H).

3. Preparation of Compounds D25~D28

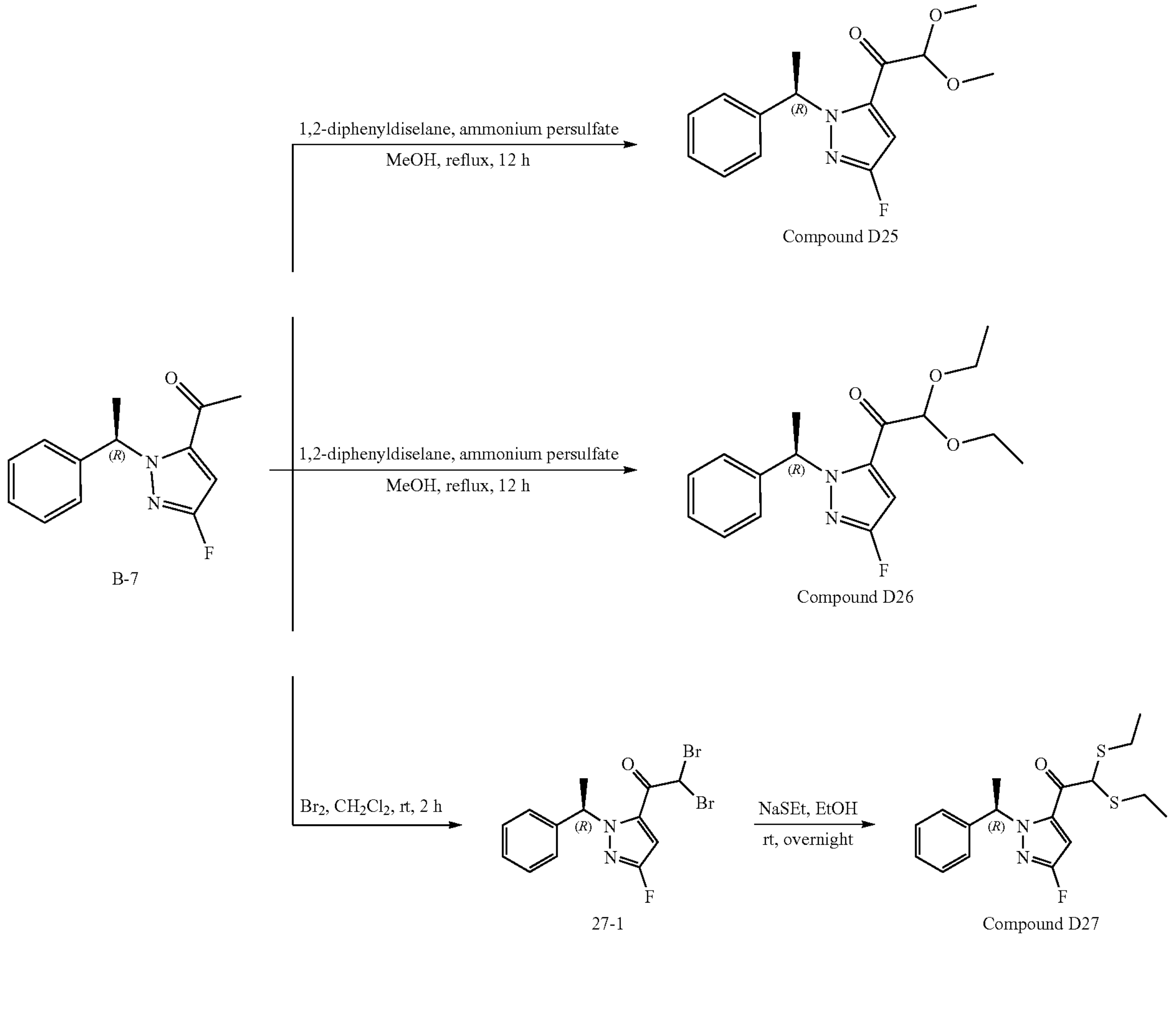

Compound D25

B-7

Compound D26

27-1

Compound D27

-continued

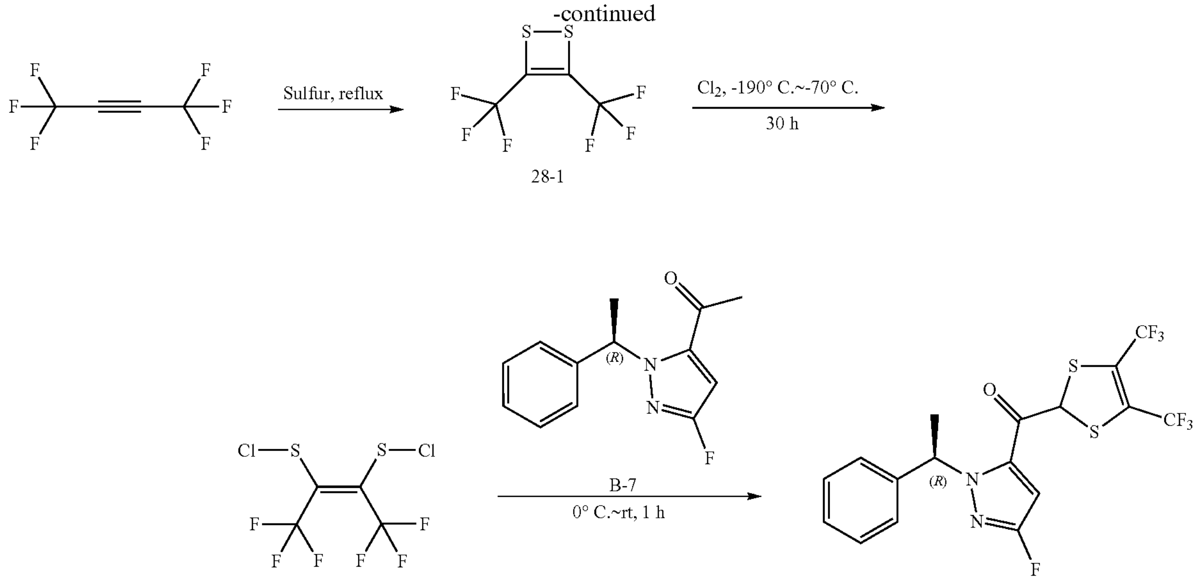

28-1

28-2

Compound D28

The title compounds D25~D27 were prepared according to the operation method of preparing compounds D13~D15 described in Example 4, using B-7 as the raw material.

Compound D25: 12 mg, ESI[M+H]$^+$=293.0

$^1$H NMR (400 MHz, $CDCl_3$) δ 7.32-7.19 (m, 5H), 6.61 (d, J=6.2 Hz, 1H), 6.50-6.39 (m, 1H), 4.87 (s, 1H), 3.37 (s, 3H), 3.33 (s, 3H), 1.85 (d, J=7.0 Hz, 3H).

Compound D26: 37 mg, ESI[M+H]$^+$=321.1

$^1$H NMR (400 MHz, $CDCl_3$) δ 7.34-7.20 (m, 5H), 6.75 (d, J=6.2 Hz, 1H), 6.47-6.39 (m, 1H), 5.02 (s, 1H), 3.70-3.61 (m, 4H), 1.87 (d, J=7.0 Hz, 3H), 1.23 (t, J=7.0 Hz, 6H).

Compound D27: 34 mg, ESI[M+H]$^+$353.1

$^1$H NMR (400 MHz, $CDCl_3$) δ 7.36-7.21 (m, 5H), 6.77 (d, J=6.2 Hz, 1H), 6.48-6.38 (m, 1H), 5.23 (s, 1H), 2.78-2.46 (m, 4H), 1.86 (d, J=7.0 Hz, 3H), 1.25 (t, J=7.1 Hz, 6H).

At room temperature, sulfur (10 g) was placed in a three-necked flask. The system was replaced with nitrogen three times, and then heated to reflux. Perfluorobut-2-yne (1.44 g, 8.9 mmol) was added slowly into the system within 5 minutes. The product was blown out from the system by nitrogen and cooled to give 28-1 (1.0 g, yield 50%). 28-1 (905 mg, 4.0 mmol) and dry chlorine (284 mg, 4.0 mmol) were cooled to −190° C. with liquid nitrogen, then the mixture was stirred at −70° C. for about 30 hrs. The crude product was distilled under reduced pressure and cooled to give 28-2 (501 mg, yield 42%).

In an ice-water bath, 28-2 (297 mg, 1.0 mmol) was added slowly into B-7 (232 mg, 1.0 mmol) at 0° C. After addition, the mixture was stirred at room temperature for 1 hour. The crude product was purified by Prep-TLC (ethyl acetate/petroleum ether (v/v)=1/5) and the fraction with Rf=0.5~0.6 was collected to give the title compound D28 (27 mg, yield 6%). ESI[M+H]$^+$=457.1

$^1$H NMR (400 MHz, $CDCl_3$) δ 7.37-7.22 (m, 5H), 6.75 (d, J=6.2 Hz, 1H), 6.47-6.34 (m, 1H), 5.50 (s, 1H), 1.85 (d, J=7.0 Hz, 3H).

Example 7 Preparation of Compounds D29~D41

Method A

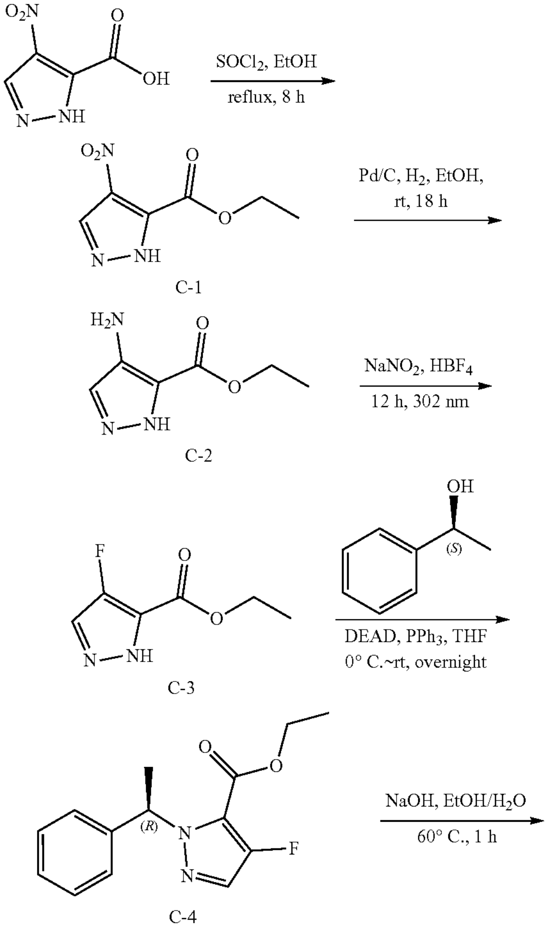

C-1

C-2

C-3

C-4

-continued
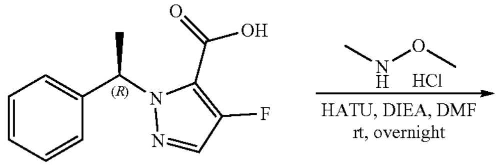
C-5
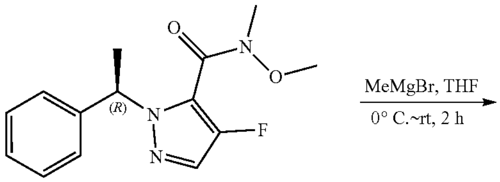
C-6
-continued
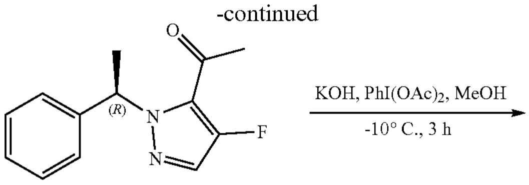
C-7
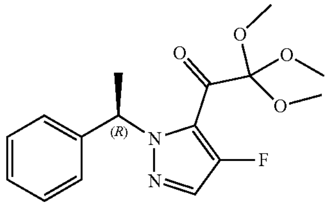
Compound D29
Method B
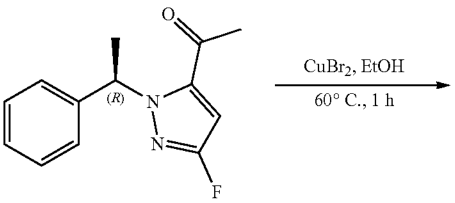
C-7
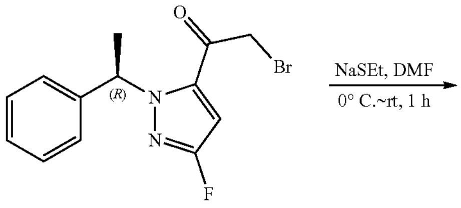
C-8
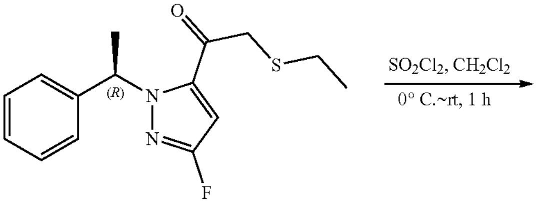
C-9
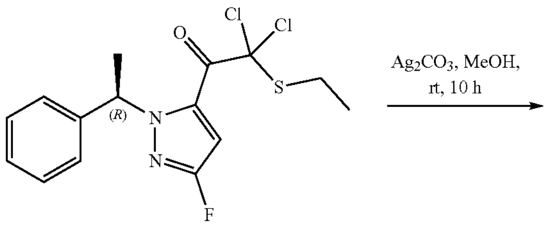
C-10
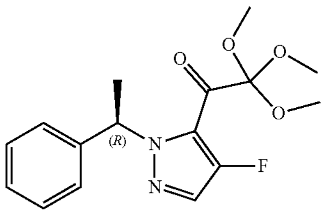
Compound D29

-continued

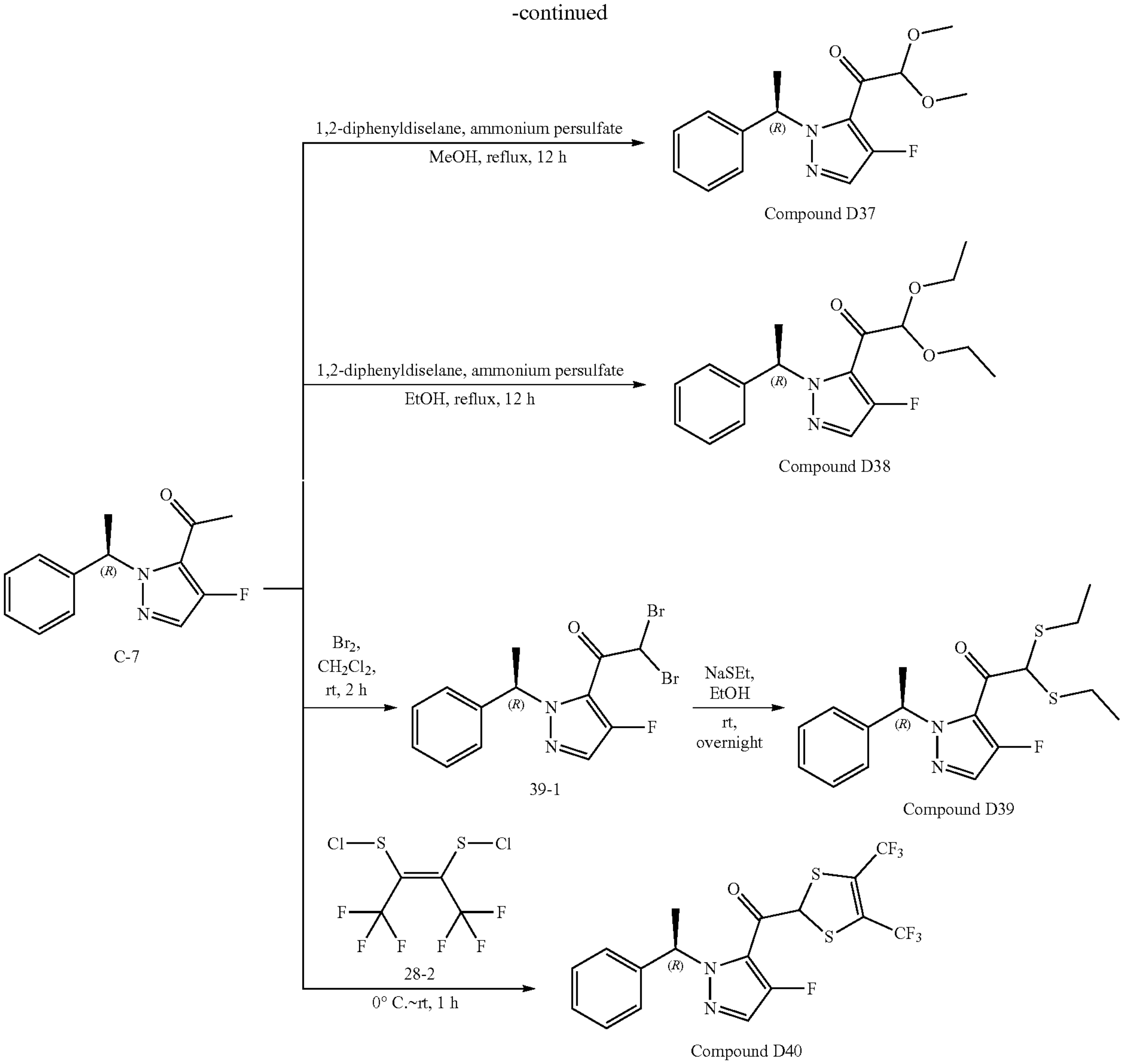

C-7

Compound D37

Compound D38

39-1

Compound D39

28-2

Compound D40

1. Preparation of ethyl 4-nitro-1H-pyrazole-5-carboxylate (C-1)

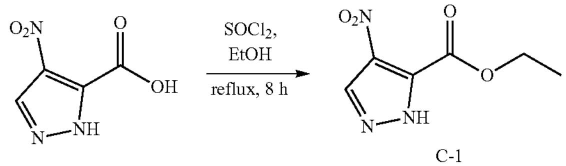

C-1

At room temperature, 4-nitro-1H-pyrazole-5-carboxylic acid (50 g, 318.3 mmol) was dissolved in ethanol (300 mL). In an ice-water bath, $SOCl_2$ (49 g, 412 mmol) was added dropwise into the mixture at 0° C. After addition, the mixture was heated to reflux for 8 hrs. The reaction was monitored by TLC until completion. The reaction mixture was concentrated under reduced pressure. The residue was dissolved in dichloromethane (30 mL) and adjusted pH to 7~8 with saturated sodium bicarbonate solution. The mixture was extracted with dichloromethane (3×30 mL). The combined organic layers were washed with saturated brine (50 mL), dried over anhydrous sodium sulfate, filtered and concentrated under reduced pressure to give compound C-1 (54.8 g, yield 93%) as a white solid. ESI[M+H]$^+$=186.1

2. Preparation of ethyl 4-amino-1H-pyrazole-5-carboxylate (C-2)

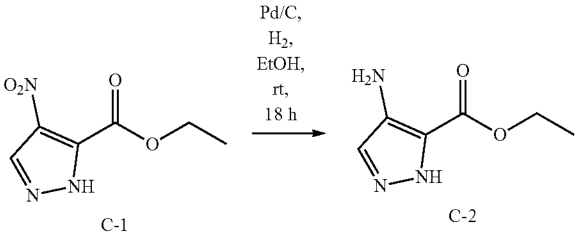

C-1

C-2

At room temperature, C-1 (54.8 g, 296 mmol) and 10% wet palladium carbon (5 g) were dissolved in ethanol (200 mL). The system was replaced three times with hydrogen, then the reaction mixture was allowed to react at room temperature for 18 hrs under hydrogen. The reaction was monitored by TLC until completion. The reaction mixture was filtered. The filter cake was washed with ethanol (3x30 mL). The filtrate was concentrated under reduced pressure. The crude product was purified by silica gel column chromatography (ethyl acetate/petroleum ether (v/v)=1/20~1/1), with TLC (ethyl acetate/petroleum ether (v/v)=1/2) monitoring, and collecting the fraction with Rf=0.4~0.5 to give compound C-2 (41.1 g, yield 89%) as a grey solid. ESI[M+H]$^+$=156.1

3. Preparation of ethyl 4-fluoro-1H-pyrazole-5-carboxylate (C-3)

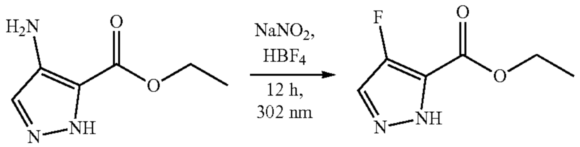

C-2 C-3

In an ice-salt bath, C-2 (35 g, 226 mmol) was dissolved in $HBF_4$ (40%) at −10° C., then the solution of $NaNO_2$ (16.4 g, 238 mmol) in the water (30 mL) was added into the mixture. The mixture was allowed to react under the irradiation of a mercury lamp (302 nm) for 12 hrs. The reaction was monitored by TLC until completion, then the reaction solution was adjusted pH to 7~8 with 1N NaOH solution in an ice-water bath. The mixture was extracted with ethyl acetate (3x50 mL). The combined organic layers were washed with saturated brine (50 mL), dried over anhydrous sodium sulfate, filtered and concentrated under reduced pressure. The crude product was purified by silica gel column chromatography (ethyl acetate/petroleum ether (v/v)= 1/20~1/5), with TLC (ethyl acetate/petroleum ether (v/v)=1/5) monitoring, and collecting the fraction with Rf=0.4~0.5 to give compound C-3 (6 g, yield 17%) as a grey solid compound.

4. Preparation of ethyl (R)-4-fluoro-1-(1-phenylethyl)-1H-pyrazole-5-carboxylate (C-4)

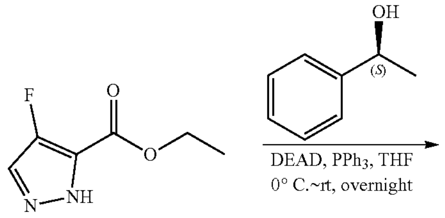

C-3

-continued

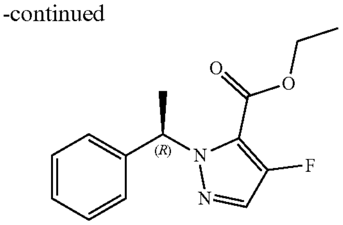

C-4

In an ice-water bath, (S)-1-phenylethan-1-ol (6.0 g, 49.1 mmol) was added into the mixture of C-3 (6 g, 37.9 mmol) and $PPh_3$ (14.9 g, 56.8 mmol) in THF (50 mL) at 0° C., then the solution of DEAD (9.9 g, 56.8 mmol) in THF (15 mL) was added dropwise into the mixture at the rate of 1.5 mmol/min After addition, the reaction mixture was warmed slowly to room temperature and stirred overnight. The reaction was monitored by TLC until completion. The reaction mixture was quenched with the saturated brine (30 mL) and extracted with ethyl acetate (3x15 mL). The combined organic layers were washed with saturated brine (30 mL), dried over anhydrous sodium sulfate, filtered and concentrated under reduced pressure to give the crude product. The crude product was purified by silica gel column chromatography (ethyl acetate/petroleum ether (v/v)=1/20~1/10), with TLC (ethyl acetate/petroleum ether (v/v)=1/2) monitoring, and collecting the fraction with Rf=0.5~0.6 to give the product C-4 (5.9 g, yield 59%). ESI[M+H]$^+$=263.1

$^1H$ NMR (400 MHz, $CDCl_3$) δ 7.44 (d, J=4.5 Hz, 1H), 7.35-7.20 (m, 5H), 6.46 (q, J=7.1 Hz, 1H), 4.53-4.09 (m, 2H), 1.88 (d, J=7.1 Hz, 3H), 1.34 (t, J=7.1 Hz, 3H).

5. Preparation of (R)-4-fluoro-1-(1-phenylethyl)-1H-pyrazole-5-carboxylic acid (C-5)

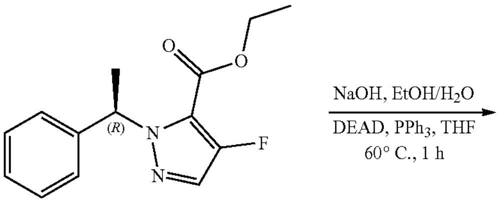

C-4

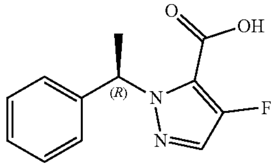

C-5

At room temperature, the solution of NaOH (3.1 g, 77.5 mmol) in water (12 mL) was added into the solution of C-4 (9.5 g, 38.9 mmol) in ethanol (12 mL), then the mixture was stirred at 60° C. for 1 hour. The reaction was monitored by TLC until completion. The reaction mixture was concentrated under reduced pressure. Water (20 mL) was poured into the residue. The mixture was adjusted pH to 4~5 with 1N HCl and extracted with dichloromethane (3x15 mL). The combined organic layers were dried over anhydrous sodium sulfate, filtered and concentrated to give the compound C-5 (6.7 g, yield 80%) as a white solid. ESI[M+H]$^+$=217.1

$^1$H NMR (400 MHz, $CDCl_3$) δ 7.62 (d, J=2.0 Hz, 1H), 7.39-7.16 (m, 5H), 7.00 (d, J=2.0 Hz, 1H), 6.56 (q, J=7.0 Hz, 1H), 1.93 (d, J=7.1 Hz, 3H).

6. Preparation of (R)-4-fluoro-N-methoxy-N-methyl-1-(1-phenylethyl)-1H-pyrazole-5-carboxamide (C-6)

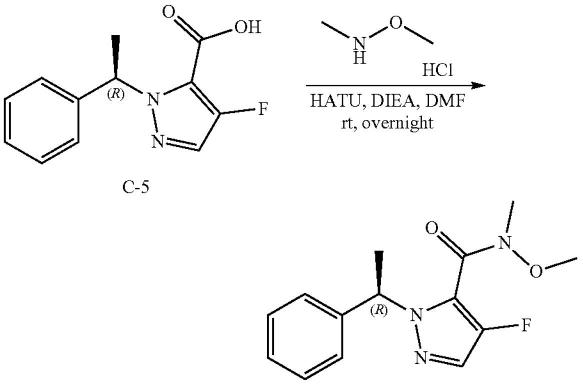

C-5

C-6

At room temperature, C-5 (2.0 g, 8.5 mmol), N, O-dimethylhydroxylamine hydrochloride (1.2 g, 12.3 mmol), DIEA (1.7 g, 13.2 mmol) and HATU (4.7 g, 12.4 mmol) were dissolved in DMF (30 mL), then the mixture was stirred at room temperature overnight. The reaction was monitored by TLC until completion. The mixture was quenched with water (100 mL) and extracted with ethyl acetate (3×30 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5-0.6 to give the title compound C-6 (1.8 g, yield 76%) as a white solid. ESI[M+H]$^+$=278.1

7. Preparation of (R)-1-(4-fluoro-1-(1-phenylethyl)-1H-pyrazol-5-yl)ethan-1-one (C-7)

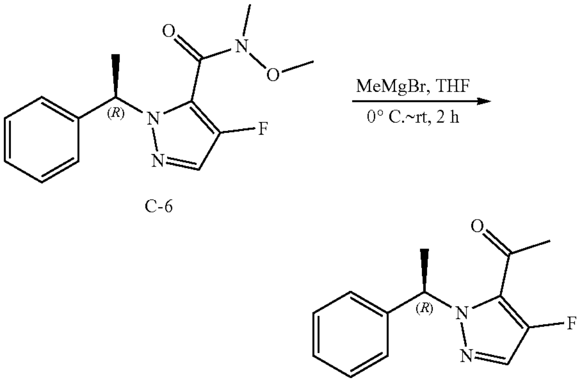

C-6

C-7

At room temperature, C-6 (1.8 g, 6.5 mmol) was dissolved in anhydrous THF (20 mL). The mixture was cooled to 0° C. with an ice-water bath. Methylmagnesium bromide (13 mL, 1 mol/L in THF, 13.0 mmol) was added dropwise into the mixture at the rate of 2 mmol/min, then the mixture was reacted at room temperature for 2 hrs. The reaction was monitored by TLC until completion. The mixture was cooled to 0° C. with an ice-water bath, quenched with saturated ammonium chloride solution (50 mL) and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give the title compound C-7 (1.2 g, yield 79%) as a white solid. ESI[M+H]$^+$=233.1

8. Preparation of (R)-2-bromo-1-(3-fluoro-1-(1-phenylethyl)-1H-pyrazol-5-yl) ethan-1-one (C-8)

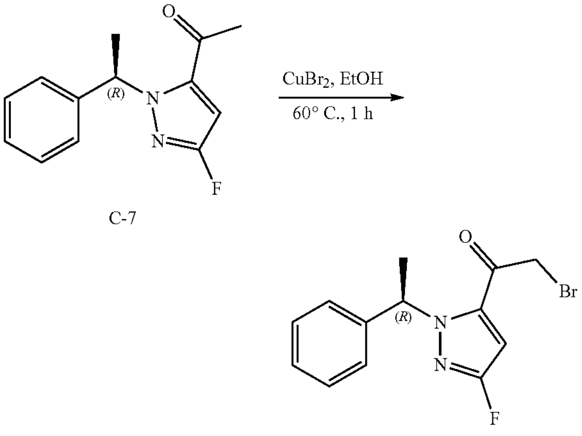

C-7

C-8

At room temperature, $CuBr_2$ (3.8 g, 17.0 mmol) was added into the solution of C-7 (2.0 g, 8.6 mmol) in ethanol (50 mL), then the mixture was stirred at 60° C. for 1 hour. The reaction was monitored by TLC until completion. The mixture was cooled to room temperature, quenched with water (50 mL) and extracted with ethyl acetate (3×10 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give the title compound C-8 (1.6 g, yield 60%) as a white solid. ESI[M+H]$^+$=311.0

9. Preparation of (R)-2-(ethylthio)-1-(3-fluoro-1-(1-phenylethyl)-1H-pyrazol-5-yl)ethan-1-one (C-9)

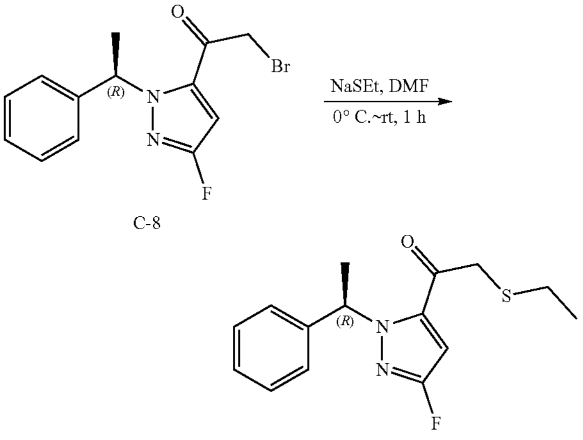

C-8

C-9

In an ice-water bath, NaSEt (405 mg, 4.82 mmol) was added into the solution of C-8 (1.5 g, 4.82 mmol) in DMF (20 mL) at 0° C., then the mixture was reacted at room temperature for 1 hour. The reaction was monitored by TLC until completion. The mixture was quenched with ice-water (10 mL) and extracted with ethyl acetate (3×5 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/10~1/3), with collecting the fraction with Rf=0.4~0.6 to give the title compound C-9 (723 mg, yield 51%). ESI$[M+H]^+$=293.0

10. Preparation of (R)-2,2-dichloro-2-(ethylthio)-1-(3-fluoro-1-(1-phenylethyl)-1H-pyrazol-5-yl)ethan-1-one (C-10)

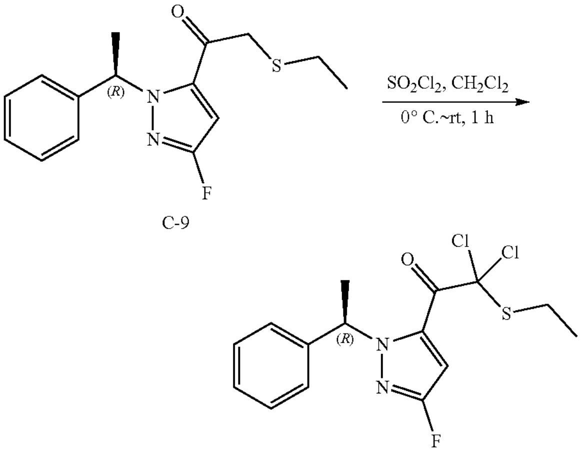

C-9

C-10

In an ice-water bath, $SO_2Cl_2$ (646 mg, 4.79 mmol) was added into the solution of C-9 (700 mg, 2.39 mmol) in dichloromethane (20 mL) at 0° C., then the mixture was stirred at room temperature for 1 hour. The reaction was monitored by TLC until completion. The reaction mixture was concentrated under reduced pressure to give the crude product C-10 (720 mg), which was used for next step directly without further purification.

11. Preparation of Compound D29

Method A

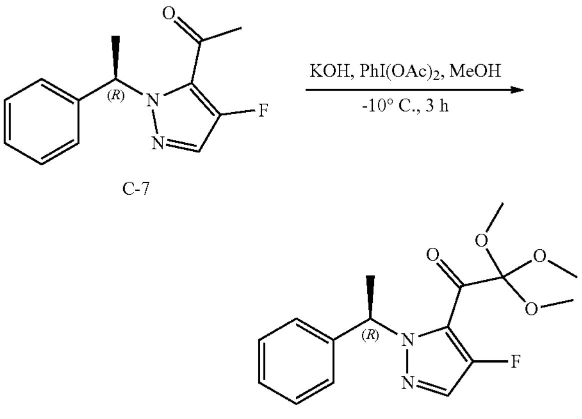

C-7

Compound D29

At room temperature, C-7 (500 mg, 2.15 mmol) and $PhI(OAc)_2$ (1.04 g, 3.23 mmol) were dissolved in methanol (20 mL), then the mixture was cooled to −10° C. with an ice-salt bath. KOH (1.45 g, 25.84 mmol) was added in portions into the mixture within 30 mins, then the reaction mixture was reacted at −10° C. for 3 hrs. The reaction was monitored by TLC until completion. The reaction mixture was quenched with saturated brine (100 mL) and extracted with ethyl acetate (3×20 mL). The combined organic layers were dried over anhydrous sodium sulfate, filtered, and concentrated under reduced pressure. The residue was purified by silica gel column chromatography (ethyl acetate/petroleum ether (v/v)=1/20~1/10), with TLC (ethyl acetate/petroleum ether (v/v)=1/8) monitoring, and collecting the fraction with Rf=0.5~0.6 to give title compound D29 (19 mg, yield 2.7%).

Method B

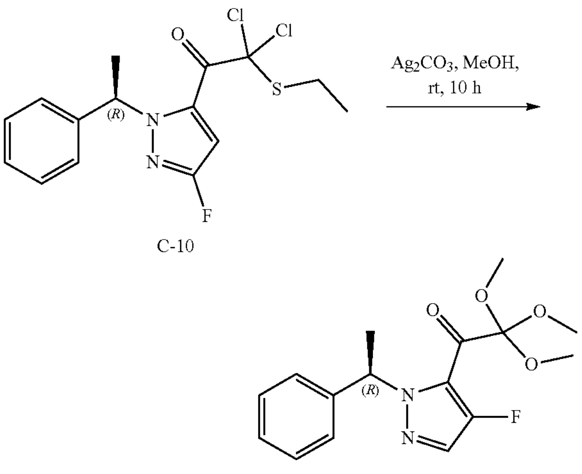

C-10

Compound D29

At room temperature, crude compound C-10 (100 mg, 0.28 mmol) and $Ag_2CO_3$ (115 mg, 0.42 mmol) were dissolved methanol (10 mL), then the mixture was stirred at room temperature for 10 hrs. The reaction was monitored by TLC until completion. The mixture was quenched with saturated sodium bicarbonate solution (10 mL) at 0° C. and extracted with ethyl acetate (3×5 mL). The combined organic layers were dried over anhydrous sodium sulfate, filtered and concentrated under reduced pressure. The residue was purified by Prep-TLC (ethyl acetate/petroleum ether (v/v)=1/5) and the fraction with Rf=0.5~0.6 was collected to give the title compound D29 (47 mg, yield 52%). ESI[M+H]$^+$=323.0

$^1$H NMR (400 MHz, $CDCl_3$) δ 7.48 (d, J=4.5 Hz, 1H), 7.35-7.20 (m, 5H), 6.34 (q, J=7.0 Hz, 1H), 3.92 (s, 3H), 3.49 (s, 6H), 1.89 (d, J=7.1 Hz, 3H).

12. Preparation of Compounds D30~D41

The title compounds D30~D36 were prepared according to the operation method of preparing compounds D2~D16 described in Example 2.

The title compounds D37~D39 were prepared according to the operation method of preparing compounds D13~D15 described in Example 4, using C-7 as the raw material.

The title compound D40 was prepared according to the operation method of preparing compound D28 described in Example 6, using C-7 as the raw material.

The title compound D41 was prepared according to the operation method of preparing compound D29, using ethyl 3,4-difluoro-1H-pyrazole-5-carboxylate as the raw material.

Compound D30: 38 mg, ESI[M+H]$^+$=321.0

$^1$H NMR (400 MHz, $CDCl_3$) δ 7.46 (d, J=4.5 Hz, 1H), 7.34-7.21 (m, 5H), 6.33 (q, J=7.0 Hz, 1H), 4.07-3.78 (m, 4H), 3.26 (s, 3H), 1.86 (d, J=7.0 Hz, 3H).

Compound D31: 26 mg, ESI[M+H]$^+$=361.0

$^1$H NMR (400 MHz, $CDCl_3$) δ 7.45 (d, J=4.5 Hz, 1H), 7.35-7.21 (m, 5H), 6.32 (q, J=7.0 Hz, 1H), 4.22-4.16 (m, 1.5H), 3.94 (s, 2H), 3.47 (m, 3H), 3.28-3.08 (m, 1.5H), 2.02-1.82 (m, 6H).

Compound D32: 17 mg, ESI[M+H]$^+$=359.0

$^1$H NMR (400 MHz, $CDCl_3$) δ 7.45 (d, J=4.5 Hz, 1H), 7.35-7.20 (m, 5H), 6.33 (q, J=7.0 Hz, 1H), 4.08-3.78 (m, 6H), 2.02-1.82 (m, 6H).

Compound D33: 25 mg, ESI[M+H]$^+$=379.1

$^1$H NMR (400 MHz, $CDCl_3$) δ 7.47 (d, J=4.5 Hz, 1H), 7.37-7.20 (m, 5H), 6.34 (q, J=7.0 Hz, 1H), 4.03 (s, 1.5H), 3.95 (s, 1H), 3.53 (s, 4.5H), 3.32 (s, 1H), 1.88 (d, J=7.0 Hz, 3H), 1.04 (s, 5.5H), 0.96 (s, 3.5H).

Compound D34: 27 mg, ESI[M+H]$^+$=377.1

$^1$H NMR (400 MHz, $CDCl_3$) δ 7.44 (d, J=4.5 Hz, 1H), 7.35-7.22 (m, 5H), 6.34 (q, J=7.0 Hz, 1H), 4.05-3.78 (m, 5H), 3.31 (s, 1H), 1.89 (d, J=7.0 Hz, 3H), 1.03 (s, 5.5H), 0.95 (s, 3.5H).

Compound D35: 31 mg, ESI[M+H]$^+$=351.0

$^1$H NMR (400 MHz, $CDCl_3$) δ 7.49 (d, J=4.5 Hz, 1H), 7.34-7.20 (m, 5H), 6.32 (q, J=7.0 Hz, 1H), 4.45-4.40 (m, 2H), 3.94 (s, 1H), 3.78-3.72 (m, 1.5H), 3.53 (s, 2.5H), 1.86 (d, J=7.0 Hz, 3H), 1.46-1.41 (m, 3H), 1.28-1.24 (m, 3H).

Compound D36: 14 mg, ESI[M+H]$^+$=365.1

$^1$H NMR (400 MHz, $CDCl_3$) δ 7.47 (d, J=4.5 Hz, 1H), 7.36-7.20 (m, 5H), 6.33 (q, J=7.0 Hz, 1H), 4.43-4.40 (m, 1H), 3.92 (s, 1H), 3.73-3.70 (m, 1.5H), 3.52 (s, 2.5H), 1.86 (d, J=7.0 Hz, 3H), 1.45-1.40 (m, 4.5H), 1.28-1.22 (m, 4.5H).

Compound D37: 23 mg, ESI[M+H]$^+$=293.0

$^1$H NMR (400 MHz, $CDCl_3$) δ 7.48 (d, J=4.5 Hz, 1H), 7.35-7.20 (m, 5H), 6.34 (q, J=7.0 Hz, 1H), 4.87 (s, 1H), 3.37 (s, 3H), 3.33 (s, 3H), 1.85 (d, J=7.0 Hz, 3H).

Compound D38: 24 mg, ESI[M+H]$^+$=321.1

$^1$H NMR (400 MHz, $CDCl_3$) δ 7.49 (d, J=4.5 Hz, 1H), 7.36-7.20 (m, 5H), 6.35 (q, J=7.0 Hz, 1H), 5.01 (s, 1H), 3.72-3.61 (m, 4H), 1.87 (d, J=7.0 Hz, 3H), 1.21-1.15 (m, 6H).

Compound D39: 26 mg, ESI[M+H]$^+$=353.0

$^1$H NMR (400 MHz, $CDCl_3$) δ 7.44 (d, J=4.5 Hz, 1H), 7.35-7.23 (m, 5H), 6.31 (q, J=7.0 Hz, 1H), 5.12 (s, 1H), 2.79-2.56 (m, 4H), 1.86 (d, J=7.0 Hz, 3H), 1.25-1.14 (m, 6H).

Compound D40: 16 mg, ESI[M+H]$^+$=457.2

$^1$H NMR (400 MHz, $CDCl_3$) δ 7.47 (d, J=4.5 Hz, 1H), 7.36-7.20 (m, 5H), 6.32 (q, J=7.0 Hz, 1H), 5.51 (s, 1H), 1.84 (d, J=7.0 Hz, 3H).

Compound D41: 11 mg, ESI[M+H]$^+$=341.0

$^1$H NMR (400 MHz, $CDCl_3$) δ 7.35-7.20 (m, 5H), 6.24 (q, J=7.0 Hz, 1H), 3.82 (s, 3H), 3.39 (s, 6H), 1.81 (d, J=7.1 Hz, 3H).

Example 8 Preparation of Compounds D42~D52

Preparation Route of Target Compound D42

Method A

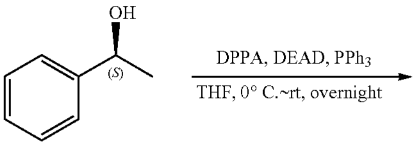

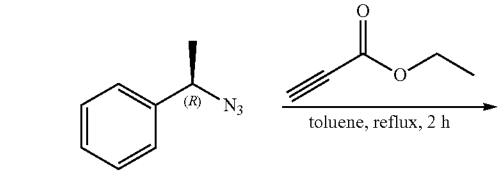

D-1

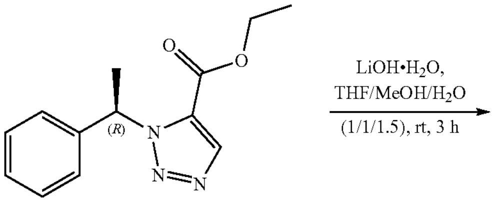

D-2

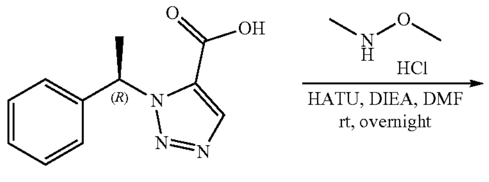

D-3

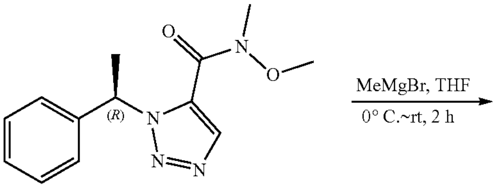

D-4

-continued
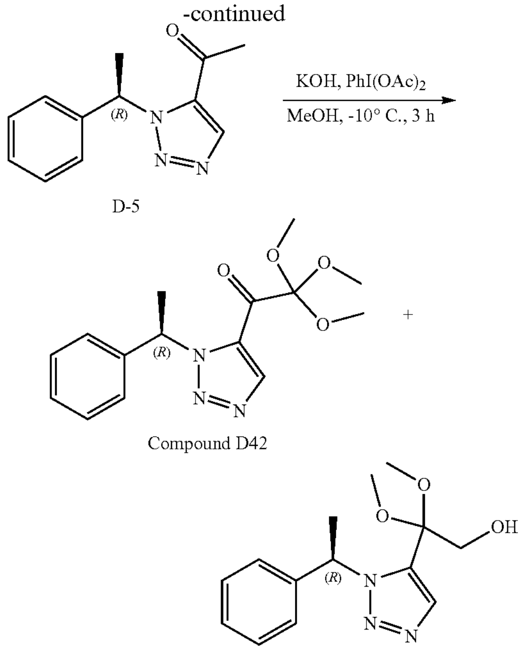
D-5
Compound D42
D-6
Method B
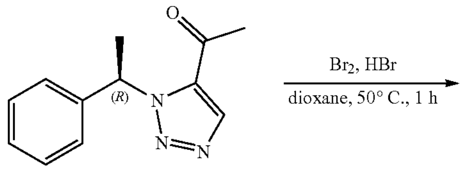
D-5
-continued
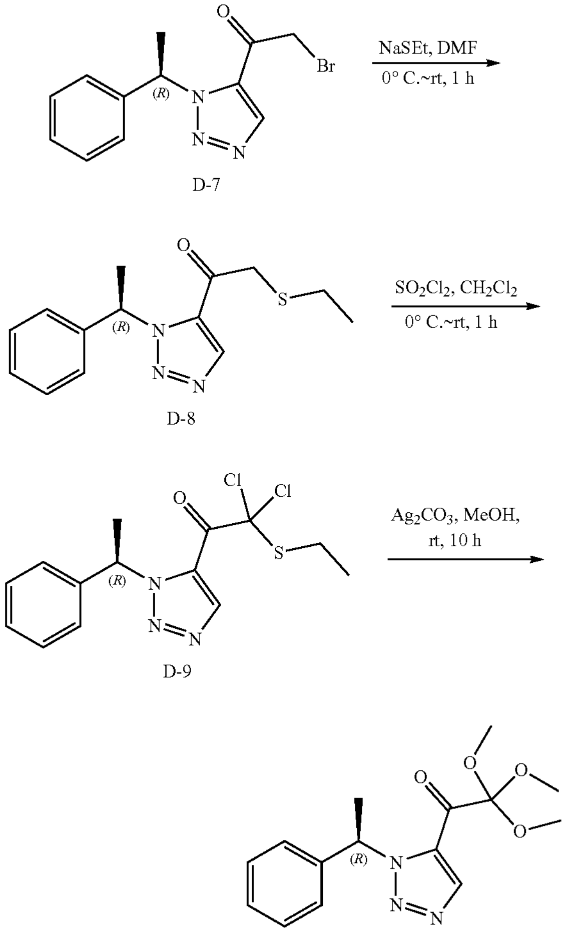
D-7
D-8
D-9
Compound D42
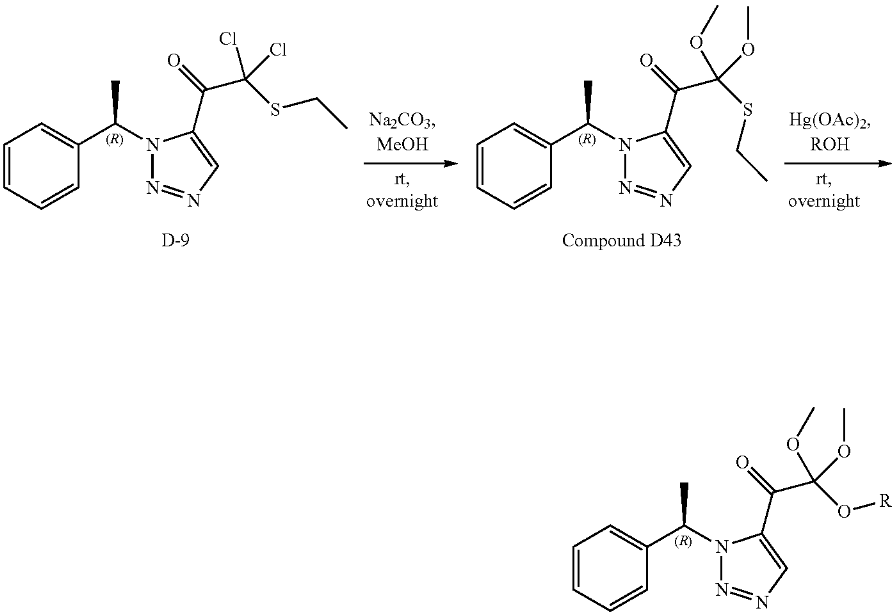
D-9
Compound D43
Compound D44~D48

-continued
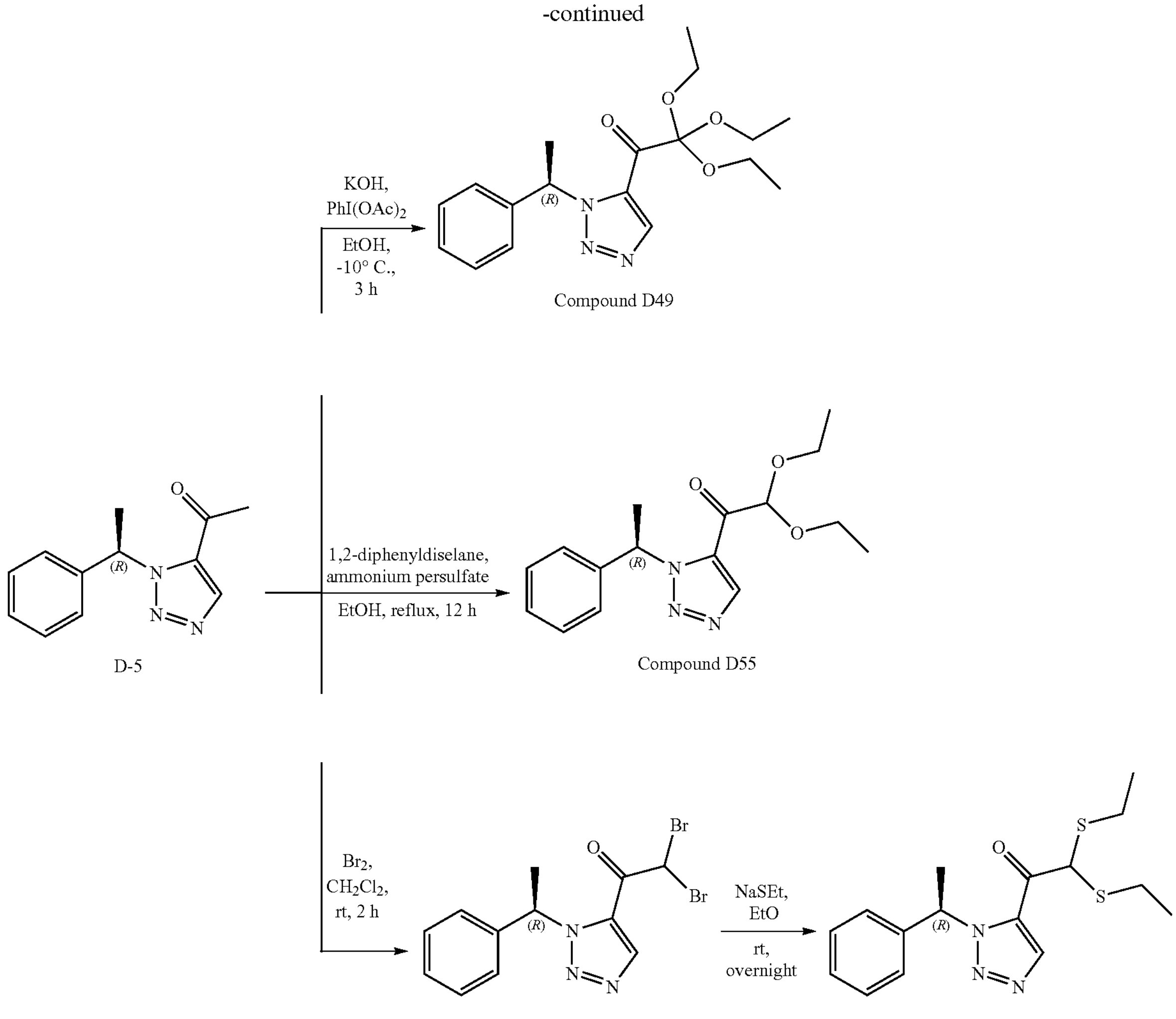
D-5
Compound D49
Compound D55
15-1
Compound D51
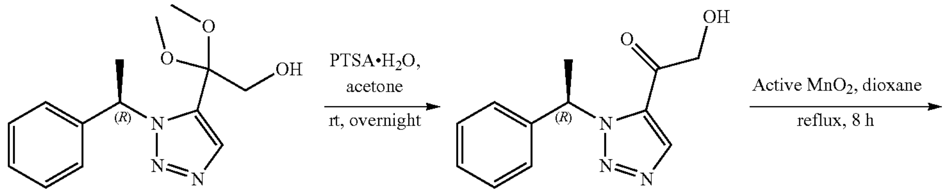
D-6
52-1
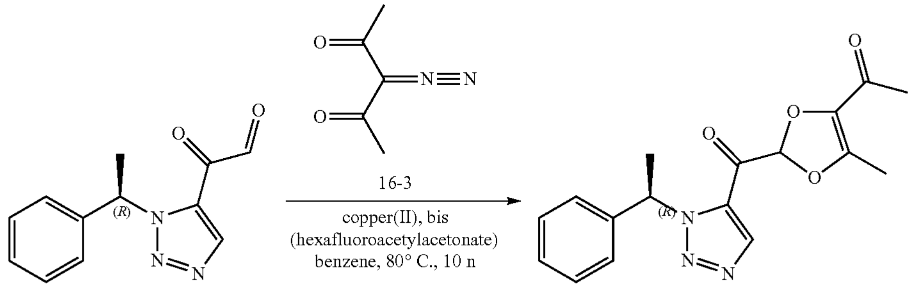
16-3
52-2
Compound D52

1. Preparation of (R)-(1-azidoethyl)benzene (D-1)

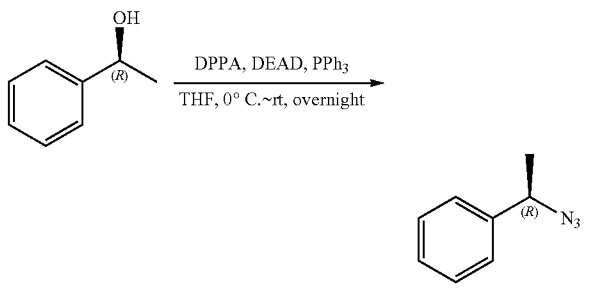

D-1

In an ice-water bath, (S)-1-phenylethan-1-ol (20 g, 164 mmol) and $PPh_3$ (85.9 g, 328 mmol) was dissolved in THF (300 mL) at 0° C., then the solution of DEAD (57.1 g, 328 mmol) in THF (50 ml) was added dropwise into the reaction mixture at the rate of 10 mmol/min, and then DPPA (54.1 g, 197 mmol) was added dropwise into the mixture at the rate of 6 mmol/min. After addition, the reaction mixture was warmed slowly to room temperature and stirred overnight. The reaction was monitored by TLC until completion. The reaction mixture was quenched with the saturated brine (150 mL) and extracted with hexane (3×50 mL). The combined organic layers were washed with saturated brine (50 mL), dried over anhydrous sodium sulfate, filtered and concentrated under reduced pressure to give crude product. The residue was purified by silica gel column chromatography (ethyl acetate/petroleum ether (v/v)=1/100~1/50), with TLC (ethyl acetate/petroleum ether (v/v)=1/10) monitoring, and collecting the fraction with Rf=0.5~0.6 to give the product D-1 (20 g, yield 83%).

2. Preparation of ethyl (R)-1-(1-phenylethyl)-1H-1,2,3-triazole-5-carboxylate (D-2)

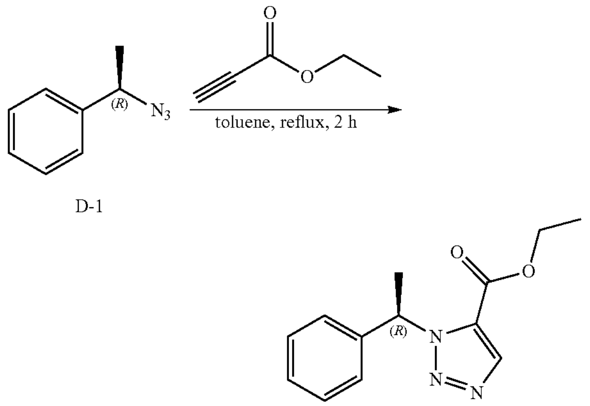

D-1

D-2

At room temperature, D-1 (4.8 g, 32.6 mmol) and ethyl propiolate (6.4 g, 65.2 mmol) were dissolved in toluene (100 mL), then the mixture was heated to reflux for 2 hrs. The reaction was monitored by TLC until completion. The reaction mixture was quenched with saturated brine (30 mL) and extracted with ethyl acetate (3×50 mL). The combined organic layers were washed with saturated brine (50 mL), dried over anhydrous sodium sulfate, filtered, and concentrated under reduced pressure. The residue was purified by silica gel column chromatography (ethyl acetate/petroleum ether (v/v)=1/10~1/1), with TLC (ethyl acetate/petroleum ether (v/v)=1/5) monitoring, and collecting the fraction with Rf=0.5~0.6 to give title compound D-2 (1.3 g, yield 16%). ESI$[M+H]^+$=246.3

$^1H$ NMR (400 MHz, $CDCl_3$) δ 8.17 (s, 1H), 7.42-7.29 (m, 5H), 6.58 (q, J=7.1 Hz, 1H), 4.45-4.26 (m, 2H), 2.08 (d, J=7.1 Hz, 3H), 1.37 (t, J=7.1 Hz, 3H).

3. Preparation of (R)-1-(1-phenylethyl)-1H-1,2,3-triazole-5-carboxylic acid (D-3)

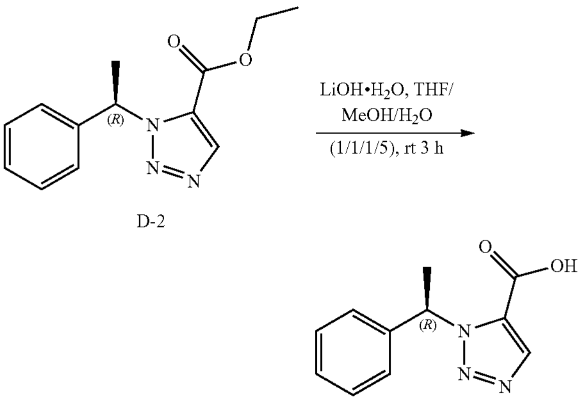

D-2

D-3

At room temperature, $LiOH·H_2O$ (220 mg, 5.24 mmol) was added into the solution of D-2 (643 mg, 2.62 mmol) in $MeOH/THF/H_2O$ (3.5 mL, v/v/v=1/1/1.5), then the mixture was stirred at room temperature overnight. The reaction was monitored by TLC until completion. The reaction mixture was concentrated under reduced pressure. Water (10 mL) was poured into the residue. The mixture was adjusted pH to 4~5 with 1N HCl and extracted with dichloromethane (3×15 mL). The combined organic layers were dried over anhydrous sodium sulfate, filtered and concentrated to give the compound D-3 (545 mg, yield 96%) as a white solid. $[M+H]^+$=218.2

$^1H$ NMR (400 MHz, $CDCl_3$) δ 8.25 (s, 1H), 7.38-7.30 (m, 5H), 6.58-6.52 (m, 1H), 2.10 (d, J=7.0 Hz, 3H).

4. Preparation of (R)—N-methoxy-N-methyl-1-(1-phenylethyl)-1H-1,2,3-triazole-5-carboxamide (D-4)

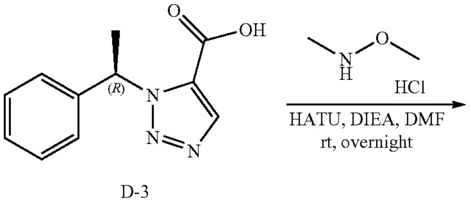

D-3

-continued

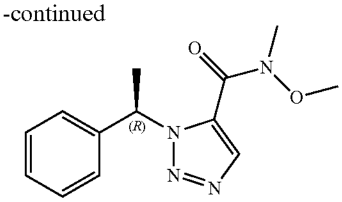

D-4

At room temperature, D-3 (4.0 g, 18.4 mmol), N, O-dimethylhydroxylamine hydrochloride (2.7 g, 27.7 mmol), DIEA (3.6 g, 27.9 mmol) and HATU (10.5 g, 27.6 mmol) were dissolved in DMF (80 mL), then the mixture was stirred at room temperature overnight. The reaction was monitored by TLC until completion. The mixture was quenched with water (100 mL) and extracted with ethyl acetate (3x30 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5-0.6 to give the title compound D-4 (3.8 g, yield 79%) as a white solid. ESI[M+H]$^+$=261.1

5. Preparation of (R)-1-(1-(1-phenylethyl)-1H-1,2,3-triazol-5-yl)ethan-1-one (D-5)

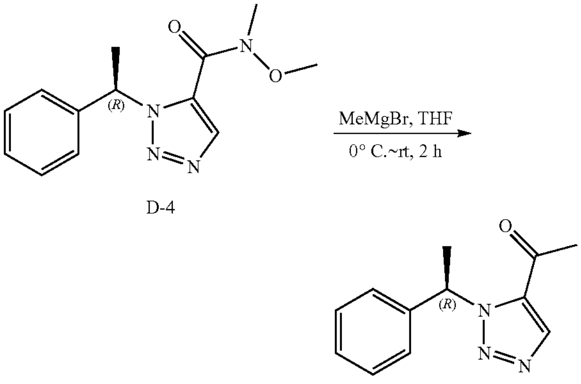

D-4

D-5

At room temperature, D-4 (3.7 g, 14.2 mmol) was dissolved in anhydrous THF (50 mL). The mixture was cooled to 0° C. with ice-water bath. Methylmagnesium bromide (28 mL, 1 mol/L in THF, 28.0 mmol) was added dropwise into the mixture at the rate of 1.5 mmol/min, then the mixture was reacted at room temperature for 2 hrs. The reaction was monitored by TLC until completion. The mixture was cooled to 0° C. with an ice-water bath, quenched with saturated ammonium chloride solution (100 mL) and extracted with ethyl acetate (3x20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give the title compound D-5 (2.3 g, yield 75%) as a white solid. ESI[M+H]$^+$=216.1

6. Preparation of (R)-2-bromo-1-(1-(1-phenylethyl)-1H-1,2,3-triazol-5-yl)ethan-1-one (D-7)

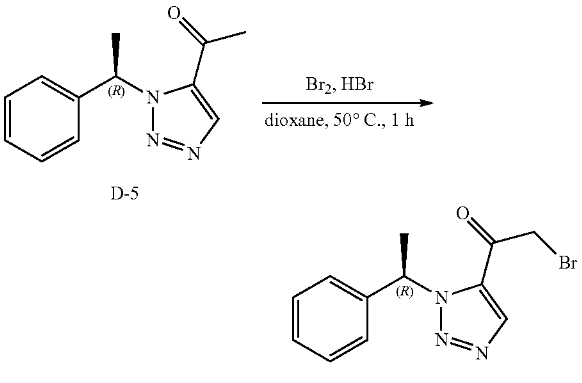

D-5

D-7

At room temperature, $Br_2$ (2.2 g, 13.8 mmol) was added into the mixture of D-5 (2.0 g, 9.3 mmol) and hydrobromic acid solution (5 mL, 40%) in dioxane (20 mL), then the mixture was stirred at 50° C. for 1 hour. The reaction was monitored by TLC until completion. The reaction mixture was cooled to room temperature, quenched with ice-water (30 mL) and saturated sodium bicarbonate solution (10 mL), extracted with ethyl acetate (3x10 mL). The combined organic layers washed with saturated brine (10 mL), dried over anhydrous sodium sulfate, filtered and concentrated under reduced pressure to give the crude compound D-7, which was used for next step directly without further purification.

7. Preparation of (R)-2-(ethylthio)-1-(1-(1-phenylethyl)-1H-1,2,3-triazol-5-yl)ethan-1-one (D-8)

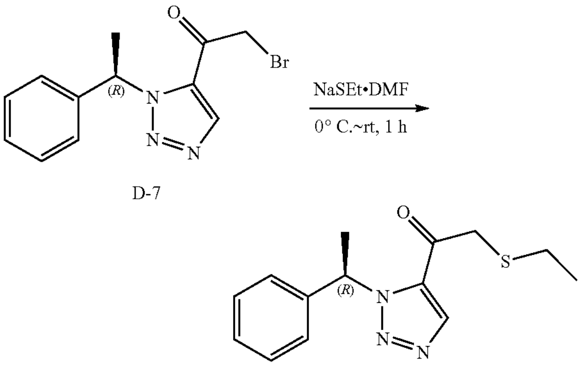

D-7

D-8

In an ice-water bath, NaSEt (942 mg, 11.2 mmol) was added into the solution of the crude compound D-7 (calculated according to the theoretical amount of 9.3 mmol) in DMF (20 mL) at 0° C., then the mixture was reacted at room temperature for 1 hour. The reaction was monitored by TLC until completion. The mixture was quenched with ice-water (10 mL) and extracted with ethyl acetate (3x5 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/10~1/3), with collecting the fraction with Rf=0.4~0.6 to give the compound D-8 (478 mg, yield 19% for 2 steps). ESI[M+H]$^+$=276.0

-continued

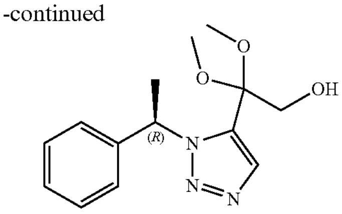

D-6

At room temperature, D-5 (200 mg, 0.93 mmol) and $PhI(OAc)_2$ (359 mg, 1.11 mmol) were dissolved in methanol (5 mL), then the mixture was cooled to −10° C. with an ice-salt bath. KOH (626 mg, 11.2 mmol) was added in portions into the mixture within 5 mins, then the reaction mixture was reacted at −10° C. for 3 hrs. The reaction was monitored by TLC until completion. The reaction mixture was quenched with saturated brine (10 mL) and extracted with ethyl acetate (3x5 mL). The combined organic layers were dried over anhydrous sodium sulfate, filtered, and concentrated under reduced pressure. The residue was purified by silica gel column chromatography (ethyl acetate/petroleum ether (v/v)=1/20~1/10), with TLC (ethyl acetate/petroleum ether (v/v)=1/8) monitoring, and collecting the fraction with Rf=0.5~0.6 to give title compound D42 (7.3 mg, yield 2.6%).

8. Preparation of (R)-2,2-dichloro-2-(ethylthio)-1-(1-(1-phenylethyl)-1H-1,2,3-triazol-5-yl)ethan-1-one (D-9

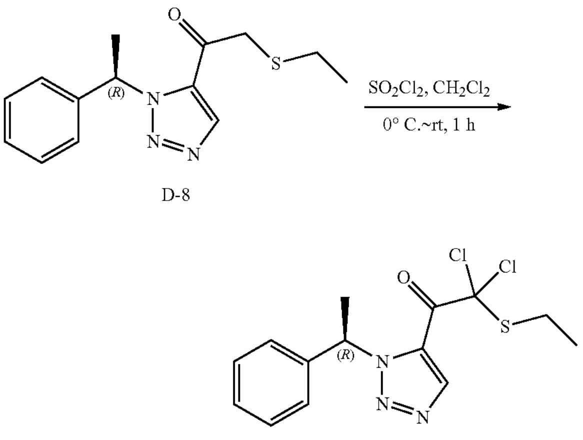

D-8

D-9

In an ice-water bath, $SO_2Cl_2$ (393 mg, 2.91 mmol) was added into the solution of D-8 (400 mg, 1.45 mmol) in dichloromethane (10 mL) at 0° C., then the mixture was stirred at room temperature for 1 hour. The reaction was monitored by TLC until completion. The reaction mixture was concentrated under reduced pressure to give the crude product D-9 (439 mg), which was used for next step directly without further purification.

9. Preparation of Compound D42

Method A

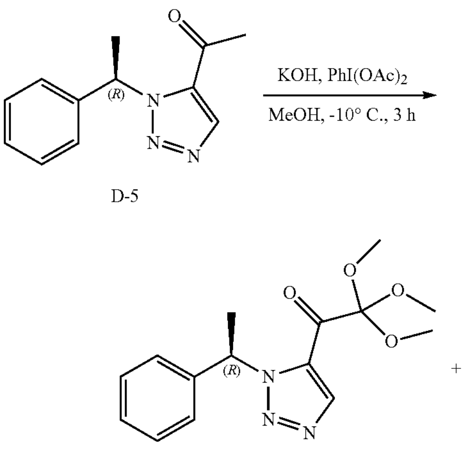

D-5

Compound D42

+

Method B

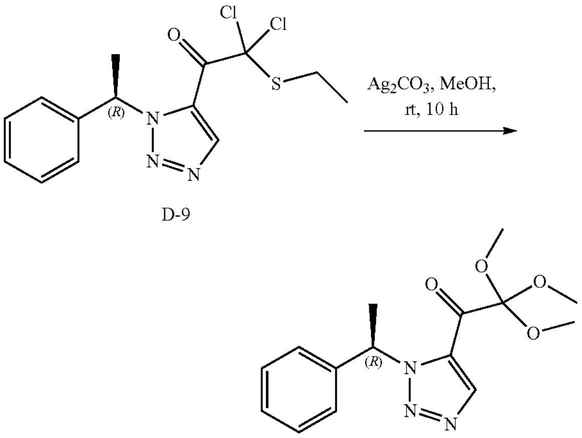

D-9

Compound D42

At room temperature, D-9 (150 mg, 0.44 mmol) and $Ag_2CO_3$ (179 mg, 0.65 mmol) were dissolved methanol (5 mL), then the mixture was stirred at room temperature for 10 hrs. The reaction was monitored by TLC until completion. In an ice-water bath, the mixture was quenched with saturated sodium bicarbonate solution (10 mL) at 0° C. and extracted with ethyl acetate (3x5 mL). The combined organic layers were dried over anhydrous sodium sulfate, filtered and concentrated under reduced pressure. The residue was purified by Prep-TLC (ethyl acetate/petroleum ether (v/v)=1/5) and the fraction with Rf=0.5~0.6 was collected to give the title compound D42 (28 mg, yield 21%). ESI[M+H]$^+$=306.0

$^1H$ NMR (400 MHz, $CDCl_3$) δ 8.68 (s, 0.61H), 8.51 (s, 0.39H), 7.35-7.28 (m, 3H), 7.26-7.18 (m, 2H), 6.55-6.46 (m, 1H), 3.95 (s, 2H), 3.49 (s, 3.5H), 3.13 (s, 3.5H), 2.13-2.03 (m, 3H).

10. Preparation of Compounds D43~D52
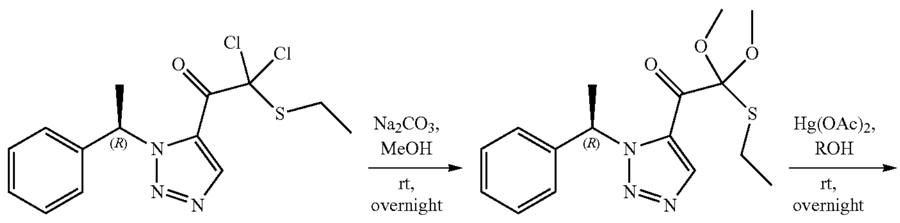
D-9
Compound D43
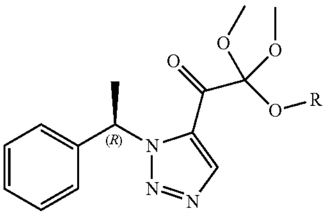
Compound D44~D48
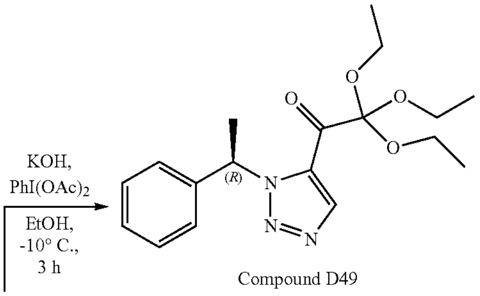
Compound D49
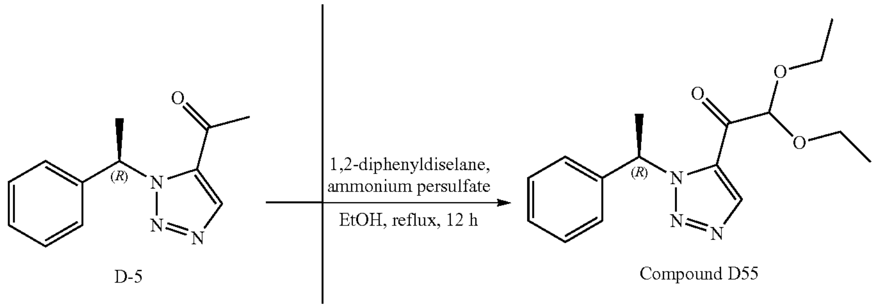
D-5
Compound D55
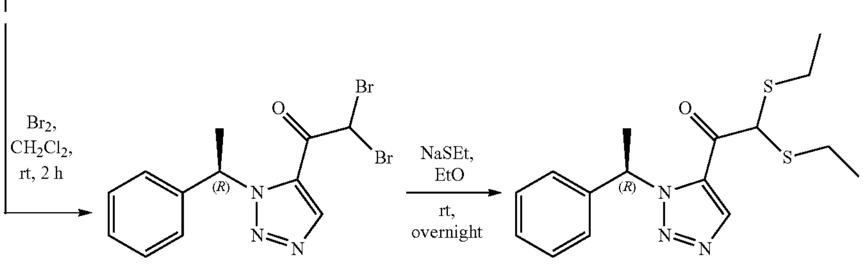
15-1
Compound D51
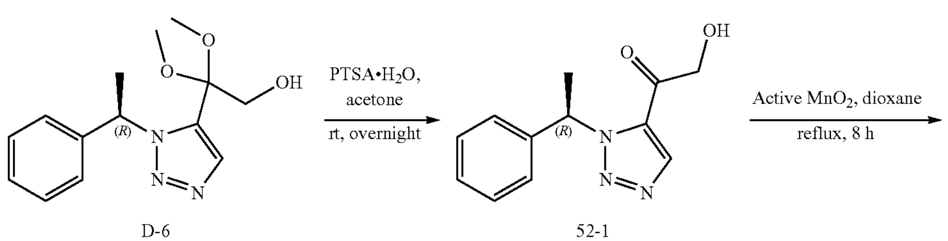
D-6
52-1

-continued

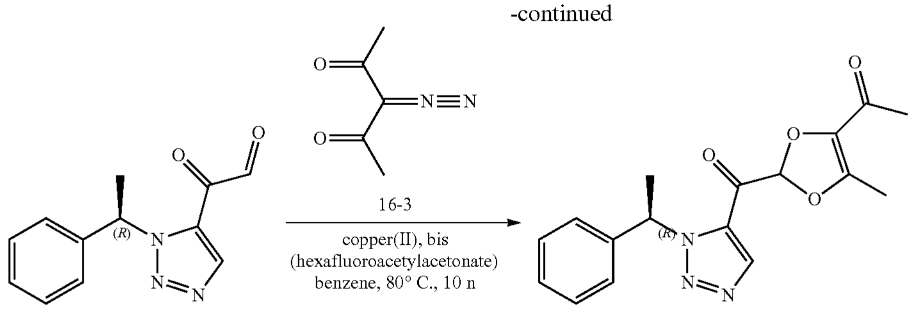

52-2

Compound D52

The title compounds D43~D49 were prepared according to the operation method of preparing compounds D2~D10 described in Example 2, and the title compounds D50~D52 were prepared according to the operation method of preparing compounds D14~D16 described in Example 4.

Compound D43: 18 mg, ESI[M+H]$^+$=336.0

$^1$H NMR (400 MHz, $CDCl_3$) δ 8.69 (s, 0.61H), 8.52 (s, 0.39H), 7.34-7.29 (m, 3H), 7.27-7.18 (m, 2H), 6.55-6.46 (m, 1H), 3.35 (s, 3H), 3.24 (s, 3H), 2.31-2.17 (m, 1H), 2.14-2.01 (m, 4H), 0.99 (t, J=7.5 Hz, 3H).

Compound D44: 32 mg, ESI[M+H]$^+$=320.1

$^1$H NMR (400 MHz, $CDCl_3$) δ 8.68 (s, 0.61H), 8.51 (s, 0.39H), 7.37-7.28 (m, 3H), 7.27-7.18 (m, 2H), 6.56-6.46 (m, 1H), 4.43-4.40 (m, 2H), 3.94 (s, 1H), 3.78-3.71 (m, 1.5H), 3.53 (s, 3.5H), 2.13-2.03 (m, 3H), 1.44 (t, J=7.1 Hz, 1.5H), 1.27 (t, J=7.0 Hz, 1.5H).

Compound D45: 22 mg, ESI[M+H]$^+$=334.1

$^1$H NMR (400 MHz, $CDCl_3$) δ 8.66 (s, 0.61H), 8.50 (s, 0.39H), 7.35-7.28 (m, 3H), 7.26-7.18 (m, 2H), 6.55-6.46 (m, 1H), 5.35-5.30 (m, 1H), 3.95 (s, 1H), 3.52 (s, 5H), 2.13-2.03 (m, 3H), 1.55 (d, J=6.5 Hz, 1H), 1.46-1.40 (m, 3H), 1.25 (t, J=10.2 Hz, 2H).

Compound D46: 16 mg, ESI[M+H]$^+$=362.1

$^1$H NMR (400 MHz, $CDCl_3$) δ 8.67 (s, 0.61H), 8.51 (s, 0.39H), 7.36-7.26 (m, 3H), 7.25-7.18 (m, 2H), 6.55-6.45 (m, 1H), 4.05 (s, 1.5H), 3.95 (s, 1H), 3.52 (s, 4.5H), 3.32 (s, 1H), 2.13-2.03 (m, 3H), 1.02 (s, 5.5H), 0.94 (s, 3.5H).

Compound D47: 19 mg, ESI[M+H]$^+$=332.1

$^1$H NMR (400 MHz, $CDCl_3$) δ 8.65 (s, 0.61H), 8.49 (s, 0.39H), 7.35-7.28 (m, 3H), 7.26-7.18 (m, 2H), 6.56-6.46 (m, 1H), 6.17-5.89 (m, 1H), 5.53-4.83 (m, 2H), 4.23-4.18 (m, 1.5H), 3.94 (s, 1.5H), 3.44 (m, 3H), 3.24-3.09 (m, 2H), 2.13-2.03 (m, 3H).

Compound D48: 35 mg, ESI[M+H]$^+$=344.1

$^1$H NMR (400 MHz, $CDCl_3$) δ 8.67 (s, 0.61H), 8.51 (s, 0.39H), 7.38-7.29 (m, 3H), 7.26-7.19 (m, 2H), 6.55-6.46 (m, 1H), 4.24-4.18 (m, 1.5H), 3.95 (s, 2H), 3.49 (s, 3H), 3.28-3.08 (m, 1.5H), 2.05-1.82 (m, 6H).

Compound D49: 33 mg, ESI[M+H]$^+$=348.1

$^1$H NMR (400 MHz, $CDCl_3$) δ 8.63 (s, 0.61H), 8.50 (s, 0.39H), 7.35-7.28 (m, 3H), 7.24-7.18 (m, 2H), 6.55-6.46 (m, 1H), 4.44-4.40 (m, 1H), 3.95 (s, 1H), 3.75-3.70 (m, 1.5H), 3.54 (s, 2.5H), 2.15-2.05 (m, 3H), 1.43-1.41 (m, 4.5H), 1.27-1.22 (m, 4.5H).

Compound D50: 24 mg, ESI[M+H]$^+$=304.1

$^1$H NMR (400 MHz, $CDCl_3$) δ 8.64 (s, 0.61H), 8.52 (s, 0.39H), 7.37-7.28 (m, 3H), 7.24-7.18 (m, 2H), 6.57-6.46 (m, 1H), 5.12 (s, 1H), 3.74-3.46 (m, 4H), 2.13-2.03 (m, 3H), 1.23 (t, J=6.9 Hz, 6H).

Compound D51: 17 mg, ESI[M+H]$^+$=336.0

$^1$H NMR (400 MHz, $CDCl_3$) δ 8.68 (s, 0.61H), 8.52 (s, 0.39H), 7.35-7.27 (m, 3H), 7.24-7.18 (m, 2H), 6.55-6.47 (m, 1H), 5.23 (s, 1H), 2.78-2.39 (m, 4H), 2.14-2.03 (m, 3H), 1.27 (t, J=7.0 Hz, 6H).

Compound D52: 20 mg, ESI[M+H]$^+$=328.2

$^1$H NMR (400 MHz, $CDCl_3$) δ 8.66 (s, 0.61H), 8.50 (s, 0.39H), 7.35-7.28 (m, 3H), 7.26-7.18 (m, 2H), 6.70 (s, 1H), 6.57-6.49 (m, 1H), 2.25 (s, 6H), 2.13-2.03 (m, 3H).

Example 9 Preparation of Compounds D53~D62

Preparation Route of Target Compound D53

Method A

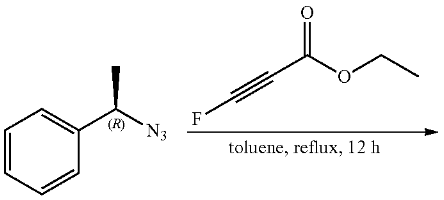

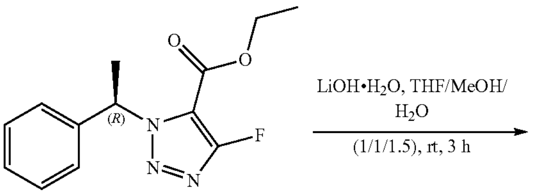

E-1

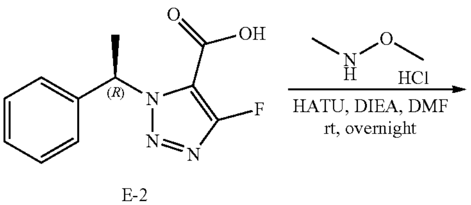

E-2

-continued
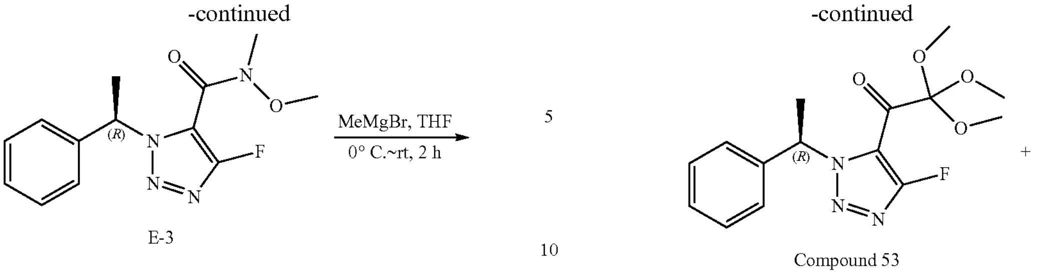
E-3
Compound 53
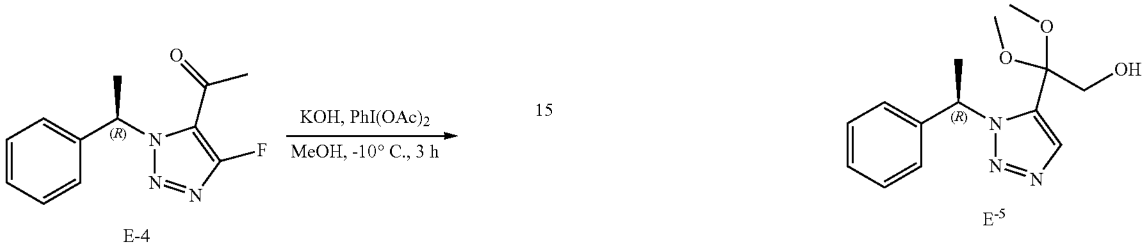
E-4
E-5
Method B
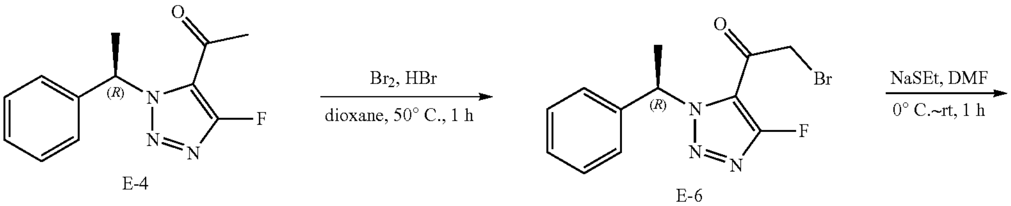
E-4
E-6
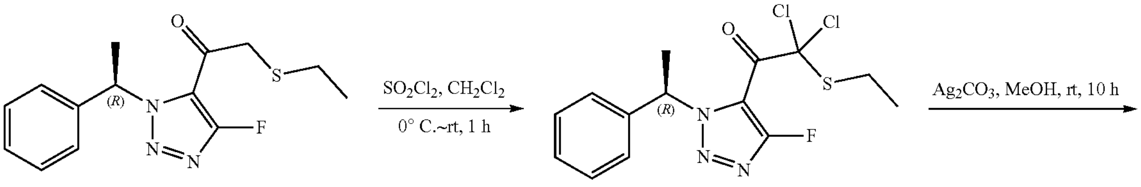
E-7
E-8
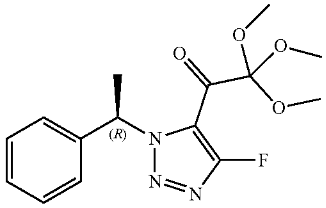
Compound 53
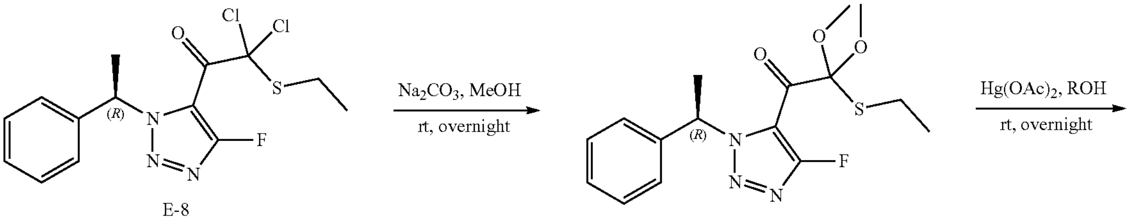
E-8
Compound D54
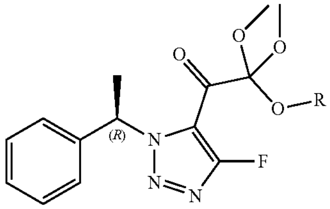
Compound D55~D59

-continued
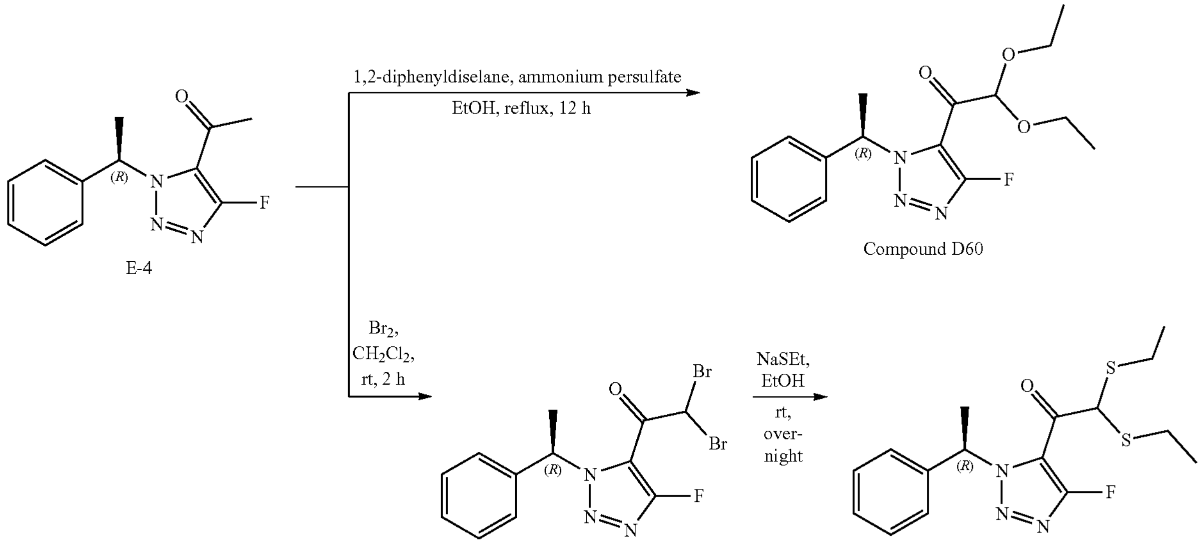
E-4
Compound D60
61-1
Compound D61
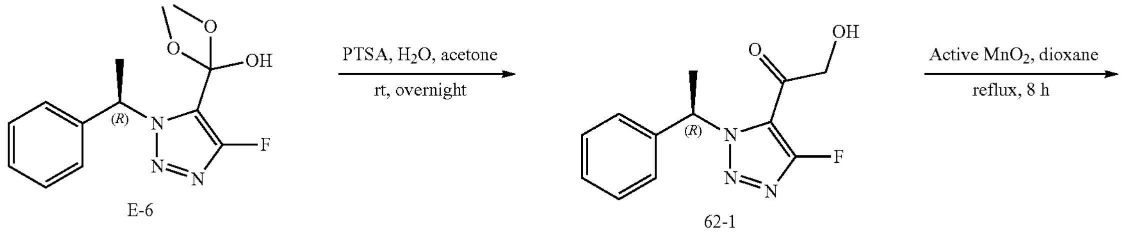
E-6
62-1
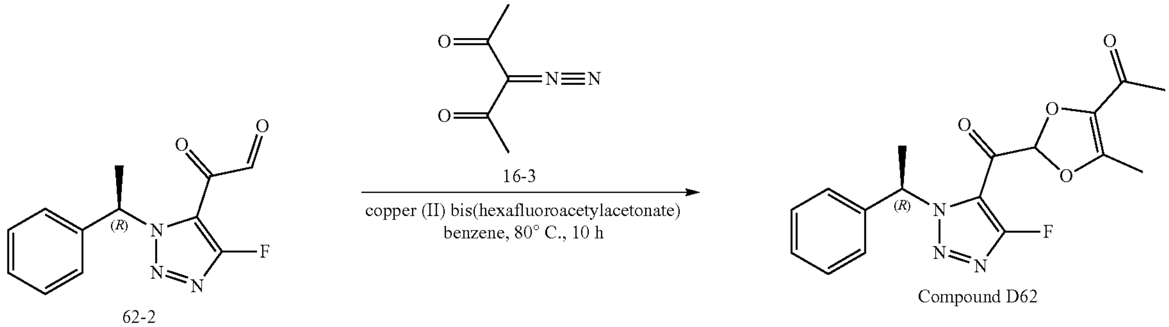
16-3
62-2
Compound D62

1. Preparation of ethyl (R)-4-fluoro-1-(1-phenylethyl)-1H-1,2,3-triazole-5-carboxylate (E-1)

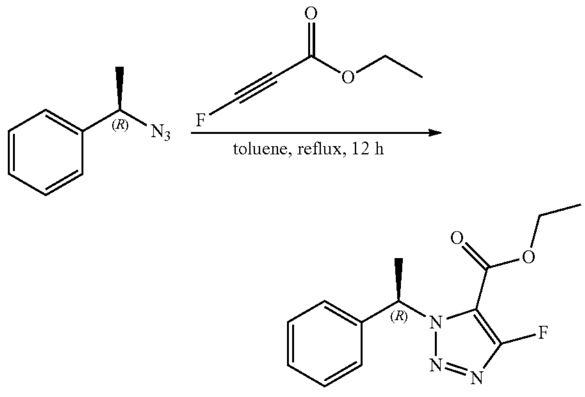

E-1

At room temperature, (R)-(1-azidoethyl) benzene (5.1 g, 34.7 mmol) and ethyl 3-fluoropropiolate (8.1 g, 69.8 mmol) were dissolved in toluene (50 mL), and then the mixture was heated to reflux for 12 hrs. The reaction was monitored by TLC until completion. The reaction mixture was concentrated under reduced pressure. The residue was purified by silica gel column chromatography (ethyl acetate/petroleum ether (v/v)=1/10~1/1), with TLC (ethyl acetate/petroleum ether (v/v)=1/5) monitoring, and collecting the fraction with Rf=0.5~0.6 to give compound E-1 (890 mg, yield 10%). ESI[M+H]$^+$=264.2

$^1$H NMR (400 MHz, $CDCl_3$) δ 7.42-7.21 (m, 5H), 6.57-6.53 (m, 1H), 4.45-4.26 (m, 2H), 2.02 (d, J=7.1 Hz, 3H), 1.37 (t, J=7.1 Hz, 3H).

2. Preparation of (R)-4-fluoro-1-(1-phenylethyl)-1H-1,2,3-triazole-5-carboxylic acid (E-2)

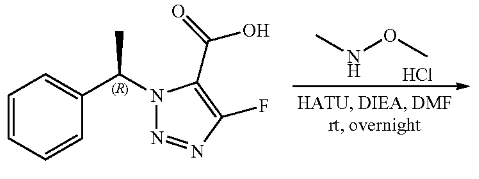

E-2

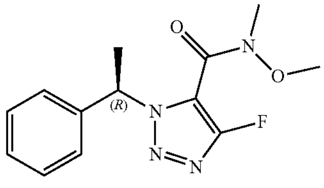

E-3

At room temperature, LiOH·$H_2O$ (223 mg, 5.32 mmol) was added into the solution of E-1 (700 mg, 2.66 mmol) in MeOH/THF/$H_2O$ (3 mL, v/v/v=1/1/1), then the mixture was stirred at room temperature for 3 hrs. The reaction was monitored by TLC until completion. The reaction mixture was concentrated under reduced pressure. Water (10 mL) was poured into the residue. The mixture was adjusted pH to 4~5 with 1N HCl and extracted with dichloromethane (3×15 mL). The combined organic layers were dried over anhydrous sodium sulfate, filtered and concentrated to give compound E-2 (586 mg, yield 94%) as a white solid. ESI[M+H]$^+$=236.0

$^1$H NMR (400 MHz, $CDCl_3$) δ 7.41-7.14 (m, 5H), 6.55-6.49 (m, 1H), 2.03 (d, J=7.1 Hz, 3H).

3. Preparation of (R)-4-fluoro-N-methoxy-N-methyl-1-(1-phenylethyl)-1H-1,2,3-triazole-5-carboxamide (E-3)

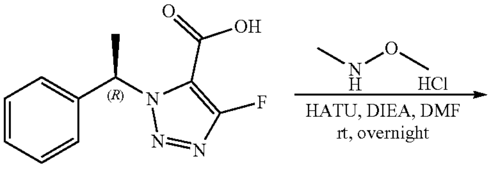

E-2

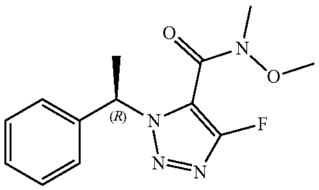

E-3

At room temperature, E-2 (4.0 g, 17.01 mmol), N, O-dimethylhydroxylamine hydrochloride (2.5 g, 25.63 mmol), DIEA (3.3 g, 25.51 mmol) and HATU (9.7 g, 27.6 mmol) were dissolved in DMF (80 mL), then the mixture was stirred at room temperature overnight. The reaction was monitored by TLC until completion. The mixture was quenched with water (100 mL) and extracted with ethyl acetate (3×30 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5-0.6 to give compound E-3 (3.1 g, yield 65%) as a white solid. ESI[M+H]$^+$=279.0

4. Preparation of (R)-1-(4-fluoro-1-(1-phenylethyl)-1H-1,2,3-triazol-5-yl)ethan-1-one (E-4)

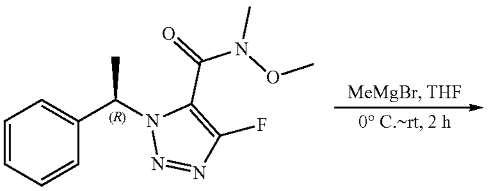

E-3

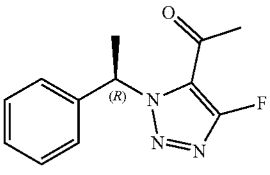

E-4

At room temperature, E-3 (2.6 g, 9.34 mmol) was dissolved in anhydrous THF (50 mL). The mixture was cooled to 0° C. with an ice-water bath. Methylmagnesium bromide (18.7 mL, 1 mol/L in THF, 18.7 mmol) was added dropwise into the mixture at the rate of 1.5 mmol/min, and then the mixture was reacted at room temperature for 2 hrs. The reaction was monitored by TLC until completion. The mixture was cooled to 0° C., quenched with saturated ammonium chloride solution (100 mL) and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give compound E-4 (1.4 g, yield 64%) as a white solid. ESI$[M+H]^+$=234.0

5. Preparation of (R)-2-bromo-1-(4-fluoro-1-(1-phenylethyl)-1H-1,2,3-triazol-5-yl)ethan-1-one (E-6)

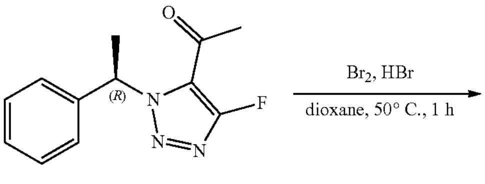

E-4

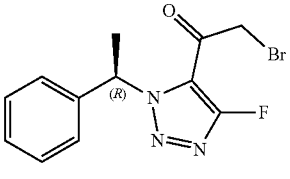

E-6

At room temperature, Bra (1.4 g, 8.76 mmol) was added into the mixture of E-4 (1.0 g, 4.29 mmol) and hydrobromic acid solution (5 mL, 40%) in dioxane (20 mL), then the mixture was stirred at 50° C. for 1 hour. The reaction was monitored by TLC until completion. The reaction mixture was cooled to room temperature, quenched with ice-water (30 mL) and saturated sodium bicarbonate solution (10 mL), and extracted with ethyl acetate (3×10 mL). The combined organic layers washed with saturated brine (10 mL), dried over anhydrous sodium sulfate, filtered and concentrated under reduced pressure to give the crude compound E-6, which was used for next step directly without further purification.

6. Preparation of (R)-2-(ethylthio)-1-(4-fluoro-1-(1-phenylethyl)-1H-1,2,3-triazol-5-yl)ethan-1-one (E-7)

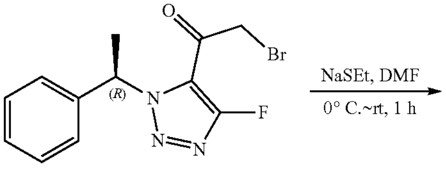

E-5

-continued

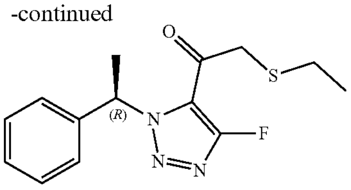

E-7

In an ice-water bath, NaSEt (433 mg, 5.15 mmol) was added into the solution of the crude compound E-6 (calculated according to the theoretical amount of 4.29 mmol) in DMF (10 mL) at 0° C., and then the mixture was reacted at room temperature for 1 hour. The reaction was monitored by TLC until completion. The mixture was quenched with ice-water (10 mL) and extracted with ethyl acetate (3×5 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/10~1/3), with collecting the fraction with Rf=0.4~0.6 to give the compound E-7 (286 mg, yield 23% for 2 steps). ESI$[M+H]^+$=294.0

7. Preparation of (R)-2,2-dichloro-2-(ethylthio)-1-(4-fluoro-1-(1-phenylethyl)-1H-1,2,3-triazol-5-yl)ethan-1-one (E-8)

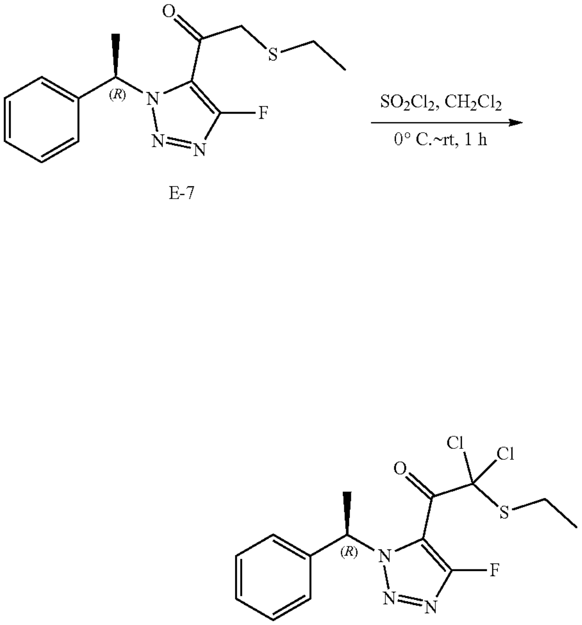

E-7

E-8

In an ice-water bath, $SO_2Cl_2$ (184 mg, 1.36 mmol) was added into the solution of E-7 (200 mg, 0.68 mmol) in dichloromethane (5 mL) at 0° C., then the mixture was stirred at room temperature for 1 hour. The reaction was monitored by TLC until completion. The reaction mixture was concentrated under reduced pressure to give the crude product E-8 (205 mg), which was used for next step directly without further purification.

8. Preparation of Compound D53

Method A

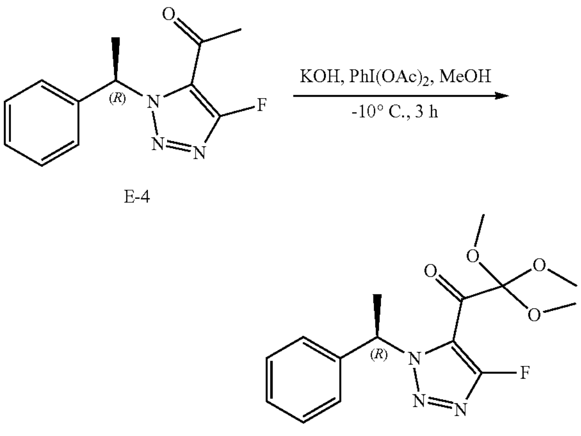

E-4

化合物 D53

At room temperature, E-4 (300 mg, 1.29 mmol) and $PhI(OAc)_2$ (621 mg, 1.93 mmol) were dissolved in methanol (10 mL), then the mixture was cooled to −10° C. with an ice-salt bath. KOH (869 mg, 15.49 mmol) was added in portions into the mixture within 5 mins, then the reaction mixture was reacted at −10° C. for 3 hrs. The reaction was monitored by TLC until completion. The reaction mixture was quenched with saturated brine (10 mL) and extracted with ethyl acetate (3×5 mL). The combined organic layers were dried over anhydrous sodium sulfate, filtered, and concentrated under reduced pressure. The residue was purified by Prep-TLC (ethyl acetate/petroleum ether (v/v)=1/5) and the fraction with Rf=0.5~0.6 was collected to give the title compound D53 (17 mg, yield 4%).

Method B

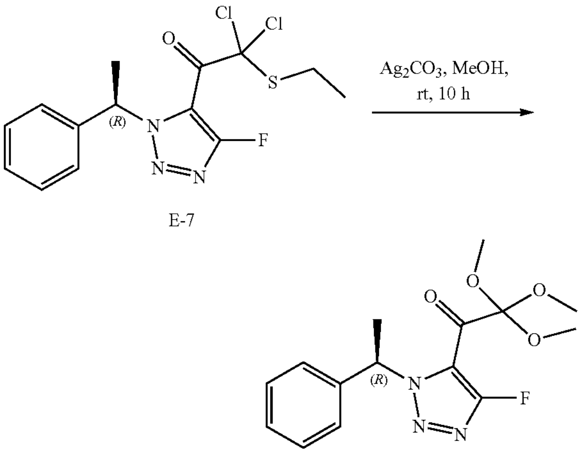

E-7

化合物 D53

At room temperature, E-7 (150 mg, 0.41 mmol) and $Ag_2CO_3$ (171 mg, 0.62 mmol) were dissolved methanol (5 mL), then the mixture was stirred at room temperature for 10 hrs. The reaction was monitored by TLC until completion. The mixture was quenched with saturated sodium bicarbonate solution (10 mL) at 0° C. and extracted with ethyl acetate (3×5 mL). The combined organic layers were dried over anhydrous sodium sulfate, filtered and concentrated under reduced pressure. The residue was purified by Prep-TLC (ethyl acetate/petroleum ether (v/v)=1/5) and the fraction with Rf=0.5~0.6 was collected to give the title compound D53 (31 mg, yield 23%). ESI[M+H]$^+$=324.0

$^1$H NMR (400 MHz, $CDCl_3$) δ 7.38-7.29 (m, 5H), 6.52 (q, J=7.1 Hz, 1H), 3.92 (s, 0.7H), 3.49 (s, 1.3H), 3.13 (s, 7H), 2.07 (d, J=7.1 Hz, 3H).

9. Preparation of Compounds D54~D62

The title compounds D54~D59 were prepared according to the operation method of preparing compounds D2~D10 described in Example 2.

The title compounds D60~D62 were prepared according to the operation method of preparing compounds D14~D16 described in Example 4.

Compound D54: 42 mg, ESI[M+H]$^+$=354.0

$^1$H NMR (400 MHz, $CDCl_3$) δ 7.39-7.28 (m, 5H), 6.51 (q, J=7.1 Hz, 1H), 3.35 (s, 3H), 3.24 (s, 3H), 2.33-2.17 (m, 1H), 2.15-2.01 (m, 4H), 0.99 (t, J=7.5 Hz, 3H).

Compound D55: 31 mg, ESI[M+H]$^+$=338.0

$^1$H NMR (400 MHz, $CDCl_3$) δ 7.38-7.29 (m, 5H), 6.52 (q, J=7.1 Hz, 1H), 4.43-4.40 (m, 2H), 3.95 (s, 1H), 3.78-3.71 (m, 1.5H), 3.52 (s, 3.5H), 2.07 (d, J=7.1 Hz, 3H), 1.42 (t, J=7.1 Hz, 1.5H), 1.27 (t, J=7.0 Hz, 1.5H).

Compound D56: 12 mg, ESI[M+H]$^+$=352.1

$^1$H NMR (400 MHz, $CDCl_3$) δ 7.37-7.28 (m, 5H), 6.53 (q, J=7.1 Hz, 1H), 5.35-5.30 (m, 1H), 3.92 (s, 1H), 3.51 (s, 5H), 2.06 (d, J=7.1 Hz, 3H), 1.56 (d, J=6.5 Hz, 1H), 1.47-1.40 (m, 3H), 1.24 (t, J=10.2 Hz, 2H).

Compound D57: 21 mg, ESI[M+H]$^+$366.1

$^1$H NMR (400 MHz, $CDCl_3$) δ 7.38-7.27 (m, 5H), 6.50 (q, J=7.1 Hz, 1H), 4.43-4.40 (m, 1H), 3.94 (s, 1H), 3.74-3.70 (m, 1.5H), 3.50 (s, 2.5H), 2.07 (d, J=7.1 Hz, 3H), 1.42-1.40 (m, 4.5H), 1.25-1.21 (m, 4.5H).

Compound D58: 12 mg, ESI[M+H]$^+$=350.0

$^1$H NMR (400 MHz, $CDCl_3$) δ 7.38-7.29 (m, 5H), 6.52 (q, J=7.1 Hz, 1H), 6.17-5.89 (m, 1H), 5.51-4.83 (m, 2H), 4.21-4.18 (m, 1.5H), 3.94 (s, 1.5H), 3.46 (m, 3H), 3.26-3.09 (m, 2H), 2.08 (d, J=7.1 Hz, 3H).

Compound D59: 35 mg, ESI[M+H]$^+$=362.0

$^1$H NMR (400 MHz, $CDCl_3$) δ 7.36-7.29 (m, 5H), 6.50 (q, J=7.1 Hz, 1H), 4.22-4.18 (m, 1.5H), 3.96 (s, 2H), 3.49 (s, 3H), 3.28-3.08 (m, 1.5H), 2.07 (d, J=7.1 Hz, 3H), 2.05-1.82 (m, 3H).

Compound D60: 24 mg, ESI[M+H]$^+$=322.0

$^1$H NMR (400 MHz, $CDCl_3$) δ 7.38-7.28 (m, 5H), 6.52 (q, J=7.1 Hz, 1H), 5.17 (s, 1H), 3.80-3.55 (m, 4H), 2.05 (d, J=7.1 Hz, 3H), 1.28-1.15 (m, 6H).

Compound D61: 34 mg, ESI[M+H]$^+$=354.0

$^1$H NMR (400 MHz, $CDCl_3$) δ 7.37-7.30 (m, 5H), 6.53 (q, J=7.1 Hz, 1H), 5.35 (s, 1H), 2.79-2.47 (m, 4H), 2.07 (d, J=7.1 Hz, 3H), 1.27-1.13 (m, 6H).

Compound D62: 21 mg, ESI[M+H]$^+$=346.2

$^1$H NMR (400 MHz, $CDCl_3$) δ 7.38-7.29 (m, 5H), 6.68 (s, 1H), 6.52 (q, J=7.1 Hz, 1H), 2.27 (s, 6H), 2.07 (d, J=7.1 Hz, 3H).

Example 10 Preparation of Compounds D63~D72
Preparation Route of Target Compound D63
Method A
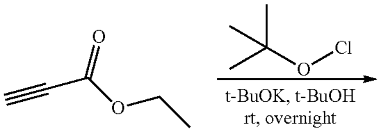
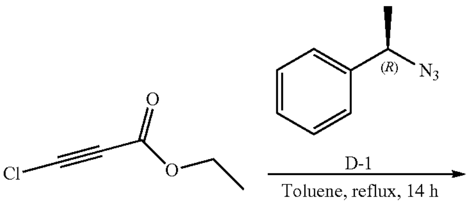
F-1
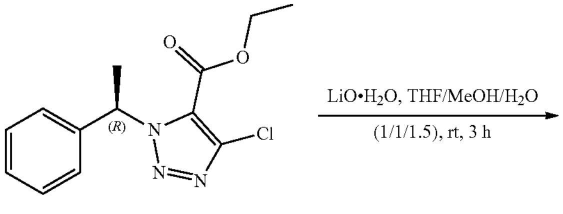
F-2
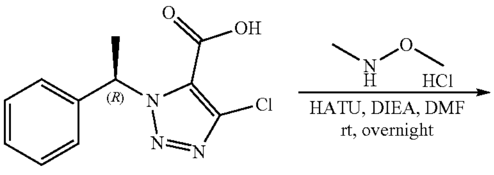
F-3
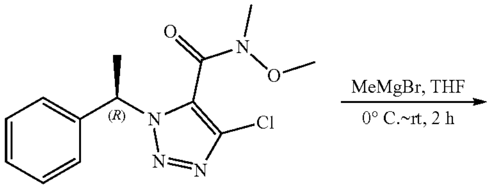
F-4
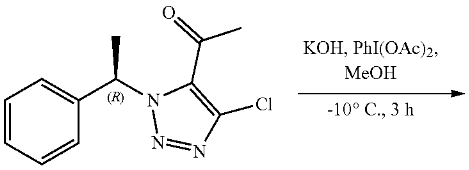
F-5
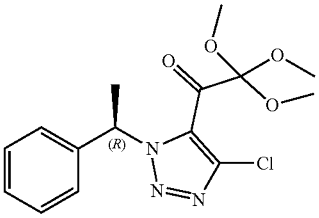
Compound D63
-continued
Method B:
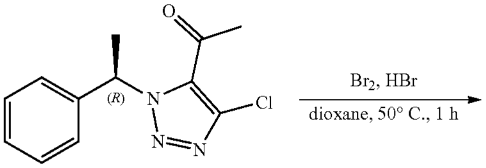
F-5
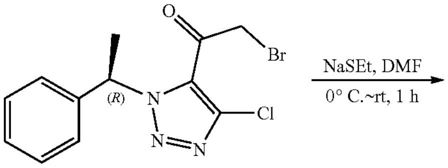
F-6
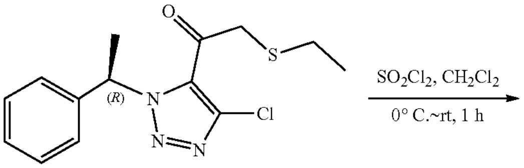
F-7
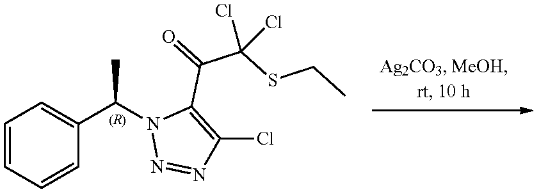
F-8
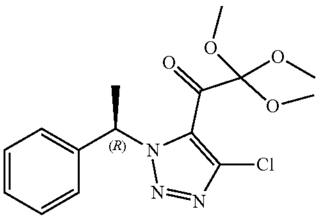
Compound D63
Preparation Route of Compounds D64~67
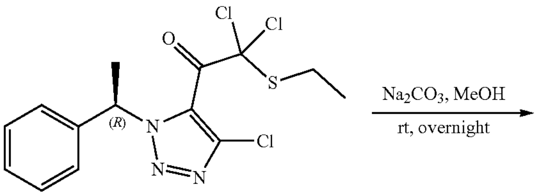
F-8
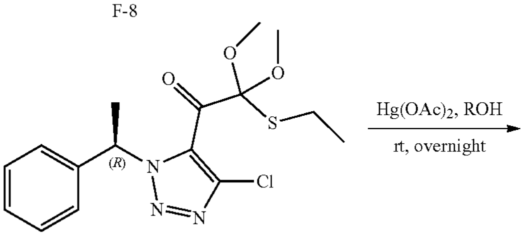
F-9

-continued
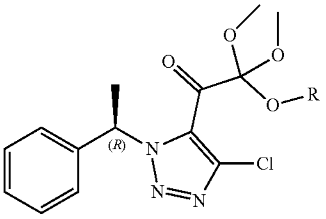
Compound D64~D67
Preparation Route of Compound D68
Method A
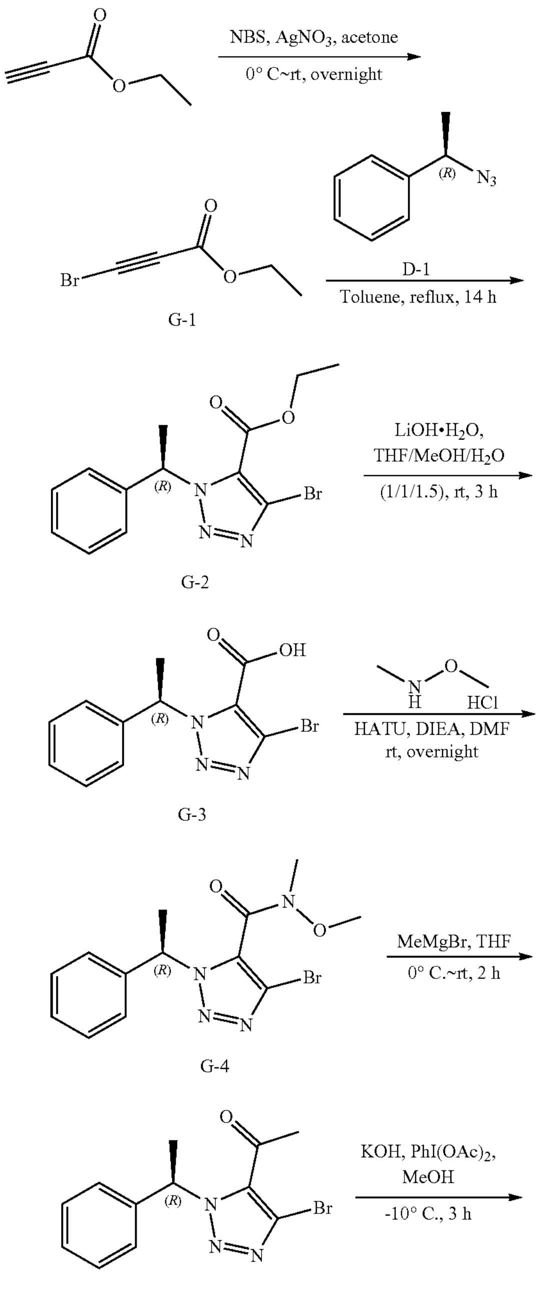
-continued
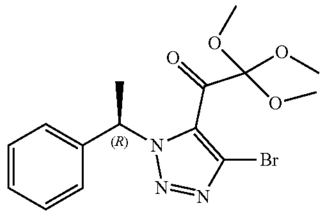
Compound D68
Method B
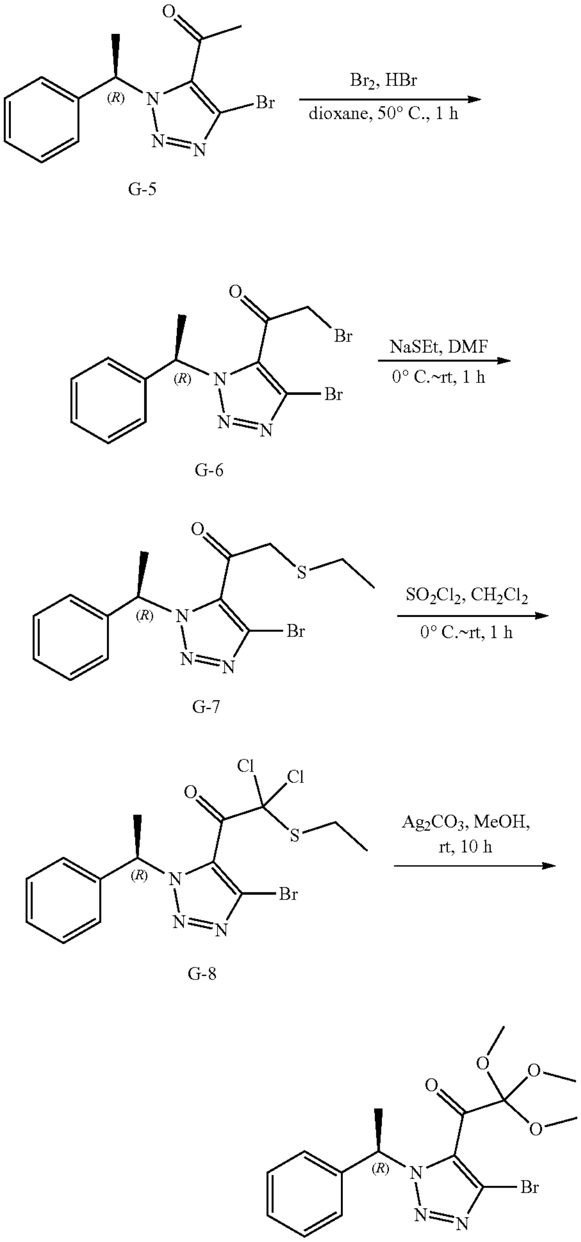
Compound D68

Preparation Route of Compounds D69~72

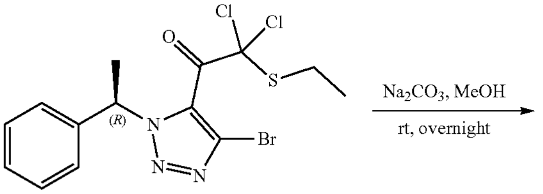

G-8

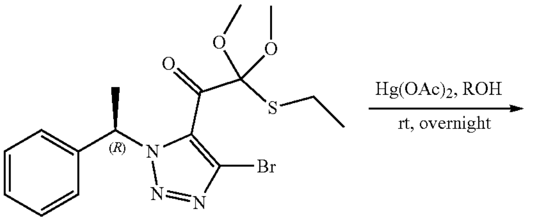

G-9

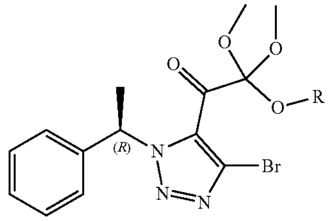

Compound D69~D72

1. Preparation of ethyl 3-chloropropiolate (F-1)

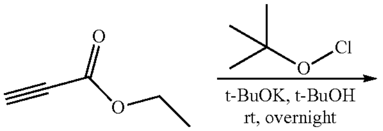

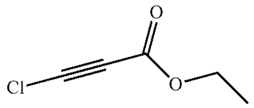

F-1

At room temperature, ethyl propiolate (9.0 g, 91.7 mmol) and tert-butyl hypochlorite (10 g, 92.1 mmol) were dissolved in t-BuOH (100 mL), then t-BuOK (2.0 g, 17.8 mmol) was added in two portions into the mixture within 5 mins After addition, the reaction mixture was stirred at room temperature overnight. The reaction was monitored by TLC until completion. The reaction mixture was filtered, and the filtrate was concentrated under reduced pressure to give the crude product F-1, which was used for next step directly without further purification.

2. Preparation of ethyl (R)-4-chloro-1-(1-phenylethyl)-1H-1,2,3-triazole-5-carboxylate (F-2)

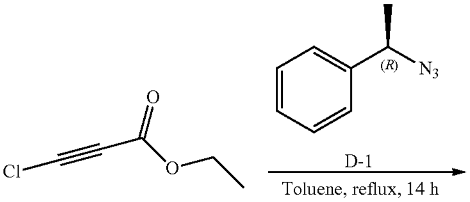

F-1

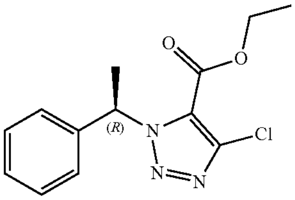

F-2

At room temperature, the crude product F-1 from the previous step and D-1 (3.2 g, 21.7 mmol) were dissolved in toluene (100 mL), and then the mixture was heated to reflux for 14 hrs. The reaction was monitored by TLC until completion. The reaction mixture was quenched with saturated brine (30 mL) and extracted with ethyl acetate (3×30 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v)=1/10-1/1), with TLC (ethyl acetate/petroleum ether (v/v)=1/5) monitoring, and collecting the fraction with Rf=0.5~0.6 to give compound F-2 (620 mg, yield 10%). ESI[M+H]$^+$=280.1

$^1$H NMR (400 MHz, CDCl$_3$) δ 7.38-7.29 (m, 5H), 6.52 (q, J=7.1 Hz, 1H), 4.43-4.33 (m, 2H), 2.07 (d, J=7.1 Hz, 3H), 1.38 (t, J=7.1 Hz, 3H).

3. Preparation of (R)-4-chloro-1-(1-phenylethyl)-1H-1,2,3-triazole-5-carboxylic acid (F-3)

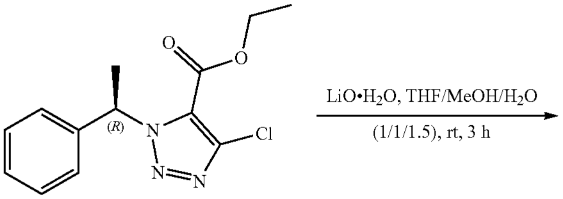

F-2

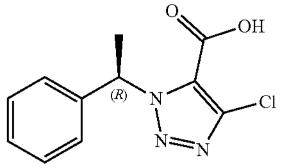

F-3

At room temperature, LiOH·H$_2$O (156 mg, 3.72 mmol) was added into the solution of F-2 (520 mg, 1.86 mmol) in MeOH/THF/H$_2$O (3 mL, v/v/v=1/1/1), then the mixture was stirred at room temperature for 3 hrs. The reaction was monitored by TLC until completion. The reaction mixture was concentrated under reduced pressure. Water (10 mL) was poured into the residue. The mixture was adjusted pH to 4~5 with 1N HCl and extracted with dichloromethane (3×15 mL). The combined organic layers were dried over anhydrous sodium sulfate, filtered and concentrated to give the compound F-3 (445 mg, yield 95%) as a white solid. ESI[M+Na]$^+$=274.1, [M+H−105]$^+$=148.1

$^1$H NMR (400 MHz, $CDCl_3$) δ 7.39-7.29 (m, 5H), 6.52 (q, J=7.1 Hz, 1H), 2.08 (d, J=7.0 Hz, 3H).

4. Preparation of Compounds D63~D67

The intermediate compounds F-4~F-9 were prepared according to the operation method of preparing intermediate compounds D-4~D-9 described in Example 8.

The title compounds D63~D67 were prepared according to the operation method of preparing compounds D42~D48 described in Example 8.

Compound D63: 30 mg, ESI[M+H]$^+$=340.0

$^1$H NMR (400 MHz, $CDCl_3$) δ 7.37-7.29 (m, 5H), 6.51 (q, J=7.1 Hz, 1H), 3.91 (s, 0.7H), 3.48 (s, 1.3H), 3.12 (s, 7H), 2.07 (d, J=7.1 Hz, 3H).

Compound D64: 18 mg, ESI[M+H]$^+$=354.0

$^1$H NMR (400 MHz, $CDCl_3$) δ 7.38-7.28 (m, 5H), 6.52 (q, J=7.1 Hz, 1H), 4.42-4.40 (m, 2H), 3.94 (s, 1H), 3.77-3.71 (m, 1.5H), 3.51 (s, 3.5H), 2.07 (d, J=7.1 Hz, 3H), 1.42 (t, J=7.1 Hz, 1.5H), 1.28 (t, J=7.0 Hz, 1.5H).

Compound D65: 12 mg, ESI[M+H]$^+$=368.0

$^1$H NMR (400 MHz, $CDCl_3$) δ 7.36-7.29 (m, 5H), 6.53 (q, J=7.1 Hz, 1H), 5.36-5.30 (m, 1H), 3.91 (s, 1H), 3.53 (s, 5H), 2.07 (d, J=7.1 Hz, 3H), 1.54 (d, J=6.5 Hz, 1H), 1.45-1.40 (m, 3H), 1.24 (t, J=10.2 Hz, 2H).

Compound D66: 10 mg, ESI[M+H]$^+$=380.0

$^1$H NMR (400 MHz, $CDCl_3$) δ 7.38-7.29 (m, 5H), 6.52 (q, J=7.1 Hz, 1H), 5.24-5.14 (m, 1H), 3.94 (s, 1H), 3.77-3.71 (m, 1.5H), 3.51 (s, 3.5H), 2.54-2.37 (m, 2H), 2.27-2.14 (m, 2H), 2.07 (d, J=7.1 Hz, 3H), 1.96-1.85 (m, 1H), 1.78-1.66 (m, 1H).

Compound D67: 24 mg, ESI[M+H]$^+$=366.0

$^1$H NMR (400 MHz, $CDCl_3$) δ 7.37-7.29 (m, 5H), 6.52 (q, J=7.1 Hz, 1H), 6.17-5.89 (m, 1H), 5.52-4.82 (m, 2H), 4.22-4.18 (m, 1.5H), 3.92 (s, 1.5H), 3.45 (m, 3H), 3.27-3.09 (m, 2H), 2.07 (d, J=7.1 Hz, 3H).

5. Preparation of ethyl 3-bromopropiolate (G-1)

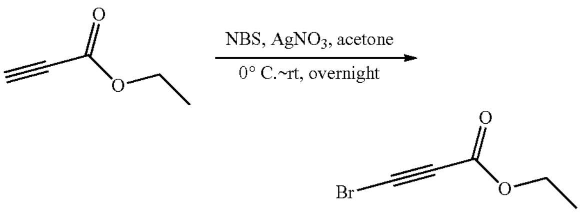

G-1

At room temperature, ethyl propiolate (12.0 g, 122 mmol), NBS (26.2 g, 147 mmol) and $AgNO_3$ (10.4 g, 61 mmol) were dissolved in acetone (400 mL), then the reaction mixture was stirred at room temperature overnight. The reaction was monitored by TLC until completion. The reaction mixture was filtered, and the filtrate was concentrated under reduced pressure to give the crude product G-1, which was used for next step directly without further purification.

6. Preparation of ethyl (R)-4-bromo-1-(1-phenylethyl)-1H-1,2,3-triazole-5-carboxylate (G-2)

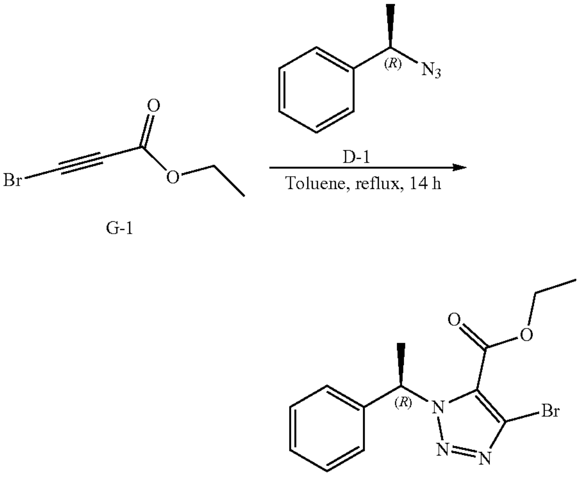

G-1

G-2

At room temperature, the crude product G-1 from the previous step and D-1 (7.1 g, 48.2 mmol) were dissolved in toluene (100 mL), then the mixture was heated to reflux for 14 hrs. The reaction was monitored by TLC until completion. The reaction mixture was quenched with saturated brine (30 mL) and extracted with ethyl acetate (3×50 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v)=1/10-1/1), with TLC (ethyl acetate/petroleum ether (v/v)=1/5) monitoring, and collecting the fraction with Rf=0.5~0.6 to give title compound G-2 (2.3 g, yield 15%). ESI[M+H]$^+$=324.1

$^1$H NMR (400 MHz, $CDCl_3$) δ 7.40-7.29 (m, 5H), 6.53 (q, J=7.1 Hz, 1H), 4.45-4.31 (m, 2H), 2.07 (d, J=7.1 Hz, 3H), 1.39 (t, J=7.1 Hz, 3H).

7. Preparation of (R)-4-bromo-1-(1-phenylethyl)-1H-1,2,3-triazole-5-carboxylic acid (G-3)

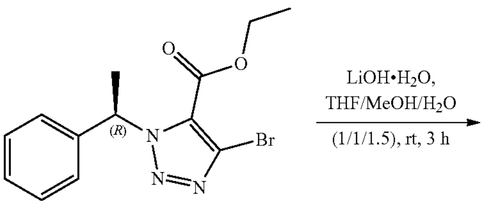

G-2

-continued

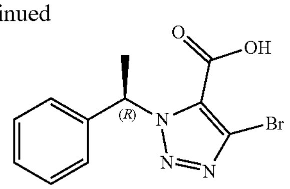

G-3

At room temperature, LiOH·$H_2O$ (337 mg, 8.0 mmol) was added into the solution of G-2 (1.3 g, 4.0 mmol) in MeOH/THF/$H_2O$ (15 mL, v/v/v=1/1/1), then the mixture was stirred at room temperature for 3 hrs. The reaction was monitored by TLC until completion. The reaction mixture was concentrated under reduced pressure. Water (10 mL) was poured into the residue. The mixture was adjusted pH to 4~5 with 1N HCl and extracted with dichloromethane (3x15 mL). The combined organic layers were dried over anhydrous sodium sulfate, filtered and concentrated to give the compound G-3 (445 mg, yield 95%) as a white solid. ESI[M+H−105]$^+$=191.0

$^1$H NMR (400 MHz, $CD_3OD$) δ 7.48-7.13 (m, 5H), 6.76-6.65 (m, 1H), 2.00 (d, J=5.5 Hz, 3H).

8. Preparation of Compounds D68~D72

The intermediate compounds G-4~G-9 were prepared according to the operation method of preparing intermediate compounds D-4~D-9 described in Example 8.

The title compounds D68~D72 were prepared according to the operation method of preparing compounds D42~D48 described in Example 8.

Compound D68: 22 mg, ESI[M+H]$^+$=384.0

$^1$H NMR (400 MHz, $CDCl_3$) δ 7.39-7.29 (m, 5H), 6.51 (q, J=7.1 Hz, 1H), 3.92 (s, 0.7H), 3.49 (s, 1.3H), 3.13 (s, 7H), 2.06 (d, J=7.1 Hz, 3H).

Compound D69: 54 mg, ESI[M+H]$^+$=398.0

$^1$H NMR (400 MHz, $CDCl_3$) δ 7.36-7.27 (m, 5H), 6.51 (q, J=7.1 Hz, 1H), 4.41-4.38 (m, 2H), 3.92 (s, 1H), 3.76-3.71 (m, 1.5H), 3.52 (s, 3.5H), 2.06 (d, J=7.1 Hz, 3H), 1.42 (t, J=7.1 Hz, 1.5H), 1.25 (t, J=7.0 Hz, 1.5H).

Compound D70: 16 mg, ESI[M+H]$^+$=412.0

$^1$H NMR (400 MHz, $CDCl_3$) δ 7.38-7.29 (m, 5H), 6.51 (q, J=7.1 Hz, 1H), 5.35-5.30 (m, 1H), 3.95 (s, 1H), 3.52 (s, 5H), 2.06 (d, J=7.1 Hz, 3H), 1.55 (d, J=6.5 Hz, 1H), 1.46-1.40 (m, 3H), 1.25 (t, J=10.2 Hz, 2H).

Compound D71: 18 mg, ESI[M+H]$^+$=424.0

$^1$H NMR (400 MHz, $CDCl_3$) δ 7.36-7.29 (m, 5H), 6.50 (q, J=7.1 Hz, 1H), 5.25-5.14 (m, 1H), 3.94 (s, 1H), 3.78-3.71 (m, 1.5H), 3.51 (s, 3.5H), 2.52-2.37 (m, 2H), 2.28-2.12 (m, 2H), 2.07 (d, J=7.1 Hz, 3H), 1.97-1.86 (m, 1H), 1.78-1.64 (m, 1H).

Compound D72: 22 mg, ESI[M+H]$^+$=410.0

$^1$H NMR (400 MHz, $CDCl_3$) δ 7.38-7.29 (m, 5H), 6.51 (q, J=7.1 Hz, 1H), 6.17-5.89 (m, 1H), 5.51-4.83 (m, 2H), 4.24-4.18 (m, 1.5H), 3.94 (s, 1.5H), 3.45 (m, 3H), 3.28-3.09 (m, 2H), 2.06 (d, J=7.1 Hz, 3H).

Example 11 Preparation of Compounds D73~D92

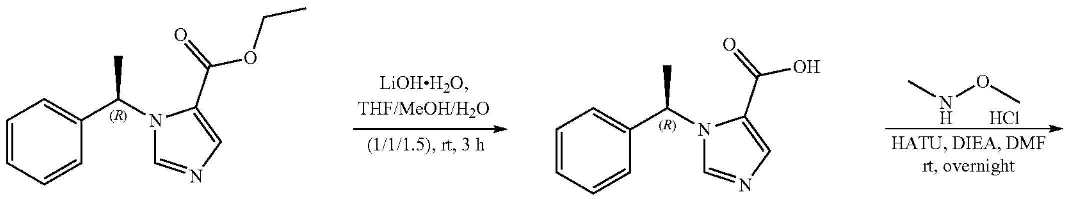

H-1

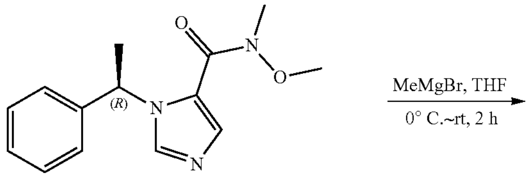

H-2

-continued
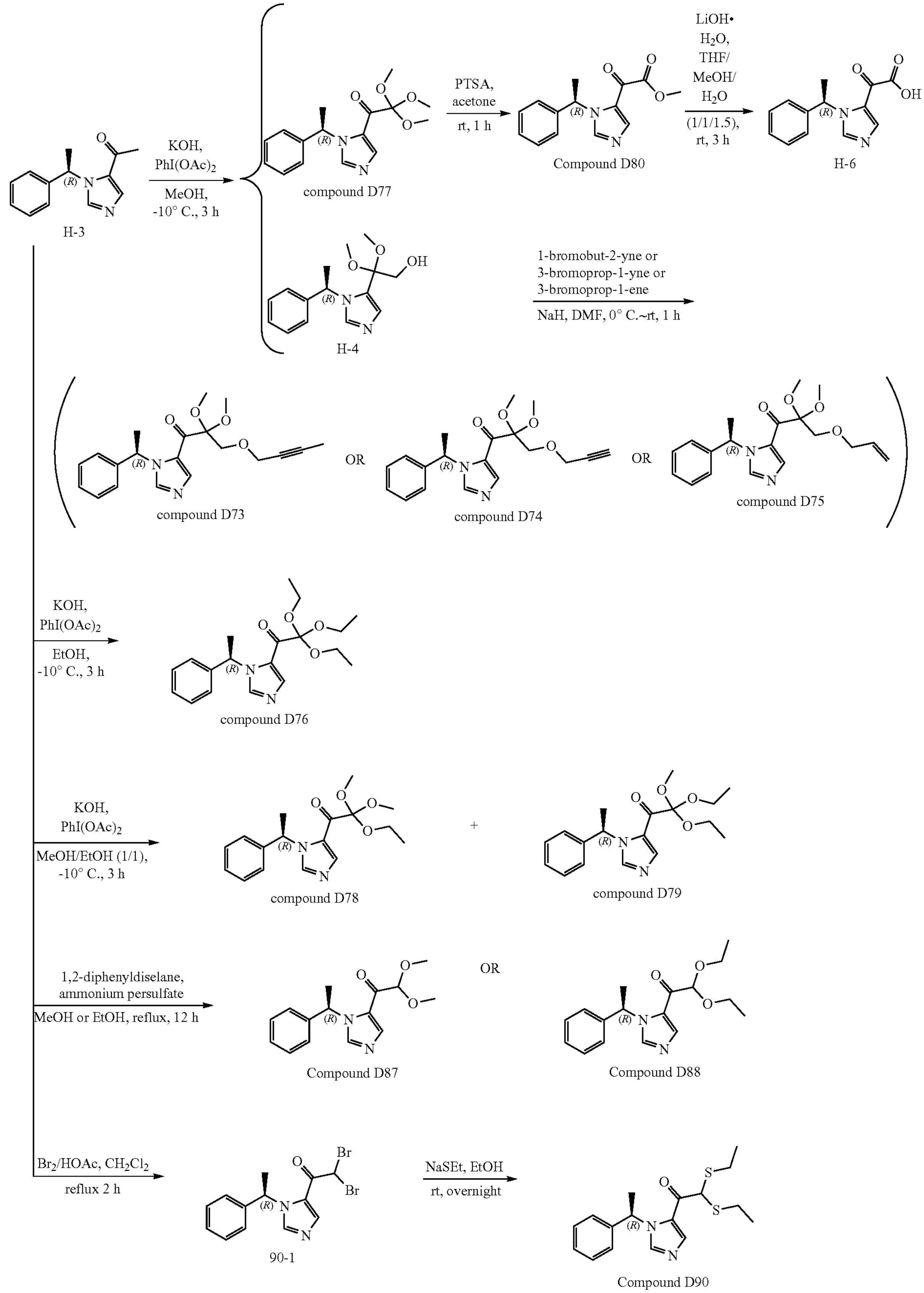
H-3
compound D77
Compound D80
H-6
H-4
compound D73
compound D74
compound D75
compound D76
compound D78
compound D79
Compound D87
Compound D88
90-1
Compound D90

-continued
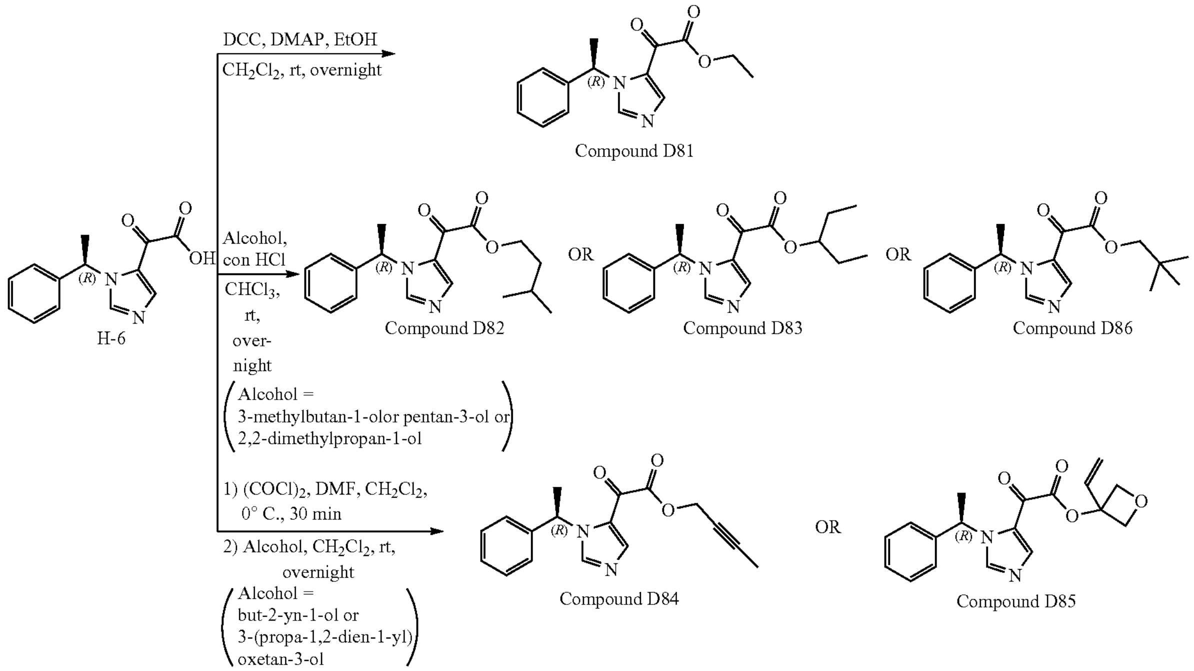
H-6
Compound D81
Compound D82 OR Compound D83 OR Compound D86
Compound D84 OR Compound D85
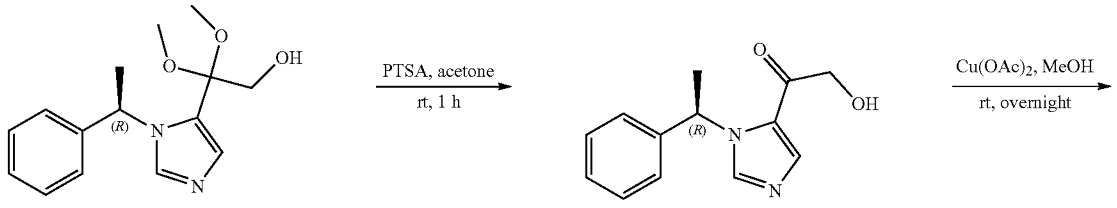
H-4
H-5
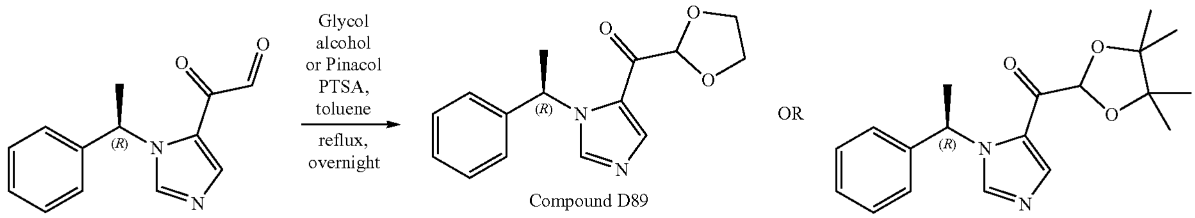
H-7
Compound D89 OR Compound D91
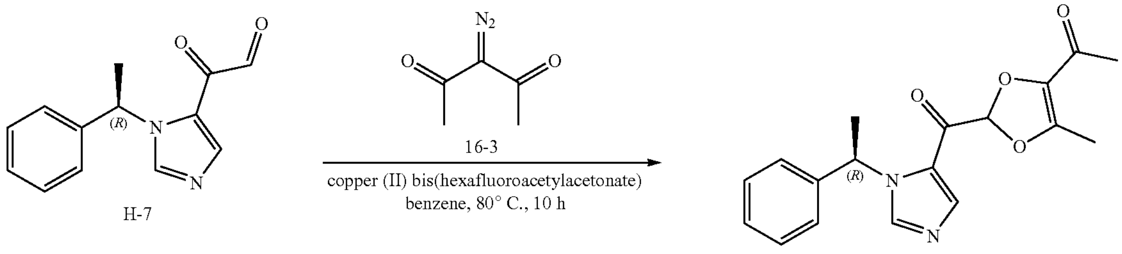
H-7
Compound D192

1. Preparation of Compound D77

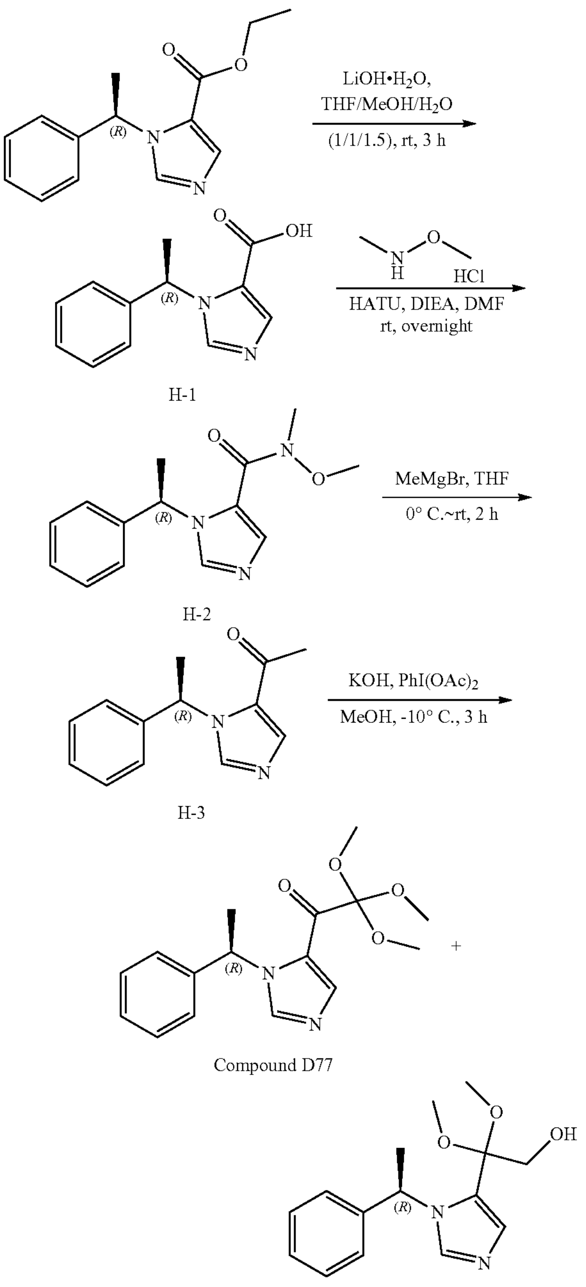

H-1

H-2

H-3

Compound D77

H-4

At room temperature, LiOH·$H_2O$ (6.9 g, 164.4 mmol) was added into the solution of ethyl (R)-1-(1-phenylethyl)-1H-imidazole-5-carboxylate (20.0 g, 81.9 mmol) in THF/MeOH/$H_2O$ (80 mL, v/v/v=1/1/1.5), then the mixture was stirred at room temperature for 3 hrs. The reaction was monitored by TLC until completion. The reaction mixture was concentrated under reduced pressure. Water (50 mL) was poured into the residue. The mixture was adjusted pH to 4~5 with 1N HCl at 0° C. and filtered. The filter cake was washed with water and methyl tert-butyl ether, transferred to a single mouth bottle and vacuum dried to give pure product H-1. The filtrate was extracted with dichloromethane (5×30 mL). The combined organic layers were dried over anhydrous sodium sulfate, filtered and concentrated. The crude product was washed with methyl tert-butyl ether to give pure product H-1. A total of two batches gave white solid compound H-1 (15 g, yield 85%). ESI[M+H]+=217.3

$^1H$ NMR (400 MHz, $CDCl_3$) δ 9.73 (brs, 1H), 7.89 (s, 1H), 7.87 (s, 1H), 7.39-7.27 (m, 3H), 7.26-7.18 (m, 2H), 6.55 (q, J=7.1 Hz, 1H), 1.87 (d, J=7.1 Hz, 3H).

At room temperature, H-1 (13 g, 60 mmol), N, O-dimethylhydroxylamine hydrochloride (11.7 g, 120 mmol), DIEA (15.5 g, 120 mmol) and HATU (45.6 g, 120 mmol) were dissolved in DMF (200 mL), then the mixture was stirred at room temperature overnight. The reaction was monitored by TLC until completion. The mixture was quenched with water (100 mL) and extracted with ethyl acetate (4×20 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5~0.6 to give the title compound H-2 (13 g, yield 84%) as a white solid. ESI[M+H]$^+$=260.1

At room temperature, H-2 (13 g, 50.1 mmol) was dissolved in anhydrous THF (100 mL). The mixture was cooled to 0° C. with an ice-water bath. Methylmagnesium bromide (100.2 mL, 1 mol/L in THF, 100.2 mmol) was added dropwise into the mixture at the rate of 5 mmol/min, then the mixture was reacted at room temperature for 2 hrs. The reaction was monitored by TLC until completion. The mixture was cooled to 0° C., quenched with saturated ammonium chloride solution (100 mL) and extracted with ethyl acetate (3×50 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give the title compound H-3 (9.1 g, yield 85%) as a white solid. ESI[M+H]$^+$215.1

At room temperature, H-3 (22 g, 0.10 mol) and $PhI(OAc)_2$ (49.6 g, 0.15 mol) were dissolved in methanol (300 mL), then the mixture was cooled to −10° C. with an ice-salt bath. KOH (67.3 g, 1.2 mol) was added in portions into the mixture within 60 mins, then the reaction mixture was reacted at −10° C. for 3 hrs. The reaction was monitored by TLC until completion. The reaction mixture was quenched with saturated brine (500 mL) and extracted with ethyl acetate (3×50 mL). The combined organic layers were dried over anhydrous sodium sulfate, filtered, and concentrated under reduced pressure. The residue was purified by silica gel column chromatography (ethyl acetate/petroleum ether (v/v)=1/20~1/5), with TLC (ethyl acetate/petroleum ether (v/v)=1/3) monitoring, and collecting the fraction with Rf=0.4~0.6 to give title compound D77 (5.1 g, yield 17%). ESI[M+H]$^+$=305.0

$^1H$ NMR (400 MHz, $CDCl_3$) δ 8.28 (s, 1H), 7.99 (s, 1H), 7.34-7.27 (m, 2H), 7.26-7.21 (m, 1H), 7.16-7.09 (m, 2H), 6.40 (q, J=6.9 Hz, 1H), 3.15 (s, 9H), 1.88 (d, J=7.1 Hz, 3H).

2. Preparation of Compounds D73, D74 and D75

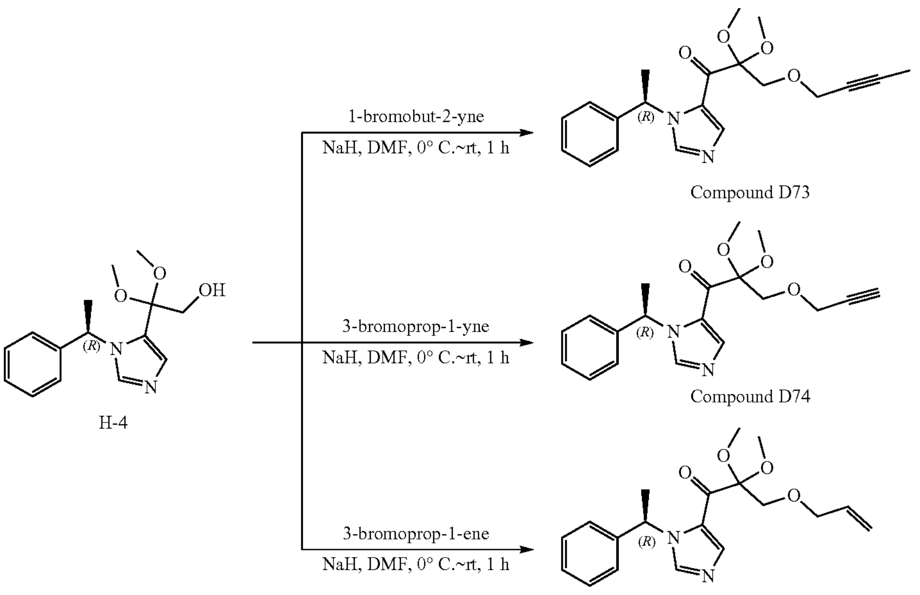

H-4

Compound D73

Compound D74

Compound D75

In an ice-water bath, NaH (18 mg, 60% in mineral oil, 0.45 mmol) was added in portions into the mixture of H-4 (100 mg, 0.36 mmol) in DMF (5 mL) at 0° C., then the mixture was stirred at 0° C. for 30 min 1-bromobut-2-yne (72 mg, 0.54 mmol) was added slowly into the mixture with a syringe. The mixture was stirred at room temperature for 1 hour. The reaction was monitored by TLC until completion. The reaction mixture was quenched with saturated ammonium chloride solution (10 mL) and extracted with ethyl acetate (3×5 mL). The combined organic layers were washed with saturated brine (10 mL), dried over anhydrous sodium sulfate, filtered, and concentrated under reduced pressure. The residue was purified by Prep-TLC (ethyl acetate/petroleum ether (v/v)=1/5) and the fraction with Rf=0.5~0.6 was collected to give the title compound D73 (65 mg, yield 51%). ESI[M+H−28]$^+$=357.3

$^1$H NMR (400 MHz, $CDCl_3$) δ 7.74 (s, 1H), 7.40-7.28 (m, 3H), 7.22-7.11 (m, 3H), 6.04 (q, J=7.0 Hz, 1H), 4.03-3.81 (m, 2H), 3.80-3.52 (m, 2H), 3.27 (s, 3H), 3.23 (s, 3H), 1.84 (d, J=7.1 Hz, 3H), 1.80 (t, J=2.3 Hz, 3H).

The title compounds D74 and D75 were prepared according to the operation method of preparing compound D73, using H-4 to react with compounds 3-bromoprop-1-yne and 3-bromoprop-1-ene respectively.

Compound D74: 85 mg, ESI[M+H]$^+$=343.3

$^1$H NMR (400 MHz, $CDCl_3$) δ 7.76 (s, 1H), 7.41-7.11 (m, 6H), 6.40 (q, J=7.1 Hz, 1H), 4.00-3.50 (m, 4H), 3.28 (s, 3H), 3.21 (s, 3H), 2.45 (t, J=2.4 Hz, 1H), 1.85 (d, J=7.1 Hz, 3H).

Compound D75: 51 mg, ESI[M+H]$^+$=345.3

$^1$H NMR (400 MHz, $CDCl_3$) δ 7.74 (s, 1H), 7.45-7.11 (m, 6H), 6.41 (q, J=7.0 Hz, 1H), 6.15-5.91 (m, 1H), 5.50-4.81 (m, 2H), 4.00-3.50 (m, 4H), 3.25 (s, 3H), 3.20 (s, 3H), 1.85 (d, J=7.1 Hz, 3H).

3. Preparation of Compounds D76, D78 and D79

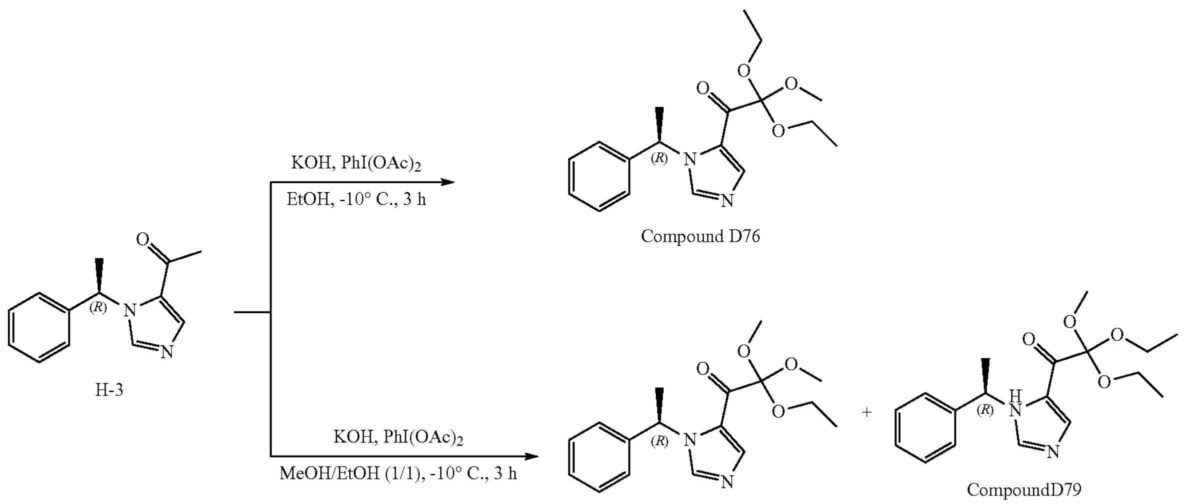

Compound D76

H-3

CompoundD78

+

CompoundD79

At room temperature, H-3 (1.0 g, 4.67 mmol) and PhI $(OAc)_2$ (2.3 g, 7.14 mmol) were dissolved in methanol (20 mL), then the mixture was cooled to −10° C. with an ice-salt bath. KOH (3.1 g, 55.25 mmol) was added in portions into the mixture within 20 mins, then the reaction mixture was reacted at −10° C. for 3 hrs. The reaction was monitored by TLC until completion. The reaction mixture was quenched with saturated brine (50 mL) and extracted with ethyl acetate (3×10 mL). The combined organic layers were dried over anhydrous sodium sulfate, filtered, and concentrated under reduced pressure. The residue was purified by Prep-TLC (ethyl acetate/petroleum ether (v/v)=1/5) and the fraction with Rf=0.5~0.6 was collected to give the title compound D76 (64 mg, yield 4%). ESI[M+H]$^+$=347.0

$^1$H NMR (400 MHz, $CDCl_3$) δ 8.34 (s, 1H), 7.91 (s, 1H), 7.32-7.27 (m, 2H), 7.26-7.22 (m, 1H), 7.13-7.06 (m, 2H), 6.41 (q, J=7.1 Hz, 1H), 3.49-3.20 (m, 6H), 1.87 (d, J=7.1 Hz, 3H), 1.14 (t, J=7.1 Hz, 9H).

Replacing the above solvent with MeOH/EtOH (20 mL, v/v=1/1) can separate the target compounds D78 and D79 at the same time.

Compound D78: 57 mg, yield 3.8%, ESI[M+H]$^+$=319.0

$^1$H NMR (400 MHz, $CDCl_3$) δ 8.31 (s, 1H), 8.03 (s, 1H), 7.41-7.19 (m, 3H), 7.17-7.07 (m, 2H), 6.41 (q, J=6.9 Hz, 1H), 3.44-3.32 (m, 1H), 3.30-3.23 (m, 1H), 3.21 (s, 3H), 3.13 (s, 3H), 1.88 (d, J=7.1 Hz, 3H), 1.12 (t, J=7.1 Hz, 3H).

Compound D79: 18 mg, yield 1.2%, ESI[M+H]$^+$=333.1

$^1$H NMR (400 MHz, $CDCl_3$) δ 8.34 (s, 1H), 8.12 (s, 1H), 7.42-7.27 (m, 3H), 7.17-7.08 (m, 2H), 6.43 (q, J=7.1 Hz, 1H), 3.46-3.32 (m, 3H), 3.22 (s, 3H), 3.20-3.09 (m, 1H), 1.89 (d, J=7.1 Hz, 3H), 1.17 (t, J=7.1 Hz, 3H), 1.10 (t, J=7.1 Hz, 3H).

4. Preparation of Compound D80

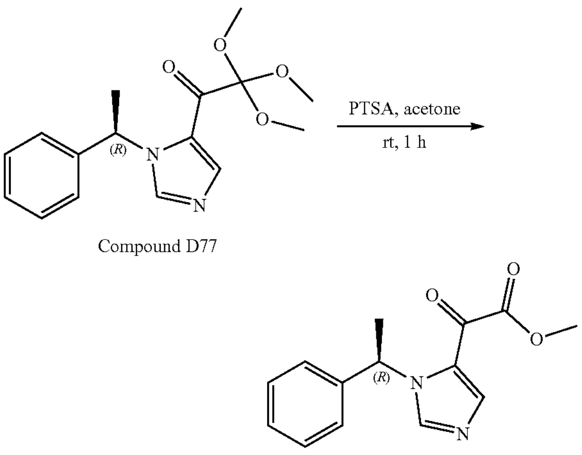

Compound D77

Compound D80

At room temperature, PTSA.$H_2O$ (9.4 g, 49.4 mmol) was added into the solution of D79 (5.0 g, 16.4 mmol) in acetone (50 mL), then the mixture was stirred at room temperature for 1 hour. The reaction was monitored by TLC until completion. The mixture was quenched with ice-water (50 mL) and extracted with ethyl acetate (3×20 mL). The combined organic layers were washed with saturated brine (20 mL), dried over anhydrous sodium sulfate, filtered and concentrated under reduced pressure. The residue was purified by silica gel column chromatography (ethyl acetate/petroleum ether (v/v)=1/20~1/5), with TLC (ethyl acetate/petroleum ether (v/v)=1/2) monitoring, and collecting the fraction with Rf=0.5~0.6 to give title compound D80 (2.5 g, yield 59%). ESI[M+H]$^+$=259.1

$^1$H NMR (400 MHz, $CDCl_3$) δ 8.42 (s, 1H), 8.10 (s, 1H), 7.42-7.30 (m, 3H), 7.25-7.20 (m, 2H), 6.39 (q, J=6.8 Hz, 1H), 3.95 (s, 3H), 1.90 (d, J=7.0 Hz, 3H).

5. Preparation of Compounds D81~D86

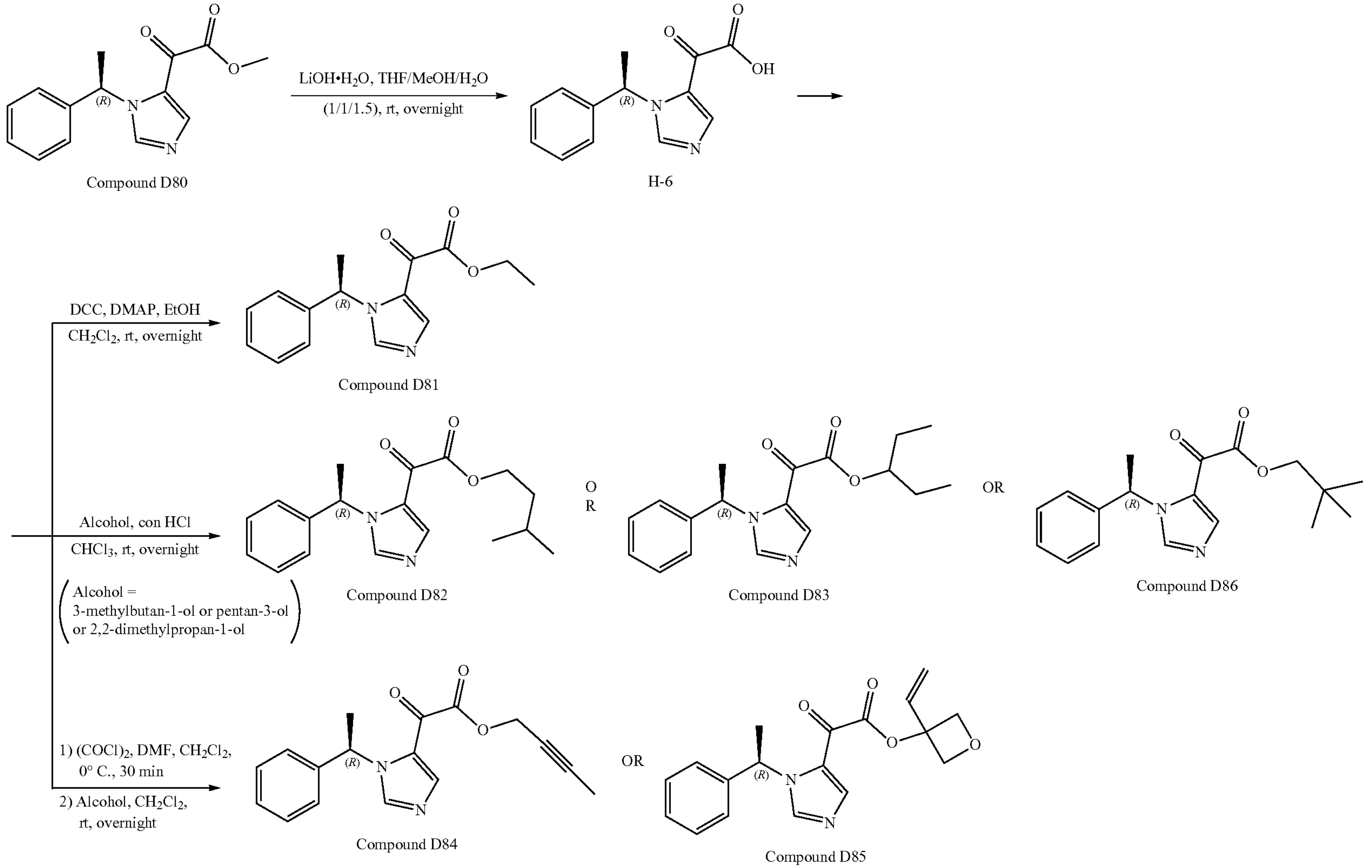
Compound D80
H-6
Compound D81
Compound D82
OR
Compound D83
OR
Compound D86
Compound D84
OR
Compound D85

At room temperature, LiOH·$H_2O$ (488 mg, 11.6 mmol) was added into the solution of D80 (1.5 g, 5.8 mmol) in THF/MeOH/$H_2O$ (14 mL, v/v/v=1/1/1.5), then the mixture was stirred at room temperature overnight. The reaction was monitored by TLC until completion. The reaction mixture was concentrated under reduced pressure. Water (10 mL) was poured into the residue. The mixture was adjusted pH to 4~5 with 1N HCl and extracted with dichloromethane (8×15 mL). The combined organic layers were dried over anhydrous sodium sulfate, filtered and concentrated to give the compound H-6 (1.1 g, yield 78%) as a grey solid. ESI[M+H]$^+$=245.0 Compound H-6 (244 mg, 1 mmol) and EtOH were condensed under the condition of DCC and DMAP to give target compound D81 (86 mg, yield 32%). ESI[M+H]$^+$= 273.1

$^1$H NMR (400 MHz, $CDCl_3$) δ 8.29 (s, 1H), 7.87 (s, 1H), 7.40-7.28 (m, 3H), 7.25-7.15 (m, 2H), 6.36 (q, J=7.0 Hz, 1H), 4.39 (q, J=7.1 Hz, 2H), 1.87 (d, J=7.1 Hz, 3H), 1.40 (t, J=7.1 Hz, 3H).

Compound H-6 (244 mg, 1 mmol) reacted with the corresponding alcohol under catalytic amount of concentrated hydrochloric acid to give target compounds D82, D83 and D86.

Compound D82: 84 mg, yield 27%, ESI[M+H]$^+$=315.1

$^1$H NMR (400 MHz, $CDCl_3$) δ 8.27 (d, J=6.7 Hz, 1H), 7.89 (s, 1H), 7.42-7.28 (m, 3H), 7.25-7.16 (m, 2H), 6.37 (q, J=7.0 Hz, 1H), 4.38-4.12 (m, 2H), 1.87 (d, J=7.1 Hz, 3H), 1.80-1.69 (m, 1H), 1.69-1.39 (m, 2H), 1.01-0.90 (m, 6H).

Compound D83: 73 mg, yield 23%, ESI[M+H]$^+$=315.0

$^1$H NMR (400 MHz, $CDCl_3$) δ 8.25 (s, 1H), 7.90 (s, 1H), 7.42-7.28 (m, 3H), 7.26-7.21 (m, 2H), 6.38 (q, J=7.0 Hz, 1H), 5.00 (p, J=6.3 Hz, 1H), 1.88 (d, J=7.1 Hz, 3H), 1.78-1.60 (m, 4H), 1.01-0.89 (m, 6H).

Compound D86: 133 mg, yield 42%, ESI[M+H]$^+$=315.1

$^1$H NMR (400 MHz, $CDCl_3$) δ 8.25 (s, 1H), 7.89 (s, 1H), 7.44-7.29 (m, 3H), 7.26-7.20 (m, 2H), 6.39 (q, J=7.1 Hz, 1H), 4.11-3.98 (m, 2H), 1.88 (d, J=7.1 Hz, 3H), 1.01 (s, 9H).

Compound H-6 (100 mg, 0.41 mmol) reacted with oxalyl chloride under catalytic amount DMF to give the corresponding acyl chloride, which was concentrated under reduced pressure to give the crude product. The crude product reacted with the corresponding alcohol using $CH_2Cl_2$ as solvent to give target compounds D84 and D85.

Compound D84: 11 mg, yield 9%, ESI[M+H]$^+$=297.1

$^1$H NMR (400 MHz, $CDCl_3$) δ 7.94 (s, 1H), 7.92 (s, 1H), 7.42-7.28 (m, 3H), 7.24-7.12 (m, 2H), 6.42 (q, J=6.9 Hz, 1H), 4.65 (q, J=17.7 Hz, 2H), 2.01-1.84 (m, 6H).

Compound D85: 16 mg, yield 12%, ESI[M+H]$^+$=339.1

$^1$H NMR (400 MHz, $CDCl_3$) δ 8.22 (s, 1H), 7.94 (s, 1H), 7.34-7.27 (m, 2H), 7.25-7.21 (m, 1H), 7.16-7.09 (m, 2H), 6.40 (q, J=6.9 Hz, 1H), 5.64 (t, J=6.6 Hz, 1H), 5.05-4.86 (m, 3H), 4.86-4.69 (m, 3H), 1.87 (d, J=7.1 Hz, 3H).

6. Preparation of Compounds D87, D88 and D90

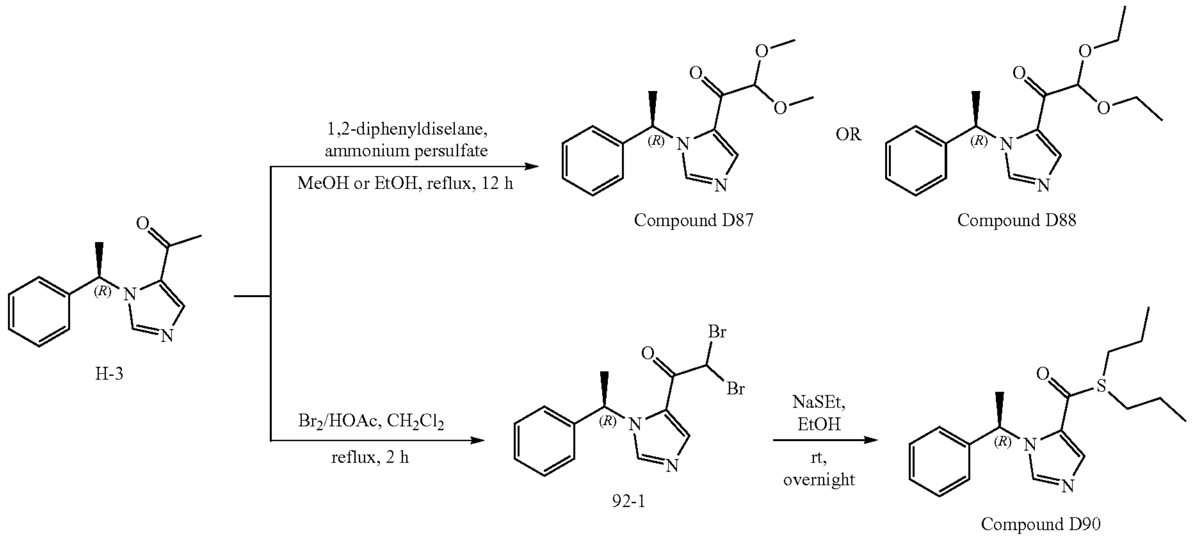

The compounds D87, D88 and D90 were prepared according to the operation method of preparing compounds D13, D14 and D15. The target compounds D87 and D88 were prepared by the reaction of H-3 with MeOH or EtOH under the conditions of 1,2-diphenyldiselane and ammonium persulfate. After bromination, H-3 reacted with NaSEt to give compound D90.

Compound D87: 63 mg, ESI[M+H]$^+$=275.0

$^1$H NMR (400 MHz, $CDCl_3$) δ 8.16 (s, 1H), 7.95 (s, 1H), 7.39-7.28 (m, 3H), 7.23-7.15 (m, 2H), 6.41 (q, J=7.1 Hz, 1H), 4.93 (s, 1H), 3.39 (s, 3H), 3.35 (s, 3H), 1.87 (d, J=7.1 Hz, 3H).

Compound D88: 168 mg, ESI[M+H]$^+$=303.0

$^1$H NMR (400 MHz, $CDCl_3$) δ 8.17 (s, 1H), 7.83 (s, 1H), 7.36-7.27 (m, 3H), 7.21-7.14 (m, 2H), 6.40 (q, J=7.1 Hz, 1H), 5.03 (s, 1H), 3.70-3.46 (m, 4H), 1.85 (d, J=7.1 Hz, 3H), 1.20 (d, J=7.1, 1.0 Hz, 6H).

Compound D90: 21 mg, ESI[M+H]$^+$=335.0

$^1$H NMR (400 MHz, $CDCl_3$) δ 8.19 (s, 1H), 7.85 (s, 1H), 7.34-7.27 (m, 2H), 7.22-7.18 (m, 1H), 7.16-7.09 (m, 2H), 6.40 (q, J=6.9 Hz, 1H), 5.23 (s, 1H), 2.79-2.39 (m, 4H), 1.86 (d, J=7.1 Hz, 3H), 1.19 (t, J=7.0 Hz, 6H).

7. Preparation of Compounds D89, D91 and D92

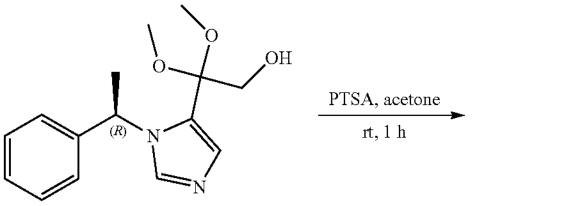

H-4

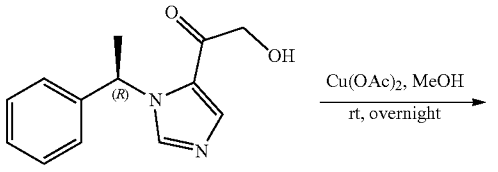

H-5

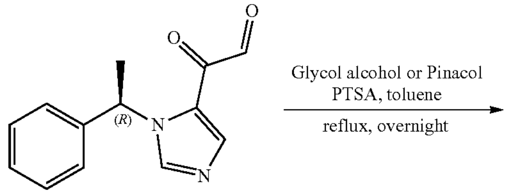

H-7

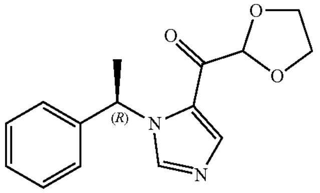

Compound D89

OR

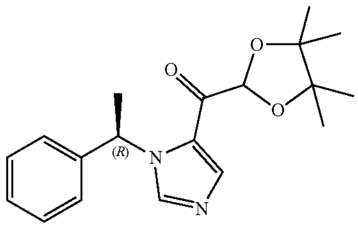

Compound D91

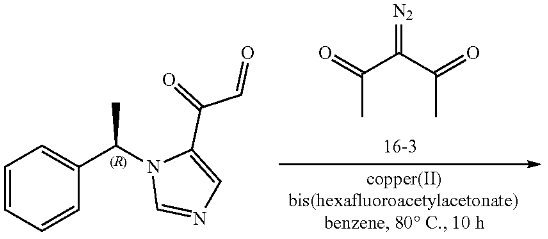

H-7

-continued

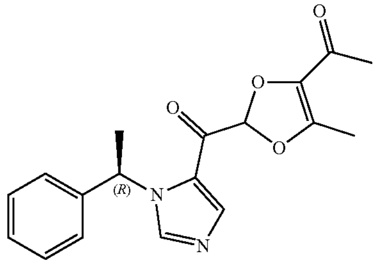

Compound D92

At room temperature, PTSA.$H_2O$ (826 mg, 4.34 mmol) was added into the solution of H-4 (400 mg, 1.45 mmol) in acetone (10 mL), then the mixture was stirred at room temperature for 1 hour. The reaction was monitored by TLC until completion. The mixture was quenched with ice-water (10 mL) and extracted with ethyl acetate (3×5 mL). The combined organic layers were washed with saturated brine (10 mL), dried over anhydrous sodium sulfate, filtered and concentrated under reduced pressure. The residue was purified by Prep-TLC (ethyl acetate/petroleum ether (v/v)=1/5) and the fraction with Rf=0.5~0.6 was collected to give the title compound H-5 (250 mg, yield 75%). ESI[M+H]$^+$231.0

H-5 was oxidized by $Cu(OAc)_2$ to give compound H-7, and then reacted with ethylene glycol or pinacol under the reflux condition of p-toluenesulfonic acid and toluene to give target compounds D89 and D91.

Compound D89: 42 mg, ESI[M+H]$^+$=273.0

$^1$H NMR (400 MHz, $CDCl_3$) δ 8.21 (s, 1H), 7.91 (s, 1H), 7.34-7.27 (m, 2H), 7.25-7.21 (m, 1H), 7.15-7.09 (m, 2H), 6.41 (q, J=6.9 Hz, 1H), 5.01 (p, J=6.3 Hz, 1H), 4.06-3.76 (m, 4H), 1.88 (d, J=7.1 Hz, 3H).

Compound D91: 12 mg, ESI[M+H]$^+$=329.3

$^1$H NMR (400 MHz, $CDCl_3$) δ 8.18 (s, 1H), 7.90 (s, 1H), 7.34-7.27 (m, 2H), 7.26-7.24 (m, 1H), 7.16-7.09 (m, 2H), 6.41 (q, J=6.9 Hz, 1H), 5.03 (s, 1H), 1.85 (d, J=7.1 Hz, 3H), 1.20 (s, 12H).

Compound D92 was prepared according to the operation method of preparing compound D16 described in Example 4.

Compound D92: 24 mg, ESI[M+H]$^+$=327.2

$^1$H NMR (400 MHz, $CDCl_3$) δ 8.28 (s, 1H), 7.99 (s, 1H), 7.34-7.27 (m, 2H), 7.26-7.21 (m, 1H), 7.16-7.09 (m, 2H), 6.65 (s, 1H), 6.40 (q, J=6.9 Hz, 1H), 2.21 (s, 6H), 1.85 (d, J=7.1 Hz, 3H).

Example 12 Preparation of Compounds D93~D107
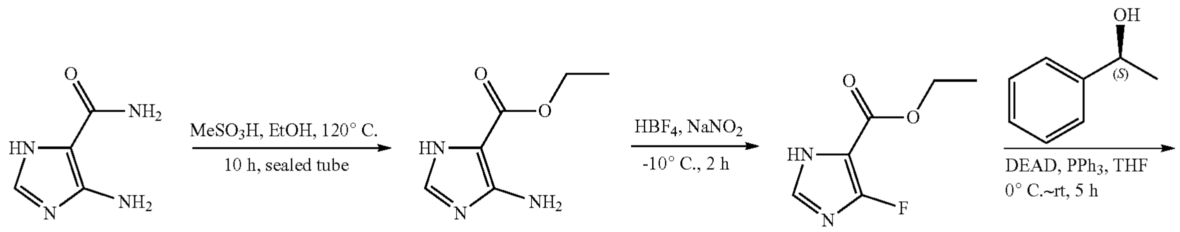
I-1 I-2
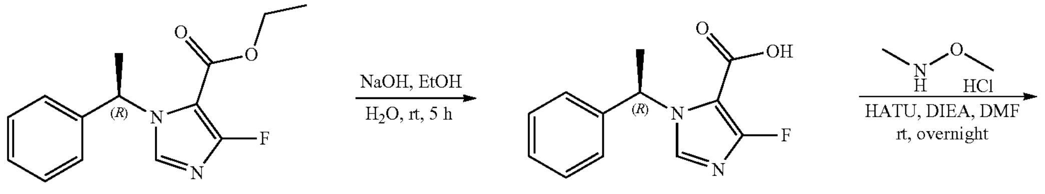
I-3 I-4
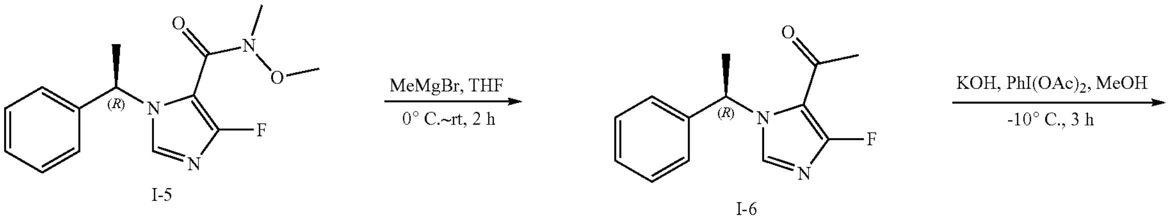
I-5 I-6
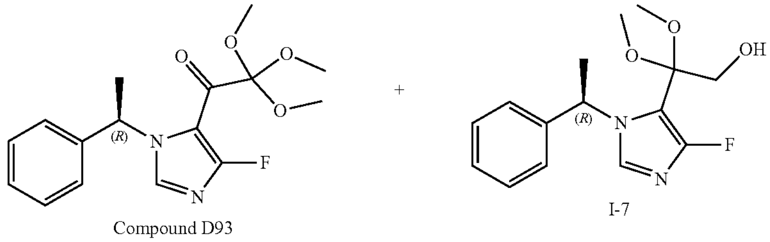
Compound D93 + I-7
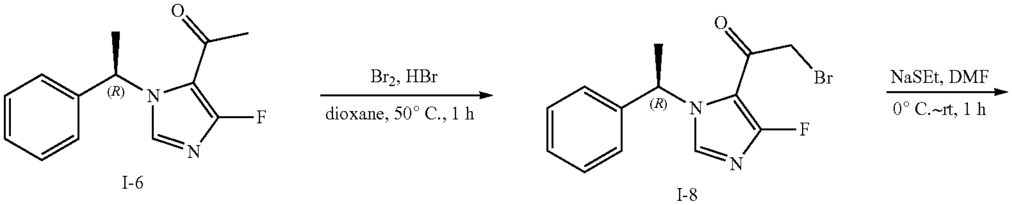
I-6 I-8
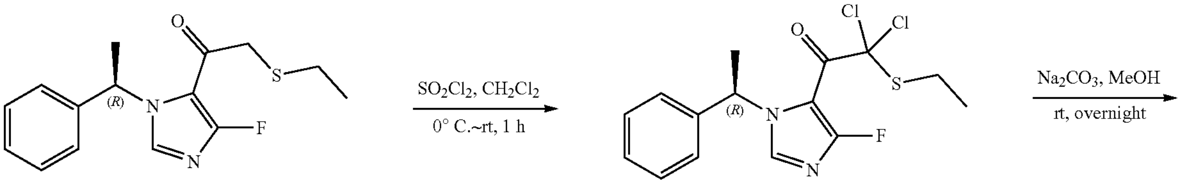
I-9 I-10
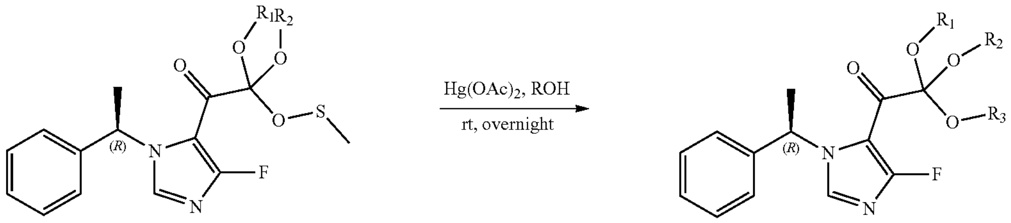
I-11 Compound D94~D100

-continued
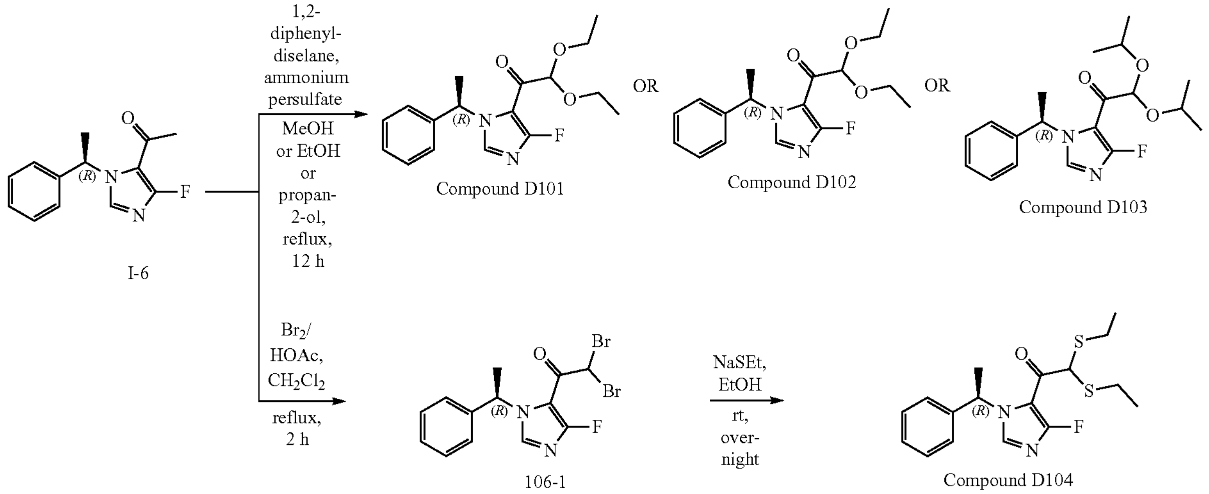
I-6
Compound D101
Compound D102
Compound D103
106-1
Compound D104
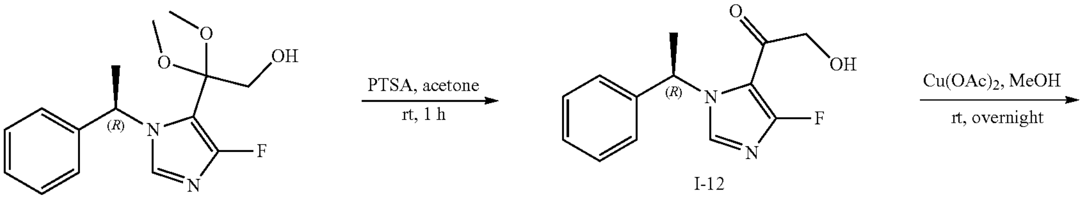
I-7
I-12
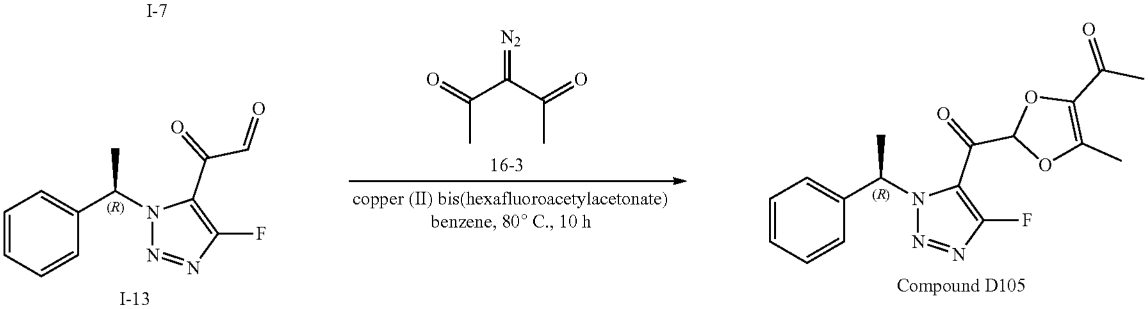
I-13
Compound D105
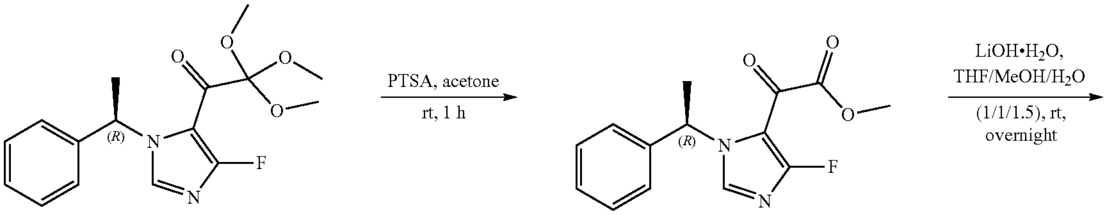
compound D93
I-14
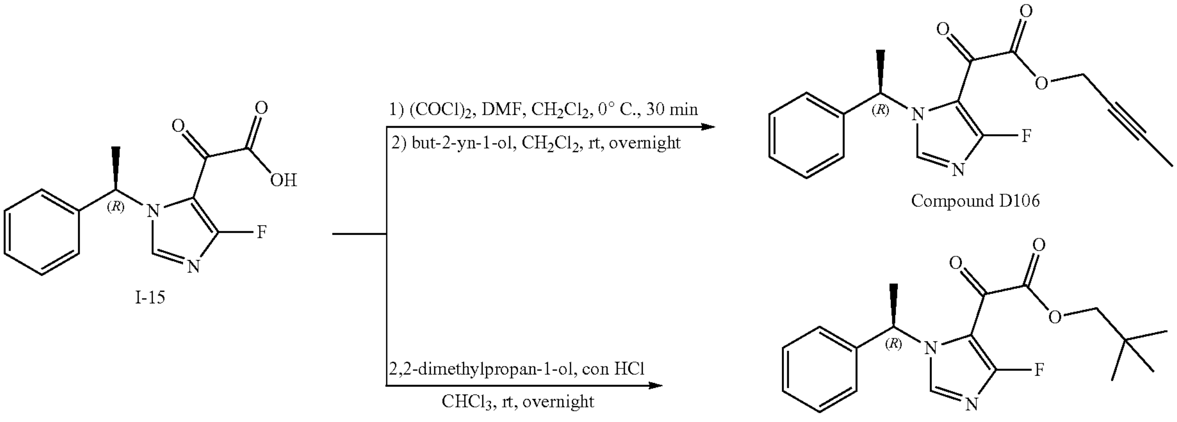
I-15
Compound D106
Compound D107

1. Preparation of ethyl 4-amino-1H-imidazole-5-carboxylate (I-1)

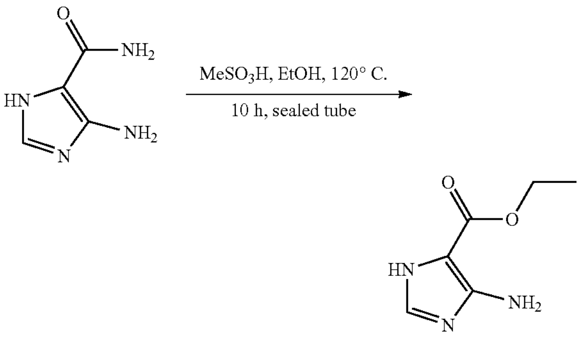

I-1

At room temperature, 4-amino-1H-imidazole-5-carboxamide (3.0 g, 23.8 mmol), ethanol (30 mL) and $MeSO_3H$ (6 mL) were successively added into the 200 mL sealed tube, then the reaction mixture was allowed to react at 120° C. for 10 hrs. The reaction was monitored by TLC until completion. The reaction mixture was concentrated under reduced pressure, adjusted pH to 7~8 with saturated sodium bicarbonate solution and extracted with ethyl acetate (3×150 mL). The combined organic layers were washed with saturated brine (100 mL), dried over anhydrous sodium sulfate, filtered and concentrated under reduced pressure to give compound I-1 (3.0 g, yield 81%) as a white solid.

2. Preparation of ethyl 4-fluoro-1H-imidazole-5-carboxylate (I-2)

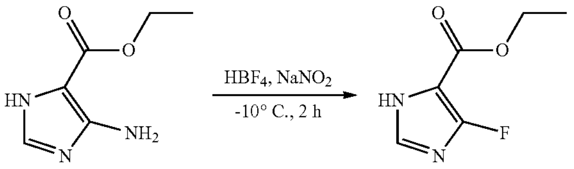

I-1 I-2

In an ice-salt bat, I-1 (250 mg, 1.61 mmol) was dissolved in $HBF_4$ (40%) at −10° C., and then the solution of $NaNO_2$ (117 mg, 1.69 mmol) in water (0.15 mL) was added into the mixture. The mixture was allowed to react under the irradiation of a mercury lamp (302 nm) for 2 hrs. The reaction was monitored by TLC until completion, and then the reaction solution was adjusted pH to 7~8 with 1N NaOH solution in an ice-water bath. The mixture was extracted with ethyl acetate (3×10 mL). The combined organic layers were washed with saturated brine (10 mL), dried over anhydrous sodium sulfate, filtered and concentrated under reduced pressure. The crude product was purified by silica gel column chromatography (ethyl acetate/petroleum ether (v/v)=1/20~1/1), with TLC (ethyl acetate/petroleum ether (v/v)=1/2) monitoring, and collecting the fraction with Rf=0.4~0.5 to give compound I-2 (100 mg, yield 39%) as colorless oil.

3. Preparation of (R)-Ethyl 4-fluoro-1-(1-phenylethyl)-1H-imidazole-5-carboxylate (I-3)

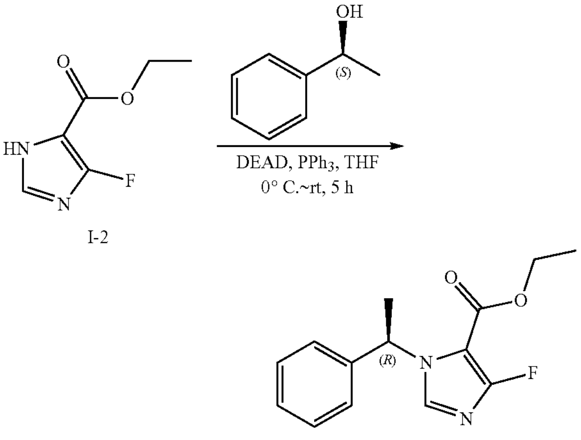

I-2

I-3

In an ice-water bath, (S)-1-phenylethan-1-ol (134 mg, 1.1 mmol) was added into the mixture of I-2 (158 mg, 1.1 mmol) and $PPh_3$ (346 mg, 1.32 mmol) in THF (10 mL) at 0° C., then the solution of DEAD (230 mg, 1.32 mmol) in THF (1 mL) was added dropwise into the mixture at the rate of 0.5 mmol/min After addition, the reaction mixture was warmed slowly to room temperature and stirred for 5 hrs. The reaction was monitored by TLC until completion. The reaction mixture was concentrated under reduced pressure. The residue was purified by silica gel column chromatography (ethyl acetate/petroleum ether (v/v)=1/3), with TLC (ethyl acetate/petroleum ether (v/v)=1/1) monitoring, and collecting the fraction with Rf=0.5~0.6 to give the product I-3 (70 mg, yield 27%) as colorless oil. ESI$[M+H]^+$=263.0 $^1H$ NMR (400 MHz, $CDCl_3$) δ 7.42-7.28 (m, 4H), 7.23-7.16 (m, 2H), 6.28 (q, J=7.1 Hz, 1H), 4.39-4.17 (m, 2H), 1.84 (d, J=7.1 Hz, 3H), 1.32 (t, J=7.1 Hz, 3H).

4. Preparation of (R)-4-fluoro-1-(1-phenylethyl)-1H-imidazole-5-carboxylic acid (I-4)

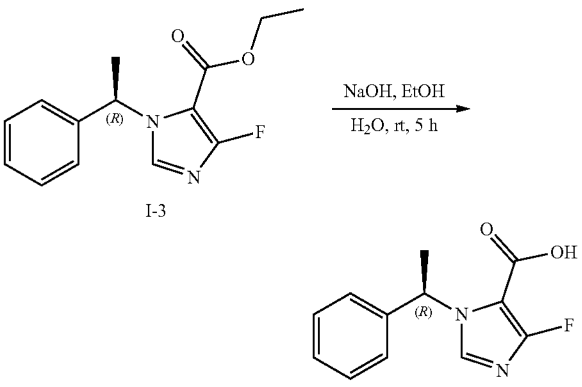

I-3

I-4

At room temperature, the solution of NaOH (21.6 mg, 0.54 mmol) in water (5 mL) was added into the solution of I-3 (70 mg, 0.27 mmol) in ethanol (5 mL), then the mixture was stirred at room temperature for 5 hrs. The reaction was monitored by TLC until completion. The reaction mixture was concentrated under reduced pressure, cooled and adjusted pH to 4~5 with 1N HCl. The mixture was extracted with ethyl acetate (3×20 mL). The combined organic layers were washed with saturated brine (20 mL), dried over anhydrous sodium sulfate, filtered and concentrated to give the compound I-4 (58 mg, yield 93%) as a grey solid. ESI[M+H]$^+$=235.0

$^1$H NMR (400 MHz, $CDCl_3$) δ 7.43-7.28 (m, 4H), 7.24-7.16 (m, 2H), 6.24 (q, J=7.0 Hz, 1H), 1.85 (d, J=7.1 Hz, 3H).

5. Preparation of (R)-4-fluoro-N-methoxy-N-methyl-1-(1-phenylethyl)-1H-imidazole-5-carboxamide (I-5)

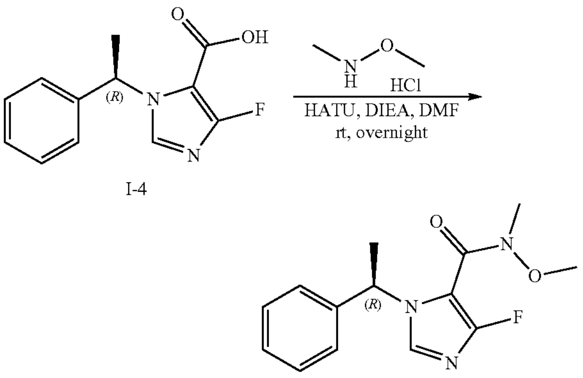

I-4

I-5

At room temperature, I-4 (4.4 g, 18.8 mmol), N, O-dimethylhydroxylamine hydrochloride (2.8 g, 28.7 mmol), DIEA (3.7 g, 28.6 mmol) and HATU (10.9 g, 28.7 mmol) were dissolved in DMF (50 mL), then the mixture was stirred at room temperature overnight. The reaction was monitored by TLC until completion. The mixture was quenched with water (100 mL) and extracted with ethyl acetate (4×30 mL). The combined organic layers were dried over anhydrous sodium sulfate, filtered and concentrated under reduced pressure. The residue was purified by silica gel column chromatography (ethyl acetate/petroleum ether (v/v)=1/10~1/3), with TLC (ethyl acetate/petroleum ether (v/v)=1/1) monitoring, and collecting the fraction with Rf=0.5-0.6 to give the title compound I-5 (4.7 g, yield 90%) as a white solid. ESI[M+H]$^+$=278.1

6. Preparation of (R)-1-(4-fluoro-1-(1-phenylethyl)-1H-imidazol-5-yl)ethan-1-one (I-6)

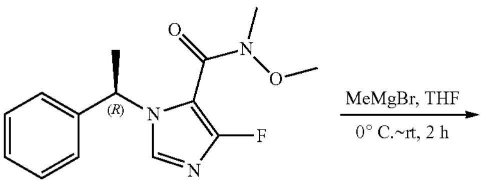

I-5

-continued

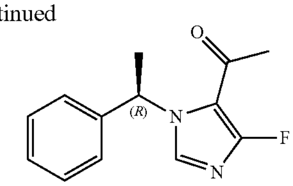

I-6

At room temperature, I-5 (4.7 g, 16.9 mmol) was dissolved in anhydrous THF (50 mL). The mixture was cooled to 0° C. with an ice-water bath. Methylmagnesium bromide (33.9 mL, 1 mol/L in THF, 33.9 mmol) was added dropwise into the mixture at the rate of 3 mmol/min, then the mixture was reacted at room temperature for 2 hrs. The reaction was monitored by TLC until completion. The mixture was cooled to 0° C. with ice-water bath, quenched with saturated ammonium chloride solution (100 mL) and extracted with ethyl acetate (3×20 mL). The combined organic layers were dried over anhydrous sodium sulfate, filtered and concentrated under reduced pressure. The residue was purified by silica gel column chromatography (ethyl acetate/petroleum ether (v/v)=1/20~1/10), with TLC (ethyl acetate/petroleum ether (v/v)=1/5) monitoring, and collecting the fraction with Rf=0.5~0.6 to give the title compound I-6 (3.9 g, yield 99%) as a white solid. ESI[M+H]$^+$=233.1

7. Preparation of D93 and Intermediate I-7

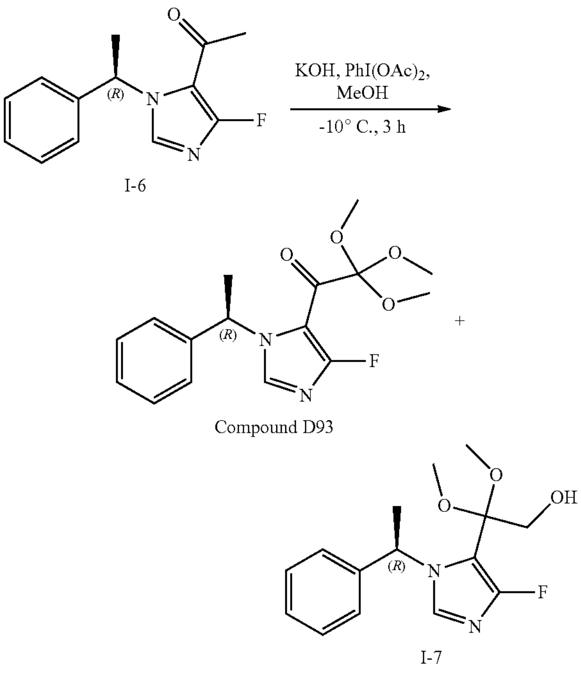

I-6

Compound D93

I-7

At room temperature, I-6 (3.9 g, 16.8 mmol) and PhI$(OAc)_2$ (8.1 g, 25.1 mmol) were dissolved in methanol (30 mL), then the mixture was cooled to −10° C. with an ice-salt bath. KOH (11.3 g, 201.4 mol) was added in portions into the mixture within 50 mins, then the reaction mixture was reacted at −10° C. for 3 hrs. The reaction was monitored by TLC until completion. The reaction mixture was quenched with saturated brine (100 mL) and extracted with ethyl acetate (3×50 mL). The combined organic layers were dried over anhydrous sodium sulfate, filtered, and concentrated under reduced pressure. The residue was purified by silica gel column chromatography (ethyl acetate/petroleum ether (v/v)=1/20~1/5), with TLC (ethyl acetate/petroleum ether (v/v)=1/3) monitoring, and collecting the fraction with Rf=0.3~0.6 to give compound I-7 (684 mg, yield 14%) as colorless oil, ESI[M+H]$^+$=295.2 and the title compound D93 (52 mg, yield 0.96%), ESI[M+H]$^+$=323.0

$^1$H NMR (400 MHz, $CDCl_3$) δ 7.44 (d, J=1.5 Hz, 1H), 7.42-7.30 (m, 3H), 7.29-7.23 (m, 2H), 6.23 (q, J=7.0 Hz, 1H), 3.93 (s, 3H), 3.49 (s, 6H), 1.86 (d, J=7.0 Hz, 3H).

8. Preparation of Compounds D94~D107

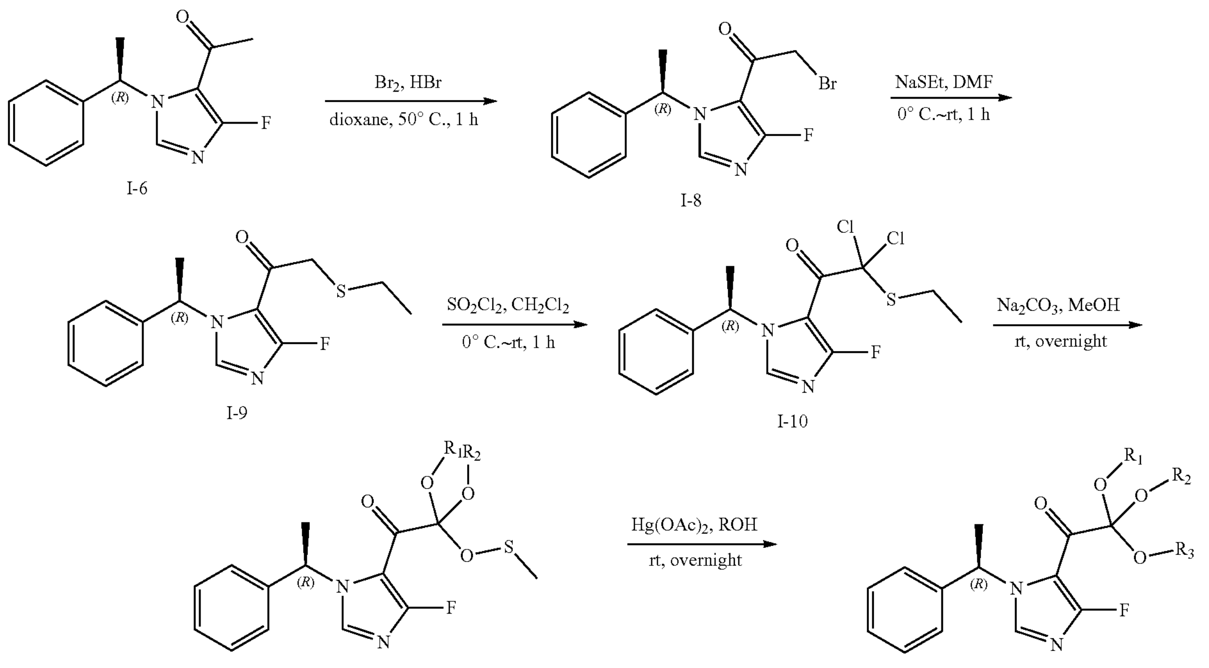

I-6

I-8

I-9

I-10

I-11

Compound D94~D100

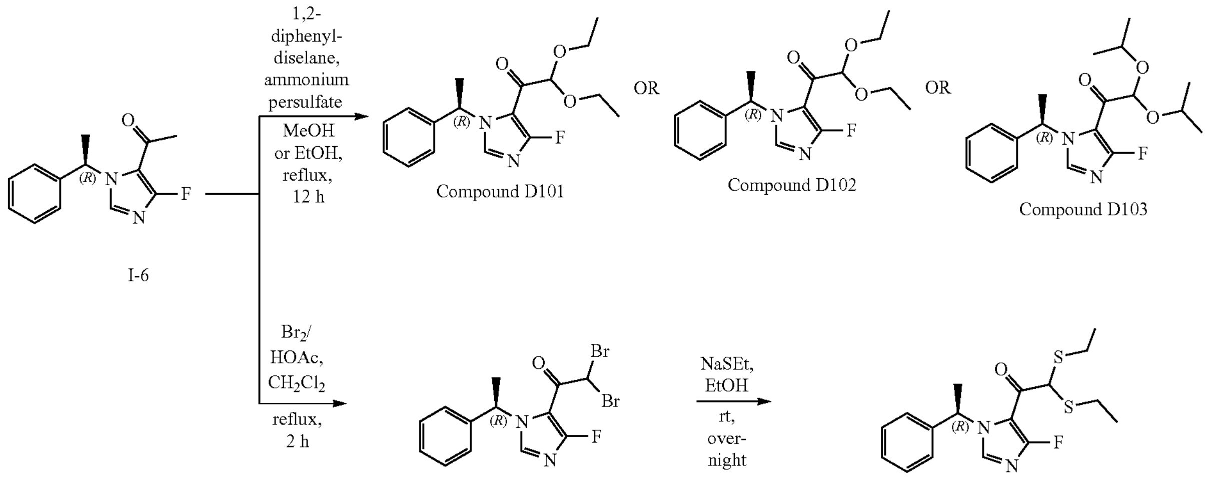

Compound D101

OR

Compound D102

OR

Compound D103

I-6

106-1

Compound D104

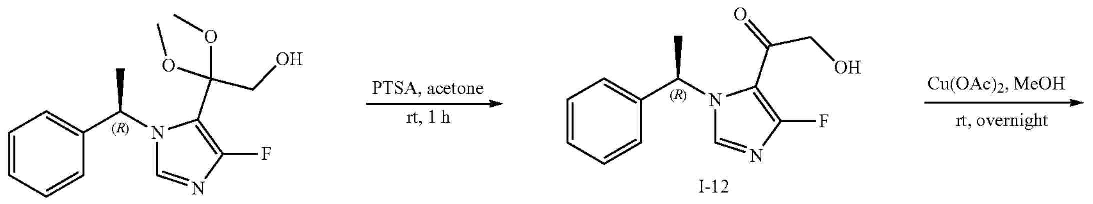

I-7

I-12

-continued

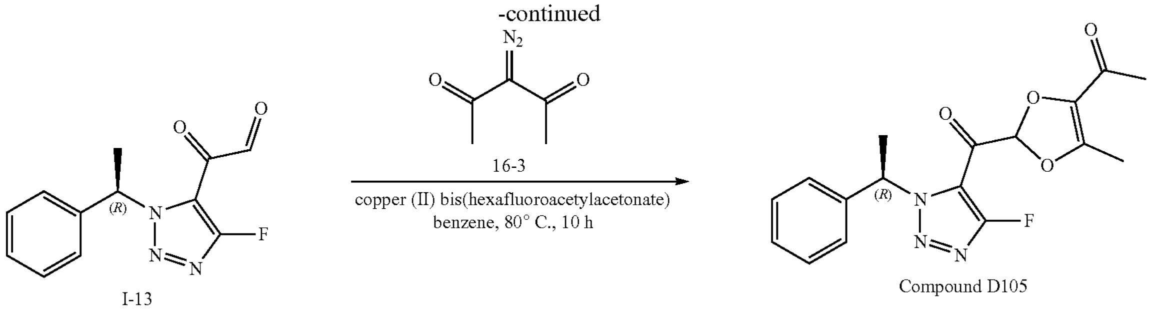

I-13

Compound D105

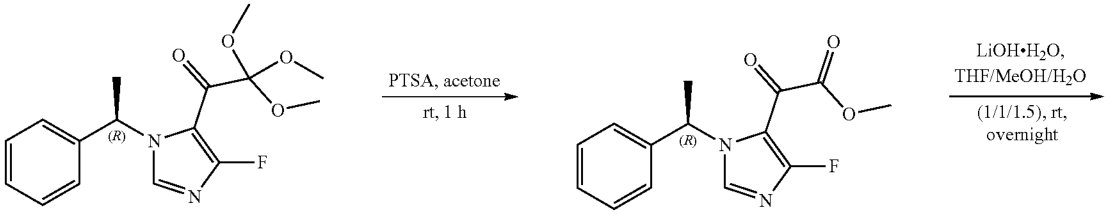

compound D93

I-14

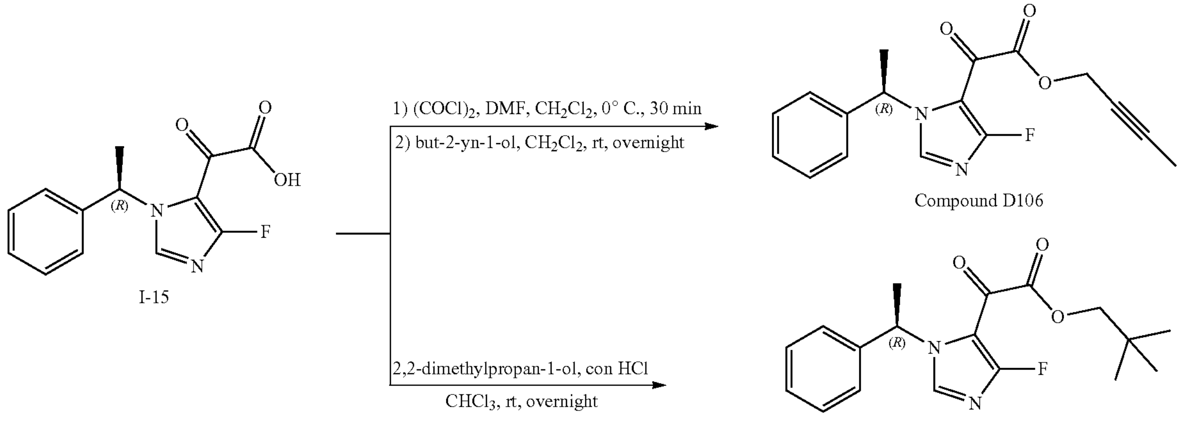

I-15

Compound D106

Compound D107

The title compounds D94~D100 were prepared according to the operation method of preparing compounds D2~D10 described in Example 2.

The title compounds D101~D105 were prepared according to the operation method of preparing compounds D13~D16 described in Example 4.

The title compounds D106~D107 were prepared according to the operation method of preparing compounds D84 and D86 described in Example 11.

Compound D94: 19 mg, ESI$[M+H]^+$=351.1

$^1$H NMR (400 MHz, $CDCl_3$) δ 7.44 (d, J=1.5 Hz, 1H), 7.41-7.30 (m, 3H), 7.28-7.23 (m, 2H), 6.23 (q, J=7.0 Hz, 1H), 4.45-4.40 (m, 2H), 3.94 (s, 1H), 3.76-3.72 (m, 1.5H), 3.54 (s, 2.5H), 1.86 (d, J=7.0 Hz, 3H), 1.43-1.41 (m, 3H), 1.27-1.24 (m, 3H).

Compound D95: 12 mg, ESI$[M+H]^+$=365.1

$^1$H NMR (400 MHz, $CDCl_3$) δ 7.47 (d, J=1.5 Hz, 1H), 7.45-7.30 (m, 3H), 7.27-7.23 (m, 2H), 6.25 (q, J=7.0 Hz, 1H), 4.42-4.41 (m, 1H), 3.93 (s, 1H), 3.75-3.72 (m, 1.5H), 3.51 (s, 2.5H), 1.88 (d, J=7.0 Hz, 3H), 1.43-1.40 (m, 4.5H), 1.25-1.20 (m, 4.5H).

Compound D96: 22 mg, ESI$[M+H]^+$=321.0

$^1$H NMR (400 MHz, $CDCl_3$) δ 7.45 (d, J=1.5 Hz, 1H), 7.42-7.31 (m, 3H), 7.29-7.23 (m, 2H), 6.23 (q, J=7.0 Hz, 1H), 4.07-3.78 (m, 4H), 3.26 (s, 3H), 1.86 (d, J=7.0 Hz, 3H).

Compound D97: 32 mg, ESI$[M+H]^+$=361.0

$^1$H NMR (400 MHz, $CDCl_3$) δ 7.46 (d, J=1.5 Hz, 1H), 7.44-7.33 (m, 3H), 7.30-7.24 (m, 2H), 6.24 (q, J=7.0 Hz, 1H), 4.22-4.18 (m, 1.5H), 3.97 (s, 2H), 3.48 (s, 3H), 3.28-3.09 (m, 1.5H), 2.05-1.82 (m, 6H).

Compound D98: 42 mg, ESI$[M+H]^+$=359.0

$^1$H NMR (400 MHz, $CDCl_3$) δ 7.44 (d, J=1.5 Hz, 1H), 7.41-7.30 (m, 3H), 7.28-7.23 (m, 2H), 6.23 (q, J=7.0 Hz, 1H), 4.04-3.78 (m, 6H), 2.03-1.82 (m, 6H).

Compound D99: 18 mg, ESI$[M+H]^+$=379.1

$^1$H NMR (400 MHz, $CDCl_3$) δ 7.46 (d, J=1.5 Hz, 1H), 7.42-7.30 (m, 3H), 7.27-7.23 (m, 2H), 6.22 (q, J=7.0 Hz, 1H), 4.03 (s, 1.5H), 3.95 (s, 1H), 3.54 (s, 4.5H), 3.30 (s, 1H), 1.86 (d, J=7.0 Hz, 3H), 1.05 (s, 5.5H), 0.94 (s, 3.5H).

Compound D100: 16 mg, ESI$[M+H]^+$=377.1

$^1$H NMR (400 MHz, $CDCl_3$) δ 7.45 (d, J=1.5 Hz, 1H), 7.43-7.32 (m, 3H), 7.29-7.23 (m, 2H), 6.24 (q, J=7.0 Hz, 1H), 4.07-3.78 (m, 5H), 3.31 (s, 1H), 1.85 (d, J=7.0 Hz, 3H), 1.03 (s, 5.5H), 0.96 (s, 3.5H).

Compound D101: 46 mg, ESI$[M+H]^+$=321.1

$^1$H NMR (400 MHz, $CDCl_3$) δ 7.42 (s, 1H), 7.37-7.28 (m, 3H), 7.24-7.17 (m, 2H), 6.34 (q, J=6.9 Hz, 1H), 5.28 (d, J=1.8 Hz, 1H), 3.88-3.24 (m, 4H), 1.83 (d, J=7.1 Hz, 3H), 1.25 (t, J=7.1 Hz, 3H), 1.12 (t, J=7.1 Hz, 3H).

Compound D102: 27 mg, ESI$[M+H]^+$=293.0

$^1$H NMR (400 MHz, $CDCl_3$) δ 7.48 (d, J=1.5 Hz, 1H), 7.44-7.30 (m, 3H), 7.29-7.23 (m, 2H), 6.23 (q, J=7.0 Hz, 1H), 4.87 (s, 1H), 3.36 (s, 3H), 3.32 (s, 3H), 1.85 (d, J=7.0 Hz, 3H).

Compound D103: 31 mg, ESI[M+H]$^+$=349.2

$^1$H NMR (400 MHz, $CDCl_3$) δ 7.47 (d, J=1.5 Hz, 1H), 7.43-7.30 (m, 3H), 7.29-7.23 (m, 2H), 6.27 (q, J=7.0 Hz, 1H), 5.00 (s, 1H), 3.98-3.90 (m, 2H), 1.87 (d, J=7.0 Hz, 3H), 1.18-1.15 (m, 12H).

Compound D104: 28 mg, ESI[M+H]$^+$=353.0

$^1$H NMR (400 MHz, $CDCl_3$) δ 7.45 (d, J=1.5 Hz, 1H), 7.42-7.30 (m, 3H), 7.28-7.23 (m, 2H), 6.23 (q, J=7.0 Hz, 1H), 5.35 (d, J=1.8 Hz, 1H), 2.78-2.39 (m, 4H), 1.85 (d, J=7.0 Hz, 3H), 1.27 (t, J=7.1 Hz, 3H), 1.20 (t, J=7.1 Hz, 3H).

Compound D105: 37 mg, ESI[M+H]$^+$=345.3

$^1$H NMR (400 MHz, $CDCl_3$) δ 7.44 (d, J=1.5 Hz, 1H), 7.41-7.30 (m, 3H), 7.28-7.23 (m, 2H), 6.68 (s, 1H), 6.23 (q, J=7.0 Hz, 1H), 2.23 (s, 6H), 1.86 (d, J=7.0 Hz, 3H).

Compound D106: 28 mg, ESI[M+H]$^+$=315.0

$^1$H NMR (400 MHz, $CDCl_3$) δ 7.46 (d, J=1.5 Hz, 1H), 7.44-7.30 (m, 3H), 7.29-7.23 (m, 2H), 6.23 (q, J=7.0 Hz, 1H), 4.65 (q, J=17.7 Hz, 2H), 2.01-1.84 (m, 6H).

Compound D107: 35 mg, ESI[M+H]$^+$=333.0

$^1$H NMR (400 MHz, $CDCl_3$) δ 7.43 (d, J=1.5 Hz, 1H), 7.40-7.30 (m, 3H), 7.29-7.23 (m, 2H), 6.21 (q, J=7.0 Hz, 1H), 4.11-3.99 (m, 2H), 1.88 (d, J=7.1 Hz, 3H), 1.00 (s, 9H).

Example 13 Preparation of Compound D108

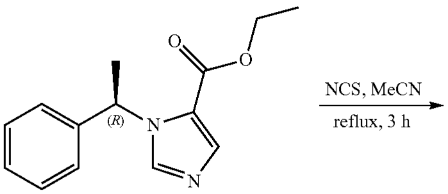

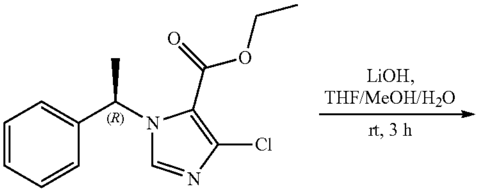

108-1

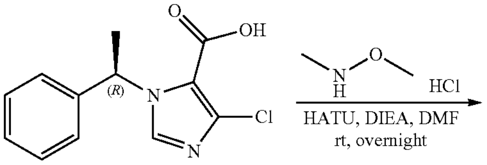

108-2

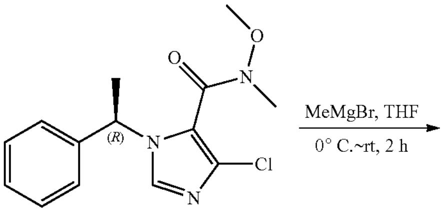

108-3

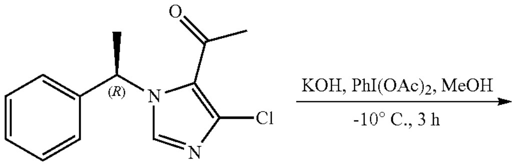

108-4

-continued

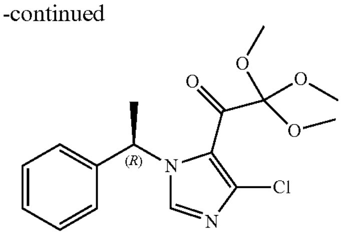

Compound D108

1. Preparation of ethyl (R)-4-chloro-1-(1-phenylethyl)-1H-imidazole-5-carboxylate (108-1)

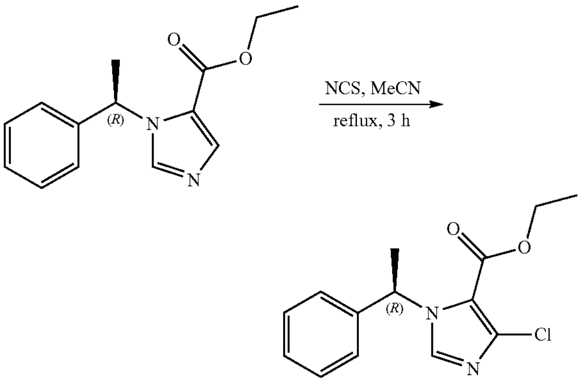

108-1

At room temperature, ethyl (R)-1-(1-phenylethyl)-1H-imidazole-5-carboxylate (5.0 g, 20.5 mmol) and NCS (3.3 g, 24.7 mmol) were dissolved in acetonitrile (50 mL), then the reaction mixture was heated to reflux for 3 hrs. The reaction was monitored by TLC until completion. The reaction mixture was cooled to room temperature, quenched with water (100 mL) and extracted with ethyl acetate (3×20 mL). The combined organic layers were washed with saturated brine (50 mL), dried over anhydrous sodium sulfate, filtered and concentrated under reduced pressure to give the crude colorless oil. The oil was purified by silica gel column chromatography (ethyl acetate/petroleum ether (v/v)=1/200~1/50), with TLC (ethyl acetate/petroleum ether (v/v)=1/30) monitoring, and collecting the fraction to give compound 108-1 (1.56 g, yield 39%). ESI[M+H]$^+$=279.0, 175.1

$^1$H NMR (400 MHz, $CDCl_3$) δ 7.72 (s, 1H), 7.38-7.27 (m, 3H), 7.21-7.14 (m, 2H), 6.73 (q, J=7.1 Hz, 1H), 4.29 (q, J=7.1 Hz, 2H), 1.98 (d, J=7.2 Hz, 3H), 1.34 (t, J=7.1 Hz, 3H).

2. Preparation of Compound D108

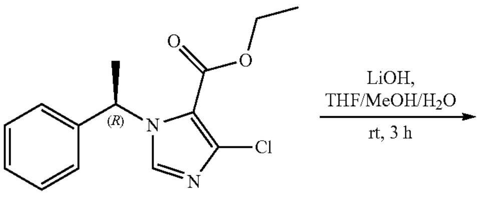

108-1

-continued

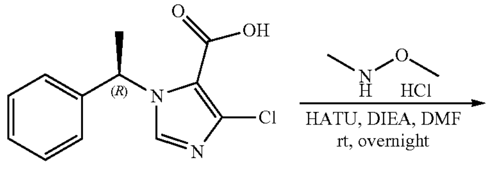

108-2

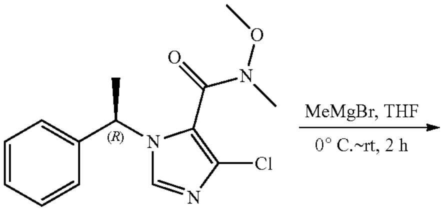

108-3

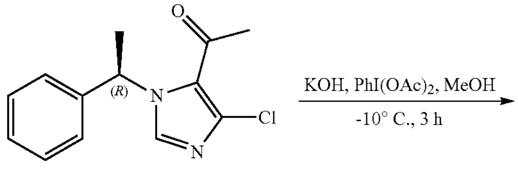

108-4

-continued

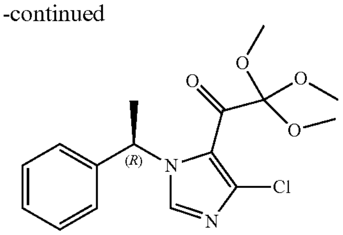

Compound D108

The intermediate compounds 108-2~108-4 were prepared according to the operation method of preparing intermediate compounds 1-4, 1-5 and 1-6 described in Example 12.

The title compound D108 was prepared according to the operation method of preparing compound D93 described in Example 12, using 108-4 as the raw material.

4.6 g of compound 108-1 was used as the starting material to finally obtain the target compound D108 (38 mg, yield 0.68% four steps). ESI[M+H]$^+$=339.0

$^1$H NMR (400 MHz, $CDCl_3$) δ 8.23 (s, 0.48H), 8.22 (s, 0.56H), 7.40-7.27 (m, 3H), 7.22-7.10 (m, 2H), 6.73-6.62 (m, 0.50H), 6.62-6.52 (m, 0.48H), 3.94 (s, 1H), 3.49 (s, 3H), 3.22 (s, 5H), 2.02 (d, J=7.1 Hz, 1.5H), 1.98 (d, J=7.2 Hz, 1.5H).

Example 14 Preparation of Compounds D109~118

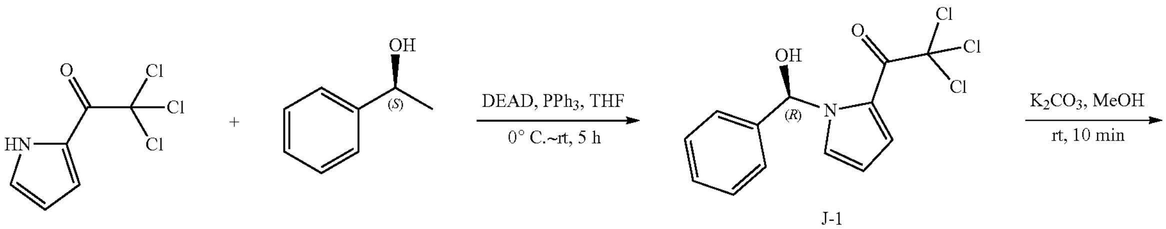

J-1

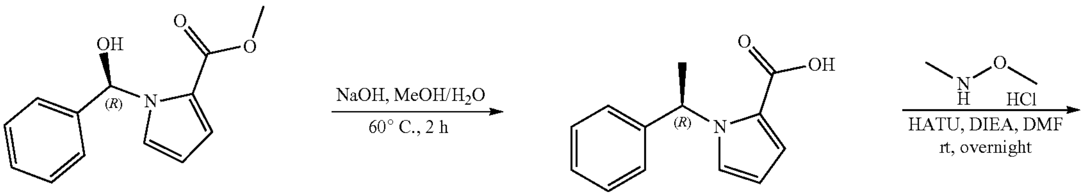

J-2

J-3

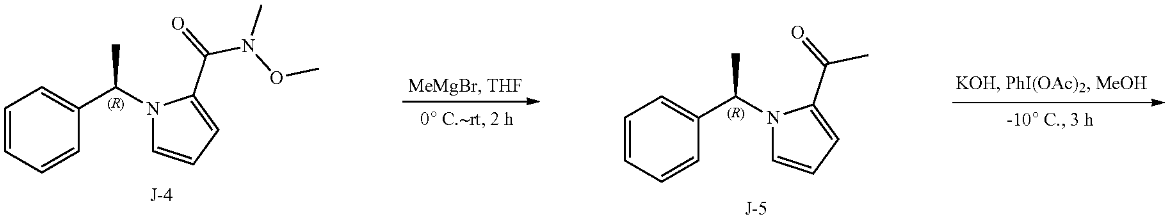

J-4

J-5

-continued
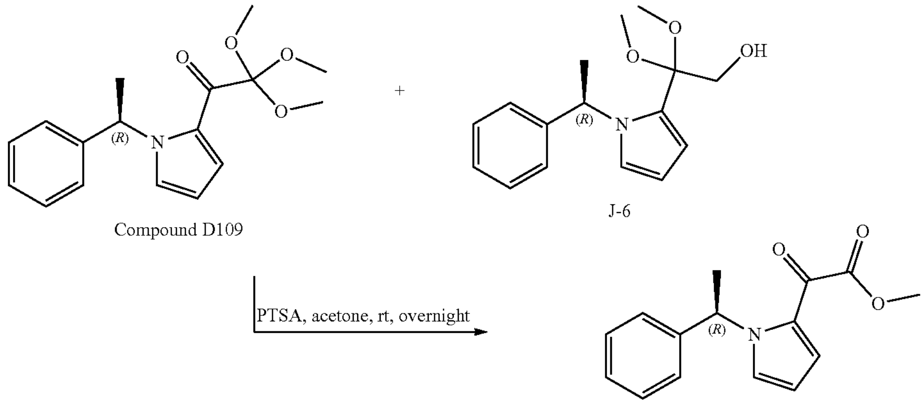
Compound D109
J-6
Compound D117
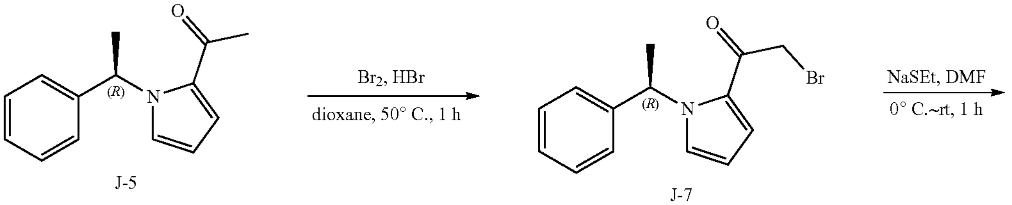
J-5
J-7
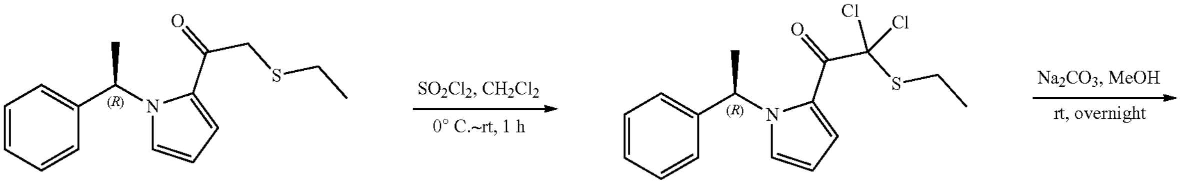
J-8
J-9
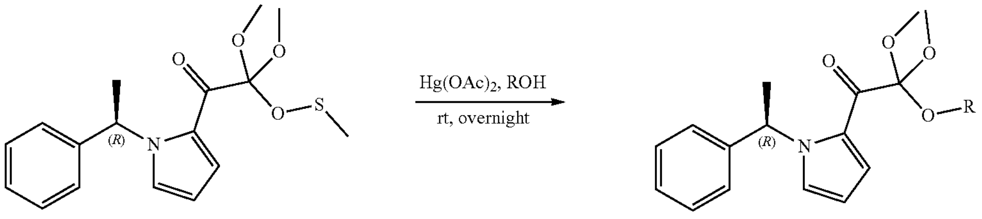
Compound D110
Compound D111~D116
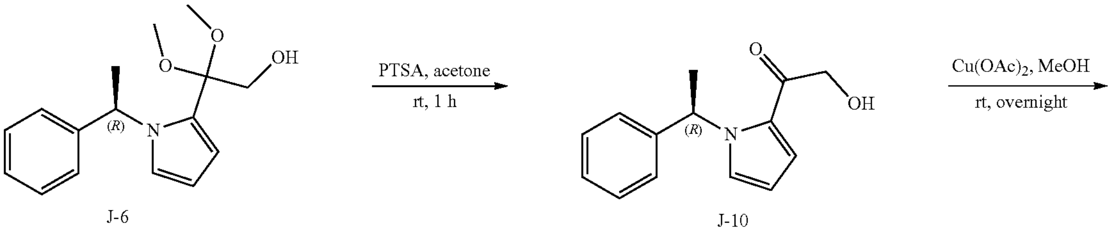
J-6
J-10
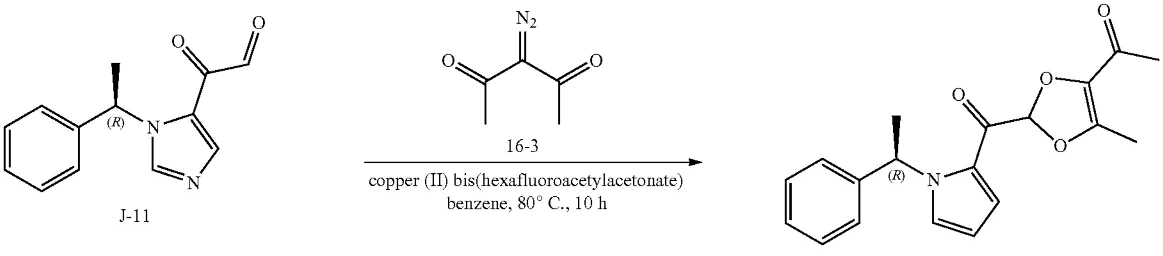
J-11
Compound D118

1. Preparation of (R)-2,2,2-trichloro-1-(1-(1-phenylethyl)-1H-pyrrol-2-yl)ethan-1-one (J-1)

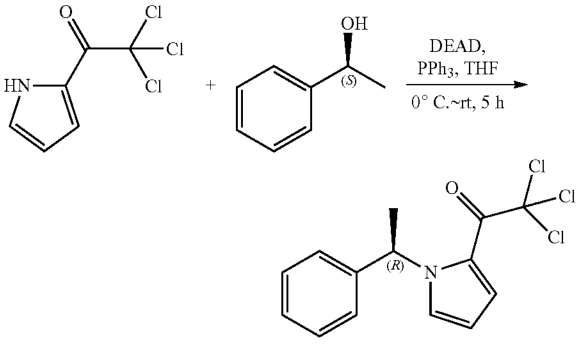

J-1

At room temperature, (S)-1-phenylethan-1-ol (1.7 g, 14.1 mmol) was added into the mixture of 2,2,2-trichloro-1-(1H-pyrrol-2-yl)ethan-1-one (3.0 g, 14.1 mmol) and $PPh_3$ (4.5 g, 17.0 mmol) in anhydrous THF (20 mL) under nitrogen protection, then the solution of DEAD (0.44 mL, 17.0 mmol) was added dropwise into the mixture at the rate of 1 mmol/min. After addition, the reaction mixture was stirred at room temperature for 5 hrs. The reaction was monitored by TLC until completion. The reaction mixture was quenched with saturated ammonium chloride solution (20 mL) and extracted with ethyl acetate (3×15 mL). The combined organic layers were washed with saturated brine (50 mL), dried over anhydrous sodium sulfate, filtered and concentrated under reduced pressure to give crude product. The residue was purified by silica gel column chromatography (ethyl acetate/petroleum ether (v/v)=1/100~1/15), with TLC (ethyl acetate/petroleum ether (v/v)=1/15) monitoring, and collecting the fraction with Rf=0.6~0.7 to give J-1 (2.66 g, yield 60%) as colorless oil.

2. Preparation of methyl (R)-1-(1-phenylethyl)-1H-pyrrole-2-carboxylate (J-2)

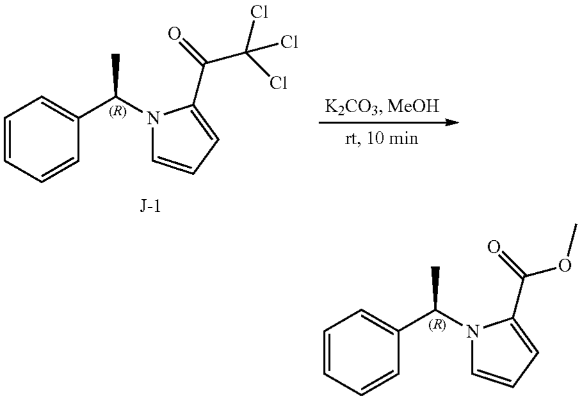

J-1

J-2

At room temperature, J-1 (2.3 g, 7.3 mmol) and $K_2CO_3$ (4.0 g, 29.2 mmol) were dissolved in methanol (20 mL), then the mixture was stirred at room temperature for 10 mins. The reaction was monitored by TLC until completion. The reaction mixture was filtered. The filter cake was washed with methanol (10 mL). The filtrate was used for next step directly without further purification.

3. Preparation of (R)-1-(1-phenylethyl)-1H-pyrrole-2-carboxylic acid (J-3)

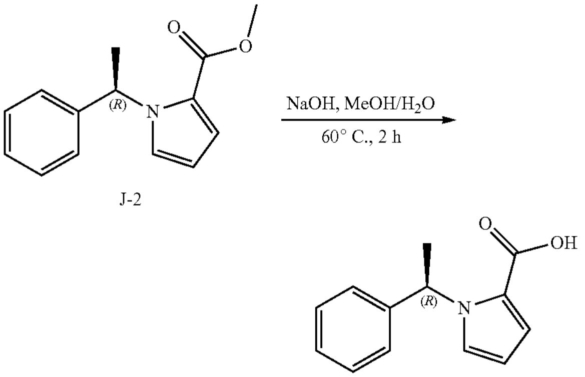

J-2

J-3

At room temperature, the solution of NaOH (584 mg, 29.2 mmol) in water (10 mL) was added into the solution of J-2 in methanol, then the mixture was stirred at 60° C. for 2 hrs. The reaction was monitored by TLC until completion. The reaction mixture was cooled and adjusted pH to 4~5 with concentrated hydrochloric acid. The reaction mixture was extracted with dichloromethane (3×15 mL). The combined organic layers were washed with saturated brine (10 mL), dried over anhydrous sodium sulfate, filtered and concentrated under reduced pressure. The residue was purified by silica gel column chromatography (ethyl acetate/petroleum ether (v/v)=1/20~1/2), with TLC (ethyl acetate/petroleum ether (v/v)=1/2) monitoring, and collecting the fraction with Rf=0.3~0.4 to give compound J-3 (1.2 g, yield 76% for two steps) as a grey solid. ESI$[M+H]^+$=216.1

$^1H$ NMR (400 MHz, $CDCl_3$) δ 7.34-7.27 (m, 1H), 7.26-7.21 (m, 1H), 7.18-7.10 (m, J=5.7, 2.7, 1.1 Hz, 1H), 7.06-7.02 (m, J=2.5, 1.9 Hz, 0H), 6.56 (q, J=7.0 Hz, 0H), 6.21 (dd, J=3.9, 2.7 Hz, 0H), 1.81 (d, J=7.1 Hz, 2H).

4. Preparation of Compounds D109~D118

The title compound D109 was prepared according to the operation method of preparing compound D1 described in Example 1.

The title compounds D110~D116 were prepared according to the operation method of preparing compounds D2~D8 described in Example 2.

The title compound D117 was prepared according to the operation method of preparing compound D11 described in Example 3.

The title compound D118 was prepared according to the operation method of preparing compound D16 described in Example 4.

Compound D109: 82 mg, ESI$[M+H]^+$=304.0

$^1H$ NMR (400 MHz, $CDCl_3$) δ 7.34-7.27 (m, 2H), 7.26-7.20 (m, 1H), 7.15 (d, J=7.3 Hz, 2H), 7.00 (d, J=3.0 Hz, 2H), 6.61 (q, J=7.0 Hz, 1H), 6.20-6.15 (m, 1H), 3.92 (s, 0.7H), 3.49 (s, 1.3H), 3.13 (s, 7H), 1.80 (d, J=7.1 Hz, 3H).

Compound D110: 34 mg, ESI[M+H]$^+$=334.0

$^1$H NMR (400 MHz, $CDCl_3$) δ 7.34-7.27 (m, 2H), 7.26-7.20 (m, 1H), 7.15 (d, J=7.3 Hz, 2H), 7.00 (d, J=3.0 Hz, 2H), 6.61 (q, J=7.0 Hz, 1H), 6.20-6.15 (m, 1H), 3.35 (s, 3H), 3.24 (s, 3H), 2.31-2.17 (m, 1H), 2.14-2.01 (m, 1H), 1.80 (d, J=7.1 Hz, 3H), 0.99 (t, J=7.5 Hz, 3H).

Compound D111: 22 mg, ESI[M+H]$^+$=318.1

$^1$H NMR (400 MHz, $CDCl_3$) δ 7.35-7.28 (m, 2H), 7.26-7.20 (m, 1H), 7.12 (d, J=7.3 Hz, 2H), 7.00 (d, J=3.0 Hz, 2H), 6.63 (q, J=7.0 Hz, 1H), 6.20-6.15 (m, 1H), 4.43-4.40 (m, 2H), 3.95 (s, 1H), 3.78-3.71 (m, 1.5H), 3.50 (s, 3.5H), 1.80 (d, J=7.1 Hz, 3H), 1.42 (t, J=7.1 Hz, 1.5H), 1.28 (t, J=7.0 Hz, 1.5H).

Compound D112: 42 mg, ESI[M+H]$^+$=332.1

$^1$H NMR (400 MHz, $CDCl_3$) δ 7.30-7.26 (m, 2H), 7.25-7.20 (m, 1H), 7.14 (d, J=7.3 Hz, 2H), 7.00 (d, J=3.0 Hz, 2H), 6.61 (q, J=7.0 Hz, 1H), 6.22-6.17 (m, 1H), 5.35-5.30 (m, 1H), 3.95 (s, 1H), 3.52 (s, 5H), 1.80 (d, J=7.1 Hz, 3H), 1.55 (d, J=6.5 Hz, 1H), 1.45-1.40 (m, 3H), 1.25 (t, J=10.2 Hz, 2H).

Compound D113: 22 mg, ESI[M+H]$^+$=360.1

$^1$H NMR (400 MHz, $CDCl_3$) δ 7.32-7.27 (m, 2H), 7.26-7.20 (m, 1H), 7.13 (d, J=7.3 Hz, 2H), 7.00 (d, J=3.0 Hz, 2H), 6.61 (q, J=7.0 Hz, 1H), 6.20-6.15 (m, 1H), 4.87 (s, 1H), 3.95 (s, 1H), 3.51 (s, 5H), 1.80 (d, J=7.1 Hz, 3H), 1.65-1.62 (m, 2.5H), 1.60-1.55 (m, 1.5H), 1.50-1.45 (m, 1.5H), 1.40-1.35 (m, 3.5H), 1.24-1.20 (m, 1H).

Compound D114: 22 mg, ESI[M+H]$^+$=360.1

$^1$H NMR (400 MHz, $CDCl_3$) δ 7.34-7.27 (m, 2H), 7.25-7.20 (m, 1H), 7.15 (d, J=7.3 Hz, 2H), 7.02 (d, J=3.0 Hz, 2H), 6.62 (q, J=7.0 Hz, 1H), 6.20-6.15 (m, 1H), 4.04 (s, 1.5H), 3.95 (s, 1H), 3.52 (s, 4.5H), 3.32 (s, 1H), 1.82 (d, J=7.1 Hz, 3H), 1.02 (s, 5.5H), 0.94 (s, 3.5H).

Compound D115: 32 mg, ESI[M+H]$^+$=330.1

$^1$H NMR (400 MHz, $CDCl_3$) δ 7.35-7.27 (m, 2H), 7.24-7.20 (m, 1H), 7.15 (d, J=7.3 Hz, 2H), 7.01 (d, J=3.0 Hz, 2H), 6.61 (q, J=7.0 Hz, 1H), 6.20-5.89 (m, 2H), 5.51-4.83 (m, 2H), 4.21-4.18 (m, 1.5H), 3.92 (s, 1.5H), 3.45 (m, 3H), 3.26-3.09 (m, 2H), 1.80 (d, J=7.1 Hz, 3H).

Compound D116: 42 mg, ESI[M+H]$^+$=342.0

$^1$H NMR (400 MHz, $CDCl_3$) δ 7.35-7.27 (m, 2H), 7.26-7.21 (m, 1H), 7.15 (d, J=7.3 Hz, 2H), 7.05 (d, J=3.0 Hz, 2H), 6.61 (q, J=7.0 Hz, 1H), 6.21-6.15 (m, 1H), 4.22-4.18 (m, 1.5H), 3.96 (s, 2H), 3.49 (s, 3H), 3.28-3.08 (m, 1.5H), 2.04-1.82 (m, 3H), 1.81 (d, J=7.1 Hz, 3H).

Compound D117: 122 mg, ESI[M+H]$^+$=258.0

$^1$H NMR (400 MHz, $CDCl_3$) δ 7.34-7.27 (m, 2H), 7.26-7.20 (m, 1H), 7.17 (d, J=7.3 Hz, 2H), 7.04 (d, J=3.0 Hz, 2H), 6.61 (q, J=7.0 Hz, 1H), 6.25-6.19 (m, 1H), 3.94 (s, 3H), 1.83 (d, J=7.1 Hz, 3H).

Compound D118: 28 mg, ESI[M+H]$^+$=326.2

$^1$H NMR (400 MHz, $CDCl_3$) δ 7.34-7.29 (m, 2H), 7.26-7.22 (m, 1H), 7.15 (d, J=7.3 Hz, 2H), 7.06 (d, J=3.0 Hz, 2H), 6.70 (s, 1H), 6.61 (q, J=7.0 Hz, 1H), 6.20-6.15 (m, 1H), 2.24 (s, 6H), 1.83 (d, J=7.1 Hz, 3H).

Example 15 Preparation of Compounds D119~D129

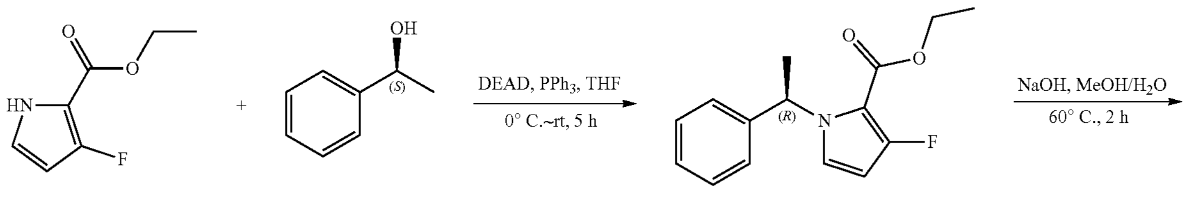

K-1

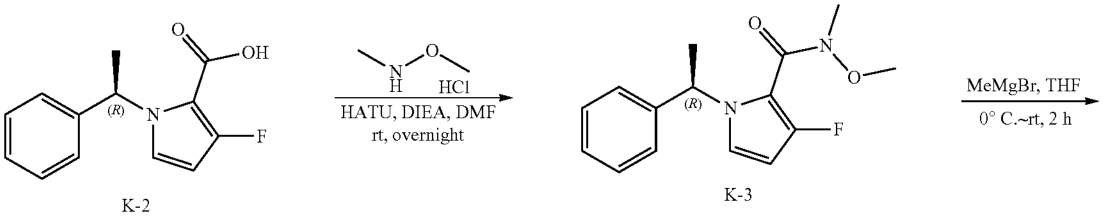

K-2 K-3

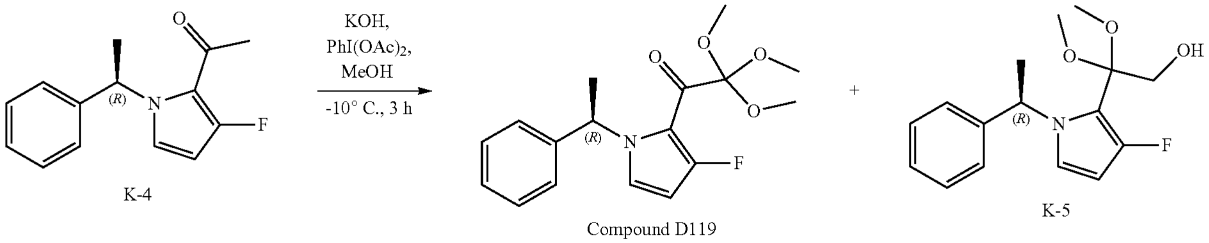

K-4 Compound D119 K-5

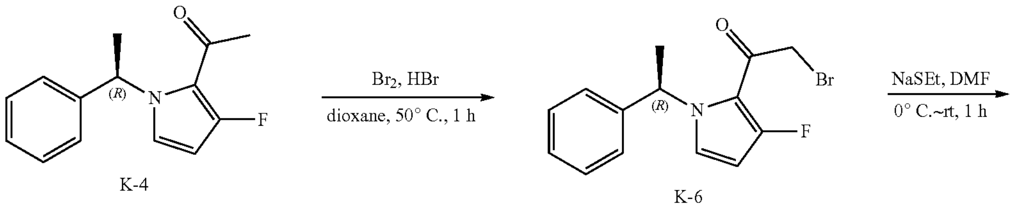

K-4 K-6

-continued
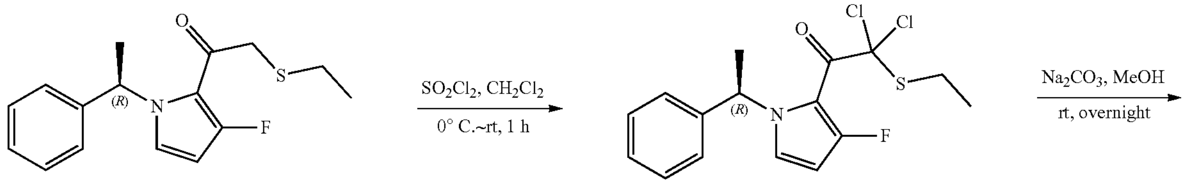
K-7 K-8
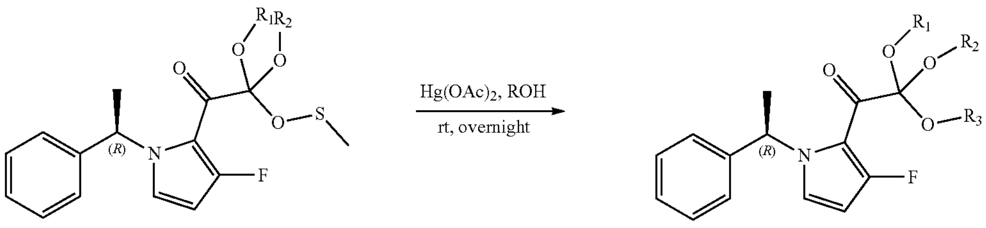
Compound D123 Compound D120~D122
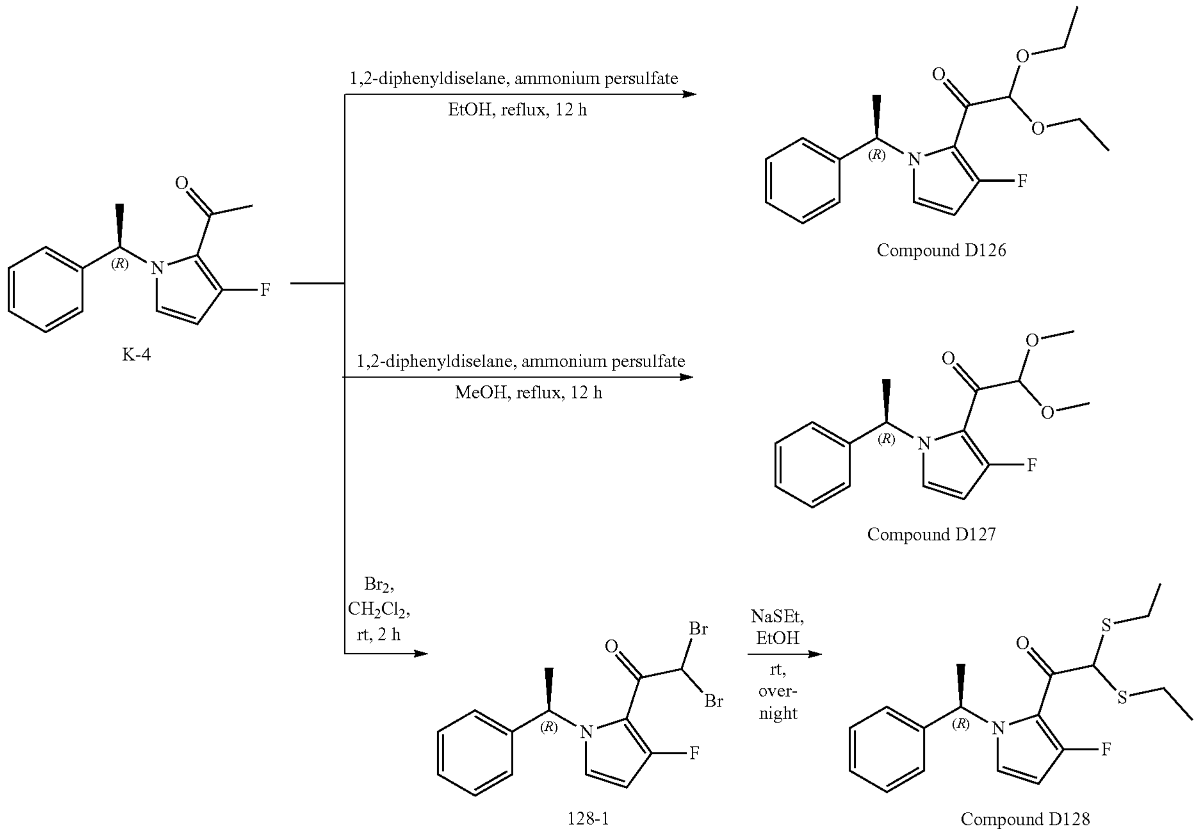
K-4
Compound D126
Compound D127
128-1
Compound D128
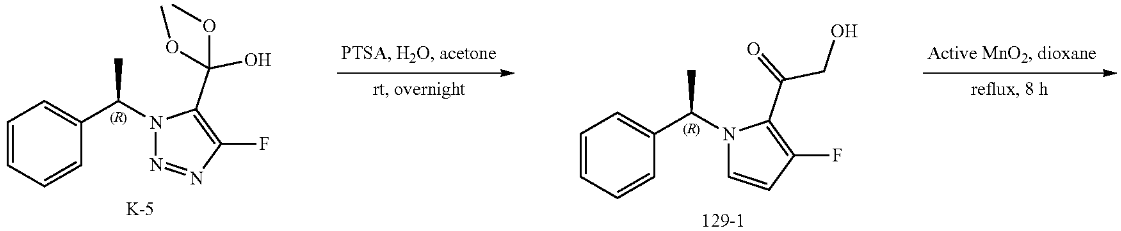
K-5 129-1

-continued

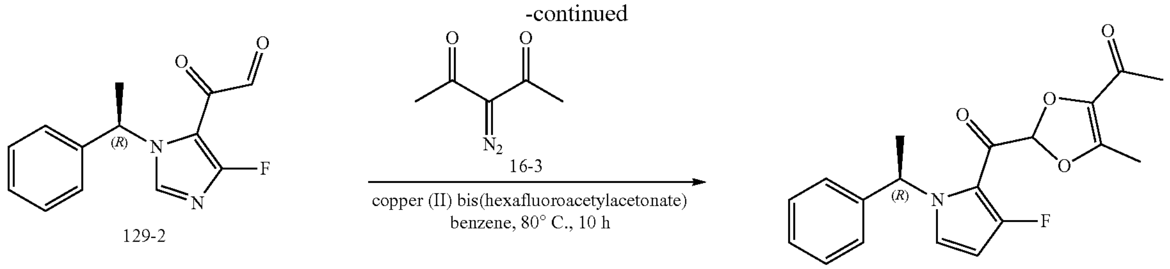

129-2

Compound D129

1. Preparation of ethyl (R)-3-fluoro-1-(1-phenylethyl)-1H-pyrrole-2-carboxylate (K-1)

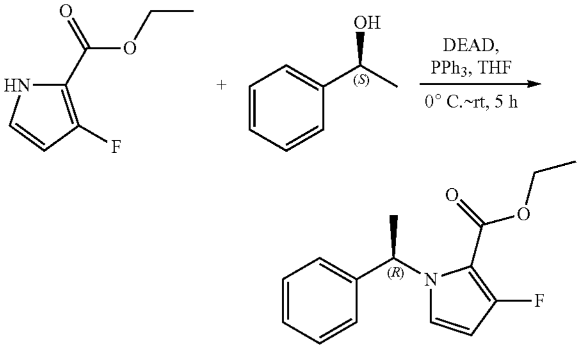

K-1

In an ice-water bath, (S)-1-phenylethan-1-ol (5.8 g, 47.5 mmol) was added into the mixture of ethyl 3-fluoro-1H-pyrrole-2-carboxylate (5.0 g, 31.8 mmol) and $PPh_3$ (12.5 g, 47.7 mmol) in THF (50 mL) at 0° C., then the solution of DEAD (8.3 g, 47.7 mmol) in THF (100 mL) was added dropwise into the mixture at the rate of 2 mmol/min. After addition, the reaction mixture was warmed slowly to room temperature and stirred overnight. The reaction was monitored by TLC until completion. The reaction mixture was quenched with the saturated brine (30 mL) and extracted with ethyl acetate (3×50 mL). The combined organic layers were washed with saturated brine (30 mL), dried over anhydrous sodium sulfate, filtered and concentrated under reduced pressure to give crude product. The crude product was purified by silica gel column chromatography (ethyl acetate/petroleum ether (v/v)=1/20~1/10), with TLC (ethyl acetate/petroleum ether (v/v)=1/2) monitoring, and collecting the fraction with Rf=0.5~0.6 to give the product K-1 (7.0 g, yield 84%). ESI[M+H]$^+$=262.2

$^1$H NMR (400 MHz, $CDCl_3$) δ 7.38-7.21 (m, 3H), 7.12 (d, J=7.2 Hz, 2H), 6.76 (dd, J=5.1, 3.3 Hz, 1H), 6.45 (q, J=7.1 Hz, 1H), 5.93 (d, J=3.2 Hz, 1H), 4.37-4.11 (m, 2H), 1.76 (d, J=7.1 Hz, 3H), 1.31 (t, J=7.1 Hz, 3H).

2. Preparation of Compounds D119~129

The title compound D119 was prepared according to the operation method of preparing compounds D1 described in Example 1.

The title compounds D120~D125 were prepared according to the operation method of preparing compounds D2~D10 described in Example 2.

The title compounds D126~D129 were prepared according to the operation method of preparing compounds D13~D16 described in Example 4.

Compound D119: 111 mg, ESI[M+H]$^+$=322.0

$^1$H NMR (400 MHz, $CDCl_3$) δ 7.35-7.28 (m, 2H), 7.26-7.21 (m, 1H), 7.17-7.09 (m, 2H), 6.83-6.76 (m, 1H), 6.44 (q, J=7.1 Hz, 1H), 5.94 (d, J=3.2 Hz, 1H), 3.92 (s, 0.7H), 3.49 (s, 1.3H), 3.13 (s, 7H), 1.76 (d, J=7.1 Hz, 3H).

Compound D120: 27 mg, ESI[M+H]$^+$=358.0

$^1$H NMR (400 MHz, $CDCl_3$) δ 7.33-7.28 (m, 2H), 7.26-7.21 (m, 1H), 7.15-7.09 (m, 2H), 6.83-6.76 (m, 1H), 6.44 (q, J=7.1 Hz, 1H), 5.94 (d, J=3.2 Hz, 1H), 4.07-3.78 (m, 6H), 2.03-1.82 (m, 3H), 1.74 (d, J=7.1 Hz, 3H).

Compound D121: 33 mg, ESI[M+H]$^+$=320.0

$^1$H NMR (400 MHz, $CDCl_3$) δ 7.35-7.28 (m, 2H), 7.26-7.21 (m, 1H), 7.19-7.09 (m, 2H), 6.83-6.76 (m, 1H), 6.41 (q, J=7.1 Hz, 1H), 5.94 (d, J=3.2 Hz, 1H), 4.07-3.78 (m, 4H), 3.26 (s, 3H), 1.78 (d, J=7.1 Hz, 3H).

Compound D122: 34 mg, ESI[M+H]$^+$=360.0

$^1$H NMR (400 MHz, $CDCl_3$) δ 7.32-7.28 (m, 2H), 7.25-7.21 (m, 1H), 7.17-7.09 (m, 2H), 6.83-6.76 (m, 1H), 6.41 (q, J=7.1 Hz, 1H), 5.94 (d, J=3.2 Hz, 1H), 4.23-4.16 (m, 1.5H), 3.95 (s, 2H), 3.47 (m, 3H), 3.27-3.08 (m, 1.5H), 2.03-1.82 (m, 3H), 1.73 (d, J=7.1 Hz, 3H).

Compound D123: 31 mg, ESI[M+H]$^+$=352.0

$^1$H NMR (400 MHz, $CDCl_3$) δ 7.30-7.27 (m, 2H), 7.25-7.21 (m, 1H), 7.17-7.09 (m, 2H), 6.83-6.76 (m, 1H), 6.45 (q, J=7.1 Hz, 1H), 5.94 (d, J=3.2 Hz, 1H), 3.35 (s, 3H), 3.24 (s, 3H), 2.31-2.17 (m, 1H), 2.11-2.01 (m, 1H), 1.74 (d, J=7.1 Hz, 3H), 0.99 (t, J=7.5 Hz, 3H).

Compound D124: 28 mg, ESI[M+H]$^+$=350.1

$^1$H NMR (400 MHz, $CDCl_3$) δ 7.34-7.28 (m, 2H), 7.24-7.21 (m, 1H), 7.17-7.09 (m, 2H), 6.83-6.76 (m, 1H), 6.40 (q, J=7.1 Hz, 1H), 5.92 (d, J=3.2 Hz, 1H), 4.43-4.40 (m, 2H), 3.95 (s, 1H), 3.77-3.71 (m, 1.5H), 3.51 (s, 2.5H), 1.78 (d, J=7.1 Hz, 3H), 1.44-1.40 (m, 3H), 1.28-1.24 (m, 3H).

Compound D125: 11 mg, ESI[M+H]$^+$=364.0

$^1$H NMR (400 MHz, $CDCl_3$) δ 7.32-7.28 (m, 2H), 7.25-7.21 (m, 1H), 7.18-7.09 (m, 2H), 6.83-6.76 (m, 1H), 6.44 (q, J=7.1 Hz, 1H), 5.94 (d, J=3.2 Hz, 1H), 4.42-4.40 (m, 1H), 3.94 (s, 1H), 3.75-3.70 (m, 1.5H), 3.52 (s, 2.5H), 1.74 (d, J=7.1 Hz, 3H), 1.43-1.41 (m, 4.5H), 1.25-1.22 (m, 4.5H).

Compound D126: 27 mg, ESI[M+H]$^+$=320.1

$^1$H NMR (400 MHz, $CDCl_3$) δ 7.34-7.28 (m, 2H), 7.26-7.21 (m, 1H), 7.16-7.08 (m, 2H), 6.83-6.76 (m, 1H), 6.42 (q, J=7.1 Hz, 1H), 5.92 (d, J=3.2 Hz, 1H), 5.25 (s, 1H), 3.70-3.46 (m, 4H), 1.76 (d, J=7.1 Hz, 3H), 1.17-1.15 (m, 6H).

Compound D127: 22 mg, ESI[M+H]$^+$=292.0

$^1$H NMR (400 MHz, $CDCl_3$) δ 7.35-7.27 (m, 2H), 7.25-7.21 (m, 1H), 7.17-7.09 (m, 2H), 6.83-6.76 (m, 1H), 6.41 (q, J=7.1 Hz, 1H), 5.92 (d, J=3.2 Hz, 1H), 5.05 (s, 1H), 3.35 (s, 3H), 3.31 (s, 3H), 1.75 (d, J=7.1 Hz, 3H).

Compound D128: 34 mg, ESI$[M+H]^+$=352.0
$^1$H NMR (400 MHz, $CDCl_3$) δ 7.36-7.28 (m, 2H), 7.26-7.21 (m, 1H), 7.18-7.09 (m, 2H), 6.83-6.76 (m, 1H), 6.43 (q, J=7.1 Hz, 1H), 5.92 (d, J=3.2 Hz, 1H), 5.36 (s, 1H), 2.80-2.39 (m, 4H), 1.76 (d, J=7.1 Hz, 3H), 1.27-1.13 (m, 6H).
Compound D129: 33 mg, ESI$[M+H]^+$=344.0
$^1$H NMR (400 MHz, $CDCl_3$) δ 7.31-7.26 (m, 2H), 7.24-7.20 (m, 1H), 7.17-7.09 (m, 2H), 6.83-6.76 (m, 1H), 6.67 (s, 1H), 6.43 (q, J=7.1 Hz, 1H), 5.91 (d, J=3.2 Hz, 1H), 2.20 (s, 6H), 1.77 (d, J=7.1 Hz, 3H).
Example 16 Preparation of Compounds D130~D134
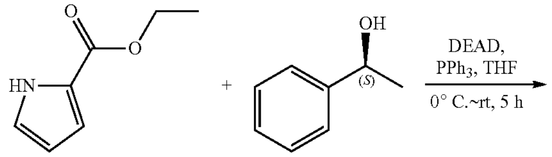
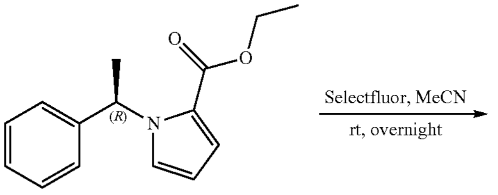
L-1
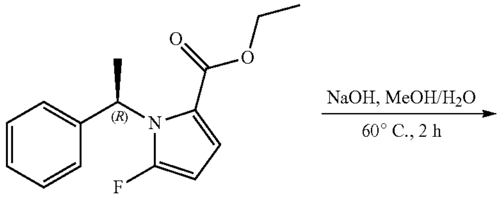
L-2
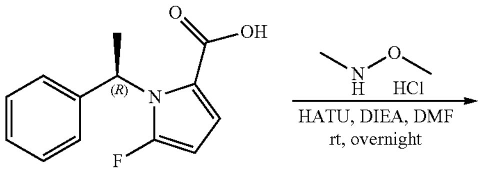
L-3
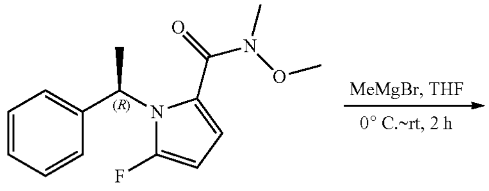
L-4
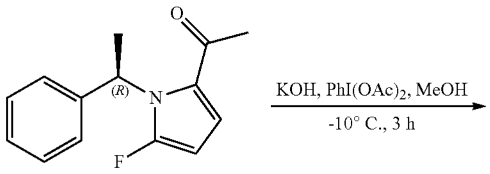
L-5
-continued
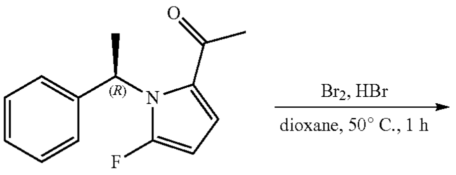
L-5
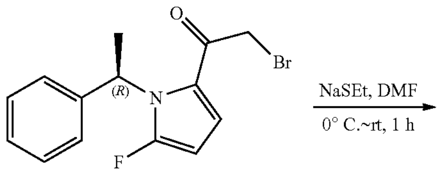
L-7
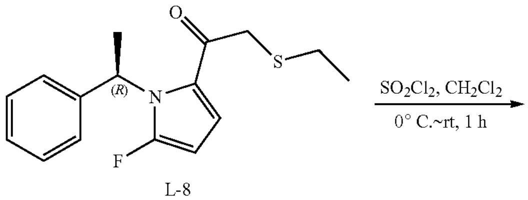
L-8
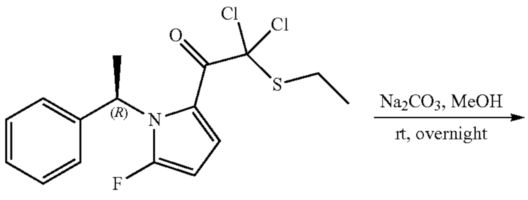
L-9
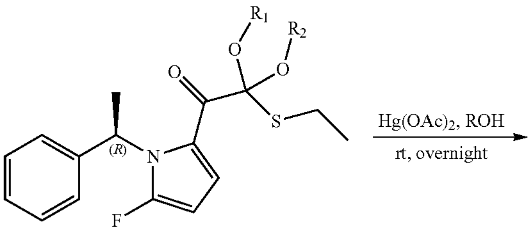
L-10
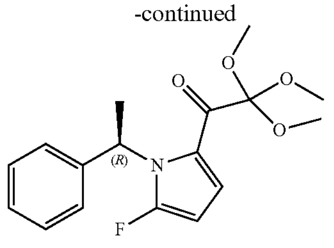
Compound D130
+
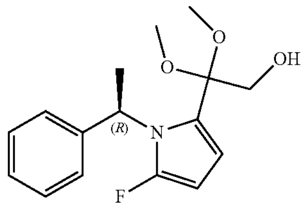
L-6

-continued

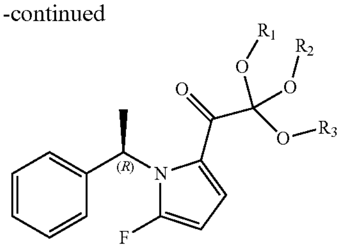

Compound D131~D132

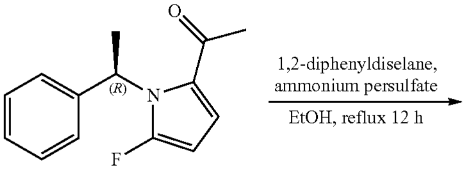

L-5

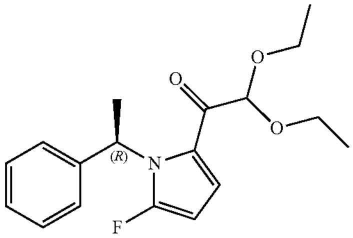

Compound D133

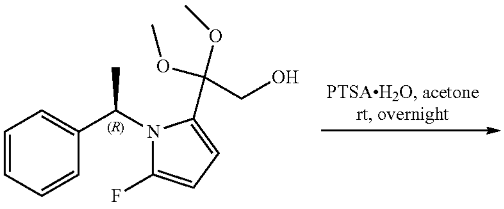

L-6

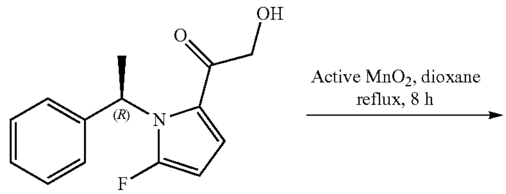

134-1

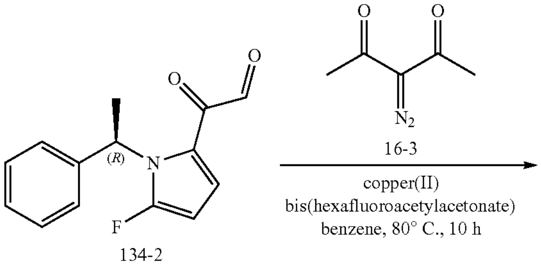

134-2

-continued

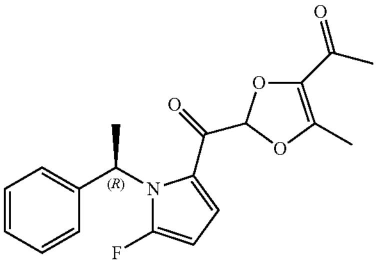

Compound D134

1. Preparation of ethyl (R)-1-(1-phenylethy)-1H-pyrrole-2-carboxylate (L-1)

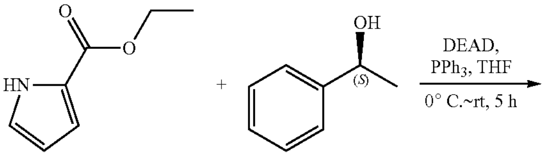

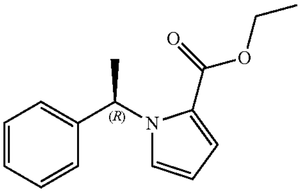

L-1

In an ice-water bath, (S)-1-phenylethan-1-ol (6.9 g, 56.5 mmol) was added into the mixture of ethyl 1H-pyrrole-2-carboxylate (5.0 g, 35.9 mmol) and $PPh_3$ (14.8 g, 56.4 mmol) in THF (50 mL) at 0° C., then the solution of DEAD (9.8 g, 56.3 mmol) in THF (20 mL) was added dropwise into the mixture at the rate of 2 mmol/min After addition, the reaction mixture was warmed slowly to room temperature and stirred overnight. The reaction was monitored by TLC until completion. The reaction mixture was quenched with the saturated brine (100 mL) and extracted with ethyl acetate (3×50 mL). The combined organic layers were washed with saturated brine (30 mL), dried over anhydrous sodium sulfate, filtered and concentrated under reduced pressure to give crude product. The crude product was purified by silica gel column chromatography (ethyl acetate/petroleum ether (v/v)=1/20~1/10), with TLC (ethyl acetate/petroleum ether (v/v)=1/2) monitoring, and collecting the fraction with Rf=0.5~0.6 to give the product L-1 (4.0 g, yield 46%). ESI$[M+H]^+$=244.3

$^1H$ NMR (400 MHz, $CDCl_3$) δ 7.37-7.29 (m, 2H), 7.28-7.22 (m, 1H), 7.20-7.12 (m, 2H), 7.07-6.99 (m, 1H), 6.63 (q, J=7.1 Hz, 1H), 6.25-6.17 (m, 1H), 4.36-4.16 (m, 2H), 1.83 (d, J=7.1 Hz, 3H), 1.33 (t, J=7.1 Hz, 3H).

2. Preparation of ethyl (R)-5-fluoro-1-(1-phenylethyl)-1H-pyrrole-2-carboxylate (L-2)

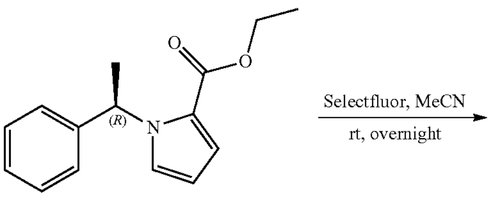

L-1

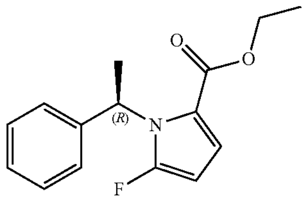

L-2

At room temperature, L-1 (2.0 g, 8.2 mmol) and Selectfluor (6.4 g, 18.1 mmol) were dissolved in acetonitrile (50 mL), then the mixture was stirred at room temperature overnight. The reaction was monitored by TLC until completion. The reaction mixture was quenched with saturated brine (100 mL) and extracted with ethyl acetate (3×10 mL). The combined organic layers were washed with saturated brine (30 mL), dried over anhydrous sodium sulfate, filtered, and concentrated under reduced pressure. The residue was purified by silica gel column chromatography (ethyl acetate/petroleum ether (v/v)=1/20~1/10), with TLC (ethyl acetate/petroleum ether (v/v)=1/2) monitoring, and collecting the fraction with Rf=0.5~0.6 to give title compound L-2 (410 mg, yield 19%). ESI[M+H]$^+$=262.1

$^1$H NMR (400 MHz, $CDCl_3$) δ 7.36-7.29 (m, 2H), 7.26-7.20 (m, 3H), 6.89 (dd, J=5.9, 4.4 Hz, 1H), 6.80 (q, J=7.1 Hz, 1H), 5.60-5.52 (m, 1H), 4.33-4.19 (m, 2H), 1.89 (dd, J=7.3, 2.3 Hz, 3H), 1.34 (t, J=7.1 Hz, 3H).

3. Preparation of Compounds D130~D13

The title compound D130 was prepared according to the operation method of preparing compounds D1 described in Example 1.

The title compounds D131~D132 were prepared according to the operation method of preparing compounds D2~D10 described in Example 2.

The title compounds D133~D134 were prepared according to the operation method of preparing compounds D14 and D16 described in Example 4.

Compound D130: 32 mg, ESI[M+H]$^+$=322.0

$^1$H NMR (400 MHz, $CDCl_3$) δ 7.35-7.22 (m, 5H), 6.94 (dd, J=6.0, 4.3 Hz, 1H), 6.80 (q, J=7.3 Hz, 1H), 5.59-5.53 (m, 1H), 3.92 (s, 0.7H), 3.49 (s, 1.3H), 3.13 (s, 7H), 1.91-1.87 (m, 3H).

Compound D131: 41 mg, ESI[M+H]$^+$=320.0

$^1$H NMR (400 MHz, $CDCl_3$) δ 7.37-7.25 (m, 5H), 6.93 (dd, J=6.0, 4.3 Hz, 1H), 6.82 (q, J=7.3 Hz, 1H), 5.59-5.54 (m, 1H), 4.07-3.78 (m, 4H), 3.26 (s, 3H), 1.91-1.85 (m, 3H).

Compound D132: 37 mg, ESI[M+H]$^+$=360.1

$^1$H NMR (400 MHz, $CDCl_3$) δ 7.36-7.24 (m, 5H), 6.92 (dd, J=6.0, 4.3 Hz, 1H), 6.83 (q, J=7.3 Hz, 1H), 5.59-5.53 (m, 1H), 4.22-4.18 (m, 1.5H), 3.94 (s, 2H), 3.46 (s, 3H), 3.28-3.08 (m, 1.5H), 2.04-1.82 (m, 6H).

Compound D133: 22 mg, ESI[M+H]$^+$=320.0

$^1$H NMR (400 MHz, $CDCl_3$) δ 7.36-7.22 (m, 5H), 6.93 (dd, J=6.0, 4.3 Hz, 1H), 6.81 (q, J=7.3 Hz, 1H), 5.58-5.53 (m, 1H), 5.24 (s, 1H), 3.76-3.42 (m, 4H), 1.91-1.86 (m, 3H), 1.25-1.11 (m, 6H).

Compound D134: 32 mg, ESI[M+H]$^+$=344.0

$^1$H NMR (400 MHz, $CDCl_3$) δ 7.37-7.24 (m, 5H), 6.94 (dd, J=6.0, 4.3 Hz, 1H), 6.83 (q, J=7.3 Hz, 1H), 6.65 (s, 1H), 5.57-5.53 (m, 1H), 2.27 (s, 6H), 1.92-1.86 (m, 3H).

Example 17 Preparation of Compounds D135~D144

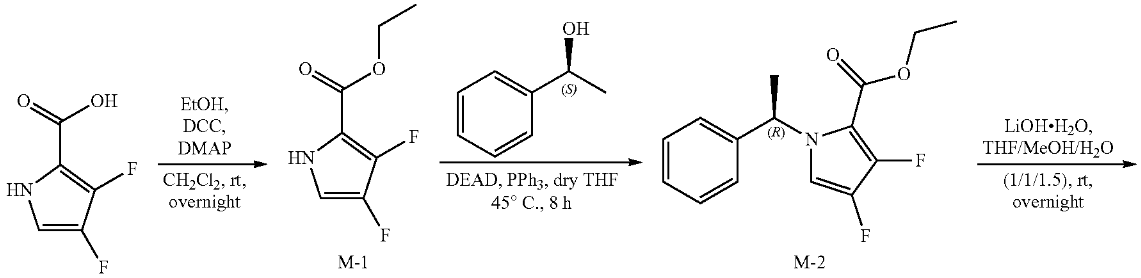

M-1

M-2

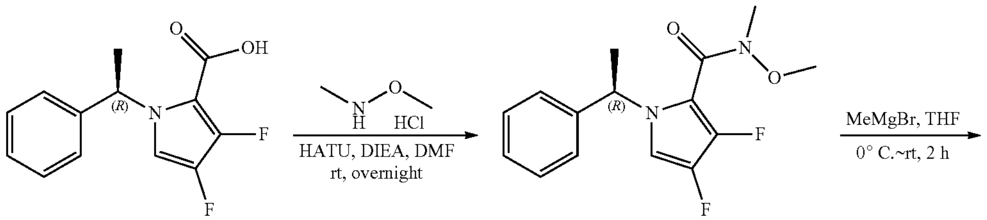

M-3

M-4

-continued
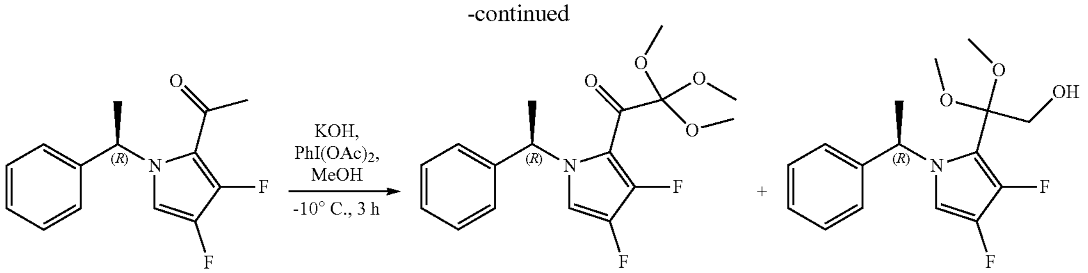
M-5 Compound D135 M-6
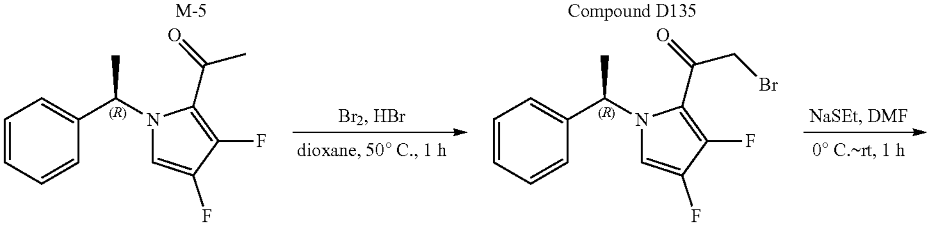
M-5 M-7
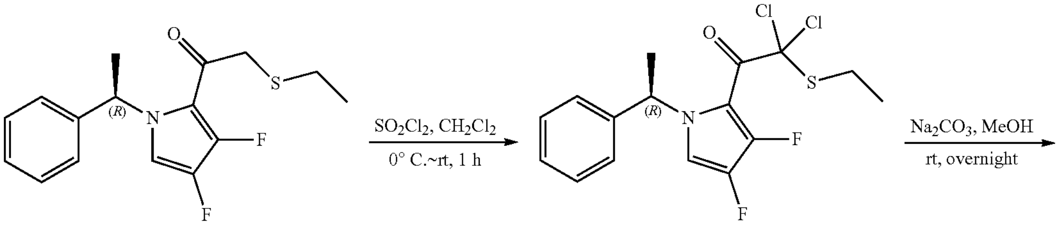
M-8 M-9
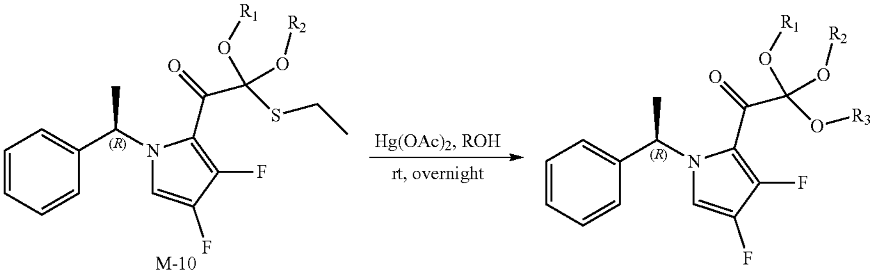
M-10
(Compound 137: $R_1 = R_2 = Me$)
Compound D136, D140~D141
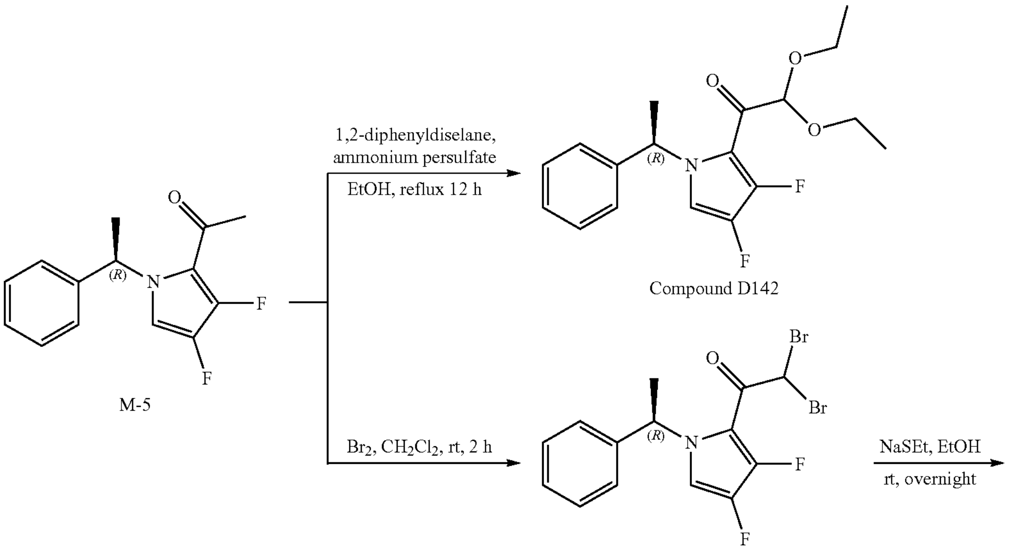
Compound D142
M-5
143-1

-continued

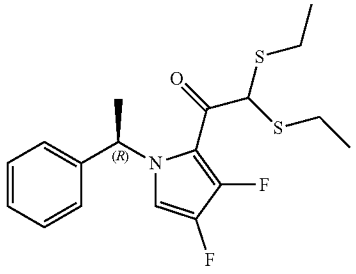

Compound D143

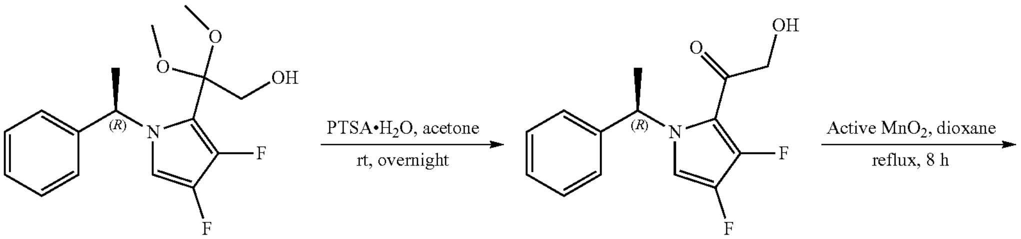

M-6

144-1

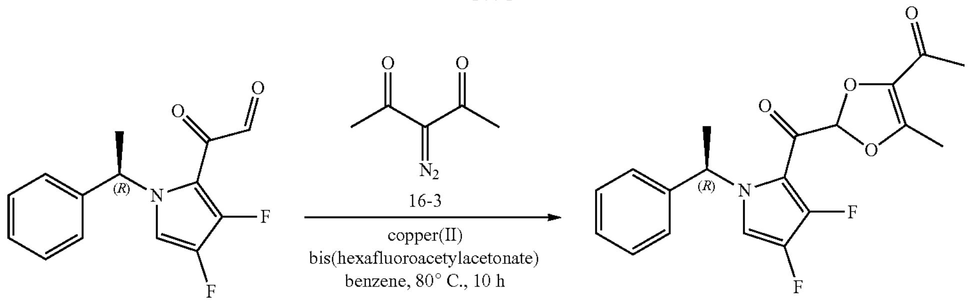

144-2

Compound D144

1. Preparation of ethyl 3,4-difluoro-1H-pyrrole-2-carboxylate (M-1)

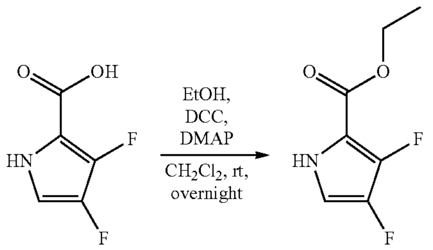

M-1

At room temperature, 3,4-difluoro-1H-pyrrole-2-carboxylic acid (1.0 g, 6.8 mmol), DCC (2.1 g, 10.2 mmol) and DMAP (1.3 g, 10.6 mmol) were dissolved in dichloromethane (10 mL), then the mixture was stirred at room temperature for 5 mins. Ethanol (470 mg, 10.2 mmol) was added slowly into the above mixture using a syringe and the reaction mixture was stirred at room temperature overnight. The reaction was monitored by TLC until completion. The reaction mixture was concentrated under reduced pressure. Methyl tert-butyl ether was added into the residue and stirred, filtered. The filter cake was washed with methyl tert-butyl ether, and the filtrate was concentrated under reduced pressure. The residue was purified by silica gel column chromatography (ethyl acetate/petroleum ether (v/v)= 1/20~1/10), with TLC (ethyl acetate/petroleum ether (v/v)=1/2) monitoring, and collecting the fraction with Rf=0.5-0.6 to give compound M-1 (800 mg, yield 67%). ESI$[M+H]^+$=176.1

2. Preparation of ethyl (R)-3,4-difluoro-1-(1-phenylethyl)-1H-pyrrole-2-carboxylate (M-2)

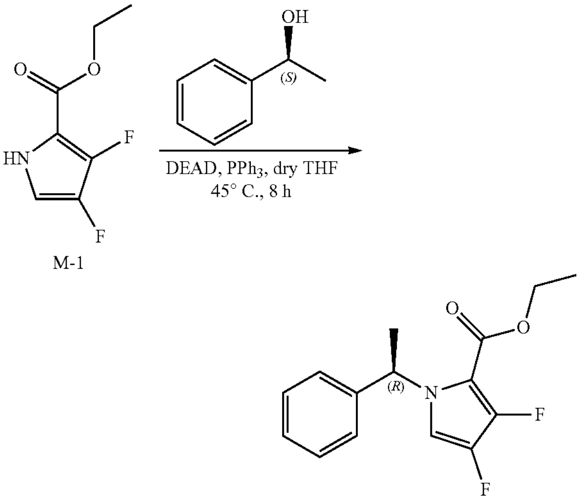

M-2

In an ice-water bath, (S)-1-phenylethan-1-ol (6.9 g, 56.5 mmol) was added into the mixture of M-1 (800 mg, 35.9 mmol) and PPh3 (14.8 g, 56.4 mmol) in THF (50 mL) at 0° C., then the solution of DEAD (9.8 g, 56.3 mmol) in THF (20 mL) was added dropwise into the mixture at the rate of 2 mmol/min. After addition, the reaction mixture was warmed slowly to room temperature and stirred overnight. The reaction was monitored by TLC until completion. The reaction mixture was quenched with the saturated brine (100 mL) and extracted with ethyl acetate (3×50 mL). The combined organic layers were washed with saturated brine (30 mL), dried over anhydrous sodium sulfate, filtered and concentrated under reduced pressure to give crude product. The crude product was purified by silica gel column chromatography (ethyl acetate/petroleum ether (v/v)=1/20~1/10), with TLC (ethyl acetate/petroleum ether (v/v)=1/2) monitoring, and collecting the fraction with Rf=0.5~0.6 to give the product M-2 (1.0 g, yield 46%). ESI[M+H]$^+$=280.2

$^1$H NMR (400 MHz, $CDCl_3$) δ 7.38-7.28 (m, 3H), 7.17-7.12 (m, 2H), 6.63 (dd, J=4.6, 2.2 Hz, 1H), 6.53-6.46 (m, 1H), 4.33-4.23 (m, 2H), 1.72 (d, J=7.1 Hz, 3H), 1.32 (t, J=7.1 Hz, 3H).

3. Preparation of Compounds D135~144

The title compound D135 was prepared according to the operation method of preparing compound D1 described in Example 1.

The title compounds D136~D141 were prepared according to the operation method of preparing compounds D2~D10 described in Example 2.

The title compounds D142~D144 were prepared according to the operation method of preparing compounds D13~D16 described in Example 4.

Compound D135: 27 mg, ESI[M+H]$^+$=340.0

$^1$H NMR (400 MHz, $CDCl_3$) δ 7.38-7.28 (m, 3H), 7.17-7.12 (m, 2H), 6.63 (dd, J=4.7, 2.2 Hz, 1H), 6.53-6.46 (m, 1H), 3.92 (s, 0.7H), 3.49 (s, 1.3H), 3.13 (s, 7H), 1.72 (d, J=7.1 Hz, 3H).

Compound D136: 28 mg, ESI[M+H]$^+$=378.0

$^1$H NMR (400 MHz, $CDCl_3$) δ 7.36-7.28 (m, 3H), 7.17-7.12 (m, 2H), 6.60 (dd, J=4.7, 2.2 Hz, 1H), 6.53-6.46 (m, 1H), 4.22-4.18 (m, 1.5H), 3.96 (s, 2H), 3.48 (s, 3H), 3.28-3.08 (m, 1.5H), 2.04-1.82 (m, 3H), 1.70 (d, J=7.1 Hz, 3H).

Compound D137: 40 mg, ESI[M+H]$^+$=370.0

$^1$H NMR (400 MHz, $CDCl_3$) δ 7.36-7.28 (m, 3H), 7.16-7.12 (m, 2H), 6.63 (dd, J=4.7, 2.2 Hz, 1H), 6.52-6.46 (m, 1H), 3.35 (s, 3H), 3.25 (s, 3H), 2.33-2.17 (m, 1H), 2.14-2.01 (m, 1H), 1.75 (d, J=7.1 Hz, 3H), 0.99 (t, J=7.5 Hz, 3H).

Compound D138: 22 mg, ESI[M+H]$^+$=368.1

$^1$H NMR (400 MHz, $CDCl_3$) δ 7.38-7.28 (m, 3H), 7.17-7.12 (m, 2H), 6.61 (dd, J=4.7, 2.2 Hz, 1H), 6.52-6.42 (m, 1H), 4.43-4.40 (m, 2H), 3.93 (s, 1H), 3.74-3.71 (m, 1.5H), 3.54 (s, 2.5H), 1.72 (d, J=7.1 Hz, 3H), 1.44-1.41 (m, 3H), 1.29-1.24 (m, 3H).

Compound D139: 32 mg, ESI[M+H]$^+$=382.1

$^1$H NMR (400 MHz, $CDCl_3$) δ 7.34-7.28 (m, 3H), 7.15-7.10 (m, 2H), 6.63 (dd, J=4.7, 2.2 Hz, 1H), 6.51-6.46 (m, 1H), 4.42-4.40 (m, 1H), 3.92 (s, 1H), 3.75-3.70 (m, 1.5H), 3.52 (s, 2.5H), 1.73 (d, J=7.1 Hz, 3H), 1.43-1.41 (m, 4.5H), 1.26-1.22 (m, 4.5H).

Compound D140: 42 mg, ESI[M+H]$^+$=338.0

$^1$H NMR (400 MHz, $CDCl_3$) δ 7.35-7.28 (m, 3H), 7.16-7.12 (m, 2H), 6.61 (dd, J=4.7, 2.2 Hz, 1H), 6.52-6.46 (m, 1H), 4.07-3.78 (m, 4H), 3.26 (s, 3H), 1.71 (d, J=7.1 Hz, 3H).

Compound D141: 23 mg, ESI[M+H]$^+$=376.0

$^1$H NMR (400 MHz, $CDCl_3$) δ 7.35-7.28 (m, 3H), 7.15-7.12 (m, 2H), 6.63 (dd, J=4.7, 2.2 Hz, 1H), 6.53-6.46 (m, 1H), 4.07-3.78 (m, 6H), 2.03-1.82 (m, 3H), 1.71 (d, J=7.1 Hz, 3H).

Compound D142: 34 mg, ESI[M+H]$^+$=338.0

$^1$H NMR (400 MHz, $CDCl_3$) δ 7.39-7.29 (m, 3H), 7.18-7.12 (m, 2H), 6.63 (dd, J=4.7, 2.2 Hz, 1H), 6.53-6.46 (m, 1H), 5.24 (s, 1H), 3.80-3.46 (m, 4H), 1.71 (d, J=7.1 Hz, 3H), 1.29-1.15 (m, 6H).

Compound D143: 31 mg, ESI[M+H]$^+$=370.0

$^1$H NMR (400 MHz, $CDCl_3$) δ 7.38-7.28 (m, 3H), 7.16-7.11 (m, 2H), 6.62 (dd, J=4.7, 2.2 Hz, 1H), 6.54-6.46 (m, 1H), 5.45 (s, 1H), 2.88-2.39 (m, 4H), 1.72 (d, J=7.1 Hz, 3H), 1.26-1.13 (m, 6H).

Compound D144: 62 mg, ESI[M+H]$^+$=362.2

$^1$H NMR (400 MHz, $CDCl_3$) δ 7.36-7.28 (m, 3H), 7.17-7.10 (m, 2H), 6.71 (s, 1H), 6.61 (dd, J=4.7, 2.2 Hz, 1H), 6.53-6.44 (m, 1H), 2.28 (s, 6H), 1.75 (d, J=7.1 Hz, 3H).

The following examples illustrate the beneficial effects of the present invention:

Example 1

The Anesthetic Activity of Group a Compounds was Assessed in Rats Using a Loss of Righting Reflexes (LORR) Assay Adult male Sprague-Dawley rats (250-300 g) were selected for the experiment. The compounds in the above examples and the control drugs, etomidate and CPMM, were dissolved in dimethyl sulfoxide (DMSO), and the same volume of DMSO was given as the blank control group. The anesthesia effects of the compounds were assessed in rats using a LORR assay and a period >30 s was considered as an indicator of general anesthesia. Then the up and down method was used to determine 50% effective dose (EDO. The drugs were administered through the tail vein of rats in a volume of 0.6 mL and at a rate of 0.1 mL/s. As shown in Tables A1-E1, the results suggest that the compounds of the present invention, similar to the control etomidate and CPMM, provide a definite and transient effect of general anesthesia. Besides the compounds have the same or better potency as etomidate and CPMM.

TABLE 1

The $ED_{50}$ value with LORR and minimal lethal dose of the present invention compounds in rats

| Compound/drug | $ED_{50}$(mg/kg) | Minimal lethal dose (mg/kg) | Approximate therapeutic index |
|---|---|---|---|
| Etomidate | 0.75(0.72-0.77)* | 12.75 | 17 |
| CPMM | 0.78(0.74-0.82)* | >7.8 | >10 |
| Propofol | 5.51(5.39-5.64)* | 28 | 5 |
| DMSO | / | / | / |
| Compound A1 | C | >16 | >8 |
| Compound A3 | C | >8 | >6 |
| Compound A4 | C | >15 | >11 |
| Compound A6 | D | >13 | >5 |
| Compound A8 | C | >9 | >7 |
| Compound A10 | D | >12 | >5 |
| Compound A11 | C | >8 | >4 |
| Compound A12 | C | >6 | >4 |
| Compound A14 | C | >11 | >8 |
| Compound A15 | D | >9 | >4 |
| Compound A16 | D | >12 | >4 |
| Compound A18 | D | >8 | >3 |
| Compound A20 | C | >12 | >10 |
| Compound A21 | D | >6 | >16 |
| Compound A23 | D | >11 | >5 |
| Compound A24 | A | >6 | >31 |
| Compound A25 | A | >5 | >21 |
| Compound A30 | C | >7 | >6 |
| Compound A34 | B | >4 | >6 |
| Compound A49 | D | >9 | >2 |
| Compound A52 | B | >11 | >16 |
| Compound A53 | D | >14 | >6 |
| Compound A54 | C | >12 | >9 |
| Compound A57 | D | >15 | >7 |

TABLE 1-continued

The $ED_{50}$ value with LORR and minimal lethal dose of the present invention compounds in rats

| Compound/drug | $ED_{50}$(mg/kg) | Minimal lethal dose (mg/kg) | Approximate therapeutic index |
|---|---|---|---|
| Compound A65 | D | >16 | >7 |
| Compound A70 | C | >12 | >6 |
| Compound A72 | A | >11 | >100 |
| Compound A73 | A | >2 | >25 |
| Compound A76 | A | >2 | >10 |
| Compound A83 | C | >12 | >10 |
| Compound A87 | B | >13 | >18 |
| Compound A90 | C | >10 | >5 |
| Compound A92 | A | >1 | >14 |
| Compound A94 | B | >12 | >12 |
| Compound A98 | C | >10 | >7 |
| Compound A100 | D | >14 | >6 |
| Compound A101 | C | >13 | >8 |
| Compound A108 | D | >15 | >5 |

Notes:
*The values in brackets indicate 95% confidence limit (mg/kg);
A indicates that the measured $ED_{50}$ is in the range of 0.04-0.50 mg/kg (including 0.04 and 0.50 mg/kg);
B means that the measured $ED_{50}$ is in the range of 0.50-1.00 mg/kg (excluding 0.50 mg/kg, including 1.00 mg/kg);
C indicates that the measured $ED_{50}$ is in the range of 1.00-2.00 mg/kg (excluding 1.00 mg/kg, including 2.00 mg/kg);
D indicates that the measured $ED_{50}$ is in the range of 2.00-6.00 mg/kg (excluding 2.00 mg/kg, including 6.00 mg/kg).

Example 2 Comparison of Pharmacological Characteristics of the Group A Compounds at Equivalent Doses ($2ED_{50}$) in Rats Adult male Sprague-Dawley rats (250-300 g) were selected for the experiment (n=8). The compounds and the control drugs, etomidate and CPMM, were dissolved in DMSO, and the same volume of DMSO was given as the blank control group. The drugs were administered at a dose twice their $ED_{50}$ through the tail vein of rats in a volume of 0.6 mL and at a rate of 0.1 mL/s. In addition, the time of LORR was recorded as the onset time of anesthesia.

The results show that the compounds of the present invention, similar to the etomidate and CPMM, exhibit rapid onset and recovery (Tables 2). Furthermore, the duration of the pharmacological effects is sufficient to meet the time requirements for rapid induction of general anesthesia and for diagnostic examinations, some short invasive clinical examinations, or operations. In the experiment, the types and incidence of adverse reactions of the compounds of the present invention are less than those of etomidate and CPMM.

TABLE 2

Comparison of pharmacological characteristics of the compounds at equivalent doses ($2ED_{50}$) in rats

| Compound/drug | $2ED_{50}$ (mg/kg) | Onset time (min) | Righting reflex duration (min) | Sedation duration (mg/kg) | Types and incidence of adverse reactions |
|---|---|---|---|---|---|
| Etomidate | 1.49 | 0.11 ± 0.03 | 4.92 ± 1.19 | 11.08 ± 2.16 | Tremor(10/10), Facial muscle twitching(4/10), Tongue stretching(8/10) |
| CPMM | 1.56 | 0.26 ± 0.08 | 1.62 ± 0.63 | 4.99 ± 0.87 | Convulsions(4/10), Tremor(5/10), Myoclonus (5/10) |
| Propofol | 11.02 | 0.19 ± 0.03 | 8.36 ± 2 | 16.02 ± 2.58 | Intermittent Tremor(6/8), Bucking (5/8), Tongue stretching(4/8), Forelimb rigidity (2/8), Hindlimb rigidity(2/8) |
| DMSO | / | / | / | / | Red urine(10/10) |
| Compound A1 | 2C | 0.56 ± 0.26 | 2.24 ± 1.29 | 8.37 ± 2.63 | Red urine(8/8), Convulsions(7/8) |
| Compound A3 | 2C | 0.13 ± 0.04 | 2.73 ± 1.08 | 5.76 ± 0.80 | Red urine(8/8), Hindlimb rigidity (1/8) |
| Compound A4 | 2C | 0.52 ± 0.21 | 1.39 ± 0.66 | 6.75 ± 1.43 | Red urine(6/6), Euphoria(5/6), Hindlimb rigidity(1/6) |
| Compound A6 | 2D | 0.38 ± 0.12 | 3.81 ± 2.17 | 9.72 ± 3.29 | Red urine(8/8), Facial muscle twitching(2/8), Hindlimb rigidity (1/8) |
| Compound A8 | 2C | 0.57 ± 0.20 | 2.70 ± 2.52 | 14.81 ± 5.21 | Red urine(8/8), Tremor(2/8), Euphoria(1/8) |
| Compound A10 | 2D | 0.43 ± 0.22 | 1.32 ± 0.61 | 8.31 ± 2.76 | Red urine(8/8), Tremor(3/8), Forelimb clonic convulsion(2/8), Hindlimb rigidity(2/8), Facial muscle twitching(2/8), Nod(1/8) |

TABLE 2-continued

Comparison of pharmacological characteristics of the compounds at equivalent doses ($2ED_{50}$) in rats

| Compound/drug | $2ED_{50}$ (mg/kg) | Onset time (min) | Righting reflex duration (min) | Sedation duration (mg/kg) | Types and incidence of adverse reactions |
|---|---|---|---|---|---|
| Compound A11 | 2C | 0.41 ± 0.15 | 2.65 ± 1.10 | 10.46 ± 2.46 | Red urine(6/6), General Tremor(4/6), Hindlimb rigidity (2/6), Convulsion(1/6), Euphoria(1/6) |
| Compound A12 | 2C | 0.69 ± 0.22 | 3.16 ± 2.13 | 8.71 ± 1.57 | Red urine(8/8), Tremor(3/8), Euphoria(1/8), Hindlimb rigidity (1/8), Clonic convulsion(1/8), Tetany convulsion (1/8), Apnea(1/8), Nod(1/8) |
| Compound A14 | 2C | 0.78 ± 0.22 | 1.20 ± 0.72 | 12.29 ± 2.59 | Red urine(5/5), Four limbs Tremor(1/5) |
| Compound A15 | 2D | 0.40 ± 0.10 | 1.82 ± 0.76 | 11.26 ± 1.51 | Red urine(8/8), Euphoria(2/8), Hindlimb rigidity(2/8), Hindlimb Tremor(1/8) |
| Compound A16 | 2D | 0.55 ± 0.21 | 2.55 ± 1.54 | 8.28 ± 1.30 | Red urine(8/8) Euphoria(2/8), Tremor(2/8), Apnea (1/8), Hindlimb rigidity (1/8) |
| Compound A18 | 2D | 0.73 ± 0.10 | 1.19 ± 0.64 | 10.44 ± 1.49 | Red urine(8/8), Hindlimb rigidity(5/8) |
| Compound A20 | 2C | 0.67 ± 0.14 | 1.15 ± 0.66 | 7.05 ± 3.95 | Red urine(8/8), Hindlimb rigidity(3/8), General Tremor(1/8) |
| Compound A21 | 2D | 0.51 ± 0.10 | 1.16 ± 0.39 | 8.65 ± 2.38 | Red urine(8/8), Euphoria(3/8), Four limbs Tremor(2/8), Hindlimb rigidity (2/8) |
| Compound A23 | 2D | 0.48 ± 0.14 | 2.28 ± 1.83 | 8.27 ± 1.80 | Red urine(8/8), Euphoria(6/8), Hindlimb rigidity (2/8), Tremor(1/8), Convulsions(1/8) |
| Compound A24 | 2A | 0.47 ± 0.09 | 1.47 ± 0.63 | 5.64 ± 0.54 | Red urine(8/8), Convulsions(5/8), Hindlimb rigidity (2/8) |
| Compound A25 | 2A | 0.50 ± 0.12 | 2.6 ± 0.83 | 7.27 ± 0.80 | Red urine(8/8), Hindlimb rigidity (2/8), Tremor(1/8) |
| Compound A30 | 2C | 0.3 ± 0.22 | 2.6 ± 0.83 | 6.40 ± 1.20 | Red urine(8/8), Euphoria(3/8), Tremor(1/8) |
| Compound A34 | 2B | 0.60 ± 0.32 | 1.6 ± 0.43 | 6.27 ± 0.47 | Red urine(8/8), Hindlimb rigidity(2/8), Tremor(1/8) |
| Compound A49 | 2D | 0.28 ± 0.04 | 2.69 ± 1.18 | 7.94 ± 1.27 | Red urine(8/8), Hindlimb rigidity (2/8), broken-winded(1/8), Tremor(3/8) |
| Compound A52 | 2B | 0.50 ± 0.08 | 2.01 ± 1.00 | 9.59 ± 3.37 | Red urine(8/8), Euphoria(3/8), broken-winded(1/8) |
| Compound A53 | 2D | 0.53 ± 0.28 | 3.01 ± 1.22 | 6.59 ± 2.17 | Red urine(8/8), Tremor(2/8) |
| Compound A54 | 2C | 0.69 ± 0.11 | 2.13 ± 1.80 | 7.49 ± 1.65 | Red urine(8/8), Hindlimb rigidity (3/8), GeneralTremor(1/8) |

TABLE 2-continued

| Comparison of pharmacological characteristics of the compounds at equivalent doses ($2ED_{50}$) in rats | | | | | |
|---|---|---|---|---|---|
| Compound/drug | $2ED_{50}$ (mg/kg) | Onset time (min) | Righting reflex duration (min) | Sedation duration (mg/kg) | Types and incidence of adverse reactions |
| Compound A57 | 2D | 0.42 ± 0.16 | 1.48 ± 0.51 | 6.31 ± 2.55 | Red urine(7/7), GeneralTremor (2/7), Tetany convulsion(2/7) |
| Compound A65 | 2D | 0.36 ± 0.15 | 2.48 ± 0.67 | 8.31 ± 3.23 | Red urine(8/8), Tremor(2/8) |
| Compound A70 | 2C | 0.31 ± 0.08 | 2.51 ± 1.03 | 10.18 ± 3.27 | Red urine(8/8), Hindlimb rigidity (2/8), Tremor(1/8), Clonic convulsion(1/8), Euphoria (1/8) |
| Compound A72 | 2A | 0.41 ± 0.17 | 0.71 ± 0.20 | 4.16 ± 2.32 | Red urine(8/8), Tremor(1/8), Hindlimb rigidity (1/8) |
| Compound A73 | 2A | 0.42 ± 0.07 | 1.21 ± 0.45 | 10.08 ± 4.36 | Red urine(8/8), Tremor(3/8), Facial muscle twitching(2/8), Euphoria (1/8), Nod(1/8) |
| Compound A76 | 2A | 0.36 ± 0.12 | 2.29 ± 0.56 | 9.08 ± 2.16 | Red urine(8/8), Tremor(2/8), Euphoria(1/8) |
| Compound A83 | 2C | 0.43 ± 0.32 | 3.21 ± 0.41 | 10.08 ± 4.36 | Red urine(8/8), Facial muscle twitching(3/8), Euphoria (2/8) |
| Compound A87 | 2B | 0.30 ± 0.12 | 2.21 ± 0.24 | 7.08 ± 2.36 | Red urine(8/8), Facial muscle twitching(4/8), Tremor(1/8) |
| Compound A90 | 2C | 0.51 ± 0.07 | 5.21 ± 1.45 | 5.06 ± 1.36 | Red urine(8/8), Convulsions(2/8), Nod(1/8) |
| Compound A92 | 2A | 0.43 ± 0.22 | 2.03 ± 0.33 | 6.08 ± 1.26 | Red urine(8/8), Tremor(2/8), Euphoria(1/8) |
| Compound A94 | 2B | 0.33 ± 0.12 | 1.26 ± 0.40 | 5.03 ± 2.19 | Red urine(8/8), Tremor(3/8), Four limbs rigidity(2/8), Euphoria(1/8) |
| Compound A98 | 2C | 0.30 ± 0.06 | 1.89 ± 0.23 | 7.12 ± 1.37 | Red urine(8/8), Facial muscle twitching(2/8), Hindlimb rigidity (1/8) |
| Compound A100 | 2D | 0.49 ± 0.17 | 3.21 ± 0.89 | 11.08 ± 3.36 | Red urine(8/8), Indirect tremor Tremor(4/8), Four limbs rigidity(2/8), Euphoria(2/8) |
| Compound A101 | 2C | 0.39 ± 0.21 | 2.29 ± 0.65 | 9.11 ± 2.36 | Red urine(8/8), Euphoria(3/8), Nod(2/8) |
| Compound A108 | 2D | 0.26 ± 0.20 | 3.29 ± 1.20 | 8.22 ± 1.36 | Red urine(8/8), Hindlimb rigidity (7/8), the four limbs Tremor(3/8) |

Example 3 the Effects of the Group a Compounds on Adrenocortical Function in Vitro Test The H295R cell line was selected and treated with vehicle (i.e., DMSO) and different concentrations of etomidate, CPMM, etomidate metabolite (i.e., etomidate acid), and the compounds of the present invention. Then secretion of the cortisol and corticosterone in the supernatant, was measured using HPLC-MS/MS method to determine whether the compounds of the present invention had adrenotoxic potential. The results show that the compounds of the present invention meet the design requirements (Table 3), and none of the compounds inhibit adrenocortical function in the experiment.

TABLE 3

The effects of the compounds on adrenocortical function in vitro test
Cell line:: H295
Incubation concentration and concentration range: 0.1 nM, 1 nM, 10 nM, 50 nM, 100 nM, 500 nM, 1000 nM, 10000 nM
Cortisol and corticosterone determination: HPLC-MS/MS method
The effect determination of compounds or drugs on adrenal function:
No inhibition (using blank culture medium, or DMSO, or etomidate metabolite, i.e., etomidate acid, as a control), marked as "0" in the table.
Mild inhibition (using CPMM as a control), marked as "1" in the table.
Obvious inhibition (with etomidate as a control), marked as "2" in the table.

| Compound/drug | $EC_{50}$ (Cortisol) | Cortisol as an indicator to determine the presence of inhibition | $EC_{50}$ (Corti-costerone) | Corti-costerone as an indicator to determine the presence of inhibition |
|---|---|---|---|---|
| Etomidate | >1 nM | 2 | >10 nM | 2 |
| CPMM | >10 nM | 1 | >100 nM | 1 |
| Propofol | >10000 nM | 0 | >10000 nM | 0 |
| Etomidate acid | >10000 nM | 0 | >10000 nM | 0 |
| DMSO | >10000 nM | 0 | >10000 nM | 0 |
| Blank medium | >10000 nM | 0 | >10000 nM | 0 |
| Compound A1 | >1000 nM | 0 | >1000 nM | 0 |
| Compound A3 | >1000 nM | 0 | >1000 nM | 0 |
| Compound A4 | >1000 nM | 0 | >1000 nM | 0 |
| Compound A6 | >1000 nM | 0 | >1000 nM | 0 |
| Compound A8 | >1000 nM | 0 | >1000 nM | 0 |
| Compound A10 | >1000 nM | 0 | >1000 nM | 0 |
| Compound A11 | >100 nM | 0 | >100 nM | 0 |
| Compound A12 | >100 nM | 0 | >100 nM | 0 |
| Compound A14 | >1000 nM | 0 | >1000 nM | 0 |
| Compound A15 | >100 nM | 0 | >100 nM | 0 |
| Compound A16 | >100 nM | 0 | >100 nM | 0 |
| Compound A18 | >100 nM | 0 | >100 nM | 0 |
| Compound A20 | >100 nM | 0 | >100 nM | 0 |
| Compound A21 | >100 nM | 0 | >100 nM | 0 |
| Compound A23 | >100 nM | 0 | >100 nM | 0 |
| Compound A24 | >1000 nM | 0 | >1000 nM | 0 |
| Compound A25 | >1000 nM | 0 | >1000 nM | 0 |
| Compound A30 | >1000 nM | 0 | >1000 nM | 0 |
| Compound A34 | >1000 nM | 0 | >1000 nM | 0 |
| Compound A49 | >100 nM | 0 | >100 nM | 0 |
| Compound A52 | >1000 nM | 0 | >1000 nM | 0 |
| Compound A53 | >100 nM | 0 | >100 nM | 0 |
| Compound A54 | >100 nM | 0 | >100 nM | 0 |
| Compound A57 | >100 nM | 0 | >100 nM | 0 |
| Compound A65 | >100 nM | 0 | >100 nM | 0 |
| Compound A70 | >100 nM | 0 | >100 nM | 0 |
| Compound A72 | >1000 nM | 0 | >1000 nM | 0 |
| Compound A73 | >1000 nM | 0 | >1000 nM | 0 |
| Compound A76 | >1000 nM | 0 | >1000 nM | 0 |
| Compound A83 | >1000 nM | 0 | >1000 nM | 0 |
| Compound A87 | >1000 nM | 0 | >1000 nM | 0 |
| Compound A90 | >1000 nM | 0 | >1000 nM | 0 |
| Compound A92 | >1000 nM | 0 | >1000 nM | 0 |

TABLE 3-continued

The effects of the compounds on adrenocortical function in vitro test
Cell line:: H295
Incubation concentration and concentration range: 0.1 nM, 1 nM, 10 nM, 50 nM, 100 nM, 500 nM, 1000 nM, 10000 nM
Cortisol and corticosterone determination: HPLC-MS/MS method
The effect determination of compounds or drugs on adrenal function:
No inhibition (using blank culture medium, or DMSO, or etomidate metabolite, i.e., etomidate acid, as a control), marked as "0" in the table.
Mild inhibition (using CPMM as a control), marked as "1" in the table.
Obvious inhibition (with etomidate as a control), marked as "2" in the table.

| Compound/drug | $EC_{50}$ (Cortisol) | Cortisol as an indicator to determine the presence of inhibition | $EC_{50}$ (Corti-costerone) | Corti-costerone as an indicator to determine the presence of inhibition |
|---|---|---|---|---|
| Compound A94 | >1000 nM | 0 | >1000 nM | 0 |
| Compound A98 | >1000 nM | 0 | >1000 nM | 0 |
| Compound A100 | >100 nM | 0 | >100 nM | 0 |
| Compound A101 | >100 nM | 0 | >100 nM | 0 |
| Compound A108 | >100 nM | 0 | >100 nM | 0 |

Example 4 the Effects of Group a Compounds on Adrenal Cortex Function were Measured In Vivo The anesthetic activity of the compounds was assessed in rats using a LORR assay and the up and down method was used to determine $ED_{50}$. The drugs were administered at a dose twice their $ED_{50}$ hrough the tail vein of rats (n=8), The changes of serum corticosterone in rats before and after administration were measured. The serum corticosterone concentration (ng/ml) was used as the representative index to determine the effect of present invention compounds on adrenal cortex function in rats.

The main test equipment are as follows:

Multifunctional ionmeter (METTLER TOLEDO, Types: SevenMulti), Pipette (Eppendorf, Specifications: 1000 ul, 200 ul, 100 ul, 10 ul), 22 G intravenous indwelling needle (BECTON DICKINSON), 1 ml micro injection needle (Germany BD), timer. Administration procedure: The experiment was unified in the forenoon. 8:00 to 8:30 for the trial preparation stage. Rats were put into a restraint device with a 22G indwelling catheter placed into a lateral tail vein and retained with heparin, a pre-filled extension tube was attached and taped to the tail vein to secure the extension tube.

① Dexamethasone suppression: intravenous injection of dexamethasone after the placement of the retaining needle (0.5 mg/kg).

② The first blood collection was performed two hours after dexamethasone administration (S1);

③ Dexamethasone is injected after blood collection (0.2 mg/kg)+the present invention Compound ($2ED_{50}$), all drugs or compounds had a constant volume of 0.6 ml, and the speed was 0.1 ml/s. Exogenous ACTH (25 ug/kg) was injected after 15 minutes.

④ Blood samples were collected again 30 minutes after ACTH administration (S2);

⑤ After blood samples were collected, they were allowed to stand for 30-60 minutes at room temperature, then centrifuged at 3500 rpm for 10 minutes, the supernatant was centrifuged at 15000 rpm for 5 minutes, and then frozen in −20° C. refrigerator.

Data collection: The concentration of corticosterone in serum of rats was measured by high performance liquid chromatography tandem mass spectrometry (HPLC-MS/MS) within 2-3 days after sampling.

Figure 1:
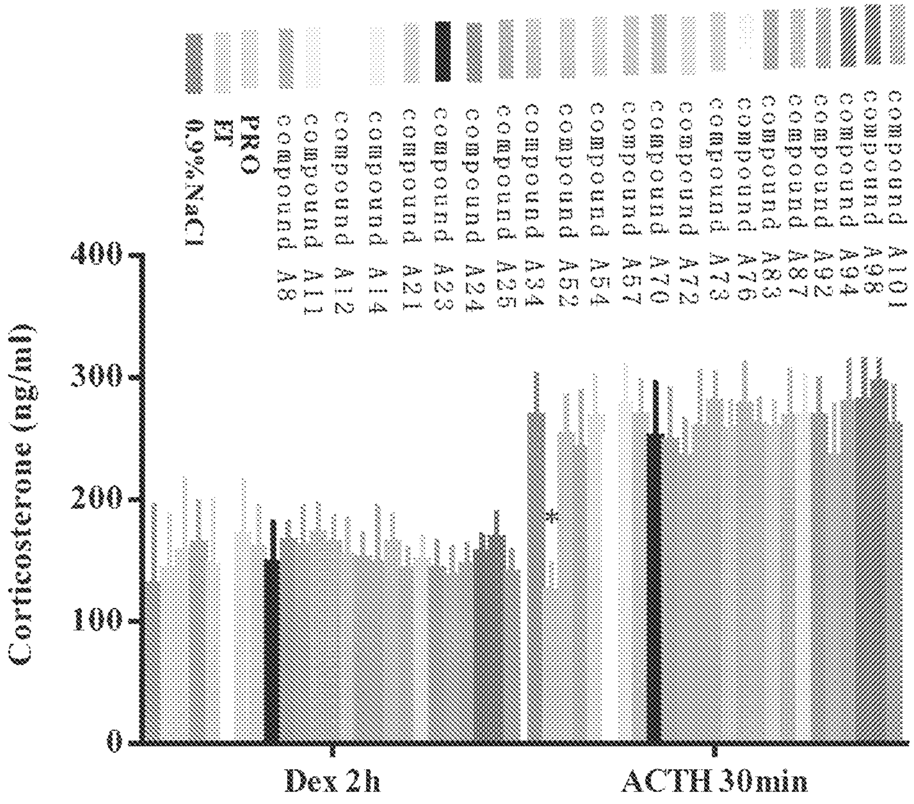
FIG. 1: Effect of the compound of the invention on the function of adrenal cortex; "*" means that it is statistically significant compared with 0.9% NaCl group.
Figure 2:
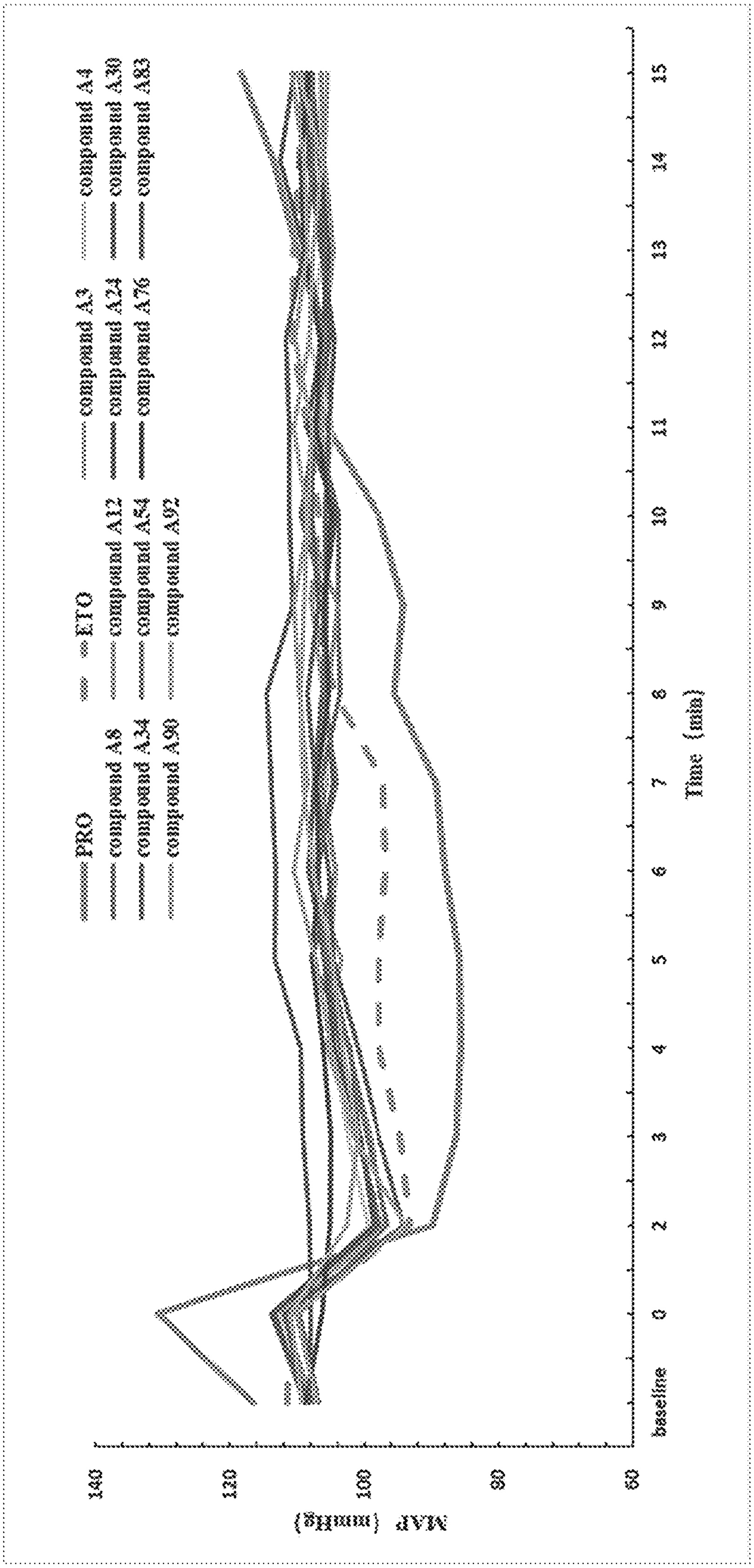
FIG. 2: Effects of the compounds of the present invention on the mean arterial pressure (MAP) (actually measured values); Notes: (1) All the test animals' righting reflex disappeared within 1 min after the administration; (2) The 0 min on the abscissa in the figure represents the end of administration; (3) The recovery time of the test animals' righting reflex for compounds or drugs were PRO: 645 s (10.75 min); ETO: 440 s (7.33 min); Compound A3: 133 s (2.22 min); Compound A4: 174 s (2.90 min); Compound A8: 139 s (2.32 min); Compound A12: 80 s (1.34 min); Compound A24: 126 s (2.10 min); Compound A30: 93 s (1.55 min); Compound A34: 94.2 s (1.57 min); Compound A54: 72 s (1.20 min); Compound A76: 203 s (3.39 min); Compound A83: 187 s (3.12 min); Compound A90: 278 s (4.63 min); Compound A92: 116 s (1.93 min).
Figure 3:
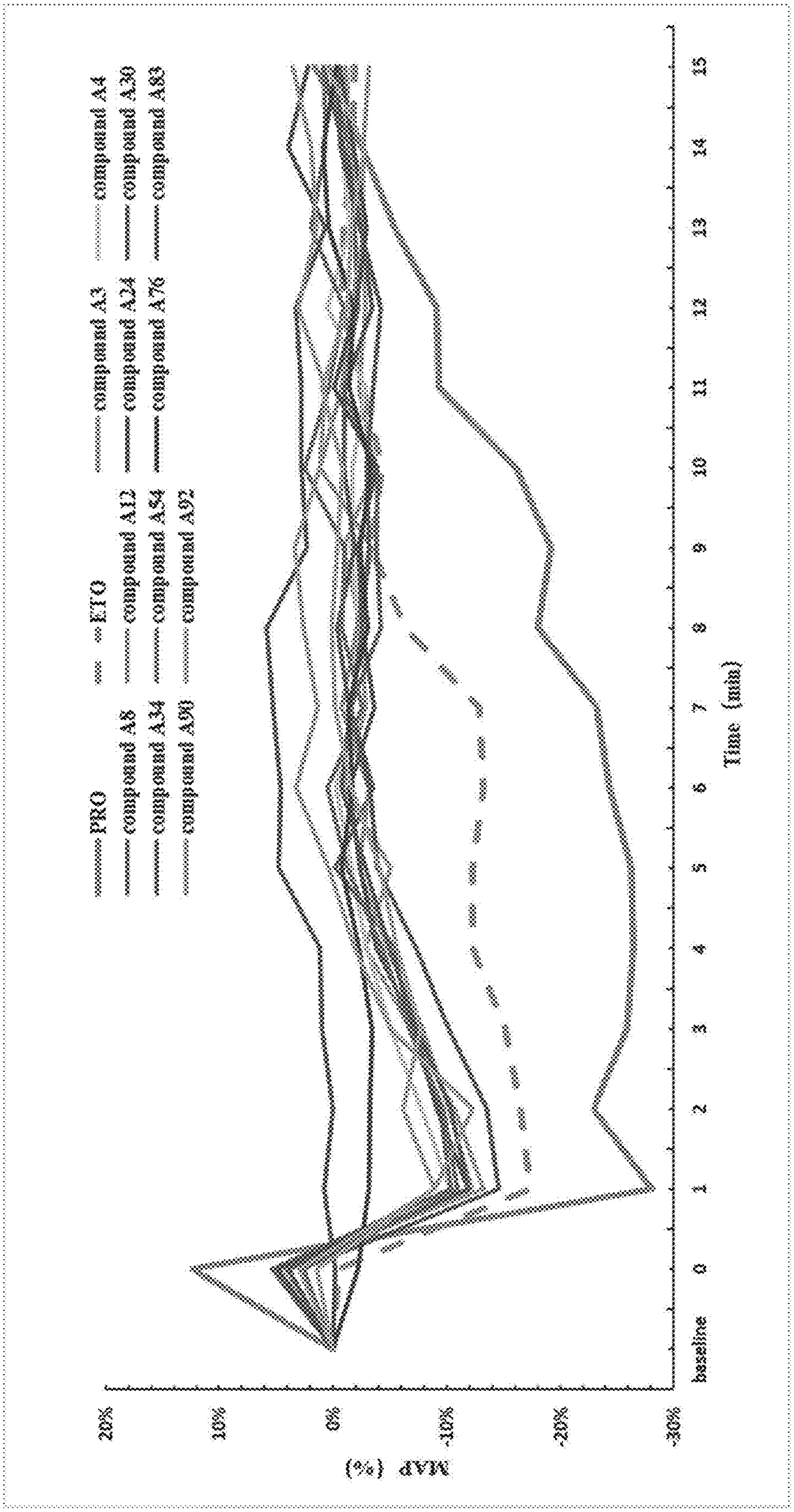
FIG. 3: Effects (rate of change) of the compounds of the present invention on the mean arterial pressure (MAP); Notes: (1) All the test animals' righting reflex disappeared within 1 min after the administration; (2) The 0 min on the abscissa in the figure represents the end of administration; (3) The recovery time of the test animals' righting reflex for compounds or drugs were PRO: 645 s (10.75 min); ETO: 440S (7.33 min); Compound A3: 133 s (2.22 min); Compound A4: 174 s (2.90 min); Compound A8: 139 s (2.32 min); Compound A12: 80 s (1.34 min); Compound A24: 126 s (2.10 min); Compound A30: 93 s (1.55 min); Compound A34: 94.2 s (1.57 min); Compound A54: 72 s (1.20 min); Compound A76: 203 s (3.39 min); Compound A83: 187 s (3.12 min); Compound A90: 278 s (4.63 min); Compound A92: 116 s (1.93 min).
Figure 4:
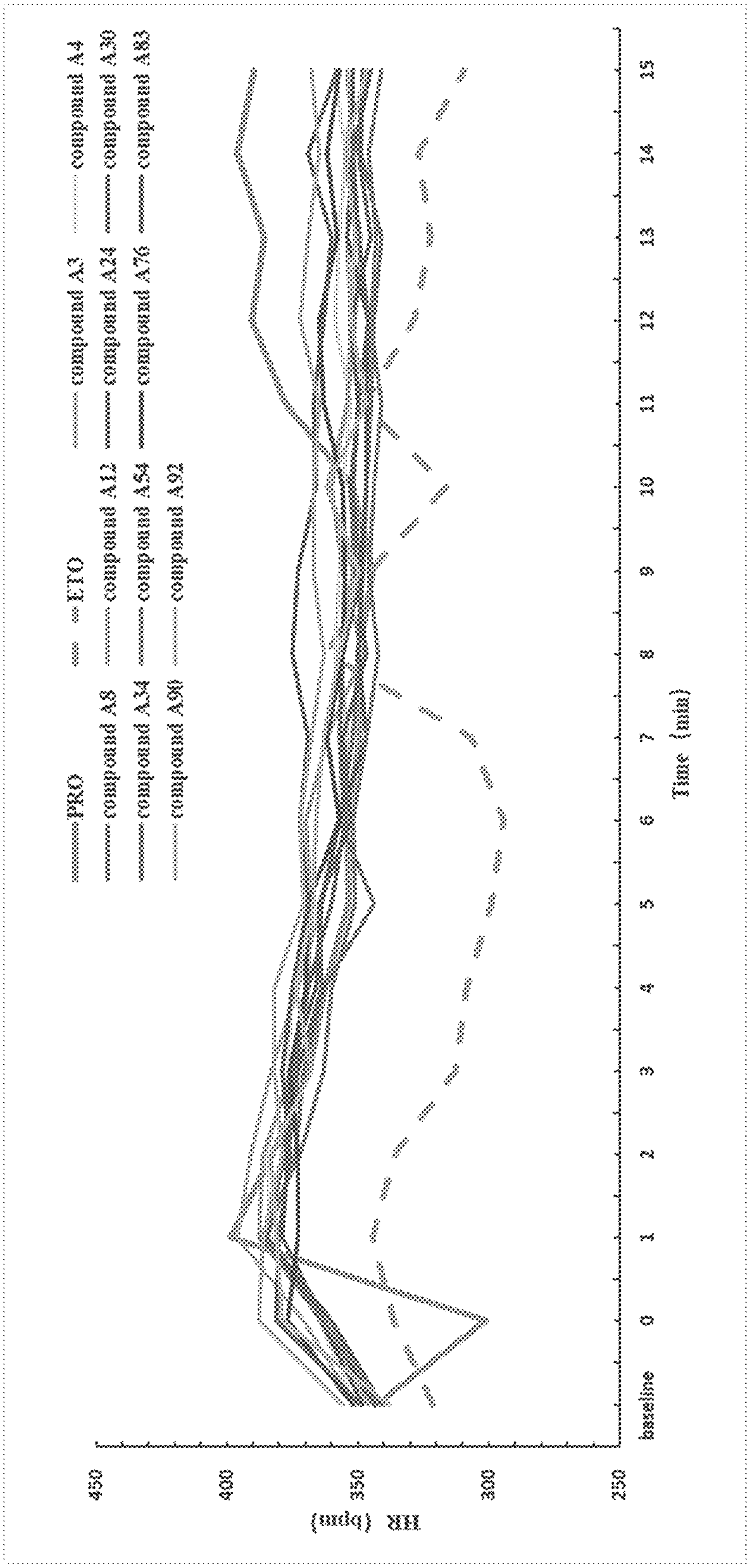
FIG. 4: Effects of the compounds of the present invention on heart rate (HR) (actually measured values); Notes: (1) All the test animals' righting reflex disappeared within 1 min after the administration; (2) The 0 min on the abscissa in the figure represents the end of administration; (3) The recovery time of the test animals' righting reflex for compounds or drugs were PRO: 645 s (10.75 min); ETO: 440 s (7.33 min); Compound A3: 133 s (2.22 min); Compound A4: 174 s (2.90 min); Compound A8: 139 s (2.32 min); Compound A12: 80 s (1.34 min); Compound A24: 126 s (2.10 min); Compound A30: 93 s (1.55 min); Compound A34: 94.2 s (1.57 min); Compound A54: 72 s (1.20 min); Compound A76: 203 s (3.39 min); Compound A83: 187 s (3.12 min); Compound A90: 278 s (4.63 min); Compound A92: 116 s (1.93 min).
Figure 5:
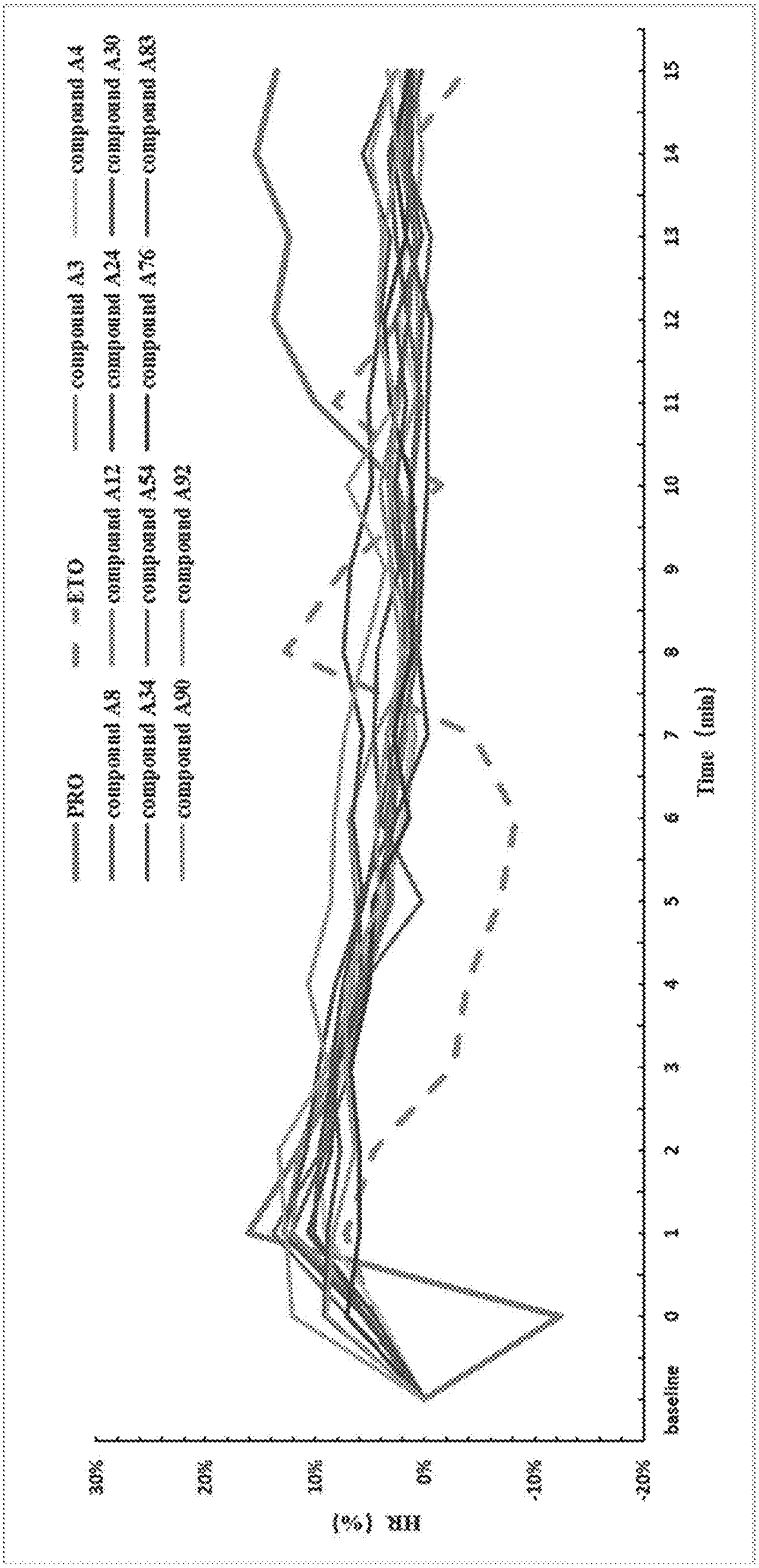
FIG. 5: Effects (rate of change) of the compounds of the present invention on heart rate (HR). Notes: (1) All the test animals' righting reflex disappeared within 1 min after the administration; (2) The 0 min on the abscissa in the figure represents the end of administration; (3) The recovery time of the test animals' righting reflex for compounds or drugs were PRO: 645 s (10.75 min); ETO: 440 s (7.33 min); Compound A3: 133 s (2.22 min); Compound A4: 174 s (2.90 min); Compound A8: 139 s (2.32 min); Compound A12: 80 s (1.34 min); Compound A24: 126 s (2.10 min); Compound A30: 93 s (1.55 min); Compound A34: 94.2 s (1.57 min); Compound A54: 72 s (1.20 min); Compound A76: 203 s (3.39 min); Compound A83: 187 s (3.12 min); Compound A90: 278 s (4.63 min); Compound A92: 116 s (1.93 min).

The result: the compounds of this invention did not inhibit the synthesis of adrenal cortex hormone as compared with normal saline (0.9% NaCl) and propofol (PRO), while the control of etomidate (ET) showed obvious inhibitory effect on adrenal cortex function (FIG. 1).

Example 5 the Effects of the Group a Compounds on the Circulatory Function were Measured in Rats Using a Small Animal Implanted Physiological Signal Telemetry System The anesthetic activity of the compounds was assessed in rats using a LORR assay and the up and down method was used to determine $ED_{50}$. The drugs were administered at a dose twice their $ED_{50}$ through the tail vein of rats (n=6). A small animal implantable physiological signal telemetry system from DSI (Data Science International, Inc.) was used to measure the changes in heart rate (HR) and blood pressure in rats during 30 min after administration. Then mean arterial pressure (MAP) and HR were used as representative indicators to determine hemodynamic stability of the compounds of the present invention in rats.

The main test equipment are as follows:

A small animal implantable physiological signal telemetry system from DSI (Data Science International, Inc.) including implants (RATHD-S21, DSI, United States), receiver boards (RPC-1, DSI, United States), signal conversion devices (DEM, DSI, USA), perfusion glue (DSI, USA), fibrin membrane (DSI, USA), etc.

A small animal ventilator (HX-101E, Chengdu Taimeng Technology Co., Ltd.); An electronic balance (ME215S, Sartorius, Germany).

First, animal models were established. A left ventricular catheter, an abdominal aortic catheter and ECG wires were placed into rats. At least one week after surgery, data were recorded.

Administration procedure: rats were put into a restraint device with a 20G indwelling catheter placed into a lateral tail vein. After administration of 0.2 mL heparin, a pre-filled extension tube was attached and taped to the tail vein to secure the extension tube. Then the rats were removed from the restraint device to a cage before placing them together on the signal receiver. After the rats acclimatized for 30 min, the compounds were injected with a dose at 2-fold the $ED_{50}$ via the catheter. Finally, the pharmacological effects, adverse reactions, and behavioural manifestations of the rats were observed and recorded Data collection: After setting the data collection parameters on the software, the power of the implant was turned on to start data collection. In this experiment, data recording frequency was set to 15 s. Data collection was continuously recorded for 30 min before and after administration of the drugs in rats. After data acquisition, the test was stopped. The results: the compounds of the present invention had almost no inhibitory effect on the circulatory function as does the control etomidate, while the control propofol exhibit significant inhibition of the circulatory function (FIG. 2, FIG. 3, FIG. 4, FIG. 5).

Example 6 Pharmacological Effects of the Group a Compounds on Continuous Infusion in Rats Adult male Sprague-Dawley rats with body weight ranging from 250 to 300 gm were selected for continuous infusion test. The compounds of the present invention and the control drugs, etomidate and CPMM, were prepared as emulsion before the test, which was continuously infused through the tail vein of the rats at 2 times the MIR (minimum infusion rate) and the LORR was maintained for 1 hour. Time to recovery of righting reflex from stopping infusion, and time to fully awake from stopping infusion were recorded. The results are shown in Table A.

The results are shown which illustrate that the recovery time after 1 hour of continuous infusion under 2×MIR conditions is not significantly longer than that of the compounds of the present invention after a single intravenous injection of $2ED_{50}$, and the recovery time is considerably shorter than that of etomidate. Furthermore, the types and incidence of adverse reactions are also significantly less than etomidate and CPMM.

TABLE 4

Pharmacological effects of the compounds on continuous infusion in rats

| Compound/drug | Onset time (min) | Recovery time after stopping infusion (min) | Types and incidence of adverse reactions |
|---|---|---|---|
| Etomidate | 4-5 | 25-30 | Tremor(6/6), Facial muscle twitching (4/6), Tonguestretching(5/6) |
| CPMM | 3-4 | 7-8 | Convulsions(3/6), Tremor(5/6), Myoclonus(5/6), |
| DMSO | / | / | Hematuria(8/8) |
| Compound A4 | 4-5 | 14-16 | Tremor(3/6), Tongue stretching(4/6) |
| Compound A14 | 6-7 | 10-14 | Tremor(1/6), |
| Compound A20 | 5-6 | 12-15 | Tremor(5/6) |
| Compound A24 | 4-5 | 8-12 | Tremor(2/6), Tongue stretching(4/6) |
| Compound A30 | 3-4 | 8-14 | Tremor(2/6) |
| Compound A52 | 5-6 | 13-18 | Tongue stretching(4/6), Tremor(4/6) |
| Compound A76 | 3-4 | 14-16 | Tremor(1/6), Tongue stretching(2/6) |
| Compound A90 | 5-6 | 2-15 | Tremor(3/6) |

Example 7 the Anesthetic Activity of the Group B Compounds was Assessed in Rats Using a Loss of Righting Reflexes (LORR) Assay Adult male Sprague-Dawley rats (250-300 g) were selected for the experiment. The compounds in the above examples and the control drugs, etomidate and CPMM, were dissolved in dimethyl sulfoxide (DMSO), and the same volume of DMSO was given as the blank control group. The anesthesia effects of the compounds were assessed in rats using a LORR assay and a period >30 s was considered as an indicator of general anesthesia. Then the up and down method was used to determine 50% effective dose (EDO. The drugs were administered through the tail vein of rats in a volume of 0.6 mL and at a rate of 0.1 mL/s. As shown in Tables A1-E1, the results suggest that the compounds of the present invention, similar to the control etomidate and CPMM, provide a definite and transient effect of general anesthesia. Besides the compounds have the same or better potency as etomidate and CPMM.

TABLE 5

The $ED_{50}$ value with LORR and minimal lethal dose of the compounds in rats

| Compound/drug | $ED_{50}$ (mg/kg) | Minimal lethal dose (mg/kg) | Approximate therapeutic index |
|---|---|---|---|
| Etomidate | 0.75(0.72-0.77)* | 12.75 | 17 |
| CPMM | 0.78(0.74-0.82)* | >7.8 | >10 |
| Propofol | 5.51(5.39-5.64)* | 28 | 5 |
| DMSO | / | / | / |
| Compound B1 | A | >8 | >20 |
| Compound B3 | A | >6 | >32 |
| Compound B6 | A | >10 | >71 |
| Compound B7 | B | >24 | >31 |
| Compound B8 | B | >8 | >9 |
| Compound B10 | B | >11 | >16 |
| Compound B11 | B | >6 | >8 |
| Compound B12 | A | >5 | >16 |
| Compound B13 | B | >1 | >2 |
| Compound B14 | C | >7 | >5 |
| Compound B15 | B | >9 | >9 |
| Compound B17 | A | >16 | >56 |
| Compound B18 | C | >14 | >12 |
| Compound B21 | B | >8 | >11 |
| Compound B26 | C | >12 | >10 |
| Compound B30 | B | >10 | >10 |
| Compound B35 | A | >8 | >29 |
| Compound B36 | B | >5 | >7 |
| Compound B40 | B | >6 | >6 |
| Compound B47 | C | >13 | >9 |
| Compound B51 | C | >14 | >12 |
| Compound B65 | B | >9 | >13 |
| Compound B70 | D | >15 | >2 |
| Compound B80 | D | >16 | >3 |
| Compound B99 | A | >8 | >16 |
| Compound B100 | D | >18 | >2 |
| Compound B101 | C | >13 | >7 |
| Compound B104 | C | >11 | >10 |
| Compound B108 | B | >14 | >20 |
| Compound B110 | D | >16 | >7 |
| Compound B115 | B | >18 | >25 |
| Compound B116 | C | >12 | >9 |
| Compound B118 | C | >17 | >12 |
| Compound B120 | B | >15 | >21 |
| Compound B121 | D | >20 | >3 |
| Compound B127 | B | >16 | >23 |
| Compound B132 | B | >12 | >16 |
| Compound B133 | B | >14 | >20 |
| Compound B136 | D | >18 | >6 |
| Compound B137 | C | >12 | >9 |
| Compound B140 | E | >30 | >2 |
| Compound B144 | E | >24 | >2 |
| Compound B145 | D | >18 | >4 |
| Compound B146 | C | >14 | >8 |

Notes:
*The values in brackets indicate 95% confidence limit (mg/kg);
A indicates that the measured $ED_{50}$ is in the range of 0.04-0.50 mg/kg (including 0.04 and 0.50 mg/kg);
B indicates that the measured $ED_{50}$ is in the range of 0.50-1.00 mg/kg (excluding 0.50 mg/kg, including 1.00 mg/kg);
C indicates that the measured $ED_{50}$ is in the range of 1.00-2.00 mg/kg (excluding 1.00 mg/kg, including 2.00 mg/kg);
D indicates that the measured $ED_{50}$ is in the range of 2.00-10.00 mg/kg (excluding 2.00 mg/kg, including 10.00 mg/kg);
E indicates that the measured $ED_{50}$ is in the range of 10.00-20.00 mg/kg (excluding 10.00 mg/kg, including 20.00 mg/kg).

Example 8 Comparison of Pharmacological Characteristics of the Group B Compounds at Equivalent Doses ($2ED_{50}$) in Rats Adult male Sprague-Dawley rats (250-300 g) were selected for the experiment (n=8).

The compounds and the control drugs, etomidate and CPMM, were dissolved in DMSO, and the same volume of DMSO was given as the blank control group. The drugs were administered at a dose twice their $ED_{50}$ through the tail vein of rats in a volume of 0.6 mL and at a rate of 0.1 mL/s. In addition, the time of LORR was recorded as the onset time of anesthesia. The results show that the compounds of the present invention, Similar to the etomidate and CPMM, exhibit rapid onset and recovery (Tables 2). Furthermore, the duration of the pharmacological effects is sufficient to meet the time requirements for rapid induction of general anesthesia and for diagnostic examinations, some short invasive clinical examinations, or operations. In the experiment, the types and incidence of adverse reactions of the compounds of the present invention are less than those of etomidate and CPMM.

TABLE 6

Comparison of pharmacological characteristics of the compounds at equivalent doses ($2ED_{50}$) in rats

| Compound/drug | $2ED_{50}$ (mg/kg) | Minimal lethal dose (mg/kg) | Approximate therapeutic index | Compound/ drug | $ED_{50}$ (mg/kg) |
|---|---|---|---|---|---|
| Etomidate | 1.49 | 0.11 ± 0.03 | 4.92 ± 1.19 | 11.08 ± 2.16 | Tremor(10/10), Facial muscle twitching(4/10), Tongue stretching(8/10) |
| CPMM | 1.56 | 0.26 ± 0.08 | 1.62 ± 0.63 | 4.99 ± 0.87 | Convulsions(4/10), Tremor(5/10), Myoclonus(5/10) |
| Propofol | 11.02 | 0.19 ± 0.03 | 8.36 ± 2 | 16.02 ± 2.58 | IntermittentTremor(6/8), Cough(5/8), Tongue stretching(4/8), Forelimb rigidity(2/8), Hindlimb rigidity(2/8) |
| DMSO | / | / | / | / | Red urine(10/10) |
| Compound B1 | 2A | 0.45 ± 0.16 | 1.11 ± 1.25 | 4.46 ± 1.41 | Red urine(8/8), Hindlimb rigidity(4/8), Euphoria(2/8) |
| Compound B3 | 2A | 0.24 ± 0.12 | 3.69 ± 1.35 | 10.32 ± 2.08 | Red urine(8/8), Hindlimb rigidity(4/8), Tremor(1/8), Euphoria(1/8) |

TABLE 6-continued

Comparison of pharmacological characteristics of the compounds at equivalent doses ($2ED_{50}$) in rats

| Compound/drug | $2ED_{50}$ (mg/kg) | Minimal lethal dose (mg/kg) | Approximate therapeutic index | Compound/drug | $ED_{50}$ (mg/kg) |
|---|---|---|---|---|---|
| Compound B6 | 2A | 0.46 ± 0.07 | 1.89 ± 0.71 | 6.13 ± 0.98 | Red urine(8/8), Euphoria(1/8) |
| Compound B7 | 2B | 0.44 ± 0.18 | 1.78 ± 0.89 | 6.18 ± 2.17 | Red urine(8/8), Euphoria(3/8) |
| Compound B8 | 2B | 0.44 ± 0.11 | 2.01 ± 0.63 | 7.06 ± 1.70 | Red urine(10/10), Euphoria(1/10), |
| Compound B10 | 2B | 0.39 ± 0.20 | 2.03 ± 0.73 | 7.14 ± 1.05 | Red urine(8/8), Facial muscle twitching(2/8) |
| Compound B11 | 2B | 0.46 ± 0.23 | 0.85 ± 0.18 | 6.89 ± 1.01 | Red urine(8/8), Generalrigidity(1/8) |
| Compound B12 | 2A | 0.58 ± 0.23 | 1.98 ± 0.89 | 6.03 ± 0.88 | Red urine(8/8), Euphoria(4/8), Hindlimb rigidity(1/8), Tremor(1/8) |
| Compound B13 | 2B | 0.21 ± 0.08 | 3.58 ± 2.20 | 9.92 ± 3.14 | Red urine(8/8), Hindlimb rigidity(7/8), Tremor(1/8) |
| Compound B14 | 2C | 0.33 ± 0.12 | 1.16 ± 0.31 | 5.47 ± 1.14 | Red urine(8/8), Euphoria(4/8) |
| Compound B15 | 2B | 0.46 ± 0.04 | 1.57 ± 0.77 | 4.74 ± 1.38 | Red urine(3/3), Euphoria(3/3) |
| Compound B17 | 2A | 0.43 ± 0.04 | 3.27 ± 1.63 | 8.07 ± 3.09 | Red urine(8/8) |
| Compound B18 | 2C | 0.31 ± 0.14 | 3.22 ± 0.99 | 7.03 ± 1.27 | Red urine(8/8), Convulsions(4/8), Slower breathing(1/8), Hindlimb rigidity(1/8) |
| Compound B21 | 2B | 0.28 ± 0.15 | 4.26 ± 1.21 | 6.03 ± 0.97 | Red urine(8/8), Hindlimb rigidity(3/8) |
| Compound B26 | 2C | 0.33 ± 0.05 | 3.26 ± 1.23 | 5.67 ± 2.03 | Red urine(8/8), Tremor(2/8), Hindlimb rigidity(2/8) |
| Compound B30 | 2B | 0.27 ± 0.04 | 4.50 ± 1.32 | 6.32 ± 1.15 | Red urine(8/8), Facial muscle twitching(2/8), Hindlimb rigidity(1/8) |
| Compound B35 | 2A | 0.38 ± 0.58 | 3.88 ± 1.08 | 5.39 ± 0.97 | Red urine(8/8), Convulsions(4/8), Slower breathing(1/8), Hindlimb rigidity(1/8) |
| Compound B36 | 2B | 0.29 ± 0.67 | 4.67 ± 1.24 | 6.61 ± 2.54 | Red urine(8/8), Slower breathing(1/8), Tremor(1/8) |
| Compound B40 | 2B | 0.21 ± 0.09 | 3.68 ± 1.21 | 6.22 ± 1.61 | Red urine(8/8), Generalrigidity(1/8), Cough(1/8), |
| Compound B47 | 2C | 0.18 ± 0.12 | 3.90 ± 0.29 | 3.21 ± 0.97 | Red urine(8/8), broken-winded(1/8), Forelimb rigidity(1/8) |
| Compound B51 | 2C | 0.29 ± 0.33 | 2.98 ± 0.28 | 4.20 ± 1.62 | Red urine(8/8), IntermittentTremor(4/8), Hindlimb rigidity(2/8) |
| Compound B65 | 2B | 0.45 ± 0.14 | 0.94 ± 0.25 | 5.30 ± 2.17 | Red urine(8/8), Hindlimb rigidity(4/8), Tremor(2/8) |
| Compound B70 | 2D | 0.51 ± 0.33 | 1.94 ± 0.61 | 4.21 ± 1.76 | Red urine(8/8), Tremor(3/8) |
| Compound B80 | 2D | 0.39 ± 0.21 | 3.20 ± 0.31 | 4.90 ± 1.27 | Red urine(8/8), Hindlimb rigidity(4/8), Tremor(2/8) |
| Compound B99 | 2A | 0.78 ± 0.24 | 1.02 ± 0.58 | 6.34 ± 1.04 | Red urine(8/8), Euphoria(3/8), Hindlimb rigidity(2/8), Tremor(1/8) |
| Compound B100 | 2D | 0.13-0.45 | 0.75-1.12 | 7.27-10.52 | Red urine(2/2), Euphoria(1/2) |
| Compound B101 | 2C | 0.44 ± 0.12 | 3.02 ± 1.32 | 5.32 ± 1.76 | Red urine(8/8), Euphoria(4/8), General rigidity(2/8), Tremor(1/8) |
| Compound B104 | 2C | 0.59 ± 0.11 | 1.18 ± 0.65 | 6.34 ± 1.33 | Red urine(8/8), Hindlimb rigidity(1/8), Tremor(1/8) |
| Compound B108 | 2B | 0.60 ± 0.12 | 0.96 ± 0.26 | 6.14 ± 1.70 | Red urine(8/8), Hindlimb rigidity(3/3) |
| Compound B110 | 2D | 0.44 ± 0.32 | 3.83 ± 0.69 | 5.32 ± 1.09 | Red urine(8/8), broken-winded(3/8), Tremor(2/8) |
| Compound B115 | 2B | 0.62 ± 0.25 | 1.95 ± 1.55 | 6.39 ± 2.85 | Red urine(8/8), Hindlimb rigidity(2/8) |
| Compound B116 | 2C | 0.49 ± 0.13 | 1.44 ± 0.73 | 5.66 ± 1.91 | Red urine(8/8), Hindlimb rigidity(2/8), Tremor(1/8) |
| Compound B118 | 2C | 0.63 ± 0.27 | 0.77 ± 0.17 | 4.89 ± 2.09 | Red urine(8/8), Tremor(1/8) |

TABLE 6-continued

Comparison of pharmacological characteristics of the compounds at equivalent doses ($2ED_{50}$) in rats

| Compound/drug | $2ED_{50}$ (mg/kg) | Minimal lethal dose (mg/kg) | Approximate therapeutic index | Compound/drug | $ED_{50}$ (mg/kg) |
|---|---|---|---|---|---|
| Compound B120 | 2B | 0.53 ± 0.17 | 1.26 ± 0.44 | 7.46 ± 1.51 | Red urine(8/8), Hindlimb rigidity(8/8), Tremor(1/8) |
| Compound B121 | 2D | 0.7 | 1.53 | 7.83 | Red urine(1/1), Tremor(1/1) |
| Compound B127 | 2B | 0.59 ± 0.15 | 1.23 ± 0.41 | 6.74 ± 2.39 | Red urine(8/8) |
| Compound B132 | 2B | 0.55 ± 0.20 | 0.91 ± 0.42 | 7.65 ± 2.60 | Red urine(8/8), Hindlimb rigidity(2/8) |
| Compound B133 | 2B | 0.63 ± 0.14 | 2.10 ± 1.17 | 8.34 ± 0.90 | Red urine(8/8), Hindlimb rigidity(4/8), Tremor(2/8) |
| Compound B136 | 2D | 0.71 ± 0.15 | 1.60 ± 0.70 | 7.22 ± 2.06 | Red urine(8/8) |
| Compound B137 | 2C | 0.50 ± 0.20 | 0.73 ± 0.13 | 6.65 ± 3.03 | Red urine(4/4), Hindlimb rigidity(2/4), Tremor(1/4) |
| Compound B140 | 2E | 0.55 ± 0.43 | 3.90 ± 0.43 | 6.56 ± 1.87 | Red urine(8/8), Euphoria(3/8) |
| Compound B144 | 2E | 0.43 ± 0.12 | 4.43 ± 0.12 | 5.07 ± 1.42 | Red urine(8/8), Tremor(4/8), Euphoria(1/8) |
| Compound B145 | 2D | 0.59 ± 0.16 | 0.57 ± 0.13 | 7.71 ± 1.03 | Red urine(8/8), Hindlimb rigidity(5/8), Euphoria(1/8) |
| Compound B146 | 2C | 0.60 ± 0.23 | 1.08 ± 0.45 | 10.21 ± 2.52 | Red urine(8/8), Hindlimb rigidity(6/8), Tremor(1/8) |

Example 9 the Effects of the Group B Compounds on Adrenocortical Function In Vitro Test The H295R cell line was selected and treated with vehicle (i.e., DMSO) and different concentrations of etomidate, CPMM, etomidate metabolite (i.e., etomidate acid), and the compounds of the present invention. Then secretion of the cortisol and corticosterone in the supernatant, was measured using HPLC-MS/MS method to determine whether the compounds of the present invention had adrenotoxic potential. The results show that the compounds of the present invention meet the design requirements (Tables 3), and none of the compounds inhibit adrenocortical function in the experiment.

TABLE 7

The effects of the compounds on adrenocortical function in vitro test

Cell line:: H295R
Incubation concentration and concentration range: 0.1 nM, 1 nM, 10 nM, 50 nM, 100 nM, 500 nM, 1000 nM, 10000 nM
Cortisol and corticosterone determination: HPLC-MS/MS method
The effect determination of compounds or drugs on adrenal function:
No inhibition (using blank culture medium, or DMSO, or etomidate metabolite, i.e., etomidate acid, as a control), marked as "0" in the table.
Mild inhibition (using CPMM as a control), marked as "1" in the table.
Obvious inhibition (with etomidate as a control), marked as "2" in the table.

| Compound/drug | $EC_{50}$ (Cortisol) | Cortisol as an indicator to determine the presence of inhibition | $EC_{50}$ (Corticosterone) | Corticosterone as an indicator to determine the presence of inhibition |
|---|---|---|---|---|
| Etomidate | >1 nM | 2 | >10 nM | 2 |
| CPMM | >10 nM | 1 | >100 nM | 1 |
| Etomidate acid | >10000 nM | 0 | >10000 nM | 0 |
| Propofol | >10000 nM | 0 | >10000 nM | 0 |
| DMSO | >10000 nM | 0 | >10000 nM | 0 |
| Blank medium | >10000 nM | 0 | >10000 nM | 0 |
| Compound B1 | >50 nM | 0 | >100 nM | 0 |
| Compound B3 | >1000 nM | 0 | >1000 nM | 0 |
| Compound B6 | >100 nM | 0 | >100 nM | 0 |
| Compound B7 | >100 nM | 0 | >100 nM | 0 |
| Compound B8 | >1000 nM | 0 | >1000 nM | 0 |
| Compound B10 | >100 nM | 0 | >100 nM | 0 |
| Compound B11 | >1000 nM | 0 | >1000 nM | 0 |
| Compound B12 | >1000 nM | 0 | >1000 nM | 0 |
| Compound B13 | >1000 nM | 0 | >1000 nM | 0 |
| Compound B14 | >1000 nM | 0 | >1000 nM | 0 |
| Compound B15 | >1000 nM | 0 | >1000 nM | 0 |
| Compound B17 | >1000 nM | 0 | >1000 nM | 0 |
| Compound B18 | >100 nM | 0 | >100 nM | 0 |
| Compound B21 | >100 nM | 0 | >100 nM | 0 |

TABLE 7-continued

The effects of the compounds on adrenocortical function in vitro test

Cell line:: H295R
Incubation concentration and concentration range: 0.1 nM, 1 nM, 10 nM, 50 nM, 100 nM, 500 nM, 1000 nM, 10000 nM
Cortisol and corticosterone determination: HPLC-MS/MS method
The effect determination of compounds or drugs on adrenal function:
No inhibition (using blank culture medium, or DMSO, or etomidate metabolite, i.e., etomidate acid, as a control), marked as "0" in the table.
Mild inhibition (using CPMM as a control), marked as "1" in the table.
Obvious inhibition (with etomidate as a control), marked as "2" in the table.

| Compound/drug | $EC_{50}$ (Cortisol) | Cortisol as an indicator to determine the presence of inhibition | $EC_{50}$ (Corticosterone) | Corticosterone as an indicator to determine the presence of inhibition |
|---|---|---|---|---|
| Compound B26 | >100 nM | 0 | >100 nM | 0 |
| Compound B30 | >1000 nM | 0 | >1000 nM | 0 |
| Compound B35 | >1000 nM | 0 | >1000 nM | 0 |
| Compound B36 | >1000 nM | 0 | >1000 nM | 0 |
| Compound B40 | >100 nM | 0 | >100 nM | 0 |
| Compound B47 | >100 nM | 0 | >100 nM | 0 |
| Compound B51 | >1000 nM | 0 | >1000 nM | 0 |
| Compound B65 | >1000 nM | 0 | >1000 nM | 0 |
| Compound B70 | >1000 nM | 0 | >1000 nM | 0 |
| Compound B80 | >1000 nM | 0 | >1000 nM | 0 |
| Compound B99 | >3000 nM | 0 | >3000 nM | 0 |
| Compound B100 | >1000 nM | 0 | >1000 nM | 0 |
| Compound B101 | >1000 nM | 0 | >1000 nM | 0 |
| Compound B104 | >3000 nM | 0 | >3000 nM | 0 |
| Compound B108 | >3000 nM | 0 | >3000 nM | 0 |
| Compound B110 | >3000 nM | 0 | >3000 nM | 0 |
| Compound B115 | >3000 nM | 0 | >3000 nM | 0 |
| Compound B116 | >3000 nM | 0 | >3000 nM | 0 |
| Compound B118 | >1000 nM | 0 | >1000 nM | 0 |
| Compound B120 | >1000 nM | 0 | >1000 nM | 0 |
| Compound B121 | >1000 nM | 0 | >1000 nM | 0 |
| Compound B127 | >3000 nM | 0 | >3000 nM | 0 |
| Compound B132 | >1000 nM | 0 | >1000 nM | 0 |
| Compound B133 | >1000 nM | 0 | >1000 nM | 0 |
| Compound B136 | >1000 nM | 0 | >1000 nM | 0 |
| Compound B137 | >1000 nM | 0 | >1000 nM | 0 |
| Compound B140 | >1000 nM | 0 | >1000 nM | 0 |
| Compound B144 | >1000 nM | 0 | >1000 nM | 0 |
| Compound B145 | >3000 nM | 0 | >3000 nM | 0 |
| Compound B146 | >3000 nM | 0 | >3000 nM | 0 |

Example 10 the Effects of Group B Compounds on Adrenal Cortex Function were Measured In Vivo The anesthetic activity of the compounds was assessed in rats using a LORR assay and the up and down method was used to determine $ED_{50}$. The drugs were administered at a dose twice their $ED_{50}$ through the tail vein of rats (n=8), The changes of serum corticosterone in rats before and after administration were measured. The serum corticosterone concentration (ng/ml) was used as the representative index to determine the effect of present invention compounds on adrenal cortex function in rats.

The main test equipment are as follows:

Multifunctional ionmeter (METTLER TOLEDO, type: SevenMulti), Pipette (Eppendorf, Specifications: 1000 ul, 200 ul, 100 ul, 10 ul), 22 G intravenous indwelling needle (BECTON DICKINSON), 1 ml micro injection needle (Germany BD), timer.

Administration procedure: The experiment was unified in the forenoon. 8:00 to 8:30 for the trial preparation stage. Rats were put into a restraint device with a 22G indwelling catheter placed into a lateral tail vein and retained with heparin, a pre-filled extension tube was attached and taped to the tail vein to secure the extension tube.

① Dexamethasone suppression: intravenous injection of dexamethasone after the placement of the retaining needle (0.5 mg/kg).

② The first blood collection was performed two hours after dexamethasone administration (S1);

③ Dexamethasone is injected after blood collection (0.2 mg/kg)+the present invention Compound (2ED50), all drugs compounds had a constant volume of 0.6 ml, and the speed was 0.1 ml/s. Exogenous ACTH (25 ug/kg) was injected after 15 minutes.

④ Blood samples were collected again 30 minutes after ACTH administration (S2);

⑤ After blood samples were collected, they were allowed to stand for 30-60 minutes at room temperature, then centrifuged at 3500 rpm for 10 minutes, the supernatant was centrifuged at 15000 rpm for 5 minutes, and then frozen in −20° C. refrigerator.

Data collection: The concentration of corticosterone in serum of rats was measured by high performance liquid chromatography tandem mass spectrometry (HPLC-MS/MS) within 2-3 days after sampling.

Figure 6:
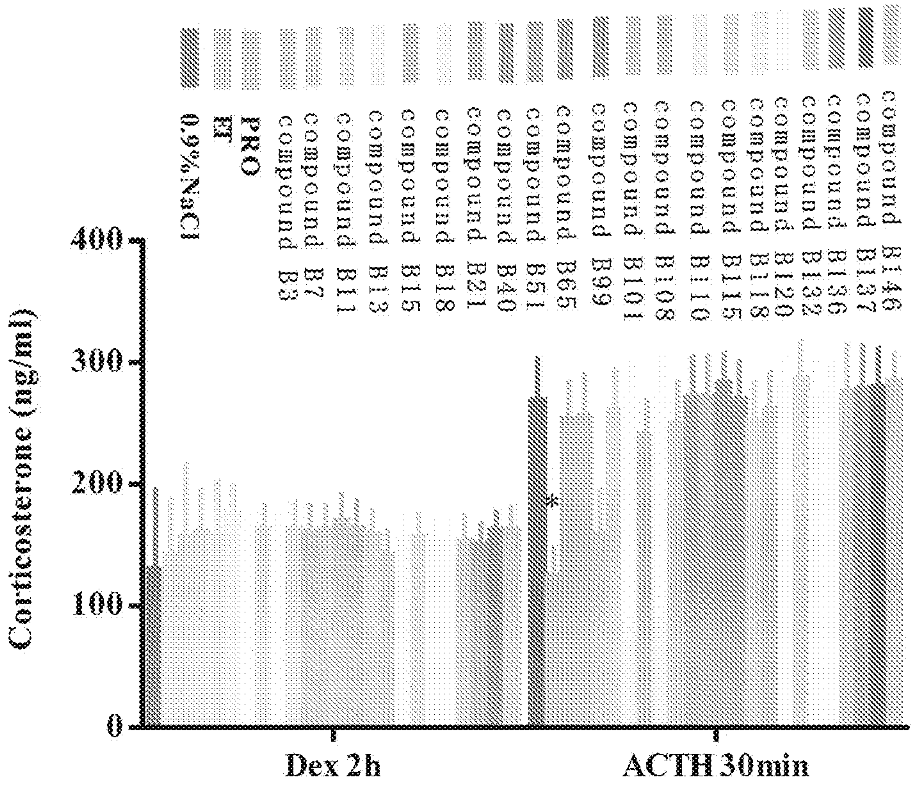
FIG. 6: Effect of the compound of the invention on the function of adrenal cortex; "*" means that it is statistically significant compared with 0.9% NaCl group.
Figure 7:
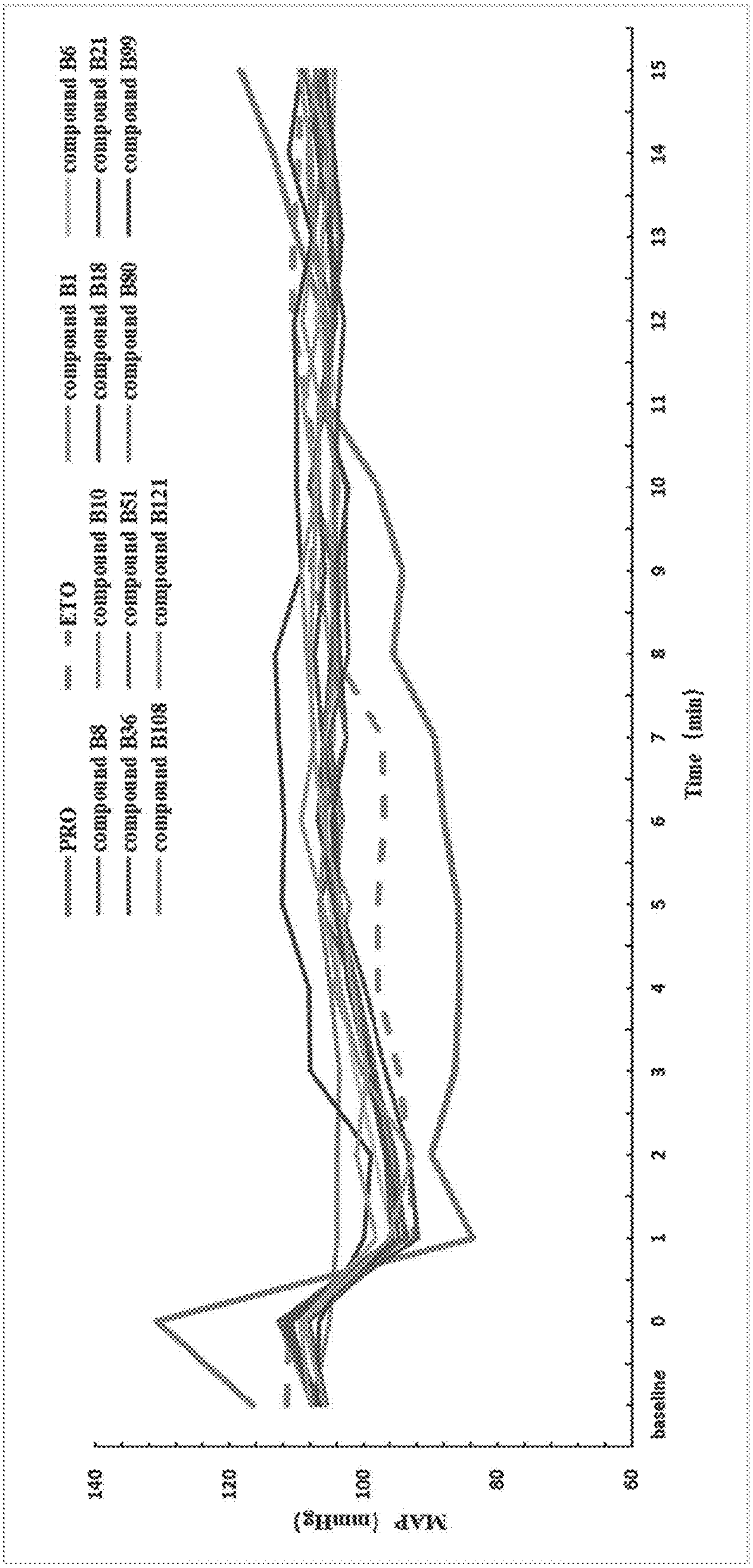
FIG. 7: Effects of the compounds of the present invention on the mean arterial pressure (MAP) (actually measured values); Notes: (1) All the test animals' righting reflex disappeared within 1 min after the administration; (2) The 0 min on the abscissa in the figure represents the end of administration; (3) The recovery time of the test animals' righting reflex for compounds or drugs were PRO: 645 s (10.75 min); ETO: 440 s (7.33 min); Compound B1: 120.6 s (2.01 min); Compound B6: 133 s (2.22 min); Compound B8: 139 s (2.32 min); Compound B10: 80 s (1.34 min); Compound B18: 186 s (3.10 min); Compound B21: 251 s (4.19 min); Compound B36: 214 s (3.57 min); Compound B51: 132 s (2.20 min); Compound B80: 203 s (3.39 min); Compound B99: 127 s (2.12 min); Compound B108: 100 s (1.63 min); Compound B127: 116 s (1.93 min).
Figure 8:
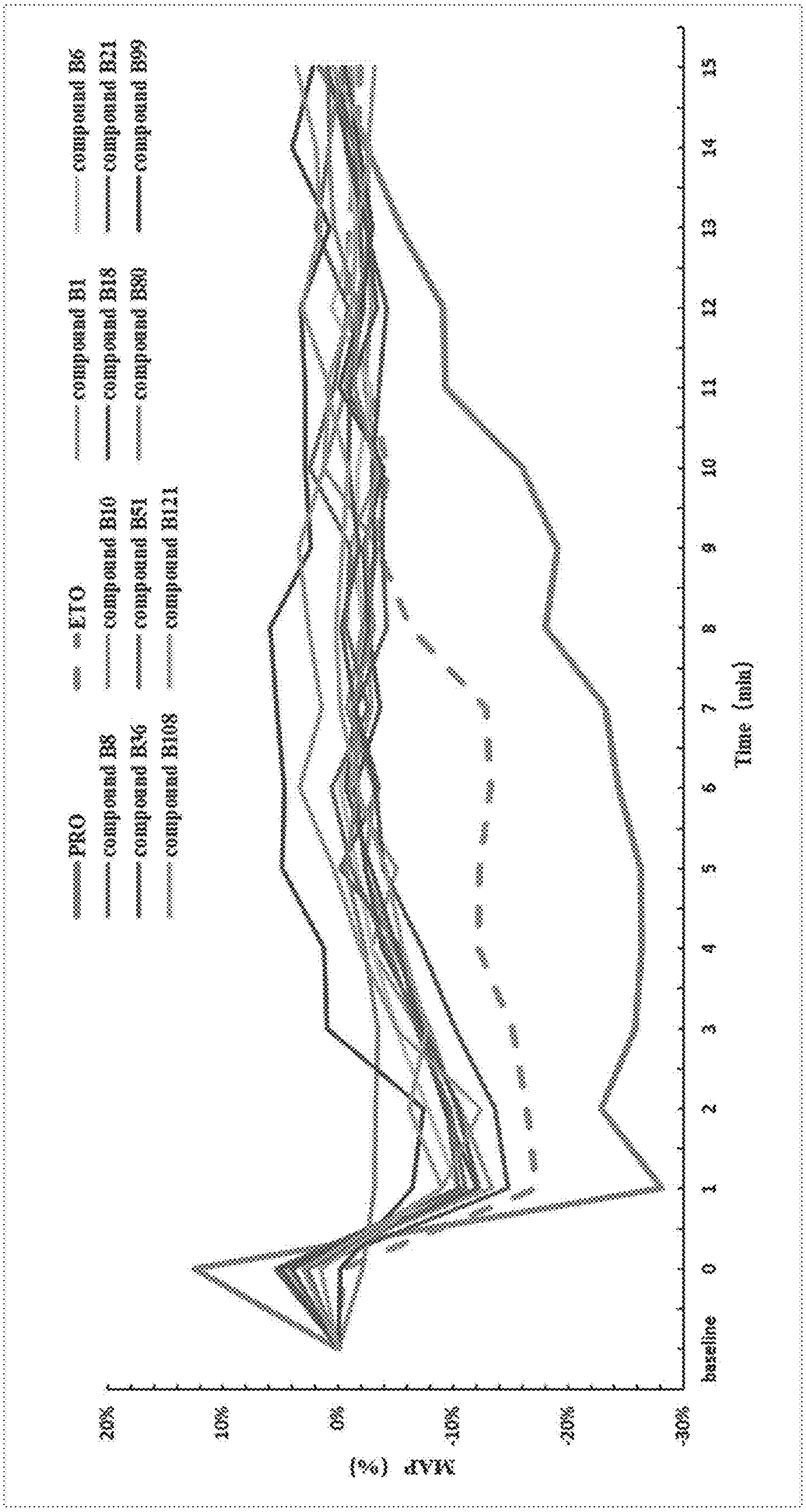
FIG. 8: Effects (rate of change) of the compounds of the present invention on the mean arterial pressure (MAP); Notes: (1) All the test animals' righting reflex disappeared within 1 min after the administration; (2) The 0 min on the abscissa in the figure represents the end of administration; (3) The recovery time of the test animals' righting reflex for compounds or drugs were PRO: 645 s (10.75 min); ETO: 440S (7.33 min); Compound B): 120.6 s (2.01 min); Compound B6: 133 s (2.22 min); Compound B8: 139 s (2.32 min); Compound B10: 80 s (1.34 min); Compound B18: 186 s (3.10 min); Compound B21: 251 s (4.19 min); Compound B36: 214 s (3.57 min); Compound B51: 132 s (2.20 min); Compound B80: 203 s (3.39 min); Compound B99: 127 s (2.12 min); Compound B108: 100 s (1.63 min); Compound B127: 116 s (1.93 min).
Figure 9:
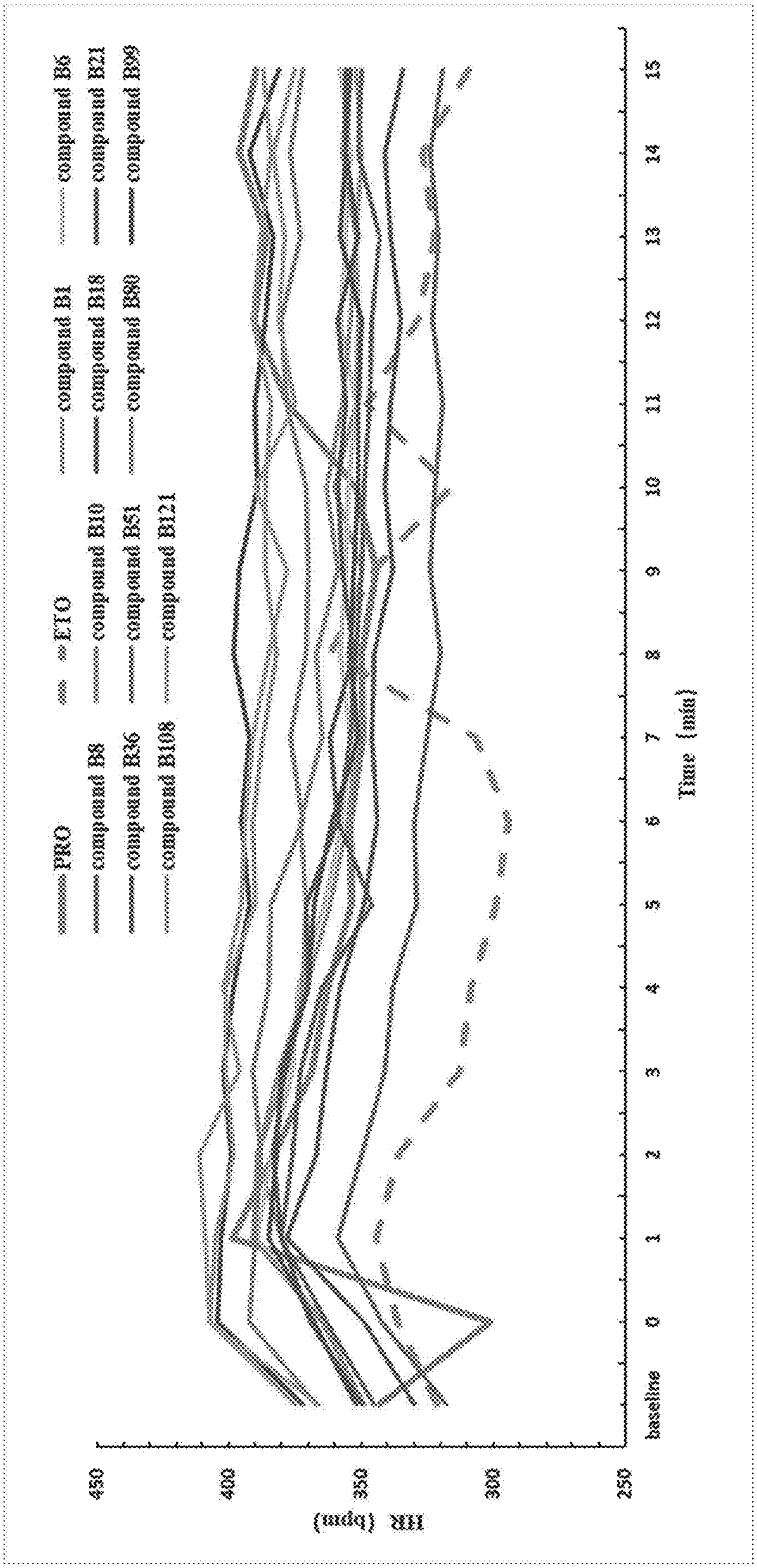
FIG. 9: Effects of the compounds of the present invention on heart rate (HR) (actually measured values); Notes: (1) All the test animals' righting reflex disappeared within 1 min after the administration; (2) The 0 min on the abscissa in the figure represents the end of administration; (3) The recovery time of the test animals' righting reflex for compounds or drugs were PRO: 645 s (10.75 min); ETO: 440 s (7.33 min); Compound B1: 120.6 s (2.01 min); Compound B6: 133 s (2.22 min); Compound B8: 139 s (2.32 min); Compound B10: 80 s (1.34 min); Compound B18: 186 s (3.10 min)

Result: the Compound of this invention did not inhibit the synthesis of adrenal cortex hormone as compared with normal saline (0.9% NaCl) and propofol (PRO), while the control of etomidate (ET) showed obvious inhibitory effect on adrenal cortex function. (FIG. 6).

Example 11 the Effects of the Group B Compounds on the Circulatory Function were Measured in Rats Using a Small Animal Implanted Physiological Signal Telemetry System The anesthetic activity of the compounds was assessed in rats using a LORR assay and the up and down method was used to determine $ED_{50}$. The drugs were administered at a dose twice their $ED_{50}$ through the tail vein of rats (n=6). A small animal implantable physiological signal telemetry system from DSI (Data Science International, Inc.) was used to measure the changes in heart rate (HR) and blood pressure in rats during 30 min after administration. Then mean arterial pressure (MAP) and HR were used as representative indicators to determine hemodynamic stability of the compounds of the present invention in rats.

The main test equipment are as follows:

A small animal implantable physiological signal telemetry system from DSI (Data Science International, Inc.) including implants (RATHD-S21, DSI, United States), receiver boards (RPC-1, DSI, United States), signal conversion devices (DEM, DSI, USA), perfusion glue (DSI, USA), fibrin membrane (DSI, USA), etc.

A small animal ventilator (HX-101E, Chengdu Taimeng Technology Co., Ltd.); An electronic balance (ME215S, Sartorius, Germany).

First, animal models were established. A left ventricular catheter, an abdominal aortic catheter and ECG wires were placed into rats. At least one week after surgery, data were recorded.

Administration procedure: rats were put into a restraint device with a 20G indwelling catheter placed into a lateral tail vein. After administration of 0.2 mL heparin, a pre-filled extension tube was attached and taped to the tail vein to secure the extension tube. Then the rats were removed from the restraint device to a cage before placing them together on the signal receiver. After the rats acclimatized for 30 min, the compounds were injected with a dose at 2-fold the $ED_{50}$ via the catheter. Finally, the pharmacological effects, adverse reactions, and behavioral manifestations of the rats were observed and recorded Data collection: After setting the data collection parameters on the software, the power of the implant was turned on to start data collection. In this experiment, data recording frequency was set to 15 s. Data collection was continuously recorded for 30 min before and after administration of the drugs in rats. After data acquisition, the test was stopped.

Results: compounds of the present invention had almost no inhibitory effect on the circulatory function as does the control etomidate and CPMM, while the control propofol exhibit significant inhibition of the circulatory function (FIG. 7, FIG. 8, FIG. 9, FIG. 10).

Example 12 Pharmacological Effects of the Group B Compounds on Continuous Infusion in Rats Adult male Sprague-Dawley rats with body weight ranging from 250 to 300 gm were selected for continuous infusion test. The compounds of the present invention and the control drugs, etomidate and CPMM, were prepared as emulsion before the test, which was continuously infused through the tail vein of the rats at 2 times the MIR (minimum infusion rate) and the LORR was maintained for 1 hour. Time to recovery of righting reflex from stopping infusion, and time to fully awake from stopping infusion were recorded. The results are shown in Table 8.

The results are shown which illustrate that the recovery time after 1 hour of continuous infusion under 2×MIR conditions is not significantly longer than that of the compounds of the present invention after a single intravenous injection of $2\times ED_{50}$, and the recovery time is considerably shorter than that of etomidate. Furthermore, the types and incidence of adverse reactions are also significantly less than etomidate and CPMM.

TABLE 8

Pharmacological effects of the compounds on continuous infusion in rats

| Compound/drug | Onset time (min) | Recovery time after stopping infusion (min) | Types and incidence of adverse reactions |
|---|---|---|---|
| Etomidate | 4-5 | 25-30 | Tremor (6/6), Facial muscle twitching (4/6), Tongue stretching (5/6) |
| CPMM | 3-4 | 7-8 | Convulsions (3/6), Tremor (5/6), Myoclonus (5/6) |
| DMSO | / | / | Red urine (8/8) |
| Compound B3 | 3-4 | 15-16 | Tremor(4/6), Tongue stretching(3/6) |
| Compound B6 | 4-6 | 14-16 | Tremor(2/6), Tongue stretching(2/6) |
| Compound B12 | 5-6 | 13-15 | Tremor(3/6) |
| Compound B14 | 5-6 | 19-12 | Tremor(3/6) |
| Compound B47 | 3-4 | 7-15 | Tremor(4/6), Forelimbrigidity(1/6) |
| Compound B80 | 3-5 | 12-16 | Tremor(5/6) |
| Compound B100 | 5-6 | 15-17 | Tremor(2/6), Tongue stretching(3/6) |
| Compound B118 | 6-7 | 13-15 | Tremor(4/6), Tongue stretching(4/6) |

Example 13 the Group C Compounds of the Invention can Produce Definite General Anesthesia in Rats Instruments and equipment: Multifunctional ionmeter (METTLER TOLEDO, types: SevenMulti), Pipette (Eppendorf, Specifications: 1000 ul, 200 ul, 100 ul, 10 ul), 22 G intravenous indwelling needle (BECTON DICKINSON), 1 ml micro injection needle (Germany BD),timer.

Experimental Method: The anesthesia effects of the compounds were assessed in rats using a loss of righting reflexes (LORR) assay and a period >30 s was considered as an indicator of general anesthesia. Then the up and down method was used to determine 50% effective dose ($ED_{50}$). Adult male Sprague-Dawley rats (250-300 g) were selected for the experiment. The compounds in the above examples and the control drugs, etomidate and CPMM, were dissolved in dimethyl sulfoxide (DMSO), and the same volume of DMSO was given as the blank control group. The drugs were administered through the tail vein of rats in a volume of 0.6 mL and at a rate of 0.1 mL/s.

Evaluating indicator: The end point of anesthesia: LORR was used as the end point of anesthesia; General anesthesia effect: the disappearance of forepaw righting reflex in rats lasting for 30 seconds is taken as the index of general anesthesia effect; Anesthesia recovery index: the recovery of rat forepaw righting reflex was used as the index of anesthesia recovery.

Experimental results are shown in Table 9:

The compound of the invention can produce definite and transient general anesthesia like the control etomidate and CPMM, and the compound of the invention shows the same or better potency as etomidate and CPMM.

TABLE 9

The effectiveness and safety window of the compound of the invention in rats

| Compound/drug | $ED_{50}$ (mg/kg) | Minimal lethal dose (mg/kg) | Approximate therapeutic index |
|---|---|---|---|
| Etomidate | 0.74(0.72-0.75)* | 13.8 | 18.7 |
| CPMM | 0.49(0.45-0.53)* | 20.6 | 42.0 |
| Propofol | 5.01(5.01-5.79)* | 22.6 | 4.0 |
| DMSO | / | / | / |
| Compound C1 | ++++ | / | / |
| Compound C2 | ++++ | >12.4 | >2.5 |
| Compound C9 | ++++ | >10.2 | >2.1 |
| Compound C14 | ++++ | >14.5 | >6.0 |
| Compound C15 | ++++ | >16.8 | >3.4 |
| Compound C16 | ++++ | >17.0 | >12.0 |
| Compound C27 | ++ | >13.6 | >16.6 |
| Compound C28 | ++++ | >11.8 | >2.4 |
| Compound C29 | ++++ | / | / |
| Compound C33 | ++++ | >14.2 | >2.8 |
| Compound C34 | ++++ | >12.8 | >2.6 |
| Compound C35 | ++ | >10.3 | >12.9 |
| Compound C36 | ++++ | >15.2 | >3.0 |
| Compound C40 | ++ | >8.3 | >13.8 |
| Compound C45 | ++++ | >10.8 | >2.2 |
| Compound C46 | ++++ | >11.8 | >2.4 |
| Compound C51 | +++ | >12.5 | >8.3 |
| Compound C53 | +++++ | / | / |
| Compound C54 | ++++++ | / | / |
| Compound C55 | ++++ | >13.61 | >16.6 |
| Compound C56 | ++++ | >13.61 | >16.6 |
| Compound C57 | ++++ | >13.61 | >16.6 |
| Compound C69 | + | >4.2 | >19.2 |
| Compound C70 | + | >6.4 | >18.2 |
| Compound C71 | ++ | >6.6 | >8.0 |
| Compound C72 | + | >8.9 | >27.7 |
| Compound C73 | + | >4.0 | >23.4 |
| Compound C74 | + | >6.0 | >42.9 |
| Compound C76 | ++ | >15.6 | >21.9 |
| Compound C78 | ++ | >11.5 | >14.3 |
| Compound C84 | +++++ | / | / |

Notes:
*The values in brackets indicate 95% confidence limit (mg/kg);
+ indicates that the measured $ED_{50}$ is in the range of 0.04-0.50 mg/kg (including 0.04 and 0.50 mg/kg);
++ means that the measured $ED_{50}$ is in the range of 0.50-1.00 mg/kg (excluding 0.50 mg/kg, including 1.00 mg/kg);
+++ indicates that the measured $ED_{50}$ is in the range of 1.00-2.00 mg/kg (excluding 1.00 mg/kg, including 2.00 mg/kg);
++++ indicates that the measured $ED_{50}$ is in the range of 2.00-10.00 mg/kg (excluding 2.00 mg/kg, including 6.00 mg/kg);
+++++ indicates that the measured $ED_{50}$ is in the range of 10.00-20.00 mg/kg (excluding 10.00 mg/kg, including 20.00 mg/kg);
++++++ indicates that the measured $ED_{50}$ is in the range of 20.00-30.00 mg/kg (excluding 20.00 mg/kg, including 30.00 mg/kg).

Example 14 the Group C Compounds of the Invention Shows the Pharmacological Effect of Rapid Onset and Rapid Recovery Under the Equivalent Dose ($2ED_{50}$)

Instruments and equipment: multi-function ion meter (METTLER TOLEDO, models: SevenMulti), pipetting gun (Eppendorf, specifications: 1000 ul, 200 ul, 100 ul, 10 ul), electronic balance (model: ME215S, manufacturers: Sartorius, Germany), the timer.

Experimental methods: Adult male Sprague-Dawley rats (250-300 g) were selected for the experiment (n=8). The compounds and the control drugs, etomidate and CPMM, were dissolved in DMSO, and the same volume of DMSO was given as the blank control group. The drugs were administered at a dose twice their $ED_{50}$ through the tail vein of rats in a volume of 0.6 mL and at a rate of 0.1 mL/s.

Evaluation index: onset time: from the completion of drug injection to the disappearance of forepaw righting reflex in rats; Duration of anesthesia: the time from the disappearance of rat forepaw righting reflex to the recovery of rat forepaw righting reflex; Recovery time of anesthesia: the time from the disappearance of forepaw righting reflex to complete recovery;

Experimental results (table 10, 11):

The compound of the invention, like the control etomidate and CPMM, shows the characteristics of rapid onset and rapid recovery. The duration of pharmacological action can meet the time needs of rapid induction of general anesthesia and diagnostic examination, short traumatic examination or operation. In the experiment, the types and incidence of adverse reactions of the compound of the invention are mostly less than those of the control etomidate and CPMM.

TABLE 10

Pharmacological effects of the present invention compound in rats

| Compound/drug | Onset time (min) | Righting reflex duration (min) | Sedation duration (min) |
|---|---|---|---|
| Etomidate | <30 s | 6.03 ± 1.93 | 15.35 ± 3.57 |
| CPMM | <30 s | 2.71 ± 0.97 | 8.48 ± 2.58 |
| Propofol | <30 s | 8.53 ± 1.52 | 14.77 ± 3.50 |
| DMSO | / | / | / |
| Compound C1 | <1 min | 0.90 ± 0.30 | 9.06 ± 1.21 |
| Compound C2 | <30 s | 1.78 ± 0.53 | 5.38 ± 0.78 |
| Compound C9 | <30 s | 1.56 ± 0.89 | 6.62 ± 0.72 |
| Compound C14 | <1 min | 1.38 ± 0.47 | 9.03 ± 1.58 |
| Compound C15 | <30 s | 2.13 ± 0.59 | 5.3 ± 0.92 |
| Compound C16 | <30 s | 2.26 ± 0.81 | 4.89 ± 0.98 |
| Compound C27 | <30 s | 1.48 ± 0.14 | 4.39 ± 0.94 |
| Compound C28 | <30 s | 1.91 ± 0.65 | 5.63 ± 0.62 |
| Compound C29 | / | / | / |
| Compound C33 | <30 s | 1.62 ± 0.85 | 4.43 ± 0.92 |
| Compound C34 | <30 s | 2.26 ± 0.81 | 4.89 ± 0.98 |
| Compound C35 | <30 s | 2.26 ± 0.81 | 4.89 ± 0.98 |
| Compound C36 | <30 s | 4.02 ± 1.09 | 15.57 ± 4.94 |
| Compound C40 | <30 s | 3.76 ± 1.75 | 10.48 ± 2.58 |
| Compound C45 | <30 s | 3.00 ± 1.02 | 7.74 ± 0.85 |
| Compound C46 | <30 s | 1.82 ± 0.64 | 5.63 ± 1.52 |
| Compound C51 | <30 s | 2.89 ± 0.68 | 4.62 ± 1.02 |
| Compound C53 | / | / | / |
| Compound C54 | / | / | / |
| Compound C55 | <30 s | 1.83 ± 0.30 | 6.26 ± 2.45 |
| Compound C56 | <1 min | 1.49 ± 0.62 | 5.32 ± 1.21 |
| Compound C57 | <1 min | 1.89 ± 0.29 | 6.12 ± 1.14 |
| Compound C69 | <30 s | 1.91 ± 0.68 | 6.28 ± 1.62 |
| Compound C70 | <30 s | 1.35 ± 0.61 | 5.30 ± 1.14 |
| Compound C71 | <30 s | 2.00 ± 0.81 | 5.11 ± 1.64 |
| Compound C72 | <1 min | 1.29 ± 0.64 | 5.70 ± 1.51 |
| Compound C73 | <30 s | 1.24 ± 0.56 | 6.76 ± 1.49 |
| Compound C74 | <1 min | 1.37 ± 0.63 | 5.68 ± 1.10 |
| Compound C76 | <30 s | 1.72 ± 0.61 | 4.32 ± 0.96 |
| Compound C78 | <30 s | 2.59 ± 0.99 | 7.30 ± 1.85 |
| Compound C84 | / | / | / |

TABLE 11

Adverse reaction of the present invention compound of the under equivalent dose($2ED_{50}$)(n = 8)

| Compound/drug | Red urine | Euphoria | Tongue stretching | Tremor | the four limbs rigidity | Slower breathing, Tetany convulsion | Cough, broken-winded | Convulsions | Systemic stiffness, Convulsions, Opisthotonus |
|---|---|---|---|---|---|---|---|---|---|
| Etomidate | / | 0 | 4 | 6 | 0 | 0 | 0 | 0 | 0 |
| CPMM | 8 | 0 | 4 | 5 | 4 | 3 | 0 | 0 | 0 |
| Propofol | / | 0 | 0 | 0 | 2 | 2 | 0 | 0 | 0 |
| DMSO | 8 | 0 | 0 | 0 | 1 | 0 | 0 | 0 | 0 |
| Compound C1 | 8 | 2 | 1 | 0 | 0 | 0 | 0 | 0 | 0 |
| Compound C2 | 8 | 0 | 2 | 0 | 0 | 0 | 0 | 0 | 0 |
| Compound C9 | 8 | 0 | 0 | 0 | 0 | 0 | 0 | 0 | 0 |
| Compound C14 | 8 | 1 | 0 | 1 | 0 | 0 | 0 | 0 | 0 |
| Compound C15 | 8 | 0 | 0 | 1 | 0 | 0 | 0 | 0 | 0 |
| Compound C16 | 8 | 0 | 1 | 2 | 4 | 0 | 0 | 0 | 0 |
| Compound C27 | 8 | 0 | 2 | 0 | 0 | 0 | 0 | 0 | 1 |
| Compound C28 | 8 | 0 | 0 | 1 | 0 | 0 | 0 | 0 | 0 |
| Compound C29 | / | / | / | / | / | / | / | / | / |
| Compound C33 | 8 | 0 | 0 | 1 | 0 | 0 | 0 | 0 | 0 |
| Compound C34 | 8 | 1 | 1 | 0 | 0 | 0 | 0 | 0 | 6 |
| Compound C35 | 8 | 0 | 1 | 0 | 0 | 0 | 0 | 0 | 7 |
| Compound C36 | 8 | 0 | 0 | 0 | 3 | 0 | 0 | 0 | 0 |
| Compound C40 | 8 | 0 | 0 | 0 | 0 | 1 | 0 | 1 | 1 |
| Compound C45 | 8 | 0 | 0 | 0 | 1 | 0 | 0 | 0 | 7 |
| Compound C46 | 8 | 0 | 1 | 1 | 0 | 0 | 0 | 0 | 0 |
| Compound C51 | 8 | 0 | 0 | 2 | 0 | 0 | 0 | 0 | 0 |
| Compound C53 | / | / | / | / | / | / | / | / | / |
| Compound C54 | / | / | / | / | / | / | / | / | / |
| Compound C55 | 8 | 0 | 0 | 0 | 0 | 0 | 0 | 0 | 7 |
| Compound C56 | 8 | 0 | 1 | 1 | 0 | 0 | 0 | 0 | 0 |
| Compound C57 | 8 | 0 | 2 | 1 | 0 | 0 | 0 | 0 | 0 |
| Compound C69 | 8 | 0 | 0 | 0 | 0 | 0 | 0 | 0 | 1 |
| Compound C70 | 8 | 4 | 0 | 0 | 6 | 0 | 0 | 0 | 0 |
| Compound C71 | 8 | 0 | 0 | 1 | 1 | 0 | 0 | 2 | 0 |
| Compound C72 | 8 | 0 | 0 | 0 | 0 | 0 | 0 | 0 | 0 |
| Compound C73 | 8 | 0 | 0 | 0 | 1 | 0 | 0 | 0 | 2 |
| Compound C74 | 8 | 0 | 0 | 1 | 0 | 0 | 0 | 0 | 0 |
| Compound C76 | 8 | 0 | 0 | 1 | 1 | 0 | 0 | 0 | 0 |
| Compound C78 | 8 | 0 | 1 | 0 | 1 | 0 | 0 | 0 | 0 |
| Compound C84 | / | / | / | / | / | / | / | / | / |

Example 15 the Group C Compounds have No Inhibition on Adrenocortical Function In Vitro Cell Test Instruments and Equipment: multi-function ion meter (METTLER TOLEDO, models: SevenMulti), pipetting gun (Eppendorf, specifications: 1000 ul, 200 ul, 100 ul, 10 ul), centrifuge (model: Allegra, manufacturers: BECKMAN COULTER, American).

Experimental methods: The H295R cell line was selected to evaluate the ability of compounds to inhibit steroid synthesis in vitro. Cells are treated with vehicle (i.e., DMSO) and different concentrations of etomidate, CPMM, etomidate metabolite (i.e., etomidate acid), and the compounds of the present invention. Incubation concentration and concentration range are 0.1 nM, 1 nM, 10 nM, 50 nM, 100 nM, 500 nM, 1000 nM, 10000 nM. Then secretion of the cortisol and corticosterone in the supernatant, was measured using HPLC-MS/MS method to determine whether the compounds of the present invention had adrenotoxic potential.

Evaluation indexes: $EC_{50}$ (Cortisol): The drug concentration required to reduce the concentration of corticosterone in the culture medium by 50%; $EC_{50}$ (Corticosterone): The drug concentration required to reduce the concentration of cortisol in the culture medium by 50%.

Experimental results (FIG. 11):

The results show that the compounds of the present invention meet the design requirements. $EC_{50}$ of all compounds is obvious greater then etomidate, little or obvious greater then CPMM, the compounds less inhibit adrenocortical function in the experiment.

Example 16 the Present Invention of Group C Compounds have No Inhibitory Effect on the Function of Adrenocortical in Rats Instruments and equipment: multi-function ion meter (METTLER TOLEDO, models: SevenMulti), pipetting gun (Eppendorf, specifications: 1000 ul, 200 ul, 100 ul, 10 ul), electronic balance (model: ME215S, manufacturers: Sartorius, Germany), the timer. Experimental Method: Adult male Sprague-Dawley rats (250-300 g) were selected for the experiment (n=8), all the experiment were started in the morning. Place indwelling needles in tail vein of rats and inject dexamethasone (0.5 mg/kg). The first time of blood collection (S1) is in two hours later, and give dexamethasone (0.2 mg/kg). The compounds and the control drugs, etomidate and PRO were given at a dose twice their $ED_{50}$, and using the same volume of 0.9% NaCl as the blank control group. All the drugs were administered in a volume of 0.6 ml and at a rate of 0.1 ml/s. 15 min later, exogenous ACTH (25 ug/kg) was injected. Another blood sample was collected after 30 min(S2). The blood samples were left standing at room temperature for 30-60 min, followed by centrifugation at 3500 rpm for 10 min. The supernatant was taken and centrifuged again at 15000 rpm for 5 min before being frozen and stored in a −20° C. refrigerator. The concentration of the corticosterone in the supernatant, was measured using HPLC-MS/MS method 2-3 days later, to determine whether the compounds of the present invention had inhibition of adrenal cortex function.

Evaluation indexes: The concentration of the corticosterone in the supernatant of rats before and after given drugs.

Result (Tables 12, FIG. 12): After given ACTH stimulation, the concentration of the corticosterone in the supernatant of rats obviously increased after given the compounds of the present invention, similar to the 0.9% NaCl and PRO; but didn't change and even going down after using etomidate. The results show that the compounds hardly inhibit adrenocortical function in the experiment.

TABLE 12

The effects of the compounds on adrenocortical function in rats

| Group | Baseline(S1) | Give ACTH 30min later(S2) |
|---|---|---|
| 0.9% NaCl | 130.10 ± 56.00 | 268.12 ± 34.77 |
| ET | 142.31 ± 45.33 | 124.34 ± 23.11 |
| PRO | 156.98 ± 59.41 | 253.11 ± 31.56 |
| Compound C2 | 163.22 ± 35.11 | 242.12 ± 46.22 |
| Compound C15 | 145.90 ± 54.33 | 267.99 ± 33.20 |
| Compound C27 | 180.33 ± 46.70 | 253.11 ± 34.56 |
| Compound C34 | 169.77 ± 45.66 | 278.33 ± 32.45 |
| Compound C40 | 159.54 ± 34.52 | 268.56 ± 29.46 |
| Compound C74 | 147.00 ± 34.56 | 250.77 ± 45.30 |

Example 17 the Group C Compound of the Present Invention has Slight Influence on the Circulatory Function of Rats Instruments and Equipment: A small animal implantable physiological signal telemetry system from DSI (Data Science International, Inc.), including implants (RATHD-S21, DSI, United States), receiver boards (RPC-1, DSI, United States), signal conversion devices (DEM, DSI, USA), perfusion glue (DSI, USA), fibrin membrane (DSI, USA), etc. A small animal ventilator (HX-101E, Chengdu Taimeng Technology Co., Ltd.); An electronic balance (ME215S, Sartorius, Germany).

Experimental Methods: The circulatory function of rats was monitored by A small animal implantable physiological signal telemetry system from DSI (Data Science International, Inc.). Adult male Sprague-Dawley rats (250-300 g) were selected for the experiment (n=6). First, the animal model was established, and the left ventricular catheter, abdominal aorta catheter and electrocardiogram wire were placed. At least one week after the operation, the signal can be collected to start the test. At the beginning of the experiment, after the placement of the indwelling needle in the tail vein of rats, connect the extension tube, put the rats together with the feeding cage on the signal receiver and start collecting data. After 30 minutes, the compound in the example and the control drugs etomidate and propofol in the dose of $2ED_{50}$ were given respectively. All compounds or drugs were given at a constant volume of 0.6 ml at a uniform rate of 0.1 ml/s. The pharmacological effects, adverse reactions and behavior of rats were observed and recorded after drug injection.

Data Collection: After setting the data collection parameters on the software, the power of the implant was turned on to start data collection. In this experiment, data recording frequency was set to 15 s once time. Data collection was continuously recorded for 15 min before and after administration of the drugs in rats. After data acquisition, the test was stopped.

Evaluation Indexes: Collect the blood pressure, heart rate and other data of rats during and 15 minutes after administration, and judge the effect of the compound of the invention on the circulatory function of rats with the indexes of mean arterial pressure (MAP) and heart rate (HR).

Experimental Results (FIG. 13,14,15,16):

Like the control etomidate, the compound of the invention has a slight inhibitory effect on the circulatory function after administration, but soon rises to near the baseline, while the control propofol shows a significant inhibition on the circulatory system function.

Example 18 the Group C Compounds of the Present Invention can Still Recover Rapidly after Continuous Infusion in Rats for 1 Hour Instrument and Equipment: micro injection pump (model: SN-50F6, manufacturer: Shenzhen Shengnuo Medical Equipment Co., LTD.), multi-functional ion meter (METTLER TOLEDO, model: SevenMulti), pipette gun (Eppendorf, specification: 1000 ul, 200 ul, 100 ul, 10 ul), timer.

Experimental Methods: Adult male SD rats with body weight ranging from 250 g to 350 g were selected for continuous infusion test. The compound of the invention, the control drug etomidate and CPMM were continuously injected through the tail vein of rats at a dose of 2 times the MIR (minimum infusion speed), and the absence of righting reflex was maintained for 1 hour from the time of the disappearance of righting reflex, and the awakening time and complete recovery time of the experimental animals were recorded after stopping the infusion.

Evaluation indexes: the time from the beginning of continuous infusion to the disappearance of sedation in rats; the time from the cessation of infusion to the restoration of the forepaw turning reflex after 1 hour of continuous infusion; the time from the cessation of infusion to the complete restoration of rats after 1 hour of continuous infusion.

Experimental results (table 13):

The recovery time of the compound in the invention is not significantly longer than or equal to etomidate in terms of recovery time after continuous infusion of 2 times the dose of MIR (minimum infusion rate) for 1 hour compared with a single intravenous injection of $2ED_{50}$ dose. The types and incidence of adverse reactions were significantly less than etomidate and CPMM.

TABLE 13

| Pharmacological effects of continuous infusion of the compounds of the present invention | | | | |
|---|---|---|---|---|
| Compound/drug | Sedation onset time(min) | After the infusion is stopped Righting reflex recovery time(min) | Recovery time after stopping infusion(min) | Types and incidence of adverse reactions |
| Etomidate | <5 | 15-20 | 30-40 | Tremor(6/6), Myoclonus(4/6), Tongue stretching(2/6), Hindlimb rigidity(2/6) |
| CPMM | <5 | 8-10 | 10-15 | Red urine(6/6), Tremor(4/6), Hindlimb rigidity(4/6) |
| DMSO | / | / | / | Red urine(6/6) |
| Compound C2 | <5 | 10-15 | 20-30 | Red urine(6/6), Tremor(3/6), Tongue stretching(4/6) |
| Compound C15 | <5 | 16-18 | 30-36 | Red urine(6/6), Tremor(1/6), |
| Compound C27 | <5 | 12-16 | 15-20 | Red urine(6/6), Tremor(5/6) |
| Compound C34 | <5 | 15-20 | 22-28 | Red urine(6/6), Tremor(2/6), Tongue stretching(4/6) |
| Compound C40 | <5 | 16-20 | 27-35 | Red urine(6/6), Tremor(2/6) |
| Compound C74 | <5 | 13-18 | 18-24 | Red urine(6/6), Tremor(4/6), Tongue stretching(4/6) |

Example 19 the Group D Compounds of the Present Invention can Produce Definite General Anesthesia in Rats Instrument and Equipment: Multifunctional ionmeter (METTLER TOLEDO, types: SevenMulti), Pipette (Eppendorf, Specifications: 1000 ul, 200 ul, 100 ul, 10 ul), 22 G intravenous indwelling needle (BECTON DICKINSON), 1 ml micro injection needle (Germany BD),timer.

Experimental Method: The anesthesia effects of the compounds were assessed in rats using a LORR assay and a period >30 s was considered as an indicator of general anesthesia. Then the up and down method was used to determine 50% effective dose ($ED_{50}$). Adult male Sprague-Dawley rats (250-300 g) were selected for the experiment. The compounds in the above examples and the control drugs, etomidate and CPMM, were dissolved in dimethyl sulfoxide (DMSO), and the same volume of DMSO was given as the blank control group. The drugs were administered through the tail vein of rats in a volume of 0.6 mL and at a rate of 0.1 mL/s.

Evaluating indicator: The end point of anesthesia: the disappearance of forepaw righting reflex (lorr) was used as the end point of anesthesia; General anesthesia effect: the disappearance of forepaw righting reflex in rats lasting for 30 seconds is taken as the index of general anesthesia effect; Anesthesia recovery index: the recovery of rat forepaw righting reflex was used as the index of anesthesia recovery.

Experimental results (Table 14):

The compound of the invention can produce definite and transient general anesthesia like the control etomidate and CPMM, and the compound of the invention shows the same or better potency as etomidate and CPMM.

TABLE 14

| The effectiveness and safety window of the compound of the present invention in rats | | | |
|---|---|---|---|
| Compound/drug | $ED_{50}$(mg/kg) | Minimal lethal dose (mg/kg) | Approximate therapeutic index |
| Etomidate | 0.74(0.72-0.75)* | 13.8 | 18.7 |
| CPMM | 0.49(0.45-0.53)* | 20.6 | 42.0 |
| Propofol | 5.01(5.01-5.79)* | 22.6 | 4.0 |
| DMSO | / | / | / |

TABLE 14-continued

| The effectiveness and safety window of the compound of the present invention in rats | | | |
|---|---|---|---|
| Compound/drug | $ED_{50}$(mg/kg) | Minimal lethal dose (mg/kg) | Approximate therapeutic index |
| Compound D1 | ++ | >11.2 | >8.4 |
| Compound D2 | ++++ | >10.5 | >6.6 |
| Compound D3 | ++++ | / | / |
| Compound D4 | ++++ | >10.1 | >5.0 |
| Compound D6 | ++++ | >12.4 | >7.3 |
| Compound D7 | ++ | >3.2 | >5.4 |
| Compound D11 | +++++ | >30.2 | >4.6 |
| Compound D17 | ++ | >11.9 | >4.5 |
| Compound D25 | ++ | >8.4 | >10.2 |
| Compound D29 | + | >3.6 | >4.1 |
| Compound D42 | + | >1.8 | >4.2 |
| Compound D73 | +++++ | / | / |
| Compound D74 | +++++ | >10.2 | >16.6 |
| Compound D75 | +++++ | >11.2 | >5.4 |
| Compound D76 | ++ | >11.5 | >31.8 |
| Compound D77 | + | >1.4 | >21.0 |
| Compound D78 | ++ | >6.8 | >6.2 |
| Compound D79 | ++ | >2.7 | >6.4 |
| Compound D80 | +++++ | >12.2 | >2.9 |
| Compound D81 | ++ | >12.6 | >15.2 |
| Compound D82 | ++++ | >7.8 | >6.3 |
| Compound D83 | +++++ | / | / |
| Compound D84 | ++++ | / | / |
| Compound D86 | +++ | >9.8 | >7.3 |
| Compound D87 | +++ | >13.2 | >6.8 |
| Compound D88 | +++ | >2.6 | >10.3 |
| Compound D93 | + | >1.8 | >25.1 |
| Compound D101 | + | >9.3 | >10.5 |
| Compound D108 | ++++ | >8.5 | >10.2 |

Notes:

*The values in brackets indicate 95% confidence limit (mg/kg);

\+ indicates that the measured $ED_{50}$ is in the range of 0.04-0.50 mg/kg (including 0.04 and 0.50 mg/kg);

++ indicates that the measured $ED_{50}$ is in the range of 0.50-1.00 mg/kg (excluding 0.50 mg/kg, including 1.00 mg/kg);

+++ indicates that the measured $ED_{50}$ is in the range of 1.00-2.00 mg/kg (excluding 1.00 mg/kg, including 2.00 mg/kg);

++++ indicates that the measured $ED_{50}$ is in the range of 2.00-6.00 mg/kg (excluding 2.00 mg/kg, including 6.00 mg/kg).

+++++ indicates that the measured $ED_{50}$ is greater than 6.00 mg/kg (excluding 6.00 mg/kg).

Example 20 the Group D Compound of the Present Invention Shows the Pharmacological Effect of Rapid Onset and Rapid Recovery Under the Equivalent Dose ($2ED_{50}$)

Instruments and Equipment: multi-function ion meter (METTLER TOLEDO, models: SevenMulti), pipetting gun (Eppendorf, specifications: 1000 ul, 200 ul, 100 ul, 10 ul), electronic balance (model: ME215S, manufacturers: Sartorius, Germany), the timer.

Experimental Methods: Adult male Sprague-Dawley rats (250-300 g) were selected for the experiment (n=8). The compounds and the control drugs, etomidate and CPMM, were dissolved in DMSO, and the same volume of DMSO was given as the blank control group. The drugs were administered at a dose twice their $ED_{50}$ through the tail vein of rats in a volume of 0.6 mL and at a rate of 0.1 mL/s.

Evaluation index: onset time: from the completion of drug injection to the disappearance of forepaw righting reflex in rats; Duration of anesthesia: the time from the disappearance of rat forepaw righting reflex to the recovery of rat forepaw righting reflex; Recovery time of anesthesia: the time from the disappearance of forepaw righting reflex to complete recovery;

Experimental results (table 15, 16):

The compound of the invention, like the control etomidate and CPMM, shows the characteristics of rapid onset and rapid recovery. The duration of pharmacological action can meet the time needs of rapid induction of general anesthesia and diagnostic examination, short traumatic examination or operation. In the experiment, the types and incidence of adverse reactions of the compound of the invention are mostly less than those of the control etomidate and CPMM.

TABLE 15

Pharmacological effects of the compound of the present invention in rats

| Compound/drug | Onset time (min) | Righting reflex duration (min) | Sedation duration (min) |
|---|---|---|---|
| Etomidate | <30 s | 6.03 ± 1.93 | 15.35 ± 3.57 |
| CPMM | <30 s | 2.71 ± 0.97 | 8.48 ± 2.58 |
| Propofol | <30 s | 8.53 ± 1.52 | 14.77 ± 3.50 |
| DMSO | / | / | / |
| Compound D1 | <1 min | 1.18 ± 0.43 | 7.96 ± 2.14 |
| Compound D2 | <1 min | 5.82 ± 1.87 | 13.71 ± 3.89 |
| Compound D3 | <1 min | 1.25 ± 0.27 | 6.26 ± 1.50 |
| Compound D4 | <1 min | 0.98 ± 0.35 | 7.28 ± 1.56 |
| Compound D6 | <1 min | 1.33 ± 0.19 | 7.35 ± 1.45 |
| Compound D7 | <1 min | 0.55 ± 0.59 | 8.52 ± 2.29 |
| Compound D11 | / | / | / |
| Compound D17 | <1 min | 0.86 ± 0.23 | 5.48 ± 0.50 |
| Compound D25 | <1 min | 1.52 ± 0.26 | 6.82 ± 0.27 |
| Compound D29 | <30 s | 1.24 ± 0.06 | 2.26 ± 0.59 |
| Compound D42 | <1 min | 1.38 ± 0.15 | 3.83 ± 0.74 |
| Compound D73 | / | / | / |
| Compound D74 | <1 min | 1.29 ± 0.49 | 4.78 ± 1.24 |
| Compound D75 | <30 s | 1.59 ± 0.67 | 5.28 ± 0.68 |
| Compound D76 | <1 min | 1.67 ± 1.32 | 6.44 ± 1.82 |
| Compound D77 | <30 s | 1.43 ± 0.22 | 3.68 ± 0.56 |
| Compound D78 | <30 s | 4.02 ± 1.35 | 7.29 ± 1.20 |
| Compound D79 | <30 s | 1.75 ± 0.76 | 5.84 ± 1.46 |
| Compound D80 | <30 s | 1.58 ± 0.61 | 6.42 ± 1.68 |
| Compound D81 | <1 min | 1.35 ± 0.12 | 4.87 ± 0.39 |
| Compound D82 | <1 min | 0.98 ± 0.31 | 6.70 ± 1.46 |
| Compound D83 | / | / | / |
| Compound D84 | / | / | / |
| Compound D86 | <1 min | 1.24 ± 0.12 | 7.88 ± 1.94 |
| Compound D87 | <30 s | 4.34 ± 0.54 | 8.26 ± 2.74 |
| Compound D88 | <30 s | 1.86 ± 1.02 | 7.08 ± 1.06 |
| Compound D93 | <30 s | 2.50 ± 0.30 | 6.89 ± 0.80 |
| Compound D101 | <30 s | 1.80 ± 0.58 | 7.20 ± 3.21 |
| Compound D108 | <30 s | 2.30 ± 1.76 | 5.90 ± 2.13 |

TABLE 16

Adverse reaction of the compound of the invention under equivalent dose(2 × ED50)(n = 8)

| Compound/drug | Red urine | Euphoria | Tongue stretching | Tremor | Four limbs rigidity | Slower breathing, Tetany convulsion | Cough, broken-winded | Convulsions | Systemic stiffness, Convulsions, opisthotonus |
|---|---|---|---|---|---|---|---|---|---|
| Etomidate | / | 0 | 4 | 3 | 2 | 0 | 0 | 0 | 0 |
| CPMM | / | 0 | 4 | 2 | 2 | 0 | 0 | 0 | 0 |
| Propofol | / | 0 | 0 | 2 | 1 | 2 | 0 | 0 | 0 |
| DMSO | 8 | 0 | 0 | 1 | 1 | 0 | 0 | 0 | 0 |
| Compound D1 | 8 | 0 | 1 | 0 | 0 | 0 | 0 | 0 | 0 |
| Compound D2 | 8 | 3 | 2 | 8 | 0 | 1 | 2 | 0 | 0 |
| Compound D3 | 8 | 0 | 0 | 1 | 1 | 0 | 0 | 0 | 0 |
| Compound D4 | 8 | 0 | 0 | 0 | 0 | 0 | 0 | 0 | 0 |
| Compound D6 | 8 | 0 | 0 | 2 | 1 | 0 | 0 | 0 | 0 |
| Compound D7 | 8 | 0 | 1 | 1 | 1 | 0 | 0 | 0 | 0 |
| Compound D11 | / | / | / | / | / | / | / | / | / |
| Compound D17 | 8 | 0 | 0 | 0 | 1 | 0 | 0 | 0 | 0 |
| Compound D25 | 8 | 0 | 0 | 2 | 1 | 0 | 0 | 0 | 0 |
| Compound D29 | 8 | 0 | 0 | 4 | 3 | 0 | 0 | 0 | 0 |
| Compound D42 | 8 | 0 | 1 | 1 | 0 | 0 | 0 | 6 | 0 |
| Compound D73 | / | / | / | / | / | / | / | / | / |
| Compound D74 | 8 | 0 | 0 | 1 | 1 | 0 | 0 | 0 | 0 |
| Compound D75 | 8 | 0 | 0 | 0 | 0 | 0 | 0 | 0 | 0 |
| Compound D76 | 8 | 0 | 0 | 0 | 2 | 0 | 0 | 0 | 8 |
| Compound D77 | 8 | 0 | 1 | 0 | 0 | 0 | 0 | 0 | 8 |
| Compound D78 | 8 | 0 | 1 | 0 | 0 | 0 | 0 | 0 | 2 |
| Compound D79 | 8 | 0 | 0 | 1 | 0 | 0 | 0 | 6 | 0 |
| Compound D80 | 8 | 0 | 0 | 0 | 4 | 0 | 0 | 0 | 0 |
| Compound D81 | 8 | 0 | 0 | 1 | 1 | 0 | 0 | 0 | 0 |
| Compound D82 | 8 | 0 | 1 | 0 | 2 | 0 | 0 | 0 | 0 |
| Compound D83 | / | / | / | / | / | / | / | / | / |
| Compound D84 | / | / | / | / | / | / | / | / | / |

TABLE 16-continued

Adverse reaction of the compound of the invention under equivalent dose(2 × ED50)(n = 8)

| Compound/drug | Red urine | Euphoria | Tongue stretching | Tremor | Four limbs rigidity | Slower breathing, Tetany convulsion | Cough, broken-winded | Convulsions | Systemic stiffness, Convulsions, opisthotonus |
|---|---|---|---|---|---|---|---|---|---|
| Compound D86 | 8 | 0 | 0 | 0 | 0 | 0 | 0 | 0 | 2 |
| Compound D87 | 8 | 0 | 0 | 0 | 0 | 0 | 0 | 0 | 5 |
| Compound D88 | 8 | 0 | 1 | 1 | 1 | 0 | 0 | 0 | 7 |
| Compound D93 | 8 | 0 | 1 | 0 | 0 | 0 | 0 | 0 | 8 |
| Compound D101 | 8 | 0 | 0 | 0 | 0 | 0 | 0 | 0 | 2 |
| Compound D108 | 8 | 2 | 0 | 0 | 0 | 0 | 0 | 0 | 0 |

Example 21 the Effects of the Group D Compounds on Adrenocortical Function in Vitro Test Instruments and Equipment: multi-function ion meter (METTLER TOLEDO, models: SevenMulti), pipetting gun (Eppendorf, specifications: 1000 ul, 200 ul, 100 ul, 10 ul), centrifuge (model: Allegra, manufacturers: BECKMAN COULTER, American).

Experimental Methods: The H295R cell line was selected to evaluate the ability of compounds to inhibit steroid synthesis in vitro. Cells are treated with vehicle (i.e., DMSO) and different concentrations of etomidate, CPMM, etomidate metabolite (i.e., etomidate acid), and the compounds of the present invention. Incubation concentration and concentration range are 0.1 nM, 1 nM, 10 nM, 50 nM, 100 nM, 500 nM, 1000 nM, 10000 nM. Then secretion of the cortisol and corticosterone in the supernatant, was measured using HPLC-MS/MS method to determine whether the compounds of the present invention had adrenotoxic potential.

Evaluation Indexes: $EC_{50}$ (Cortisol): The drug concentration required to reduce the concentration of corticosterone in the culture medium by 50%; $EC_{50}$ (Corticosterone): The drug concentration required to reduce the concentration of cortisol in the culture medium by 50%.

Experimental Results (FIG. 17):

The results show that the compounds of the present invention meet the design requirements. $EC_{50}$ of all compounds is obvious greater then etomidate, little or obvious greater then CPMM, the compounds less inhibit adrenocortical function in the experiment.

Example 22 Compounds D Hardly Inhibit Adrenocortical Function

Instruments and Equipment: multi-function ion meter (METTLER TOLEDO, models: SevenMulti), pipetting gun (Eppendorf, specifications: 1000 ul, 200 ul, 100 ul, 10 ul), electronic balance (model: ME215S, manufacturers: Sartorius, Germany), the timer. Experimental Method: Adult male Sprague-Dawley rats (250-300 g) were selected for the experiment (n=8), all the experiment were started in the morning. Place indwelling needles in tail vein of rats and inject dexamethasone (0.5 mg/kg). The first time of blood collection (S1) is in two hours later, and give dexamethasone (0.2 mg/kg). The compounds and the control drugs, etomidate and PRO were given at a dose twice their $ED_{50}$, and using the same volume of 0.9% NaCl as the blank control group. All the drugs were administered in a volume of 0.6 ml and at a rate of 0.1 ml/s. 15 min later, exogenous ACTH (25 ug/kg) was injected. Another blood sample was collected after 30 min (S2). The blood samples were left standing at room temperature for 30-60 min, followed by centrifugation at 3500 rpm for 10 min. The supernatant was taken and centrifuged again at 15000 rpm for 5 min before being frozen and stored in a −20° C. refrigerator. The concentration of the corticosterone in the supernatant, was measured using HPLC-MS/MS method 2-3 days later, to determine whether the compounds of the present invention had inhibition of adrenal cortex function.

Evaluation indexes: The concentration of the corticosterone in the supernatant of rats before and after given drugs.

Experimental Results (Tables 17, FIG. 18): After given ACTH stimulation, the concentration of the corticosterone in the supernatant of rats obviously increased after given the compounds of the present invention, similar to the 0.9% NaCl and PRO; but didn't change and even going down after using etomidate. The results show that the compounds hardly inhibit adrenocortical function in the experiment.

TABLE 17

The effects of the compounds on adrenocortical function in rats

| Group | Baseline(S1) | Give ACTH 30 min later(S2) |
|---|---|---|
| 0.9% NaCl | 130.10 ± 43.28 | 268.12 ± 34.77 |
| ET | 142.31 ± 45.33 | 124.34 ± 23.11 |
| PRO | 156.98 ± 59.41 | 253.11 ± 31.56 |
| Compound D1 | 165.43 ± 15.99 | 247.90 ± 43.21 |
| Compound D17 | 160.98 ± 33.09 | 248.55 ± 32.33 |
| Compound D25 | 171.66 ± 24.66 | 259.09 ± 36.77 |
| Compound D29 | 163.98 ± 22.11 | 279.76 ± 24.67 |
| Compound D76 | 153.23 ± 30.91 | 277.88 ± 34.56 |
| Compound D79 | 151.11 ± 21.00 | 277.88 ± 30.56 |
| Compound D81 | 147.99 ± 46.90 | 260.99 ± 21.77 |
| Compound D87 | 163.22 ± 35.11 | 242.12 ± 40.22 |
| Compound D88 | 172.33 ± 46.70 | 253.11 ± 33.20 |

Example 23 the Group D Compound of the Present Invention has Slight Influence on the Circulatory Function of Rats Instruments and Equipment: A small animal implantable physiological signal telemetry system from DSI (Data Science International, Inc.) including implants (RATHD-S21, DSI, United States), receiver boards (RPC-1, DSI, United States), signal conversion devices (DEM, DSI, USA), perfusion glue (DSI, USA), fibrin membrane (DSI, USA), etc. A small animal ventilator (HX-101E, Chengdu Taimeng Technology Co., Ltd.); An electronic balance (ME215S, Sartorius, Germany).

Experimental Methods: The circulatory function of rats was monitored by A small animal implantable physiological signal telemetry system from DSI (Data Science International, Inc.). Adult male Sprague-Dawley rats (250-300 g) were selected for the experiment (n=6). First, the animal model was established, and the left ventricular catheter, abdominal aorta catheter and electrocardiogram wire were placed. At least one week after the operation, the signal can be collected to start the test. At the beginning of the experiment, after the placement of the indwelling needle in the tail vein of rats, connect the extension tube, put the rats together with the feeding cage on the signal receiver and start collecting data. After 30 minutes, the compound in the example and the control drugs etomidate and propofol in the dose of 2ed50 were given respectively. All compounds or drugs were given at a constant volume of 0.6 ml at a uniform rate of 0.1 ml/s. The pharmacological effects, adverse reactions and behavior of rats were observed and recorded after drug injection.

Data collection: After setting the data collection parameters on the software, the power of the implant was turned on to start data collection. In this experiment, data recording frequency was set to 15 s. Data collection was continuously recorded for 15 min before and after administration of the drugs in rats. After data acquisition, the test was stopped.

Evaluation indexes: Collect the blood pressure, heart rate and other data of rats during and 15 minutes after administration, and judge the effect of the compound of the invention on the circulatory function of rats with the indexes of mean arterial pressure (MAP) and heart rate (HR).

Experimental results (FIG. 19,20,21,22):

Like the control etomidate, the compound of the invention has a slight inhibitory effect on the circulatory function after administration, but soon rises to near the baseline, while the control propofol shows a significant inhibition on the circulatory system function.

Example 24 the Group D Compounds of the Present Invention can Still Recover Rapidly after Continuous Infusion in Rats for 1 Hour Instrument and Equipment: micro injection pump (model: SN-50F6, manufacturer: Shenzhen Shengnuo Medical Equipment Co., LTD.), multi-functional ion meter (METTLER TOLEDO, model: SevenMulti), pipette gun (Eppendorf, specification: 1000 ul, 200 ul, 100 ul, 10 ul), timer.

Experimental Methods: Adult male SD rats with body weight ranging from 250 g to 350 g were selected for continuous infusion test. The compound of the invention, the control drug etomidate and CPMM were continuously injected through the tail vein of rats at a dose of 2 times the MIR (minimum infusion speed), and the absence of righting reflex was maintained for 1 hour from the time of the disappearance of righting reflex, and the awakening time and complete recovery time of the experimental animals were recorded after stopping the infusion.

Evaluation indexes: the time from the beginning of continuous infusion to the disappearance of sedation in rats; the time from the cessation of infusion to the restoration of the forepaw turning reflex after 1 hour of continuous infusion; the time from the cessation of infusion to the complete restoration of rats after 1 hour of continuous infusion.

Experimental results (Table 18):

The recovery time of the compound in the invention is not significantly longer than or equal to etomidate in terms of recovery time after continuous infusion of 2 times the dose of MIR (minimum infusion rate) for 1 hour compared with a single intravenous injection of $2ED_{50}$ dose. The types and incidence of adverse reactions were significantly less than etomidate and CPMM.

TABLE 17

The effects of the compounds on adrenocortical function in rats

| Group | Baseline (S1) | Give ACTH 30 min later (S2) |
|---|---|---|
| 0.9% NaCl | 130.10 ± 43.28 | 268.12 ± 34.77 |
| ET | 142.31 ± 45.33 | 124.34 ± 23.11 |
| PRO | 156.98 ± 59.41 | 253.11 ± 31.56 |
| Compound D1 | 165.43 ± 15.99 | 247.90 ± 43.21 |
| Compound D17 | 160.98 ± 33.09 | 248.55 ± 32.33 |
| Compound D25 | 171.66 ± 24.66 | 259.09 ± 36.77 |
| Compound D29 | 163.98 ± 22.11 | 279.76 ± 24.67 |
| Compound D76 | 153.23 ± 30.91 | 277.88 ± 34.56 |
| Compound D79 | 151.11 ± 21.00 | 277.88 ± 30.56 |
| Compound D81 | 147.99 ± 46.90 | 260.99 ± 21.77 |
| Compound D87 | 163.22 ± 35.11 | 242.12 ± 40.22 |
| Compound D88 | 172.33 ± 46.70 | 253.11 ± 33.20 |

Example 23 the Group D Compound of the Present Invention has Slight Influence on the Circulatory Function of Rats Instruments and Equipment: A small animal implantable physiological signal telemetry system from DSI (Data Science International, Inc.) including implants (RATHD-S21, DSI, United States), receiver boards (RPC-1, DSI, United States), signal conversion devices (DEM, DSI, USA), perfusion glue (DSI, USA), fibrin membrane (DSI, USA), etc. A small animal ventilator (HX-101E, Chengdu Taimeng Technology Co., Ltd.); An electronic balance (ME215S, Sartorius, Germany).

Experimental Methods: The circulatory function of rats was monitored by A small animal implantable physiological signal telemetry system from DSI (Data Science International, Inc.). Adult male Sprague-Dawley rats (250-300 g) were selected for the experiment (n=6). First, the animal model was established, and the left ventricular catheter, abdominal aorta catheter and electrocardiogram wire were placed. At least one week after the operation, the signal can be collected to start the test. At the beginning of the experiment, after the placement of the indwelling needle in the tail vein of rats, connect the extension tube, put the rats together with the feeding cage on the signal receiver and start collecting data. After 30 minutes, the compound in the example and the control drugs etomidate and propofol in the dose of 2ed50 were given respectively. All compounds or drugs were given at a constant volume of 0.6 ml at a uniform rate of 0.1 ml/s. The pharmacological effects, adverse reactions and behavior of rats were observed and recorded after drug injection.

Data collection: After setting the data collection parameters on the software, the power of the implant was turned on to start data collection. In this experiment, data recording frequency was set to 15 s. Data collection was continuously recorded for 15 min before and after administration of the drugs in rats. After data acquisition, the test was stopped. Evaluation indexes: Collect the blood pressure, heart rate and other data of rats during and 15 minutes after administration, and judge the effect of the compound of the invention on the circulatory function of rats with the indexes of mean arterial pressure (MAP) and heart rate (HR).

Experimental results (FIG. 19, 20,21,22):

Like the control etomidate, the compound of the invention has a slight inhibitory effect on the circulatory function after administration, but soon rises to near the baseline, while the control propofol shows a significant inhibition on the circulatory system function.

Example 24 the Group D Compound of the Present Invention can Still Recover Rapidly after Continuous Infusion in Rats for 1 Hour Instrument and Equipment: micro injection pump (model: SN-50F6, manufacturer: Shenzhen Shengnuo Medical Equipment Co., LTD.), multi-functional ion meter (METTLER TOLEDO, model: SevenMulti), pipette gun (Eppendorf, specification: 1000 ul, 200 ul, 100 ul, 10 ul), timer.

Experimental Methods: Adult male SD rats with body weight ranging from 250 g to 350 g were selected for continuous infusion test. The compound of the invention, the control drug etomidate and CPMM were continuously injected through the tail vein of rats at a dose of 2 times the MIR (minimum infusion speed), and the absence of righting reflex was maintained for 1 hour from the time of the disappearance of righting reflex, and the awakening time and complete recovery time of the experimental animals were recorded after stopping the infusion.

Evaluation indexes: the time from the beginning of continuous infusion to the disappearance of sedation in rats; the time from the cessation of infusion to the restoration of the forepaw turning reflex after 1 hour of continuous infusion; the time from the cessation of infusion to the complete restoration of rats after 1 hour of continuous infusion.

Experimental results (table 18):

The recovery time of the compound in the invention is not significantly longer than or equal to etomidate in terms of recovery time after continuous infusion of 2 times the dose of MIR (minimum infusion rate) for 1 hour compared with a single intravenous injection of $2ED_{50}$ dose. The types and incidence of adverse reactions were significantly less than etomidate and CPMM.

TABLE 18

Pharmacological effects of continuous infusion of the compound of present the invention

| Compound/drug | Sedation onset time(min) | After the infusion is stopped Righting reflex recovery time(min) | Recovery time after stopping infusion(min) | Types and incidence of adverse reactions |
|---|---|---|---|---|
| Etomidate | <5 | 15-20 | 30-40 | Tremor(6/6), Myoclonus(4/6), Tongue stretching(2/6), Hindlimb rigidity(2/6) |
| CPMM | <5 | 8-10 | 10-15 | Red urine(6/6), Tremor(4/6), Hindlimb rigidity(4/6) |
| DMSO | / | / | / | Red urine(6/6) |
| Compound D1 | <5 | 18-24 | 35-45 | Red urine(6/6), Tremor(2/6), Tongue stretching(2/6) |
| Compound D17 | <5 | 15-22 | 25-35 | Red urine(6/6), Tremor(1/6), |
| Compound D25 | <5 | 16-24 | 30-40 | Red urine(6/6), Tremor(2/6), Hindlimb rigidity(1/6) |
| Compound D29 | <5 | 12-20 | 20-25 | Red urine(6/6), Tongue stretching(4/6) |
| Compound D76 | <5 | 15-25 | 25-40 | Red urine(6/6), Hindlimb rigidity(2/6) |
| Compound D77 | <5 | 12-16 | 20-30 | Red urine(6/6), Tongue stretching(3/6), Tremor(3/6) |
| Compound D81 | <5 | 13-14 | 15-25 | Red urine(6/6), Tremor(2/6), the four limbs rigidity(2/6) |

In summary, the present invention discloses a class of structurally novel substituted nitrogen heterocyclic compounds. The substituted nitrogen heterocyclic compounds have better depressant effects on the central nervous system and produce sedative, hypnotic and/or anesthetic action as well as control of epilepsy persistence; The substituted nitrogen heterocyclic compounds not only maintains excellent anesthetic activity, but also has the characteristics of rapid onset and rapid recovery; At the same time, the substituted nitrogen heterocyclic compounds have almost no inhibitory effect on the function of adrenal cortex and has little side effects, which solves the technical problems in the field. The present invention provides a new choice for clinically screening and/or preparing sedative, hypnotic and/or general anesthesia drugs and drugs for controlling status epilepticus.

The invention claimed is:

1. A compound, or a stereoisomer thereof, or a pharmaceutically acceptable salt thereof, or a solvate thereof, or a deuterated derivative thereof, characterized in that: the compound is a compound of formula I;

Formula I

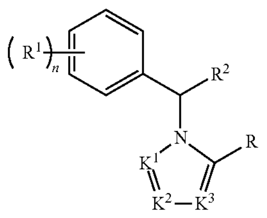

$R^1$ is deuterium, or substituted or unsubstituted $C_{1-8}$ alkyls;

for above $R^1$, said substituents are deuterium;

n is an integer of 0~5;

$R^2$ is $C_{1-8}$ alkyls;

$K^1$ is N, $K^2$ is N or $CR^{k2}$;

$K^3$ is $CR^{k3}$,

R is selected from the group consisting of

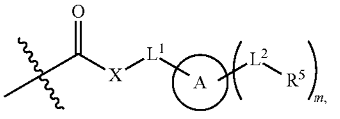

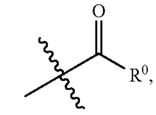

and

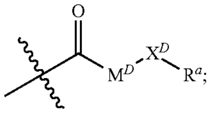

$R^{k2}$ and $R^{k3}$ are independently selected from the group consisting of hydrogen, deuterium, halogen, and $C_{1-8}$ alkyls;

X is O or S;

$L^1$ and $L^2$ are each independently none, or substituted or unsubstituted $C_{1-8}$ alkylene; said substituents are selected from the group consisting of deuterium, cyano, hydroxyl, carboxyl, halogen, CH, $CH_2$, $C_{3-8}$ alkyls or their halogenated or deuterated derivative, $C_{2-8}$ alkenyls or their halogenated or deuterated derivative, $C_{2-8}$ alkynyls or their halogenated or deuterated derivative, $C_{1-8}$ alkoxyls or their halogenated or deuterated derivative, $C_{3-8}$ cycloalkyls or their halogenated or deuterated derivative, 3~8-membered heterocyclic groups or their halogenated or deuterated derivative, aryls or their halogenated or deuterated derivative, and heteroaryls or their halogenated or deuterated derivative;

$L^1$ and $L^2$ can be connected to the homotopic or heterotopic atoms on the A ring;

m is an integer of 0~4;

ring A is none, or ring A is selected from the group consisting of 3~8-membered saturated carbocycles, 3~8-membered unsaturated carbocycles, 3~8-membered saturated heterocycles, and 3~8-membered unsaturated heterocycles;

$R^5$ is selected from the group consisting of hydrogen, deuterium, halogen, propadienyl,

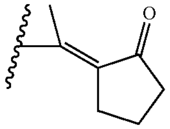

substituted or unsubstituted $C_{1-8}$ alkyls, $—OR^{33}$, $—SR^{33}$, $—OC(O)R^{34}$, $C_{3-8}$-membered cycloalkyls, 3~8-membered heterocyclyls aryls, heteroaryls, $—N(R^{33})_2$, $—C(O)R^{34}$, $—C(S)R^{34}$, $—S(O)R^{34}$, $—CON(R^{33})_2$, $—SO_2R^{34}$, substituted or unsubstituted $C_{2-8}$ alkenyls, substituted or unsubstituted $C_{2-8}$ alkynyls, cyano, isocyano, isothiocyano, nitro, $-L^{33}-R^{36}$ and $=R^{39}$;

$L^{33}$ is $C_{1-4}$ alkylene;

$R^{36}$ is selected from the group consisting of cyano, nitro, $—OC(O)\ R^{34}$, $—C(O)R^{34}$, $—S(O)R^{34}$, and $—C(O)N(R^{33})_2$;

$R^{33}$ is selected from the group consisting of hydrogen, methylsulfonyl, $-L^{31}-COO-L^{32}$, and the following substituted or unsubstituted groups: $C_{1-8}$ alkyls, $C_{3-8}$ cycloalkyls, 3~8-membered heterocyclyls, aryls, or heteroaryls;

$R^{34}$is selected from the group consisting of $R^{33}$, deuterium, and the following substituted or unsubstituted groups: $C_{1-8}$ alkoxyl, $C_{2-8}$ alkenyls, $C_{2-8}$ alkynyls, or $—S—C_{1-8}$ alkyls;

$L^{31}$ is substituted or unsubstituted $C_{1-8}$ alkylene;

$L^{32}$ is substituted or unsubstituted $C_{1-8}$ alkyls;

for above $R^5$, $R^{33}$, $R^{34}$, said substituents are selected from the group consisting of deuterium, cyano, hydroxyl, carboxyl, halogen, $C_{1-4}$ alkyls or their halogenated or the deuterated derivative, $C_{1-4}$ alkoxyl or their halogenated or the deuterated derivative, $C_{3-8}$-membered cycloalkyls or their halogenated or the deuterated derivative, 3-8-membered heterocyclyls or their halogenated or the deuterated derivative, aryls or their halogenated or deuterated derivative, heteroaryls or their halogenated or deuterated derivative, $—S—C_{1-4}$ alkyls, di-substituted cyclic carbonyls, $=R^{39}$, $C_{2-8}$ alkenyls, and $C_{2-8}$ alkynyls;

$R^{39}$ is selected from the group consisting of O, S, $NR^{40}$, and $C(R^{41})_2$; wherein $R^{40}$ is selected from the group consisting of hydrogen, halogen, and $C_{1-4}$ alkyls or their halogenated or deuterated derivative; $R^{41}$ is $R^{40}$ or deuterium;

$R^0$ is $L^{C3}R^{C4}$, or $L^{C1}X^CL^{C2}R^{C5}$;

$L^{C3}$ is none, or substituted or unsubstituted $C_{1-4}$ alkylene, said substituents in $C_{1-4}$ alkylenyls are selected from the group consisting of $C_{1-5}$ alkyls, $C_{1\sim5}$ alkoxyl, halogen, and hydroxyl;

$R^{C4}$ is selected from the group consisting of substituted or unsubstituted $C_2$~6 alkenyls, substituted or unsubstituted $C_{2-6}$ alkynyls, substituted or unsubstituted 3~6-membered saturated or unsaturated heterocyclyls, substituted or unsubstituted 3~6-membered saturated or unsaturated cycloalkyls, and $COR^{4d}$; said substituents are each independently $L^{C4}R^{4e}$; $R_{4d}$ is $C_{1\sim6}$ alkyls; $L^{C4}$ is none, or substituted or unsubstituted $C_{1-4}$ alkylene; $R^{4e}$ is selected from the group consisting of $C_{1-5}$ alkyls, $C_{1\sim5}$ alkoxyl, halogen, and hydroxyl;

$L^{C1}$ is substituted or unsubstituted $C_{1-3}$ alkylene, said substituents is $C_{1-5}$ alkyls;

$X^C$ is O or S;

$L^{C2}$ is none, or substituted or unsubstituted $C_{1-3}$ alkylene, said substituents are selected from the group consisting of $C_{1-4}$ alkyls, $C_{1-4}$ alkoxyl, and $L^{2a}R^{5g}$; wherein $L^{2a}$ is none, or $C_{1\sim2}$ alkylene; $R^{5g}$ is halogen, or $C_{1\sim4}$ alkoxyls;

$R^{C5}$ is selected from the group consisting of hydrogen, halogen, $C_{1\sim5}$ alkyls, $C_{2\sim4}$ alkenyls, $C_{2\sim4}$ alkynyls, $COR^{4d}$, $C_{3\sim6}$ di-alkenyls, $C_{1\sim5}$ alkoxyl, 3~6-membered saturated or unsaturated heterocyclyls optionally substituted by one or more $R^{5c}$, 3~6-membered saturated or unsaturated cycloalkyls optionally substituted by one or more $R^{5c}$; wherein $R^{4d}$ is $C_{1-6}$ alkyls, $R^{5c}$ is selected from the group consisting of halogen, $=R^{5d}$, $L^{1a}R^{5e}$, and $C_{3\sim6}$di-alkenyls; $R^{5d}$ is $CH_2$, O or S, $L^{1a}$ is $C_{1-3}$ alkylene, and $R^{5e}$ is $C_{1\sim5}$ alkyls, or $C_{1\sim5}$ alkoxyl;

$M^D$ is CO or $CR^{D6}R^{D7}$, wherein $R^{D6}$ is hydrogen, or $X^{Db}R^{D4b}$, $R^{D7}$ is hydrogen, or $X^{Dc}R^{D4c}$;

$X^D$ is O or S; $X^{Db}$ is O or S; $X^{Dc}$ is O or S;

$R^a$ is selected from the group consisting of substituted or unsubstituted $C_{1\sim6}$ alkyls, substituted or unsubstituted $C_{2\sim6}$ alkynyls, substituted or unsubstituted $C_{2\sim6}$ alkenyls, substituted or unsubstituted 3~6-membered saturated or unsaturated heterocyclyls, and substituted or unsubstituted 3~6-membered saturated or unsaturated cycloalkyls; said substituents are each independently selected from the group consisting of $C_{3\sim6}$ di-alkenyls, $C_{1\sim5}$ alkyls, $C_{1\sim5}$ alkoxyl, halogen, and hydroxyl;

$R^{D4b}$ and $R^{D4c}$ are each independently selected from the group consisting of substituted or unsubstituted $C_{1-6}$ alkyls, substituted or unsubstituted $C_{2\sim6}$ alkynyls, substituted or unsubstituted $C_{2\sim6}$ alkenyls, $COR^{Df}$, substituted or unsubstituted 3≡6-membered saturated or unsaturated heterocyclyls groups, and substituted or unsubstituted 3~6-membered saturated or unsaturated cycloalkyls; said substituents are each independently selected from the group consisting of $C_{3-6}$ dialkenyls, $C_{1\sim5}$ alkyls, $C_{1\sim5}$ alkoxyl, halogen, and hydroxyl; $R^{Df}$ is $C_{1-5}$ alkyls.

2. Compounds according to claim 1, or the stereoisomer thereof, or the pharmaceutically acceptable salt thereof, or the solvate thereof, or the deuterated derivative thereof, characterized in that: said compound is a compound of formula A-I:

Formula A-I

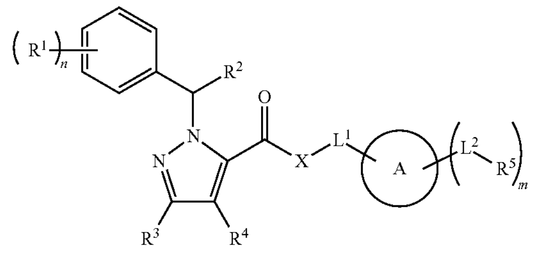

$R^1$ is deuterium, or substituted or unsubstituted $C_{1-8}$ alkyls;

for above $R^1$, said substituents are deuterium;

n is an integer of 0-5;

$R^2$ is $C_{1-8}$ alkyls;

$R^3$ and $R^4$ are each independently selected from the group consisting of hydrogen, deuterium, halogen, and substituted or unsubstituted $C_{1-8}$ alkyls; said substituents is deuterium, halogen, $C_{1-8}$ alkyls or their halogenated or deuterated derivative, $C_{1-8}$ alkoxyl or their halogenated or deuterated derivative;

X is O or S;

$L^1$ is none, or substituted or unsubstituted $C_{1-8}$ alkylene; said substituents are selected from the group consisting of deuterium, cyano, halogen, $C_{1-8}$ alkyls or their halogenated or deuterated derivative, $C_{2-8}$ alkenyls or their halogenated or deuterated derivative, and $C_{2-8}$ alkynyls or their halogenated or deuterated derivative;

$L^2$ is none;

$L^1$ and $L^2$ can be connected to the homotopic or heterotopic atoms on the A ring;

m is 0 or 1;

ring A is none, or ring A is 3~8-membered saturated carbocycles, or 3~8-membered unsaturated carbocycles;

$R^5$ is as defined in claim 1.

3. The compound according to claim 1, or the stereoisomer thereof, or the pharmaceutically acceptable salt thereof, or the solvate thereof, or the deuterated derivative thereof, characterized in that: said compound is a compound of formula A-II:

Formula A-II

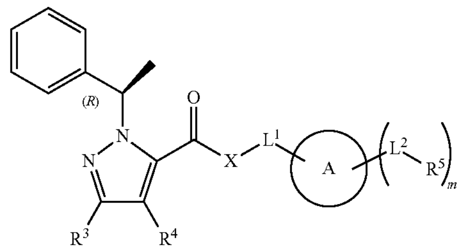

wherein $R^3$ and $R^4$ are each independently selected from the group consisting of hydrogen, deuterium, halogen, and substituted or unsubstituted $C_{1-4}$ alkyls; said substituents is selected from the group consisting of deuterium, halogen, and $C_{1-4}$ alkyls or their halogenated or deuterated derivative;

X is O or S;

$L^1$ is none, or substituted or unsubstituted $C_{1-4}$ alkylene; said substituents are selected from the group consisting of deuterium, $C_{1-4}$ alkyls, $C_{2-4}$ alkenyls;

$L^2$ is none;

$L^1$ and $L^2$ can be connected to the homotopic or heterotopic atoms on the A ring;

m is 0 or 1;

ring A is none, or ring A is selected from the group consisting of 3~6-membered saturated carbocycles, 3~6-membered unsaturated carbocycles, 3~6-membered saturated heterocycles, and 3~6-membered unsaturated heterocycles;

$R^5$ is as defined in claim 1.

4. The compounds according to claim 1, or the stereoisomer thereof, or the pharmaceutically acceptable salt thereof, or the solvate thereof, or the deuterated derivative thereof, characterized in that: said compound is a compound of formula A-II:

Formula A-II

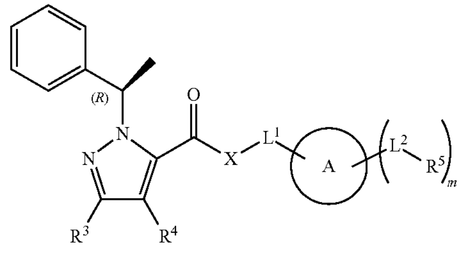

(a) in formula A-II:

ring A is 3~6-membered saturated carbocycles;

X is O;

m is 0 or 1;

$R^3$ and $R^4$ are each independently selected from the group consisting of hydrogen, deuterium, F, Cl, and $CF_3$;

$L^1$ is none, or substituted by 1~2 substituents or unsubstituted methylene; said substituents are selected from the group consisting of deuterium, $C_{1-4}$ alkyls, and $C_{2-3}$ alkenyls;

$L^2$ is none;

$L^1$ and $L^2$ can be connected to the homotopic or heterotopic atoms on the A ring;

$R^5$ is selected from the group consisting of hydrogen, deuterium, $C_{1-2}$ alkyls, propadienyl, $C_{2-4}$ alkenyls, $C_{2-4}$ alkynyls, —$OR^{33}$, —$C(O)R^{34}$, and =$R^{39}$;

$R^{33}$ is $C_{1-3}$ alkyls;

$R^{34}$is selected from the group consisting of hydrogen, deuterium, $C_{1-3}$ alkyls, and $C_{1-3}$ alkoxyl; and $R^{39}$ is O or $CH_2$;

or, (b) in formula A-II:

ring A is

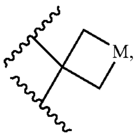

M is O or S;

X is O;

m is 0 or 1;

$R^3$ and $R^4$ are each independently selected from the group consisting of hydrogen, deuterium, F, Cl, and $CF_3$;

$L^1$ is none, or substituted by 1~2 substituents or unsubstituted methylene; said substituents are deuterium, $C_{1-4}$ alkyls, and $C_{2-3}$ alkenyls;

$L^2$ is none;

$R^5$ is selected from the group consisting of hydrogen, deuterium, $C_{1-2}$ alkyls, propadienyl, $C_{2-4}$ alkenyls, $C_{2-4}$ alkynyls, —$OR^{33}$, —$C(O)R^{34}$, and =$R^{39}$;

$R^{33}$ is $C_{1-3}$ alkyls;

$R^{34}$is selected from the group consisting of hydrogen, deuterium, $C_{1-3}$ alkyls, and $C_{1-3}$ alkoxyl;

and $R^{39}$ is selected from the group consisting of O, S, and $CH_2$;

or, (c) in formula A-II:

ring A is

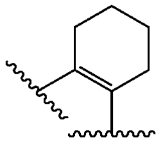

or

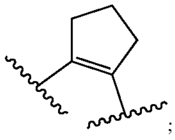

;

X is O;

m is 0 or 1;

$R^3$ and $R^4$ are each independently selected from the group consisting of hydrogen, deuterium, F, Cl, and $CF_3$;

$L^1$ is none, or substituted by 1~2 substituents or unsubstituted methylene; said substituents are selected from the group consisting of deuterium, $C_{1-4}$ alkyls, and $C_{2-3}$ alkenyls;

$L^2$ is none;

$R^5$ is —$C(O)R^{34}$; and $R^{34}$is selected from the group consisting of hydrogen, deuterium, $C_{1-2}$ alkyl, and $C_{1-2}$ alkoxyl;

or, (d) in formula A-II:

ring A is none;

X is O;

m is 1;

$R^3$ and $R^4$ are each independently selected from the group consisting of hydrogen, deuterium, F, Cl, and $CF_3$;

$L^1$ is none, or substituted by 1~2 substituents or unsubstituted methylene; said substituents are selected from the group consisting of deuterium, $C_{1-4}$ alkyls, and $C_{2-3}$ alkenyls;

$L^2$ is none;

$R^5$ is selected from the group consisting of hydrogen, deuterium, $C_{1-4}$ alkyls, propadienyl,

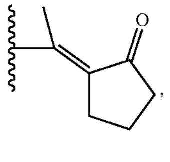 [SMILES: */C(C)=C1\CCCC1=O]

$C_{2-4}$ alkenyls, $C_{2-4}$ alkynyls, —$OR^{33}$, and —$OC(O)R^{34}$;

$R^{33}$ is $C_{1-3}$ alkyls; and $R^{34}$is selected from the group consisting of hydrogen, deuterium, $C_{1-3}$ alkyls, and $C_{1-3}$ alkoxyl.

5. The compound according to claim 1, or the stereoisomer thereof, or the pharmaceutically acceptable salt thereof, or the solvate thereof, or the prodrug thereof, or the metabolite thereof, or the deuterated derivative thereof, characterized in that: said compound is a compound of formula B—I:

Formula B-I

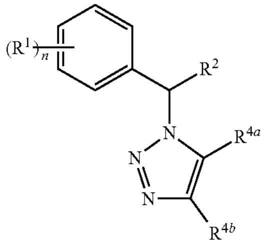

wherein $R^1$ is each independently deuterium, or substituted or unsubstituted $C_{1-8}$ alkyls;

for above $R^1$, said substituents are deuterium;

n is an integer of 0~5;

$R^2$ is $C_{1-8}$ alkyls;

$R^{4a}$ is

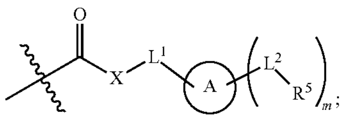

$R^{4b}$ is $R^4$;

$R^4$ is selected from the group consisting of hydrogen, deuterium, halogen, and substituted or unsubstituted $C_{1-8}$ alkyls; said substituents are selected from the group consisting of deuterium, halogen, $C_{1-8}$ alkyls or their halogenated or the deuterated derivative, and $C_{1-8}$ alkoxyls or their halogenated or the deuterated derivative;

X is O, or S;

$L^1$ and $L^2$ are each independently none, or substituted or unsubstituted $C_{1-8}$ alkylene; said substituents are deuterium, cyano, $C_{1-8}$ alkyls or their halogenated or deuterated derivative, $C_{2-8}$ alkenyls or their halogenated or deuterated derivative, and $C_{2-8}$ alkynyls or their halogenated or;

$L^1$ and $L^2$ can be connected to the homotopic or heterotopic atoms on the A ring;

m is 0 or 1;

Ring A is none, or ring A is selected from the group consisting of 3~8-membered saturated carbocycles, 3~8-membered unsaturated carbocycles, and 3~8-membered saturated heterocycles or 3~8-membered unsaturated heterocycles;

$R^5$ is as defined in claim 1.

6. The compound according to claim 1, or the stereoisomer thereof, or the pharmaceutically acceptable salt thereof, or the solvate thereof, or the prodrug thereof, or the metabolite thereof, or the deuterated derivative thereof, characterized in that: said compound is a compound of formula B-II-1:

Formula B-II-1

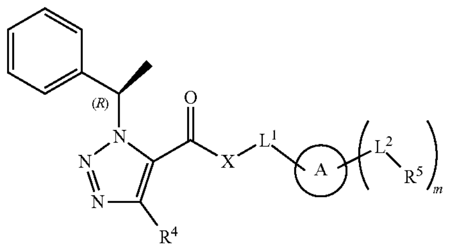

wherein $R^4$ is selected from the group consisting of hydrogen, deuterium, halogen, and substituted or unsubstituted $C_{1-4}$ alkyls; said substituents are selected from the group consisting of deuterium, halogen, and $C_{1-4}$ alkyls or their halogenated or the deuterated derivative;

X is O or S;

$L^1$ and $L^2$ are each independently none, or substituted or unsubstituted $C_{1-4}$ alkylene; said substituents are each independently selected from the group consisting of deuterium, $C_{1-4}$ alkyls, and $C_{2-4}$ alkenyls;

$L^1$ and $L^2$ can be connected to the homotopic or heterotopic atoms on the A ring;

m is 0 or 1;

Ring A is none, or; ring A is selected from the group consisting of 3~6-membered saturated carbocycles, 3~6-membered unsaturated carbocycles, and 3~6-membered saturated heterocycles;

$R^5$ is as defined in claim 1.

7. The compounds according to claim 1, or the stereoisomer thereof, or the pharmaceutically acceptable salt thereof, or the solvate thereof, or the prodrugs thereof, or the metabolites thereof, or the deuterated derivative thereof, characterized in that: said compound is a compound of formula B-II-1:

Formula B-II-1

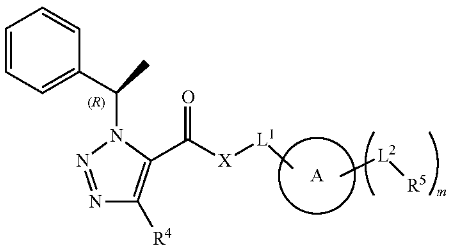

(a) wherein:

Ring A is 3~6-membered saturated carbocycles;

X is O, or S;

m is 1;

$R^4$ is selected from the group consisting of hydrogen, deuterium, and halogen;

$L^1$ and $L^2$ are each independently none, or substituted by 1 substituent or unsubstituted methylenes; said substituents are each independently selected from the group consisting of deuterium, $C_{1-4}$ alkyls, and $C_{2-3}$ alkenyls;

$L^1$ and $L^2$ can be connected to the homotopic or heterotopic atoms on the A ring;

$R^5$ is selected from the group consisting of hydrogen, deuterium, $—OR^{33}$, and $—C(O)R^{34}$;

$R^{33}$ is $C_{1-3}$ alkyls;

$R^{34}$is $C_{1-3}$ alkoxyls;

or, (b) wherein:

Ring A is

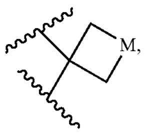

M is s O;

X is O or S;

m is 1;

$R^4$ is selected from the group consisting of hydrogen, deuterium, and halogen;

$L^1$ and $L^2$ are none;

$R^5$ is selected from the group consisting of $C_{1-2}$ alkyls, propadienyl, $C_{2-4}$ alkenyls, and $=R^{39}$;

said substituents for $R^5$ is selected from the group consisting of $=R^{39}$, $C_{2-4}$ alkenyls, and $C_{2-4}$ alkynyls;

$R^{39}$ is $CH_2$;

or, (c) wherein:

Ring A is

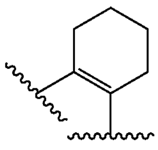

or

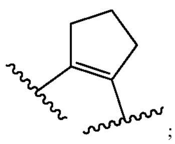

;

X is O or S;

m is 1;

$R^4$ is selected from the group consisting of hydrogen, deuterium, and halogen;

$L^1$ and $L^2$ are none;

$R^5$ is —C(O)$R^{34}$; and $R^{34}$ is $C_{1-2}$ alkyls, or $C_{1-2}$ alkoxyl;

or, (d) wherein:

Ring A is none,

X is O, or S;

m is 1;

$R^4$ is each independently selected from the group consisting of hydrogen, deuterium, halogen, and halogenated or un-halogenated methyl;

$L^1$ and $L^2$ are each independently none, or substituted by 1~2 substituents or unsubstituted $C_{1-2}$ methylene; said substituents are deuterium, or $C_{1-4}$ alkyls;

$R^5$ is $C_{1-4}$ alkyls, or $C_{2-4}$ alkenyls.

8. Compounds according to claim 1, or the stereoisomer thereof, or the pharmaceutically acceptable salt thereof, or the solvate thereof, or the prodrug thereof, or the metabolite thereof, or the deuterated derivative thereof, characterized in that: said compound is a compound of formula C-I:

Formula C-I

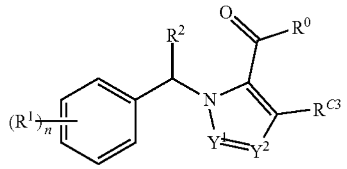

wherein, n is an integer of 0~3;

$R^1$ is $C_{1-5}$ alkoxyls;

$R^2$ is $C_{1-5}$ alkyls;

$Y^1$ is N, $Y^2$ is selected from N or $CR^{c5b}$;

$R^{c5b}$, $R^{c3}$ are each independently selected from the group consisting of hydrogen, halogens, and $C_{1-5}$ alkyls;

$R^0$ is $L^{C3}R^{C4}$ or $L^{C1}X^CL^{C2}R^{C5}$;

$L^{C3}$ is none, or substituted or unsubstituted $C_{1-4}$ alkylene; said substituents for $C_{1-4}$ alkylenyls are selected from the group consisting of $C_{1-5}$ alkyls, $C_{1-5}$ alkoxyls, halogens, and hydroxyl;

$R^{C4}$is selected from the group consisting of substituted or unsubstituted $C_{2-6}$ alkenyls, substituted or unsubstituted $C_{2-6}$ alkynyls, substituted or unsubstituted 3~6-membered saturated or unsaturated heterocyclyls, substituted or unsubstituted 3~6-membered saturated or unsaturated cycloalkyls, and $COR^{4d}$; said substituents are each independently $L^{C4}R^{4e}$; wherein $R^{4d}$ is $C_{1-6}$ alkyls; $L^{C4}$is none, or substituted or unsubstituted $C_{1-4}$ alkylene; and $R^{4e}$ is selected from the group consisting of $C_{1-5}$ alkyls, $C_{1-5}$ alkoxyl, halogen, and hydroxyl;

$L^{C1}$ is the substituted or unsubstituted $C_{1-3}$ alkylene, said substituents are the $C_{1-5}$ alkyls;

$X^C$ is O or S;

$L^{C2}$is none, or substituted or unsubstituted $C_{1-3}$ alkylene, said substituents are selected from the group consisting of $C_{1-4}$ alkyls, $C_{1-4}$ alkoxyls, and $L^{2a}R^{5g}$; wherein $L^{2a}$ is none, or $C_{1-2}$ alkylene, and $R^{5g}$ is halogen, or $C_{1-4}$ alkoxyls;

$R^{c5}$ is selected from the group consisting of hydrogen, halogen, $C_{1-5}$ alkyls, $C_{2-4}$ alkenyls, $C_{2-4}$ alkynyls, $COR^{4d}$, $C_{3\sim6}$ dienyls, $C_{1\sim5}$ alkoxyl, 3~6-membered saturated or unsaturated heterocyclyls substituted by one or more $R^{5c}$, and 3~6-membered saturated or unsaturated cycloalkyls substituted by one or more $R^{5c}$; wherein $R^{4d}$ is $C_{1-6}$ alkyls, $R^{5c}$ is selected from the group consisting of halogen, $=R^{5d}$, $L^{1a}R^{5e}$, and $C_{3\sim6}$ dienyls; wherein $R^{5d}$ is $CH_2$, O or S; $L^{1a}$ is $C_{1-3}$ alkylenyls; and $R^{5e}$ is $C_{1-5}$ alkyls, $C_{1-5}$ alkoxyls.

9. The compounds according to claim 1, or the stereoisomer thereof, or the pharmaceutically acceptable salt thereof, or the solvate thereof, or the prodrug thereof, or the metabolite thereof, or the deuterated derivative thereof, characterized in that:

(a) said compound is a compound of formula C-II-a:

Formula C-II-a

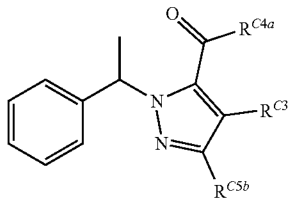

in formula C-II-a, $R^{C4a}$ is selected from the group consisting of substituted or unsubstituted $C_{2-3}$ alkenyls, substituted or unsubstituted $C_{2-3}$ alkynyls, and substituted or unsubstituted 3~4-membered saturated epoxyls; said substituents are each independently $C_{1-3}$ alkyls;

$R^{c5b}$ and $R^{C3}$ are each independently selected from the group consisting of hydrogen, halogen, and $C_{1-3}$ alkyls;

or, (b) said compound is a compound of formula C-III-a:

Formula C-III-a

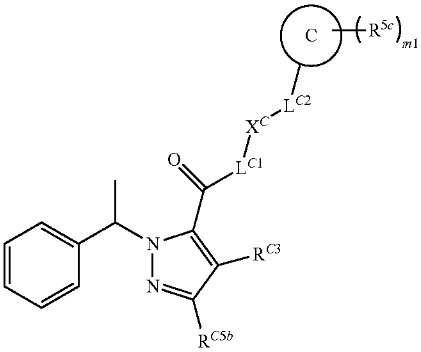

wherein, $X^C$ is O or S;

$L^{C1}$ is substituted or unsubstituted $C_{1-3}$ alkylene, said substituents are $C_{1-3}$ alkyls;

$L^{C2}$is none, or substituted or unsubstituted $C_{1-2}$ alkylene, said substituents are $C_{1-3}$ alkyls;

Ring C is 3~4-membered saturated heterocyclyls, or 3~4-membered saturated cycloalkyls;

m1 is selected from the group consisting of 0, 1, and 2;

$R^5$, is selected from the group consisting of halogen, $=R^{5d}$, $L^{1a}R^{5e}$, and propadienyl; wherein $R^{5d}$ is $CH_2$; $L^{1a}$ is $C_{1\sim3}$ alkylenyls, $R^{5e}$ is $C_{1\sim3}$ alkyls, $C_{1\sim3}$ alkoxyls;

$R^{C5b}$ and $R^{C3}$ are each independently selected from the group consisting of hydrogen, halogen, and $C_{1\sim3}$ alkyls;

or, (c) said compounds is a compound of formula C-III-c:

Formula C-III-c

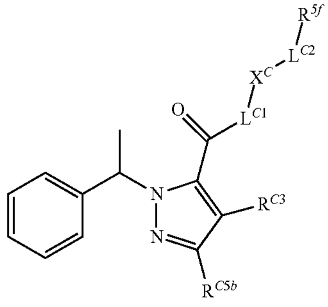

wherein, $X^C$ is O or S;

$L^{C1}$ is substituted or unsubstituted $C_{1-3}$ alkylene, said substituents are $C_{1-3}$ alkyls;

$L^{C2}$ is none, or substituted or unsubstituted $C_{1-2}$ alkylene, said substituents are selected from the group consisting of $C_{1-4}$ alkyls, $C_{1-4}$ alkoxyls, and $L^{2a}R^{5g}$; wherein $L^{2a}$ is none, or $C_{1-2}$ alkylene; $R^{5g}$ is halogen, or $C_{1-4}$ alkoxyls;

$R^{5f}$ is selected from the group consisting of hydrogen, halogen, $C_{1-4}$ alkyls, $C_{2-3}$ alkenyls, $C_{2-3}$ alkynyls, $COR^{4d}$, propadienyl, and $C_{1\sim4}$ alkoxyls; wherein $R^{4d}$ $C_{1\sim4}$ alkyls;

$R^{C5b}$ and $R^{C3}$ are each independently selected from the group consisting of hydrogen, halogen, and $C_{1\sim3}$ alkyls;

or, (d) said compounds is a compound of formula C-IV-a:

Formula C-IV-a

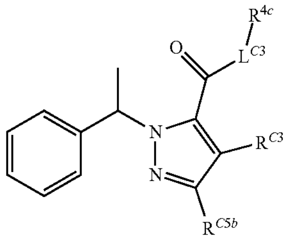

wherein $L^{C3}$ is substituted or unsubstituted $C_{1-3}$ alkylene, said substituents is $C_{1-3}$ alkyls, or $C_{1\sim3}$ alkoxyl;

$R^{4c}$ is selected from the group consisting of substituted or unsubstituted $C_{2-4}$alkenyls, substituted or unsubstituted $C_{2-4}$ alkynyls, substituted or unsubstituted 4-membered saturated cycloalkyls, and $COR^{4d}$; wherein said substituents are each independently $L^{C4}R^{4e}$; wherein $R^{4d}$ is $C_{1\sim3}$ alkyls, $L^{C4}$ is none or $C_{1-2}$ alkylene; and $R^{4e}$ is $C_{1\sim3}$ alkyls, or $C_{1\sim3}$ alkoxyl.

10. The compounds according to claim 1, or the stereoisomer thereof, or the pharmaceutically acceptable salt thereof, or the solvate thereof, or the prodrug thereof, or the metabolite thereof, or the deuterated derivative thereof, characterized in that:

said compound is a compound of formula D-I:

Formula D-I

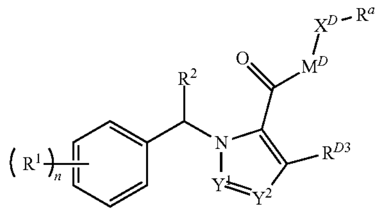

wherein, n is an integer of 0~3;

$R^1$ is $C_{1-5}$ alkyls;

$R^2$ is $C_{1-5}$ alkyls;

$Y^1$ is N, $Y^2$ is N or $CR^{D5b}$;

$R^{D5b}$ and $R^{D3}$ are independently selected from the group consisting of hydrogen, halogen, and $C_{1-5}$ alkyls;

$M^D$ is CO or $CR^{D6}R^{D7}$; wherein $R^{D6}$ is hydrogen, or $X^{Db}R^{D4b}$; and $R_7$ is hydrogen, or $X^{Dc}R^{D4c}$;

$X^D$ is O or S; $X^{Db}$ is O or S; $X^DC$ is O or S;

$R^a$ is selected from the group consisting of substituted or unsubstituted $C_{1-6}$ alkyls, substituted or unsubstituted $C_{2-6}$ alkynyls, substituted or unsubstituted $C_{2-6}$ alkenyls, substituted or unsubstituted 3~6-membered saturated or unsaturated heterocyclyls, and substituted or unsubstituted 3~6-membered saturated or unsaturated cycloalkyls; said substituents are each independently selected from the group consisting of $C_{1\sim5}$ alkyls, $C_{1\sim5}$ alkoxyl, halogen, and hydroxyl;

$R^{D4b}$ and $R^{D4c}$ are each independently selected from the group consisting of substituted or unsubstituted $C_{1\sim6}$ alkyls, substituted or unsubstituted $C_{2\sim6}$ alkynyls, substituted or unsubstituted $C_{2-6}$ alkenyls, substituted or unsubstituted 3~6-membered saturated or unsaturated heterocyclyls, and substituted or unsubstituted 3~6-membered saturated or unsaturated cycloalkyls; said substituents are each independently selected from the group consisting of $C_{1\sim5}$ alkyls, $C_{1\sim5}$ alkoxyl, halogen, and hydroxyl.

11. The compound according to claim 1, or the stereoisomer thereof, or the pharmaceutically acceptable salt thereof, or the solvate thereof, or the prodrug thereof, or the metabolite thereof, or the deuterated derivative thereof, characterized in that:

(a) said compound is a compound of formula D-II:

Formula D-II

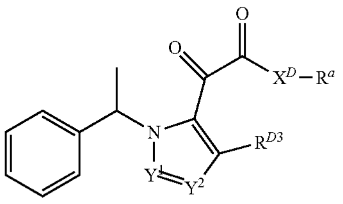

in formula D-II, $X^D$ is O or S;

$R^a$ is selected from the group consisting of substituted or unsubstituted $C_{1-6}$ alkyls, substituted or unsubstituted $C_{2-6}$ alkynyls, substituted or unsubstituted $C_{2-6}$ alkenyls, substituted or unsubstituted 3~6-membered saturated or unsaturated heterocyclyls, and substituted or unsubstituted 3~6-membered saturated or unsaturated cycloalkyls; said substituents are each independently of each other selected from the group consisting of $C_{1\sim5}$ alkyls, $C_{1\sim5}$ alkoxyls, halogen, and hydroxyl;

$Y^1$ is N, $Y^2$ is N or $CR^{C5b}$;

$R^{D5b}$, $R^{D3}$ are each independently selected from the group consisting of hydrogen, halogen, and $C_{1\sim5}$ alkyls;

or, (b) said compound is a compound of formula D-III:

Formula D-III

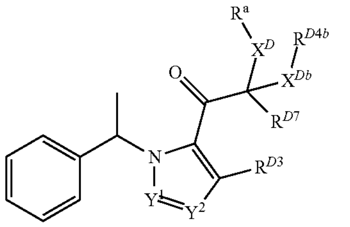

wherein, $R^{D7}$ is hydrogen or $X^{Dc}R^{D4c}$;

$X^D$, $X^{Db}$, $X^{Dc}$ are independently O or S;

$R^a$, $R^{D4b}$, $R^{D4c}$ are each independently selected from the group consisting of $C_{1-6}$ alkyls, $C_{2-6}$ alkynyls, $C_{2-6}$ alkenyls, substituted or unsubstituted 3~6-membered saturated or unsaturated heterocyclyls, and substituted or unsubstituted 3~6-membered saturated or unsaturated cycloalkyls; said substituents are each independently selected from the group consisting of $C_{1\sim3}$ alkyls, $C_{1\sim3}$ alkoxyl, halogen, and hydroxyl;

$Y^1$ is N, $Y^2$is N or $CR^{D5b}$;

$R^{D5b}$, $R^{D3}$ are each independently selected from the group consisting of hydrogen, halogen, and $C_1\sim_5$ alkyls.

12. The compounds according to claim 1, or the stereoisomer thereof, or pharmaceutically acceptable salt thereof, or the solvate thereof, or the prodrug thereof, or the metabolite thereof, or the deuterated derivative thereof, characterized in that:

(a) said compound is a compound of formula D-II-2 or formula D-II-4:

Formula D-II-2

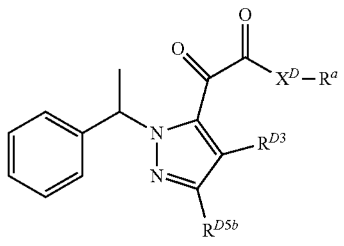

Formula D-II-4

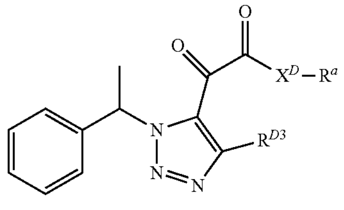

wherein, $X^D$ is O or S;

$R^a$ is selected from the group consisting of substituted or unsubstituted $C_{1-5}$ alkyls, substituted or unsubstituted $C_{2-4}$ alkynyls, substituted or unsubstituted $C_{2-4}$ alkenyls, substituted or unsubstituted 4-membered saturated epoxyls groups, and substituted or unsubstituted 4-membered saturated cycloalkyls; said substituents are each independently $C_{1\sim3}$ alkyls, or $C_{1\sim3}$ alkoxys;

$R^{D5b}$ and $R^{D3}$ are each independently selected from the group consisting of hydrogen, halogen, and $C_{1\sim3}$ alkyls;

or, (b) said compound is a compound of formula D-III-2, or formula D-III-4:

Formula D-III-2

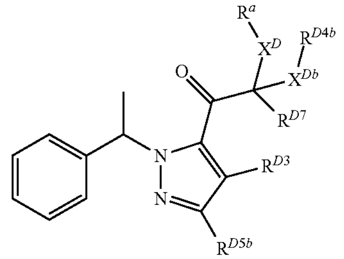

Formula D-III-4

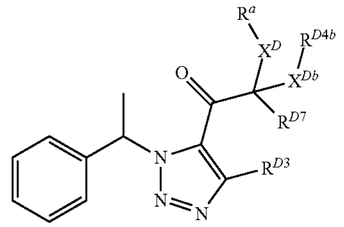

wherein, $R^{D7}$ is hydrogen or $X^{Dc}R^{D4c}$;

$X^D$, $X^{Db}$, and $X^{Dc}$ are each independently O or S;

$R^a$, $R^{D4b}$, and $R^{D4c}$ are each independently selected from the group consisting of $C_{1-5}$ alkyls, $C_{2-4}$ alkynyls, $C_{2-3}$ alkenyls, and 4-membered saturated cycloalkyls;

$R^{D5b}$ and $R^{D3}$ are each independently selected from the group consisting of hydrogen, halogen, and $C_{1\sim3}$ alkyls.

13. The compounds according to claim 1, or the stereoisomer thereof, or the pharmaceutically acceptable salt thereof, or the solvate thereof, or the deuterated derivative thereof, characterized in that, said compounds are selected from the group consisting of:

Compound A1

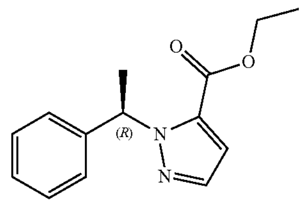

Compound A2

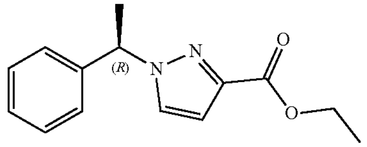

-continued
Compound A3
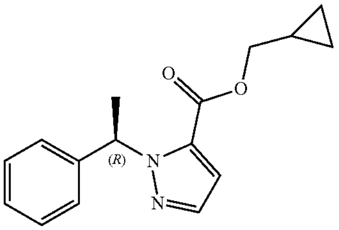
Compound A4
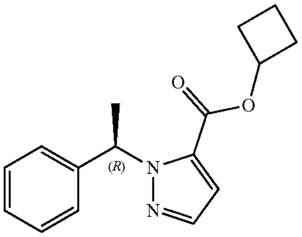
Compound A5
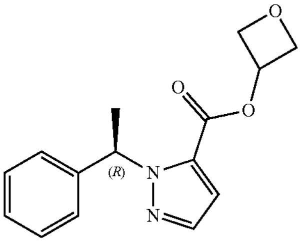
Compound A6
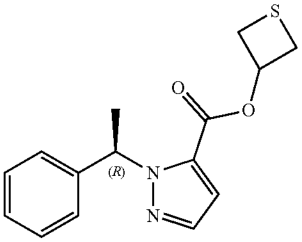
Compound A7
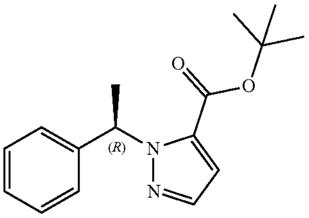
Compound A8
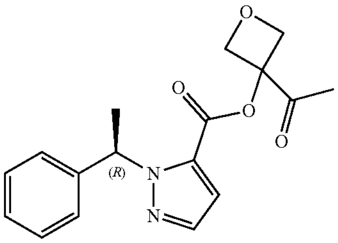
-continued
Compound A9
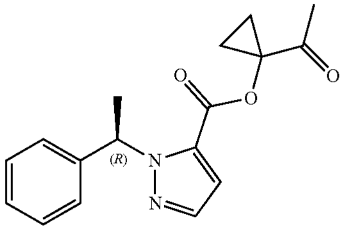
Compound A10
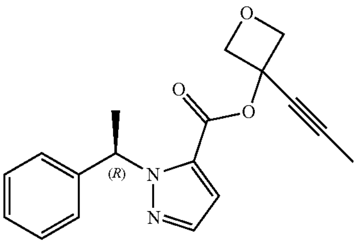
Compound A11
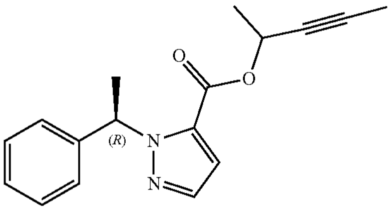
Compound A12
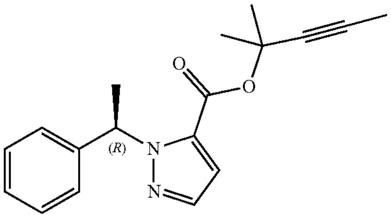
Compound A13
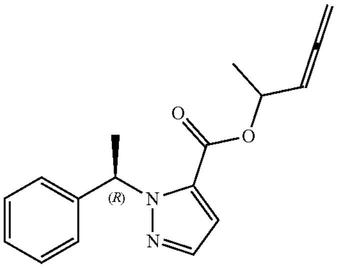
Compound A14
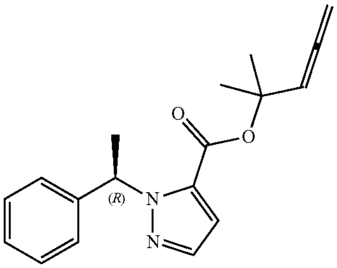

-continued
Compound A15
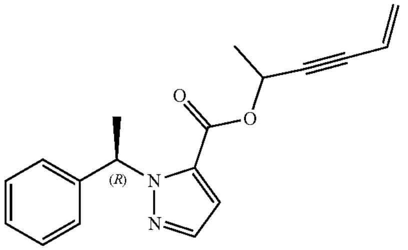
Compound A16
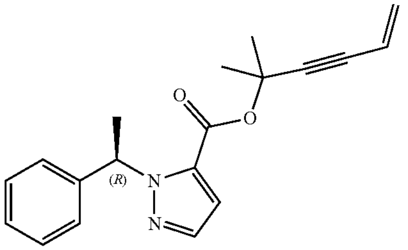
Compound A17
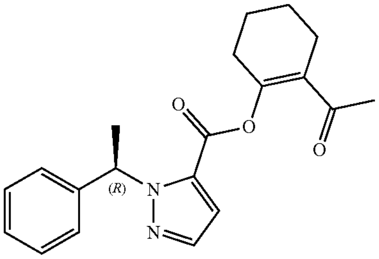
Compound A18
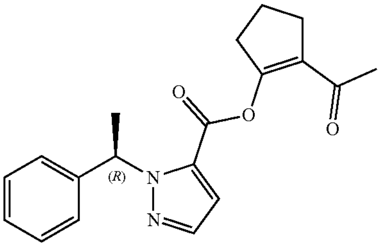
Compound A19
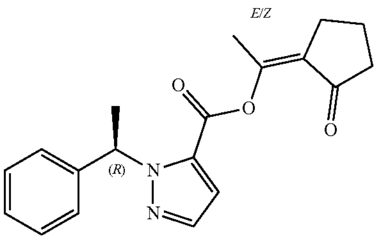
Compound A20
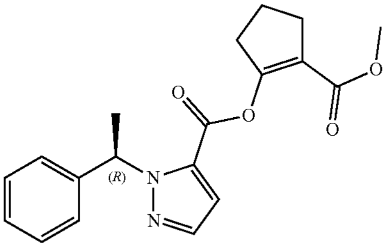
-continued
Compound A21
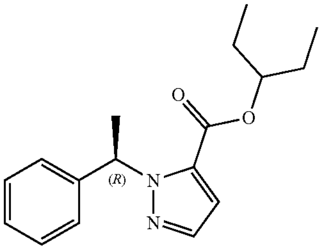
Compound A22
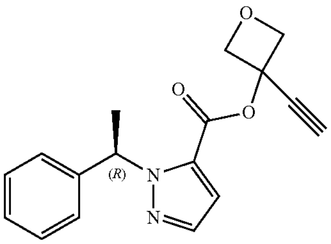
Compound A23
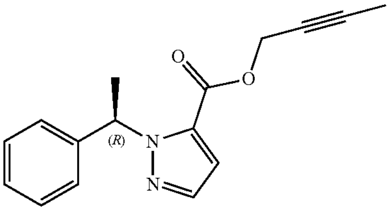
Compound A24
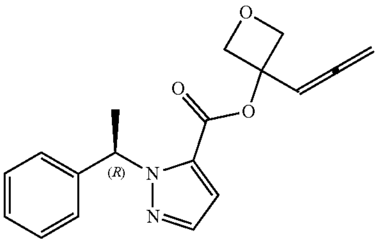
Compound A25
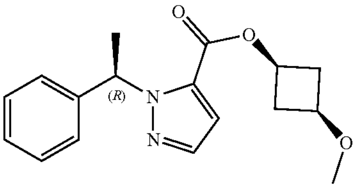
Compound A26
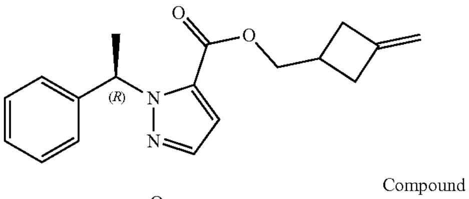
Compound A27
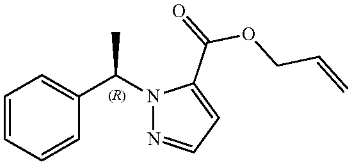

-continued
Compound A28
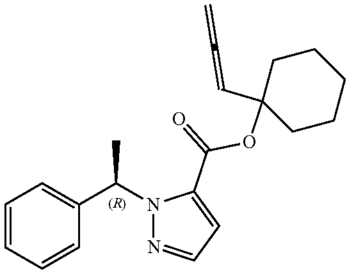
Compound A29
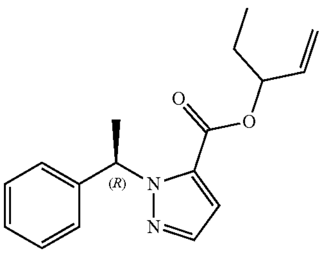
Compound A30
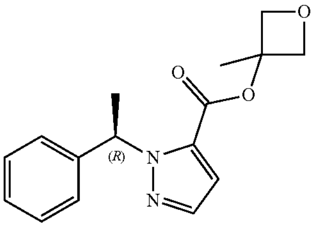
Compound A31
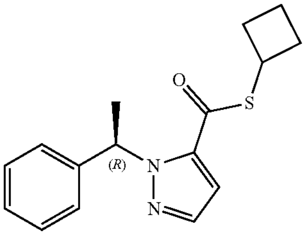
Compound A32
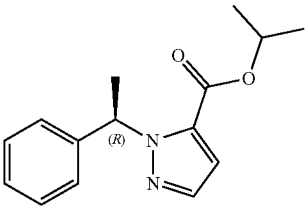
Compound A33
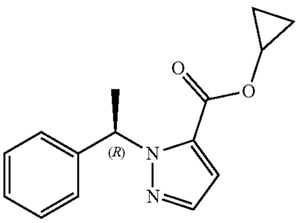
-continued
Compound A34
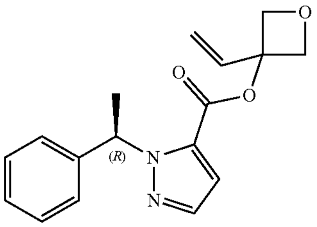
Compound A35
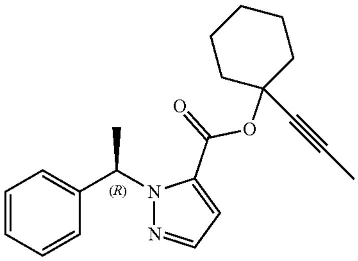
Compound A36
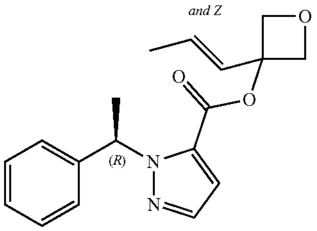
Compound A37
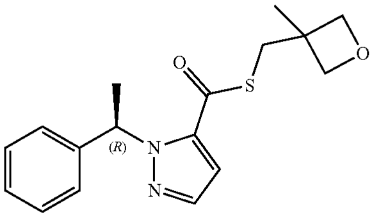
Compound A38
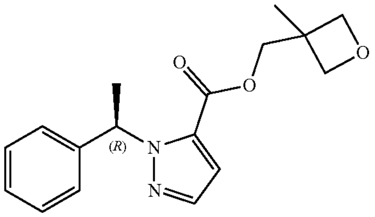
Compound A39
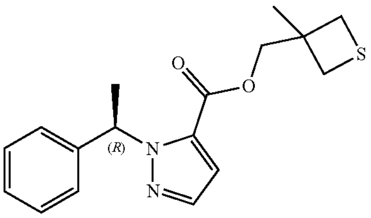

-continued
Compound A40
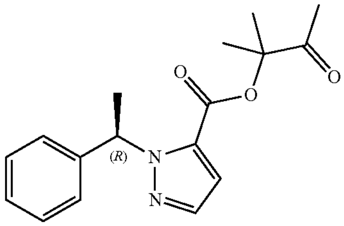
Compound A41
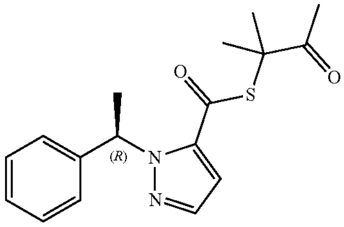
Compound A42
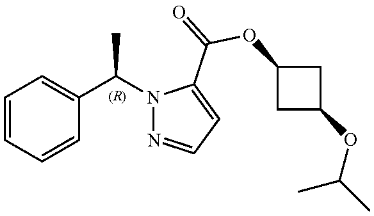
Compound A43
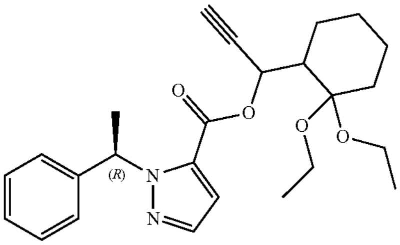
Compound A44
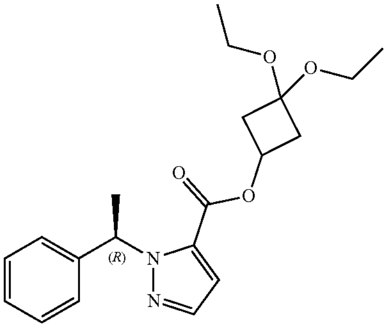
Compound A45
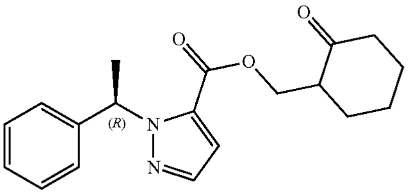
-continued
Compound A46
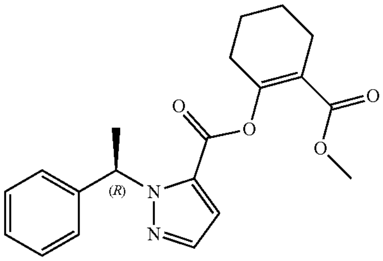
Compound A47
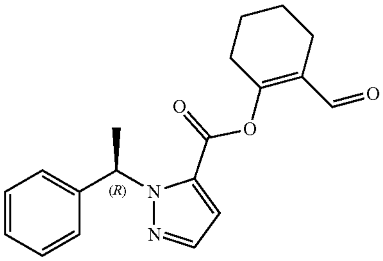
Compound A48
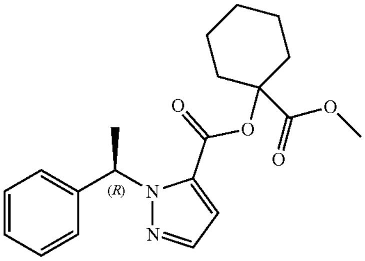
Compound A49
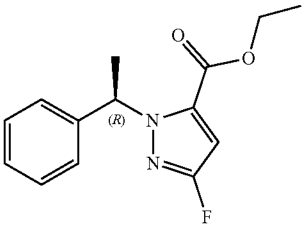
Compound A50
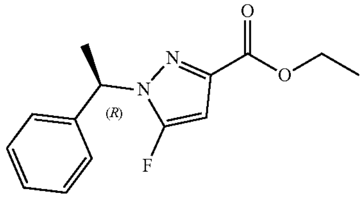
Compound A51
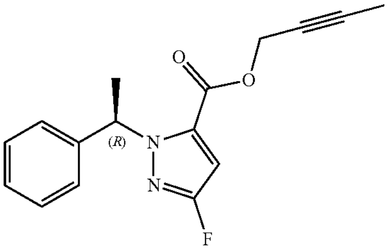

-continued
Compound A52
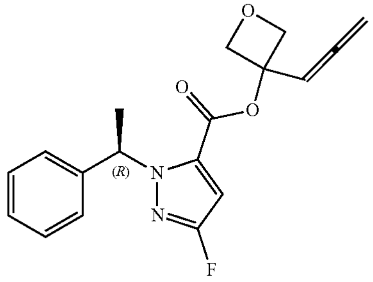
Compound A53
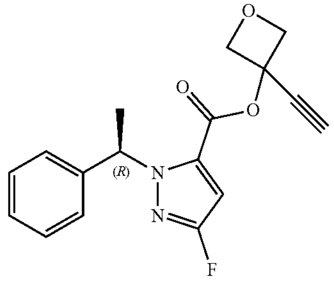
Compound A54
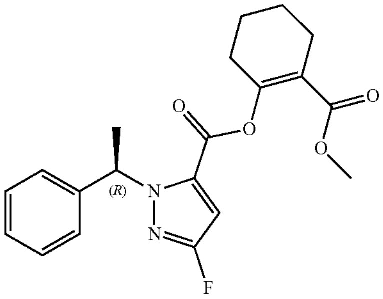
Compound A55
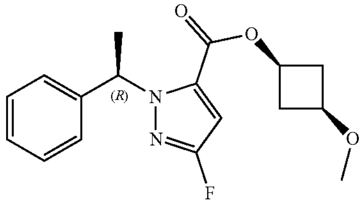
Compound A56
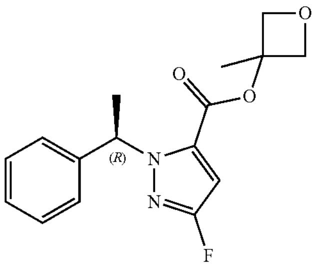
Compound A57
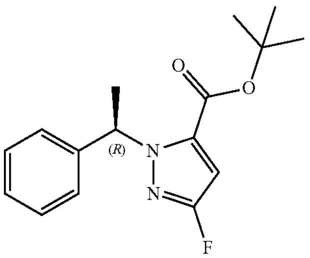
-continued
Compound A58
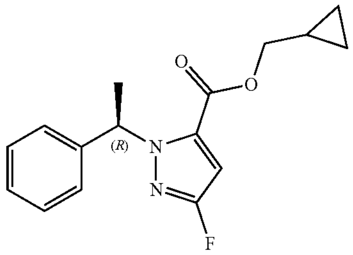
Compound A59
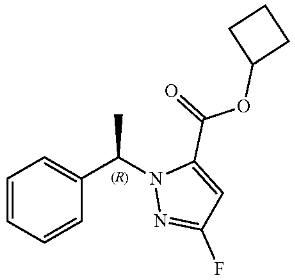
Compound A60
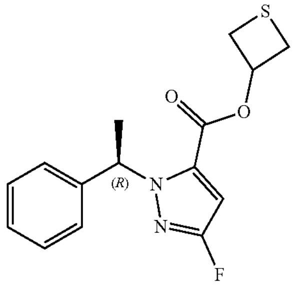
Compound A61
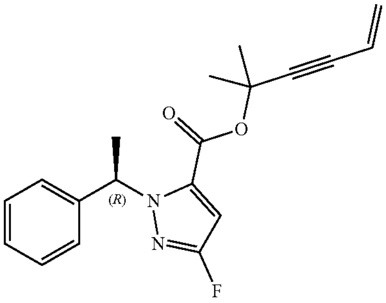
Compound A62
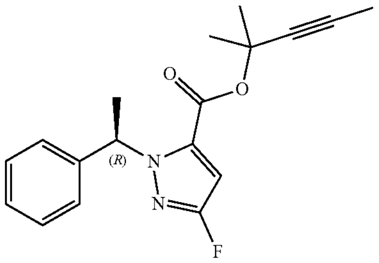

-continued
Compound A63
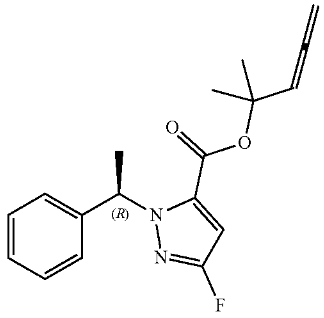
Compound A64
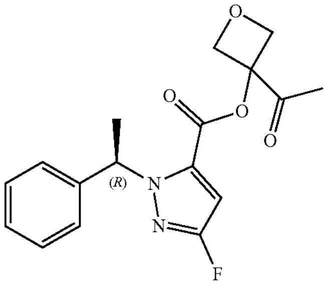
Compound A65
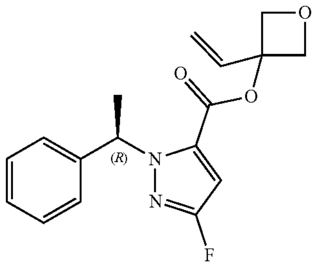
Compound A66
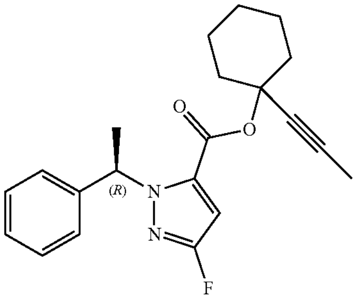
Compound A67
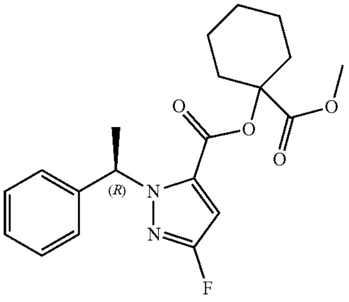
-continued
Compound A68
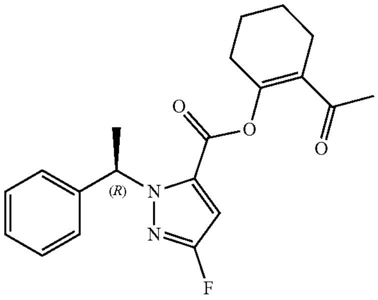
Compound A69
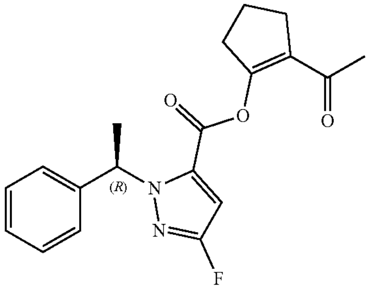
Compound A70
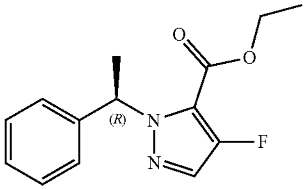
Compound A71
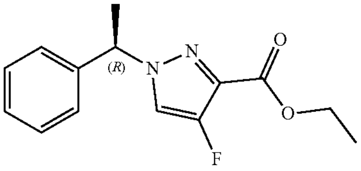
Compound A72
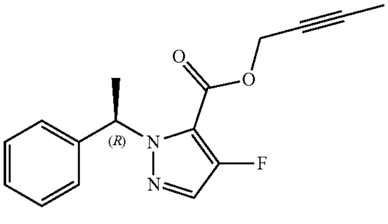
Compound A73
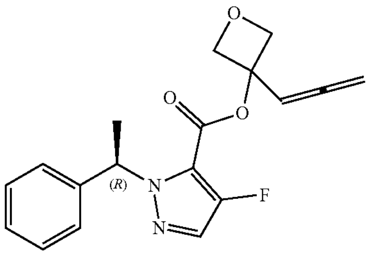

-continued
Compound A74
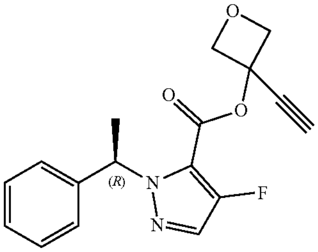
Compound A75
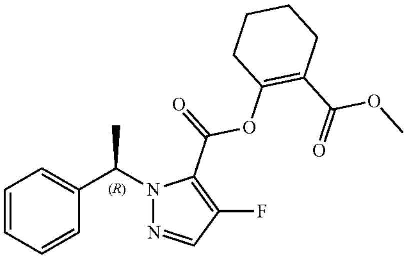
Compound A76
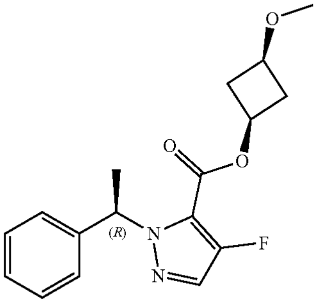
Compound A77
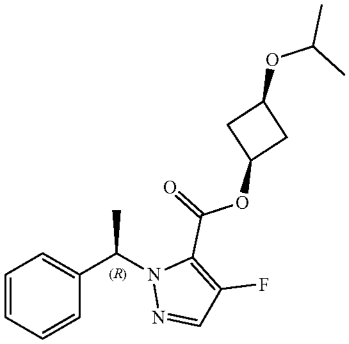
Compound A78
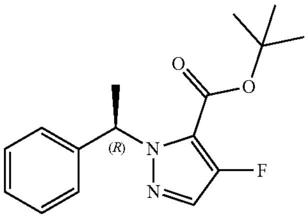
-continued
Compound A79
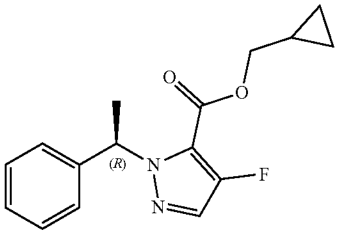
Compound A80
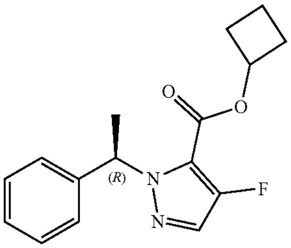
Compound A81
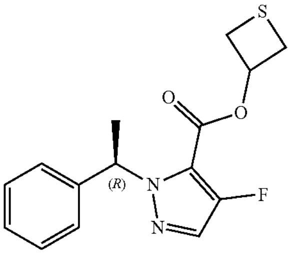
Compound A82
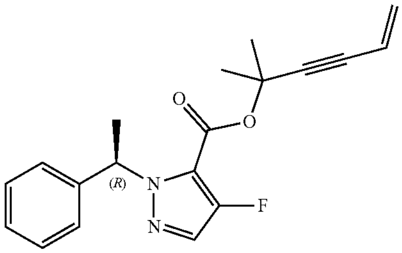
Compound A83
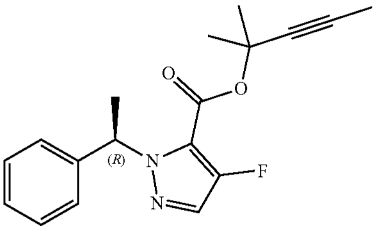
Compound A84
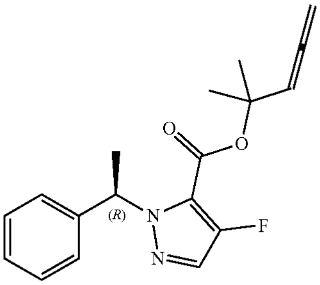

-continued
Compound A85
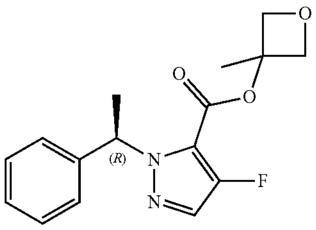
Compound A86
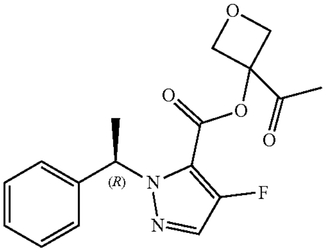
Compound A87
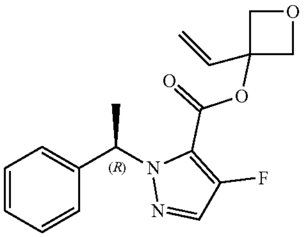
Compound A88
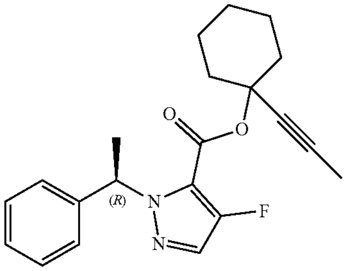
Compound A89
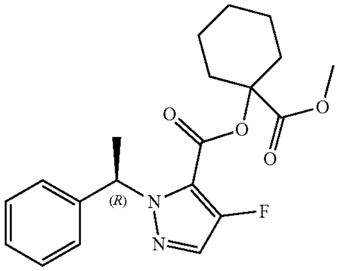
Compound A90
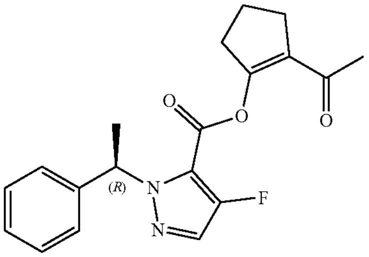
-continued
Compound A91
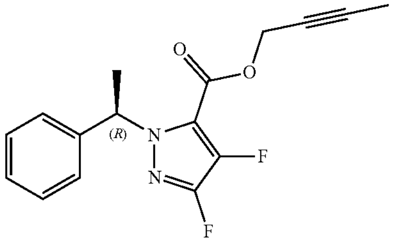
Compound A92
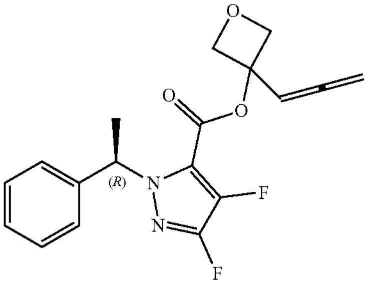
Compound A93
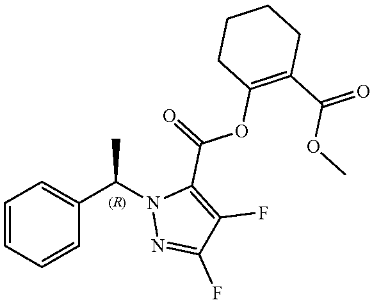
Compound A94
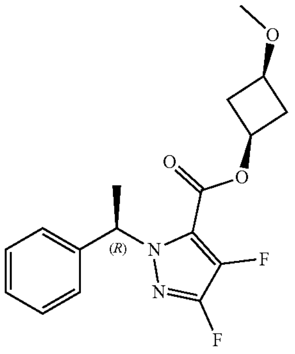
Compound A95
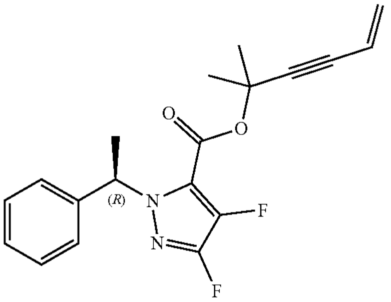

-continued
Compound A96
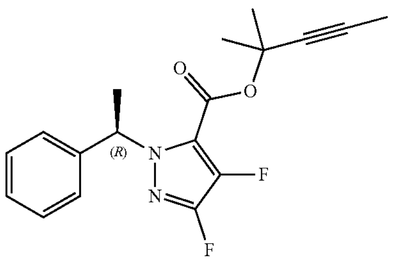
Compound A97
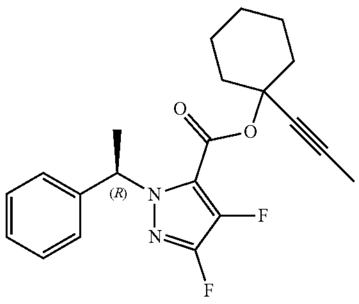
Compound A98
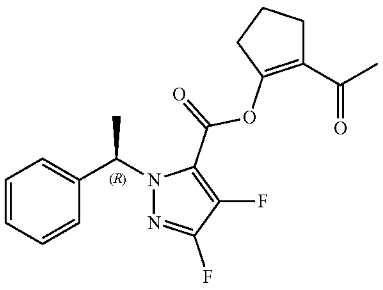
Compound A99
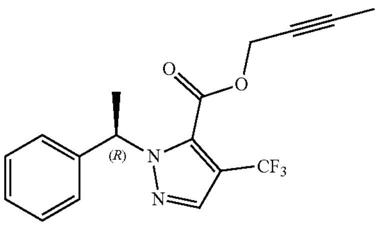
Compound A100
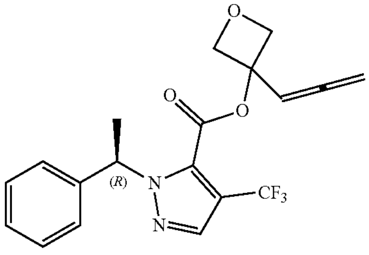
-continued
Compound A101
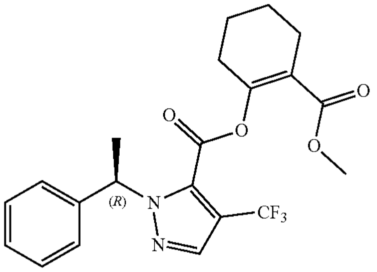
Compound A102
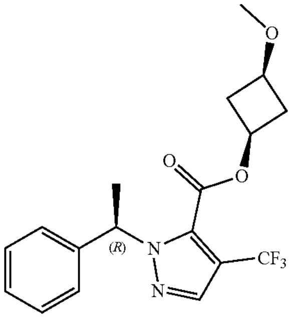
Compound A103
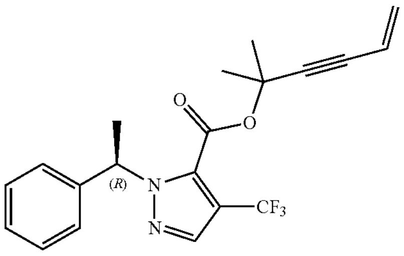
Compound A104
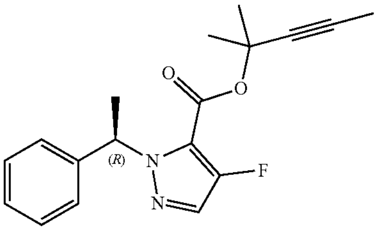
Compound A105
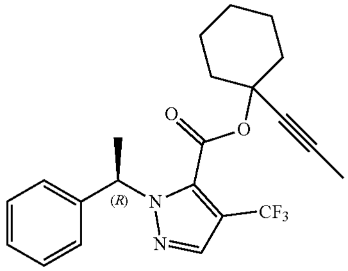

-continued
Compound A106
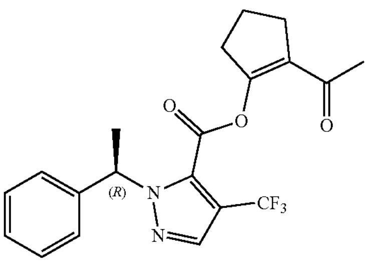
Compound A107
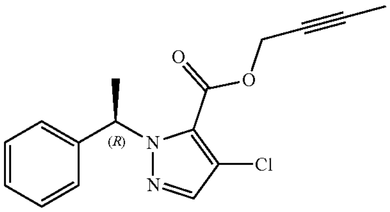
Compound A108
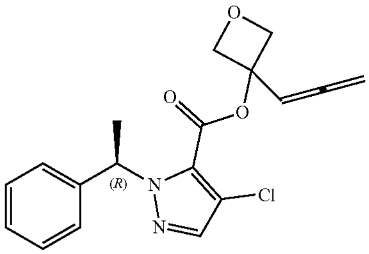
Compound A109
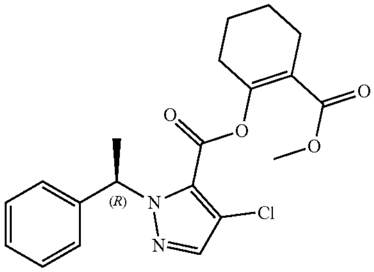
Compound A110
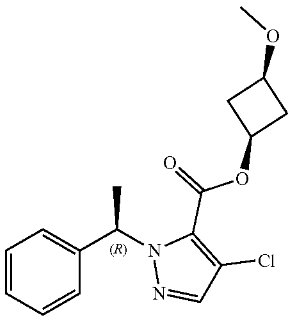
-continued
Compound A111
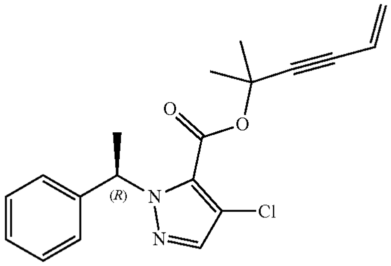
Compound A112
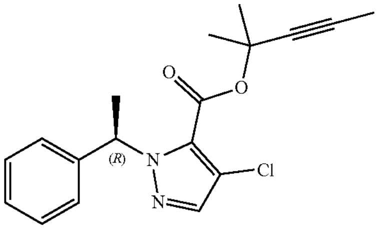
Compound A113
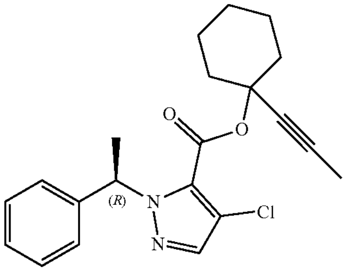
Compound A114
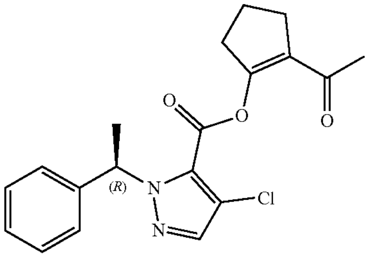
Compound B1
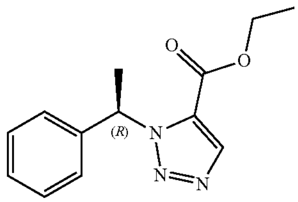
Compound B2
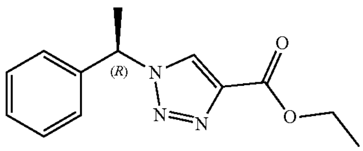

-continued
Compound B3
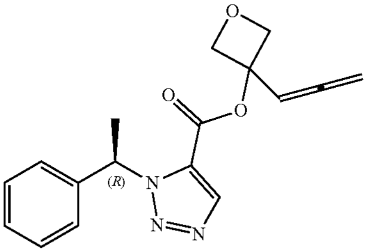
Compound B4
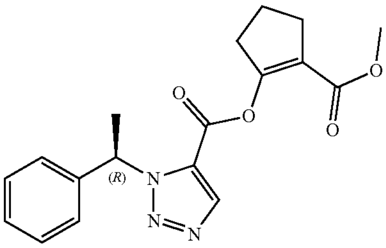
Compound B5
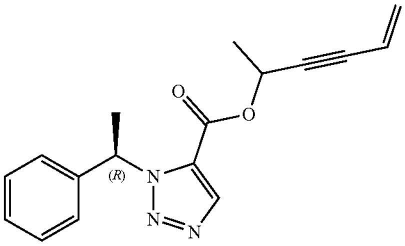
Compound B6
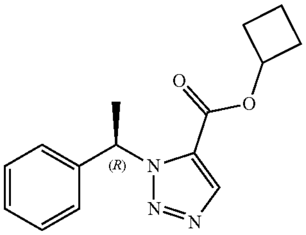
Compound B7
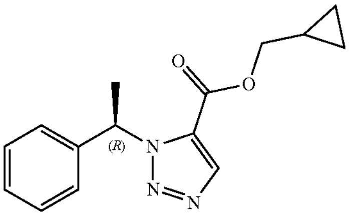
Compound B8
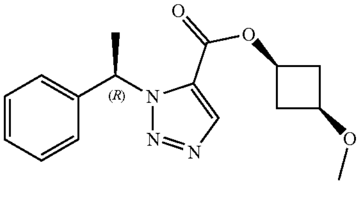
-continued
Compound B9
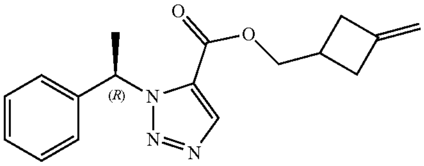
Compound B10
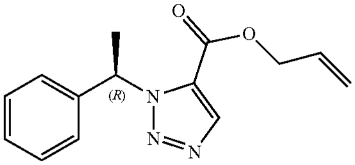
Compound B11
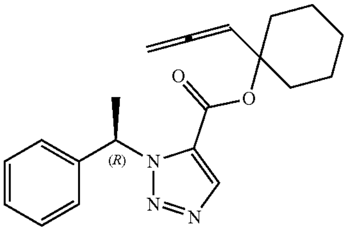
Compound B12
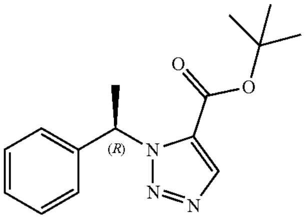
Compound B13
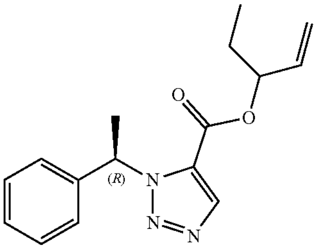
Compound B14
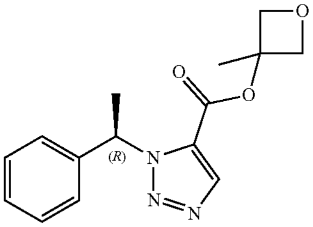
Compound B15
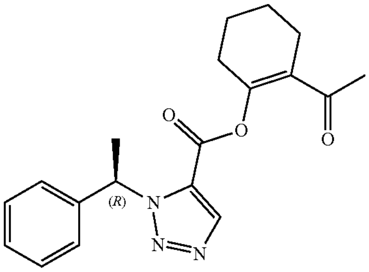

-continued
Compound B16
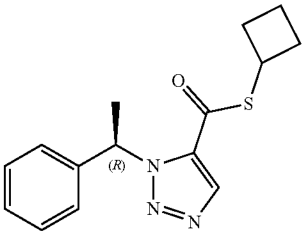
Compound B17
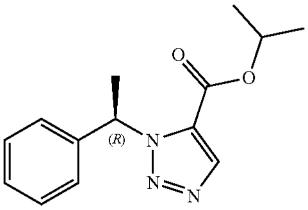
Compound B18
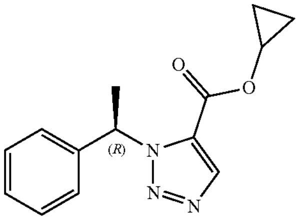
Compound B19
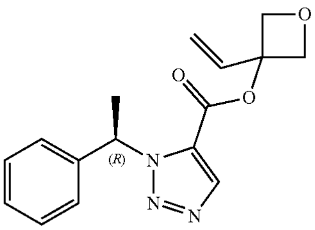
Compound B20
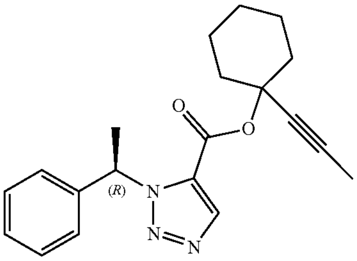
Compound B21
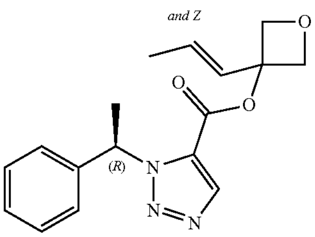
-continued
Compound B22
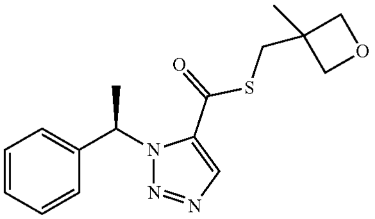
Compound B23
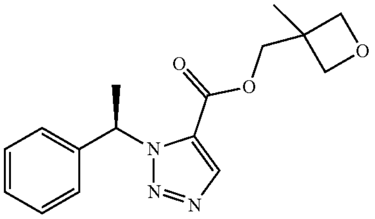
Compound B24
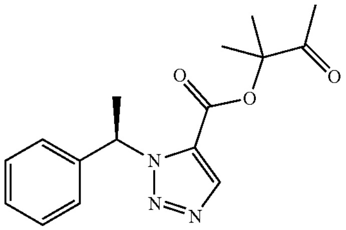
Compound B25
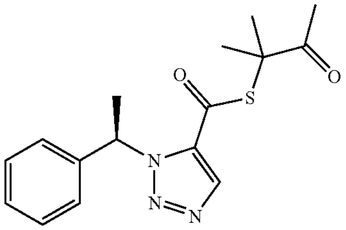
Compound B26
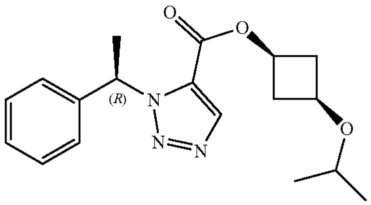
Compound B27
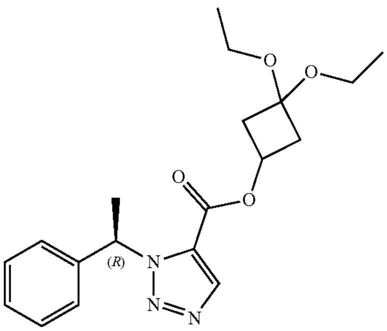

-continued
Compound B28
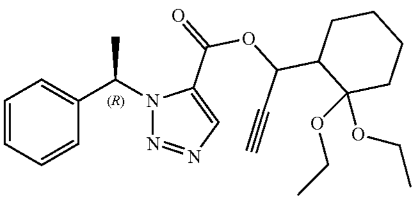
Compound B29
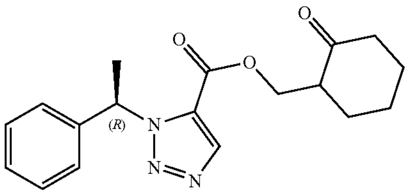
Compound B30
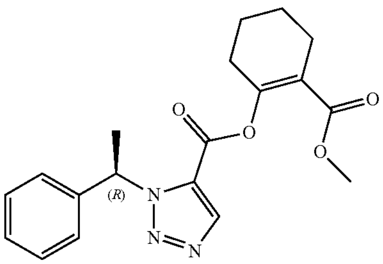
Compound B31
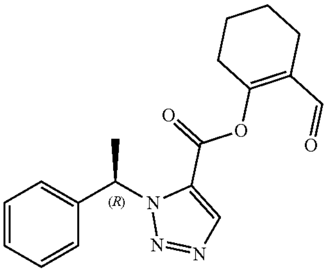
Compound B32
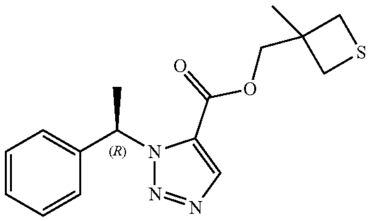
Compound B33
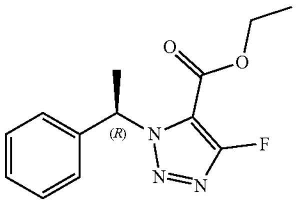
Compound B34
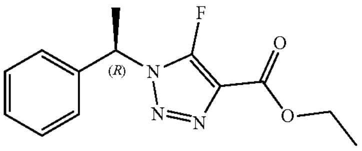
-continued
Compound B35
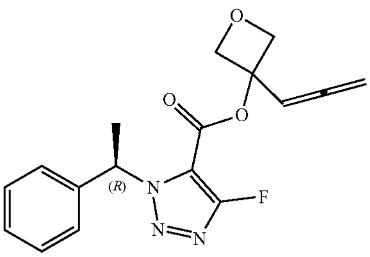
Compound B36
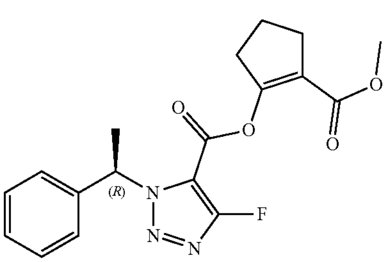
Compound B37
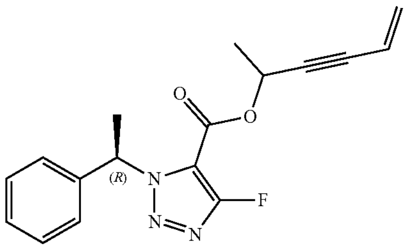
Compound B38
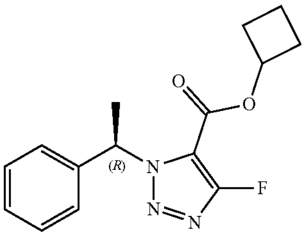
Compound B39
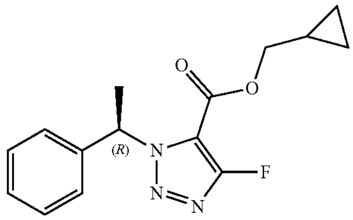
Compound B40
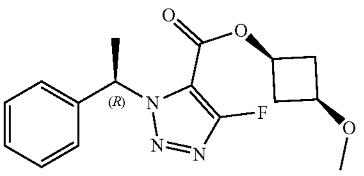

-continued
Compound B41
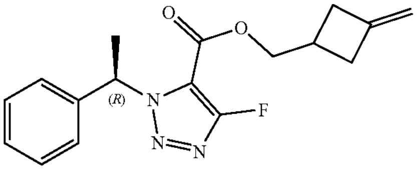
Compound B42
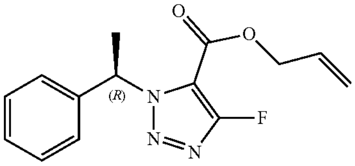
Compound B43
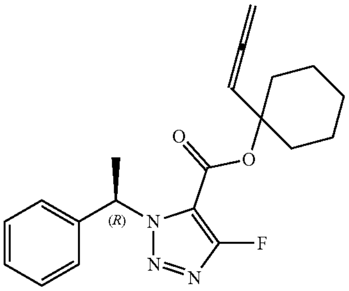
Compound B44
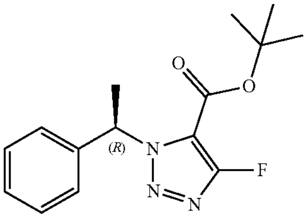
Compound B45
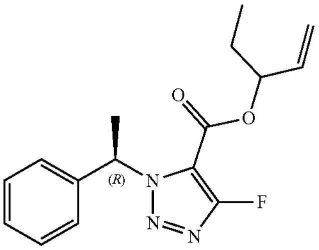
Compound B46
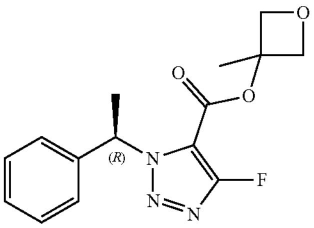
-continued
Compound B47
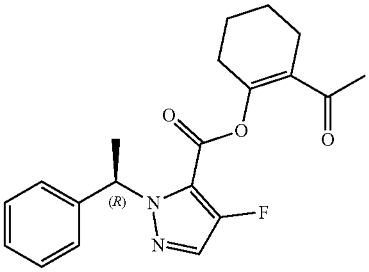
Compound B48
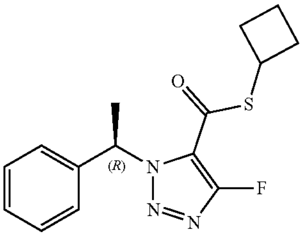
Compound B49
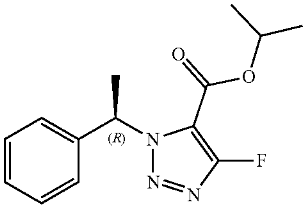
Compound B50
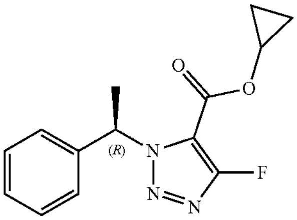
Compound B51
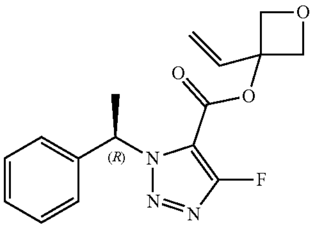
Compound B52
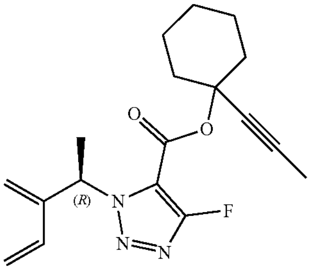

-continued
Compound B53
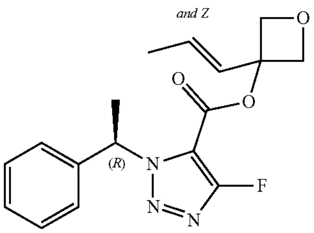
Compound B54
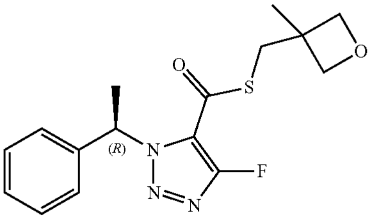
Compound B55
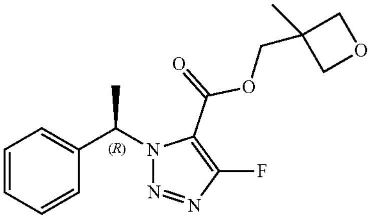
Compound B56
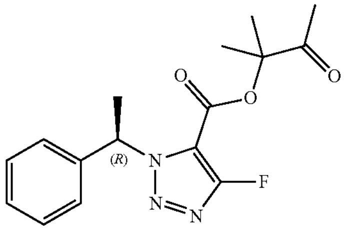
Compound B57
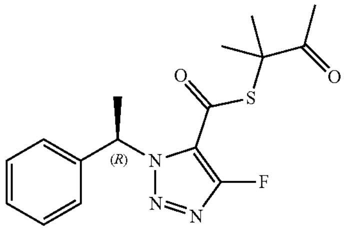
Compound B58
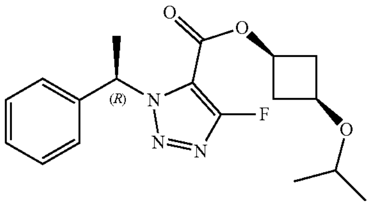
-continued
Compound B59
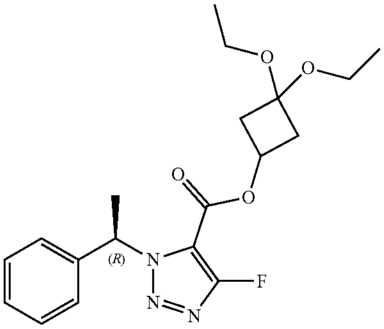
Compound B60
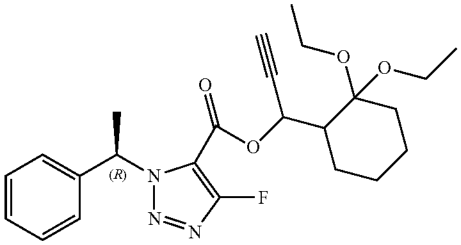
Compound B61
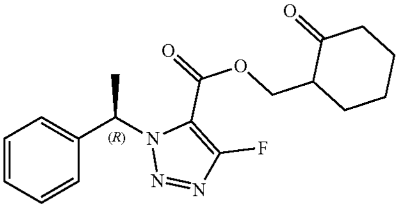
Compound B62
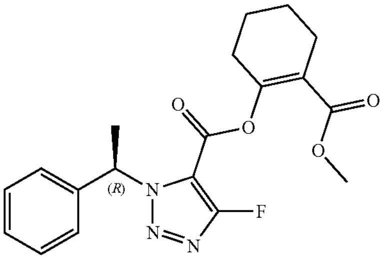
Compound B63
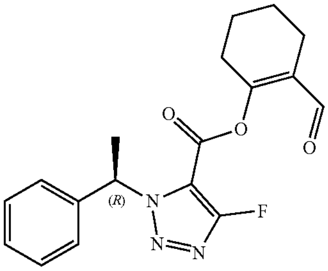
Compound B64
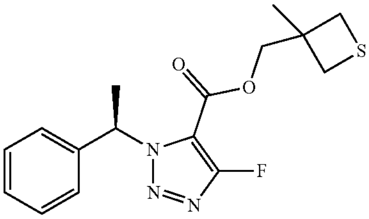

-continued
Compound B65
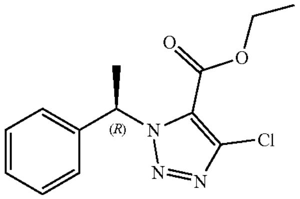
Compound B66
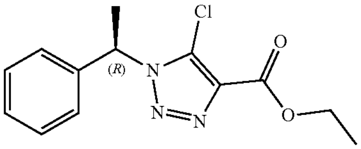
Compound B67
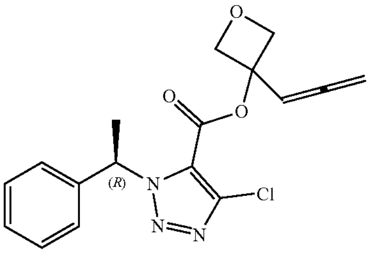
Compound B68
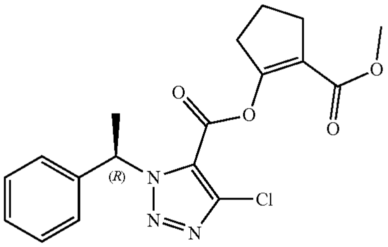
Compound B69
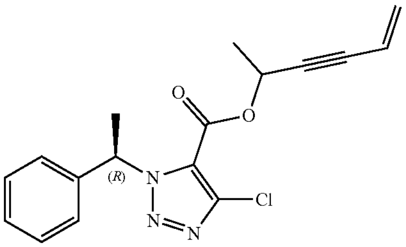
Compound B70
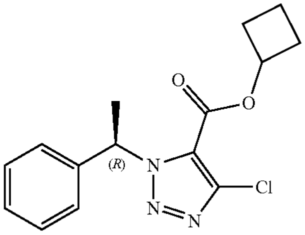
-continued
Compound B71
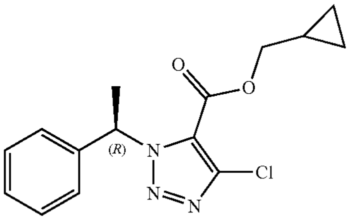
Compound B72
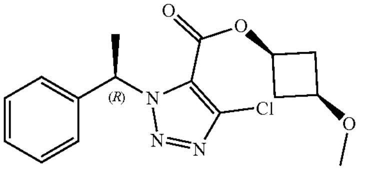
Compound B73
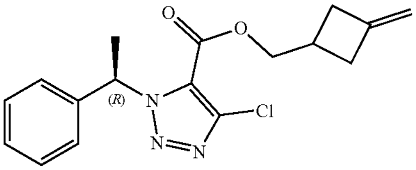
Compound B74
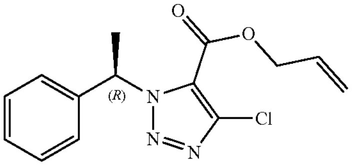
Compound B75
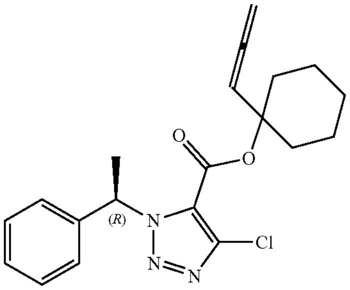
Compound B76
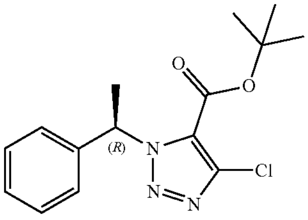
Compound B77
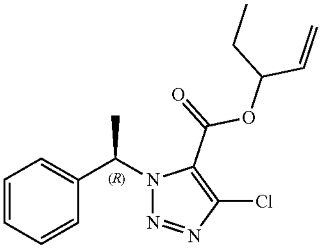

-continued
Compound B78
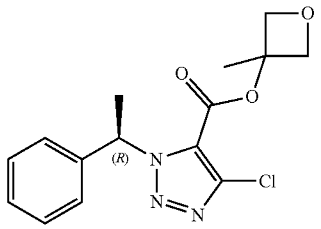
Compound B79
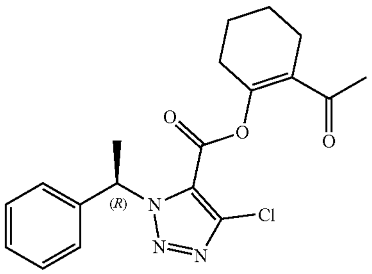
Compound B80
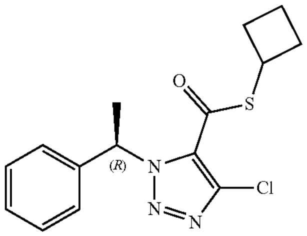
Compound B81
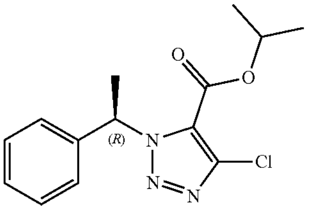
Compound B82
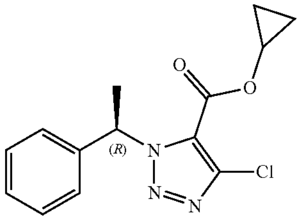
Compound B83
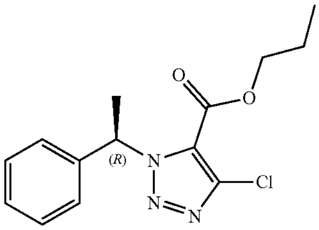
-continued
Compound B84
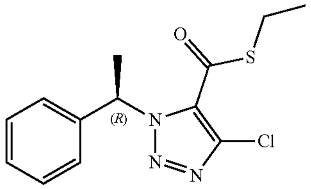
Compound B85
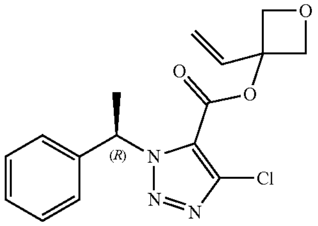
Compound B86
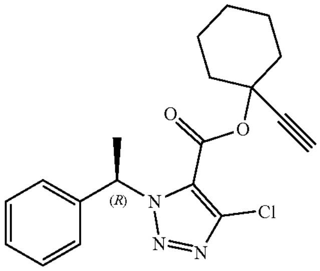
Compound B87
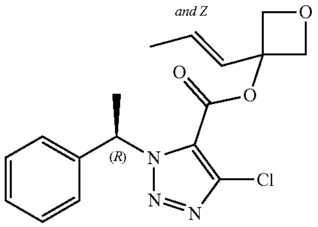
Compound B88
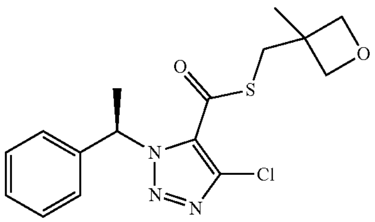
Compound B89
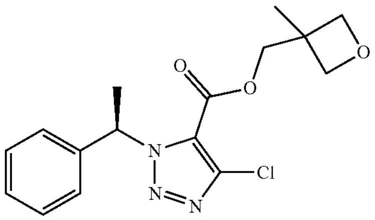

-continued
Compound B90
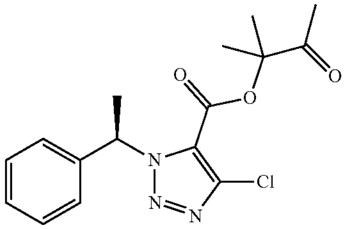
Compound B91
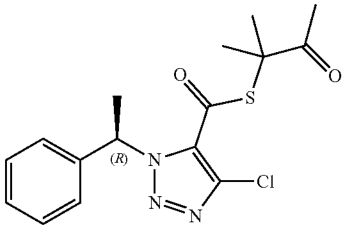
Compound B92
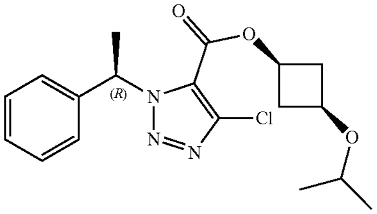
Compound B93
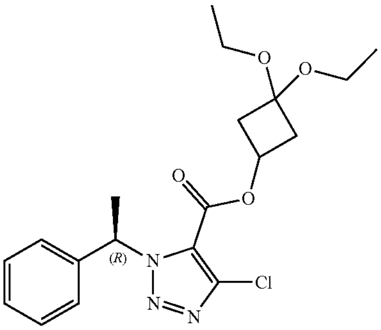
Compound B94
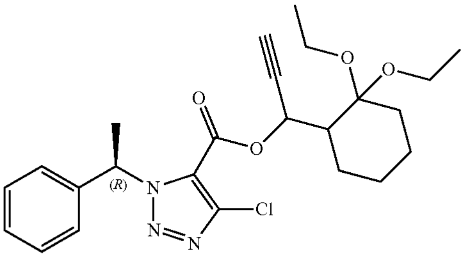
Compound B95
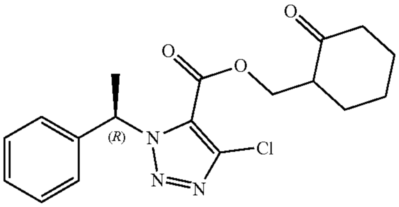
-continued
Compound B96
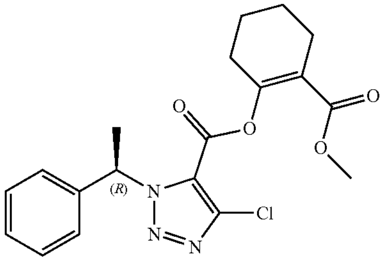
Compound B97
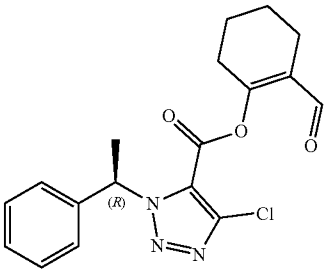
Compound B98
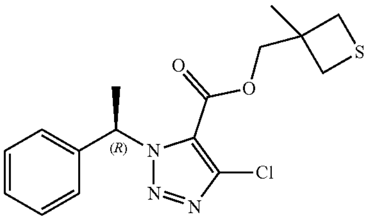
Compound B99
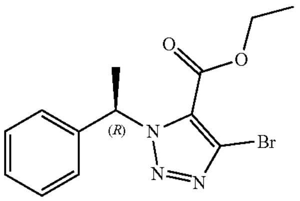
Compound B100
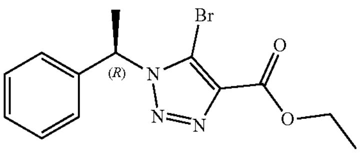
Compound B101
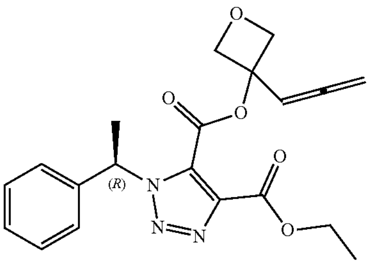

-continued
Compound B102
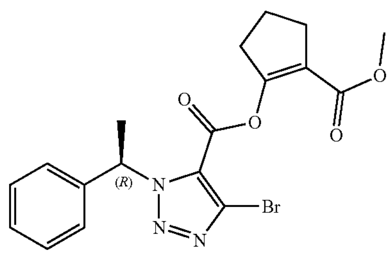
Compound B103
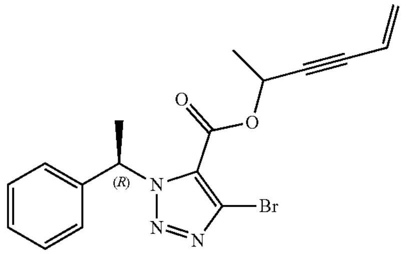
Compound B104
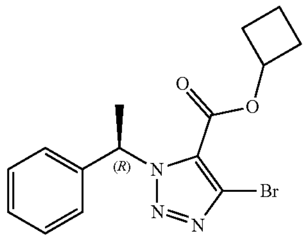
Compound B105
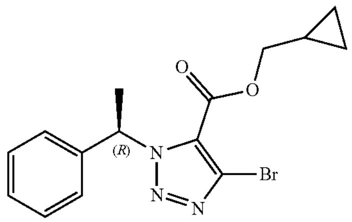
Compound B106
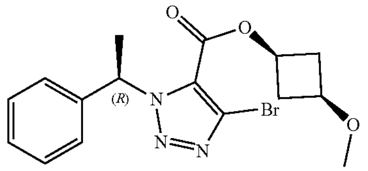
Compound B107
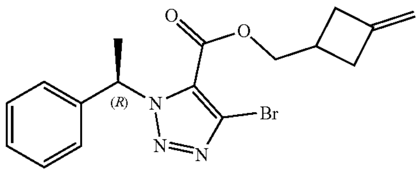
Compound B108
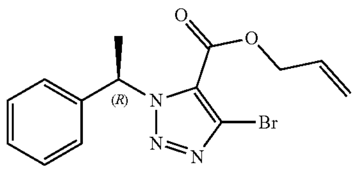
-continued
Compound B109
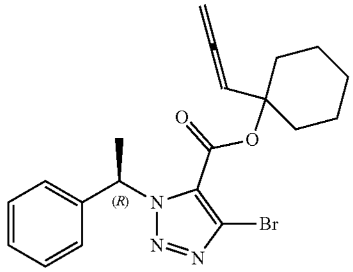
Compound B110
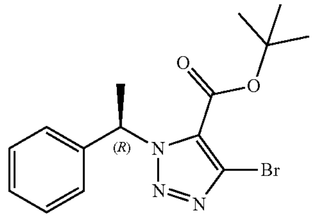
Compound B111
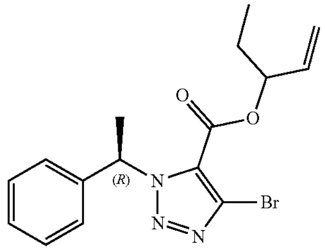
Compound B112
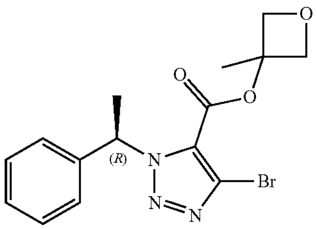
Compound B113
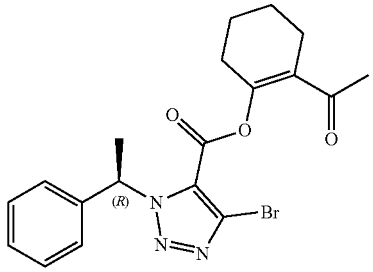
Compound B114
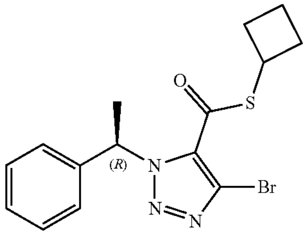

-continued
Compound B115
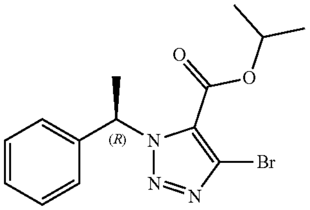
Compound B116
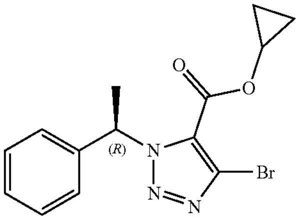
Compound B117
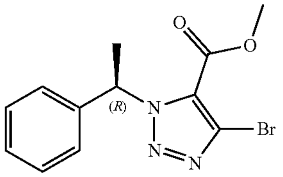
Compound B118
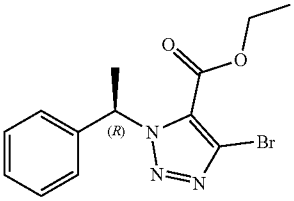
Compound B119
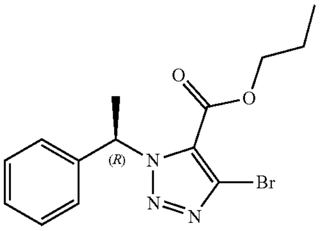
Compound B120
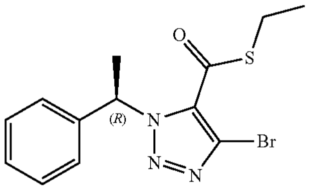
Compound B121
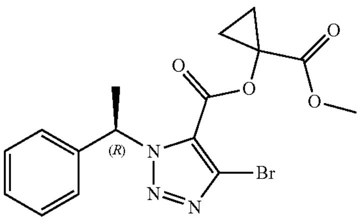
-continued
Compound B122
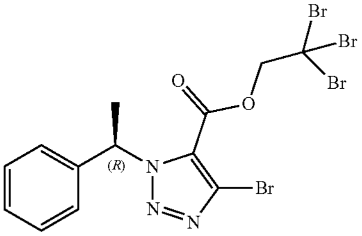
Compound B123
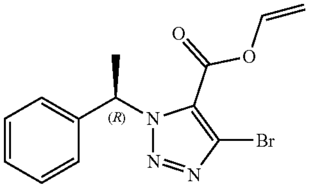
Compound B124
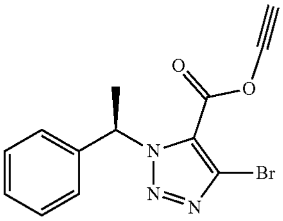
Compound B125
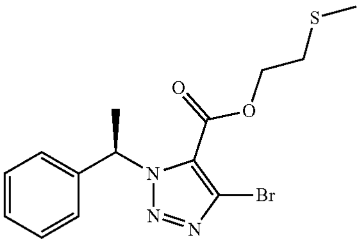
Compound B126
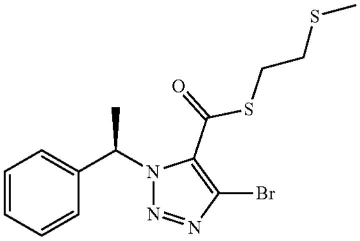
Compound B127
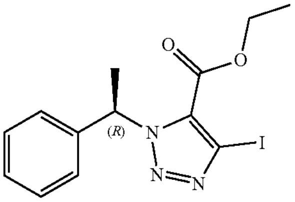
Compound B128
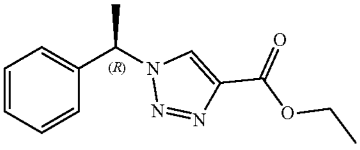

-continued
Compound B129
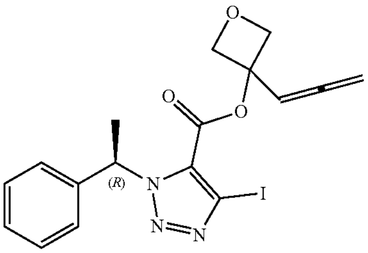
Compound B130
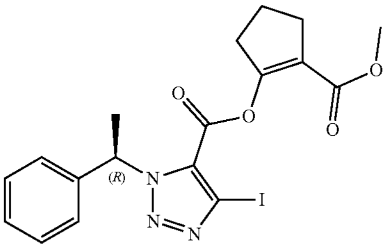
Compound B131
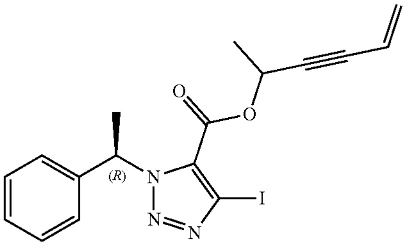
Compound B132
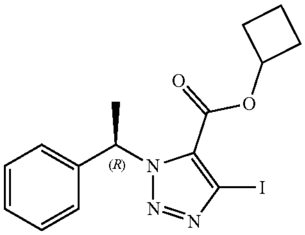
Compound B133
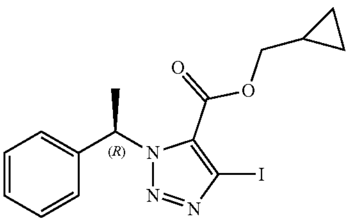
Compound B134
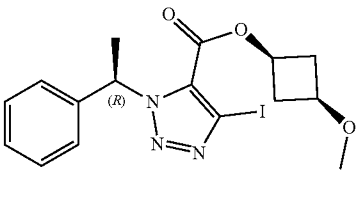
-continued
Compound B135
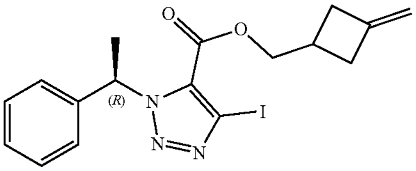
Compound B136
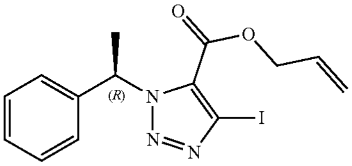
Compound B137
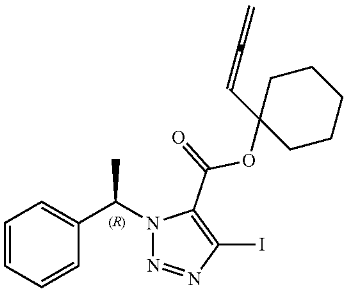
Compound B138
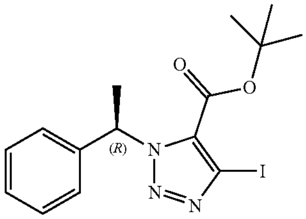
Compound B139
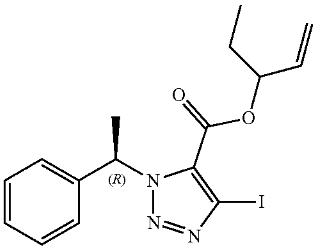
Compound B140
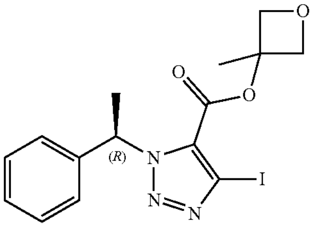

-continued
Compound B141
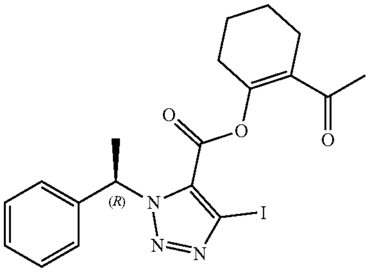
Compound B142
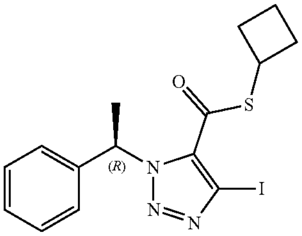
Compound B143
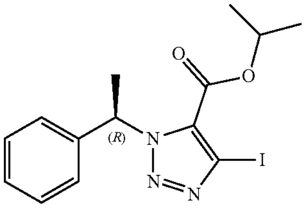
Compound B144
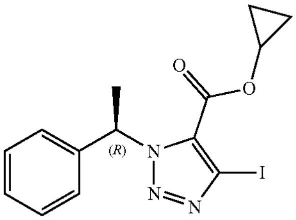
Compound B145
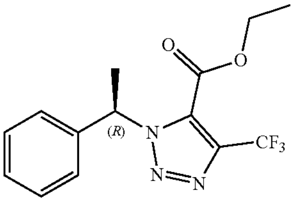
Compound B146
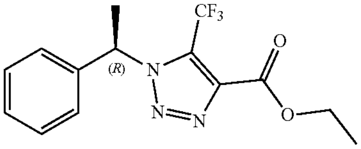
Compound B147
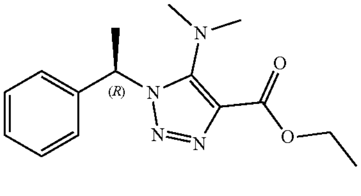
Compound C1
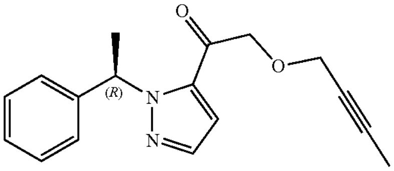
Compound C2
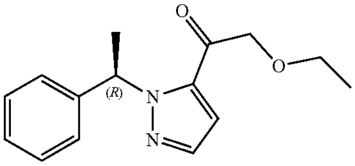
Compound C3
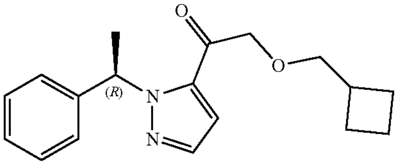
Compound C4
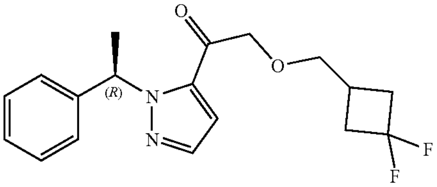
Compound C5
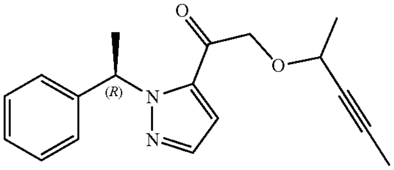
Compound C6
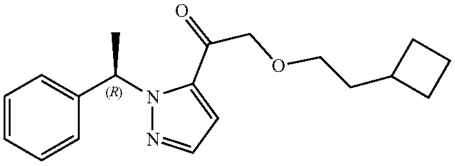
Compound C7
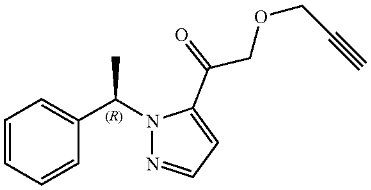
Compound C8
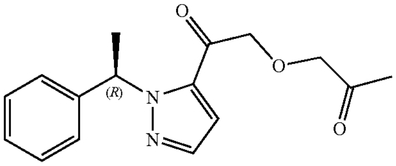

-continued
Compound C9
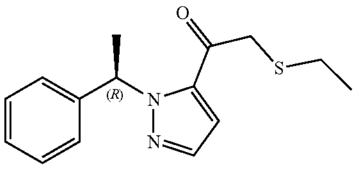
Compound C10
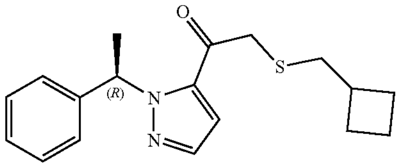
Compound C11
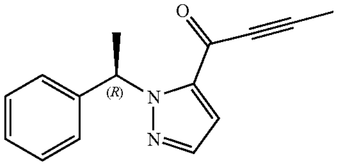
Compound C12
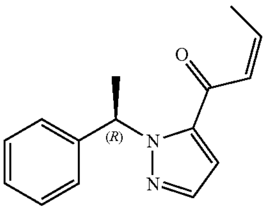
Compound C13
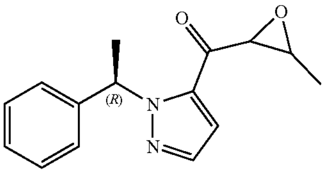
Compound C14
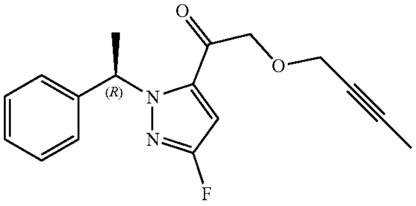
Compound C15
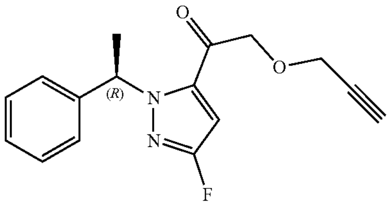
Compound C16
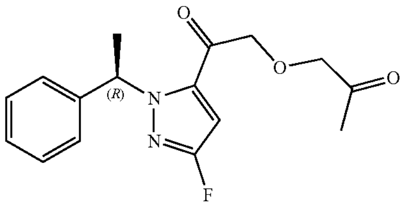
-continued
Compound C17
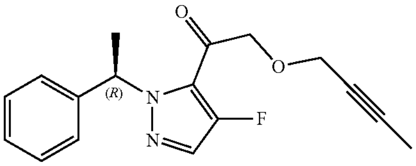
Compound C18
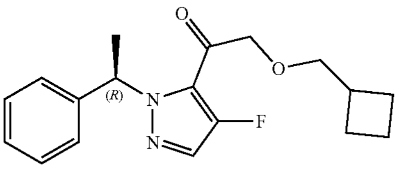
Compound C19
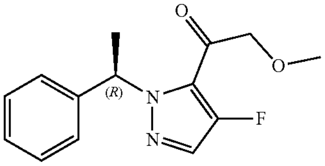
Compound C20
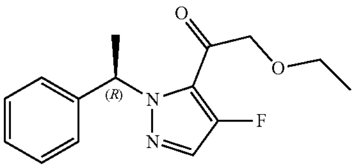
Compound C21
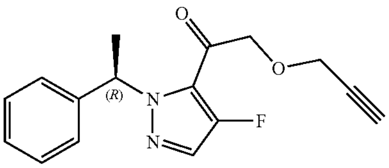
Compound C22
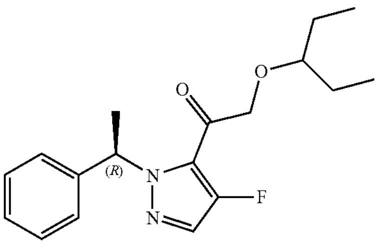
Compound C23
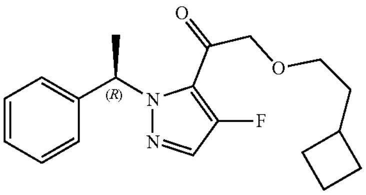
Compound C24
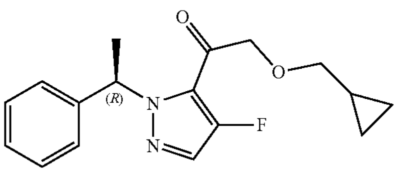

Compound C25
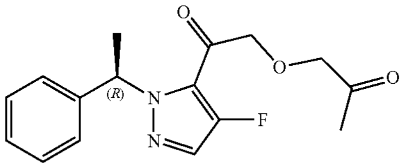
Compound C26
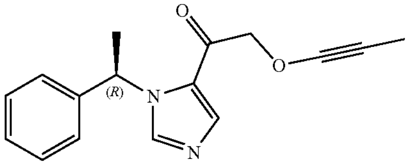
Compound C27
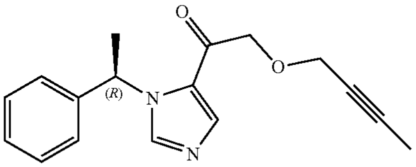
Compound C28
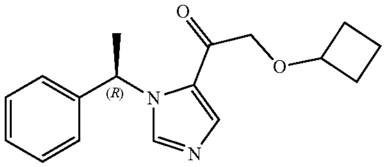
Compound C29
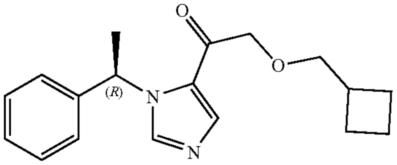
Compound C30
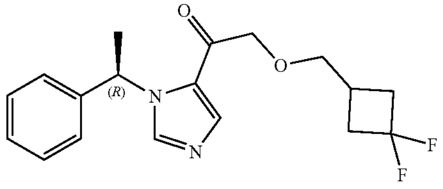
Compound C31
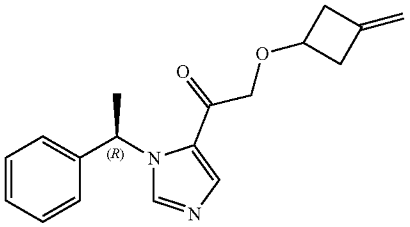
Compound C32
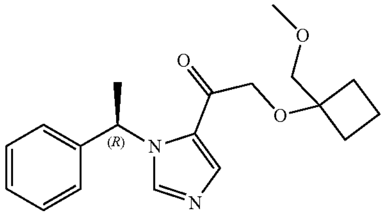
Compound C33
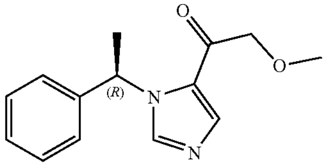
Compound C34
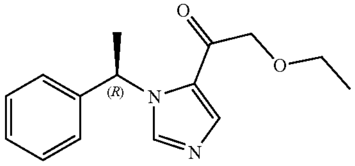
Compound C35
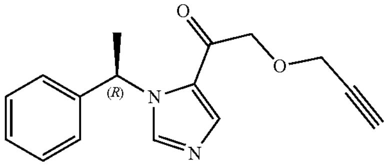
Compound C36
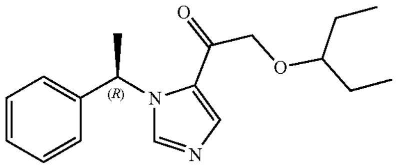
Compound C37
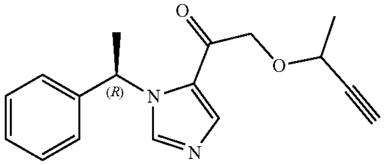
Compound C38
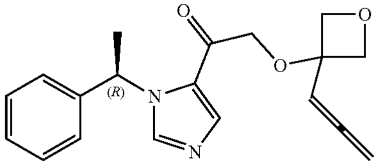
Compound C39
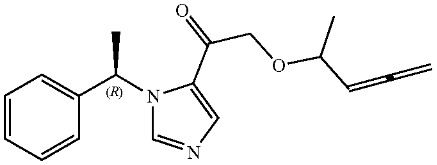
Compound C40
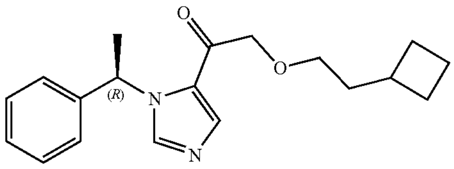
Compound C41
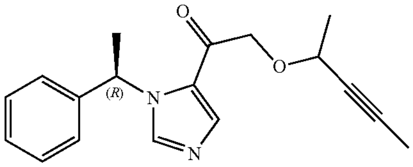

-continued
Compound C42
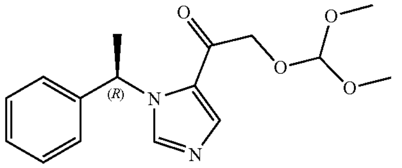
Compound C43
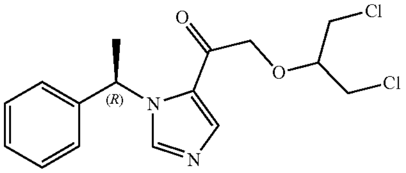
Compound C44
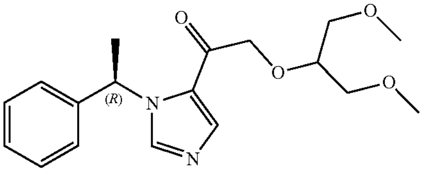
Compound C45
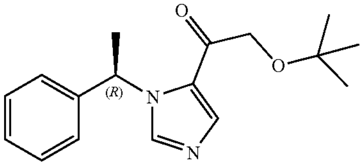
Compound C46
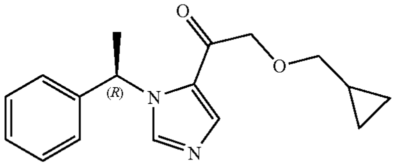
Compound C47
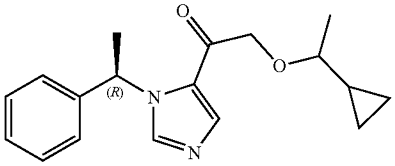
Compound C48
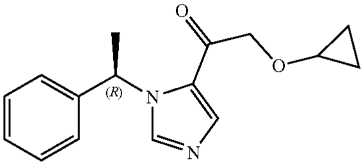
Compound C49
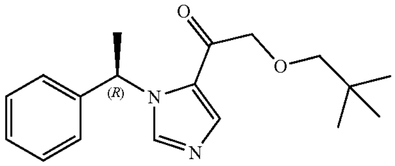
Compound C50
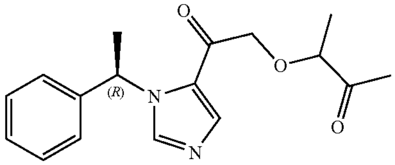
-continued
Compound C51
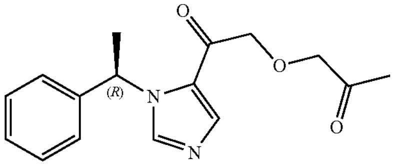
Compound C52
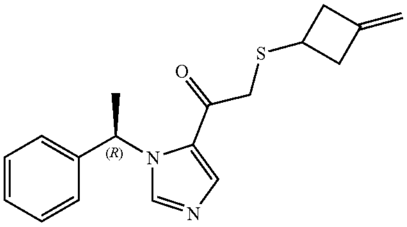
Compound C53
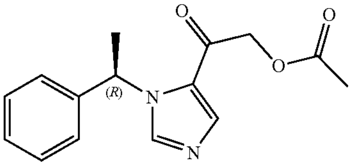
Compound C54
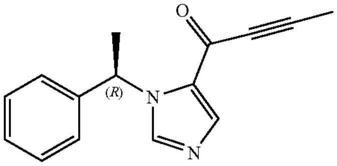
Compound C55
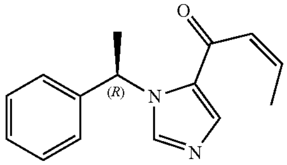
Compound C56
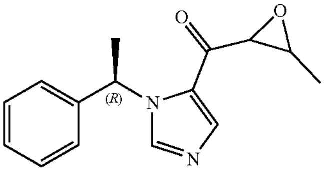
Compound C57
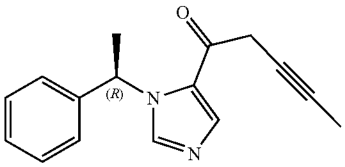
Compound C58
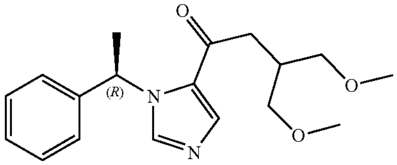

-continued
Compound C59
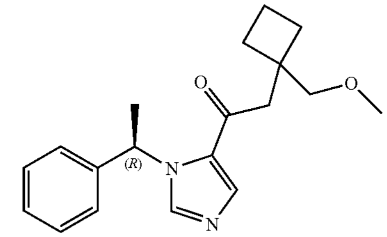
Compound C60
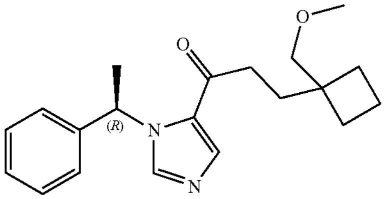
Compound C61
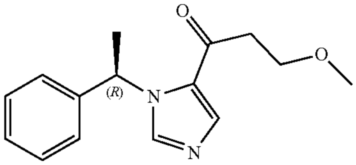
Compound C62
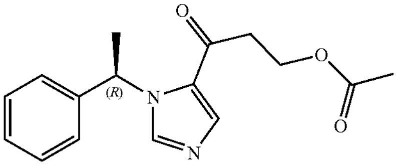
Compound C63
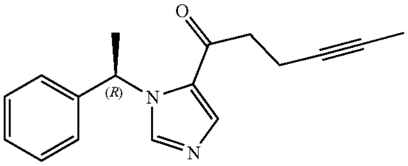
Compound C64
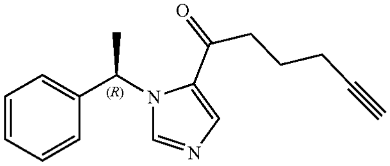
Compound C65
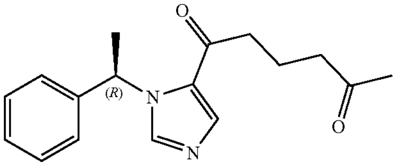
Compound C66
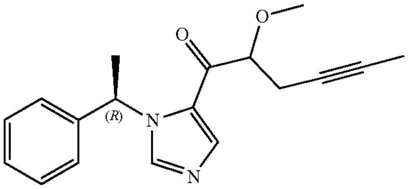
-continued
Compound C67
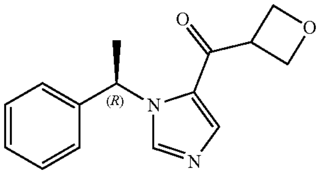
Compound C68
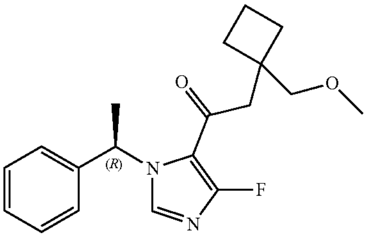
Compound C69
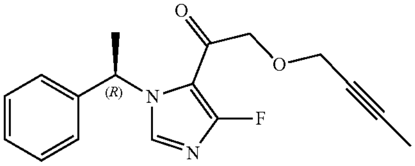
Compound C70
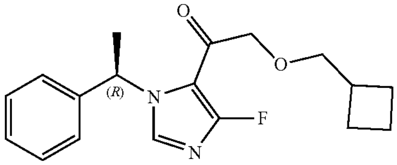
Compound C71
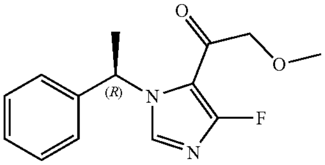
Compound C72
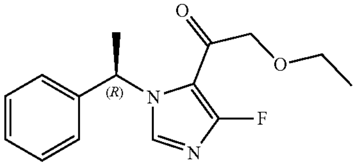
Compound C73
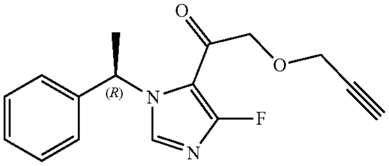
Compound C74
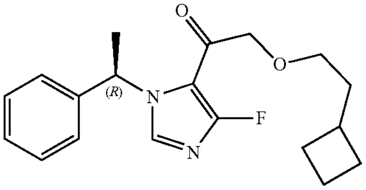

-continued
Compound C75
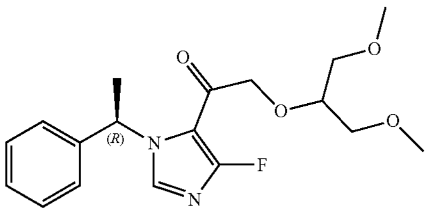
Compound C76
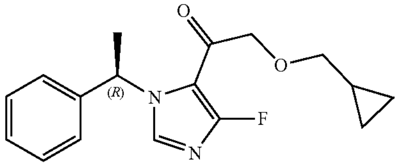
Compound C77
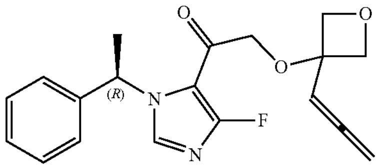
Compound C78
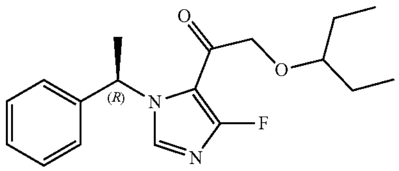
Compound C79
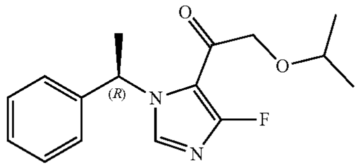
Compound C80
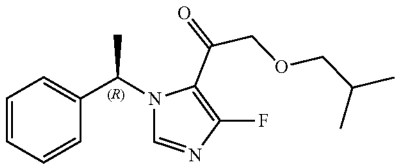
Compound C81
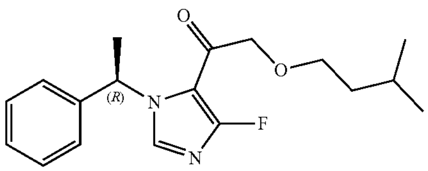
Compound C82
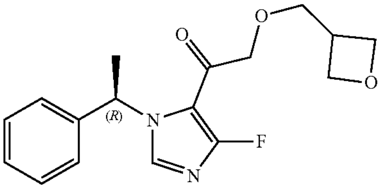
-continued
Compound C83
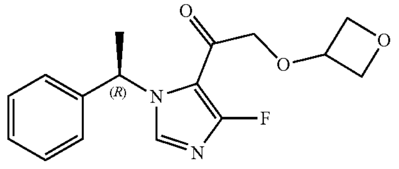
Compound C84
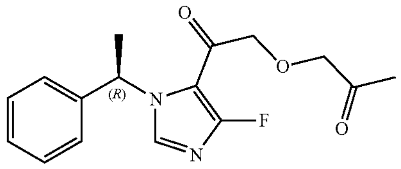
Compound C85
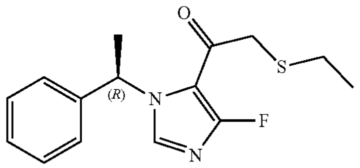
Compound D1
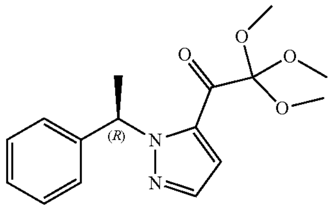
Compound D2
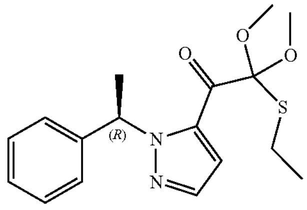
Compound D3
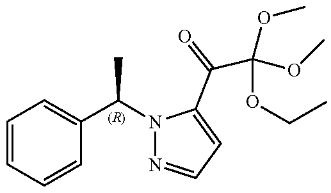
Compound D4
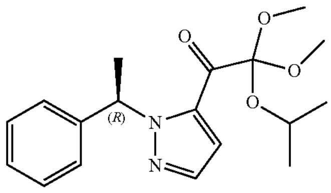
Compound D5
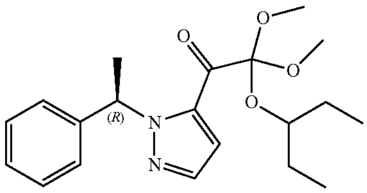

-continued
Compound D6
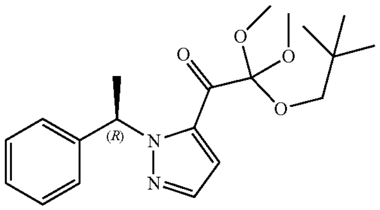
Compound D7
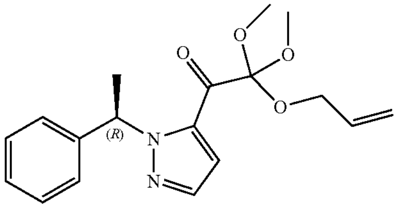
Compound D8
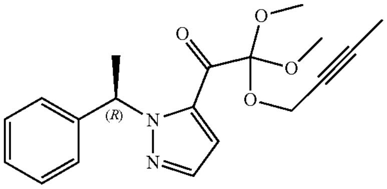
Compound D9
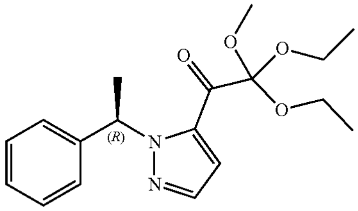
Compound D10
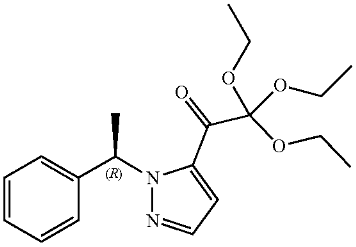
Compound D11
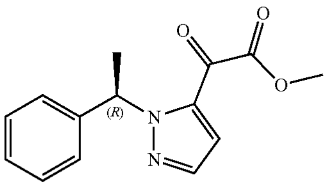
Compound D12
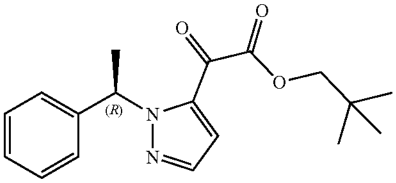
-continued
Compound D13
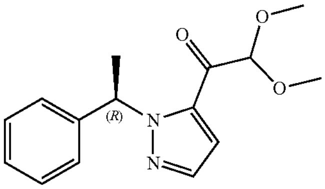
Compound D14
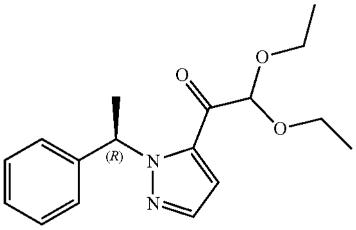
Compound D15
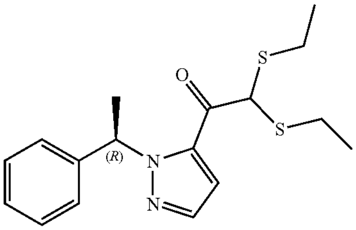
Compound D16
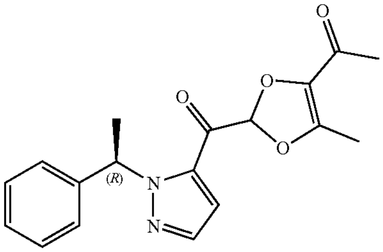
Compound D17
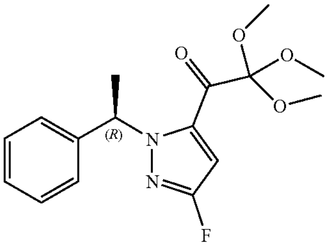
Compound D18
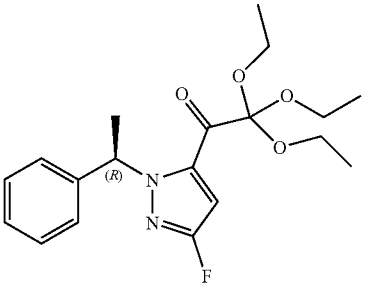

-continued
Compound D19
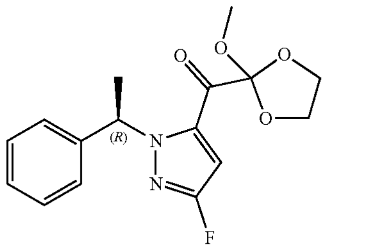
Compound D20
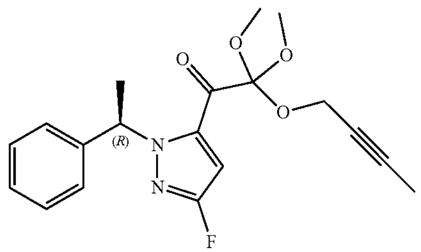
Compound D21
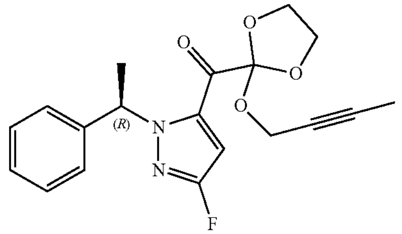
Compound D22
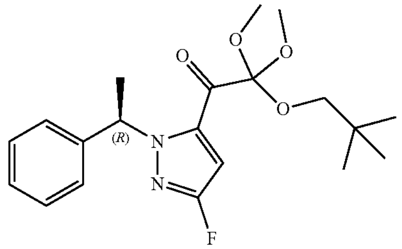
Compound D23
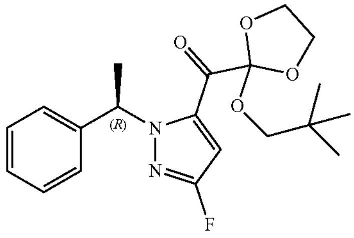
Compound D24
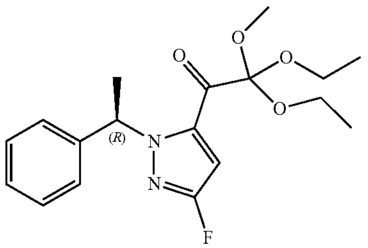
Compound D25
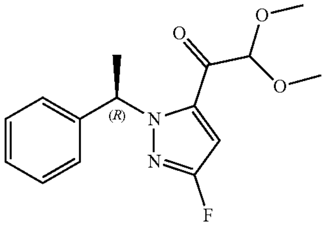
Compound D26
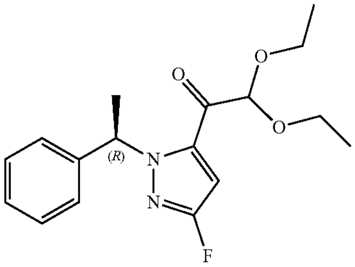
Compound D27
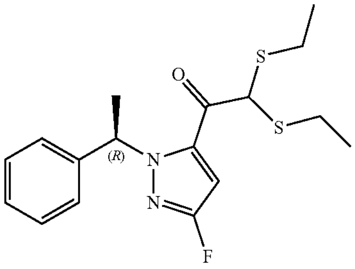
Compound D28
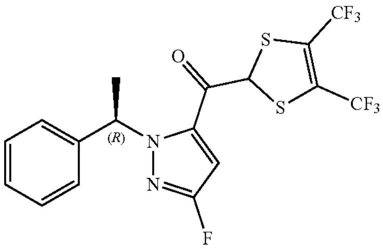
Compound D29
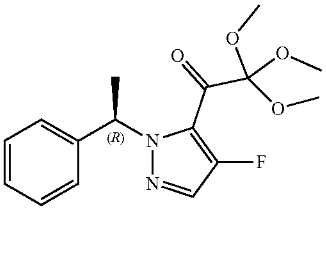
Compound D30
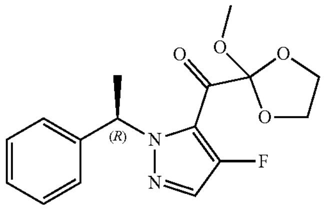

-continued
Compound D31
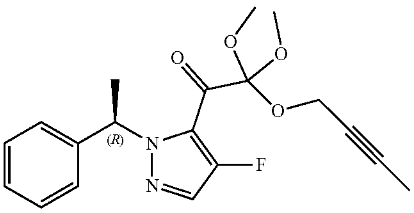
Compound D32
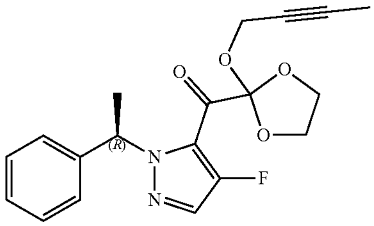
Compound D33
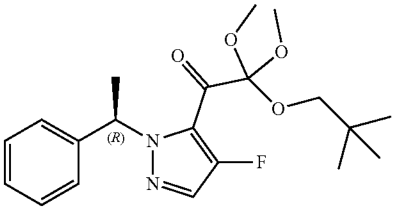
Compound D34
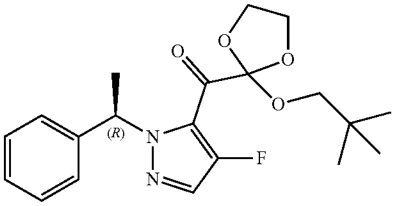
Compound D35
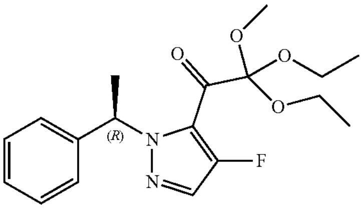
Compound D36
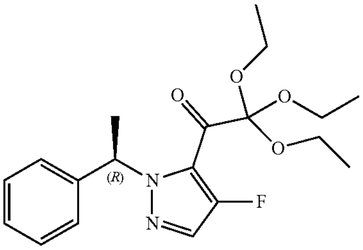
Compound D37
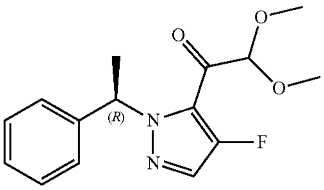
-continued
Compound D38
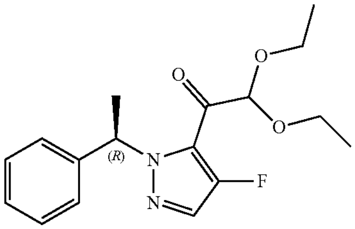
Compound D39
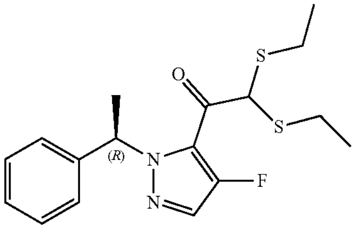
Compound D40
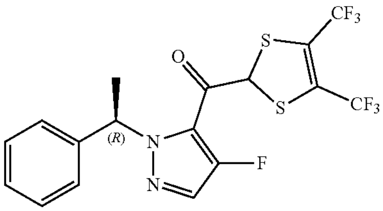
Compound D41
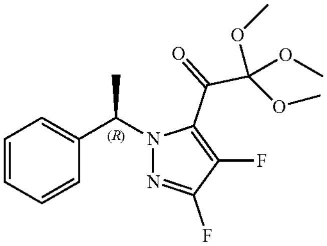
Compound D42
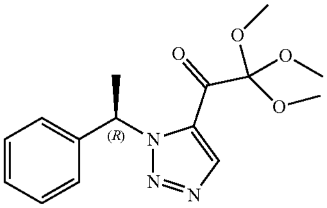
Compound D43
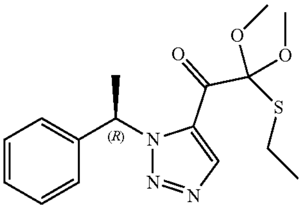
Compound D44
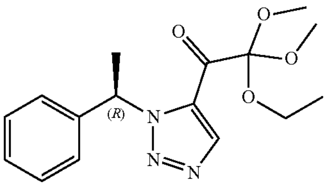

-continued
Compound D45
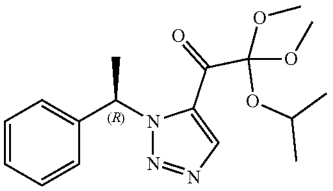
Compound D46
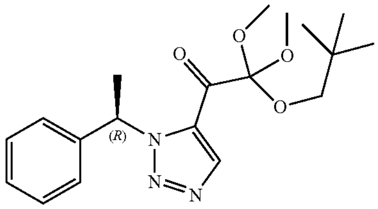
Compound D47
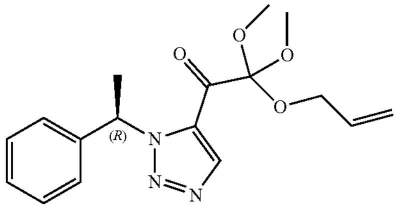
Compound D48
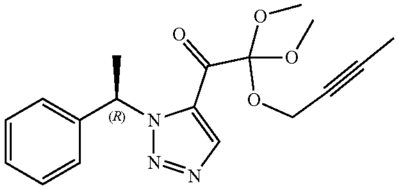
Compound D49
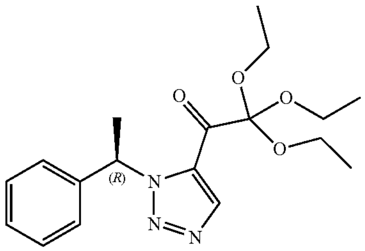
Compound D50
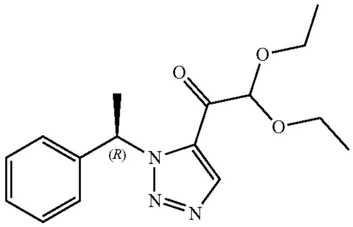
Compound D51
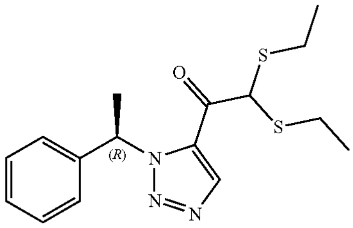
-continued
Compound D52
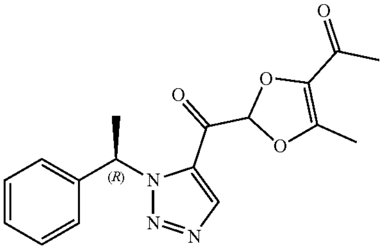
Compound D53
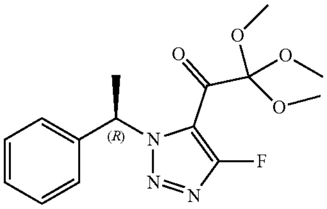
Compound D54
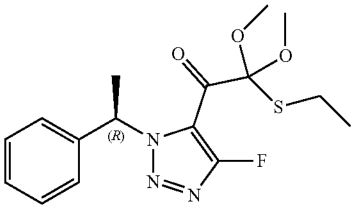
Compound D55
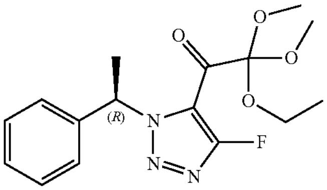
Compound D56
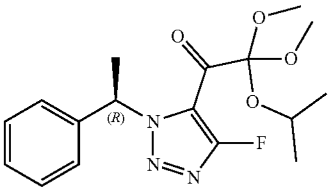
Compound D57
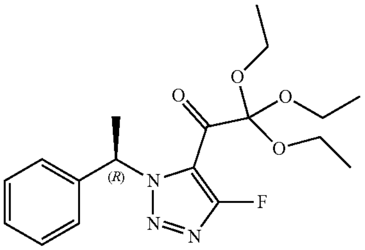
Compound D58
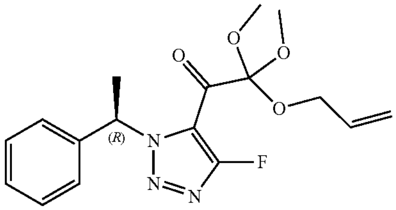

-continued
Compound D59
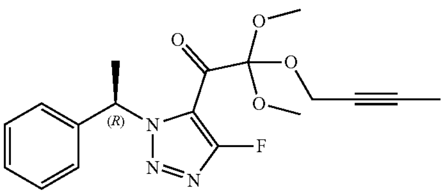
Compound D60
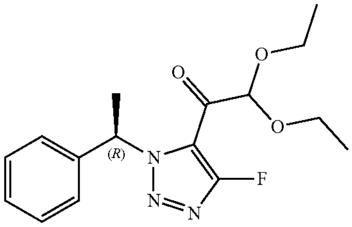
Compound D61
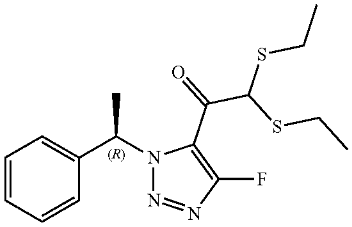
Compound D62
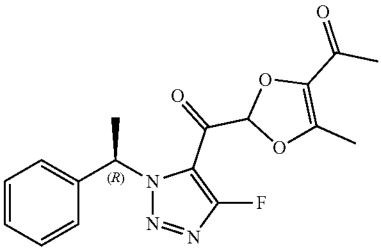
Compound D63
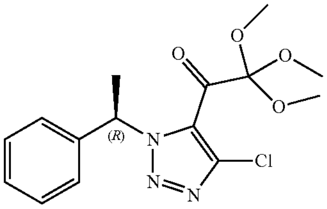
Compound D64
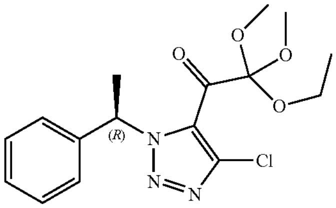
Compound D65
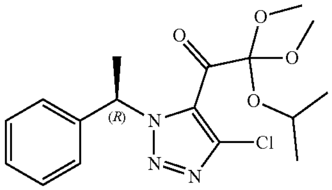
-continued
Compound D66
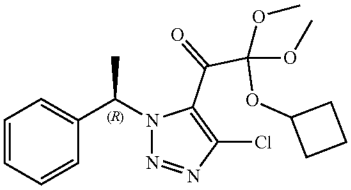
Compound D67
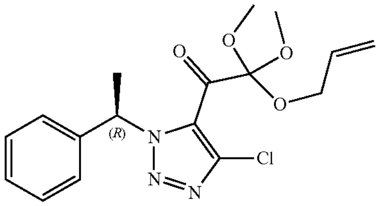
Compound D68
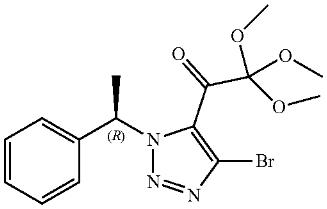
Compound D69
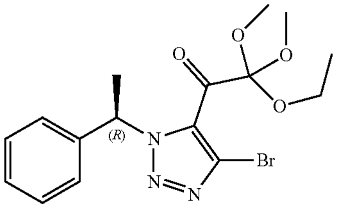
Compound D70
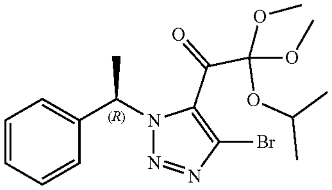
Compound D71
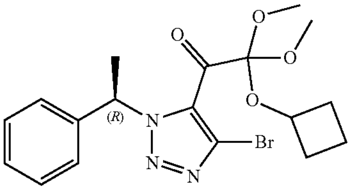
Compound D72
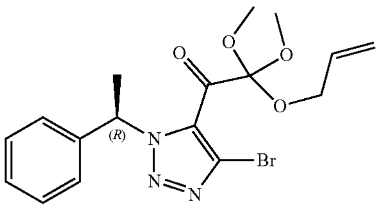

-continued
Compound D73
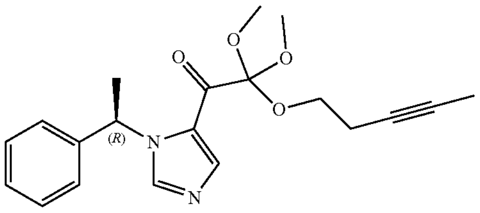
Compound D74
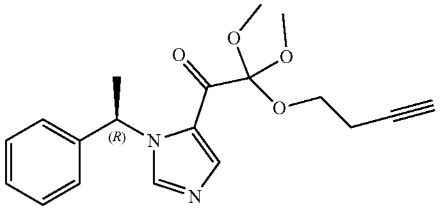
Compound D75
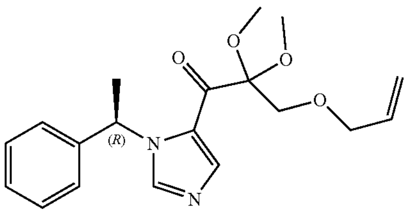
Compound D76
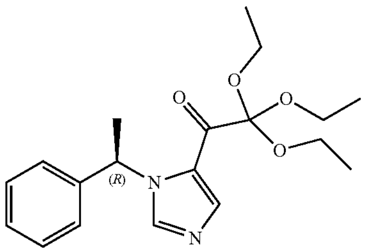
Compound D77
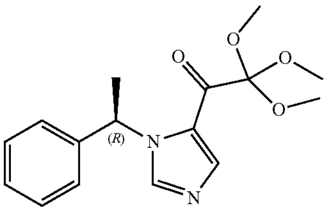
Compound D78
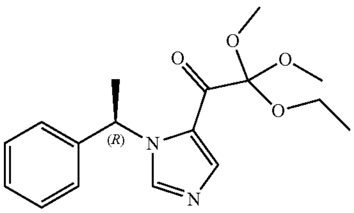
Compound D79
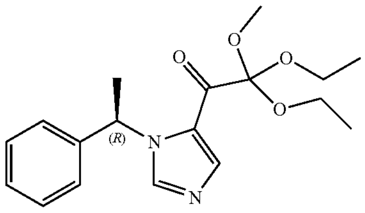
-continued
Compound D80
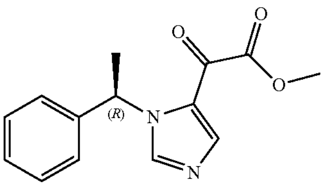
Compound D81
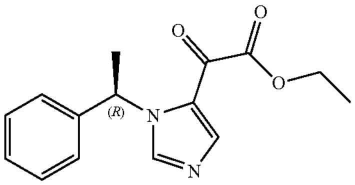
Compound D82
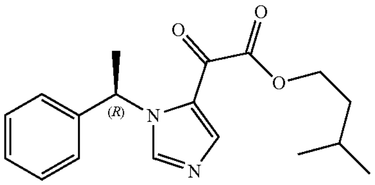
Compound D83
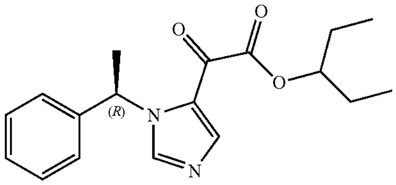
Compound D84
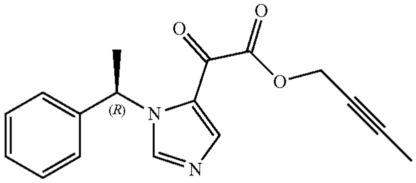
Compound D85
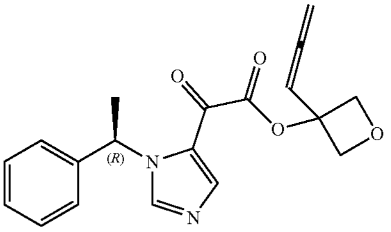
Compound D86
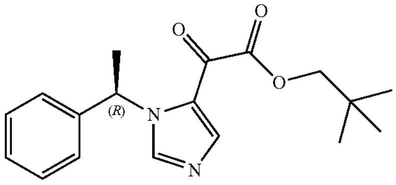
Compound D87
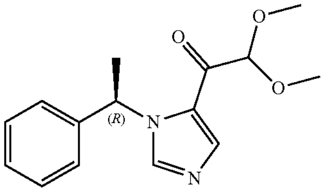

Compound D88
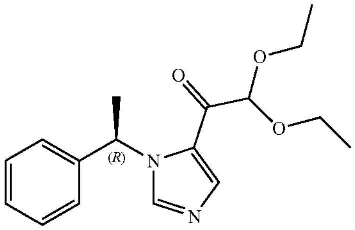
Compound D89
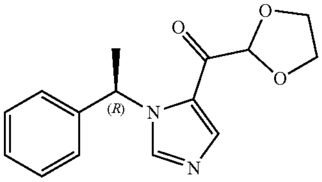
Compound D90
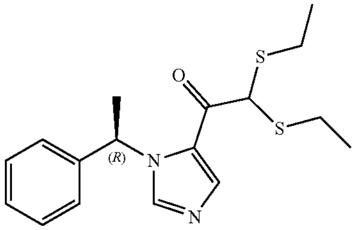
Compound D91
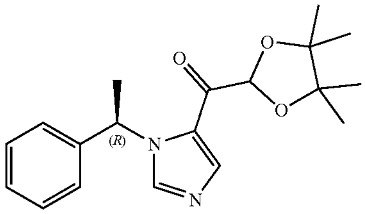
Compound D92
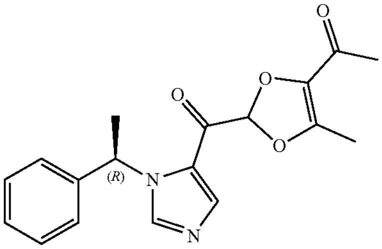
Compound D93
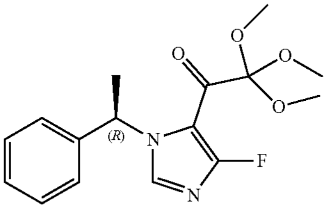
Compound D94
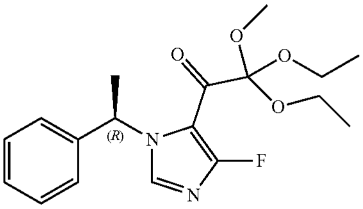
Compound D95
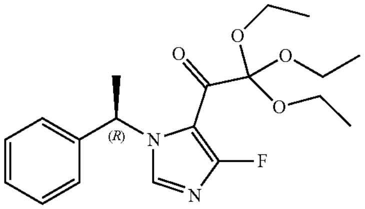
Compound D96
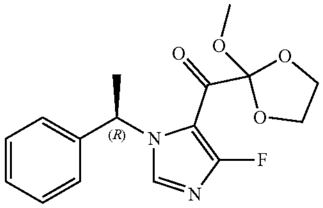
Compound D97
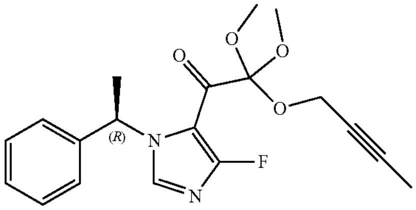
Compound D98
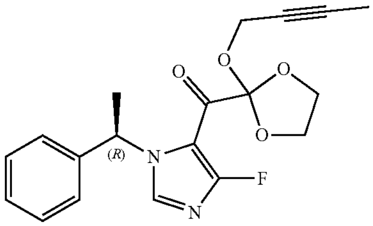
Compound D99
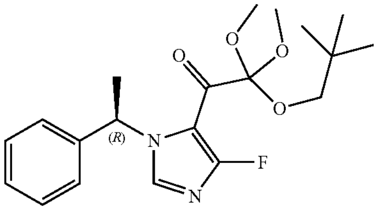
Compound D100
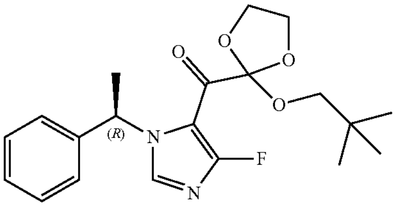
Compound D101
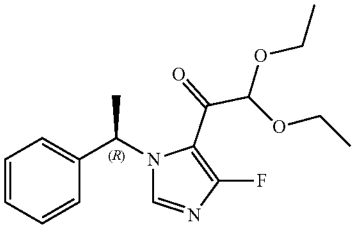

-continued
Compound D102
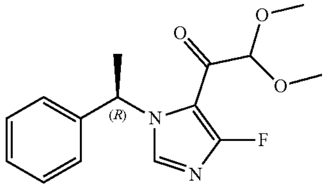
Compound D103
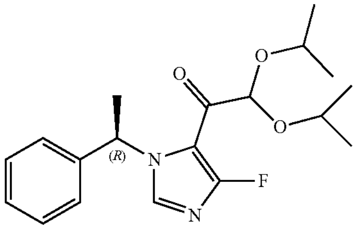
Compound D104
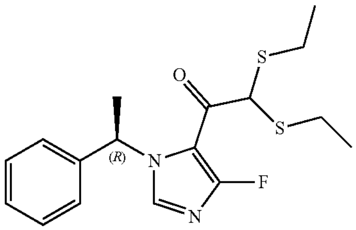
Compound D105
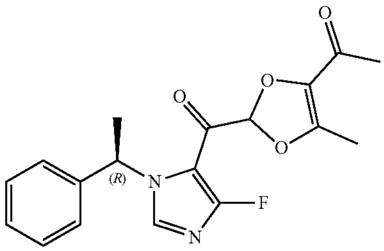
Compound D106
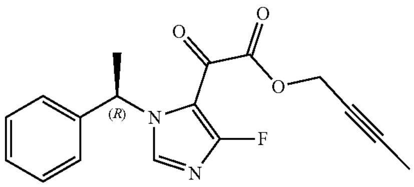
Compound D107
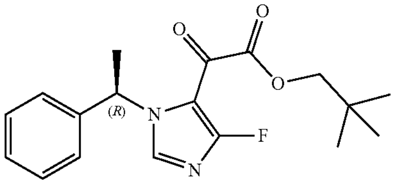
Compound D108
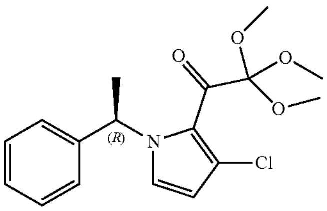
-continued
Compound D109
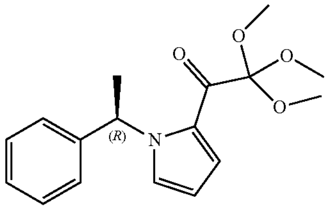
Compound D110
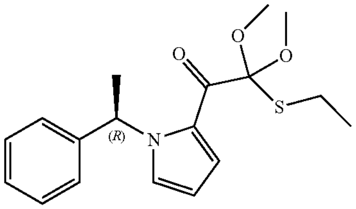
Compound D111
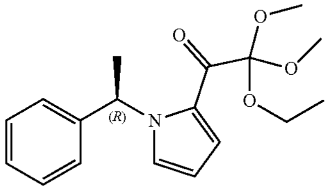
Compound D112
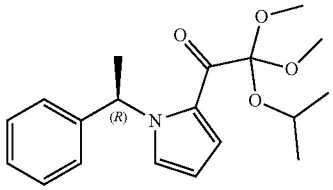
Compound D113
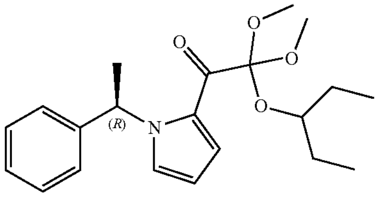
Compound D114
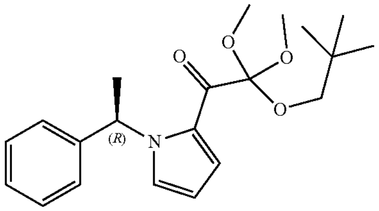
Compound D115
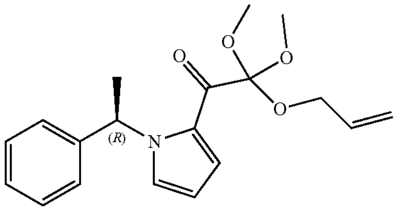

-continued
Compound D116
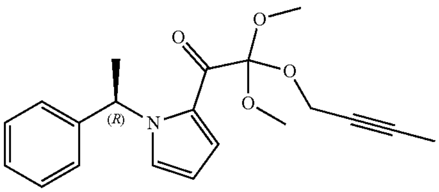
Compound D117
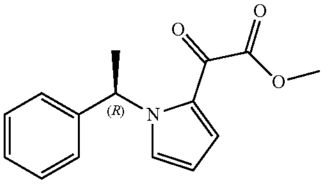
Compound D118
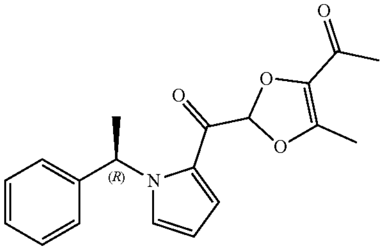
Compound D119
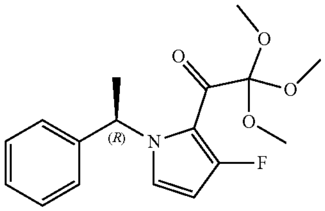
Compound D120
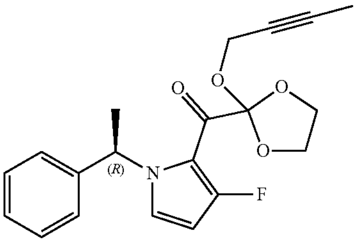
Compound D121
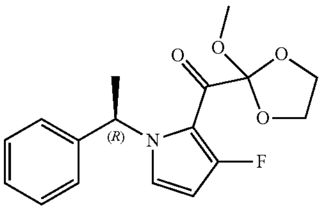
-continued
Compound D122
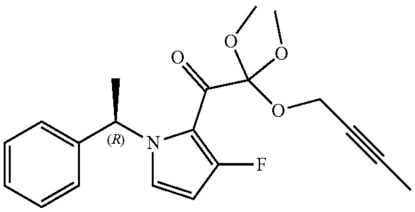
Compound D123
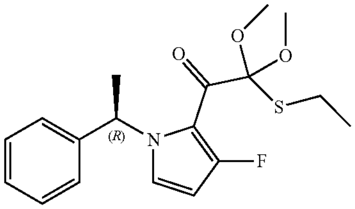
Compound D124
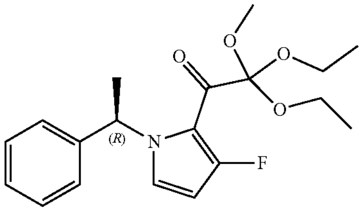
Compound D125
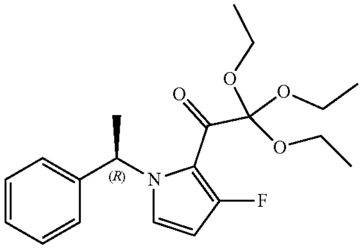
Compound D126
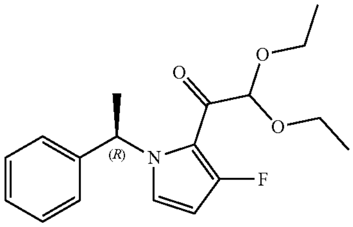
Compound D127
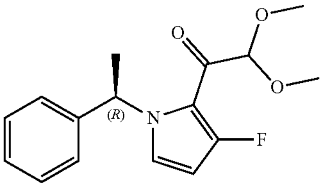
Compound D128
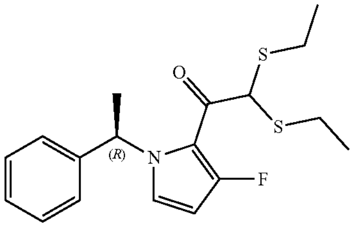

-continued
Compound D129
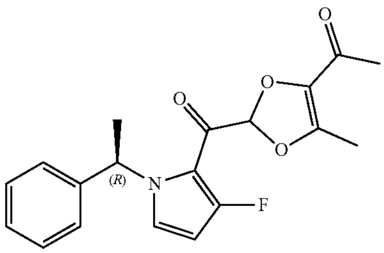
Compound D130
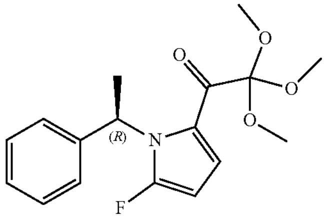
Compound D131
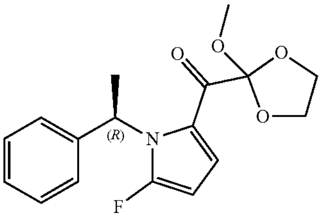
Compound D132
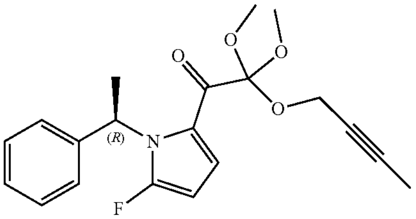
Compound D133
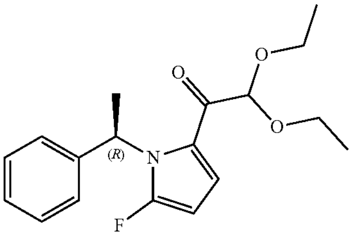
Compound D134
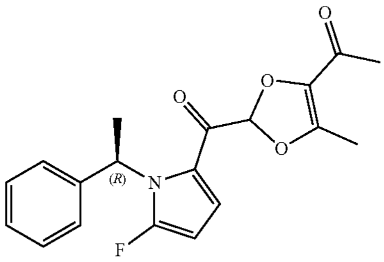
-continued
Compound D135
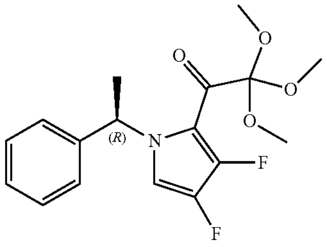
Compound D136
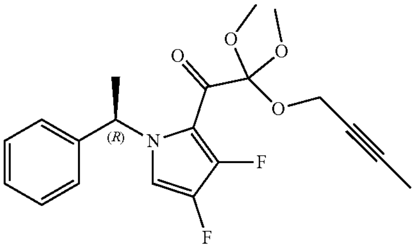
Compound D137
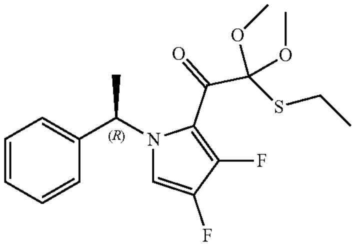
Compound D138
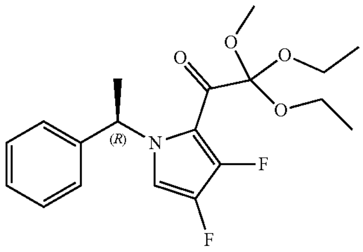
Compound D139
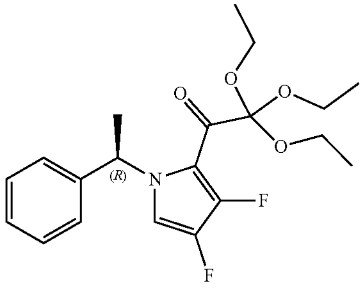
Compound D140
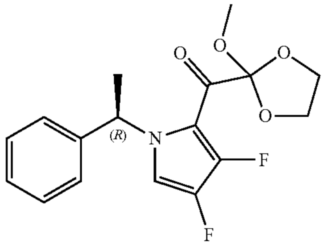

-continued

Compound D141

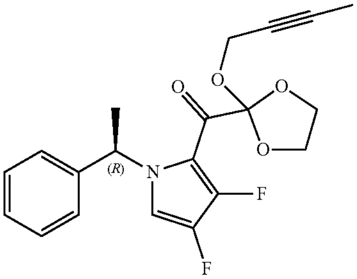

Compound D142

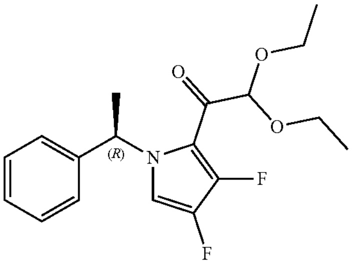

Compound D143

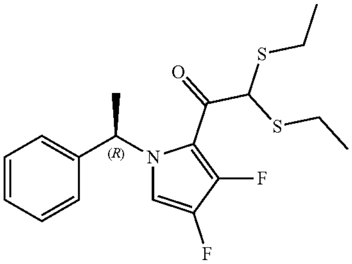

-continued

Compound D144

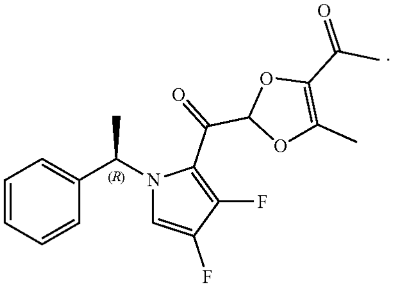

14. A drug, comprising (i) the compound according to claim 1, or the stereoisomer thereof, or the pharmaceutically acceptable salt thereof, or the solvate thereof, or the prodrug thereof, or the metabolite thereof, or the deuterated derivative thereof, or their combinations as active ingredients, and (ii) pharmaceutically acceptable excipients.

15. A method for sedating, hypnotizing or anesthetizing a subject in need thereof, comprising a step of:

administering to the subject in need thereof a therapeutically effective amount of the compound according to claim 1, or the stereoisomer thereof, or the pharmaceutically acceptable salt thereof, or the solvate thereof, or the deuterated derivative thereof, or the drug comprising the same.

16. The compound according to claim 1, or the stereoisomer thereof, or the pharmaceutically acceptable salt thereof, or the solvate thereof, or the deuterated derivative thereof, characterized in that: $K^1$ is N, and $K^2$ is $CR^{k2}$.

17. The compound according to claim 1, or the stereoisomer thereof, or the pharmaceutically acceptable salt thereof, or the solvate thereof, or the deuterated derivative thereof, characterized in that: $K^1$ is N, and $K^2$ is $CR^{k2}$, n is 0, and $R^2$ is methyl.

* * * * *